(12) United States Patent
Hatanaka et al.

(10) Patent No.: US 11,633,365 B2
(45) Date of Patent: Apr. 25, 2023

(54) NUCLEIC ACID-CONTAINING LIPID NANOPARTICLE

(71) Applicant: KYOWA KIRIN CO., LTD., Tokyo (JP)

(72) Inventors: Kentaro Hatanaka, Tokyo (JP); Michihiro Maemoto, Tokyo (JP); Shintaro Hosoe, Tokyo (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 428 days.

(21) Appl. No.: 16/636,177

(22) PCT Filed: Aug. 6, 2018

(86) PCT No.: PCT/JP2018/029446
§ 371 (c)(1),
(2) Date: Feb. 3, 2020

(87) PCT Pub. No.: WO2019/027055
PCT Pub. Date: Feb. 7, 2019

(65) Prior Publication Data
US 2020/0368173 A1    Nov. 26, 2020

(30) Foreign Application Priority Data
Aug. 4, 2017   (JP) .............. JP2017-151525

(51) Int. Cl.
| *A61K 9/51* | (2006.01) |
| *C07C 323/25* | (2006.01) |
| *C07D 205/04* | (2006.01) |
| *C12N 15/113* | (2010.01) |

(52) U.S. Cl.
CPC .......... *A61K 9/5123* (2013.01); *C07C 323/25* (2013.01); *C07D 205/04* (2013.01); *C12N 15/113* (2013.01); *C12N 2310/14* (2013.01)

(58) Field of Classification Search
CPC ............... A61K 9/0019; A61K 9/127; A61K 39/55555; A61K 47/543; C12N 15/111; C12N 15/113; C12N 2310/14; C12N 2320/32
USPC ...... 424/9.1; 435/6.1, 91.1, 91.31, 455, 458; 514/44 A; 536/23.1, 24.5
See application file for complete search history.

(56) References Cited

U.S. PATENT DOCUMENTS

| 5,976,567 | A | 11/1999 | Wheeler et al. |
| 6,287,591 | B1 | 9/2001 | Semple et al. |
| 6,858,225 | B2 | 2/2005 | Semple et al. |
| 7,341,738 | B2 | 3/2008 | Semple et al. |
| 7,901,708 | B2 | 3/2011 | MacLachlan et al. |
| 8,021,686 | B2 | 9/2011 | Semple et al. |
| 8,236,770 | B2 | 8/2012 | Endert et al. |
| 8,329,070 | B2 | 12/2012 | MacLachlan et al. |
| 9,492,386 | B2 | 11/2016 | MacLachlan et al. |
| 9,504,651 | B2 | 11/2016 | MacLachlan et al. |
| 10,143,758 | B2 | 12/2018 | Guild et al. |
| 10,272,041 | B2 | 4/2019 | Kester et al. |
| 10,576,166 | B2 | 3/2020 | DeRosa et al. |
| 2003/0129221 | A1 | 7/2003 | Semple et al. |
| 2004/0142025 | A1 | 7/2004 | MacLachlan et al. |
| 2005/0008689 | A1 | 1/2005 | Semple et al. |
| 2005/0255153 | A1 | 11/2005 | Semple et al. |
| 2006/0286161 | A1 | 12/2006 | Panzner et al. |
| 2008/0200417 | A1 | 8/2008 | Semple et al. |
| 2008/0311181 | A1 | 12/2008 | Endert et al. |
| 2010/0041152 | A1 | 2/2010 | Wheeler et al. |
| 2011/0216622 | A1 | 9/2011 | MacLachlan et al. |
| 2011/0244026 | A1 | 10/2011 | Guild et al. |
| 2012/0114831 | A1 | 5/2012 | Semple et al. |
| 2013/0149374 | A1 | 6/2013 | Lee et al. |
| 2013/0195967 | A1 | 8/2013 | Guild et al. |
| 2014/0044772 | A1 | 2/2014 | MacLachlan et al. |
| 2014/0271824 | A1 | 9/2014 | Kester et al. |
| 2014/0294937 | A1 | 10/2014 | MacLachlan et al. |
| 2014/0294940 | A1 | 10/2014 | Guild et al. |
| 2016/0287725 | A1 | 10/2016 | DeRosa et al. |
| 2017/0210698 | A1* | 7/2017 | Benenato ............. A61K 9/5146 |
| 2017/0258719 | A1 | 9/2017 | MacLachlan et al. |
| 2018/0353434 | A1* | 12/2018 | Hatanaka ........... C07D 295/088 |
| 2019/0167586 | A1 | 6/2019 | MacLachlan et al. |
| 2019/0192690 | A1 | 6/2019 | Guild et al. |
| 2020/0268664 | A1 | 8/2020 | MacLachlan et al. |

FOREIGN PATENT DOCUMENTS

| CN | 106540271 | 3/2017 |
| JP | 2002-501511 | 1/2002 |
| JP | 2007-501850 | 2/2007 |
| JP | 2007-530462 | 11/2007 |
| WO | 96/40964 | 12/1996 |
| WO | 2004/002453 | 1/2004 |
| WO | 2009/002719 | 12/2008 |
| WO | 2010/014895 | 2/2010 |

(Continued)

OTHER PUBLICATIONS

Structures provided. (Year: 2017).*
Roberts et al (Nature Reviews: Drug Discovery, vol. 19, pp. 673-694 (2020)) (Year: 2020).*
Damase et al (Frontiers in Bioengineering and Biotech., vol. 9, article 628137, pp. 1-24 (2021)) (Year: 2021).*
International Search Report dated Oct. 23, 2018 in International (PCT) Application No. PCT/JP2018/029446 with English-language translation.

(Continued)

*Primary Examiner* — Jane J Zara
(74) *Attorney, Agent, or Firm* — Wenderoth, Lind & Ponack, L.L.P.

(57) ABSTRACT

The present invention provides a nucleic acid-containing lipid nanoparticle comprising an analog of a fatty acid ester of glycerol, and a nucleic acid, wherein the analog is not hydrolyzable by a lipase.

18 Claims, 2 Drawing Sheets

Specification includes a Sequence Listing.

(56) References Cited

FOREIGN PATENT DOCUMENTS

| WO | 2010/056403 | 5/2010 |
| WO | 2011/068810 | 6/2011 |
| WO | 2013/143555 | 10/2013 |
| WO | 2014/143806 | 9/2014 |
| WO | 2016/153012 | 9/2016 |
| WO | 2016/180467 | 11/2016 |
| WO | 2018/062413 | 4/2018 |

OTHER PUBLICATIONS

Mokhtarieh et al., "Asymmetric liposome particles with highly efficient encapsulation of siRNA and without nonspecific cell penetration suitable for target-specific delivery", Biochimica et Biophysica Acta, 2012, vol. 1818, pp. 1633-1641.

Semple et al., "Efficient encapsulation of antisense oligonucleotides in lipid vesicles using ionizable aminolipids: formation of novel small multilamellar vesicle structure", Biochimica et Biophysica Acta, 2001, vol. 1510, pp. 152-166.

Mamusa et al., "Cationic liposomal vectors incorporating a bolaamphiphile for oligonucleotide antimicrobials", Biochimica et Biophisica Acta, 2017, vol. 1859, pp. 1767-1777.

* cited by examiner

[Figure 1]
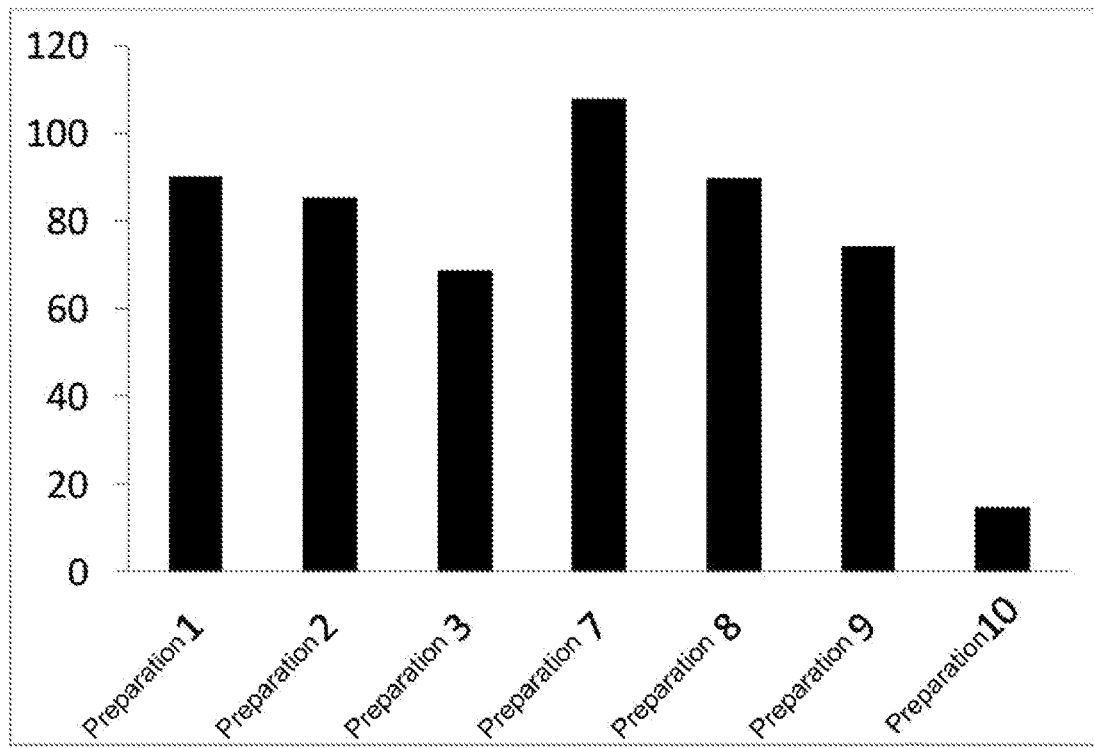
[Figure 2]
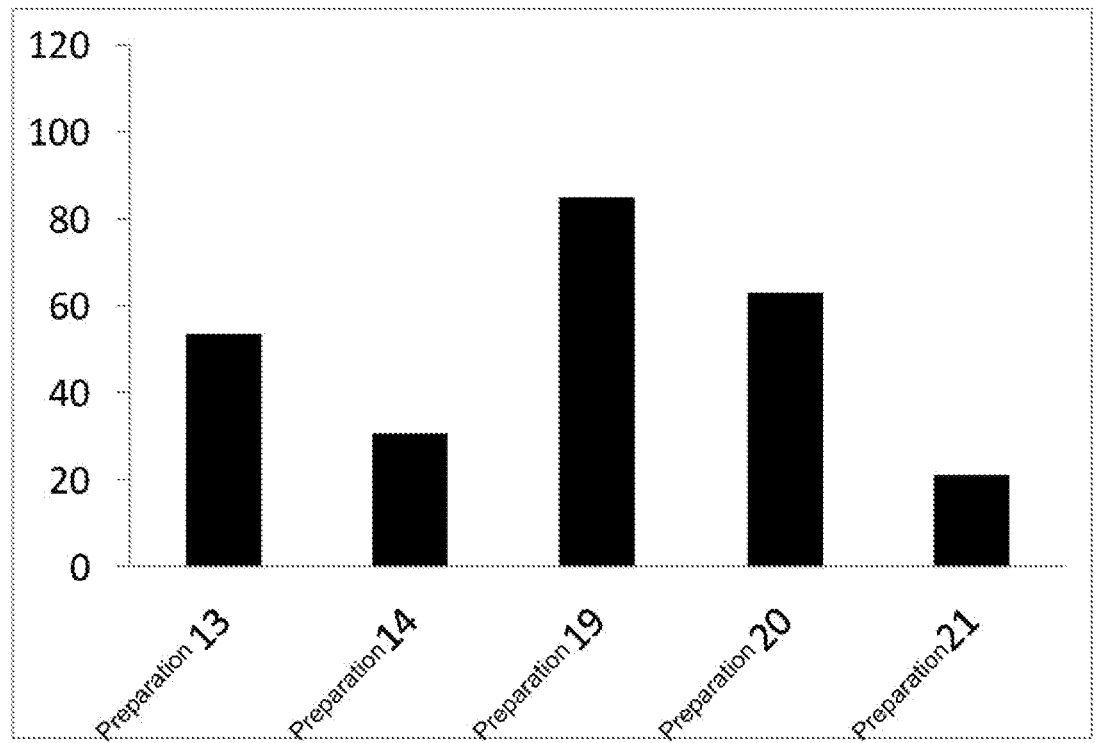

[Figure 3]
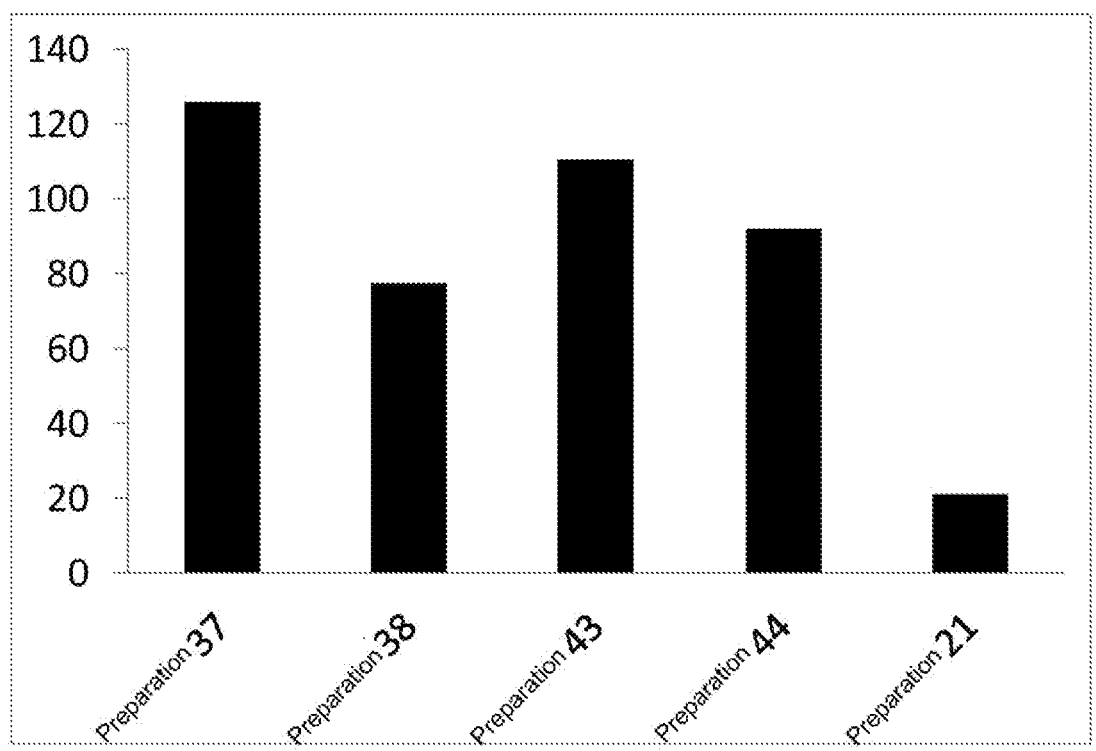

NUCLEIC ACID-CONTAINING LIPID NANOPARTICLE

TECHNICAL FIELD

The present invention relates to a nucleic acid-containing lipid nanoparticle.

BACKGROUND ART

In order to achieve gene therapy, carriers have been developed for efficiently delivering nucleic acids such as plasmid DNA (pDNA), antisense oligodeoxynucleic acid (ODN) and short interfering RNA (siRNA) to target cells in vivo. A method which involves allowing lipid particles to contain nucleic acids in order to protect the nucleic acids from in vivo nucleases and the like, and administering the complexes is known as an approach thereof.

Patent Literature 1 and Non Patent Literature 1 have reported, as a method for producing a liposome containing a nucleic acid or the like, for example, a method for producing a liposome containing siRNA by dissolving a dried cationic lipid, an aqueous sodium citrate solution of siRNA and a neutral lipid, and a polyethylene glycolated phospholipid in HEPES [N-(2-hydroxyethyl)piperazine-N'-(2-ethanesulfonic acid)] buffered saline (hereinafter, referred to as "HBS") and ethanol, adding the resulting solution to diethyl ether to form a water-in-oil (W/O) emulsion, then mixing the solution, and treating the solution by a reverse-phase evaporation method.

Patent Literature 2 and Non Patent Literature 2 have reported a method for producing a liposome containing ODN by dissolving ODN in an aqueous citric acid solution of pH 3.8, adding a solution of a lipid in ethanol to the solution, decreasing the ethanol concentration to 20 v/v % to prepare a liposome containing ODN, filtering the solution through a sizing membrane, removing an excess of ethanol by dialysis, and then further dialyzing the sample at pH 7.5 to remove ODN attached to the liposome surface.

Patent Literature 3 has reported, for example, a method for producing a liposome containing pDNA by mixing a solution containing pDNA dissolved in an aqueous citric acid solution with a solution containing a lipid dissolved in ethanol using a T-shaped mixer, decreasing the ethanol concentration to 45 v/v %, then further adding thereto a citrate buffer solution so that the ethanol concentration is decreased to 20 v/v % to prepare a liposome containing pDNA, removing residual pDNA through an anion-exchange resin, and removing an excess of ethanol by ultra-filtration.

Patent Literature 4 has reported a method for producing a liposome containing pDNA by complexing pDNA with a cationic lipid as micelle in an organic solvent containing water, further adding a lipid thereto, and then removing the organic solvent by dialysis.

Patent Literature 5 has reported a method for producing a liposome containing pDNA by complexing pDNA with a cationic lipid as micelle in an aqueous solution of a surfactant, further adding a lipid thereto, and then removing the surfactant by dialysis.

Meanwhile, Non Patent Literature 3 has reported that in a test using lipid nanoparticles containing doxorubicin, the contents are efficiently released by hydrolyzing an ester bond at position sn-2 of phospholipid with phospholipase A2 (hereinafter, also referred to as "PLA2"). This means that when phospholipid, a constituent of the lipid nanoparticles, is metabolized with phospholipase A2 in vivo, the stability of the particles carrying a drug is reduced. When the drug is a low-molecular drug, the reduced stability of the particles facilitates smoothly releasing the drug so that the drug exhibits activity. On the other hand, when the contents are a nucleic acid, the nucleic acid is poorly taken up into cells even after release and is enzymatically degraded, leading to the disappearance of its activity. Nanoparticles containing the nucleic acid mentioned above generally employ a lipid served as a substrate of PLA2. Thus, it has been difficult to prepare a lipid particle having high stability.

Patent Literature 6 discloses that 1,2-di-O-hexadecyl-sn-glycero-3-phosphocholine is used in a composition for the oral administration and transport of bioactive drugs, and states that such a composition is stable against acids. However, the literature does not state that this composition was used for nucleic acid transport.

CITATION LIST

Patent Literature

Patent Literature 1: U.S. Patent Application Publication No. 2013/0149374
Patent Literature 2: Japanese Unexamined Patent Application Publication (Translation of PCT Application) No. 2002-501511
Patent Literature 3: WO 2004/002453
Patent Literature 4: WO 96/40964
Patent Literature 5: U.S. Patent Application Publication No. 2010/0041152
Patent Literature 6: WO 2014/143806

Non Patent Literature

Non Patent Literature 1: Biochimica et Biophysica Acta, 2012, Vol. 1818, p. 1633-1641
Non Patent Literature 2: Biochimica et Biophysica Acta, 2001, Vol. 1510, p. 152-166

SUMMARY OF INVENTION

Technical Problem

An object of the present invention is to provide a nucleic acid-containing lipid nanoparticle that is useful as a medicament and is more stable than conventional particles.

Solution to Problem

The present invention relates to the following:

[1]
A nucleic acid-containing lipid nanoparticle comprising an analog of a fatty acid ester of glycerol, and a nucleic acid,
wherein the analog is not hydrolyzable by a lipase.

[2]
The nucleic acid-containing lipid nanoparticle according to [1], wherein the analog of the fatty acid ester of glycerol is an analog of a glycerophospholipid.

[3]
The nucleic acid-containing lipid nanoparticle according to [1] or [2], wherein the lipase is phospholipase A2.

[4]
The nucleic acid-containing lipid nanoparticle according to any one of [1] to [3], wherein the analog of the fatty acid ester of glycerol is a lipid represented by the following formula (1) or (2):

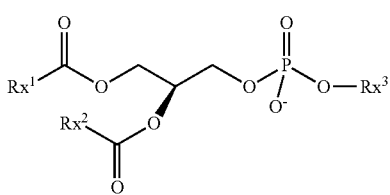
(1)

wherein $Rx^1$ and $Rx^2$ are the same or different and are each optionally substituted linear or branched C7-C23 alkyl, C7-C23 alkenyl or C7-C23 alkynyl; and $Rx^3$ is a negative charge, a hydrogen atom, or any of the following groups:

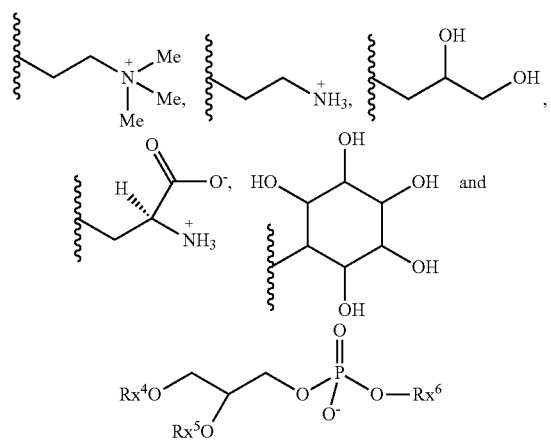
(2)

wherein $Rx^4$ is optionally substituted linear or branched C8-C24 alkyl, C8-C24 alkenyl or C8-C24 alkynyl or $Rx^{41}$-CO—;

$Rx^{41}$ is optionally substituted linear or branched C7-C23 alkyl, C7-C23 alkenyl or C7-C23 alkynyl;

$Rx^5$ is optionally substituted linear or branched C8-C24 alkyl, C8-C24 alkenyl or C8-C24 alkynyl; and $Rx^6$ is a negative charge, a hydrogen atom, or any of the following groups:

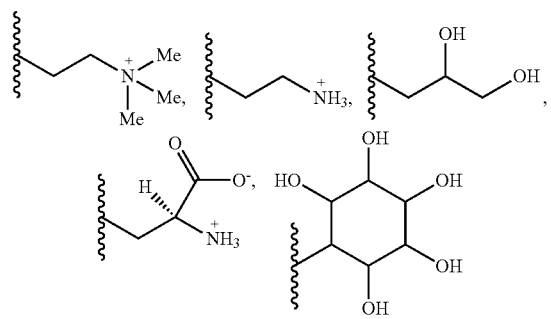

[5]
The nucleic acid-containing lipid nanoparticle according to any one of [1] to [4], wherein a content of the analog of the fatty acid ester of glycerol is 0.001-fold molar amount or more with respect to the molar number of total lipid.

[6]
The nucleic acid-containing lipid nanoparticle according to any one of [1] to [5], further comprising a cationic lipid.

[7]
The nucleic acid-containing lipid nanoparticle according to [6], wherein the cationic lipid is lipid A represented by at least one of formulas (I), (II), (III), (IV), (V') and (V'') given below, and/or lipid B represented by at least one of formulas (CL-I), (CL-II), (CL-III), (CL-IV), (CL-V), (CL-VI), (CL-VII), (CL-VIII), (CL-IX), (CL-X), (CL-XI), (CL-XII), (CL-XIII), (CL-XIV), (CL-XV), (CL-XVI), (CL-XVII), (CL-XVIII) and (CL-XIX) given below (wherein the formulas (I), (II), (III), (IV), (V') and (V'') are represented by structures described in Description of Embodiments mentioned later, and the formulas (CL-I), (CL-II), (CL-III), (CL-IV), (CL-V), (CL-VI), (CL-VII), (CL-VIII), (CL-IX), (CL-X), (CL-XI), (CL-XII), (CL-XIII), (CL-XIV), (CL-XV), (CL-XVI), (CL-XVII), (CL-XVIII) and (CL-XIX) are represented by structures described in Description of Embodiments mentioned later; the same holds true for the description below).

[8]
The nucleic acid-containing lipid nanoparticle according to [7], wherein the cationic lipid is the lipid B.

[9]
The nucleic acid-containing lipid nanoparticle according to any one of [1] to [8], further comprising a lipid derivative or a fatty acid derivative of a water-soluble polymer.

[10]
The nucleic acid-containing lipid nanoparticle according to [9], wherein the water-soluble polymer moiety of the lipid derivative or the fatty acid derivative of the water-soluble polymer is selected from the group consisting of polyethylene glycol, polyglycerin, polyethyleneimine, polyvinyl alcohol, polyacrylic acid and polyacrylamide.

[11]
The nucleic acid-containing lipid nanoparticle according to any one of [1] to [10], further comprising a neutral lipid.

[12]
The nucleic acid-containing lipid nanoparticle according to [11], wherein the neutral lipid is selected from the group consisting of phospholipid, sterol, glyceroglycolipid, sphingoglycolipid and sphingoid.

[13]
The nucleic acid-containing lipid nanoparticle according to any one of [1] to [12], wherein the nucleic acid is a nucleic acid having a silencing effect on a target gene through the use of RNA interference (RNAi).

[14]
The nucleic acid-containing lipid nanoparticle according to [13], wherein the target gene is a gene related to tumor or inflammation.

[15]
A method for stabilizing a nucleic acid-containing lipid nanoparticle using an analog of a fatty acid ester of glycerol, wherein the analog is not hydrolyzable by a lipase. Here, the analog may be the analog referred in any of [1] to [5], and the nucleic acid-containing lipid nanoparticle may be the nucleic acid-containing lipid nanoparticle according to any of [1] to [14].

[16]
A method for introducing a nucleic acid into a cell using the nucleic acid-containing lipid nanoparticle according to any one of [1] to [14].

[17]
The method according to [16], wherein the cell is a cell residing at a mammalian tumor or inflammation site.

[18]

The method according to [16] or [17], wherein the cell is a cell residing in the mammalian liver, stomach, lung, kidney, pancreas or spleen.

[19]

The method according to any one of [16] to [18], wherein a method for the introduction into the cell is a method of introduction into the cell by intravenous administration or subcutaneous administration.

[20]

A method for treating a cancer or an inflammatory disease, comprising administering the nucleic acid-containing lipid nanoparticle according to any one of [1] to [14] to a mammal.

[21]

The method for treating method according to [20], wherein the administration is intravenous administration or subcutaneous administration.

[22]

A medicament comprising the nucleic acid-containing lipid nanoparticle according to any one of [1] to [14].

[23]

The medicament according to [22], wherein the medicament is intended for intravenous administration or subcutaneous administration.

[24]

A therapeutic agent for a cancer or an inflammatory disease comprising the nucleic acid-containing lipid nanoparticle according to any one of [1] to [14].

[25]

The therapeutic agent according to [24], wherein the therapeutic agent is intended for intravenous administration or subcutaneous administration.

[26]

A compound represented by formula (CL-XVIII), or a pharmaceutically acceptable salt thereof (the cationic lipid):

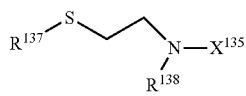

(CL-XVIII)

wherein $R^{137}$ and $R^{138}$ are the same or different and are each linear or branched C8-C24 alkyl, C8-C24 alkenyl, C8-C24 alkynyl, C8-C24 alkylthioethyl, C8-24 alkenylthioethyl, or C8-C24 alkynylthioethyl; and $X^{135}$ is a hydrogen atom, C1-C3 alkyl, hydroxy C2-C4 alkyl, formula (C):

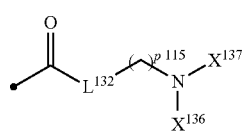

(C)

wherein $X^{136}$ and $X^{137}$ are the same or different and are each a hydrogen atom or C1-C3 alkyl, or $X^{136}$ and $X^{137}$ optionally form a C2-C6 nitrogen-containing hetero ring together with the nitrogen atom to which they are bonded; $L^{132}$ is S or O; and $p^{115}$ is an integer from 2 to 4, formula (D):

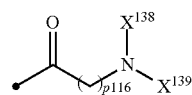

(D)

wherein $X^{138}$ and $X^{139}$ are the same or different and are each a hydrogen atom or C1 to C3 alkyl, or $X^{138}$ and $X^{139}$ optionally form a C3-C6 nitrogen-containing hetero ring together with the nitrogen atom to which they are bonded; and $p^{116}$ is an integer from 1 to 4, or formula (E):

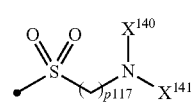

(E)

wherein $X^{140}$ and $X^{141}$ are the same or different and are each a hydrogen atom or C1 to C3 alkyl, or $X^{140}$ and $X^{141}$ optionally form a C3-C6 nitrogen-containing hetero ring together with the nitrogen atom to which they are bonded; and $p^{117}$ is an integer from 1 to 4.

[27]

A compound represented by formula (CL-XIX), or a pharmaceutically acceptable salt thereof (the cationic lipid):

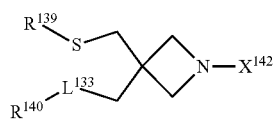

(CL-XIX)

wherein $R^{139}$ and $R^{140}$ are the same or different and are each linear or branched C8-C24 alkyl, C8-C24 alkenyl or C8-C24 alkynyl;

$L^{133}$ is S or O; and $X^{142}$ is a hydrogen atom, C1-C3 alkyl, hydroxy C2-C4 alkyl, formula (F):

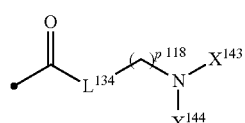

(F)

wherein $X^{143}$ and $X^{144}$ are the same or different and are each a hydrogen atom or C1-C3 alkyl, or $X^{143}$ and $X^{144}$ optionally form a C2-C6 nitrogen-containing hetero ring together with the nitrogen atom to which they are bonded; $L^{134}$ is S or O; and $p^{118}$ is an integer from 2 to 4, or formula (G):

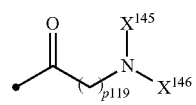

(G)

wherein $X^{145}$ and $X^{146}$ are the same or different and are each a hydrogen atom or C1 to C3 alkyl, or $X^{145}$ and $X^{146}$ optionally form a C3-C6 nitrogen-containing hetero ring together with the nitrogen atom to which they are bonded; and $p^{119}$ is an integer from 1 to 4.

Advantageous Effects of Invention

The present invention can provide a nucleic acid-containing lipid nanoparticle that is useful as a medicament and is more stable than conventional particles.

BRIEF DESCRIPTION OF DRAWINGS

FIG. 1 shows a graph showing the amount of lipids remaining in each preparation. The ordinate of the graph depicts the amount of lipids remaining (%) with that in a PLA2-untreated group defined as 1. The abscissa depicts each preparation.

FIG. 2 shows a graph showing the amount of lipids remaining in each preparation. The ordinate of the graph depicts the amount of lipids remaining (%) with that in a PLA2-untreated group defined as 1. The abscissa depicts each preparation.

FIG. 3 shows a graph showing the amount of lipids remaining in each preparation. The ordinate of the graph depicts the amount of lipids remaining (%) with that in a PLA2-untreated group defined as 1. The abscissa depicts each preparation.

DESCRIPTION OF EMBODIMENTS

Hereinafter, the mode for carrying out the present invention will be described in detail. The embodiments described below do not limit the present invention.

The nucleic acid-containing lipid nanoparticle of the present invention comprises an analog of a fatty acid ester of glycerol, and a nucleic acid. The analog is not hydrolyzable by a lipase.

The nucleic acid-containing lipid nanoparticle of the present invention can be stably present even if contacted with a lipase, because the lipid in the particle resists degradation.

In a lipid having a fatty acid ester structure of glycerol (hereinafter, also referred to as a natural glycerol lipid), at least one hydroxy group of glycerol, and a fatty acid form an ester bond. This ester bond is hydrolyzed by the action of a lipase.

The analog of the fatty acid ester of glycerol according to the present invention is a lipid having a structure modified from a partial structure in the natural glycerol lipid, and is not hydrolyzable by a lipase.

In the present invention, the phrase "not hydrolyzable by a lipase" means that when the nucleic acid-containing lipid nanoparticle of the present invention is contacted with a lipase, usually 30% or more, preferably 50% or more, more preferably 70% or more, further preferably 90% or more, still further preferably 99% or more, is not degraded with respect to the total amount of the analog of the fatty acid ester of glycerol present in the nucleic acid-containing lipid nanoparticle.

The bringing into contact the analog with the lipase is performed under conditions of usually 30 to 45° C., preferably 35 to 42° C., more preferably 37° C., and usually 0 minutes to 48 hours, preferably 1 minute to 36 hours, more preferably 1 minute to 24 hours.

The analog of the fatty acid ester of glycerol according to the present invention is preferably structurally modified in the range of preferably 10 angstroms (angstrom: $10^{-10}$ m) or less, more preferably 8 angstroms or less, further preferably 6 angstroms or less, from the carbon atom at position sn-2 of a glycerol skeleton in a natural glycerol lipid represented by formula (NL1) given below. When the structural modification is in the range of 10 angstroms or less from the carbon atom at position sn-2, the nucleic acid-containing lipid nanoparticle tends to resist the hydrolytic effect of a lipase and is thus stabilized.

The lower limit value of the structural modification range is not particularly limited as long as the lower limit value is 0 angstroms or more. The range of 0 angstroms from the carbon atom at position sn-2 refers to the carbon atom at position sn-2.

In this context, the structural modification means that a structure near the glycerol skeleton of the natural glycerol lipid is changed, and is not particularly limited as long as the structural modification reduces interaction with an active site of a lipase. Examples thereof include: the inversion of the asymmetric center of the natural glycerol lipid, i.e., the conversion of an L form to a D form; the replacement of the ester bond between the glycerol skeleton and the fatty acid with a bond such as an ether bond (—O—), a thioether bond (—S—), an amino bond (—N($R^p$)— (wherein $R^p$ is a hydrogen atom or an organic group) or an amide bond (—NHCO—); the replacement of hydrogen at any one or more of positions sn-1, sn-2 and sn-3 with an organic group; and the introduction of an organic group to position α, β, γ or δ of an acyl group mentioned later.

Examples of the organic group include hydroxy, alkoxy, alkoxycarbonyl, nitro, cyano, fluoro, chloro and bromo. Among these substituents, the alkyl moiety in alkoxy and alkoxycarbonyl is a C1-C4 alkyl such as methyl, ethyl, propyl, isopropyl, cyclopropyl, butyl, isobutyl, sec-butyl, tert-butyl, cyclobutyl or cyclopropylmethyl.

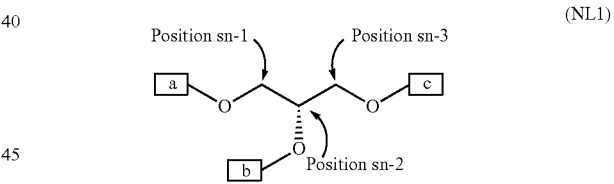

(NL1)

a and b are each independently an acyl group given below, and c is an acyl group, a phosphoric acid group, a sugar or the like. However, when both a and c are acyl groups, these acyl groups differ in the number of carbon atoms, structure, etc. and are not the same.

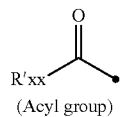

(Acyl group)

Examples of R'xx in the acyl group include optionally substituted linear or branched C7-C23 alkyl, C7-C23 alkenyl and C7-C23 alkynyl.

The analog of the fatty acid ester of glycerol according to the present invention, i.e., the analog of the natural glycerol lipid represented by formula (NL1), is preferably a glycerophospholipid analog.

The glycerophospholipid can be represented by, for example, the following formula (NL2), and the glycerophospholipid analog is a structurally modified form of the lipid represented by the following formula (NL2):

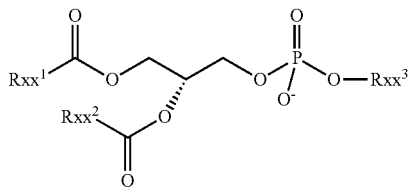

(NL2)

In formula (NL2), $Rxx^1$ and $Rxx^2$ are the same or different and are each optionally substituted linear or branched C7-C23 alkyl, C7-C23 alkenyl or C7-C23 alkynyl. Examples of $Rxx^3$ include a hydrogen atom, and the following groups:

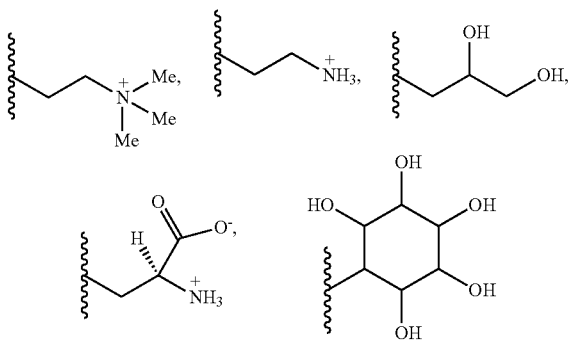

Examples of the linear or branched C7-C23 alkyl in formulas (NL1) and (NL2) include heptyl, octyl, nonyl, decyl, undecyl, dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadecan-2-yl, nonadecyl, 2,6,10,14-tetramethylpentadecyl, icosyl, 3,7,11,15-tetramethylhexadecyl, henicosyl, docosyl, tricosyl and tetracosyl.

The linear or branched C7-C23 alkenyl in formulas (NL1) and (NL2) can be linear or branched C7-C23 alkenyl containing one to three double bonds. Examples thereof include (Z)-tridec-8-enyl, (Z)-tetradec-9-enyl, (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (E)-heptadec-8-enyl, (E)-octadec-9-enyl, (Z)-heptadec-10-enyl, (Z)-octadec-11-enyl, (8Z,11Z)-heptadeca-8,11-dienyl, (9Z, 12Z)-octadeca-9,12-dienyl, (8Z,11Z,14Z)-octadeca-8,11, 14-trienyl, (9Z,12Z,15Z)-octadeca-9,12,15-trienyl, (Z)-nonadec-10-enyl, (Z)-icos-11-enyl, (10Z,13Z)-nonadeca-10,13-dienyl, (11Z,14Z)-icosa-11,14-dienyl, 2,6,10-trimethylundeca-1,5,9-trienyl, 3,7,11-trimethyldodeca-2,6,10-trienyl, 2,6,10,14-tetramethylpentadec-1-enyl and 3,7, 11,15-tetramethylhexadec-2-enyl, preferably (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (8Z,11Z)-heptadeca-8,11-dienyl and (9Z,12Z)-octadeca-9, 12-dienyl, more preferably (Z)-heptadec-8-enyl, (Z)-octadec-9-enyl, (8Z,11Z)-heptadeca-8,11-dienyl and (9Z,12Z)-octadeca-9,12-dienyl.

The linear or branched C7-C23 alkynyl in formulas (NL1) and (NL2) can be linear or branched C8-24 alkynyl containing one to three triple bonds. Examples thereof include dodec-11-ynyl, tridec-12-ynyl, pentadec-6-ynyl, hexadec-7-ynyl, pentadeca-4,6-diynyl, hexadeca-5,7-diynyl, heptadec-8-ynyl and octadec-9-ynyl, preferably pentadec-6-ynyl, hexadec-7-ynyl, pentadeca-4,6-diynyl, hexadeca-5,7-diynyl, heptadec-8-ynyl and octadec-9-ynyl, more preferably heptadec-8-ynyl and octadec-9-ynyl.

Examples of the substituent for the optionally substituted linear or branched C7-C23 alkyl, C7-C23 alkenyl or C7-C23 alkynyl in formulas (NL1) and (NL2) include hydroxy, alkoxy, alkoxycarbonyl, nitro, cyano, fluoro, chloro and bromo. Among these substituents, the alkyl moiety in alkoxy and alkoxycarbonyl is C1-C4 alkyl such as methyl, ethyl, propyl, isopropyl, cyclopropyl, butyl, isobutyl, sec-butyl, tert-butyl, cyclobutyl or cyclopropylmethyl.

Examples of the glycerophospholipid represented by formula (NL2) include, but are not limited to, natural or synthetic phospholipids such as phosphatidylcholines (PCs) (specifically, soybean phosphatidylcholine, egg phosphatidylcholine (EPC), distearoyl phosphatidylcholine, 1,2-distearoyl-sn-glycero-3-phosphocholine (DSPC), dipalmitoyl phosphatidylcholine, 1,2-dipalmitoyl-sn-glycero-3-phosphocholine (DPPC), palmitoyl oleoyl phosphatidylcholine (POPC), dimyristoyl phosphatidylcholine (DMPC), dioleoyl phosphatidylcholine (DOPC), etc.), phosphatidylethanolamines (specifically distearoyl phosphatidylethanolamine (DSPE), dipalmitoyl phosphatidylethanolamine (DPPE), dioleoyl phosphatidylethanolamine (DOPE), dimyristoyl phospoethanolamine (DMPE), 16-0-monomethyl PE, 16-0-dimethyl PE, 18-1-trans PE, palmitoyl oleoyl-phosphatidylethanolamine (POPE), 1-stearoyl-2-oleoyl-phosphatidylethanolamine (SOPE), etc.), glycerophospholipids (specifically, phosphatidylserine, phosphatidic acid, phosphatidylglycerol, phosphatidylinositol, palmitoyl oleoyl phosphatidylglycerol (POPG), lysophosphatidylcholine, etc.), sphingophospholipids (specifically, sphingomyelin, ceramide phosphoethanolamine, ceramide phosphoglycerol, ceramide phosphoglycerophosphoric acid, etc.), glycerophosphonolipids, sphingophosphonolipids, natural lecithins (specifically, egg lecithin, soybean lecithin, etc.) and hydrogenated phospholipids (specifically, hydrogenated soybean phosphatidylcholine, etc.).

The lipase according to the present invention is not particularly limited as long as the enzyme hydrolyzes the fatty acid ester contained in the natural glycerol lipid represented by formula (NL1). Examples of the lipase include phospholipase. Examples of the phospholipase specifically include phospholipase A1, phospholipase A2, phospholipase B, lysophospholipase, phospholipase C and phospholipase D.

The analog of the fatty acid ester of glycerol according to the present invention is preferably an analog of a fatty acid ester of glycerol, and the analog is not hydrolyzable by phospholipase A2.

The glycerophospholipid analog has a structure modified from a partial structure of the glycerophospholipid represented by formula (NL2) described above. Specifically, the glycerophospholipid analog is preferably a lipid represented by the following formula (1) or (2):

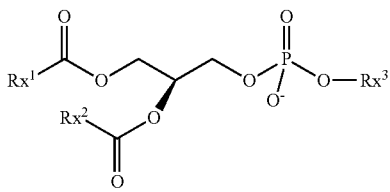

(1)

wherein

Rx$^1$ and Rx$^2$ are the same or different and are each optionally substituted linear or branched C7-C23 alkyl, C7-C23 alkenyl or C7-C23 alkynyl; and Rx$^3$ is a negative charge, a hydrogen atom, or any of the following groups:

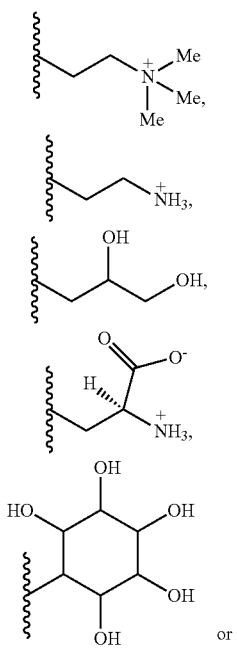

or

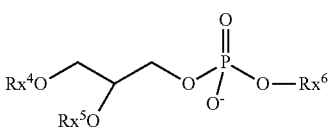

(2)

wherein

Rx$^4$ is optionally substituted linear or branched C8-C24 alkyl, C8-C24 alkenyl or C8-C24 alkynyl or Rx$^{41}$-CO—;

Rx$^{41}$ is optionally substituted linear or branched C7-C23 alkyl, C7-C23 alkenyl or C7-C23 alkynyl;

Rx$^5$ is optionally substituted linear or branched C8-C24 alkyl, C8-C24 alkenyl or C8-C24 alkynyl; and Rx$^6$ is a negative charge, a hydrogen atom, or any of the following groups:

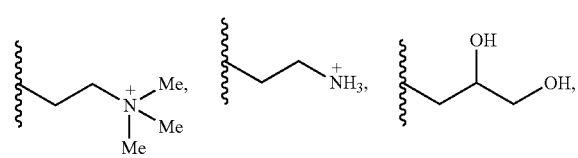

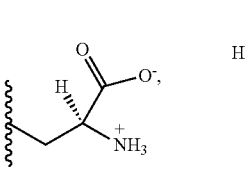 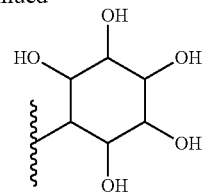

Examples of the linear or branched C7-C23 alkyl, C1-C23 alkenyl and C7-C23 alkenyl in formulas (1) and (2) can include the same as those listed about C7-C23 alkyl, C7-C23 alkenyl and C7-C23 alkenyl in formula (NL2).

Examples of the linear or branched C8-C24 alkyl include heptyl, octyl, nonyl, decyl, undecyl, dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadecan-2-yl, nonadecyl, 2,6,10,14-tetramethylpentadecyl, icosyl, 3,7,11,15-tetramethylhexadecyl, henicosyl, docosyl, tricosyl and tetracosyl.

The linear or branched C8-C24 alkenyl can be linear or branched C8-24 alkenyl containing one to three double bonds. Examples thereof include (Z)-tridec-8-enyl, (Z)-tetradec-9-enyl, (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (E)-heptadec-8-enyl, (E)-octadec-9-enyl, (Z)-heptadec-10-enyl, (Z)-octadec-11-enyl, (8Z,11Z)-heptadeca-8,11-dienyl, (9Z,12Z)-octadeca-9,12-dienyl, (8Z,11Z,14Z)-octadeca-8,11,14-trienyl, (9Z,12Z,15Z)-octadeca-9,12,15-trienyl, (Z)-nonadec-10-enyl, (Z)-icos-11-enyl, (10Z,13Z)-nonadeca-10,13-dienyl, (11Z,14Z)-icosa-11,14-dienyl, 2,6,10-trimethylundeca-1,5,9-trienyl, 3,7,11-trimethyldodeca-2,6,10-trienyl, 2,6,10,14-tetramethylpentadec-1-enyl and 3,7,11,15-tetramethylhexadec-2-enyl, preferably (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (8Z,11Z)-heptadeca-8,11-dienyl and (9Z,12Z)-octadeca-9,12-dienyl, more preferably (Z)-heptadec-8-enyl, (Z)-octadec-9-enyl, (8Z,11Z)-heptadeca-8,11-dienyl and (9Z,12Z)-octadeca-9,12-dienyl.

The linear or branched C8-C24 alkynyl can be linear or branched C8-24 alkynyl containing one to three triple bonds. Examples thereof include dodec-11-ynyl, tridec-12-ynyl, pentadec-6-ynyl, hexadec-7-ynyl, pentadeca-4,6-diynyl, hexadeca-5,7-diynyl, heptadec-8-ynyl and octadec-9-ynyl, preferably pentadec-6-ynyl, hexadec-7-ynyl, pentadeca-4,6-diynyl, hexadeca-5,7-diynyl, heptadec-8-ynyl and octadec-9-ynyl, more preferably heptadec-8-ynyl and octadec-9-ynyl.

Examples of the substituent for the optionally substituted linear or branched C8-C24 alkyl, C8-C24 alkenyl, C8-C24 alkynyl, C7-C23 alkyl, C7-C23 alkenyl and C7-C23 alkynyl in formulas (1) and (2) include hydroxy, alkoxy, alkoxycarbonyl, nitro, cyano, fluoro, chloro and bromo. Among these substituents, the alkyl moiety in alkoxy and alkoxycarbonyl is C1-C4 alkyl such as methyl, ethyl, propyl, isopropyl, cyclopropyl, butyl, isobutyl, sec-butyl, tert-butyl, cyclobutyl or cyclopropylmethyl.

The analog of the fatty acid ester of glycerol according to the present invention may be a salt. When the analog of the fatty acid ester of glycerol is a salt, the salt is not particularly limited as long as the salt is pharmaceutically acceptable. For example, when each of Rx$^3$ and Rx$^6$ in formulas (1) and (2) is a hydrogen atom,

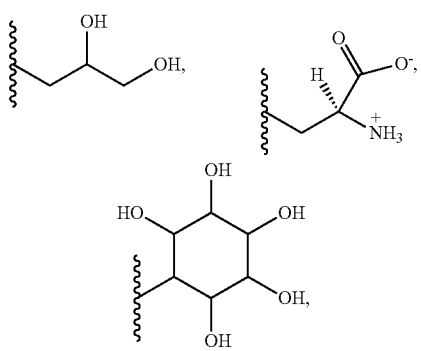

a salt of an alkali metal such as sodium or potassium, or ammonium salt ($NH_4^+$ salt) is preferred.

Each of $Rx^3$ and $Rx^6$ may be a negative charge. The negative charge represented by $Rx^3$ or $Rx^6$ means that hydrogen corresponding to $Rx^3$ or $Rx^6$ is deprotonated. Specifically, the negative charge means that a phosphoric acid ester group in formulas (1) and (2) may be $-PO_4^2$.

The lipid represented by formula (2) may be a single substance of any one optical isomer as to asymmetric carbon having a configuration that is not shown herein, or may be a mixture containing such optical isomers at an arbitrary ratio.

Specifically, an inositol skeleton in $Rxx^3$, $Rx^3$ and $Rx^6$ in formula (NL2) and formulas (1) and (2) is derived from any inositol given below. In the following inositol structures, a hydroxy group to form a bond to phosphoric acid is not particularly limited.

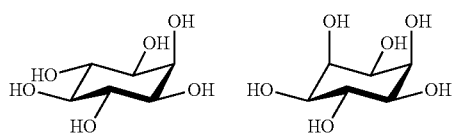

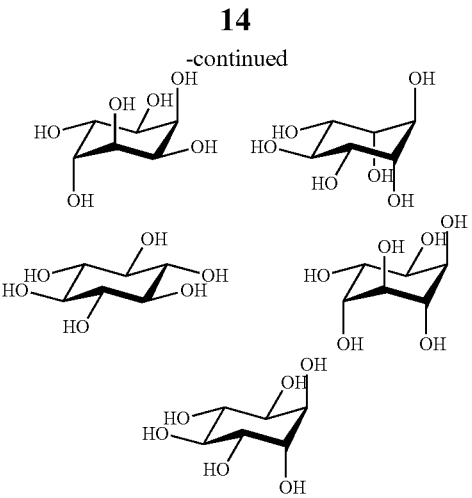

When each of $Rxx^3$, $Rx^3$ and $Rx^6$ is an inositol skeleton, the inositol skeleton is preferably represented by the following formula:

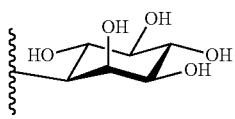

Examples of the C7-C23 alkyl, the C7-C23 alkenyl, the C7-C23 alkynyl, the C8-C24 alkyl, the C8-C24 alkenyl and the C8-C24 alkynyl in formulas (1) and (2) can include the same as those listed about their respective groups in formulas (NL1) and (NL2). Preferred examples thereof can include the same as those listed about the respective groups in formulas (NL1) and (NL2).

The groups in each of formulas (1), (2), (NL1) and (NL2) may be arbitrarily combined as described about the respective groups or may be a combination of preferred groups.

Examples of the analog of the fatty acid ester of glycerol in the nucleic acid-containing nanoparticle of the present invention can specifically include the following compounds:

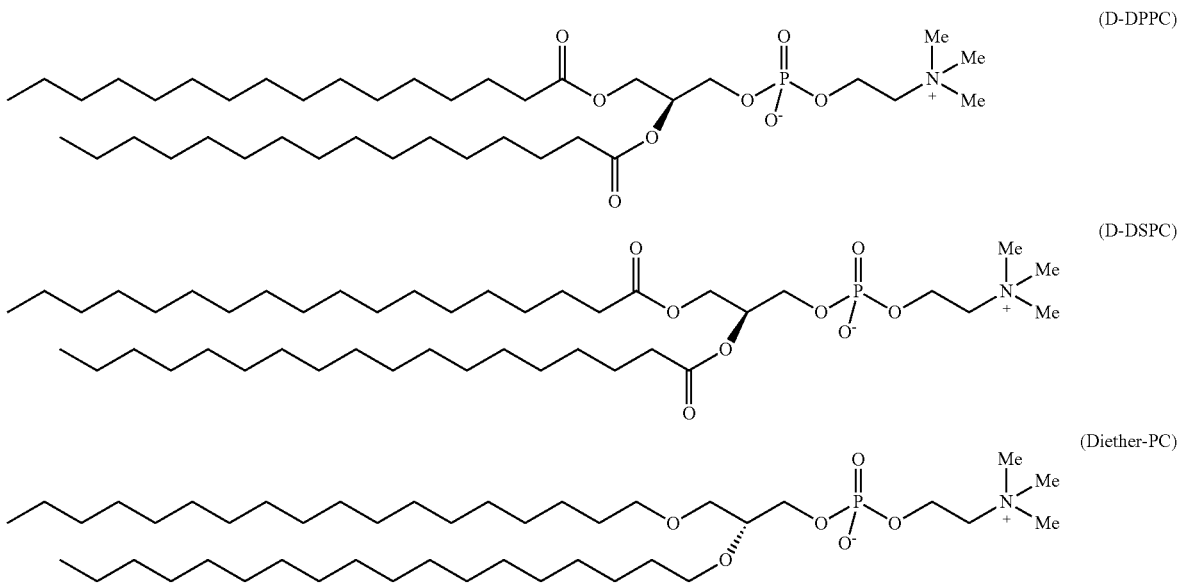

The analog of the fatty acid ester of glycerol according to the present invention may be a commercially available product or may be synthesized by use of an organic synthesis approach.

The lipid represented by formula (1) can be produced, for example, as follows, though the production method is not particularly limited.

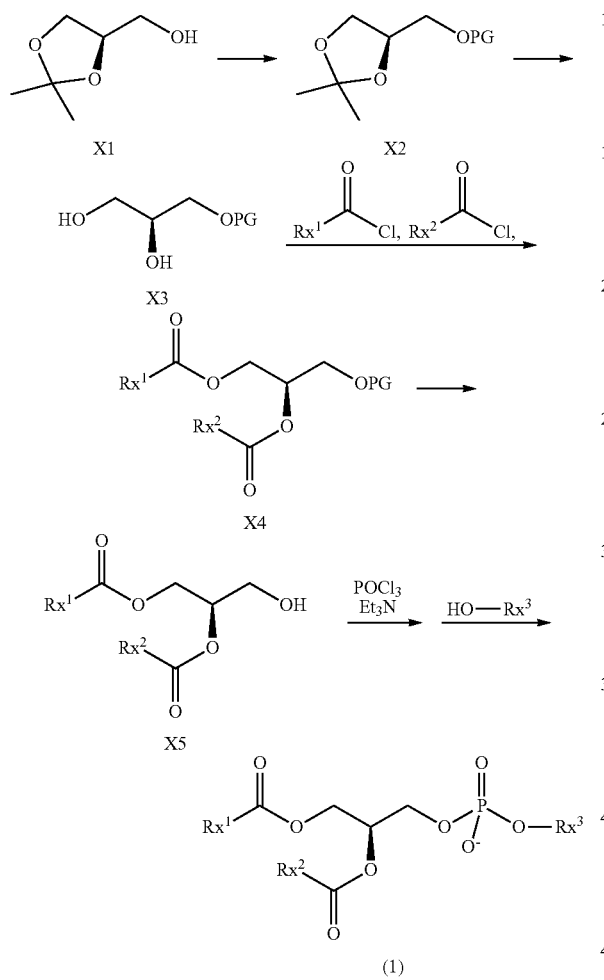

wherein PG represents a protective group; and $Rx^1$, $Rx^2$ and $Rx^3$ are as defined in $Rx^1$, $Rx^2$ and $Rx^3$ in formula (1).

Specifically, a hydroxy group of acetal X1 known in the art which is obtained from a sugar such as mannitol is protected with a protective group (PG group), and an isopropylidene group is hydrolyzed to prepare diol X3. Alternatively, diol X3 may be obtained as a commercially available product such as (S)-3-(benzyloxy)propane-1,2-diol. Subsequently, diol X3 is reacted with an acid chloride represented by $Rx^1$-CO—Cl, $Rx^2$-CO—Cl or the like to obtain compound X4. Further, the protective group (PG group) is removed, and the resulting hydroxy group can be reacted with phosphorus(V) oxychloride in the presence of a base such as triethylamine and further reacted with a compound represented by $Rx^3$-OH to obtain the lipid represented by formula (1).

The reaction for the conversion of diol X3 to compound X4 may be performed by protecting any of a primary alcohol and a secondary alcohol with a protective group.

The protective group for use in the synthesis of the lipid represented by formula (1) can be selected on the basis of reaction conditions or a substrate with reference to, for example, Protective Groups in Organic Synthesis, third edition, T. W. Greene, John Wiley & Sons Inc. (1999).

The lipid represented by formula (2) can be produced, for example, as follows, though the production method is not particularly limited.

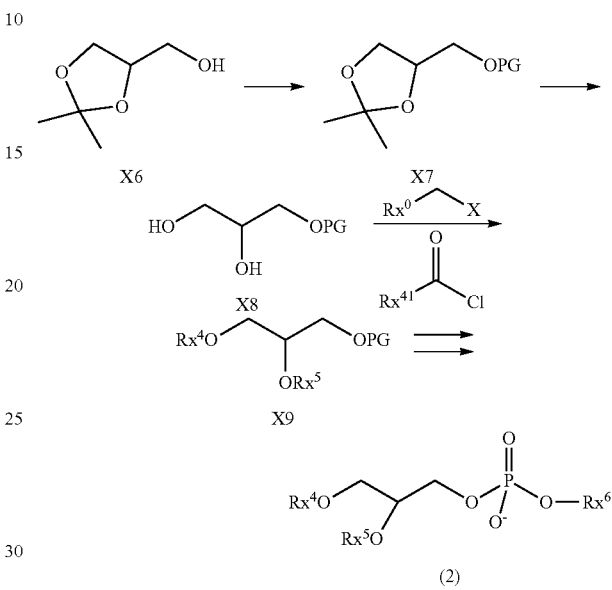

wherein PG represents a protective group; $Rx^0$ represents optionally substituted linear or branched C7-C23 alkyl, C7-C23 alkenyl or C7-C23 alkynyl; X represents a halogen atom such as chlorine, bromine or iodine, OMs, or OTs; and $Rx^4$, $Rx^5$, $Rx^6$ and $Rx^{41}$ are as defined in $Rx^4$, $Rx^5$, $Rx^6$ and $Rx^{41}$ in formula (2).

Specifically, a hydroxy group of acetal X6 known in the art which is obtained from a sugar such as mannitol is protected with a protective group (PG group), and an isopropylidene group is hydrolyzed to prepare diol X8. Subsequently, diol X8 can be reacted with an electrophile represented by, for example, $Rx^0$-$CH_2$—X (reaction conditions of Williamson etherification can be referred to and applied thereto) to obtain diether X9. Alternatively, diol X8 can be reacted with an acid chloride represented by $Rx^{42}$-CO—Cl or the like and subsequently reacted with an electrophile represented by $Rx^0$-$CH_2$—X to obtain compound X9. Further, the protective group (PG group) is removed, and the resulting hydroxy group can be reacted with phosphorus(V) oxychloride in the presence of a base such as triethylamine and further reacted with a compound represented by $Rx^3$-OH to obtain the lipid represented by formula (2).

The reaction for the conversion of diol X3 to compound X4 may be performed by protecting any of a primary alcohol and a secondary alcohol with a protective group.

The protective group for use in the synthesis of the lipid represented by formula (2) can be selected on the basis of reaction conditions or a substrate with reference to, for example, Protective Groups in Organic Synthesis, third edition, T. W. Greene, John Wiley & Sons Inc. (1999).

The nucleic acid-containing lipid nanoparticle of the present invention preferably further comprises a cationic lipid.

The cationic lipid is not particularly limited as long as the cationic lipid is an amphipathic molecule having a lipophilic region containing one or more optionally substituted hydrocarbon groups, and a cationic hydrophilic region containing at least one primary amino group, secondary amino group, tertiary amino group and/or quaternary ammonium group. Examples thereof can include a lipid having a hydrophilic unit having one quaternary ammonium group and optionally substituted three independent hydrocarbon groups (lipid A), and a lipid having a hydrophilic unit having optionally substituted one amino group or one quaternary ammonium group and a hydrophobic unit having optionally substituted two independent hydrocarbon groups (lipid B).

In the present invention, the nucleic acid-containing lipid nanoparticle is prepared using the lipid having a hydrophilic unit having one quaternary ammonium group and optionally substituted three independent hydrocarbon groups (lipid A) with a lipid derivative or a fatty acid derivative of a water-soluble polymer, and a nucleic acid. The obtained nucleic acid-containing lipid nanoparticle can have much better physicochemical stability and physiological activity.

In the present invention, the lipid having a hydrophilic unit having one quaternary ammonium group and optionally substituted three independent hydrocarbon groups (lipid A) is not particularly limited as long as the lipid is a molecule intramolecularly having one quaternary ammonium group as a hydrophilic unit and having optionally substituted three independent hydrocarbon groups. Lipid A is represented by, for example, any of structural formulas (A) to (C) given below. In structural formulas (A) to (C) given below, the "hydrophilic unit" represents a hydrophilic unit having one quaternary ammonium group, and the three "hydrophobic units" represent optionally substituted three independent hydrocarbon groups.

Zero to three out of the four bonds of the quaternary ammonium group constituting the "hydrophilic unit" are attached to any 0 to 3 of the hydrocarbon groups constituting the "hydrophobic unit", and the remaining bond(s) is attached to an optionally substituted chain and/or cyclic hydrocarbon group, etc. The optionally substituted chain and/or cyclic hydrocarbon group constituting the "hydrophilic unit" can be any group composed of carbon and hydrogen atoms and is preferably a group having 1 to 10 carbon atoms, more preferably a group having 1 to 6 carbon atoms, further preferably a group having 1 to 3 carbon atoms.

The "hydrophilic unit" may have one or more ethers, esters, amides or the like via a carbon atom in the optionally substituted chain and/or cyclic hydrocarbon group, etc. constituting this hydrophilic unit. Examples of the substituent for the optionally substituted chain and/or cyclic hydrocarbon group, etc. include carbamate, amino, monoalkylamino, dialkylamino, pyrrolidin-2-yl, pyrrolidin-3-yl, piperidin-2-yl, piperidin-3-yl, piperidin-4-yl, morpholin-2-yl, morpholin-3-yl, hydroxy, alkoxy, alkoxycarbonyl, hydroxycarbonyl, carbamoyl, monoalkylcarbamoyl, dialkylcarbamoyl, nitro, cyano, fluoro, chloro, and bromo.

The hydrocarbon group constituting the "hydrophobic unit" can be any group consisting of 8 to 24 carbon atoms and hydrogen atoms. Hydrocarbon groups can be classified from the viewpoint of topology. Examples thereof include linear hydrocarbon groups, branched hydrocarbon groups and cyclic hydrocarbon groups (e.g., a cholesteryl group). A linear or branched hydrocarbon group is preferred. Also, hydrocarbon groups can be classified on the basis of the presence or absence of an unsaturated bond (double bond or triple bond). Hydrocarbon groups having an unsaturated bond can also be classified on the basis of the presence or absence of aromaticity. A hydrocarbon group having only a saturated bond (alkyl) or a hydrocarbon group having an unsaturated bond and lacking aromaticity (e.g., alkenyl or alkynyl) is preferred. The hydrocarbon group in lipid A is preferably linear or branched C8-C24 alkyl, C8-C24 alkenyl or C8-C24 alkynyl.

Each hydrocarbon group constituting the "hydrophobic unit" may be bonded directly to the quaternary ammonium group of the "hydrophilic unit", or may be bonded to the quaternary ammonium group via an ether, ester or amide bond, etc. and the optionally substituted chain and/or cyclic hydrocarbon group, etc. constituting the "hydrophilic unit". As shown in structural formula (B) or (C), the hydrocarbon groups constituting two or three "hydrophobic units" may be bonded via a carbon atom, and this carbon atom may be bonded either directly to the quaternary ammonium group of the "hydrophilic unit" or to the quaternary ammonium group via an ether, ester or amide bond, etc. and the optionally substituted chain and/or cyclic hydrocarbon group, etc. constituting the "hydrophilic unit".

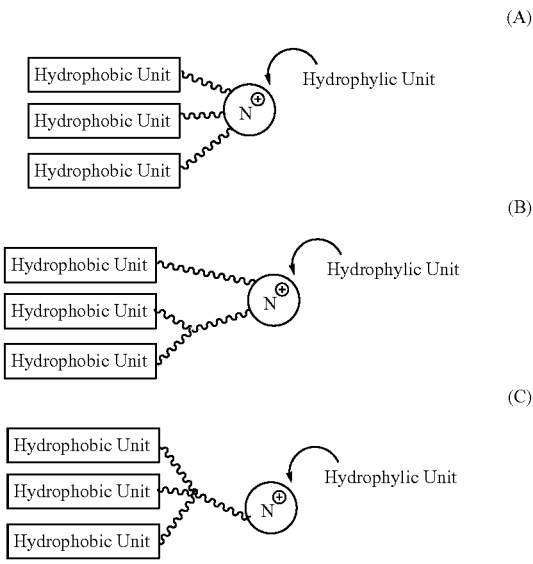

Examples of lipid A can include lipids represented by the following formulas (I) to (IV), (V') and (V"):

formula (I)

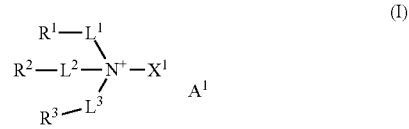

wherein $R^1$ to $R^3$ are the same or different and are each optionally substituted linear or branched C8-C24 alkyl, C8-C24 alkenyl or C8-C24 alkynyl;

$L^1$ to $L^3$ are the same or different and are each absent, or $-Z^1-(CY^1Y^2)_{p1}-$ or $-Z^2-(CY^3Y^4)_{p2}-Z^3-(CY^5Y^6)_{p3}-$ wherein $Y^1$ to $Y^6$ are the same or different and are each a hydrogen atom or optionally substituted C1-C4 alkyl; $Z^1$ to $Z^3$ are the same or different and are each $-O-$, $-NY^{7A}-$, $-CO-O-$, $-O-CO-$, $-CO-NY^{7B}-$, —NY$^{7C}$—CO— or —NY$^{7D}$—CO—O— wherein Y$^{7A}$ to Y$^{7D}$ are the same or different and are each a hydrogen atom or optionally substituted C1-C4 alkyl; and p$^1$ to p$^3$ are the same or different and are each an integer from 1 to 5;

X$^1$ is optionally substituted C1-C4 alkyl; and

A$^1$ is a pharmaceutically acceptable anion, formula (II)

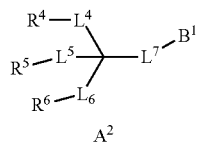

(II)

wherein

R$^4$ to R$^6$ are the same or different and are each optionally substituted linear or branched C8-C24 alkyl, C8-C24 alkenyl or C8-C24 alkynyl;

L$^4$ to L$^6$ are the same or different and are each absent, or —Z$^4$—(CY$^8$Y$^9$)$_{p4}$— or —Z$^5$—(CY$^{10}$Y$^{11}$)$_{p5}$—Z$^6$—(CY$^{12}$Y$^{13}$)$_{p6}$— wherein Y$^8$ to Y$^{13}$ are the same or different and are each a hydrogen atom or optionally substituted C1-C4 alkyl; Z$^4$ to Z$^6$ are the same or different and are each —O—, —NY$^{14A}$—, —CO—O—, —O—CO—, —CO—NY$^{14B}$—, —NY$^{14C}$—CO— or —NY$^{14D}$—CO—O— wherein Y$^{14A}$ to Y$^{14D}$ are the same or different and are each a hydrogen atom or optionally substituted C1-C4 alkyl; p$^4$ is an integer from 0 to 5; p$^5$ is an integer from 1 to 5; and p$^6$ is an integer from 0 to 5;

L$^7$ is absent, or —(CY$^{15}$Y$^{16}$)$_{p7}$—, —(CY$^{17}$Y$^{18}$)$_{p8}$—Z$^7$—(CY$^{19}$Y$^{20}$)$_{p9}$— or —(CY$^{21}$Y$^{22}$)$_{p10}$—Z$^8$—(CY$^{23}$Y$^{24}$)$_{p11}$—Z$^9$—(CY$^{25}$Y$^{26}$)$_{p12}$— wherein Y$^{15}$ to Y$^{26}$ are the same or different and are each a hydrogen atom or optionally substituted C1-C4 alkyl; Z$^7$ to Z$^9$ are the same or different and are each —O—, —NY$^{27A}$—, —CO—O—, —O—CO—, —CO—NY$^{27B}$—, —NY$^{27C}$—CO— or —NY$^{27D}$—CO—O— wherein Y$^{27A}$ to Y$^{27D}$ are the same or different and are each a hydrogen atom or optionally substituted C1-C4 alkyl; p$^7$ is an integer from 1 to 5; p$^8$ is an integer from 0 to 5; p$^9$ is an integer from 1 to 5; p$^{10}$ is an integer from 0 to 5; p$^{11}$ is an integer from 1 to 5; and p$^{12}$ is an integer from 1 to 5;

B$^1$ is

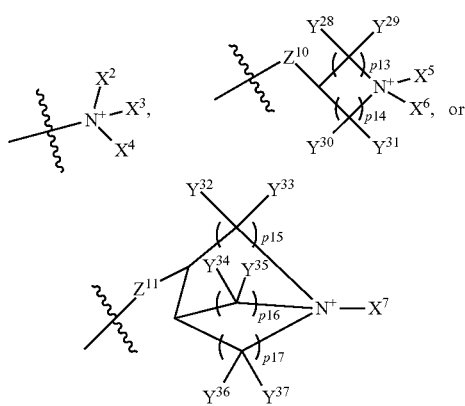

wherein X$^2$ and X$^3$ are the same or different and are each optionally substituted C1-C4 alkyl, or together form an optionally substituted C4-C6 hetero ring with the adjacent nitrogen atom; X$^4$ is optionally substituted C1-C4 alkyl; X$^5$ and X$^6$ are the same or different and are each optionally substituted C1-C4 alkyl, or together form an optionally substituted C4-C6 hetero ring with the adjacent nitrogen atom; X$^7$ is optionally substituted C1-C4 alkyl; Y$^{28}$ to Y$^{37}$ are the same or different and are each a hydrogen atom or optionally substituted C1-C4 alkyl; Z$^{10}$ and Z$^{11}$ are the same or different and are each —O—, —NY$^{38A}$—, —CO—O—, —O—CO—, —CO—NY$^{38B}$—, —NY$^{38C}$—CO— or —NY$^{38D}$—CO—O— wherein Y$^{38A}$ to Y$^{38D}$ are the same or different and are each a hydrogen atom or optionally substituted C1-C4 alkyl; p$^{13}$ is an integer from 0 to 5; and p$^{14}$ to p$^{17}$ are the same or different and are each an integer from 1 to 5; and A$^2$ is a pharmaceutically acceptable anion, formula (III)

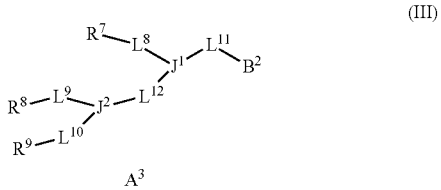

(III)

wherein

R$^7$ to R$^9$ are the same or different and are each optionally substituted linear or branched C8-C24 alkyl, C8-C24 alkenyl or C8-C24 alkynyl;

L$^8$ to L$^{10}$ are the same or different and are each absent, or —Z$^{12}$—(CY$^{39}$Y$^{40}$)$_{p18}$— or —Z$^{13}$—(CY$^{41}$Y$^{42}$)$_{p19}$—Z$^{14}$—(CY$^{43}$Y$^{44}$)$_{p20}$— wherein Y$^{39}$ to Y$^{44}$ are the same or different and are each a hydrogen atom or optionally substituted C1-C4 alkyl; Z$^{12}$ to Z$^{14}$ are the same or different and are each —O—, —NY$^{45A}$—, —CO—O—, —O—CO—, —CO—NY$^{45B}$—, —NY$^{45C}$—CO—, —NY$^{45D}$—CO—O— or —CO— wherein Y$^{45A}$ to Y$^{45D}$ are the same or different and are each a hydrogen atom or optionally substituted C1-C4 alkyl; p$^{18}$ is an integer from 0 to 5; p$^{19}$ is an integer from 1 to 5; and p$^{20}$ is an integer from 0 to 5;

L$^{11}$ is absent, or —(CY$^{46}$Y$^{47}$)$_{p21}$—, —(CY$^{48}$Y$^{49}$)$_{p22}$—Z$^{15}$—(CY$^{50}$Y$^{51}$)$_{p23}$— or —(CY$^{52}$Y$^{53}$)$_{p24}$—Z$^{16}$—(CY$^{54}$Y$^{55}$)$_{p25}$—Z$^{17}$—(CY$^{56}$Y$^{57}$)$_{p26}$— wherein Y$^{46}$ to Y$^{57}$ are the same or different and are each a hydrogen atom or optionally substituted C1-C4 alkyl; Z$^{15}$ to Z$^{17}$ are the same or different and are each —O—, —NY$^{58A}$—, —CO—O—, —O—CO—, —CO—NY$^{58B}$—, —NY$^{58C}$—CO—, —NY$^{58D}$—CO—O— or —CO— wherein Y$^{58A}$ to Y$^{58D}$ are the same or different and are each a hydrogen atom or optionally substituted C1-C4 alkyl; p$^{21}$ is an integer from 1 to 5; p$^{22}$ is an integer from 0 to 5; p$^{23}$ is an integer from 1 to 5; p$^{24}$ is an integer from 0 to 5; p$^{25}$ is an integer from 1 to 5; and p$^{26}$ is an integer from 1 to 5;

L$^{12}$ is absent, or —(CY$^{59}$Y$^{60}$)$_{p27}$—, —(CY$^{61}$Y$^{62}$)$_{p28}$—Z$^{18}$—(CY$^{63}$Y$^{64}$)$_{p29}$— or —(CY$^{65}$Y$^{66}$)$_{p30}$—Z$^{19}$—(CY$^{67}$Y$^{68}$)$_{p31}$—Z$^{20}$—(CY$^{69}$Y$^{70}$)$_{p32}$— wherein Y$^{59}$ to Y$^{70}$ are the same or different and are each a hydrogen atom or optionally substituted C1-C4 alkyl; Z$^{18}$ to Z$^{20}$ are the same or different and are each —O—, —NY$^{71A}$—, —CO—O—, —O—CO—, —CO—NY$^{71B}$—, —NY$^{71C}$—CO—, —NY$^{71D}$—CO—O— or —CO— wherein Y$^{71A}$ to Y$^{71D}$ are the same or different and are each a hydrogen atom or optionally substituted C1-C4 alkyl; p$^{27}$ is an integer from 1 to 5; p$^{28}$ is an integer from 0 to 5; p$^{29}$ is an integer from 0 to 5; p$^{30}$ is an integer from 0 to 5; p$^{31}$ is an integer from 1 to 5; and p$^{32}$ is an integer from 0 to 5;

$J^1$ and $J^2$ are the same or different and are each $CY^{72}$ or N wherein $Y^{72}$ is a hydrogen atom, hydroxy, optionally substituted C1-C4 alkyl, optionally substituted C1-C4 alkoxy, or optionally substituted C1-C4 acyloxy;

$B^2$ is

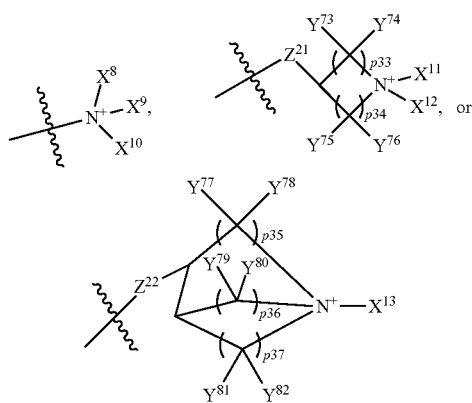

wherein $X^8$ and $X^9$ are the same or different and are each optionally substituted C1-C4 alkyl, or together form an optionally substituted C4-C6 hetero ring with the adjacent nitrogen atom; $X^{10}$ is optionally substituted C1-C4 alkyl; $X^{11}$ and $X^{12}$ are the same or different and are each optionally substituted C1-C4 alkyl, or together form an optionally substituted C4-C6 hetero ring with the adjacent nitrogen atom; $X^{13}$ is optionally substituted C1-C4 alkyl; $Y^{73}$ to $Y^{82}$ are the same or different and are each a hydrogen atom or optionally substituted C1-C4 alkyl; $Z^{21}$ and $Z^{22}$ are the same or different and are each —O—, —$NY^{83A}$—, —CO—O—, —O—CO—, —CO—$NY^{83B}$—, —$NY^{83C}$—CO— or —$NY^{83D}$—CO—O— wherein $Y^{83A}$ to $Y^{83D}$ are the same or different and are each a hydrogen atom or optionally substituted C1-C4 alkyl; $p^{33}$ is an integer from 0 to 5; and $p^{34}$ to $p^{37}$ are the same or different and are each an integer from 1 to 5; and $A^3$ is a pharmaceutically acceptable anion, formula (IV)

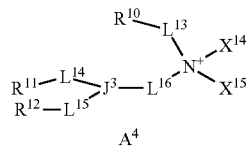

wherein $R^{10}$ to $R^{12}$ are the same or different and are each optionally substituted linear or branched C8-C24 alkyl, C8-C24 alkenyl or C8-C24 alkynyl;

$L^{13}$ is absent, or —$Z^{23}$—$(CY^{84}Y^{85})_{p38}$— or —$Z^{24}$—$(CY^{86}Y^{87})_{p39}$—$Z^{25}$—$(CY^{88}Y^{89})_{p40}$— wherein $Y^{84}$ to $Y^{89}$ are the same or different and are each a hydrogen atom or optionally substituted C1-C4 alkyl; $Z^{23}$ to $Z^{25}$ are the same or different and are each —O—, —$NY^{90A}$—, —CO—O—, —O—CO—, —CO—$NY^{90B}$—, —$NY^{90C}$—CO— or —$NY^{90D}$—CO—O— wherein $Y^{90A}$ to $Y^{90D}$ are the same or different and are each a hydrogen atom or optionally substituted C1-C4 alkyl; and $p^{38}$ to $p^{40}$ are the same or different and are each an integer from 1 to 5;

$L^{14}$ and $L^{15}$ are the same or different and are each absent, or —$Z^{26}$—$(CY^{91}Y^{92})_{p41}$— or —$Z^{27}$—$(CY^{93}Y^{94})_{p42}$—$Z^{28}$—$(CY^{95}Y^{96})_{p43}$— wherein $Y^{91}$ to $Y^{96}$ are the same or different and are each a hydrogen atom or optionally substituted C1-C4 alkyl; $Z^{26}$ to $Z^{28}$ are the same or different and are each —O—, —$NY^{97A}$—, —CO—O—, —O—CO—, —CO—$NY^{97B}$—, —$NY^{97C}$—CO—, —$NY^{97D}$—CO—O— or —CO— wherein $Y^{97A}$ to $Y^{97D}$ are the same or different and are each a hydrogen atom or optionally substituted C1-C4 alkyl; $p^{41}$ is an integer from 0 to 5; $p^{42}$ is an integer from 1 to 5; and $p^{43}$ is an integer from 0 to 5;

$L^{16}$ is absent, or —$(CY^{98}Y^{99})_{p44}$—, —$(CY^{100}Y^{101})_{p45}$—$Z^{29}$—$(CY^{102}Y^{103})_{p46}$— or —$(CY^{104}Y^{105})_{p47}$—$Z^{30}$—$(CY^{106}Y^{107})_{p48}$—$Z^{31}$—$(CY^{108}Y^{109})_{p49}$— wherein $Y^{98}$ to $Y^{109}$ are the same or different and are each a hydrogen atom or optionally substituted C1-C4 alkyl; $Z^{29}$ to $Z^{31}$ are the same or different and are each —O—, —$NY^{110A}$—, —CO—O—, —O—CO—, —CO—$NY^{110B}$—, —$NY^{110C}$—CO—, —$NY^{110D}$—CO—O— or —CO— wherein $Y^{110A}$ to $Y^{110D}$ are the same or different and are each a hydrogen atom or optionally substituted C1-C4 alkyl; $p^{44}$ is an integer from 1 to 5; $p^{45}$ is an integer from 0 to 5; $p^{46}$ is an integer from 1 to 5; $p^{47}$ is an integer from 0 to 5; $p^{48}$ is an integer from 1 to 5; and $p^{49}$ is an integer from 1 to 5;

$J^3$ is $CY^{111}$ or N wherein $Y^{111}$ is a hydrogen atom, hydroxy, optionally substituted C1-C4 alkyl, optionally substituted C1-C4 alkoxy, or optionally substituted C1-C4 acyloxy;

$X^{14}$ and $X^{15}$ are the same or different and are each optionally substituted C1-C4 alkyl, or together form an optionally substituted C4-C6 hetero ring with the adjacent nitrogen atom; and $A^4$ is a pharmaceutically acceptable anion, and formula (V') or formula (V")

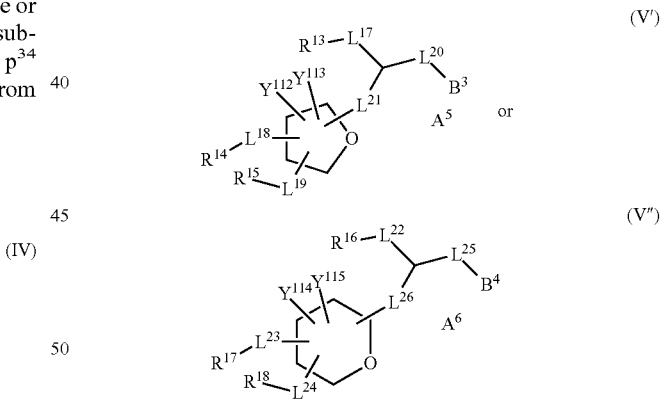

wherein $R^{13}$ to $R^{18}$ are the same or different and are each optionally substituted linear or branched C8-C24 alkyl, C8-C24 alkenyl or C8-C24 alkynyl;

$Y^{112}$ to $Y^{115}$ are the same or different and are each a hydrogen atom, hydroxy or optionally substituted C1-C4 alkyl;

$L^{17}$ to $L^{19}$ and $L^{22}$ to $L^{24}$ are the same or different and are each absent, or —$Z^{32}$—$(CY^{116}Y^{117})_{p51}$— or —$Z^{33}$—$(CY^{118}Y^{119})_{p52}$—$Z^{34}$—$(CY^{120}Y^{121})_{p53}$— wherein $Y^{116}$ to $Y^{121}$ are the same or different and are each a hydrogen atom or optionally substituted C1-C4 alkyl; $Z^{32}$ to $Z^{34}$ are the same or different and are each —O—, —$NY^{122A}$—, —CO—O—, —O—CO—, —CO—$NY^{122B}$—, —NY$^{122C}$—CO—, —NY$^{122D}$—CO—O— or —CO— wherein Y$^{122A}$ to Y$^{122D}$ are the same or different and are each a hydrogen atom or optionally substituted C1-C4 alkyl; $p^{51}$ is an integer from 0 to 5; $p^{52}$ is an integer from 1 to 5; and $p^{53}$ is an integer from 0 to 5;

L$^{20}$ and L$^{25}$ are the same or different and are each absent, or —(CY$^{123}$Y$^{124}$)$_{p54}$—, —(CY$^{125}$Y$^{126}$)$_{p55}$—Z$^{35}$— (CY$^{127}$Y$^{128}$)$_{p56}$— or —(CY$^{129}$Y$^{130}$)$_{p57}$—Z$^{36}$— (CY$^{131}$Y$^{132}$)$_{p58}$—Z$^{37}$—(CY$^{133}$Y$^{134}$)$_{p59}$— wherein Y$^{123}$ to Y$^{134}$ are the same or different and are each a hydrogen atom or optionally substituted C1-C4 alkyl; Z$^{35}$ to Z$^{37}$ are the same or different and are each —O—, —NY$^{135A}$—, —CO—O—, —O—CO—, —CO—NY$^{135B}$—, —NY$^{135C}$—CO—, —NY$^{135D}$—CO—O— or —CO— wherein Y$^{135A}$ to Y$^{135D}$ are the same or different and are each a hydrogen atom or optionally substituted C1-C4 alkyl; $p^{54}$ is an integer from 1 to 5; $p^{55}$ is an integer from 0 to 5; $p^{56}$ is an integer from 1 to 5; $p^{57}$ is an integer from 0 to 5; $p^{58}$ is an integer from 1 to 5; and $p^{59}$ is an integer from 1 to 5;

L$^{21}$ and L$^{26}$ are the same or different and are each absent, or —(CY$^{136}$Y$^{137}$)$_{p60}$—, —(CY$^{138}$Y$^{139}$)$_{p61}$—Z$^{38}$— (CY$^{140}$Y$^{141}$)$_{p62}$— or —(CY$^{142}$Y$^{143}$)$_{p63}$—Z$^{39}$— (CY$^{144}$Y$^{145}$)$_{p64}$—Z$^{40}$—(CY$^{146}$Y$^{147}$)$_{p65}$— wherein Y$^{136}$ to Y$^{147}$ are the same or different and are each a hydrogen atom or optionally substituted C1-C4 alkyl; Z$^{38}$ to Z$^{40}$ are the same or different and are each —O—, —NY$^{148A}$—, —CO—O—, —O—CO—, —CO—NY$^{148B}$—, —NR$^{148C}$—CO—, —NY$^{148D}$—CO—O— or —CO— wherein Y$^{148A}$ to Y$^{148D}$ are the same or different and are each a hydrogen atom or optionally substituted C1-C4 alkyl; $p^{60}$ is an integer from 1 to 5; $p^{61}$ is an integer from 0 to 5; $p^{62}$ is an integer from 0 to 5; $p^{63}$ is an integer from 0 to 5; $p^{64}$ is an integer from 1 to 5; and $p^{65}$ is an integer from 0 to 5;

B$^3$ and B$^4$ are the same or different and are each

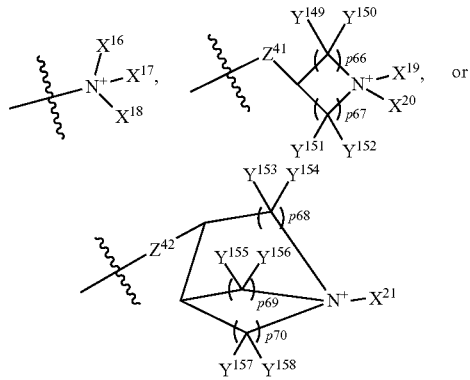

wherein X$^{16}$ and X$^{17}$ are the same or different and are each optionally substituted C1-C4 alkyl, or together form an optionally substituted C4-C6 hetero ring with the adjacent nitrogen atom; X$^{18}$ is optionally substituted C1-C4 alkyl; X$^{19}$ and X$^{20}$ are the same or different and are each optionally substituted C1-C4 alkyl, or together form an optionally substituted C4-C6 hetero ring with the adjacent nitrogen atom; X$^{21}$ is optionally substituted C1-C4 alkyl; Y$^{149}$ to Y$^{158}$ are the same or different and are each a hydrogen atom or optionally substituted C1-C4 alkyl; Z$^{41}$ and Z$^{42}$ are the same or different and are each —O—, —NY$^{159A}$—, —CO—O—, —O—CO—, —CO—NY$^{159B}$—, —NY$^{159C}$—CO— or —NY$^{159D}$—CO—O— wherein Y$^{159A}$ to Y$^{159D}$ are the same or different and are each a hydrogen atom or optionally substituted C1-C4 alkyl; $p^{66}$ is an integer from 0 to 5; and $p^{67}$ to $p^{70}$ are the same or different and are each an integer from 1 to 5; and A$^5$ and A$^6$ are the same or different and are each a pharmaceutically acceptable anion.

Hereinafter, the compounds represented by formulas (I) to (IV), (V') and (V") are also referred to as compounds (I) to (IV), (V') and (V"), respectively. The same holds true for compounds of other formula numbers.

The definition of each group in formulas (I) to (V") will be described below.

Examples of the linear or branched C8-C24 alkyl include octyl, nonyl, decyl, undecyl, dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadecan-2-yl, nonadecyl, 2,6,10,14-tetramethylpentadecyl, icosyl, 3,7,11,15-tetramethylhexadecyl, henicosyl, docosyl, tricosyl and tetracosyl, preferably nonyl, decyl, undecyl, dodecyl, tridecyl, tetradecyl, pentadecyl, hexadecyl, heptadecyl and octadecyl, more preferably undecyl, dodecyl, tridecyl, tetradecyl, pentadecyl and hexadecyl.

Examples of the linear or branched C9-C18 alkyl include nonyl, decyl, undecyl, dodecyl, tridecyl, tetradecyl, 2,6,10-trimethylundecyl, pentadecyl, 3,7,11-trimethyldodecyl, hexadecyl, heptadecyl, octadecyl and 6,10,14-trimethylpentadecan-2-yl, preferably nonyl, decyl, undecyl, dodecyl, tridecyl, tetradecyl, pentadecyl, hexadecyl, heptadecyl and octadecyl, more preferably undecyl, dodecyl, tridecyl, tetradecyl, pentadecyl and hexadecyl.

The linear or branched C8-C24 alkenyl can be linear or branched C8-24 alkenyl containing one to three double bonds. Examples thereof include (Z)-tridec-8-enyl, (Z)-tetradec-9-enyl, (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (E)-heptadec-8-enyl, (E)-octadec-9-enyl, (Z)-heptadec-10-enyl, (Z)-octadec-11-enyl, (8Z,11Z)-heptadeca-8,11-dienyl, (9Z,12Z)-octadeca-9,12-dienyl, (8Z,11Z,14Z)-octadeca-8,11,14-trienyl, (9Z,12Z,15Z)-octadeca-9,12,15-trienyl, (Z)-nonadec-10-enyl, (Z)-icos-11-enyl, (10Z,13Z)-nonadeca-10,13-dienyl, (11Z,14Z)-icosa-11,14-dienyl, 2,6,10-trimethylundeca-1,5,9-trienyl, 3,7,11-trimethyldodeca-2,6,10-trienyl, 2,6,10,14-tetramethylpentadec-1-enyl and 3,7,11,15-tetramethylhexadec-2-enyl, preferably (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (8Z,11Z)-heptadeca-8,11-dienyl and (9Z,12Z)-octadeca-9,12-dienyl, more preferably (Z)-heptadec-8-enyl, (Z)-octadec-9-enyl, (8Z,11Z)-heptadeca-8,11-dienyl and (9Z,12Z)-octadeca-9,12-dienyl.

Examples of the linear or branched C15-C20 alkenyl include (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (E)-heptadec-8-enyl, (E)-octadec-9-enyl, (Z)-heptadec-10-enyl, (Z)-octadec-11-enyl, (8Z,11Z)-heptadeca-8,11-dienyl, (9Z,12Z)-octadeca-9,12-dienyl, (8Z,11Z,14Z)-octadeca-8,11,14-trienyl, (9Z,12Z,15Z)-octadeca-9,12,15-trienyl, (Z)-nonadec-10-enyl, (Z)-icos-11-enyl, (10Z,13Z)-nonadeca-10,13-dienyl, (11Z,14Z)-icosa-11,14-dienyl and 3,7,11,15-tetramethylhexadec-2-enyl, preferably (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (8Z,11Z)-heptadeca-8,11-dienyl and (9Z,12Z)-octadeca-9,12-dienyl, more preferably (Z)-heptadec-8-enyl, (Z)-octadec-9-enyl, (8Z,11Z)-heptadeca-8,11-dienyl and (9Z,12Z)-octadeca-9,12-dienyl.

In the present invention, a group having a cyclopropane ring formed by adding formally a methylene biradical to a double bond of the optionally substituted linear or branched C8-C24 alkenyl is also included in the C8-C24 alkenyl. Examples thereof include groups having the following cyclopropane rings corresponding to (Z)-hexadec-9-enyl, (9Z,12Z)-octadeca-9,12-dienyl and (8Z,11Z)-heptadeca-8,11-dienyl:

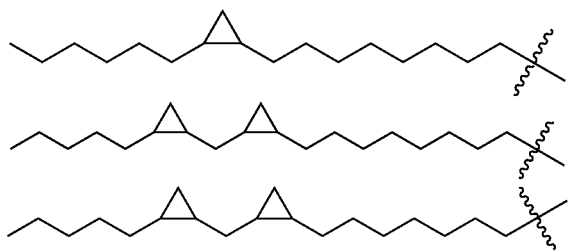

The linear or branched C8-C24 alkynyl can be linear or branched C8-24 alkynyl containing one to three triple bonds. Examples thereof include dodec-11-ynyl, tridec-12-ynyl, pentadec-6-ynyl, hexadec-7-ynyl, pentadeca-4,6-diynyl, hexadeca-5,7-diynyl, heptadec-8-ynyl and octadec-9-ynyl, preferably pentadec-6-ynyl, hexadec-7-ynyl, pentadeca-4,6-diynyl, hexadeca-5,7-diynyl, heptadec-8-ynyl and octadec-9-ynyl, more preferably heptadec-8-ynyl and octadec-9-ynyl.

Examples of the C1-C4 alkyl include methyl, ethyl, propyl, isopropyl, cyclopropyl, butyl, isobutyl, sec-butyl, tert-butyl, cyclobutyl and cyclopropylmethyl, preferably methyl and ethyl, more preferably methyl.

The alkyl moiety in the optionally substituted C1-C4 alkoxy is as defined in the C1-C4 alkyl.

Examples of the substituent for the optionally substituted linear or branched C8-C24 alkyl, C8-C24 alkenyl or C8-C24 alkynyl include hydroxy, alkoxy, alkoxycarbonyl, nitro, cyano, fluoro, chloro and bromo. Among these substituents, the alkyl moiety in alkoxy and alkoxycarbonyl is as defined in the C1-C4 alkyl.

Examples of the substituent for the optionally substituted C1-C4 alkyl include amino, monoalkylamino, dialkylamino, pyrrolidin-2-yl, pyrrolidin-3-yl, piperidin-2-yl, piperidin-3-yl, piperidin-4-yl, morpholin-2-yl, morpholin-3-yl, hydroxy, alkoxy, alkoxycarbonyl, hydroxycarbonyl, carbamoyl, monoalkylcarbamoyl, dialkylcarbamoyl, nitro, cyano, fluoro, chloro and bromo. Among these substituents, the alkyl moiety in monoalkylamino, dialkylamino, alkoxy, alkoxycarbonyl, monoalkylcarbamoyl and dialkylcarbamoyl is as defined in the C1-C4 alkyl. Two alkyl moieties in dialkylamino and dialkylcarbamoyl may be the same as or different from each other.

In the present invention, each of the pyrrolidin-2-yl, the pyrrolidin-3-yl, the piperidin-2-yl, the piperidin-3-yl, the piperidin-4-yl, the morpholin-2-yl and the morpholin-3-yl includes a group formed by adding C1-C3 alkyl such as methyl or ethyl to a nitrogen atom in a ring.

Examples of the C1-C3 alkyl include methyl, ethyl, propyl, isopropyl and cyclopropyl, preferably methyl and ethyl, more preferably methyl.

Examples of the C4-C6 hetero ring together formed by $X^2$ and $X^3$ with the adjacent nitrogen atom include pyrrolidine, piperidine, morpholine and azepane, preferably pyrrolidine and piperidine. Examples of the substituent for the optionally substituted C4-C6 hetero ring together formed by $X^2$ and $X^3$ with the adjacent nitrogen atom include optionally substituted C1-C4 alkyl (as defined above), amino, monoalkylamino, dialkylamino, pyrrolidin-2-yl, pyrrolidin-3-yl, piperidin-2-yl, piperidin-3-yl, piperidin-4-yl, morpholin-2-yl, morpholin-3-yl, hydroxy, alkoxy, alkoxycarbonyl, hydroxycarbonyl, carbamoyl, monoalkylcarbamoyl, dialkylcarbamoyl, nitro, cyano, fluoro, chloro and bromo. Among these substituents, the alkyl moiety in monoalkylamino, dialkylamino, alkoxy, alkoxycarbonyl, monoalkylcarbamoyl and dialkylcarbamoyl is as defined in the C1-C4 alkyl. Two alkyl moieties in dialkylamino and dialkylcarbamoyl may be the same as or different from each other.

The hetero ring moiety and the substituent moiety in the optionally substituted C4-C6 hetero ring together formed by $X^5$ and $X^6$ with the adjacent nitrogen atom are each as defined above.

The hetero ring moiety and the substituent moiety in the optionally substituted C4-C6 hetero ring together formed by $X^8$ and $X^9$ with the adjacent nitrogen atom are each as defined above.

The hetero ring moiety and the substituent moiety in the optionally substituted C4-C6 hetero ring together formed by $X^{11}$ and $X^{12}$ with the adjacent nitrogen atom are each as defined above.

The hetero ring moiety and the substituent moiety in the optionally substituted C4-C6 hetero ring together formed by $X^{14}$ and $X^{15}$ with the adjacent nitrogen atom are each as defined above.

The hetero ring moiety and the substituent moiety in the optionally substituted C4-C6 hetero ring together formed by $X^{16}$ and $X^{17}$ with the adjacent nitrogen atom are each as defined above.

The hetero ring moiety and the substituent moiety in the optionally substituted C4-C6 hetero ring together formed by $X^{19}$ and $X^{20}$ with the adjacent nitrogen atom are each as defined above.

Examples of the acyl in the C1-C4 acyloxy include formyl, acetyl, propanoyl, 2-methylpropanoyl, cyclopropanoyl and butanoyl, preferably acetyl.

Examples of the substituent for the optionally substituted C1-C4 acyloxy include amino, monoalkylamino, dialkylamino, pyrrolidin-2-yl, pyrrolidin-3-yl, piperidin-2-yl, piperidin-3-yl, piperidin-4-yl, morpholin-2-yl, morpholin-3-yl, hydroxy, alkoxy, alkoxycarbonyl, hydroxycarbonyl, carbamoyl, monoalkylcarbamoyl, dialkylcarbamoyl, nitro, cyano, fluoro, chloro and bromo. Among these substituents, the alkyl moiety in monoalkylamino, dialkylamino, alkoxy, alkoxycarbonyl, monoalkylcarbamoyl and dialkylcarbamoyl is as defined in the C1-C4 alkyl. Two alkyl moieties in dialkylamino and dialkylcarbamoyl may be the same as or different from each other.

The quaternary ammonium group means a group having a nitrogen atom having four covalent bonds to four carbon atoms. Unlike a hydrogen atom added to primary to tertiary amines, the quaternary ammonium group always has a positive charge irrespective of ambient pH.

Examples of the pharmaceutically acceptable anion include, but are not limited to: inorganic ions such as chloride ions, bromide ions, iodide ions, nitrate ions, sulfate ions and phosphate ions; and organic acid ions such as acetate ions, oxalate ions, maleate ions, fumarate ions, citrate ions, benzoate ions and methanesulfonate ions.

In formula (I), $R^1$ to $R^3$ are preferably the same linear or branched C8-C24 alkyl, C8-C24 alkenyl or C8-C24 alkynyl, more preferably the same linear or branched C8-C24 alkyl or C8-C24 alkenyl, further preferably the same linear or branched C15-C20 alkenyl or the same linear or branched C9-C18 alkyl, most preferably the same linear C15-C20 alkenyl or the same linear C9-C18 alkyl.

$L^1$ to $L^3$ are the same or different and are each absent, or $-Z^1-(CY^1Y^2)_{p1}-$ or $-Z^2-(CY^3Y^4)_{p2}-Z^3-(CY^5Y^6)_{p3}-$, preferably $-Z^1-(CY^1Y^2)_{p2}-$. $Y^1$ to $Y^6$ are the same or different and are each a hydrogen atom or optionally substituted C1-C4 alkyl, preferably a hydrogen atom. $Z^1$ to $Z^3$ are the same or different and are each $-O-$, $-NY^{7A}-$, $-CO-O-$, $-O-CO-$, $-CO-NY^{7B}-$, $-NY^{7C}-CO-$ or $-NY^{7D}-CO-O-$, preferably $-O-$, $-CO-O-$, $-O-CO-$, $-CO-NY^{7B}-$ or $-NY^{7C}-CO-$. $Y^{7A}$ to $Y^{7D}$ are the same or different and are each a hydrogen atom or optionally substituted C1-C4 alkyl, preferably a hydrogen atom or methyl, $p^1$ to $p^3$ are the same or different and are each an integer from 1 to 5, preferably 1 or 2.

$L^1$ to $L^3$ are preferably the same or different and are each $-O-(CY^1Y^2)_{p1}-$, $-CO-O-(CY^1Y^2)_{p1}-$, $-O-CO-(CY^1Y^2)_{p1}-$, $-CO-NY^{73}-(CY^1Y^2)_{p1}-$ or $-NY^{7C}-CO-(CY^1Y^2)_{p1}-$, more preferably are the same or different and are each $-CO-O-(CY^1Y^2)_{p2}-$ or $-O-CO-(CY^1Y^2)_{p1}-$, further preferably are the same and $-CO-O-(CH_2)_2-$.

In formula (I), preferably, one or more of $L^1$ to $L^3$ are the same or different and are each $-CO-O-(CY^1Y^2)_{p1}-$ or $-O-CO-(CY^1Y^2)_{p1}-$, and $R^1$ to $R^3$ are the same linear C15-C20 alkenyl or the same linear C9-C18 alkyl.

When at least one of $L^1$ to $L^3$ is absent, or $-O-(CY^1Y^2)_{p1}-$, $-O-CO-(CY^1Y^2)_{p1}-$ or $-NY^{7C}-CO-(CY^1Y^2)_{p1}-$, $R^1$ to $R^3$ bonded to the positively charged nitrogen atom (N+), $-O-(CY^1Y^2)_{p1}-$, $-O-CO-(CY^1Y^2)_{p1}-$ or $-NR^6-CO-(CY^1Y^2)_{p2}-$ are the same or different and are each more preferably octyl, decyl, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl, 3,7,11,15-tetramethylhexadec-2-enyl or the like, further preferably dodecyl, tetradecyl, hexadecyl, (Z)-hexadec-9-enyl, (Z)-octadec-6-enyl, (Z)-octadec-9-enyl, (9Z,12Z)-octadeca-9,12-dienyl or the like.

When at least one of $L^1$ to $L^3$ is $-CO-O-(CY^1Y^2)_{p2}-$ or $-CO-NY^{7B}-(CY^2Y^2)_{p1}-$, $R^1$ to $R^3$ bonded to $-CO-O-(CY^1Y^2)_{p1}-$ or $-CO-NY^{7B}-(CY^1Y^2)_{p1}-$ are the same or different and are each more preferably nonyl, undecyl, tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-octadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl, 2,6,10,14-tetramethylpentadec-1-enyl or the like, further preferably undecyl, tridecyl, pentadecyl, (Z)-pentadec-8-enyl, (Z)-heptadec-5-enyl, (Z)-heptadec-8-enyl, (8Z,11Z)-heptadeca-8,11-dienyl or the like.

$X^1$ is preferably methyl, hydroxypropyl or hydroxyethyl, more preferably methyl.

In formula (II), $R^4$ to $R^6$ are preferably the same linear or branched C8-C24 alkyl, C8-C24 alkenyl or C8-C24 alkynyl, more preferably the same linear or branched C8-C24 alkyl or C8-C24 alkenyl, further preferably the same linear or branched C15-C20 alkenyl or the same linear or branched C9-C18 alkyl, most preferably the same linear C15-C20 alkenyl or the same linear C9-C18 alkyl.

$L^4$ to $L^6$ are the same or different and are each absent, or $-Z^4-(CY^8Y^9)_{p4}-$ or $-Z^5-(CY^{10}Y^{11})_{p5}-Z^6-(CY^{12}Y^{13})_{p6}-$, preferably $-Z^4-(CY^8Y^9)_{p4}-$ or $-Z^5-(CY^{10}Y^{11})_{p5}-Z^6-(CY^{12}Y^{13})_{p6}-$, more preferably $-Z^4-(CY^8Y^9)_{p4}-$. $Y^8$ to $Y^{13}$ are the same or different and are each a hydrogen atom or optionally substituted C1-C4 alkyl, preferably a hydrogen atom. $Z^4$ to $Z^6$ are the same or different and are each $-O-$, $-NY^{14A}-$, $-CO-O-$, $-O-CO-$, $-CO-NY^{14B}-$, $-NY^{14C}-CO-$ or $-NY^{14D}-CO-O-$, preferably $-O-$, $-CO-O-$, $-O-CO-$, $-CO-NY^{14B}-$ or $-NY^{14C}-CO-$. $Y^{27A}$ to $Y^{27D}$ are the same or different and are each a hydrogen atom or optionally substituted C1-C4 alkyl, preferably a hydrogen atom or methyl, $p^4$ is an integer from 0 to 5. $p^5$ is an integer from 1 to 5. $p^6$ is an integer from 0 to 5. All of $p^4$ to $p^6$ are preferably 1 or 2.

$L^4$ to $L^6$ are preferably the same or different and are each $-O-(CY^8Y^9)_{p4}-$, $-CO-O-(CY^8Y^9)_{p4}-$, $-O-CO-(CY^8Y^9)_{p4}-$, $-CO-NY^{14B}-(CY^8Y^9)_{p4}-$, $-NY^{14C}-CO-(CY^8Y^9)_{p4}-$, $-NY^{14D}-CO-Q-(CY^8Y^9)_{p4}-$ or $-O-CO-(CY^{10}Y^{11})_{p5}-Z^6-(CY^{12}Y^{13})_{p6}-$, more preferably are the same or different and are each $-CO-O-(CY^8Y^9)_{p4}-$, $-O-CO-(CY^8Y^9)_{p4}-$ or $-O-CO-(CY^{10}Y^{11})_{p5}-O-(CY^{12}Y^{13})_{p6}-$, further preferably are the same and $-CO-O-CH_2-$.

In formula (II), preferably, one or more of $L_4$ to $L_6$ are the same or different and are each $-CO-O-(CY^8Y^9)_{p4}-$, $-O-CO-(CY^8Y^9)_{p4}-$, or $-O-CO-(CY^{10}Y^{11})_{p5}-O-(CY^{12}Y^{13})_{p6}-$, and $R^4$ to $R^6$ are the same linear C15-C20 alkenyl or the same linear C9-C18 alkyl.

When at least one of $L^4$ to $L^6$ is absent, or $-O-(CY^8Y^9)_{p4}-$, $-O-CO-(CY^8Y^9)_{p4}-$, $-NY^{14C}-CO-(CY^8Y^9)_{p4}-$, $-NY^{14D}-CO-O-$ or $-O-CO-(CY^{10}Y^{11})_{p5}-(CY^{12}Y^{13})_{p6}-$, $R^7$ to $R^9$ bonded to the carbon atom adjacent to $L^7$, $-O-(CY^8Y^9)_{p4}-$, $-O-CO-(CY^8Y^9)_{p4}-$, $-NY^{14C}-CO-(CY^8Y^9)_{p4}-$, $-NY^{14D}-CO-O-$ or $-O-CO-(CY^{10}Y^{11})_{p5}-Z^6-(CY^{12}Y^{13})_{p6}-$ are the same or different and are each preferably octyl, decyl, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl, 3,7,11,15-tetramethylhexadec-2-enyl or the like, more preferably dodecyl, tetradecyl, hexadecyl, (Z)-hexadec-9-enyl, (Z)-octadec-6-enyl, (Z)-octadec-9-enyl, (9Z,12Z)-octadeca-9,12-dienyl or the like.

When at least one of $L^4$ to $L^6$ is $-CO-O-(CY^8Y^9)_{p4}-$ or $-CO-NY^{14B}-(CY^8Y^9)_{p4}-$, $R^4$ to $R^6$ bonded to $-CO-O-(CY^8Y^9)_{p4}-$ or $-CO-NY^{14B}-(CY^8Y^9)_{p4}-$ are the same or different and are each preferably nonyl, undecyl, tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-octadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl, 2,6,10,14-tetramethylpentadec-1-enyl or the like, more preferably undecyl, tridecyl, pentadecyl, (Z)-pentadec-8-enyl, (Z)-heptadec-5-enyl, (Z)-heptadec-8-enyl, (8Z,11Z)-heptadeca-8,11-dienyl or the like.

$L^7$ is preferably absent, or $-(CY^{15}Y^{16})_{p7}-$, $-(CY^{17}Y^{18})_{p8}-O-CO-(CY^{19}Y^{20})_{p9}-$ or $-(CY^{17}$ $Y^{18})_{p8}$—$NY^{27C}$—CO—$(CY^{19}Y^{20})_{p9}$—, more preferably absent, or —$(CY^{15}Y^{16})_{p7}$—. In this case, $B^1$ is preferably

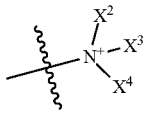

more preferably —$N^+(CH_3)_3$.

When $L^7$ is —$(CY^{15}Y^{16})_{p7}$—, $p^7$ is preferably 1 to 3, more preferably 1 or 2, further preferably 1. Each of $Y^{15}$ and $Y^{16}$ is preferably a hydrogen atom. $B^1$ is preferably —$N^+(CH_3)_3$.

When $L^7$ is —$(CY^{17}Y^{18})_{p8}$—O—CO—$(CY^{19}Y^{20})_{p9}$— or —$(CY^{17}Y^{18})_{p8}$—$NY^{27C}$—CO—$(CY^{19}Y^{20})_{p9}$—, preferably, $p^8$ is 0 to 3, and $p^9$ is 1 to 3. More preferably, $p^8$ is 0 to 1, and $p^9$ is 1 to 3. Preferably, each of $Y^{17}$ to $Y^{20}$ is a hydrogen atom, and $Y^{27C}$ is a hydrogen atom or methyl. $B^1$ is preferably —$N^+(CH_3)_3$.

Preferably, $X^2$ and $X^3$ are the same or different and are each methyl or ethyl, or together form an optionally substituted C4-C6 hetero ring with the adjacent nitrogen atom. More preferably, $X^2$ and $X^3$ are the same and methyl, or together form pyrrolidine or piperidine with the adjacent nitrogen atom. Further preferably, $X^2$ and $X^3$ are the same and methyl.

$X^4$ is preferably methyl, ethyl, hydroxypropyl, hydroxyethyl or the like, more preferably methyl.

Preferably, $X^2$ and $X^3$ are the same or different and are each methyl or ethyl, and $X^4$ is methyl, ethyl, hydroxypropyl, hydroxyethyl or the like. Each of $X^2$ to $X^4$ is more preferably methyl.

In another preferred mode of the present invention, $B^1$ is

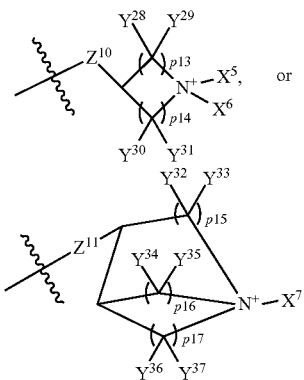

and $L^7$ is absent, or —$(CY^{15}Y^{16})_{p7}$—, —$(CY^{17}Y^{18})_{p8}$—O—CO—$(CY^{19}Y^{20})_{p9}$— or —$(CY^{17}Y^{18})_{p8}$—$NY^{27C}$—CO—$(CY^{19}Y^{20})_{p9}$—. In this case, more preferably, $B^1$ is

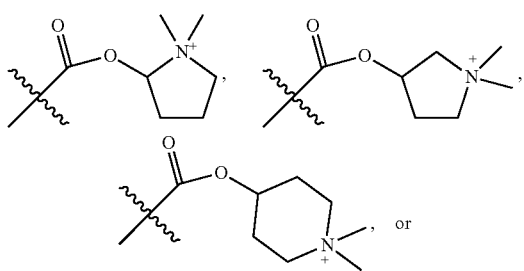

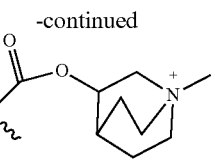

and $L^7$ is absent, or —NH—CO—$(CH_2)_{p9}$—, —O—CO—$(CH_2)_{p9}$—, —$CH_2$—NH—CO—$(CH_2)_{p9}$— or —$CH_2$—O—CO—$(CH_2)_{p9}$—.

In formula (III), $R^7$ is preferably linear or branched C8-C24 alkyl or C8-C24 alkenyl, more preferably linear or branched C15-C20 alkenyl or linear or branched C9-C18 alkyl, most preferably the same linear C15-C20 alkenyl or the same linear C9-C18 alkyl. $R^8$ and $R^9$ are preferably the same linear or branched C8-C24 alkyl, C8-C24 alkenyl or C8-C24 alkynyl, more preferably the same linear or branched C15-C20 alkenyl or linear or branched C9-C18 alkyl, most preferably the same linear C15-C20 alkenyl or linear C9-C18 alkyl.

$L^8$ is absent, or —$Z^{12}$—$(CY^{39}Y^{40})_{p19}$— or —$Z^{13}$—$(CY^{41}Y^{42})_{p19}$—$Z^{14}$—$(CY^{43}Y^{44})_{p20}$—, preferably absent or —$Z^{12}$—$(CY^{39}Y^{40})_{p19}$—. $L^9$ and $L^{10}$ are the same or different and are each absent, or —$Z^{12}$—$(CY^{39}Y^{40})_{p18}$— or —$Z^{13}$—$(CY^{41}Y^{42})_{p19}$—$Z^{14}$—$(CY^{43}Y^{44})_{p20}$—, preferably are the same or different and are each absent or —$Z^{12}$—$(CY^{39}Y^{40})_{p18}$—. $Y^{39}$ to $Y^{44}$ are the same or different and are each a hydrogen atom or optionally substituted C1-C4 alkyl, preferably a hydrogen atom. $Z^{12}$ to $Z^{14}$ are the same or different and are each —O—, —$NY^{45A}$—, —CO—O—, —O—CO—, —CO—$NY^{45B}$—, —$NY^{45C}$—CO—, —$NY^{45D}$—CO—O— or —CO—, preferably —CO—O—, —O—CO—, —CO—$NY^{45B}$—, —$NY^{45C}$—CO— or —CO—. $Y^{45A}$ to $Y^{45D}$ are the same or different and are each a hydrogen atom or optionally substituted C1-C4 alkyl, preferably a hydrogen atom or methyl, $p^{18}$ is an integer from 0 to 5, preferably 0 or 1. $p^{19}$ is an integer from 1 to 5, preferably 1 or 2. $p^{20}$ is an integer from 0 to 5, preferably 0 or 1.

Preferably, one of $L^8$ to $L^{10}$ is —CO—O—$(CY^{39}Y^{40})_{p18}$— or —O—CO—$(CY^{39}Y^{40})_{p18}$—, or two or more of $L^8$ to $L^{10}$ are the same or different and are each —CO—O—$(CY^{39}Y^{40})_{p18}$— or —O—CO—$(CY^{39}Y^{40})_{p18}$—, and each of $R^7$ to $R^9$ is linear C15-C20 alkenyl or C9-C18 alkyl. $R^8$ and $R^9$ are preferably the same.

$L^8$ is preferably absent, or —CO—O—$(CY^{39}Y^{40})_{p18}$—, —O—CO—$(CY^{39}Y^{40})_{p18}$—, —CO—$NY^{45B}$—$(CY^{39}Y^{40})_{p18}$— or —$NY^{45C}$—CO—$(CY^{39}Y^{40})_{p18}$—, more preferably absent, or —CO—O—$(CY^{39}Y^{40})_{p18}$—, —O—CO—$(CY^{39}Y^{40})_{p28}$— or —CO—$NY^{45B}$—$(CY^{39}Y^{40})_{p28}$—, further preferably absent, or —CO—O—$(CH_2)_{p18}$—, —O—CO—$(CH_2)_{p18}$— or —CO—NH—$(CH_2)_{p18}$—.

$L^9$ and $L^{10}$ are preferably the same or different and are each absent, or —CO—O—$(CY^{39}Y^{40})_{p18}$—, —O—CO—$(CY^{39}Y^{40})_{p18}$—, —CO—$NY^{45B}$—$(CY^{39}Y^{40})_{p18}$— or —$NY^{45C}$—CO—$(CY^{39}Y^{40})_{p18}$—, more preferably are the same or different and are each absent, or —CO—O—$(CY^{39}Y^{40})_{p18}$— or —O—CO—$(CY^{39}Y^{40})_{p18}$—, further preferably are the same or different and are each absent or —CO—O—$(CH_2)_{p18}$—, most preferably are the same and absent or —CO—O—$(CH_2)_{p18}$—.

In formula (III), preferably, one of $L^8$ to $L^{10}$ is absent, or —CO—O—$(CY^{39}Y^{40})_{p18}$—, —O—CO—$(CY^{39}Y^{40})_{p18}$—, —CO—$NY^{45b}$—$(CY^{39}Y^{40})_{p18}$— or —$NY^{45C}$—CO—$(CY^{39}Y^{40})_{p18}$—, or two or more of $L^8$ to $L^{10}$ are the same or different and are each absent, or —CO—O—$(CY^{39}$ $Y^{40})_{p18}$—, —O—CO—$(CY^{39}Y^{40})_{p18}$—, —CO—NY$^{45b}$—$(CY^{39}Y^{40})_{p18}$— or —NY$^{45C}$—CO—$(CY^{39}Y^{40})_{p18}$—, and each of $R^7$ to $R^9$ is preferably linear C15-C20 alkenyl or C9-C18 alkyl. $R^8$ and $R^9$ are preferably the same.

When at least one of $L^8$ to $L^{10}$ is absent, or —O—$(CY^{39}Y^{40})_{p18}$—, —O—CO—$(CY^{39}Y^{40})_{p18}$—, —NY$^{45C}$—CO—$(CY^{39}Y^{40})_{p18}$— or —NY$^{45D}$—CO—O—$(CY^{39}Y^{40})_{p18}$—, $R^7$ to $R^9$ bonded to $J^1$ or $J^2$, —O—$(CY^{39}Y^{40})_{p18}$—, —O—CO—$(CY^{39}Y^{40})_{p18}$—, —NY$^{45C}$—CO—$(CY^{39}Y^{40})_{p18}$— or —NY$^{45D}$—CO—O—$(CY^{39}Y^{40})_{p18}$— are the same or different and are each preferably octyl, decyl, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl, 3,7,11,15-tetramethylhexadec-2-enyl or the like, more preferably dodecyl, tetradecyl, hexadecyl, (Z)-hexadec-9-enyl, (Z)-octadec-6-enyl, (Z)-octadec-9-enyl, (9Z,12Z)-octadeca-9,12-dienyl or the like.

When at least one of $L^8$ to $L^{10}$ is —CO—O—$(CY^{39}Y^{40})_{p18}$—, —CO—NY$^{45B}$—$(CY^{39}Y^{40})_{p18}$— or —CO—$(CY^{39}Y^{40})_{p18}$, $R^7$ to $R^9$ bonded to —CO—O—$(CY^{39}Y^{40})_{p18}$—, —CO—NY$^{45B}$—$(CY^{39}Y^{40})_{p18}$— or —CO—$(CY^{39}Y^{40})_{p18}$ are the same or different and are each preferably nonyl, undecyl, tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-octadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl or 2,6,10,14-tetramethylpentadec-1-enyl, more preferably undecyl, tridecyl, pentadecyl, (Z)-pentadec-8-enyl, (Z)-heptadec-5-enyl, (Z)-heptadec-8-enyl, (8Z,11Z)-heptadeca-8,11-dienyl or the like.

$L^{11}$ is absent, or —$(CY^{46}Y^{47})_{p21}$—, —$(CY^{48}Y^{49})_{p22}$—$Z^{15}$—$(CY^{50}Y^{51})_{p23}$— or —$(CY^{52}Y^{53})_{p24}$—$Z^{16}$—$(CY^{54}Y^{55})_{p25}$—$Z^{17}$—$(CY^{56}Y^{57})_{p26}$—, preferably absent, or —$(CY^{46}Y^{47})_{p21}$— or —$(CY^{48}Y^{49})_{p22}$—$Z^{15}$—$(CY^{50}Y^{51})_{p23}$—. $Y^{46}$ to $Y^{57}$ are the same or different and are each a hydrogen atom or optionally substituted C1-C4 alkyl, preferably a hydrogen atom. $Z^{15}$ to $Z^{17}$ are the same or different and are each —O—, —NY$^{58A}$—, —CO—O—, —O—CO—, —CO—NY$^{58B}$—, —NY$^{58C}$—CO—, —NY$^{58D}$—CO—O— or —CO—, preferably —CO—O—, —O—CO—, —CO—NY$^{58B}$—, —NY$^{58C}$—CO— or —CO—, more preferably —O—CO— or —NY$^{58C}$—CO—. $p^{21}$ is an integer from 1 to 5, preferably 1 to 3. $p^{22}$ is an integer from 0 to 5, preferably 0 to 3. $p^{23}$ is an integer from 1 to 5, preferably 1 or 2.

$L^{11}$ is preferably absent, or —$(CY^{46}Y^{47})_{p21}$—, —$(CY^{48}Y^{49})_{p22}$—O—CO—$(CY^{50}Y^{51})_{p23}$—, or —$(CY^{48}Y^{49})_{p22}$—NY$^{58C}$—CO—$(CY^{50}Y^{51})_{p23}$—, more preferably absent or —$(CY^{46}Y^{47})_{p21}$—, further preferably absent or —$(CH_2)_{p2}$—.

$L^{12}$ is preferably absent or —$(CY^{59}Y^{60})_{p27}$—, more preferably absent or —$(CH_2)_{p27}$—, further preferably absent or —$CH_2$— or —$(CH_2)_2$—.

$J^1$ and $J^2$ are the same or different and are each $CY^{72}$ or N. Preferably, $J^1$ and $J^2$ are the same or different and are each CH, C(OH) or N.

When $L^{11}$ is absent, $J^1$ is preferably CH.

In another preferred mode of the present invention, $L^9$ and $L^{10}$ are absent; $L^{12}$ is —CO—$(CH_2)_{p29}$—; $J^1$ is CH; and $J^2$ is N. In this case, preferably, $L^8$ is —CO—NY$^{45B}$—$(CH_2)_{p18}$—, and $L^{11}$ is absent or —$(CH_2)_{p22}$—.

In an alternative preferred mode of the present invention, $L^9$ and $L^{10}$ are absent; $L^{12}$ is —O—CO—$(CH_2)_{p18}$—; and each of $J^1$ and $J^2$ is CH. In this case, preferably, $L^8$ is —O—CO—$(CH_2)_{p18}$—, and $L^{11}$ is absent.

$B^2$ is preferably

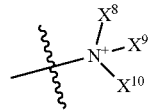

more preferably —N$^+$(CH$_3$)$_3$.

$X^8$ to $X^{10}$ are as defined above in $X^2$ to $X^4$, respectively.

In formula (IV), $R^{10}$ is preferably linear or branched C8-C24 alkyl or C8-C24 alkenyl, more preferably linear or branched C15-C20 alkenyl or linear or branched C9-C18 alkyl, most preferably linear C15-C20 alkenyl or linear C9-C18 alkyl. $R^{11}$ and $R^{12}$ are preferably the same linear or branched C8-C24 alkyl, C8-C24 alkenyl or C8-C24 alkynyl, more preferably the same linear or branched C15-C20 alkenyl or linear or branched C9-C18 alkyl, most preferably the same linear C15-C20 alkenyl or linear C9-C18 alkyl.

$L^{13}$ is absent, or —$Z^{23}$—$(CY^{84}Y^{85})_{p38}$— or —$Z^{24}$—$(CY^{86}Y^{87})_{p39}$—$Z^{25}$—$(CY^{88}Y^{89})_{p40}$—, preferably absent, or —$Z^{23}$—$(CY^{84}Y^{85})_{p38}$—. $Y^{84}$ to $Y^{89}$ are the same or different and are each a hydrogen atom or optionally substituted C1-C4 alkyl, preferably a hydrogen atom. $Z^{23}$ to $Z^{25}$ are the same or different and are each —O—, —NY$^{90A}$—, —CO—O—, —O—CO—, —CO—NY$^{90B}$—, —NY$^{90C}$—CO— or —NY$^{90D}$—CO—O—, preferably —CO—O—, —O—CO—, —CO—NY$^{90B}$— or —NY$^{90C}$—CO—, more preferably —CO—NY$^{90B}$—. $Y^{90A}$ to $Y^{90D}$ are the same or different and are each a hydrogen atom or optionally substituted C1-C4 alkyl, preferably a hydrogen atom or methyl, $p^{38}$ to $p^{40}$ are the same or different and are each an integer from 1 to 5, preferably 1 or 2.

$L^{13}$ is preferably absent, or —CO—O—$(CY^{84}Y^{85})_{p38}$—, —O—CO—$(CY^{84}Y^{85})_{p38}$—, —CO—NY$^{90B}$—$(CY^{84}Y^{85})_{p38}$—, or —NY$^{90C}$—CO—$(CY^{84}Y^{85})_{p38}$—, more preferably absent, or —CO—O—$(CH_2)_{p38}$—, —O—CO—$(CH_2)_{p38}$— or —CO—NCH$_3$—$(CH_2)_{p38}$—, further preferably absent, or —CO—NCH$_3$—$(CH_2)_{p38}$—.

$L^{14}$ and $L^{15}$ are the same or different and are each absent, or —$Z^{26}$—$(CY^{91}Y^{92})_{p41}$— or —$Z^{27}$—$(CY^{93}Y^{94})_{p42}$—$Z^{28}$—$(CY^{95}Y^{96})_{p43}$—, preferably absent, or —$Z^{26}$—$(CY^{91}Y^{92})_{p41}$—. $Y^{91}$ to $Y^{96}$ are the same or different and are each a hydrogen atom or optionally substituted C1-C4 alkyl, preferably a hydrogen atom. $Z^{26}$ to $Z^{28}$ are the same or different and are each —O—, —NY$^{97A}$—, —CO—O—, —O—CO—, —CO—NY$^{97B}$—, —NY$^{97C}$—CO—, —NY$^{97D}$—CO—O— or —CO—, preferably —CO—O—, —O—CO—, —CO—NY$^{97B}$—, —NY$^{97C}$—CO—, or —CO—. $Y^{97A}$ to $Y^{97D}$ are the same or different and are each a hydrogen atom or optionally substituted C1-C4 alkyl, preferably a hydrogen atom or methyl, $p^{41}$ is an integer from 0 to 5, preferably 0 to 2. $p^{42}$ is an integer from 1 to 5, preferably 1 or 2. $p^{43}$ is an integer from 0 to 5, preferably 0 to 2.

$L^{14}$ and $L^{15}$ are preferably the same or different and are each absent, or —CO—O—$(CY^{91}Y^{92})_{p41}$—, —O—CO—$(CY^{91}Y^{92})_{p41}$—, —CO—NY$^{97B}$—$(CY^{91}Y^{92})_{p41}$—, —NY$^{97C}$—CO—$(CY^{91}Y^{92})_{p41}$— or —CO—$(CY^{91}Y^{92})_{p41}$—, more preferably are the same or different and are each absent, or —CO—O—$(CY^{91}Y^{92})_{p41}$—, —O—CO—$(CY^{91}Y^{92})_{p41}$— or —CO—$(CY^{91}Y^{92})_{p41}$—, further preferably are the same or different and are each absent, or —CO—O—$(CH_2)_{p41}$—, —O—CO—$(CH_2)_{p41}$— or —CO—.

In formula (IV), more preferably, $L^{13}$ is —CO—O—$(CY^{84}Y^{85})_{p38}$—, —O—CO—$(CY^{84}Y^{85})_{p38}$— or —CO—$NY^{90B}$—$(CY^{84}Y^{85})_{p38}$—; one of $L^{14}$ and $L^{15}$ is —CO—O—$(CY^{91}Y^{92})_{p41}$— or —O—CO—$(CY^{91}Y^{92})_{p41}$—; $L^{13}$ is —CO—O—$(CY^{84}Y^{85})_{p38}$—, —O—CO—$(CY^{84}Y^{85})_{p38}$— or —CO—$NY^{89B}$—$(CY^{84}Y^{85})_{p38}$—, and one of $L^{14}$ and $L^{15}$ is —CO—O—$(CY^{91}Y^{92})_{p41}$— or —O—CO—$(CY^{91}Y^{92})_{p41}$—; $L^{14}$ and $L^{15}$ are the same or different and are each —CO—O—$(CY^{91}Y^{92})_{p41}$— or —O—CO—$(CY^{91}Y^{92})_{p41}$—; or $L^{13}$ is —CO—O—$(CY^{84}Y^{85})_{p38}$—, —O—CO—$(CY^{84}Y^{85})_{p38}$— or —CO—$NY^{89B}$—$(CY^{84}Y^{85})_{p38}$—, and $L^{14}$ and $L^{15}$ are the same or different and are each —CO—O—$(CY^{91}Y^{92})_{p41}$— or —O—CO—$(CY^{91}Y^{92})_{p41}$—; and each of $R^{10}$ to $R^{12}$ is linear or branched C15-C20 alkenyl or C9-C18 alkyl. $R^{11}$ and $R^{12}$ are preferably the same.

When $L^{13}$ is absent, or —O—$(CY^{84}Y^{85})_{p38}$—, —$NY^{90A}$—$(CY^{84}Y^{85})_{p38}$—, —O—CO—$(CY^{84}Y^{85})_{p38}$—, —$NY^{90C}$—CO—$(CY^{84}Y^{85})_{p38}$— or —$NY^{90D}$—CO—$(CY^{84}Y^{85})_{p38}$—, $R^{10}$ is preferably octyl, decyl, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl or 3,7,11,15-tetramethylhexadec-2-enyl, more preferably dodecyl, tetradecyl, hexadecyl, (Z)-hexadec-9-enyl, (Z)-octadec-6-enyl, (Z)-octadec-9-enyl or (9Z,12Z)-octadeca-9,12-dienyl.

When $L^{13}$ is —CO—O—$(CY^{84}Y^{85})_{p38}$— or —CO—$NY^{90B}$—$(CY^{84}Y^{85})_{p38}$—, $R^{10}$ is more preferably nonyl, undecyl, tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-octadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl or 2,6,10,14-tetramethylpentadec-1-enyl, further preferably undecyl, tridecyl, pentadecyl, (Z)-pentadec-8-enyl, (Z)-heptadec-5-enyl, (Z)-heptadec-8-enyl or (8Z,11Z)-heptadeca-8,11-dienyl.

When at least one of $L^{14}$ and $L^{15}$ is absent, or —O—$(CY^{91}Y^{92})_{p41}$—, —$NY^{97A}$—$(CY^{91}Y^{92})_{p41}$—, —O—CO—$(CY^{91}Y^{92})_{p41}$—, —$NY^{97C}$—CO—$(CY^{91}Y^{92})_{p41}$— or —$NY^{97D}$—CO—O—$(CY^{91}Y^{92})_{p41}$—, $R^{11}$ and $R^{12}$ bonded to $J^3$, —O—$(CY^{91}Y^{92})_{p41}$—, —$NY^{97A}$—$(CY^{91}Y^{92})_{p41}$—, —O—CO—$(CY^{91}Y^{92})_{p41}$—, —$NY^{97C}$—CO—$(CY^{91}Y^{92})_{p41}$— or —$NY^{97D}$—CO—O—$(CY^{91}Y^{92})_{p41}$— are the same or different and are each more preferably octyl, decyl, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl or 3,7,11,15-tetramethylhexadec-2-enyl, further preferably dodecyl, tetradecyl, hexadecyl, (Z)-hexadec-9-enyl, (Z)-octadec-6-enyl, (Z)-octadec-9-enyl or (9Z,12Z)-octadeca-9,12-dienyl.

When at least one of $L^{14}$ and $L^{15}$ is —CO—O—$(CY^{91}Y^{92})_{p41}$— or —CO—$NY^{97B}$—$(CY^{91}Y^{92})_{p41}$—, $R^{11}$ and $R^{12}$ bonded to —CO—O—$(CY^{91}Y^{92})_{p41}$— or —CO—$NY^{97B}$—$(CY^{91}Y^{92})_{p41}$— are the same or different and are each more preferably nonyl, undecyl, tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-octadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl or 2,6,10,14-tetramethylpentadec-1-enyl, further preferably undecyl, tridecyl, pentadecyl, (Z)-pentadec-8-enyl, (Z)-heptadec-5-enyl, (Z)-heptadec-8-enyl or (8Z,11Z)-heptadeca-8,11-dienyl.

$L^{16}$ is absent, or —$(CY^{98}Y^{99})_{p44}$—, —$(CY^{100}Y^{101})_{p45}$—$Z^{29}$—$(CY^{102}Y^{103})_{p46}$— or —$(CY^{104}Y^{105})_{p47}$—$Z^{30}$—$(CY^{106}Y^{107})_{p48}$—$Z^{31}$—$(CY^{108}Y^{109})_{p49}$—, preferably absent, or —$(CY^{98}Y^{99})_{p44}$— or —$(CY^{100}Y^{101})_{p45}$—$Z^{29}$—$(CY^{102}Y^{103})_{p46}$—, more preferably absent, or —$(CY^{98}Y^{99})_{p44}$—, —$(CY^{100}Y^{101})_{p45}$—O—CO—$(CY^{102}Y^{103})_{p46}$—, —$(CY^{100}Y^{101})_{p45}$—$NY^{109C}$—CO—$(CY^{102}Y^{103})_{p46}$— or —CO—$(CY^{102}Y^{103})_{p46}$—, further preferably absent, or —$(CH_2)_{p44}$— or —CO—$(CH_2)_{p46}$—.

$J^3$ is $CY^{111}$ or N, preferably CH or N. When $J^3$ is N, more preferably, $L^{14}$ is absent; $L^{15}$ is —CO—; and $L^{16}$ is absent, or —$(CY^{98}Y^{99})_{p44}$—, or $L^{14}$ is absent; $L^{15}$ is absent; and $L^{16}$ is —CO—$(CY^{102}Y^{103})_{p46}$—.

$X^{14}$ and $X^{15}$ are as defined above in $X^2$ and $X^3$, respectively.

In formula (V'), $R^{13}$ is preferably linear or branched C8-C24 alkyl or C8-C24 alkenyl, more preferably linear or branched C15-C20 alkenyl or linear or branched C9-C18 alkyl, most preferably linear C15-C20 alkenyl or linear C9-C18 alkyl. $R^{14}$ and $R^{15}$ are preferably the same linear or branched C8-C24 alkyl, C8-C24 alkenyl or C8-C24 alkynyl, more preferably the same linear or branched C15-C20 alkenyl or linear or branched C9-C18 alkyl, most preferably the same linear C15-C20 alkenyl or linear C9-C18 alkyl.

$L^{17}$ to $L^{19}$ are the same or different and are each absent, or —$Z^{32}$—$(CY^{116}Y^{117})_{p51}$— or —$Z^{33}$—$(CY^{118}Y^{119})_{p52}$—$Z^{34}$—$(CY^{120}Y^{121})_{p53}$—, preferably —$Z^{32}$—$(CY^{116}Y^{117})_{p51}$—, more preferably —O—$(CY^{116}Y^{117})_{p51}$— or —CO—O—$(CY^{116}Y^{117})_{p51}$—, further preferably —O— or —CO—O—.

In formula (V'), preferably, $L^{17}$ to $L^{19}$ are the same or different and are each —O— or —CO—O—, and each of $R^{13}$ to $R^{15}$ is linear C15-C20 alkenyl or C9-C18 alkyl. In this case, preferably, $L^{17}$ to $L^{19}$ are the same and —O— or —CO—O—, and $R^{13}$ to $R^{15}$ are the same and linear C15-C20 alkenyl or C9-C18 alkyl.

When at least one of $L^{17}$ to $L^{19}$ is absent, or —O—$(CY^{116}Y^{117})_{p51}$—, —O—CO—$(CY^{116}Y^{117})_{p51}$—, —$NY^{122C}$—CO—$(CY^{116}Y^{117})_{p51}$— or —$NY^{122D}$—CO—O—$(CY^{116}Y^{117})_{p51}$—, $R^{13}$ to $R^{15}$ bonded to carbon adjacent to the furanose ring or $L^{20}$, —O—$(CY^{116}Y^{117})_{p51}$—, —O—CO—$(CY^{116}Y^{117})_{p51}$—, —$NY^{122C}$—CO—$(CY^{116}Y^{117})_{p51}$— or —$NY^{122D}$—CO—O—$(CY^{116}Y^{117})_{p51}$— are the same or different and are each preferably octyl, decyl, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl, 3,7,11,15-tetramethylhexadec-2-enyl or the like, more preferably dodecyl, tetradecyl, hexadecyl, (Z)-hexadec-9-enyl, (Z)-octadec-6-enyl, (Z)-octadec-9-enyl, (9Z,12Z)-octadeca-9,12-dienyl or the like.

When at least one of $L^{17}$ to $L^{19}$ is —CO—O—$(CY^{116}Y^{117})_{p51}$—, —CO—NY$^{122B}$—$(CY^{116}Y^{117})_{p51}$— or —CO—$(CY^{116}Y^{117})_{p51}$—, $R^{13}$ to $R^{15}$ bonded to —CO—O—$(CY^{116}Y^{117})_{p51}$—, —CO—NY$^{122B}$—$(CY^{116}Y^{117})_{p51}$— or —CO—$(CY^{116}Y^{117})_{p51}$— are the same or different and are each preferably nonyl, undecyl, tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-octadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl or 2,6,10,14-tetramethylpentadec-1-enyl, more preferably undecyl, tridecyl, pentadecyl, (Z)-pentadec-8-enyl, (Z)-heptadec-5-enyl, (Z)-heptadec-8-enyl, (8Z,11Z)-heptadeca-8,11-dienyl or the like.

$L^{20}$ is absent, or —$(CY^{123}Y^{124})_{p54}$—, —$(CY^{125}Y^{126})_{p55}$—$Z^{35}$—$(CY^{127}Y^{128})_{p56}$— or —$(CY^{129}Y^{130})_{p57}$—$Z^{36}$—$(CY^{131}Y^{132})_{p58}$—$Z^{37}$—$(CY^{133}Y^{134})_{p59}$—, preferably —$(CY^{123}Y^{124})_{p54}$—, more preferably —$(CH_2)_{p54}$—, further preferably —$CH_2$—.

$L^{21}$ is absent, or —$(CY^{136}Y^{137})_{p60}$—, —$(CY^{138}Y^{139})_{p61}$—$Z^{38}$—$(CY^{140}Y^{141})_{p62}$— or —$(CY^{142}Y^{143})_{p63}$—$Z^{39}$—$(CY^{144}Y^{145})_{p64}$—$Z^{40}$—$(CY^{146}Y^{147})_{p65}$—, preferably absent or —$(CY^{136}Y^{137})_{p60}$—, more preferably absent or —$(CH_2)_{p60}$—, further preferably absent.

$B^3$ is preferably

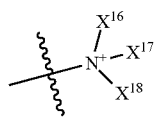

more preferably —N$^+$(CH$_3$)$_3$.

$Y^{112}$ and $Y^{113}$ are the same or different and are each a hydrogen atom, hydroxy or optionally substituted C1-C4 alkyl, preferably are the same or different and are each a hydrogen atom or hydroxy, more preferably are the same and a hydrogen atom.

In formula (V"), $R^{16}$ to $R^{18}$, $L^{22}$ to $L^{26}$, $B^4$, $Y^{114}$ to $Y^{115}$ and $A^6$ are as defined in $R^{13}$ to $R^{15}$, $L^{17}$ to $L^{21}$, $B^3$, $Y^{112}$ to $Y^{113}$ and $A^5$, respectively.

In formula (V'), when $Y^{112}$ is a hydrogen atom, four substituents on the pyran ring are preferably added on different carbon atoms, respectively, on the pyran ring. Formula (V') is more preferably

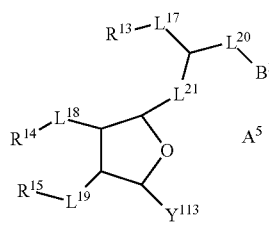

In this case, further preferably, $L^{17}$ to $L^{19}$ are the same or different and are each —O— or —CO—O—, and each of $R^{13}$ to $R^{15}$ is linear C15-C20 alkenyl or C9-C18 alkyl. Most preferably, $L^{17}$ to $L^{19}$ are the same or different and are each —O— or —CO—O—; each of $R^{13}$ to $R^{15}$ is linear C15-C20 alkenyl or C9-C18 alkyl; $L^{17}$ and $L^{21}$ are absent; and $Y^{113}$ is a hydrogen atom or hydroxy.

In formula (V'), four substituents on the furan ring are preferably added on different carbon atoms, respectively, on the furan ring. Formula (V') is more preferably

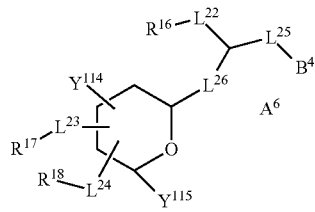

In this case, further preferably, $L^{22}$ to $L^{24}$ are the same or different and are each —O— or —CO—O—, and each of $R^{16}$ to $R^{18}$ is linear C15-C20 alkenyl or C9-C18 alkyl. Most preferably, $L^{22}$ to $L^{24}$ are the same or different and are each —O— or —CO—O—; each of $R^{16}$ to $R^{18}$ is linear C15-C20 alkenyl or C9-C18 alkyl; $L^{22}$ and $L^{26}$ are absent; and $Y^{114}$ is a hydrogen atom or hydroxy.

When $p^{13}$, $p^{33}$ and $p^{66}$ are 0 in the definition of each of the formulas:

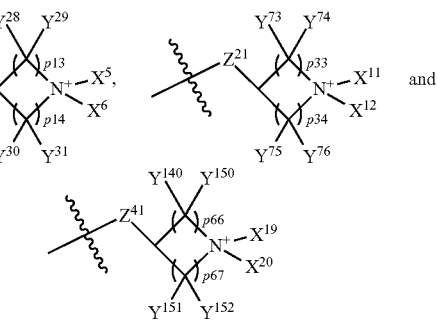

in the definition of formulas $B^1$, $B^2$, $B^3$ and $B^4$, N$^+$ is bonded to carbon adjacent to each of $Z^{10}$, $Z^{21}$ and $Z^{41}$.

The nucleic acid-containing lipid nanoparticle of the present invention preferably comprises a lipid represented by formula (II) as lipid A.

The nucleic acid-containing lipid nanoparticle of the present invention may comprise a cationic lipid other than the lipid having a hydrophilic unit having one quaternary ammonium group and optionally substituted three independent hydrocarbon groups (lipid A). The cationic lipid other than lipid A used in the present invention is not particularly limited as long as the cationic lipid is an amphipathic molecule having a lipophilic region containing one or more optionally substituted hydrocarbon groups, and a cationic hydrophilic region containing at least one primary amino group, secondary amino group, tertiary amino group and/or quaternary ammonium group (except for lipid A). The cationic lipid other than lipid A is preferably a lipid having a hydrophilic unit having optionally substituted one amino group or one quaternary ammonium group and a hydrophobic unit having optionally substituted two independent hydrocarbon groups (lipid B).

In the present invention, the lipid having, in the same molecule, a hydrophilic unit having optionally substituted one amino group or one quaternary ammonium group and a hydrophobic unit having optionally substituted two independent hydrocarbon groups (lipid B) is not particularly limited as long as the lipid is a molecule intramolecularly having optionally substituted one amino group or one quaternary ammonium group as a hydrophilic unit, and having optionally substituted two independent hydrocarbon groups. Lipid B is represented by, for example, any of structural formulas (D) and (E) given below.

In structural formulas (D) and (E) given below, the "hydrophilic unit" represents a hydrophilic unit having optionally substituted one amino group or one quaternary ammonium group, and the "hydrophobic unit" represents an optionally substituted independent hydrocarbon group.

Zero to two out of the three bonds of the amino group constituting the "hydrophilic unit" are attached to any 0 to 2 of the hydrocarbon groups constituting the "hydrophobic unit", and the remaining bond(s) is attached to hydrogen or an optionally substituted chain and/or cyclic hydrocarbon group, etc.

Zero to two out of the four bonds of the quaternary ammonium group constituting the "hydrophilic unit" are attached to any 0 to 2 of the hydrocarbon groups constituting the "hydrophobic unit", and the remaining bonds are attached to hydrogen or an optionally substituted chain and/or cyclic hydrocarbon group, etc.

The optionally substituted chain and/or cyclic hydrocarbon group constituting the "hydrophilic unit" can be any group composed of carbon and hydrogen atoms and is preferably a group having 1 to 10 carbon atoms, more preferably a group having 1 to 6 carbon atoms, further preferably a group having 1 to 3 carbon atoms.

The "hydrophilic unit" may have one or more ethers, esters, amides or the like via a carbon atom in the optionally substituted chain and/or cyclic hydrocarbon group, etc. constituting this hydrophilic unit. Examples of the substituent for the optionally substituted chain and/or cyclic hydrocarbon group, etc. include carbamate, amino, monoalkylamino, dialkylamino, pyrrolidin-2-yl, pyrrolidin-3-yl, piperidin-2-yl, piperidin-3-yl, piperidin-4-yl, morpholin-2-yl, morpholin-3-yl, hydroxy, alkoxy, alkoxycarbonyl, hydroxycarbonyl, carbamoyl, monoalkylcarbamoyl, dialkylcarbamoyl, nitro, cyano, fluoro, chloro, and bromo.

The hydrocarbon group constituting the "hydrophobic unit" can be any group consisting of 8 to 24 carbon atoms and hydrogen atoms. Hydrocarbon groups can be classified from the viewpoint of topology. Examples thereof include linear hydrocarbon groups, branched hydrocarbon groups and cyclic hydrocarbon groups (e.g., a cholesteryl group). A linear or branched hydrocarbon group is preferred. Also, hydrocarbon groups can be classified on the basis of the presence or absence of an unsaturated bond (double bond or triple bond). Hydrocarbon groups having an unsaturated bond can also be classified on the basis of the presence or absence of aromaticity. The hydrocarbon group is preferably a hydrocarbon group having only a saturated bond (alkyl) or a hydrocarbon group having an unsaturated bond and lacking aromaticity (e.g., alkenyl or alkynyl). The hydrocarbon group in lipid A is preferably linear or branched C8-C24 alkyl, C8-C24 alkenyl or C8-C24 alkynyl.

Each hydrocarbon group constituting the "hydrophobic unit" may be bonded directly to the amino group or the quaternary ammonium group of the "hydrophilic unit", or may be bonded to the amino group or the quaternary ammonium group via an ether, ester or amide bond, etc. and the optionally substituted chain and/or cyclic hydrocarbon group, etc. constituting the "hydrophilic unit". As shown in structural formula (E), the hydrocarbon groups constituting two "hydrophobic units" may be bonded via a carbon atom, and this carbon atom may be bonded either directly to the amino group or the quaternary ammonium group of the "hydrophilic unit" or to the amino group or the quaternary ammonium group via an ether, ester or amide bond, etc. and the optionally substituted chain and/or cyclic hydrocarbon group, etc. constituting the "hydrophilic unit".

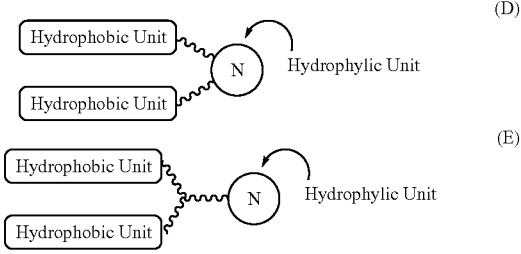

(D)

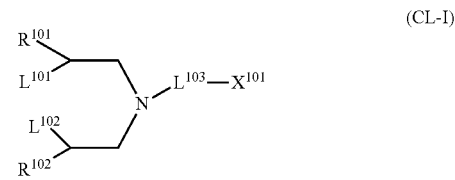

(E)

The cationic lipid in the nucleic acid-containing lipid nanoparticle of the present invention may be lipid A alone or lipid B alone and preferably comprises both lipid A and lipid B.

Examples of the cationic lipid other than lipid A used in the present invention include cationic lipids described in WO 2013/089151, WO 2011/136368, WO 2014/007398, WO 2010/042877 and WO 2010/054401.

Examples of lipid B used in the present invention can include lipids represented by the following formulas (CL-I) to (CL-XIX):

formula (CL-I)

$$\underset{R^{102}}{\overset{R^{101}}{\diagdown}} \underset{L^{102}}{\overset{L^{101}}{\diagdown}} N \underset{}{\diagup} L^{103} - X^{101}$$

(CL-I)

wherein
$R^{101}$ and $R^{102}$ are the same or different and are each linear or branched C10-C24 alkyl, C10-C24 alkenyl or C10-C24 alkynyl;
$L^{101}$ and $L^{102}$ are each a hydrogen atom, or together form a single bond or C1-C3 alkylene;
$L^{103}$ is a single bond, —CO— or —CO—O—;
when $L^{103}$ is a single bond,
  $X^{101}$ is a hydrogen atom, C1-C6 alkyl, C3-C6 alkenyl, pyrrolidin-3-yl, piperidin-3-yl, piperidin-4-yl, or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl; and
when $L^{103}$ is —CO— or —CO—O—,
  $X^{101}$ is pyrrolidin-2-yl, pyrrolidin-3-yl, piperidin-2-yl, piperidin-3-yl, piperidin-4-yl, morpholin-2-yl, morpholin-3-yl, or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl, and at least one of the substituents is amino, monoalkylamino, dialkylamino, trialkylammonio, pyrrolidinyl, piperidyl or morpholinyl, formula (CL-II)

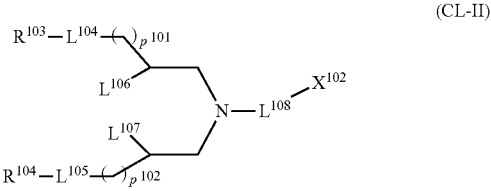

wherein $R^{103}$ and $R^{104}$ are the same or different and are each linear or branched C12-C24 alkyl, C12-C24 alkenyl or C12-C24 alkynyl;

$p^{101}$ and $p^{102}$ are the same or different and are each an integer from 0 to 3;

$L^{106}$ and $L^{107}$ are each a hydrogen atom, or together form a single bond or C2-C8 alkylene;

$L^{104}$ and $L^{105}$ are the same or different and are each —O—, —CO—O— or —O—CO—;

$L^{108}$ is a single bond, —CO— or —CO—O—;

when $L^{108}$ is a single bond, $X^{102}$ is a hydrogen atom, C1-C6 alkyl, C3-C6 alkenyl, pyrrolidin-2-yl, pyrrolidin-3-yl, piperidin-3-yl, piperidin-4-yl, or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl; and when $L^{108}$ is —CO— or —CO—O—, $X^{102}$ is pyrrolidin-2-yl, pyrrolidin-3-yl, piperidin-2-yl, piperidin-3-yl, piperidin-4-yl, morpholin-2-yl, morpholin-3-yl, or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl, and at least one of the substituents is amino, monoalkylamino, dialkylamino, trialkylammonio, pyrrolidinyl, piperidyl or morpholinyl, formula (CL-III)

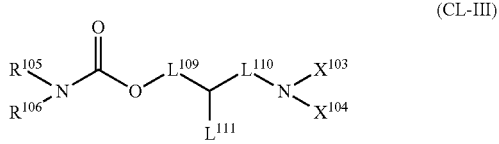

wherein $R^{105}$ is linear or branched C8-C24 alkyl, C8-C24 alkenyl or C8-C24 alkynyl; $R^{106}$ is linear or branched C8-C24 alkyl, C8-C24 alkenyl, C8-C24 alkynyl, C8-C24 alkyloxyethyl, C8-C24 alkyloxypropyl, C8-C24 alkenyloxyethyl, C8-C24 alkenyloxypropyl, C8-C24 alkynyloxyethyl or C8-C24 alkynyloxypropyl;

$X^{103}$ and $X^{104}$ are the same or different and are each C1-C3 alkyl, or together form C2-C8 alkylene, or $X^{103}$ forms C2-C8 alkylene together with $L^{111}$;

$L^{111}$ is a hydrogen atom, C1-C6 alkyl, C3-C6 alkenyl, amino, monoalkylamino, hydroxy, alkoxy, carbamoyl, monoalkylcarbamoyl, dialkylcarbamoyl, or C1-C6 alkyl or C3-C6 alkenyl substituted with one to three same or different substituents selected from amino, monoalkylamino, hydroxy, alkoxy, carbamoyl, monoalkylcarbamoyl and dialkylcarbamoyl, or forms C2-C8 alkylene together with $X^{103}$;

$L^{109}$ is C1-C6 alkylene;

$L^{110}$ is a single bond, or C1-C6 alkylene, provided that the sum of the numbers of carbon atoms of $L^{109}$ and $L^{110}$ is 7 or less; when $L^{111}$ is a hydrogen atom, $L^{110}$ is a single bond; and when $L^{111}$ forms C2-C6 alkylene together with $X^{103}$, $L^{110}$ is a single bond, or methylene or ethylene, formula (CL-IV)

wherein $R^{107}$ is linear or branched C8-C24 alkyl, C8-C24 alkenyl or C8-C24 alkynyl;

$R^{108}$ is linear or branched C8-C24 alkyl, C8-C24 alkenyl, C8-C24 alkynyl, C8-C24 alkyloxyethyl, C8-C24 alkyloxypropyl, C8-C24 alkenyloxyethyl, C8-C24 alkenyloxypropyl, C8-C24 alkynyloxyethyl, C8-C24 alkynyloxypropyl, C8-C24 alkyloxyethoxyethyl, C8-C24 alkenyloxyethoxyethyl or C8-C24 alkynyloxyethoxyethyl;

$X^{105}$ is a hydrogen atom, optionally substituted C1-C4 alkyl or —CO—$(CH_2)_n$—NY1Y2;

n represents an integer from 1 to 4; and

Y1 and Y2 are the same or different and are each C1-C3 alkyl, or together form C2-C8 alkylene, formula (CL-V)

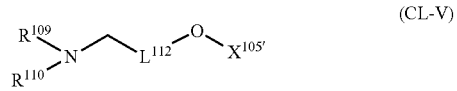

wherein $R^{109}$ is linear or branched C8-C24 alkyl, C8-C24 alkenyl or C8-C24 alkynyl;

$R^{110}$ is linear or branched C8-C24 alkyl, C8-C24 alkenyl, C8-C24 alkynyl, C8-C24 alkyloxyethyl, C8-C24 alkyloxypropyl, C8-C24 alkenyloxyethyl, C8-C24 alkenyloxypropyl, C8-C24 alkynyloxyethyl or C8-C24 alkynyloxypropyl;

$L^{112}$ is C1-C3 alkylene; and $X^{105'}$ is a hydrogen atom or C1-C3 alkyl, formula (CL-VI)

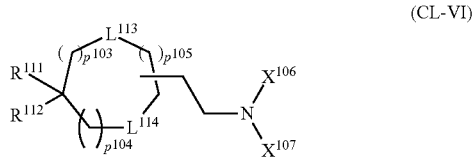

wherein $R^{111}$ and $R^{112}$ are the same or different and are each optionally substituted linear or branched C8-C24 alkyl, C8-C24 alkenyl or C8-C24 alkynyl;

$X^{106}$ and $X^{107}$ are the same or different and are each C1-C3 alkyl, or together form C2-C8 alkylene;

$p^{103}$, $p^{104}$ and $p^{105}$ are the same or different and are each 0 or 1, provided that $p^{103}$, $p^{104}$ and $p^{105}$ are not 0 at the same time; and $L^{113}$ and $L^{114}$ are the same or different and are each O, S or NH, formula (CL-VII)

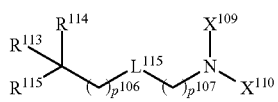

(CL-VII)

wherein $R^{113}$ and $R^{114}$ are the same or different and are each optionally substituted linear or branched C8-C24 alkyl, C8-C24 alkenyl or C8-C24 alkynyl;

$R^{115}$ is a hydrogen atom, hydroxy, optionally substituted C1-C4 alkyl, C1-C4 alkoxy or C1-C4 acyloxy;

$X^{109}$ and $X^{110}$ are the same or different and are each C1-C3 alkyl, or together form C2-C8 alkylene;

$L^{115}$ is —CO—O—, —O—CO—, —NHCO— or —CONH—;

$p^{106}$ is an integer from 0 to 3; and $p^{107}$ is an integer from 1 to 4, formula (CL-VIII)

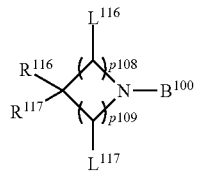

(CL-VIII)

wherein $R^{116}$ and $R^{117}$ are the same or different and are each optionally substituted linear or branched C8-C24 alkyl, C8-C24 alkenyl, C8-C24 alkynyl, C7-C20 alkyloxy C1-C3 alkyl, C7-C20 alkenyloxy C1-C3 alkyl or C7-C20 alkynyloxy C1-C3 alkyl, or the C8-C24 alkyl, the C8-C24 alkenyl or the C8-C24 alkynyl in which a biodegradable group is integrated, or the C8-C24 alkyl group, the C8-C24 alkenyl group or the C8-C24 alkynyl group in which a biodegradable group is present at the terminal;

the biodegradable group thus integrated is —C(O)O— or —OC(O)—, and the group having the biodegradable group present at the terminal is —C(O)O—C1-C4 alkyl or —OC(O)—C1-C4 alkyl;

$B^{100}$ is a hydrogen atom, C1-C3 alkyl, hydroxy C2-C4 alkyl, C1-C3 dialkylamino C2-C4 alkyl, formula (A):

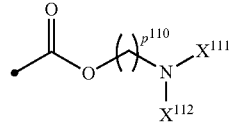

(A)

wherein $X^{111}$ and $X^{112}$ are the same or different and are each a hydrogen atom or C1-C3 alkyl, or $X^{111}$ and $X^{112}$ optionally form a C2-C6 nitrogen-containing hetero ring together with the nitrogen atom to which they are bonded; and $p^{110}$ is an integer from 2 to 6, or formula (B):

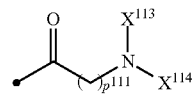

(B)

wherein $X^{113}$ and $X^{114}$ are the same or different and are each a hydrogen atom or C1 to C3 alkyl, or $X^{113}$ and $X^{114}$ optionally form a C2-C6 nitrogen-containing hetero ring together with the nitrogen atom to which they are bonded; and $p^{111}$ is an integer from 1 to 6;

$p^{108}$ is an integer from 0 to 4; $p^{109}$ is an integer from 1 to 4, provided that when $p^{108}$ is 0, $p^{109}$ is not 1;

$L^{116}$ is the same or different on each carbon to which it is bonded and is a hydrogen atom or C1-C3 alkyl; and $L^{117}$ is the same or different on each carbon to which it is bonded and is a hydrogen atom or C1-C3 alkyl, formula (CL-IX)

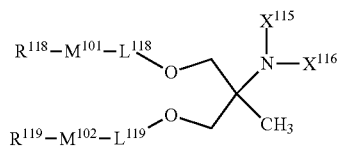

(CL-IX)

wherein $X^{115}$ and $X^{116}$ are the same or different and are each a hydrogen atom or C1-C3 alkyl;

$L^{118}$ and $L^{119}$ are the same or different and are each optionally substituted linear or branched C8-C24 alkylene or C8-C24 alkenylene;

$M^{101}$ and $M^{102}$ are the same or different and are each selected from the group consisting of —C=C—, —OC(O)—, —C(O)O—, —SC(O)—, —C(O)S—, —OC(S)—, —C(S)O—, —SS—, —C(R")=N—, —N=C(R")—, —C(R")=N—O—, —O—N=C(R")—, —N(R")C(O)—, —C(O)N(R")—, —N(R")C(S)—, —C(S)N(R")—, —N(R")C(O)N(R''')—, —N(R")C(O)O—, —OC(O)N(R")— and —OC(O)O—;

R" and R''' are the same or different and are each a hydrogen atom or C1-C3 alkyl; and $R^{118}$ and $R^{119}$ are the same or different and are each optionally substituted linear or branched C1-C16 alkyl or C2-C16 alkenyl, formula (CL-X)

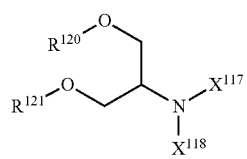

(CL-X)

wherein $X^{117}$ and $X^{118}$ are the same or different and are each hydrogen atom, optionally substituted C1-C6 alkyl, heterocyclyl or polyamine, or $X^{117}$ and $X^{118}$ optionally form, together with the nitrogen to which they are bonded, a 4- to 7-membered monocyclic hetero ring optionally containing one or two additional heteroatoms selected from N, O and S in addition to the nitrogen; and $R^{120}$ and $R^{121}$ are the same or different and are each optionally substituted linear or branched C4-C24 alkyl or C4-C24 alkenyl, formula (CL-XI)

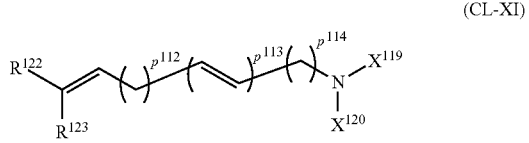

(CL-XI)

wherein $X^{119}$ and $X^{120}$ are the same or different and are each a hydrogen atom, optionally substituted linear or branched C1-C20 alkyl, C1-C20 alkenyl, C1-C20 alkynyl or C6-C20 acyl;

$R^{122}$ and $R^{123}$ are the same or different and are each optionally substituted linear or branched C1-C30 alkyl, C2-C30 alkenyl or C2-C30 alkynyl; and $p^{112}$, $p^{113}$ and $p^{114}$ are the same or different and are each 0, or an arbitrary positive integer, formula (CL-XII)

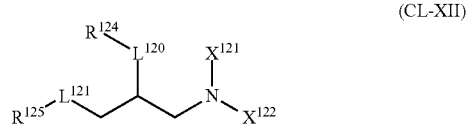

(CL-XII)

wherein $X^{121}$ and $X^{122}$ are the same or different and are each a hydrogen atom, C1-C6 alkyl, cycloalkyl or cycloalkenyl, or $X^{121}$ and $X^{122}$ optionally form a C2-C6 nitrogen-containing hetero ring together with the nitrogen atom to which they are bonded;

$L^{120}$ and $L^{121}$ are the same or different and are each —O—, —OC(O)— or —(O)CO—; and $R^{124}$ and $R^{125}$ are the same or different and are each optionally substituted linear or branched C8-C24 alkyl or C8-C24 alkenyl, formula (CL-XIII)

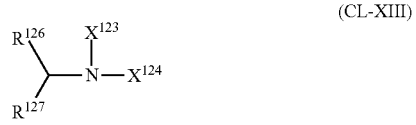

(CL-XIII)

wherein $R^{126}$ and $R^{127}$ are the same or different and are each optionally substituted linear or branched C8-C24 alkyl, C8-C24 alkenyl, C8-C24 alkynyl, C8-C24 heteroalkyl, C8-C24 heteroalkenyl or C8-C24 heteroalkynyl;

$X^{123}$ is a hydrogen atom or optionally substituted C1-C6 alkyl;

$X^{124}$ is C1-C6 alkyl, substituted C1-C6 alkyl which is substituted with —NR$^{4a}$R$^{4b}$, or optionally substituted C3-C7 heterocyclyl;

R$^{4a}$ and R$^{4b}$ are the same or different and are each a hydrogen atom, —C(=NH)NH$_2$ or optionally substituted C1-C6 alkyl, or R$^{4a}$ and R$^{4b}$ optionally form optionally substituted C3-C7 heterocyclyl together with the nitrogen atom to which they are bonded;

$X^{123}$ and $X^{124}$ optionally form optionally substituted C3-C7 heterocyclyl together with the nitrogen atom to which they are bonded, provided that $X^{123}$ and $X^{124}$ do not form imidazolyl, benzimidazolyl, or succinimidyl, and only one primary amine is allowed to be present on any one of $X^{123}$ and $X^{124}$, or any primary amine is not present on any one of $X^{123}$ and $X^{124}$, and neither $X^{123}$ nor $X^{124}$ is substituted amide;

when each of $R^{126}$ and $R^{127}$ is C11 alkyl or C15 alkyl, $X^{123}$ is not a hydrogen atom;

when each of $R^{126}$ and $R^{127}$ is C16 alkyl or C17 alkyl, $R^{126}$ and $R^{127}$ are not substituted with OH;

when each of $R^{126}$ and $R^{127}$ is C17 alkyl, $X^{123}$ and $X^{124}$ are not substituted with OH; and when each of $R^{126}$ and $R^{127}$ is C18 alkyl, $X^{124}$ is not substituted with optionally substituted imidazolyl, formula (CL-XIV)

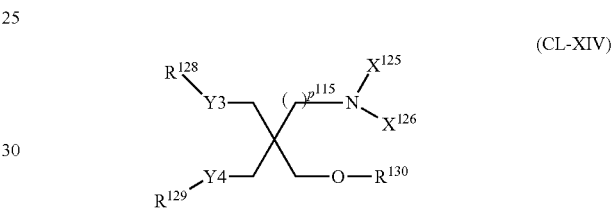

(CL-XIV)

wherein $X^{125}$ and $X^{126}$ are the same or different and are each a hydrogen atom, optionally substituted C1-C6 alkyl, heterocyclyl or polyamine, or $X^{125}$ and $X^{126}$ optionally form, together with the nitrogen to which they are bonded, a 4- to 7-membered monocyclic hetero ring optionally containing one or two additional heteroatoms selected from N, O and S in addition to the nitrogen;

$R^{130}$ is a hydrogen atom or C1-C6 alkyl;

$R^{128}$ and $R^{129}$ are the same or different and are each optionally substituted linear or branched C4-C24 alkyl or C4-C24 alkenyl;

Y3 and Y4 are the same or different and are each an oxygen atom or CH$_2$; and p115 is an integer of 0 to 2, formula (CL-XV)

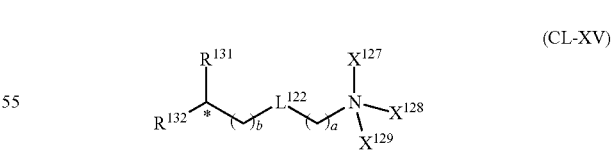

(CL-XV)

wherein $X^{127}$ and $X^{128}$ are the same or different and are each C1-C6 alkyl, C2-C6 alkenyl or C2-C6 alkynyl, or $X^{127}$ and $X^{128}$ form, together with the nitrogen atom to which they are bonded, a hetero ring having one or two nitrogen atoms;

$L^{122}$ is —C(O)O—, —OC(O)—, —C(O)N(X$^{130}$)—, —N(X$^{130}$)C(O)—, —OC(O)O—, —OC(O)N(X$^{130}$)—, —N(X$^{130}$)C(O)N(X$^{130}$)—, or —N(X$^{130}$)C(O)O—;

each $X^{130}$ present is independently a hydrogen atom or C1-C3 alkyl;

a is 1, 2, 3, 4, 5, or 6;

b is 0, 1, 2, or 3;

$X^{129}$ is absent, or hydrogen or C1-C3 alkyl;

$R^{131}$ and $R^{132}$ are the same or different and are each alkyl having 12 to 24 carbon atoms, alkenyl having 12 to 24 carbon atoms, or alkoxy having 12 to 24 carbon atoms, which has one or more biodegradable groups; the biodegradable groups are each independently integrated in the alkyl group having 12 to 24 carbon atoms, the alkenyl group having 12 to 24 carbon atoms, or the alkoxy group having 12 to 24 carbon atoms, or present at a terminal of the alkyl group having 12 to 24 carbon atoms, the alkenyl group having 12 to 24 carbon atoms, or the alkoxy group having 12 to 24 carbon atoms, wherein the biodegradable group thus integrated is —C(O)O—, —OC(O)—, —C(O)N($X^{130}$)—, or —N($X^{130}$) C(O)—, and the group having the biodegradable group present at the terminal is —C(O)O—C1-C4 alkyl, —OC(O)—C1-C4 alkyl, —C(O)N($X^{130}$)—C1-C4 alkyl, or —N($X^{130}$)C(O)—C1-C4 alkyl; and $R^{131}$ and $R^{132}$ each have at least four carbon atoms between the biodegradable group and the asterisked (*) tertiary carbon atom, formula (CL-XVI)

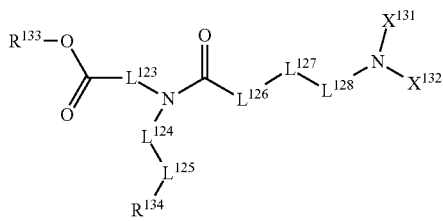

(CL-XVI)

wherein $R^{133}$ and $R^{134}$ are the same or different and are each linear or branched C1-C9 alkyl, C2-C11 alkenyl or C2-C11 alkynyl;

$L^{123}$ and $L^{124}$ are the same or different and are each linear C5-C18 alkylene or linear C5-C18 alkenylene, or forms a hetero ring with N to which they are bonded;

$L^{125}$ is a single bond or —CO—O—, and when $L^{125}$ is —CO—O—, -$L^{124}$-CO—$OR^{134}$ is formed;

$L^{127}$ is S or O;

$L^{126}$ is a single bond or linear or branched C1-C6 alkylene, or forms a hetero ring with N to which they are bonded via —C(O)—;

$L^{128}$ is linear or branched C1-C6 alkylene; and $X^{131}$ and $X^{132}$ are the same or different and are each hydrogen or linear or branched C1-C6 alkyl, formula (CL-XVII)

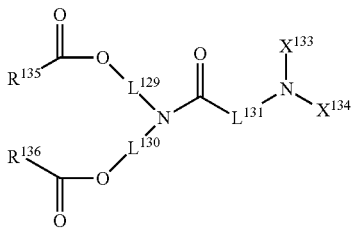

(CL-XVII)

wherein $L^{131}$ is C2-C4 alkylene or —$CH_2$—S—$CH_2CH_2$—;

$L^{129}$ and $L^{130}$ are the same or different and are each C1-C6 alkyl;

$R^{135}$ and $R^{136}$ are the same or different and are each C10-C30 alkyl or C10-C30 alkenyl; and $X^{133}$ and $X^{134}$ are the same or different and are each hydrogen, C1-C6 alkyl or —$CH_2CH_2OH$, formula (CL-XVIII)

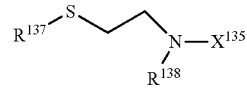

(CL-XVIII)

wherein $R^{137}$ and $R^{138}$ are the same or different and are each linear or branched C8-C24 alkyl, C8-C24 alkenyl, C8-C24 alkynyl, C8-C24 alkylthioethyl, C8-24 alkenylthioethyl, or C8-C24 alkynylthioethyl;

$X^{135}$ is a hydrogen atom, C1-C3 alkyl, hydroxy C2-C4 alkyl, formula (C):

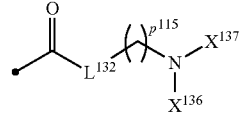

(C)

wherein $X^{136}$ and $X^{137}$ are the same or different and are each a hydrogen atom or C1-C3 alkyl, or $X^{136}$ and $X^{137}$ optionally form a C2-C6 nitrogen-containing hetero ring together with the nitrogen atom to which they are bonded; $L^{132}$ is S or O; and $p^{115}$ is an integer from 2 to 4, formula (D):

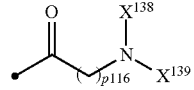

(D)

wherein $X^{138}$ and $X^{139}$ are the same or different and are each a hydrogen atom or C1 to C3 alkyl, or $X^{138}$ and $X^{139}$ optionally form a C3-C6 nitrogen-containing hetero ring together with the nitrogen atom to which they are bonded; and $p^{116}$ is an integer from 1 to 4, or formula (E):

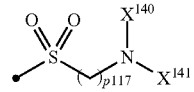

(E)

wherein $X^{140}$ and $X^{141}$ are the same or different and are each a hydrogen atom or C1 to C3 alkyl, or $X^{140}$ and $X^{141}$ optionally form a C3-C6 nitrogen-containing hetero ring together with the nitrogen atom to which they are bonded; and $p^{117}$ is an integer from 1 to 4, and formula (CL-XIX)

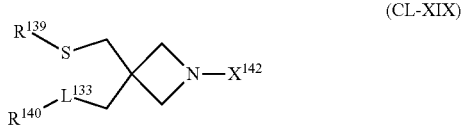

(CL-XIX)

wherein $R^{139}$ and $R^{140}$ are the same or different and are each linear or branched C8-C24 alkyl, C8-C24 alkenyl or C8-C24 alkynyl;

$L^{133}$ is S or O; and $X^{142}$ is a hydrogen atom, C1-C3 alkyl, hydroxy C2-C4 alkyl, formula (F):

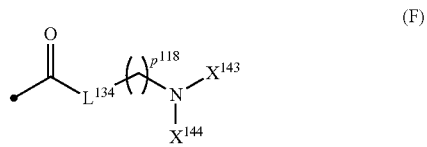

(F)

wherein $X^{143}$ and $X^{144}$ are the same or different and are each a hydrogen atom or C1-C3 alkyl, or $X^{143}$ and $X^{144}$ optionally form a C2-C6 nitrogen-containing hetero ring together with the nitrogen atom to which they are bonded; $L^{134}$ is S or O; and $p^{118}$ is an integer from 2 to 4, or formula (G):

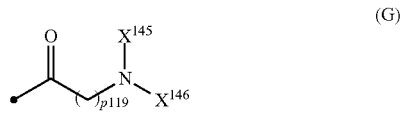

(G)

wherein $X^{145}$ and $X^{146}$ are the same or different and are each a hydrogen atom or C1 to C3 alkyl, or $X^{145}$ and $X^{146}$ optionally form a C3-C6 nitrogen-containing hetero ring together with the nitrogen atom to which they are bonded; and $p^{119}$ is an integer from 1 to 4.

One aspect of the present invention provides a compound represented by formula (CL-XVIII) or (CL-XIX), or a pharmaceutically acceptable salt thereof.

In the compound represented by formula (CL-XVIII) or (CL-XIX) of the present invention, a hydrogen ion may be coordinated on a lone pair of electrons on the nitrogen atom in the structure. In this case, the hydrogen ion may form a salt with a pharmaceutically acceptable anion. In the present invention, the compound represented by formula (CL-XVIII) or (CL-XIX), or the pharmaceutically acceptable salt thereof also encompasses a cationic lipid in which a hydrogen ion may be coordinated on a lone pair of electrons on the nitrogen atom in the structure.

In the present invention, examples of the pharmaceutically acceptable anion include: inorganic ions such as chloride ions, bromide ions, nitrate ions, sulfate ions and phosphate ions; and organic acid ions such as acetate ions, oxalate ions, maleate ions, fumarate ions, citrate ions, benzoate ions and methanesulfonate ions.

Examples of the pharmaceutically acceptable salt of the compound represented by formula (CL-XVIII) or (CL-XIX) of the present invention include hydrochloride, bromate, nitrate, sulfate, phosphate, acetate, oxalate, maleate, fumarate, citrate, benzoate and methanesulfonate.

Some compounds represented by formula (CL-XVIII) or (CL-XIX) of the present invention may have stereoisomers such as geometric isomers and optical isomers, tautomers, or the like. Compound (I) of the present invention encompasses all possible isomers including them, and mixtures thereof.

Some or all of the atoms in formula (CL-XVIII) or (CL-XIX) of the present invention may be replaced with their corresponding isotopic atoms. The compound represented by formula (CL-XVIII) or (CL-XIX) also encompasses such a compound containing isotopic atoms replaced therefor. For example, some or all of the hydrogen atoms in compound (I) may each be a hydrogen atom having an atomic weight of 2 (deuterium atom).

The compound derived from formula (CL-XVIII) or (CL-XIX) of the present invention by the replacement of some or all of the atoms with their corresponding isotopic atoms can be produced in the same way as in each production method described above by using commercially available building blocks. The compound derived from formula (CL-XVIII) or (CL-XIX) by the replacement of some or all of the hydrogen atoms with deuterium atoms can also be produced by use of, for example, a method which involves deuterating an alcohol, a carboxylic acid, or the like using an iridium complex as a catalyst and heavy water as a deuterium source [see J. Am. Chem. Soc., Vol. 124, No. 10, 2092 (2002)].

In the definition of each group in formula (CL-I), examples of the linear or branched C10-C24 alkyl include decyl, undecyl, dodecyl, tridecyl, 6,10-dimethylundec-2-yl, tetradecyl, pentadecyl, hexadecyl, heptadecyl, octadecyl, 6,10,14-trimethylpentadecan-2-yl, nonadecyl, icosyl, henicosyl, docosyl, tricosyl and tetracosyl, preferably decyl, undecyl, dodecyl, tridecyl, tetradecyl, pentadecyl, hexadecyl, heptadecyl and octadecyl, more preferably tridecyl, tetradecyl, pentadecyl, hexadecyl, heptadecyl and octadecyl.

The linear or branched C10-C24 alkenyl can be linear or branched C10-C24 alkenyl containing one to three double bonds. Examples thereof include (Z)-dodec-7-enyl, (Z)-tetradec-7-enyl, (Z)-tetradec-9-enyl, (Z)-hexadec-4-enyl, (Z)-hexadec-7-enyl, (E)-hexadec-7-enyl, (Z)-hexadec-9-enyl, (7Z,10Z)-hexadeca-7,10-dienyl, (7Z,10Z,13Z)-hexadeca-7,10,13-trienyl, (Z)-octadec-6-enyl, (Z)-octadec-9-enyl, (E)-octadec-9-enyl, (9Z,12Z)-octadeca-9,12-dienyl, (Z)-octadec-11-enyl, (9Z,12Z,15Z)-octadeca-9,12,15-trienyl, (Z)-icos-11-enyl and (11Z,14Z)-icosa-11,14-dienyl, preferably (Z)-dodec-7-enyl, (Z)-tetradec-7-enyl, (Z)-hexadec-4-enyl, (Z)-hexadec-7-enyl, (E)-hexadec-7-enyl, (Z)-hexadec-9-enyl, (7Z,10Z)-hexadeca-7,10-dienyl, (7Z,10Z, 13Z)-hexadeca-7,10,13-trienyl, (Z)-octadec-9-enyl, (9Z, 12Z)-octadeca-9,12-dienyl and (11Z,14Z)-icosa-11,14-dienyl, more preferably (7Z,10Z)-hexadeca-7,10-dienyl and (9Z,12Z)-octadeca-9,12-dienyl.

The linear or branched C10-C24 alkynyl can be linear or branched C10-C24 alkynyl containing one to three triple bonds. Examples thereof include dec-9-ynyl, dodec-4-ynyl, dodec-11-ynyl, tetradec-5-ynyl, tetradec-6-ynyl, hexadec-7-ynyl, hexadeca-3,5-diynyl, hexadeca-5,7-diynyl and octadec-9-ynyl, preferably hexadec-7-ynyl and octadec-9-ynyl, more preferably octadec-9-ynyl.

In formula (CL-I), $R^{101}$ and $R^{103}$ are preferably the same linear or branched C10-C24 alkyl, C10-C24 alkenyl or C10-C24 alkynyl, more preferably the same linear or branched C10-C24 alkyl or C10-C24 alkenyl, further preferably the same linear C10-C24 alkenyl.

Examples of the C1-C3 alkylene include methylene, ethylene and propylene, preferably methylene and ethylene, more preferably methylene.

Examples of the C1-C6 alkyl include methyl, ethyl, propyl, isopropyl, cyclopropyl, butyl, isobutyl, sec-butyl, tert-butyl, cyclobutyl, cyclopropylmethyl, pentyl, isopentyl, sec-pentyl, neopentyl, tert-pentyl, cyclopentyl, hexyl and cyclohexyl, preferably methyl, ethyl, propyl, isopropyl, butyl, isobutyl, sec-butyl, tert-butyl, pentyl, isopentyl, sec-pentyl, tert-pentyl, neopentyl and hexyl, more preferably methyl, ethyl and propyl.

Examples of the C3-C6 alkenyl include allyl, 1-propenyl, butenyl, pentenyl and hexenyl, preferably allyl.

Each of the monoalkylamino and the dialkylamino can be amino substituted with one or two same or different C1-C6 alkyl (as defined above) groups, or C1-C6 alkyl (as defined above) substituted with amino, methylamino, ethylamino, dimethylamino, diethylamino, pyrrolidinyl, piperidyl or morpholinyl. Examples thereof include methylamino, ethylamino, propylamine, butylamino, pentylamino, hexylamino, dimethylamino, diethylamino, ethylmethylamino, methylpropylamino, butylmethylamino, methylpentylamino, hexylmethylamino, aminoethylamino, aminopropylamino, (aminoethyl)methylamino and bis(aminoethyl)amino, preferably methylamino, ethylamino, dimethylamino, diethylamino, aminopropylamino and bis(aminoethyl)amino, more preferably methylamino and dimethylamino.

The trialkylammonio can be ammonio substituted by three same or different C1-C6 alkyl (as defined above) groups, or C1-C6 alkyl (as defined above) substituted with amino, methylamino, ethylamino, dimethylamino, diethylamino, pyrrolidinyl, piperidyl or morpholinyl. Examples thereof include trimethylammonio, ethyldimethylammonio, diethylmethylammonio, triethylammonio, tripropylammonio, tributylammonio, tripentylammonio, trihexylammonio, tris(aminoethyl)ammonio, (aminoethyl)dimethylammonio and bis(aminoethyl)methylammonio, preferably trimethylammonio, triethylammonio, tris(aminoethyl)ammonio, (aminoethyl)dimethylammonio and bis(aminoethyl)methylammonio, more preferably trimethylammonio.

In compound (CL-I), the trialkylammonio may form a salt with a pharmaceutically acceptable anion (as defined above).

The alkoxy can be hydroxy substituted with C1-C6 alkyl (as defined above) or C1-C6 alkyl (as defined above) substituted with amino, methylamino, ethylamino, dimethylamino, diethylamino, pyrrolidinyl, piperidyl or morpholinyl. Examples thereof include methoxy, ethoxy, propyloxy, butyloxy, pentyloxy, hexyloxy, aminoethoxy and methylaminoethoxy, preferably methoxy, ethoxy, aminoethoxy and methylaminoethoxy, more preferably methoxy.

Each of the monoalkylcarbamoyl and the dialkylcarbamoyl can be carbamoyl substituted with one or two same or different C1-C6 alkyl (as defined above) groups, or C1-C6 alkyl (as defined above) substituted with amino, methylamino, ethylamino, dimethylamino, diethylamino, pyrrolidinyl, piperidyl or morpholinyl. Examples thereof include methylcarbamoyl, ethylcarbamoyl, propylcarbamoyl, butylcarbamoyl, pentylcarbamoyl, hexylcarbamoyl, dimethylcarbamoyl, diethylcarbamoyl, ethylmethylcarbamoyl, methylpropylcarbamoyl, butylmethylcarbamoyl, methylpentylcarbamoyl, hexylmethylcarbamoyl, aminoethylcarbamoyl, aminopropylcarbamoyl, (aminoethyl)methylcarbamoyl and bis(aminoethyl)carbamoyl, preferably methylcarbamoyl, ethylcarbamoyl and dimethylcarbamoyl, more preferably methylcarbamoyl and dimethylcarbamoyl.

Each of $L^{101}$ and $L^{102}$ is more preferably a hydrogen atom. In this case, $R^{101}$ and $R^{102}$ are the same or different and are each preferably dodecyl, tetradecyl, (Z)-dodec-7-enyl, (Z)-tetradec-7-enyl, (Z)-hexadec-4-enyl, (Z)-hexadec-7-enyl, (E)-hexadec-7-enyl, (Z)-hexadec-9-enyl, (7Z,10Z)-hexadeca-7,10-dienyl, (7Z,10Z,13Z)-hexadeca-7,10,13-trienyl, (Z)-octadec-9-enyl or (9Z,12Z)-octadeca-9,12-dienyl, more preferably (Z)-tetradec-7-enyl, (Z)-hexadec-7-enyl, (7Z,10Z)-hexadeca-7,10-dienyl or (9Z,12Z)-octadeca-9,12-dienyl, further preferably are the same and (Z)-tetradec-7-enyl, (Z)-hexadec-7-enyl, (7Z,10Z)-hexadeca-7,10-dienyl or (9Z,12Z)-octadeca-9,12-dienyl.

When each of $L^{101}$ and $L^{102}$ is a hydrogen atom, $X^{101}$ is more preferably a hydrogen atom, methyl, pyrrolidin-3-yl, piperidin-3-yl, piperidin-4-yl, or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl, further preferably a hydrogen atom, methyl, or C1-C6 alkyl or C3-C6 alkenyl substituted with one to three same or different substituents selected from amino, hydroxy and carbamoyl, still further preferably a hydrogen atom, methyl or the like.

When $L^{101}$ and $L^{102}$ together form a single bond or GI-GS alkylene, $R^{101}$ and $R^{102}$ are the same or different and are each preferably tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, or (11Z,14Z)-icosa-11,14-dienyl, more preferably (Z)-octadec-9-enyl or (9Z,12Z)-octadeca-9,12-dienyl, further preferably are the same and (Z)-octadec-9-enyl or (9Z,12Z)-octadeca-9,12-dienyl.

When $L^{101}$ and $L^{102}$ together form a single bond or GI-GS alkylene, $X^{101}$ is more preferably a hydrogen atom, methyl, pyrrolidin-3-yl, piperidin-3-yl, piperidin-4-yl, or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl, further preferably a hydrogen atom, methyl, or C1-C6 alkyl or C3-C6 alkenyl substituted with one to three same or different substituents selected from amino, hydroxy and carbamoyl, most preferably a hydrogen atom, methyl or the like.

In another more preferred mode of the present invention, when $L^{101}$ and $L^{102}$ together form a single bond, $L^{103}$ is —CO— or —CO—O—, preferably —CO—. In this case, $X^{101}$ is preferably aminomethyl, 1,2-diaminoethyl, 2-aminoethyl, 1,3-diaminopropyl, 1,4-diaminobutyl, 1,5-diaminopentyl, 3-aminopropyl, 4-aminobutyl, 5-aminopentyl or the like, more preferably 1,2-diaminoethyl, 1,3-diaminopropyl, 1,4-diaminobutyl or 1,5-diaminopentyl. $R^{101}$ and $R^{102}$ are the same or different and are each preferably tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl or (11Z,14Z)-icosa-11,14-dienyl, more preferably (Z)-octadec-9-enyl or (9Z,12Z)-octadeca-9,12-dienyl, further preferably are the same and (Z)-octadec-9-enyl or (9Z,12Z)-octadeca-9,12-dienyl.

$L^{103}$ is more preferably a single bond.

When $L^{103}$ is a single bond, $X^{101}$ is more preferably a hydrogen atom, methyl, pyrrolidin-3-yl, piperidin-3-yl, piperidin-4-yl, or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl, or the like, further preferably a hydrogen atom, methyl, hydroxymethyl, 2-hydroxyethyl, 2,3-dihydroxypropyl, 2-hydroxypropyl, 3-hydroxypropyl, 2-hydroxy-3-methoxypropyl, aminomethyl, 2-aminoethyl, 3-aminopropyl, 4-aminobutyl, 5-aminopentyl, 2-(N,N-dimethylamino)ethyl, 3-(N,N-dimethylamino)propyl, 2-carbamoylethyl, 2-dimethylcarbamoylethyl, 1-methylpiperidin-4-yl or the like, most preferably a hydrogen atom or methyl.

When $L^{103}$ is —CO— or —CO—O—, more preferably, $X^{101}$ is pyrrolidin-3-yl, piperidin-3-yl, piperidin-4-yl, or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl, and at least one of the substituents is amino, monoalkylamino, dialkylamino, trialkylammonio, pyrrolidinyl, piperidyl, morpholinyl or the like. $R^3$ is further preferably aminomethyl, 1,2-diaminoethyl, 2-aminoethyl, 1,3-diaminopropyl, 3-aminopropyl, 1,4-diaminobutyl, 4-aminobutyl, 1,5-diaminopentyl, 5-aminopentyl, (N,N-dimethylamino)methyl, 2-(N,N-dimethylamino)ethyl, 3-(N,N-dimethylamino)propyl, 1-hydroxy-2-aminoethyl, 1-amino-2-hydroxyethyl or the like, most preferably 1,2-diaminoethyl, 2-aminoethyl, 1,3-diaminopropyl, 3-aminopropyl, 1,4-diaminobutyl, 4-aminobutyl, 1,5-diaminopentyl, 5-aminopentyl or the like.

In an alternative more preferred mode of the present invention, $L^{103}$ is a single bond, and $X^{101}$ is a hydrogen atom. In this case, $R^{101}$ and $R^{102}$ are the same or different and are each preferably dodecyl, tetradecyl, (Z)-dodec-7-enyl, (Z)-tetradec-7-enyl, (Z)-hexadec-4-enyl, (Z)-hexadec-7-enyl, (E)-hexadec-7-enyl, (Z)-hexadec-9-enyl, (7Z,10Z)-hexadeca-7,10-dienyl, (7Z,10Z,13Z)-hexadeca-7,10,13-trienyl, (Z)-octadec-9-enyl or (9Z,12Z)-octadeca-9,12-dienyl, more preferably are the same or different and are each (Z)-tetradec-7-enyl or (7Z,10Z)-hexadeca-7,10-dienyl, further preferably are the same and (Z)-tetradec-7-enyl, (Z)-hexadec-7-enyl or (7Z,10Z)-hexadeca-7,10-dienyl.

In an alternative more preferred mode of the present invention, $L^{103}$ is a single bond, and $X^{101}$ is methyl. In this case, $R^{101}$ and $R^{102}$ are the same or different and are each preferably dodecyl, tetradecyl, (Z)-dodec-7-enyl, (Z)-tetradec-7-enyl, (Z)-hexadec-4-enyl, (Z)-hexadec-7-enyl, (E)-hexadec-7-enyl, (Z)-hexadec-9-enyl, (7Z,10Z)-hexadeca-7,10-dienyl, (7Z,10Z,13Z)-hexadeca-7,10,13-trienyl, (Z)-octadec-9-enyl or (9Z,12Z)-octadeca-9,12-dienyl, more preferably are the same or different and are each (Z)-tetradec-7-enyl, (7Z,10Z)-hexadeca-7,10-dienyl or (9Z,12Z)-octadeca-9,12-dienyl, further preferably are the same and (Z)-tetradec-7-enyl, (7Z,10Z)-hexadeca-7,10-dienyl or (9Z,12Z)-octadeca-9,12-dienyl.

In the definition of each group in formula (CL-II), examples of the linear or branched C12-C24 alkyl include dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadecan-2-yl, nonadecyl, 2,6,10,14-tetramethylpentadecyl, icosyl, 3,7,11,15-tetramethylhexadecyl, henicosyl, docosyl, tricosyl and tetracosyl, preferably dodecyl, tridecyl, tetradecyl, pentadecyl, hexadecyl, heptadecyl, octadecyl, nonadecyl and icosyl, more preferably dodecyl, tridecyl, tetradecyl, pentadecyl, hexadecyl, heptadecyl and octadecyl.

The linear or branched C12-C24 alkenyl can be linear or branched C12-C24 alkenyl containing one to three double bonds. Examples thereof include (Z)-tridec-8-enyl, (Z)-tetradec-9-enyl, (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (E)-heptadec-8-enyl, (E)-octadec-9-enyl, (Z)-heptadec-10-enyl, (Z)-octadec-11-enyl, (8Z,11Z)-heptadeca-8,11-dienyl, (9Z,12Z)-octadeca-9,12-dienyl, (8Z,11Z,14Z)-octadeca-8,11,14-trienyl, (9Z,12Z,15Z)-octadeca-9,12,15-trienyl, (Z)-nonadec-10-enyl, (Z)-icos-11-enyl, (10Z,13Z)-nonadeca-10,13-dienyl, (11Z,14Z)-icosa-11,14-dienyl, 2,6,10-trimethylundeca-1,5,9-trienyl, 3,7,11-trimethyldodeca-2,6,10-trienyl, 2,6,10,14-tetramethylpentadec-1-enyl and 3,7,11,15-tetramethylhexadec-2-enyl, preferably (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (8Z,11Z)-heptadeca-8,11-dienyl and (9Z,12Z)-octadeca-9,12-dienyl, more preferably (Z)-heptadec-8-enyl, (Z)-octadec-9-enyl, (8Z,11Z)-heptadeca-8,11-dienyl and (9Z,12Z)-octadeca-9,12-dienyl.

The linear or branched C12-C24 alkynyl can be linear or branched C12-C24 alkynyl containing one to three triple bonds. Examples thereof include dodec-11-ynyl, tridec-12-ynyl, pentadec-6-ynyl, hexadec-7-ynyl, pentadeca-4,6-diynyl, hexadeca-5,7-diynyl, heptadec-8-ynyl and octadec-9-ynyl, preferably pentadec-6-ynyl, hexadec-7-ynyl, pentadeca-4,6-diynyl, hexadeca-5,7-diynyl, heptadec-8-ynyl and octadec-9-ynyl, more preferably heptadec-8-ynyl and octadec-9-ynyl.

In the definition of each group in formula (CL-II), the C1-C3 alkylene, the C1-C6 alkyl and the C3-C6 alkenyl are each as defined above in formula (CL-I).

The monoalkylamino, the dialkylamino, the trialkylammonio, the alkoxy, the monoalkylcarbamoyl and the dialkylcarbamoyl are each as defined above in formula (CL-I).

$R^{103}$ and $R^{104}$ are preferably the same linear or branched C12-C24 alkyl, C12-C24 alkenyl or C12-C24 alkynyl, more preferably the same linear or branched C12-C24 alkyl or C12-C24 alkenyl.

$L^{104}$ and $L^{105}$ are more preferably the same and —O—, —CO—O— or —O—CO—.

When at least one of $L^{104}$ and $L^{105}$ is —O— or —O—CO—, $R^{103}$ and $R^{104}$ are the same or different and are each more preferably dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl or 3,7,11,15-tetramethylhexadec-2-enyl, further preferably tetradecyl, hexadecyl, octadecyl, (Z)-hexadec-9-enyl, (Z)-octadec-6-enyl, (Z)-octadec-9-enyl or (9Z,12Z)-octadeca-9,12-dienyl.

When at least one of $L^{104}$ and $L^{105}$ is —CO—O—, each of $R^{103}$ and $R^{104}$ is more preferably tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-octadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl or 2,6,10,14-tetramethylpentadec-1-enyl, further preferably tridecyl, pentadecyl, heptadecyl, (Z)-pentadec-8-enyl, (Z)-heptadec-5-enyl, (Z)-heptadec-8-enyl or (8Z,11Z)-heptadeca-8,11-dienyl.

$p^{101}$ and $p^{102}$ are more preferably 0 or 1 at the same time.

$L^{106}$ and $L^{107}$ more preferably together form a single bond or C1-C3 alkylene. When $L^{106}$ and $L^{107}$ together form a single bond or C1-C3 alkylene, $X^{102}$ is more preferably a hydrogen atom, methyl, pyrrolidin-2-yl, pyrrolidin-3-yl, piperidin-2-yl, piperidin-3-yl, piperidin-4-yl, morpholin-2-yl, morpholin-3-yl, or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl, further preferably a hydrogen atom, methyl, or C1-C6 alkyl or C3-C6 alkenyl substituted with one to three same or different substituents selected from amino, trialkylammonio, hydroxy and carbamoyl, most preferably a hydrogen atom, methyl, 2,3-dihydroxypropyl, 3-hydroxypropyl, aminomethyl, 1,2-diaminoethyl, 2-aminoethyl, 1,3-diaminopropyl, 1,4-diaminobutyl, 1,5-diaminopentyl, 3-aminopropyl, 4-aminobutyl, 5-aminopentyl or 2-carbamoylethyl. Among these substituents, the alkyl moiety in monoalkylamino, dialkylamino, trialkylammonio, alkoxy, monoalkylcarbamoyl and dialkylcarbamoyl is as defined in the C1-C4 alkyl. Two or three alkyl moieties in dialkylamino, trialkylammonio and dialkylcarbamoyl are the same as or different from each other.

When $L^{106}$ and $L^{107}$ together form a single bond, $L^{108}$ is —CO— or —CO—O—, preferably —CO—.

When $L^{106}$ and $L^{107}$ together form a single bond, $p^{101}$ and $p^{102}$ are the same or different and are each preferably 1 to 3.

When each of $L^{106}$ and $L^{107}$ is a hydrogen atom, $X^{102}$ is preferably a hydrogen atom, methyl, pyrrolidin-2-yl, pyrrolidin-3-yl, piperidin-2-yl, piperidin-3-yl, piperidin-4-yl, morpholin-2-yl, morpholin-3-yl or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl, more preferably a hydrogen atom, methyl or C1-C6 alkyl or C3-C6 alkenyl substituted with one to three same or different substituents selected from amino, trialkylammonio, hydroxy and carbamoyl, further preferably a hydrogen atom, methyl, 2,3-dihydroxypropyl, 3-hydroxypropyl, aminomethyl, 1,2-diaminoethyl, 2-aminoethyl, 1,3-diaminopropyl, 1,4-diaminobutyl, 1,5-diaminopentyl, 3-aminopropyl, 4-aminobutyl, 5-aminopentyl, 2-carbamoylethyl or the like. Among these substituents, the alkyl moiety in monoalkylamino, dialkylamino, trialkylammonio, alkoxy, monoalkylcarbamoyl and dialkylcarbamoyl is as defined in the C1-C4 alkyl. Two or three alkyl moieties in dialkylamino, trialkylammonio, and dialkylcarbamoyl are the same as or different from each other.

$L^{108}$ is preferably a single bond. When $L^{108}$ is a single bond, each of $L^{104}$ and $L^{105}$ is preferably —O—.

When $L^{108}$ is a single bond, $X^{102}$ is preferably a hydrogen atom, methyl, pyrrolidin-3-yl, piperidin-3-yl, piperidin-4-yl or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl, or the like, more preferably a hydrogen atom, methyl, hydroxymethyl, 2-hydroxyethyl, 2,3-dihydroxypropyl, 2-hydroxypropyl, 3-hydroxypropyl, 2-hydroxy-3-methoxypropyl, aminomethyl, 2-aminoethyl, 3-aminopropyl, 4-aminobutyl, 5-aminopentyl, 2-(N,N-dimethylamino)ethyl, 3-(N,N-dimethylamino)propyl, 2-carbamoylethyl, 2-dimethylcarbamoylethyl, 1-methylpiperidin-4-yl or the like, further preferably a hydrogen atom, methyl, 2,3-dihydroxypropyl, 3-hydroxypropyl, 2-aminoethyl, 3-aminopropyl, 4-aminobutyl, 5-aminopentyl, 2-carbamoylethyl or the like. Among these substituents, the alkyl moiety in monoalkylamino, dialkylamino, trialkylammonio, alkoxy, monoalkylcarbamoyl and dialkylcarbamoyl is as defined in the C1-C4 alkyl. Two or three alkyl moieties in dialkylamino, trialkylammonio, and dialkylcarbamoyl are the same as or different from each other.

Each of $L^{104}$ and $L^{105}$ is more preferably —O—. However, when $L^{108}$ is a single bond and $X^{102}$ is a hydrogen atom, $L^{104}$ and $L^{105}$ are preferably the same and —CO—O— or —O—CO—, more preferably —CO—O—.

When $L^{108}$ is —CO— or —CO—O—, $L^{104}$ and $L^{105}$ are preferably the same and —CO—O— or —O—CO—, more preferably —CO—O—.

When $L^{108}$ is —CO— or —CO—O—, $X^{102}$ is preferably pyrrolidin-3-yl, piperidin-3-yl, piperidin-4-yl or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl, and at least one of the substituents is preferably amino, monoalkylamino, dialkylamino, trialkylammonio, pyrrolidinyl, piperidyl or morpholinyl. $X^{102}$ is more preferably aminomethyl, 1,2-diaminoethyl, 2-aminoethyl, 1,3-diaminopropyl, 3-aminopropyl, 1,4-diaminobutyl, 4-aminobutyl, 1,5-diaminopentyl, 5-aminopentyl, (N,N-dimethylamino)methyl, 2-(N,N-dimethylamino)ethyl, 3-(N,N-dimethylamino)propyl, 1-amino-2-hydroxyethyl or the like, further preferably aminomethyl, 1,2-diaminoethyl, 2-aminoethyl, 1,3-diaminopropyl, 3-aminopropyl, 1,4-diaminobutyl, 4-aminobutyl, 1,5-diaminopentyl, 5-aminopentyl or the like. Among these substituents, the alkyl moiety in monoalkylamino, dialkylamino, trialkylammonio, alkoxy, monoalkylcarbamoyl and dialkylcarbamoyl is as defined in the C1-C6 alkyl. Two or three alkyl moieties in dialkylamino, trialkylammonio and dialkylcarbamoyl are the same as or different from each other.

$L^{104}$ and $L^{105}$ are preferably the same and —CO—O— or —O—CO—, more preferably —CO—O—.

In the definition of each group in formulas (CL-III), (CL-IV) and (CL-V), the linear or branched C8-C24 alkyl, C8-C24 alkenyl and C8-C24 alkynyl are each as defined above in formulas (I) to (IV), and the same groups as those described therein are preferred.

In the definition of each group in formulas (CL-III), (CL-IV) and (CL-V), examples of the alkyl moiety in C8-C24 alkyloxyethyl and C8-C24 alkyloxypropyl include those listed about the linear or branched C8-C24 alkyl.

Examples of the alkynyl moiety in alkynyloxyethyl and alkynyloxypropyl include those listed about the linear or branched C8-C24 alkynyl.

$R^{105}$ and $R^{106}$ are preferably the same or different and are each linear or branched C8-C24 alkyl or C8-C24 alkenyl, more preferably are the same or different and are each linear or branched C8-C24 alkenyl, further preferably are the same or different and are each linear C8-C24 alkenyl. Also, $R^{105}$ and $R^{106}$ are more preferably the same. In this case, linear or branched C12-C24 alkyl, C12-C24 alkenyl or C12-C24 alkynyl is preferred, and linear C12-C24 alkenyl is more preferred. The linear or branched C12-C24 alkyl, C12-C24 alkenyl and C12-C24 alkynyl are each as defined above in formula (CL-II).

$R^{105}$ and $R^{106}$ are preferably the same or different and are each linear or branched C8-C24 alkyl or C8-C24 alkenyl, more preferably are the same or different and are each linear or branched C8-C24 alkenyl, further preferably are the same or different and are each linear C8-C24 alkenyl. Also, $R^{105}$ and $R^{106}$ are more preferably the same. In this, case, linear or branched C15-C20 alkyl, C15-C20 alkenyl or C15-C20 alkynyl is preferred, and linear C15-C20 alkenyl is more preferred. The linear or branched C15-C20 alkyl, C15-C20 alkenyl and C15-C20 alkynyl are each as defined above in formulas (I) to (IV), and the same groups as those described therein are preferred.

When $R^{105}$ and $R^{106}$ are different, preferably, $R^{105}$ is linear or branched C15-C20 alkyl, C15-C20 alkenyl or C15-C20 alkynyl, and $R^{106}$ is linear or branched C8-C12 alkyl. In this context, examples of the linear or branched C8-C12 alkyl include octyl, nonyl, decyl, undecyl and dodecyl, preferably octyl, decyl and dodecyl.

More preferably, $R^{105}$ is linear C15-C20 alkenyl, and $R^{106}$ is linear C8-C12 alkyl. Further preferably, $R^{105}$ is (Z)-octadec-9-enyl or (9Z,12Z)-octadeca-9,12-dienyl, and $R^{106}$ is octyl, decyl or dodecyl.

When $R^{105}$ and $R^{106}$ are different, also preferably, $R^{105}$ is linear or branched C8-C24 alkyl, C8-C24 alkenyl or C8-C24 alkynyl, and $R^{106}$ is C8-C24 alkyloxyethyl, C8-C24 alkyloxypropyl, C8-C24 alkenyloxyethyl, C8-C24 alkenyloxypropyl, C8-C24 alkynyloxyethyl or C8-C24 alkynyloxypropyl. In this case, more preferably, $R^{105}$ is linear C8-C24 alkenyl, and $R^{106}$ is C8-C24 alkenyloxyethyl. Further preferably, $R^{105}$ is (Z)-octadec-9-enyl, (9Z,12Z)-octadeca-9,12-dienyl or (11Z,14Z)-icosa-11,14-dienyl, and $R^{106}$ is (Z)-octadec-9-enyloxyethyl, (9Z,12Z)-octadeca-9,12-dienyloxyethyl or (11Z,14Z)-icosa-11,14-dienyloxyethyl. Most preferably, $R^{105}$ is (9Z,12Z)-octadeca-9,12-dienyl, and $R^{106}$ is (9Z,12Z)-octadeca-9,12-dienyloxyethyl.

When $R^{105}$ and $R^{106}$ are the same or different and are each linear or branched C8-C24 alkyl or C8-C24 alkenyl, $R^{105}$ and $R^{106}$ are preferably the same or different and are each tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl or (Z)-docos-13-enyl, more preferably are the same or different and are each hexadecyl, (Z)-hexadec-9-enyl, (Z)-octadec-6-enyl, (Z)-octadec-9-enyl, (9Z,12Z)-octadeca-9,12-dienyl, (Z)-icos-11-enyl or (11Z,14Z)-icosa-11,14-dienyl, further preferably are the same or different and are each (Z)-octadec-9-enyl, (9Z,12Z)-octadeca-9,12-dienyl or (11Z,14Z)-icosa-11,14-dienyl, most preferably are the same and (9Z,12Z)-octadeca-9,12-dienyl.

Preferably, $R^{107}$ is as defined above in $R^{105}$, and $R^{107}$ is preferably the same group as in $R^{105}$. $R^{108}$ is preferably linear C8-C24 alkyloxyethyl, C8-C24 alkyloxypropyl, C8-C24 alkenyloxyethyl, C8-C24 alkenyloxypropyl, C8-C24 alkynyloxyethyl, C8-C24 alkynyloxypropyl, C8-C24 alkyloxyethoxyethyl, C8-C24 alkenyloxyethoxyethyl or C8-C24 alkynyloxyethoxyethyl, more preferably linear C8-C24 alkyloxyethyl, C8-C24 alkenyloxyethyl or C8-C24 alkynyloxyethyl. Most preferably, $R^{107}$ is linear C15-C20 alkenyl, and $R^{108}$ is C8-C24 alkenyloxyethyl.

Preferably, $R^{109}$ and $R^{110}$ are as defined above in $R^{105}$ and $R^{106}$, respectively, and preferably the same groups as in $R^{109}$ and $R^{110}$ described above. However, $R^{109}$ and $R^{110}$ are preferably the same linear or branched C15-C20 alkyl, C15-C20 alkenyl or C15-C20 alkynyl, more preferably are the same and (9Z,12Z)-octadeca-9,12-dienyl.

Examples of the C1-C3 alkyl represented by $X^{103}$ and $X^{104}$ include methyl, ethyl, propyl, isopropyl and cyclopropyl, preferably methyl and ethyl, more preferably methyl.

Examples of the C2-C8 alkylene together formed by $X^{103}$ and $X^{104}$ include ethylene, propylene, butylene, pentylene, hexylene, heptylene and octylene, preferably butylene, pentylene and hexylene, more preferably hexylene.

Examples of the C2-C8 alkylene formed by $X^{103}$ together with $L^{111}$ include ethylene, propylene, butylene, pentylene, hexylene, heptylene and octylene, preferably propylene, butylene and pentylene, more preferably propylene and butylene, further preferably propylene.

Preferably, $X^{103}$ and $X^{104}$ are the same or different and are each methyl or ethyl, or together form butylene, pentylene or hexylene, or $X^{103}$ forms ethylene, propylene or butylene together with $L^{111}$. Preferably, $X^{103}$ and $X^{104}$ are the same or different and are each methyl or ethyl, or together form butylene, pentylene or hexylene. Also preferably, $X^{103}$ forms ethylene, propylene or butylene together with $L^{111}$, and $X^{104}$ is methyl or ethyl. More preferably, $X^{103}$ and $X^{104}$ are the same and methyl, or together form hexylene. Also more preferably, $X^{103}$ forms propylene or butylene together with $L^{111}$, and $X^{104}$ is methyl.

The C1-C6 alkyl, the C3-C6 alkenyl, the monoalkylamino, the alkoxy, the monoalkylcarbamoyl and the di alkyl carbamoyl represented by $L^{111}$ are each as defined above in formula (CL-I).

Preferably, $L^{111}$ is a hydrogen atom, C1-C6 alkyl, amino, monoalkylamino, hydroxy, alkoxy or C1-C6 alkyl substituted with one to three same or different substituents selected from amino, monoalkylamino, hydroxy and alkoxy, or forms C2-C6 alkylene together with $X^{103}$. More preferably, $L^{111}$ is a hydrogen atom, methyl, amino, methylamino, hydroxy, methoxy or methyl substituted with one to three same or different substituents selected from amino and hydroxy, or forms ethylene, propylene or butylene together with $X^{103}$. Further preferably, $L^{111}$ is a hydrogen atom, C1-C3 alkyl, or hydroxy, or forms propylene or butylene together with $X^{103}$. Most preferably, $L^{111}$ is a hydrogen atom or forms propylene together with $X^{103}$.

Examples of the C1-C6 alkylene represented by $L^{109}$ and $L^{110}$ include methylene, ethylene, propylene, butylene, pentylene and hexylene, preferably methylene and ethylene.

$L^{109}$ is preferably methylene, ethylene, propylene or the like, more preferably methylene, ethylene or the like. $L^{110}$ is preferably a single bond, methylene, ethylene or the like, more preferably a single bond, methylene or the like. The sum of the numbers of carbon atoms of $L^{109}$ and $L^{110}$ is preferably 1 to 3, more preferably 2. In any of these cases, preferably, $X^{103}$ and $X^{104}$ are the same or different and are each methyl, ethyl or the like, and $L^{111}$ is a hydrogen atom, methyl, amino, methylamino, hydroxy, methoxy or methyl substituted with one to three same or different substituents selected from amino and hydroxy, or the like; $X^{103}$ and $X^{104}$ together form pentylene, hexylene, heptylene or the like, and $L^{111}$ is a hydrogen atom, methyl, amino, methylamino, hydroxy, methoxy or methyl substituted with one to three same or different substituents selected from amino and hydroxy, or the like; or $X^{103}$ forms propylene, butylene, pentylene or the like together with $L^{111}$, and $X^{104}$ is methyl, ethyl or the like. More preferably, each of $X^{103}$ and $X^{104}$ is methyl, and $L^{111}$ is a hydrogen atom; $X^{103}$ and $X^{104}$ together form pentylene or hexylene, and $L^{111}$ is a hydrogen atom; or $X^{103}$ forms propylene together with $L^{111}$, and $X^{104}$ is methyl or the like.

Examples of the C1-C4 alkyl represented by $X^{105}$ include methyl, ethyl, propyl, isopropyl, butyl and cyclobutyl, preferably methyl. $X^{105}$ is further preferably a hydrogen atom.

In the definition of each group in formula (CL-V), examples of the C1-C3 alkyl represented by $X^{105'}$ include methyl, ethyl, propyl, isopropyl and cyclopropyl, preferably methyl, ethyl and isopropyl, more preferably methyl and ethyl. $X^{105'}$ is further preferably a hydrogen atom, methyl or the like, most preferably a hydrogen atom.

Examples of the C1-C3 alkylene represented by $L^{112}$ include methylene, ethylene and propylene, preferably methylene and ethylene.

In the definition of each group in formulas (CL-VI) and (CL-VII), the optionally substituted linear or branched C8-C24 alkyl, C8-C24 alkenyl and C8-C24 alkynyl are each as defined above in formulas (I) to (V″).

Examples of the C1-C4 alkyl in the optionally substituted C1-C4 alkyl represented by $R^{115}$ in formula (CL-VII) include methyl, ethyl, propyl, isopropyl, cyclopropyl, butyl, isobutyl, sec-butyl, tert-butyl, cyclobutyl and cyclopropylmethyl, preferably methyl and ethyl, more preferably methyl.

The alkyl moiety in the optionally substituted C1-C4 alkoxy is as defined in the C1-C4 alkyl.

Examples of the substituent for the optionally substituted C1-C4 alkyl include amino, monoalkylamino, dialkylamino, pyrrolidin-2-yl, pyrrolidin-3-yl, piperidin-2-yl, piperidin-3-yl, piperidin-4-yl, morpholin-2-yl, morpholin-3-yl, hydroxy, alkoxy, alkoxycarbonyl, hydroxycarbonyl, carbamoyl, monoalkylcarbamoyl, dialkylcarbamoyl, nitro, cyano, fluoro, chloro and bromo. Among these substituents, the alkyl moiety in monoalkylamino, dialkylamino, alkoxy, alkoxycarbonyl, monoalkylcarbamoyl and dialkylcarbamoyl is as defined in the C1-C4 alkyl. Two alkyl moieties in dialkylamino and dialkylcarbamoyl may be the same as or different from each other.

Examples of the acyl in the optionally substituted C1-C4 acyloxy include formyl, acetyl, propanoyl, 2-methylpropanoyl, cyclopropanoyl and butanoyl, preferably acetyl.

Examples of the substituent for the optionally substituted C1-C4 acyloxy include amino, monoalkylamino, dialkylamino, pyrrolidin-2-yl, pyrrolidin-3-yl, piperidin-2-yl, piperidin-3-yl, piperidin-4-yl, morpholin-2-yl, morpholin-3-yl, hydroxy, alkoxy, alkoxycarbonyl, hydroxycarbonyl, carbamoyl, monoalkylcarbamoyl, dialkylcarbamoyl, nitro, cyano, fluoro, chloro and bromo. Among these substituents, the alkyl moiety in monoalkylamino, dialkylamino, alkoxy, alkoxycarbonyl, monoalkylcarbamoyl and dialkylcarbamoyl is as defined in the C1-C4 alkyl. Two alkyl moieties in dialkylamino and dialkylcarbamoyl may be the same as or different from each other.

In formula (CL-VI), $R^{111}$ and $R^{112}$ are preferably the same linear or branched C8-C24 alkyl, C8-C24 alkenyl or C8-C24 alkynyl, more preferably the same linear or branched C8-C24 alkyl or C8-C24 alkenyl.

$R^{111}$ and $R^{112}$ are preferably the same or different and are each octyl, decyl, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl, 3,7,11,15-tetramethylhexadec-2-enyl or the like, more preferably are the same or different and are each dodecyl, tetradecyl, (Z)-hexadec-9-enyl, (Z)-octadec-6-enyl, (Z)-octadec-9-enyl, (9Z,12Z)-octadeca-9,12-dienyl or the like, further preferably are the same and (Z)-hexadec-9-enyl, (Z)-octadec-6-enyl, (Z)-octadec-9-enyl, (9Z,12Z)-octadeca-9,12-dienyl or the like.

$X^{106}$ and $X^{107}$ are preferably the same or different and are each methyl or ethyl, more preferably are the same and methyl.

Examples of the C2-C8 alkylene together formed by $X^{106}$ and $X^{107}$ include ethylene, propylene, butylene, pentylene, hexylene, heptylene and octylene, preferably butylene, pentylene and hexylene, more preferably butylene and pentylene.

Preferably, $X^{106}$ and $X^{107}$ are the same and methyl, or together form butylene, pentylene or hexylene.

$p^{103}$ and $p^{104}$ are preferably 0 at the same time, and $p^{105}$ is preferably 1.

$L^{113}$ and $L^{114}$ are preferably 0 at the same time.

In formula (CL-VII), $R^{113}$ and $R^{114}$ are preferably the same linear or branched C8-C24 alkyl, C8-C24 alkenyl or C8-C24 alkynyl, more preferably the same linear or branched C8-C24 alkyl or C8-C24 alkenyl.

The C1-C3 alkyl and the C2-C8 alkylene represented by $X^{109}$ and $X^{110}$ are each as defined above in formula (CL-VI).

$R^{115}$ is preferably a hydrogen atom, hydroxy, methyl, methoxy or the like, more preferably a hydrogen atom, hydroxy or the like, further preferably a hydrogen atom.

$L^{115}$ is preferably —O—CO— or —NH—CO—. In this case, preferably, $p^{106}$ is 0 or 1, and $p^{107}$ is an integer from 1 to 3. More preferably, $p^{106}$ is 0, and $p^{107}$ is 1 or 3.

When $L^{115}$ is —CO—O—, preferably, $p^{106}$ is 0, and $p^{107}$ is an integer from 2 to 4. More preferably, $p^{106}$ is 0, and $p^{107}$ is 3.

When $L^{115}$ is —CO—NH—, preferably, $p^{106}$ is 0, and $p^{107}$ is an integer from 2 to 4. More preferably, $p^{106}$ is 0, and $p^{107}$ is 3.

Each group in formulas (CL-VIII) to (CL-XIX) may be as defined in formulas (I) to (V″), or may be as defined in formulas (CL-I) to (CL-VIII).

In formula (CL-XVIII), $R^{137}$ and $R^{138}$ are the same or different and are each linear or branched C8-C24 alkyl, C8-C24 alkenyl, C8-C24 alkynyl, C8-C24 alkylthioethyl, C8-24 alkenylthioethyl or C8-C24 alkynylthioethyl.

Examples of the linear or branched C8-C24 alkyl represented by $R^{137}$ and $R^{138}$ include heptyl, octyl, nonyl, decyl, undecyl, dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadecan-2-yl, nonadecyl, 2,6,10,14-tetramethylpentadecyl, icosyl, 3,7,11,15-tetramethylhexadecyl, henicosyl, docosyl, tricosyl and tetracosyl.

The linear or branched C8-C24 alkenyl represented by $R^{137}$ and $R^{138}$ can be linear or branched C8-24 alkenyl containing one to three double bonds. Examples thereof include (Z)-tridec-8-enyl, (Z)-tetradec-9-enyl, (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (E)-heptadec-8-enyl, (E)-octadec-9-enyl, (Z)-heptadec-10-enyl, (Z)-octadec-11-enyl, (8Z,11Z)-heptadeca-8,11-dienyl, (9Z,12Z)-octadeca-9,12-dienyl, (8Z,11Z,14Z)-octadeca-8,11,14-trienyl, (9Z,12Z,15Z)-octadeca-9,12,15-trienyl, (Z)-nonadec-10-enyl, (Z)-icos-11-enyl, (10Z,13Z)-nonadeca-10,13-dienyl, (11Z,14Z)-icosa-11,14-dienyl, 2,6,10-trimethylundeca-1,5,9-trienyl, 3,7,11-trimethyldodeca-2,6,10-trienyl, 2,6,10,14-tetramethylpentadec-1-enyl and 3,7,11,15-tetramethylhexadec-2-enyl, preferably (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (8Z,11Z)-heptadeca-8,11-dienyl and (9Z,12Z)-octadeca-9,12-dienyl, more preferably (Z)-heptadec-8-enyl, (Z)-octadec-9-enyl, (8Z,11Z)-heptadeca-8,11-dienyl and (9Z,12Z)-octadeca-9,12-dienyl.

The linear or branched C8-C24 alkynyl represented by $R^{137}$ and $R^{138}$ can be linear or branched C8-24 alkynyl containing one to three triple bonds. Examples thereof include dodec-11-ynyl, tridec-12-ynyl, pentadec-6-ynyl, hexadec-7-ynyl, pentadeca-4,6-diynyl, hexadeca-5,7-diynyl, heptadec-8-ynyl and octadec-9-ynyl, preferably pentadec-6-ynyl, hexadec-7-ynyl, pentadeca-4,6-diynyl, hexadeca-5,7-diynyl, heptadec-8-ynyl and octadec-9-ynyl, more preferably heptadec-8-ynyl and octadec-9-ynyl.

Examples of the C8-C24 alkyl, the C8-24 alkenyl and the C8-C24 alkynyl contained in the C8-C24 alkylthioethyl, the C8-24 alkenylthioethyl and the C8-C24 alkynylthioethyl represented by $R^{137}$ and $R^{138}$ can include the same groups as those of the aforementioned C8-C24 alkyl, C8-24 alkenyl and C8-C24 alkynyl, respectively.

Examples of the C1-C3 alkyl represented by $X^{135}$ include methyl, ethyl, n-propyl and isopropyl.

Examples of the hydroxy C2-C4 alkyl represented by $X^{135}$ include hydroxyethyl, hydroxypropyl and hydroxybutyl. The position of substitution with the hydroxy group is arbitrary.

Examples of the C1 to C3 alkyl represented by $X^{136}$, $X^{137}$, $X^{138}$, $X^{139}$, $X^{140}$ and $X^{141}$ include methyl, ethyl, n-propyl and isopropyl.

Examples of the C3-C6 nitrogen-containing hetero ring that may be formed by $X^{136}$ and $X^{137}$, $X^{138}$ and $X^{139}$, or $X^{140}$ and $X^{141}$ include pyrrolidine, piperidine, morpholine and azepane.

$R^{139}$ and $R^{140}$ in formula (CL-XIX) are the same or different and are each linear or branched C8-C24 alkyl, C8-C24 alkenyl or C8-C24 alkynyl.

Examples of the linear or branched C8-C24 alkyl represented by $R^{139}$ and $R^{140}$ include heptyl, octyl, nonyl, decyl, undecyl, dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadecan-2-yl, nonadecyl, 2,6,10,14-tetramethylpentadecyl, icosyl, 3,7,11,15-tetramethylhexadecyl, henicosyl, docosyl, tricosyl and tetracosyl.

The linear or branched C8-C24 alkenyl represented by $R^{139}$ and $R^{140}$ can be linear or branched C8-C24 alkenyl containing one to three double bonds. Examples thereof include (Z)-tridec-8-enyl, (Z)-tetradec-9-enyl, (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (E)-heptadec-8-enyl, (E)-octadec-9-enyl, (Z)-heptadec-10-enyl, (Z)-octadec-11-enyl, (8Z,11Z)-heptadeca-8,11-dienyl, (9Z,12Z)-octadeca-9,12-dienyl, (8Z,11Z,14Z)-octadeca-8,11,14-trienyl, (9Z,12Z,15Z)-octadeca-9,12,15-trienyl, (Z)-nonadec-10-enyl, (Z)-icos-11-enyl, (10Z,13Z)-nonadeca-10,13-dienyl, (11Z,14Z)-icosa-11,14-dienyl, 2,6,10-trimethylundeca-1,5,9-trienyl, 3,7,11-trimethyldodeca-2,6,10-trienyl, 2,6,10,14-tetramethylpentadec-1-enyl and 3,7,11,15-tetramethylhexadec-2-enyl, preferably (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (8Z,11Z)-heptadeca-8,11-dienyl and (9Z,12Z)-octadeca-9,12-dienyl, more preferably (Z)-heptadec-8-enyl, (Z)-octadec-9-enyl, (8Z,11Z)-heptadeca-8,11-dienyl and (9Z,12Z)-octadeca-9,12-dienyl.

The linear or branched C8-C24 alkynyl represented by $R^{139}$ and $R^{140}$ can be linear or branched C8-C24 alkynyl containing one to three triple bonds. Examples thereof include dodec-11-ynyl, tridec-12-ynyl, pentadec-6-ynyl, hexadec-7-ynyl, pentadeca-4,6-diynyl, hexadeca-5,7-diynyl, heptadec-8-ynyl and octadec-9-ynyl, preferably pentadec-6-ynyl, hexadec-7-ynyl, pentadeca-4,6-diynyl, hexadeca-5,7-diynyl, heptadec-8-ynyl and octadec-9-ynyl, more preferably heptadec-8-ynyl and octadec-9-ynyl.

Examples of the C1-C3 alkyl represented by $X^{146}$ include methyl, ethyl, n-propyl and isopropyl.

Examples of the hydroxy C2-C4 alkyl represented by $X^{146}$ include hydroxyethyl, hydroxypropyl and hydroxybutyl. The position of substitution with the hydroxy group is arbitrary.

Examples of the C1 to C3 alkyl represented by $X^{143}$, $X^{144}$, $X^{145}$ and $X^{146}$ include methyl, ethyl, n-propyl and isopropyl.

Examples of the C3-C6 nitrogen-containing hetero ring that may be formed by $X^{143}$ and $X^{144}$, or $X^{145}$ and $X^{146}$ include pyrrolidine, piperidine, morpholine and azepane.

Each group in formula (CL-VIII) may be a preferred form of the corresponding group described in WO 2016/002753; each group in formula (CL-X) may be a preferred form of the corresponding group described in WO 2009/129385; each group in formula (CL-XI) may be a preferred form of the corresponding group described in WO 2013/149140; each group in formula (CL-XII) may be a preferred form of the corresponding group described in WO 2009/129395; each group in formula (CL-XIII) may be a preferred form of the corresponding group described in WO 2013/059496; each group in formula (CL-XIV) may be a preferred form of the corresponding group described in WO 2011/149733; each group in formula (CL-XV) may be a preferred form of the corresponding group described in WO 2011/153493; each group in formula (CL-XVI) may be a preferred form of the corresponding group described in WO 2015/074085; and each group in formula (CL-XVII) may be a preferred form of the corresponding group described in WO 2013/064911.

$L^{118}$ and $L^{119}$ in formula (CL-IX) are the same or different and are each preferably linear or branched C8-C24 alkylene or C8-C24 alkenylene, more preferably linear or branched C8-C20 alkylene or C8-C20 alkenylene.

The C1-C6 alkyl, the heterocyclyl or the polyamine of $X^{117}$ and $X^{118}$ in formula (CL-X) may be substituted with one to three substituents selected from a halogen atom, R', OR', SR', ON, $CO_2R'$ and $CONR'_2$.

When $X^{117}$ and $X^{118}$ in formula (CL-X) form, together with the nitrogen to which they are bonded, a 4- to 7-membered monocyclic hetero ring optionally containing one or two additional heteroatoms selected from N, O and S in addition to the nitrogen, the monocyclic hetero ring may be substituted with one to three substituents selected from a halogen atom, R', OR', SR', ON, $CO_2R'$ and $CONR'_2$.

In this context, R' is a hydrogen atom or C1-C6 alkyl, and the C1-C6 alkyl represented by R' may be substituted with a halogen atom or OH.

$R^{120}$ and $R^{121}$ in formula (CL-X) are the same or different and are each preferably linear or branched C4-C24 alkyl or C4-C24 alkenyl, more preferably linear or branched C4-C20 alkyl or C4-C20 alkenyl.

The C4-C24 alkyl or the C4-C24 alkenyl may be substituted with one or more substituents selected from a halogen atom, R', OR', SR', CN, $CO_2R'$ and $CONR'_2$.

In this context, R' is a hydrogen atom or C1-C6 alkyl, and the C1-C6 alkyl represented by R' may be substituted with a halogen atom or OH.

When each of $X^{119}$ and $X^{120}$ in formula (CL-XI) is optionally substituted linear or branched C6-C20 acyl, a structure other than the carbonyl group in the C6-C20 acyl can be C5-C19 alkyl, C5-C19 alkenyl or C5-C19 alkynyl.

$R^{124}$ and $R^{125}$ in formula (CL-XII) are the same or different and are each preferably linear or branched C8-C24 alkyl or C8-C24 alkenyl, more preferably linear or branched C14-C20 alkyl or C14-C20 alkenyl.

The C1-C6 alkyl, the heterocyclyl or the polyamine of $X^{125}$ and $X^{126}$ in formula (CL-XIV) may be substituted with one to three substituents selected from a halogen atom, R', OR', SR', CN, $CO_2R'$ and $CONR'_2$.

When $X^{125}$ and $X^{126}$ in formula (CL-XIV) form, together with the nitrogen to which they are bonded, a 4- to 7-membered monocyclic hetero ring optionally containing one or two additional heteroatoms selected from N, O and S in addition to the nitrogen, the monocyclic hetero ring may be substituted with one to three substituents selected from a halogen atom, R', OR', SR', CN, $CO_2R'$ and $CONR'_2$.

In this context, R' is a hydrogen atom or C1-C6 alkyl, and the C1-C6 alkyl represented by R' may be substituted with a halogen atom or OH.

$R^{128}$ and $R^{129}$ in formula (CL-XIV) are the same or different and are each preferably linear or branched C4-C24 alkyl or C4-C24 alkenyl, more preferably linear or branched C4-C20 alkyl or C4-C20 alkenyl.

The C4-C24 alkyl or the C4-C24 alkenyl may be substituted with one or more substituents selected from a halogen atom, R', OR', SR', CN, $CO_2R'$ and $CONR'_2$.

In this context, R' is a hydrogen atom or C1-C6 alkyl, and the C1-C6 alkyl represented by R' may be substituted with a halogen atom or OH.

$R^{137}$ and $R^{138}$ in formula (CL-XVIII) are the same or different and are each linear or branched C8-C24 alkyl, C8-C24 alkenyl, C8-C24 alkynyl, C8-C24 alkylthioethyl, 08-24 alkenylthioethyl or C8-C24 alkynylthioethyl, preferably are the same or different and are each linear C8-C24 alkenyl.

$X^{135}$ is a hydrogen atom, C1-C3 alkyl, or hydroxy C2-C4 alkyl, formula (C), formula (D) or formula (E), preferably a hydrogen atom or formula (C) or formula (D), more preferably a hydrogen atom or formula (E), further preferably a hydrogen atom.

$R^{139}$ and $R^{140}$ in formula (CL-XIX) are the same or different and are each linear or branched C8-C24 alkyl, C8-C24 alkenyl or C8-C24 alkynyl, preferably are the same or different and are each linear C8-C24 alkenyl.

$L^{133}$ is S or O, preferably S.

$X^{142}$ is a hydrogen atom, C1-C3 alkyl, hydroxy C2-C4 alkyl, formula (F) or formula (G), preferably C1-C3 alkyl, further preferably methyl.

Lipid B in the nucleic acid-containing lipid nanoparticle of the present invention is preferably a lipid represented by formula (CL-I) or a lipid represented by formula (CL-II), more preferably a lipid represented by formula (CL-I).

Specific examples of lipid B used in the present invention will be shown below in Tables 1 to 15, though lipid B used in the present invention is not limited thereto.

TABLE 1

| Compound No. | Structural formula |
|---|---|
| CL-1 | (structure) |
| CL-2 | (structure) |
| CL-3 | (structure) |
| CL-4 | (structure) |
| CL-5 | (structure) |
| CL-6 | (structure) |
| CL-7 | (structure) |

TABLE 1-continued
| Compound No. | Structural formula |
|---|---|
| CL-8 |  |
TABLE 2
| Compound No. | Structural formula |
|---|---|
| CL-9 | |
| CL-10 | |
| CL-11 | |
| CL-12 | |
| CL-13 | |
| CL-14 | |
| CL-15 | |
| CL-16 | |
TABLE 3
| Compound No. | Structural formula |
|---|---|
| CL-17 | 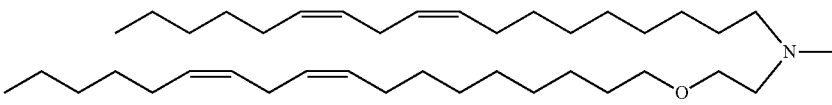 [SMILES: CCCCC/C=C\C/C=C\CCCCCCCCOCCN(C)CCCCCCCC/C=C\C/C=C\CCCCC] |

TABLE 3-continued

| Compound No. | Structural formula |
|---|---|
| CL-18 | |
| CL-19 | |
| CL-20 | |
| CL-21 | |
| CL-22 | |
| CL-23 | |
| CL-24 | |

TABLE 4

| Compound No. | Structural formula |
|---|---|
| CL-25 | |
| CL-26 | |
| CL-27 | |

TABLE 4-continued

| Compound No. | Structural formula |
| --- | --- |
| CL-28 | |
| CL-29 | |
| CL-30 | |
| CL-31 | |

TABLE 5

| Compound No. | Structural formula |
| --- | --- |
| CL-32 | |
| CL-33 | |
| CL-34 | |
| CL-35 | |
| CL-36 | |
| CL-37 | |
| CL-38 | |

TABLE 5-continued

| Compound No. | Structural formula |
| --- | --- |
| CL-39 | (structure) |

TABLE 6

| Compound No. | Structural formula |
| --- | --- |
| CL-40 | (structure) |
| CL-41 | (structure) |
| CL-42 | (structure) |
| CL-43 | (structure) |
| CL-44 | (structure) |
| CL-45 | (structure) |

TABLE 7

| Compound No. | Structural formula |
| --- | --- |
| CL-46 | (structure) |
| CL-47 | (structure) |
| CL-48 | (structure) |

TABLE 7-continued

| Compound No. | Structural formula |
|---|---|
| CL-49 | |
| CL-50 | |

TABLE 8

| Compound No. | Structural formula |
|---|---|
| CL-51 | |
| CL-52 | |
| CL-53 | |
| CL-54 | |

TABLE 9

| CL-55 | |
|---|---|
| CL-56 | |
| CL-57 | |
| CL 58 | |

TABLE 9-continued
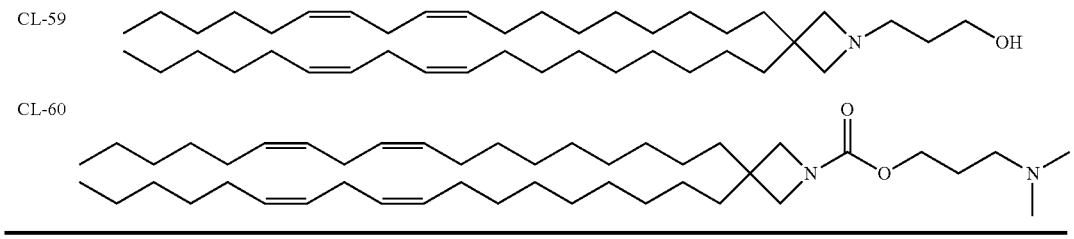
TABLE 10
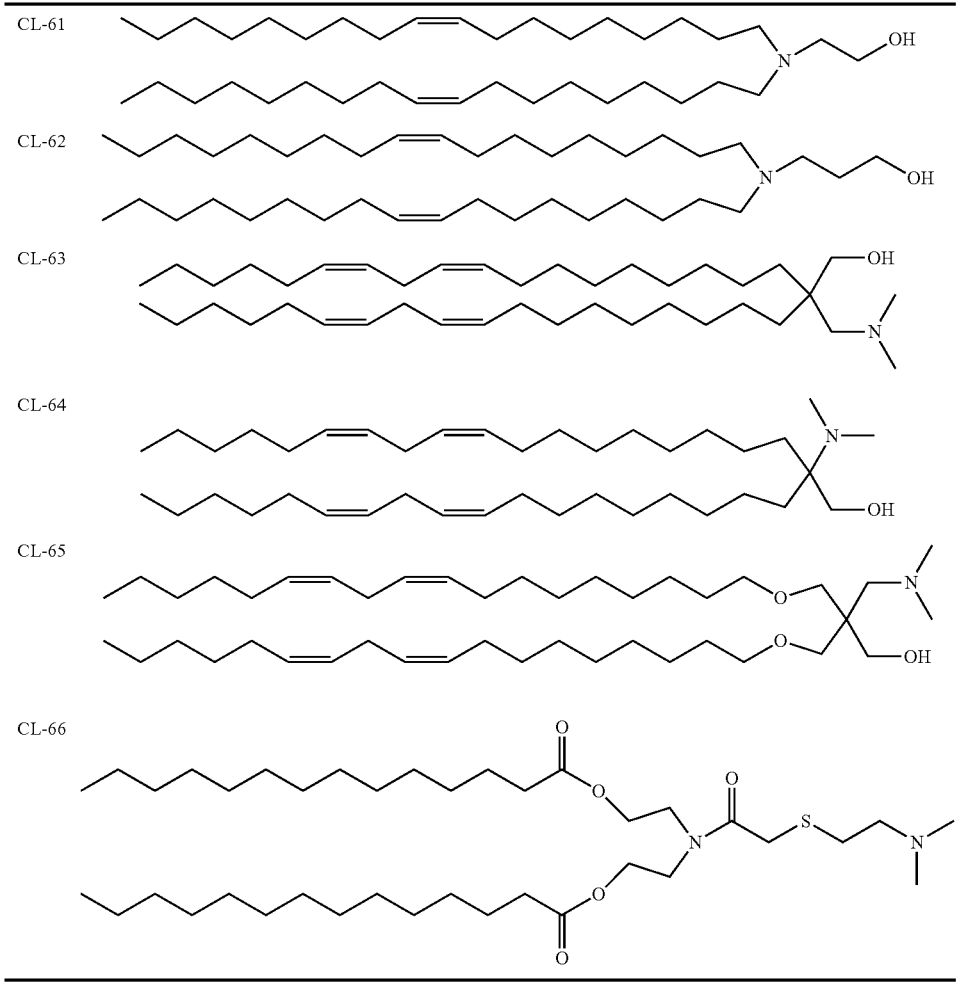
TABLE 11
| Compound No. | Structural formula |
| --- | --- |
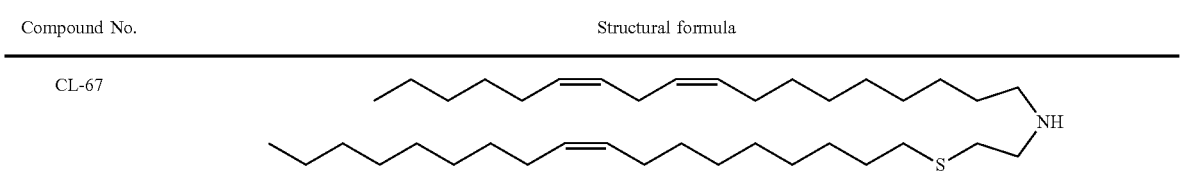

TABLE 11-continued

| Compound No. | Structural formula |
| --- | --- |
| CL-68 | |
| CL-69 | |
| CL-70 | |
| CL-71 | |
| CL-72 | |
| CL-73 | |

TABLE 12

| CL-74 | |
| --- | --- |
| CL-75 | |
| CL-76 | |
| CL-77 | |

TABLE 12-continued

| | |
|---|---|
| CL-78 | (structure) |
| CL-79 | (structure) |
| CL-80 | (structure) |
| CL-81 | (structure) |

TABLE 13

| | |
|---|---|
| CL-82 | (structure) |
| CL-83 | (structure) |
| CL-84 | (structure) |
| CL-85 | (structure) |
| CL-86 | (structure) |
| CL-87 | (structure) |

TABLE 13-continued
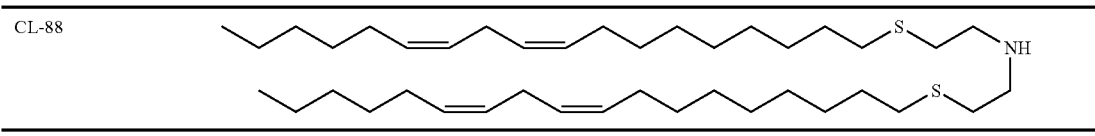
TABLE 14
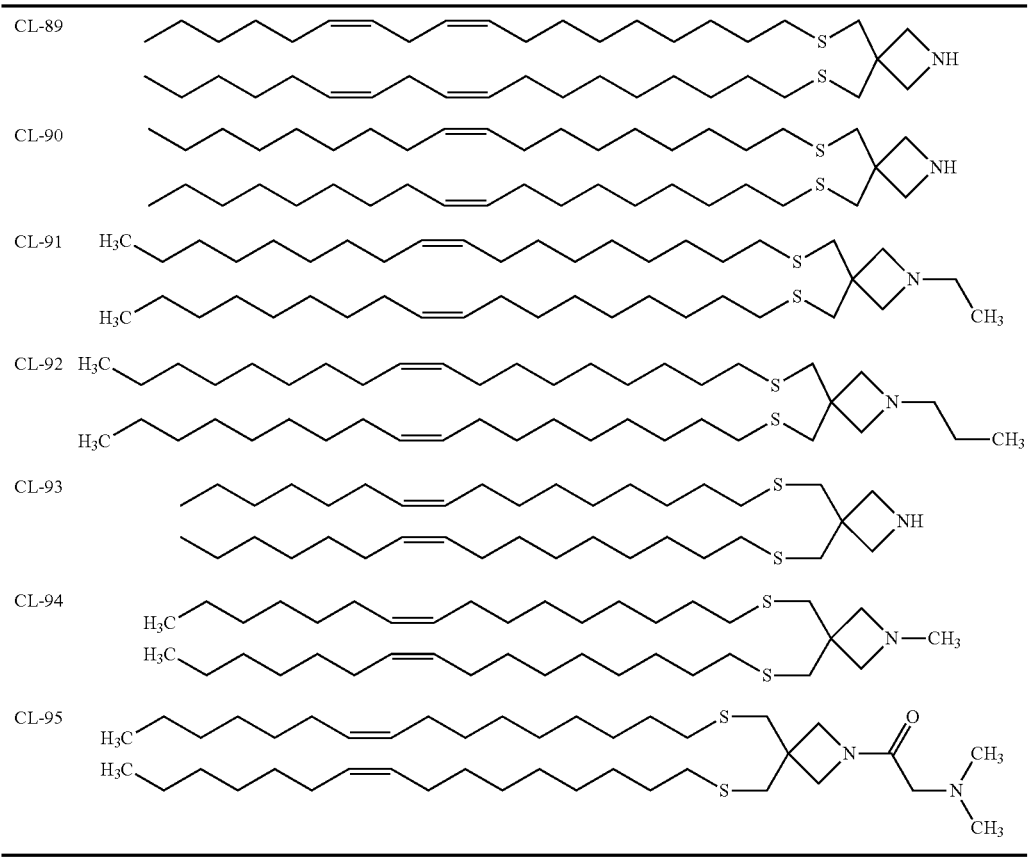
TABLE 15
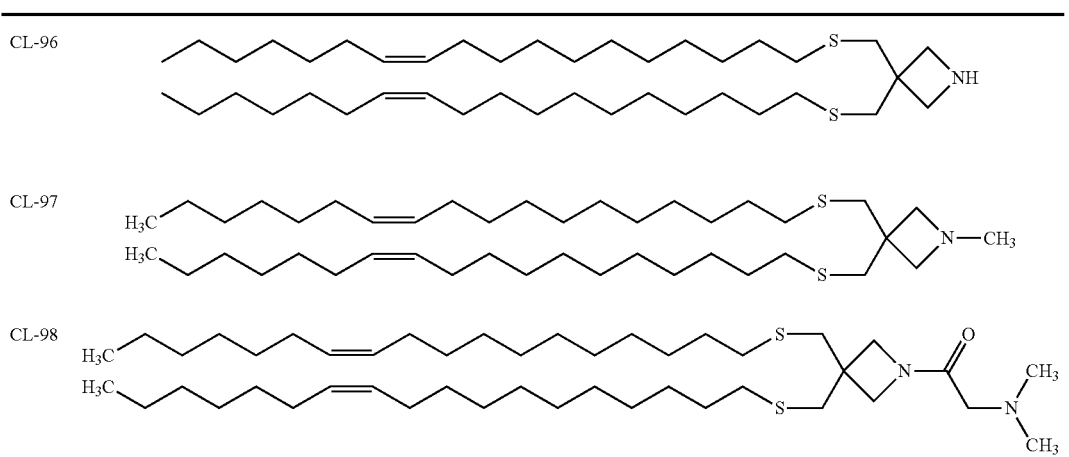

TABLE 15-continued

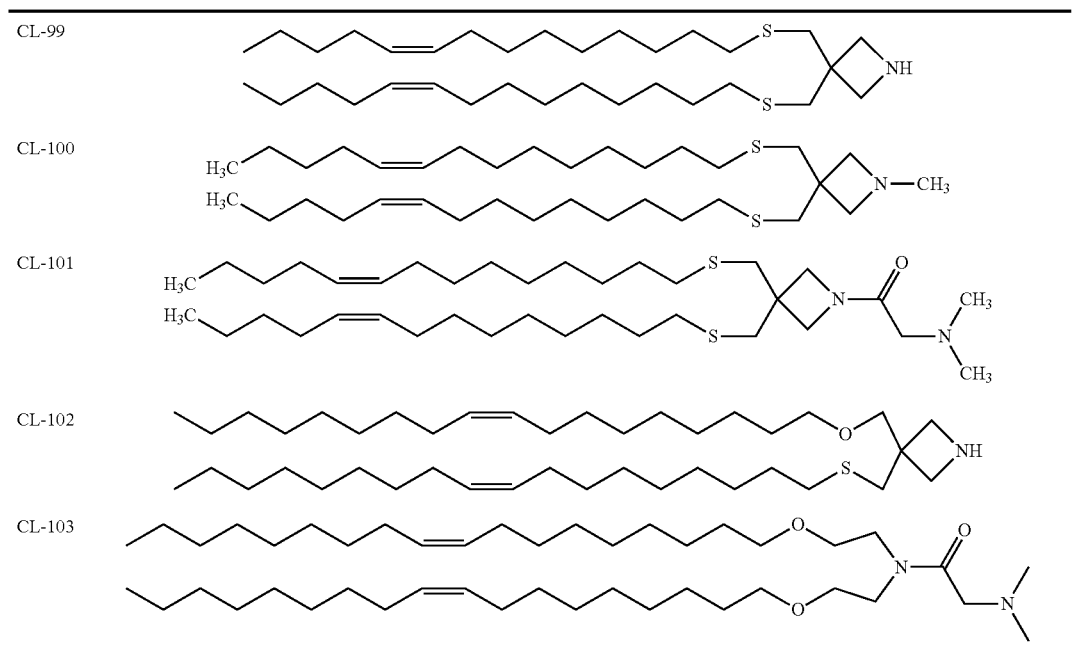

Next, methods for producing lipid A used in the present invention will be described. In the production methods shown below, if defined groups react under conditions of the production methods or are unsuitable for carrying out the production methods, the desired compounds can be obtained by use of introduction and removal methods of protective groups commonly used in organic synthetic chemistry [e.g., methods described in Protective Groups in Organic Synthesis, third edition, T. W. Greene, John Wiley & Sons Inc. (1999)] or the like. If necessary, the order of reaction steps including substituent introduction or the like may be changed.

General unit reactions such as etherification ("The Fourth Series of Experimental Chemistry 20, Synthesis of Organic Compound II", 4th edition, p. 187, Maruzen Co., Ltd. (1992), etc.), amination ("The Fourth Series of Experimental Chemistry 20, Synthesis of Organic Compound II", 4th edition, p. 279, Maruzen Co., Ltd. (1992), etc.), esterification ("The Fourth Series of Experimental Chemistry 22, Synthesis of Organic Compound IV", 4th edition, p. 43, Maruzen Co., Ltd. (1992), etc.), and amidation ("The Fourth Series of Experimental Chemistry 22, Synthesis of Organic Compound IV", 4th edition, p. 137, Maruzen Co., Ltd. (1992), etc.) described in the production methods shown below may each be performed under general reaction conditions described in the existing literatures.

Compound (I) can be obtained by any method of synthesis route 1 or 2 given below, a method equivalent to the method, or the like.

Compound (I) can be obtained from ammonia according to synthesis route 1.

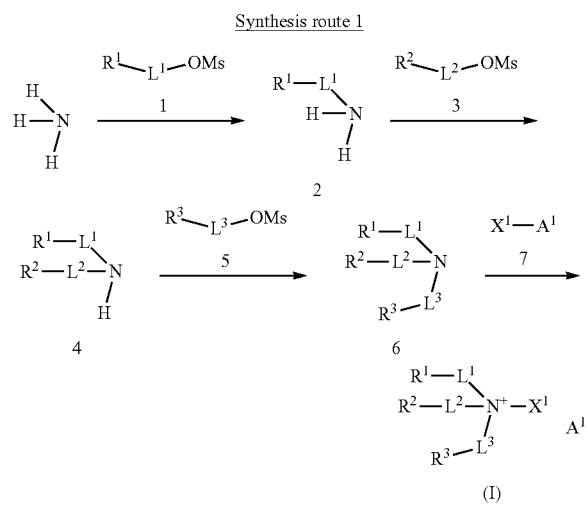

wherein Ms represents a methanesulfonyl group; and the other groups are each as defined above.

Compound 2 can be obtained by reacting ammonia with compound 1 in a solvent (e.g., polar solvents such as tetrahydrofuran and methanol) at a high temperature (e.g., 80° C. or higher).

Compound 4 is obtained by reacting compound 2 with compound 3 in the presence of a base (e.g., inorganic bases such as sodium hydroxide) at a high temperature (e.g., 100° C. or higher). Although no solvent is particularly necessary, a high-boiling solvent (e.g., polar solvents such as ethylene glycol) may be used in some cases.

Compound 6 is obtained by reacting compound 4 with compound 5 in the presence of a base (e.g., inorganic bases such as sodium hydroxide) at a high temperature (e.g., 100° C. or higher). Although no solvent is particularly necessary, a high-boiling solvent (e.g., polar solvents such as ethylene glycol) may be used in some cases.

Each of these three heating reactions may suitably employ a microwave reaction apparatus. Alternatively, a halide such as bromide or iodide corresponding to compound 1, compound 3 or compound 5 may be used instead of the compound.

Compound 4 wherein $R^1$-$L^1$ and $R^2$-$L^2$ are the same is also obtained from ammonia using excessive compound 1. Compound 6 wherein $R^2$-$L^2$ and $R^3$-$L^3$ are the same is also obtained from compound 2 using excessive compound 3. Compound 6 wherein $R^2$-$L^2$, $R^2$-$L^2$ and $R^3$-$L^3$ are the same is also obtained from ammonia using more excessive compound 1.

Compound (I) is obtained by reacting compound 6 with compound 7 in the presence or absence of a solvent (e.g., halogen-based solvents such as chloroform) at room temperature or a high temperature (e.g., 100° C. or higher). Anion $A^1$ of compound (I) may be converted to another anion, for example, by treating the compound (I) with an appropriate anion-exchange resin.

Each compound such as compound 1, compound 3, compound 5 and compound 7, etc. for use in the reactions can be obtained as a commercially available product, or by a method described in Examples or a method equivalent thereto, or by a known method described in a literature (e.g., a method described in "The Fifth Series of Experimental Chemistry 13, Synthesis of Organic Compound I", 5th edition, p. 374, Maruzen Co., Ltd. (2005)) or a method equivalent thereto.

Alternatively, compound 1 may be obtained by treating corresponding $R^1$-$L^1$-OH with mesyl anhydride or mesyl chloride.

Compound $R^1$-$L^1$-OH wherein $L^1$ is —$Z^1$—$(CY^1Y^2)_{p2}$— (wherein each group is as defined above) can be obtained by subjecting any one of $R^1$—OMs, $R^1$—OH, $R^1$—$NY^{7,4}$—H (wherein $Y^{7,4}$ is as defined above) and $R^1$—$CO_2H$ and any one of HO—$(CY^7Y^2)_{p1}$—O—$PRO^1$, MsO—$(CY^7Y^2)_{p1}$—O—$PRO^1$, $HO_2C$—$(CY^2Y^2)_{p1}$—O—$PRO^1$ and H—$NY^{7,4}$—$(CY^2Y^2)_{p1}$—O—$PRO^1$ (wherein $PRO^1$ is a silyl-based protective group (e.g., triethylsilyl (TES), tert-butyldimethylsilyl (TBS) and tert-butyldiphenylsilyl (TBDPS))) to any reaction of etherification (e.g., using a strong base such as sodium hydride), amination (e.g., substitution reaction), esterification (e.g., using a condensing agent such as 1-ethyl-3-(3-dimethylaminopropyl)carbodiimide hydrochloride), and amidation (e.g., using the same condensing agent thereas), followed by deprotection.

Likewise, compound $R^1$-$L^1$-OH wherein $L^1$ is —$Z^2$—$(CY^3Y^4)_{p2}$—$Z^3$—$(CY^5Y^6)_{p3}$— (wherein each group is as defined above) can also be obtained by the application of reaction known in the art one to several times using a reaction substrate appropriate for the desired compound.

Compounds 3 and 5 can be prepared by the same approach as in compound 1.

Compound (Ia) can be obtained from compound 8 according to synthesis route 2.

Synthesis route 2

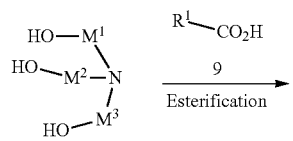

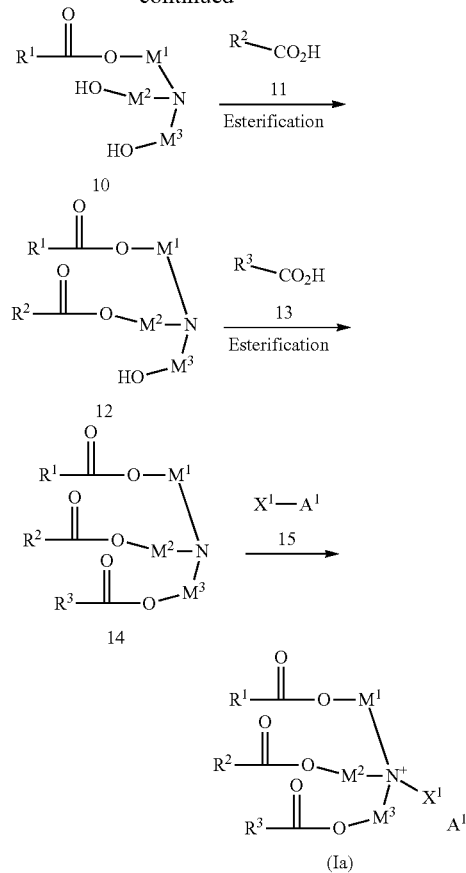

wherein $M^1$ to $M^3$ are the same or different and are each —$(CY^1Y^2)_{p1}$— or —$(CY^3Y^4)_{p2}$—$Z^3$—$(CY^5Y^6)_{p3}$— (wherein each group is as defined above); and the other groups are each as defined above.

Compound 10 is obtained by treating compound 8 and compound 9 with a base (e.g., organic bases such as triethylamine), a condensing agent (e.g., condensing agents such as 1-ethyl-3-(3-dimethylaminopropyl)carbodiimide hydrochloride and O-(7-aza-1H-benzotriazol-1-yl)-N,N,N',N'-tetramethyluronium hexafluorophosphate) and an activator (activators such as N,N-dimethylaminopyridine) in a solvent (e.g., halogen-based solvents such as chloroform).

Compound 12 is obtained by esterifying compound 10 and compound 11 in the same way as above.

Compound 14 is obtained by esterifying compound 12 and compound 13 in the same way as above.

Compound 12 wherein $R^1$ and $R^2$ are the same is also obtained from compound 8 using excessive compound 9. Compound 14 wherein $R^2$ and $R^3$ are the same is also obtained from compound 10 using excessive compound 11. Compound 14 wherein $R^1$, $R^2$ and $R^3$ are the same is also obtained from compound 8 using more excessive compound 9.

Compound (Ia) is obtained by reacting compound 14 with compound 15 in the presence or absence of a solvent (e.g., halogen-based solvents such as chloroform) at room temperature or a high temperature (e.g., 100° C. or higher). Anion $A^1$ of compound (Ia) may be converted to another anion, for example, by treating the compound (Ia) with an appropriate anion-exchange resin.

Each compound such as compound 8, compound 9, compound 11, compound 14 and compound 15, etc. for use in the reaction can be obtained as a commercially available product, or by a method described in Examples or a method equivalent thereto, or by a known method described in a literature (e.g., a method described in "The Fifth Series of Experimental Chemistry 14, Synthesis of Organic Compound II", 5th edition, p. 1, Maruzen Co., Ltd. (2005) or "The Fourth Series of Experimental Chemistry 22, Synthesis of Organic Compound IV", 4th edition, p. 1, Maruzen Co., Ltd. (1992)) or a method equivalent thereto.

Compound (II) can be obtained by any method of synthesis routes 3 to 16 shown below, a method equivalent to the method, or the like.

Compound (IIa) can be obtained from compound 15 according to synthesis route 3.

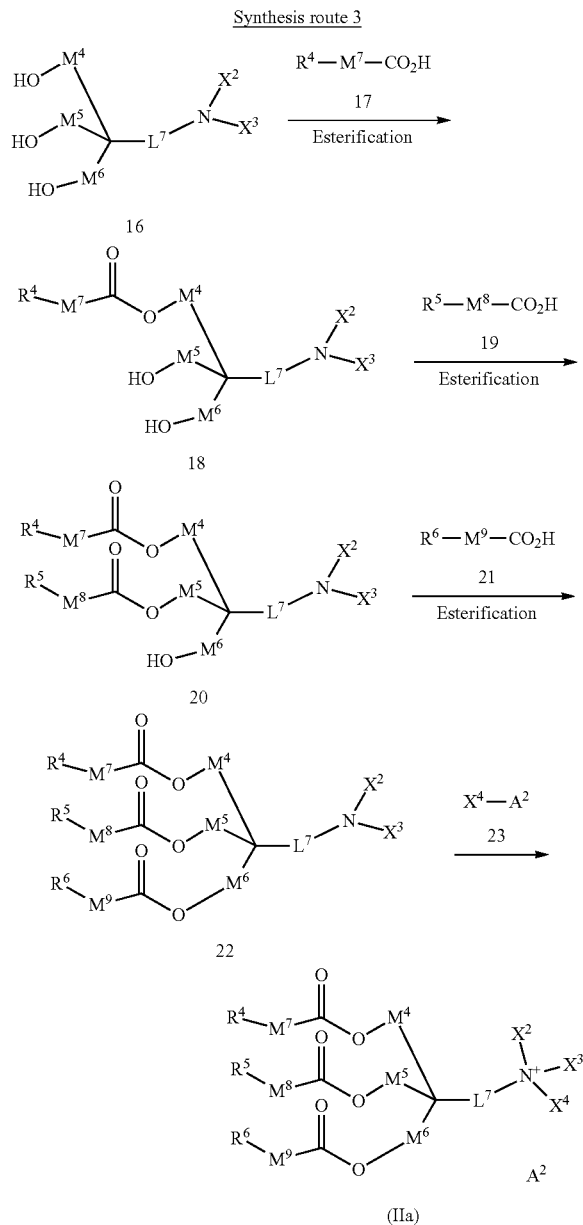

wherein $M^7$ is absent, and $M^4$ is —$(CY^8Y^9)_{p4}$—; $M^7$ is absent, and $M^4$ is —$(CY^{10}Y^{11})_{p5}$—$Z^6$—$(CY^{12}Y^{13})_{p6}$—; or $M^7$ is —$Z^5$—$(CY^{10}Y^{11})_{p5}$—, and $M^4$ is —$(CY^{12}Y^{13})_{p6}$—

(wherein each group is as defined above); $M^8$ is absent, and $M^5$ is —$(CY^8Y^9)_{p4}$—; $M^8$ is absent, and $M^5$ is —$(CY^{10}Y^{11})_{p5}$—$Z^6$—$(CY^{12}Y^{13})_{p6}$—; or $M^8$ is —$Z^5$—$(CY^{10}Y^{11})_{p5}$—, and $M^5$ is —$(CY^{12}Y^{13})_{p6}$—; $M^9$ is absent, and $M^6$ is —$(CY^8Y^9)_{p4}$—; $M^9$ is absent, and $M^6$ is —$(CY^{10}Y^{11})_{p5}$—$Z^6$—$(CY^{12}Y^{13})_{p6}$—; or $M^9$ is —$Z^5$—$(CY^{10}Y^{11})_{p5}$—, and $M^6$ is —$(CY^{12}Y^{13})_{p6}$—; and the other groups are each as defined above.

Compound 22 is obtained by reacting compound 16 with compound 17, compound 19 and compound 21 in order by the application of the same reaction conditions as in the esterification reaction of compound 8 with compound 9 in synthesis route 2.

Compound (IIa) is obtained by reacting compound 22 with compound 23 by the application of the same conditions as the reaction conditions for the synthesis of compound (Ia) through the reaction of compound 14 with compound 15 in synthesis route 2. Anion $A^2$ of compound (IIa) may be converted to another anion, for example, by treating the compound (IIa) with an appropriate anion-exchange resin.

Each compound such as compound 16, compound 17, compound 19, compound 21 and compound 23, etc. for use in the reaction can be obtained as a commercially available product, or by a method described in Examples or a method equivalent thereto, or by a known method described in a literature (e.g., a method described in "The Fifth Series of Experimental Chemistry 14, Synthesis of Organic Compound II", 5th edition, p. 1, Maruzen Co., Ltd. (2005) or "The Fourth Series of Experimental Chemistry 22, Synthesis of Organic Compound IV", 4th edition, p. 1, Maruzen Co., Ltd. (1992)) or a method equivalent thereto.

Compound 16 can also be obtained by any method of synthesis routes 11 to 15 mentioned later.

Compound 17 wherein $M^7$ is —$Z^5$—$(CY^{10}Y^{11})_{p5}$— can be obtained by subjecting any one of $R^4$—OMs, $R^4$—OH, $R^4$—$NY^{14A}$—H (wherein $Y^{14A}$ is as defined above) and $R^4$—$CO_2H$ and any one of HO—$(CY^{10}Y^{11})_{p5}$—CO—O—$PRO^2$, MsO—$(CY^{10}Y^{11})_{p5}$—CO—O—$PRO^2$, $HO_2C$—$(CY^{10}Y^{11})_{p5}$—CO—O—$PRO^2$ and H—$NY^{14A}$—$(CY^{10}Y^{11})_{p5}$-CO—O—$PRO^2$ (wherein $PRO^2$ is a protective group for carboxylic acid (e.g., methyl, tert-butyl and benzyl)) to any reaction of etherification (e.g., using a strong base such as sodium hydride), amination (e.g., substitution reaction), esterification (e.g., using a condensing agent such as 1-ethyl-3-(3-dimethylaminopropyl)carbodiimide hydrochloride), and amidation (e.g., using the same condensing agent thereas), followed by deprotection.

Compounds 19 and 21 can be prepared by the same approach as in compound 17.

In synthesis route 3, the introduction of $X^4$ may be performed first. Specifically, first, compound 23 may be allowed to act on compound 16, followed by the esterification of compounds 17, 19 and 21 in order to obtain compound (IIa).

Compound (IIb) can be obtained from compound 16 according to synthesis route 4.

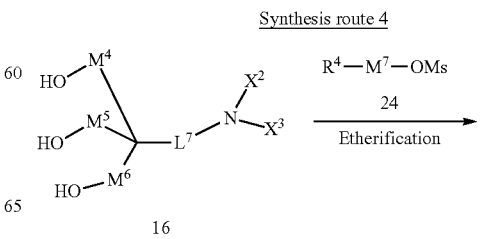

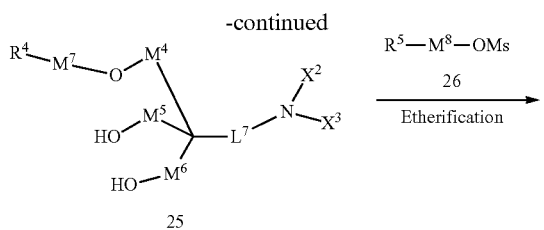

25

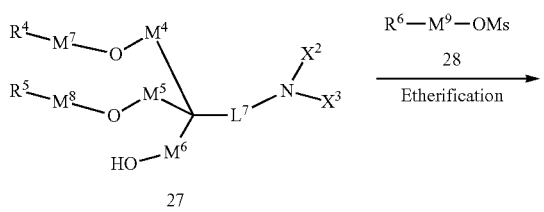

27

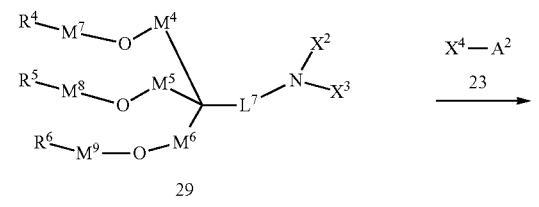

29

(IIb)

wherein each group is as defined above.

Compound 25 can be obtained by reacting compound 16 with compound 24 in the presence of a base (e.g., inorganic bases such as sodium hydride) in a solvent (e.g., aprotic solvents such as tetrahydrofuran and toluene) at a high temperature (e.g., 100° C. or higher).

Compound 27 is obtained by etherifying compound 25 and compound 26 in the same way as above.

Compound 29 is obtained by etherifying compound 27 and compound 28 in the same way as above.

Each of these three heating reactions may suitably employ a microwave reaction apparatus. Alternatively, bromide, iodide or the like corresponding to compound 24, compound 26 and compound 28 may be used instead of the compound.

Compound 27 wherein $R^4$-$M^7$ and $R^5$-$M^8$ are the same is also obtained from compound 16 using excessive compound 24. Compound 29 wherein $R^5$-$M^8$ and $R^6$-$M^9$ are the same is also obtained from compound 25 using excessive compound 26. Compound 29 wherein $R^4$-$M^7$, $R^5$-$M^8$ and $R^6$-$M^9$ are the same is also obtained from compound 16 using more excessive compound 24.

Compound (IIb) is obtained by reacting compound 29 with compound 23 in the presence or absence of a solvent (e.g., halogen-based solvents such as chloroform) at room temperature or a high temperature (e.g., 100° C. or higher). Anion $A^2$ of compound (IIb) may be converted to another anion, for example, by treating the compound (Iib) with an appropriate anion-exchange resin.

Each compound such as compound 16, compound 24, compound 26, compound 28 and compound 23, etc. for use in the reaction can be obtained as a commercially available product, or by a method described in Examples or a method equivalent thereto, or by a known method described in a literature (e.g., a method described in "The Fifth Series of Experimental Chemistry 14, Synthesis of Organic Compound II", 5th edition, p. 1, Maruzen Co., Ltd. (2005) or "The Fifth Series of Experimental Chemistry 13, Synthesis of Organic Compound I", 5th edition, p. 374, Maruzen Co., Ltd. (2005)) or a method equivalent thereto.

Alternatively, compound 24 may be obtained by treating corresponding $R^4$-$M^7$-OH with mesyl anhydride or mesyl chloride.

Compound $R^4$-$M^7$-OH wherein $M^7$ is —$Z^5$—($CY^{10}Y^{11}$)$_{p5}$— (wherein each group is as defined above) can be obtained by subjecting any one of $R^4$—OMs, $R^4$—OH, $R^4$—$NY^{14A}$—H (wherein $Y^{14A}$ is as defined above) and $R^4$—$CO_2H$ and any one of HO—($CY^{10}Y^{11}$)$_{p5}$—O—$PRO^1$, MsO—($CY^{10}Y^{11}$)$_{p5}$—O—$PRO^1$, $HO_2C$—($CY^{10}Y^{11}$)$_{p5}$—O—$PRO^1$ and H—$NY^{14A}$—($CY^{10}Y^{11}$)$_{p5}$—O—$PRO^1$ (wherein each group is as defined above) to any reaction of etherification, amination, esterification and amidation, followed by deprotection.

Compounds 26 and 28 can be prepared by the same approach as in compound 24.

As shown in synthesis route 5, compound (IIe) can be obtained from compound 25 obtained in synthesis route 4 by appropriately combining the reactions such as esterification in synthesis route 3. As shown in synthesis route 5, compound (IId) can be obtained from compound 27 obtained in synthesis route 4 by appropriately combining the reactions such as esterification in synthesis route 3.

Synthesis route 5

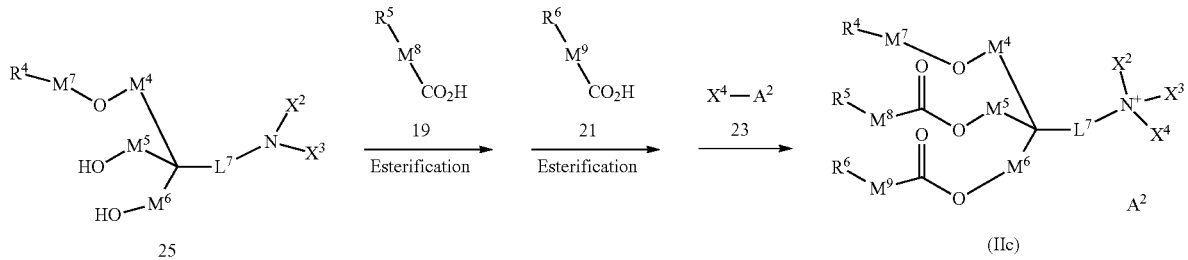

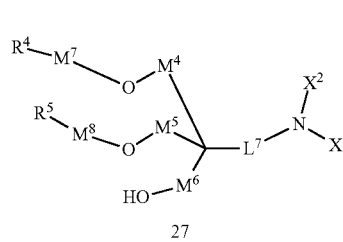

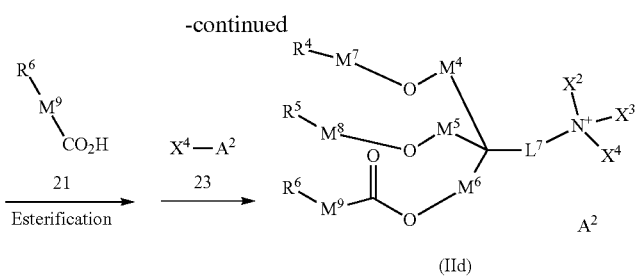

wherein each group is as defined above.

Compound (IIe) can be obtained from compound 30 according to synthesis route 6.

Synthesis route 6

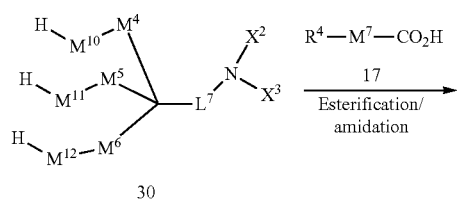

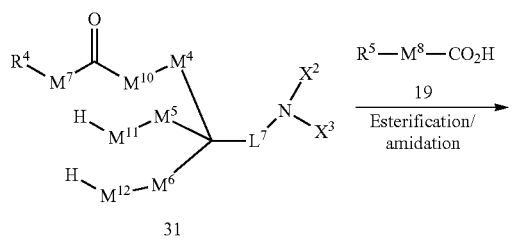

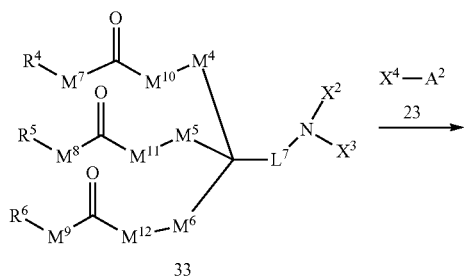

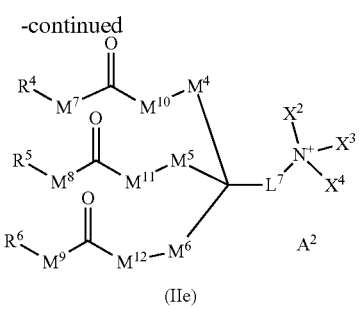

wherein $M^{10}$, $M^{11}$ and $M^{12}$ are each independently O or $NY^{14A}$; and the other groups are each as defined above.

Compound 33 is obtained through the esterification or amidation reaction of compound 30 with compound 17, compound 19 and compound 21 in order.

Compound (IIe) is obtained by reacting compound 33 with compound 23 by the application of the same conditions as the reaction conditions for the synthesis of compound (Ia) through the reaction of compound 14 with compound 15 in synthesis route 2. Anion $A^2$ of compound (IIe) may be converted to another anion, for example, by treating the compound (IIe) with an appropriate anion-exchange resin.

Compound 30 can also be obtained by any method of synthesis routes 11 to 15 mentioned later.

Compound (IIf) can be obtained from compound 34 according to synthesis route 7.

Synthesis route 7

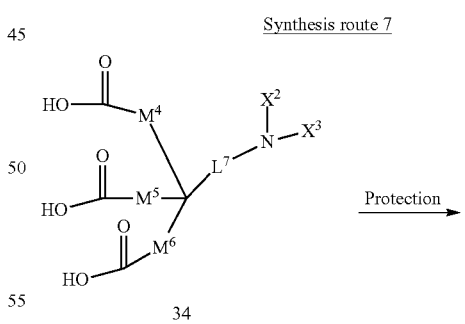

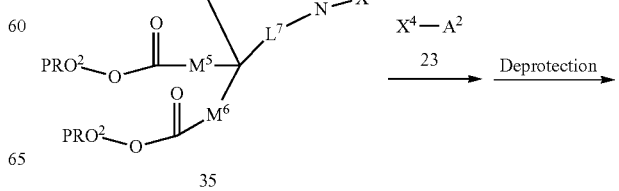

-continued

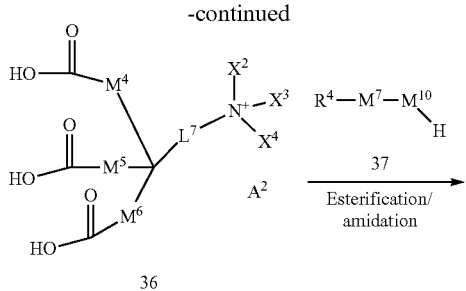

36

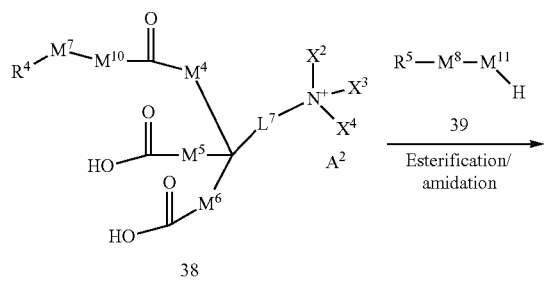

38

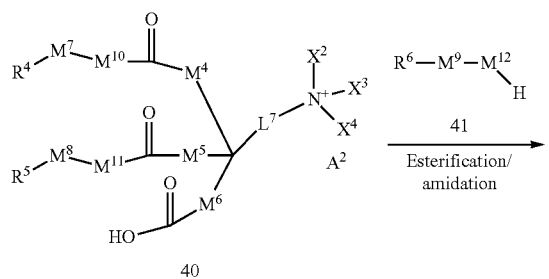

40

-continued

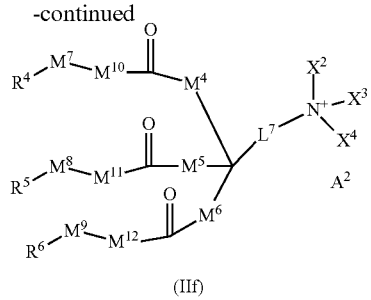

(IIf)

wherein each group is as defined above.

Compound 35 is obtained by protecting compound 34 with an appropriate protective group.

Compound 36 is obtained by reacting compound 35 with compound 23 by the application of the same conditions as the reaction conditions for the synthesis of compound (Ia) through the reaction of compound 14 with compound 15 in synthesis route 2, followed by deprotection under appropriate conditions.

Compound (IIf) is obtained by the esterification or amidation reaction of compound 36 with compound 37, compound 39 and compound 41 in order. Anion $A^2$ of compound (IIf) may be converted to another anion, for example, by treating the compound (IIf) with an appropriate anion-exchange resin.

Each of compounds 34, 35 and 36 can be obtained as a commercially available product, or by a method described in Examples or a method equivalent thereto.

Compound 37 wherein $M^{10}$ is $NY^{14.4}$ can also be obtained by reacting $R^4$-$M^7$-OMs (compound 24) with $Y^{14.4}NH_2$.

Compounds 37 and 39 can be prepared by the same approach as in compound 35.

As shown in synthesis route 8, compound (IIf) can also be obtained by performing the esterification or amidation of compound 24 with compounds 37, 39 and 41 in order, and finally introducing $X^4$ by the action of compound 23.

Synthesis route 8

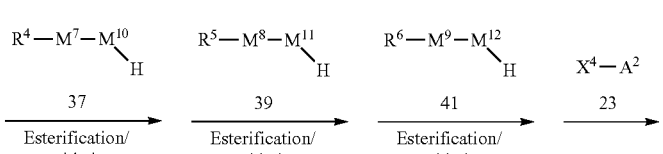

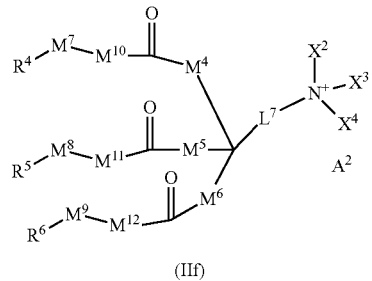

(IIf)

wherein each group is as defined above.

Compound (IIg) can be obtained from ethyl cyanoacetate according to synthesis route 9.

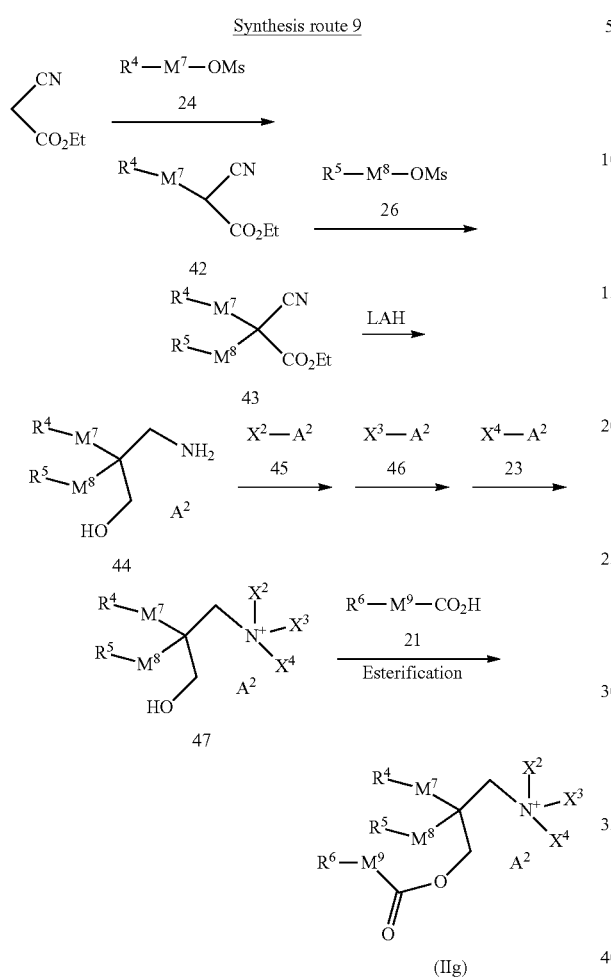

wherein Et represents an ethyl group; LAH is lithium aluminum hydride; and the other groups are each as defined above.

Compound 42 can be obtained by reacting ethyl cyanoacetate with compound 24 in the presence of a base (e.g., inorganic bases such as sodium hydride) and, in some cases, an additive (e.g., additives such as tetrabutylammonium iodide) in a solvent (e.g., aprotic solvents such as tetrahydrofuran) at a high temperature (e.g., 60° C. or higher).

Compound 43 can be obtained by reacting compound 42 with compound 26 in the presence of a base (e.g., inorganic bases such as sodium hydride) and, in some cases, an additive (e.g., additives such as tetrabutylammonium iodide) in a solvent (e.g., aprotic solvents such as tetrahydrofuran) at a high temperature (e.g., 60° C. or higher).

Compound 43 wherein $R^4$ and $R^5$ are the same can also be obtained from ethyl cyanoacetate using excessive compound 24.

Compound 44 can be obtained by reducing compound 43 with excessive lithium aluminum hydride (LAH) in a solvent (e.g., aprotic solvents such as tetrahydrofuran).

Compound 47 can be obtained by allowing compound 45, compound 46 and compound 23 in order to act on compound 44 in the presence or absence of a solvent (e.g., halogen-based solvents such as chloroform). Compound 47 wherein $X^2$, $X^3$ and $X^4$ are the same can also be obtained from compound 44 using excessive compound 45.

Compound (IIg) is obtained by reacting compound 47 with compound 21 by the application of the same reaction conditions as in the esterification reaction of compound 8 with compound 9 in synthesis route 2. Anion $A^2$ of compound (IIg) may be converted to another anion, for example, by treating the compound (IIg) with an appropriate anion-exchange resin.

Compounds 45 and 46 are obtained in the same way as in compound 23.

Compound (IIh) can be obtained from dimethyl malonate according to synthesis route 10.

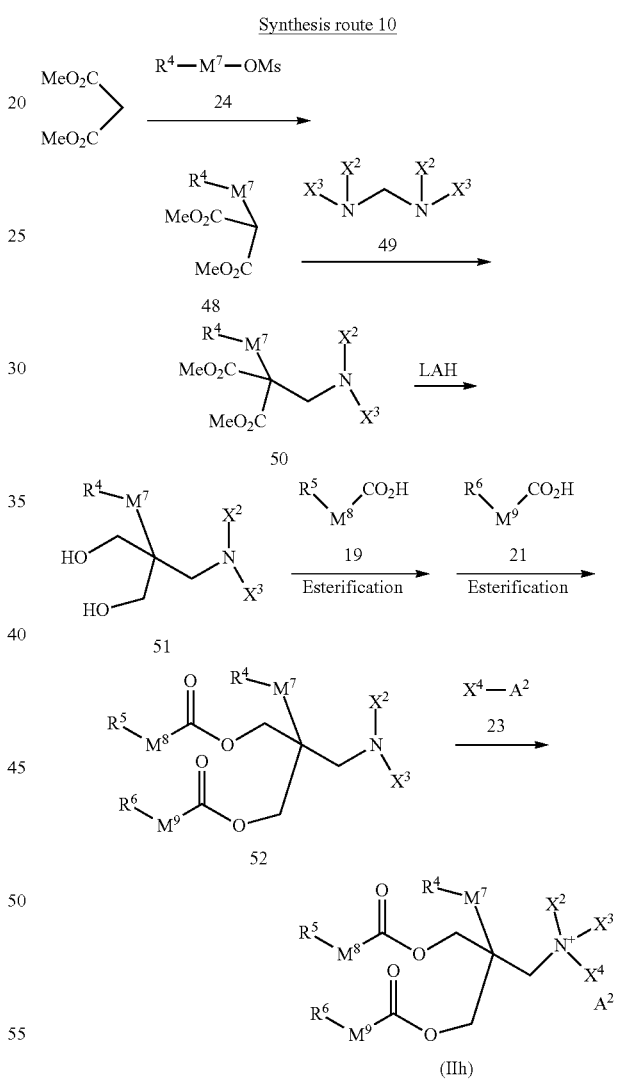

wherein Me represents a methyl group; LAH is lithium aluminum hydride; and the other groups are each as defined above.

Compound 48 can be obtained by reacting dimethyl malonate with compound 24 in the presence of a base (e.g., inorganic bases such as cesium carbonate) and, in some cases, an additive (e.g., additives such as tetrabutylammonium iodide) in a solvent (e.g., aprotic solvents such as acetonitrile) under heating (e.g., 50° C.).

Compound 50 can be obtained by reacting compound 48 with compound 49 in the presence of acetic anhydride and a base (e.g., inorganic bases such as sodium hydride) in a solvent (e.g., aprotic solvents such as acetonitrile).

Compound 51 can be obtained by reducing compound 50 with excessive lithium aluminum hydride (LAH) in a solvent (e.g., aprotic solvents such as tetrahydrofuran).

Compound 52 is obtained by reacting compound 51 with compound 19 and compound 21 by the application of the same reaction conditions as in the esterification of compound 8 and compound 9 in synthesis route 2.

Compound (IIh) is obtained by reacting compound 52 with compound 53 in the presence or absence of a solvent (e.g., halogen-based solvents such as chloroform) at room temperature or a high temperature (e.g., 100° C. or higher). Anion $A^2$ of compound (IIh) may be converted to another anion, for example, by treating the compound (IIh) with an appropriate anion-exchange resin.

Compound 49 can be obtained as a commercially available product, or by a method described in Examples or a method equivalent thereto, or by a known method described in a literature (e.g., a method described in "Helvetica Chimica Acta, Vol. 92, No. 8, p. 1644-1656, 2009") or a method equivalent thereto.

Compounds 54 and 56 can be obtained according to synthesis route 11.

Synthesis route 11

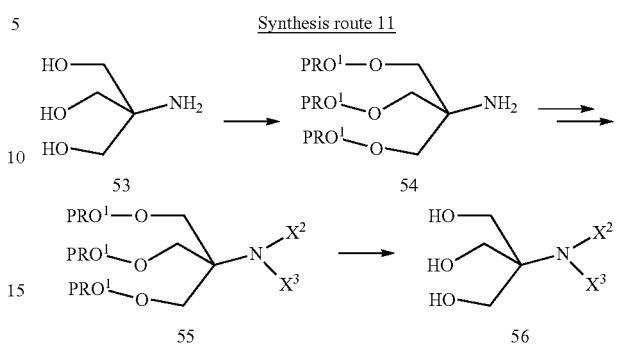

wherein each group is as defined above.

Compound 54 can be obtained by protecting hydroxy of compound 53.

Compound 53 can be obtained as a commercially available product.

Compound 55 can be obtained by allowing compound 45 and compound 46 to act on compound 54.

Compound 56 can be obtained by deprotecting compound 55.

Compounds 58 to 65 can be obtained according to synthesis route 12.

Synthesis route 12

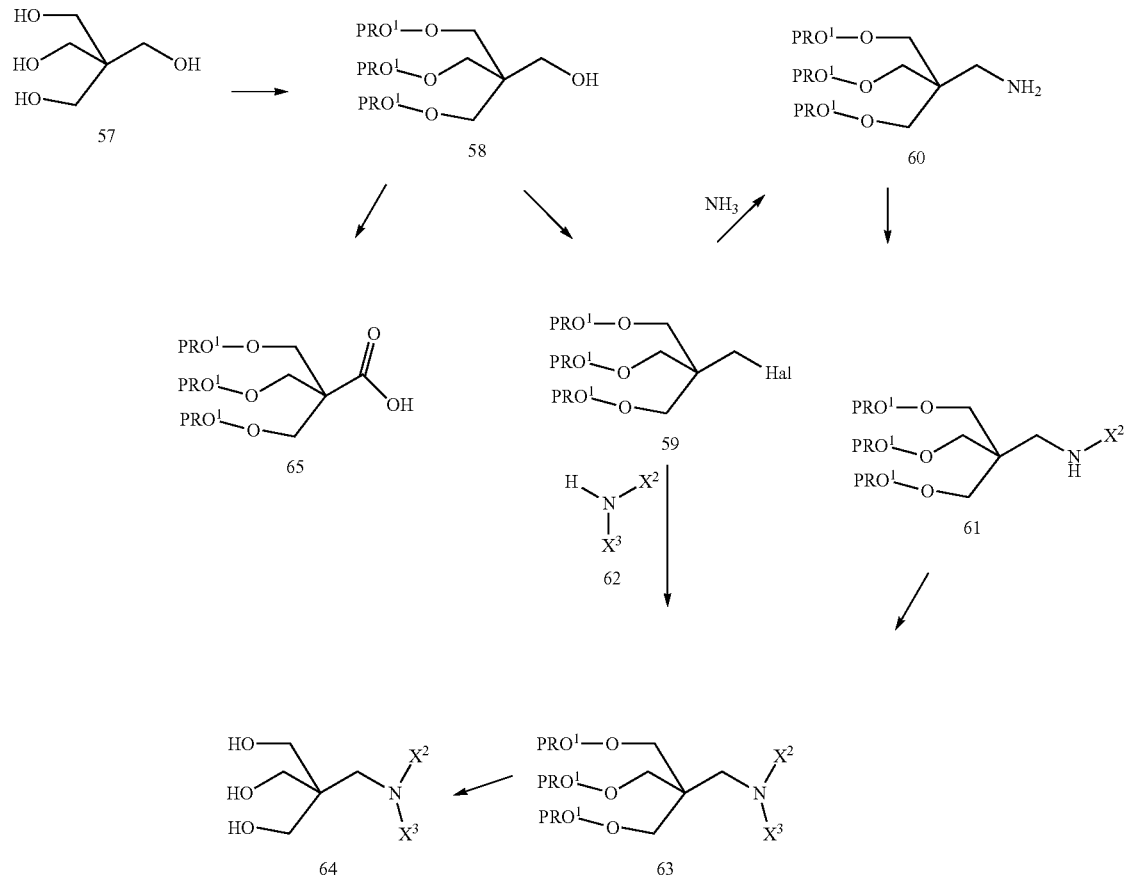

wherein Hal is a halogen atom such as chlorine, bromine or iodine; and the other groups are each as defined above.

Compound 58 can be obtained by protecting hydroxy of compound 57.

Compound 57 can be obtained as a commercially available product.

Compound 59 can be obtained by allowing a halogenation reagent (e.g., chlorine, bromine, iodine and iodine chloride) to act on compound 58.

Compound 60 is obtained by reacting compound 59 with ammonia. Compound 61 is obtained by allowing compound 45 to act on compound 60. Compound 63 is obtained by allowing compound 46 to act on compound 61.

Alternatively, compound 63 may be obtained by reacting compound 59 with compound 62.

Compound 63 is obtained by deprotecting compound 62.

Compound 64 is obtained by oxidizing compound 58 with an appropriate oxidizing agent (e.g., potassium permanganate and Jones reagent).

Compounds 67 to 73 can be obtained according to synthesis route 13.

Compound 71 is obtained by hydrolyzing compound 66 with a base (e.g., sodium hydroxide).

Compound 72 is obtained by reducing compound 71 with a reducing agent (e.g., borane).

Compound 73 can be obtained by allowing a halogenation reagent (e.g., chlorine, bromine, iodine and iodine chloride) to act on compound 72.

A compound having a further extended alkylene chain between each functional group (amino group, monoalkylamino group, dialkylamino group, carboxylic acid, hydroxy and halogen) and quaternary carbon of compounds 67, 68, 69, 71, 72 and 73 can be obtained by performing a series of reactions from compound 59 in synthesis route 13 for compound 73. Also, the alkylene chain between each functional group and quaternary carbon can be freely extended by repeating this operation.

Synthesis route 13

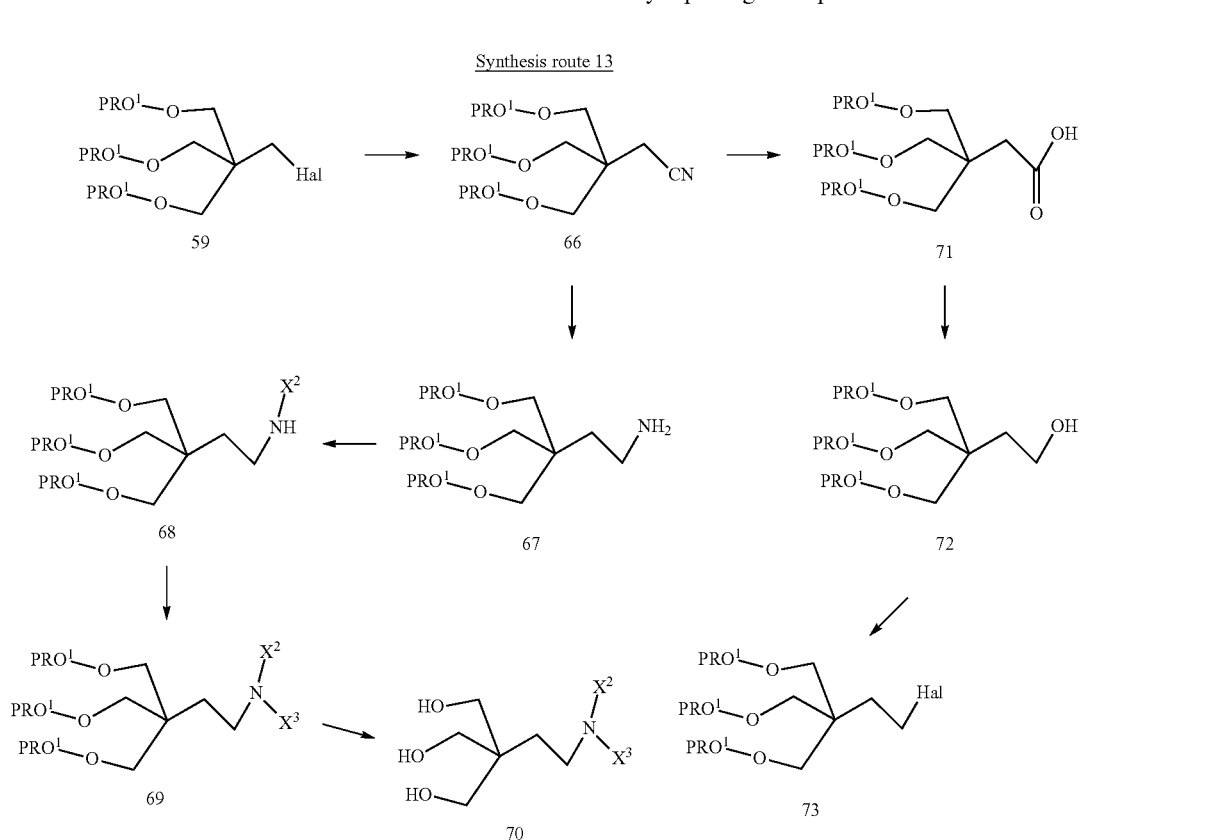

wherein each group is as defined above.

Compound 66 is obtained by allowing a cyanide (e.g., sodium cyanide, potassium cyanide and lithium cyanide) to act on compound 59.

Compound 67 is obtained by reducing compound 66 with lithium aluminum hydride or the like.

Compound 68 is obtained by allowing compound 45 to act on compound 67. Compound 69 is obtained by allowing compound 46 to act on compound 68.

Compound 70 is obtained by deprotecting compound 69.

Compound 76 can be synthesized according to synthesis route 14.

Synthesis route 14

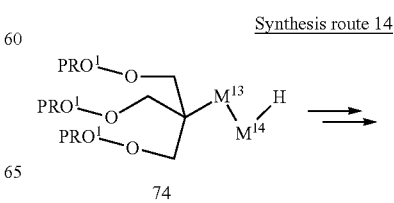

-continued

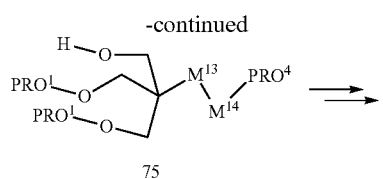

75

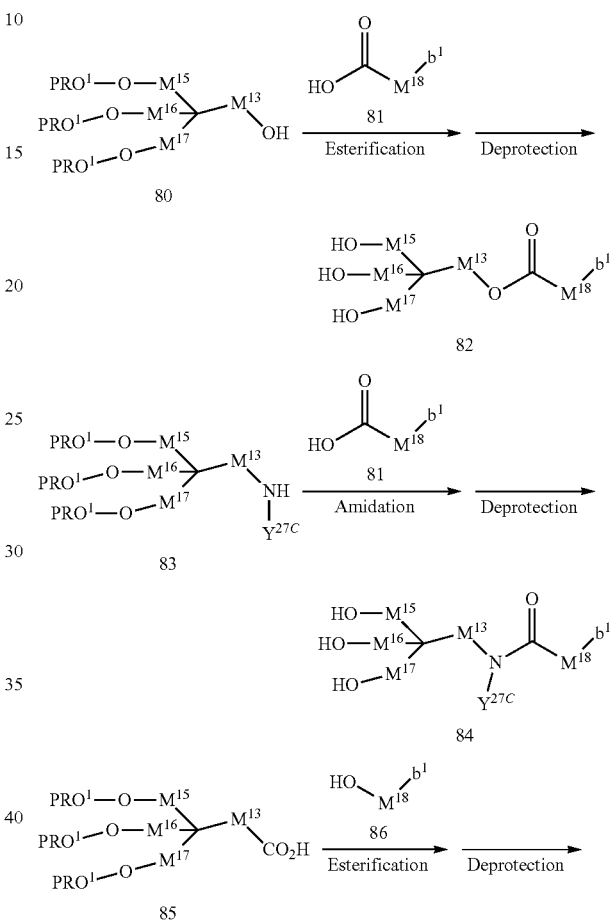

wherein $M^{16}$ and $M^{17}$ each represent $-(CH_2)_{p203}-$ and $-(CH_2)_{p204}-$ wherein each of $p^{203}$ and $p^{204}$ is an integer from 1 to 5; and the other groups are each as defined above.

Compounds 82, 84, 87, 89, 92 and 95 can be synthesized according to synthesis route 16.

wherein $M^{13}$ is $-(CH_2)_{p201}-$; $M^{15}$ is $-(CH_2)_{p202}-$ wherein each of $p^{201}$ and $p^{202}$ is an integer from 1 to 5; $M^{14}$ is $-O-$, $-CO-O-$ or $-NY^{27A}-$; and $PRO^4$ represents any of protective group $PRO^1$ for hydroxy, protective group $PRO^2$ for carboxylic acid and protective group $PRO^3$ for amine (e.g., carbamate-based protective groups such as tert-butoxycarbonyl, and benzyl) according to $M^{14}$.

Compound 74 is obtained by any method described in synthesis routes 11 to 13, or a method equivalent thereto.

Compound 75 is obtained by appropriately protecting and deprotecting compound 74.

Compound 76 is obtained by any method described in synthesis routes 11 to 13, or a method equivalent thereto with compound 75 as a starting material.

As shown in synthesis route 15, compounds 77 to 79 can be obtained by performing protection and deprotection, and a method equivalent to synthesis route 14 in order with compound 76 as a starting material.

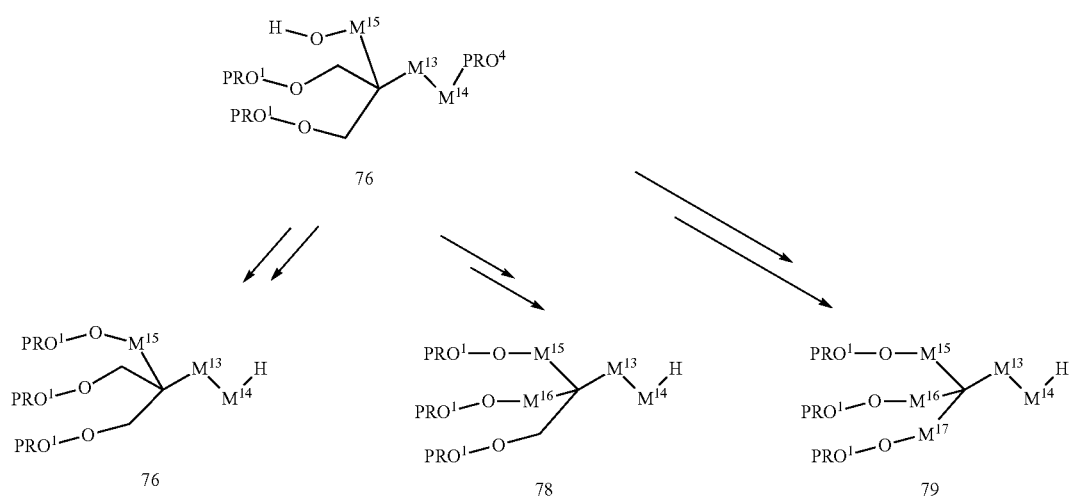

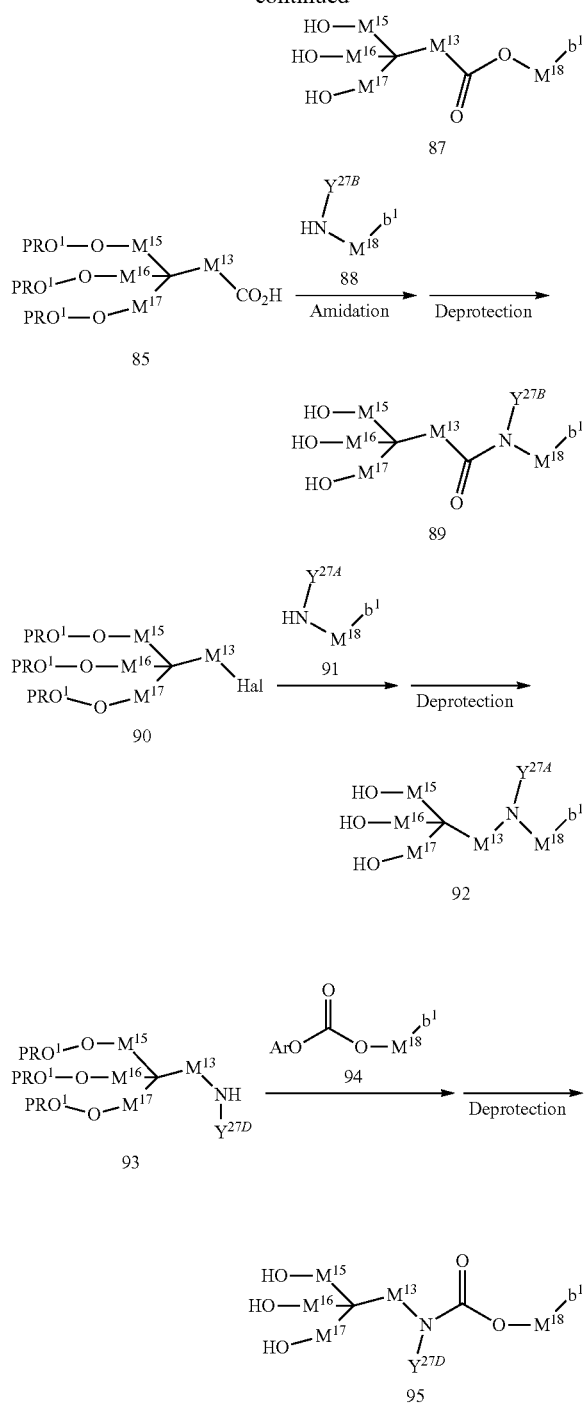

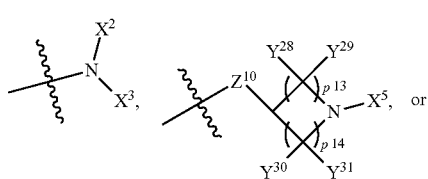

wherein $M^{18}$ is —$(CY^{19}Y^{20})_{p9}$— or —$(CY^{23}Y^{24})_{p11}$—$Z^9$—$(CY^{25}Y^{26})_{p12}$—; $b^1$ is

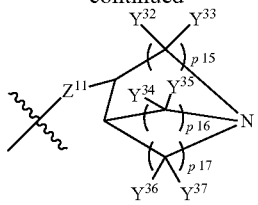

Ar is a p-nitrophenyl group; Hal is a halogen atom such as chlorine, bromine or iodine; the other groups are each as defined above; and when p13 is 0, N is directly bonded to the carbon atom adjacent to $Z^{10}$.

Compound 82 is obtained by condensing compound 80 and compound 81 through esterification, followed by deprotection.

Compound 84 is obtained by condensing compound 83 and compound 81 through amidation, followed by deprotection.

Compound 87 is obtained by condensing compound 85 and compound 86 through esterification, followed by deprotection.

Compound 89 is obtained by condensing compound 85 and compound 88 through amidation, followed by deprotection.

Compound 92 is obtained by subjecting compound 90 and compound 91 to nucleophilic substitution reaction, followed by deprotection.

Compound 95 is obtained by subjecting compound 93 and compound 94 to transesterification reaction, followed by deprotection.

Compounds 80, 83, 85, 90 and 93 can be obtained by synthesis routes 12 to 15 or a method equivalent thereto.

Each of compounds 81, 86, 88, 91 and 94 wherein $M^{18}$ is —$(CY^{19}Y^{20})_{p9}$— can be obtained as a commercially available product, or by a method described in Examples or a method equivalent thereto, or by the conversion of a functional group of a commercially available product according to a conventional method.

In this case, a compound wherein $b^1$ is

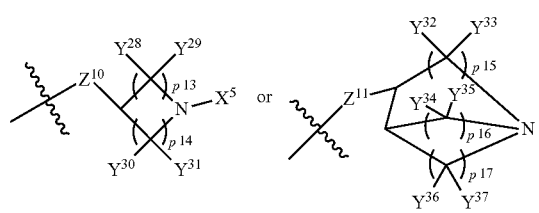

can be obtained by condensing wherein $M^{37}$ is —OH, —$CO_2H$ or $NY^{38}$ (provided that $Y^{38}$ is a hydrogen atom or optionally substituted C1-C4 alkyl)

with each corresponding appropriate fragment through etherification, amination, esterification, amidation or the like.

Compounds 81, 86, 88, 91 and 94 wherein $M^{18}$ is $-(CY^{23}Y^{24})_{p11}-Z^9-(CY^{25}Y^{26})_{p12}-$ can be obtained by condensing the same compound as compound 81, 86, 88, 91 or 94 wherein $M^{18}$ is $-(CY^{19}Y^{20})_{p9}-$ with each corresponding appropriate fragment through etherification, amination, esterification, amidation or the like.

Compound (III) can be obtained by any method of synthesis routes 17 to 21 given below, a method equivalent to the method, or the like.

Compound (IIIa) can be obtained from compound 96 according to synthesis route 17.

Synthesis route 17

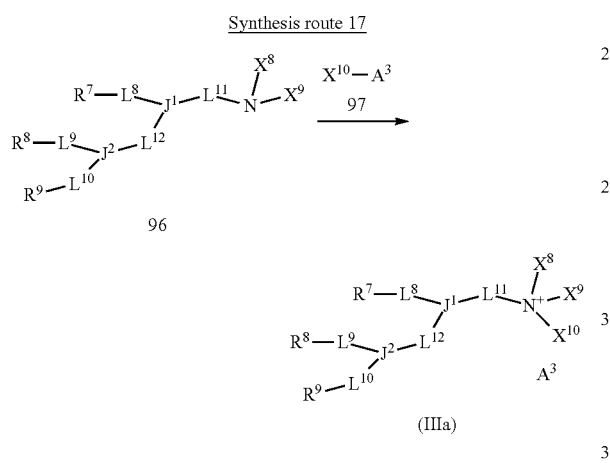

(IIIa)

wherein each group is as defined above.

Compound (IIIa) is obtained by reacting compound 96 with compound 97 in the presence or absence of a solvent (e.g., halogen-based solvents such as chloroform) at room temperature or a high temperature (e.g., 100° C. or higher). Anion $A^3$ of compound (IIIa) may be converted to another anion, for example, by treating the compound (IIIa) with an appropriate anion-exchange resin.

Compound 96 can be obtained by a method described in Examples or a method equivalent thereto, or by a method described in the literature (U.S. Patent Application Publication No. 2012/0172411) or a method equivalent thereto.

Each compound such as compound 97, etc. for use in the reaction can be obtained as a commercially available product, or by a method described in Examples or a method equivalent thereto, or by a known method described in a literature or a method equivalent thereto.

Compound (IIIb) can be obtained from ethyl glyoxylate according to synthesis route 18.

Synthesis route 18

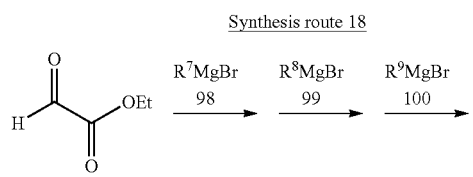

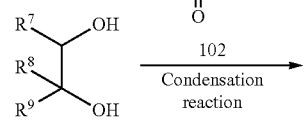

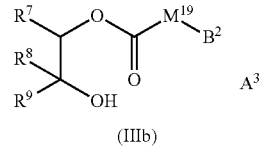

(IIIb)

wherein $M^{19}$ is $-(CY^{50}Y^{51})_{p23}-$ or $-(CY^{54}Y^{55})_{p25}-Z^{17}-(CY^{56}Y^{57})_{p26}-$ (wherein each group is as defined above); $b^2$ is

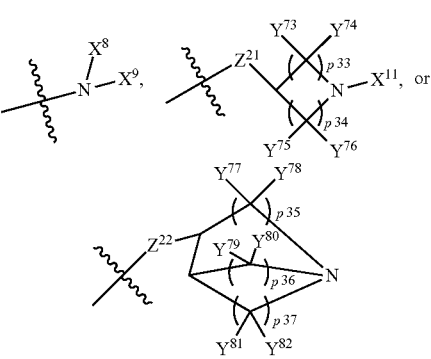

and the other groups are each as defined above; and when p33 is 0, N is directly bonded to the carbon atom adjacent to $Z^{21}$.

Compound 101 is obtained by reacting ethyl glyoxylate with Grignard reagents 98, 99 and 100 in order in a solvent (e.g., ether-based solvents such as tetrahydrofuran). Compound 101 wherein $R^7$, $R^8$ and $R^9$ are the same is also obtained by allowing excessive compound 98 to act on ethyl glyoxylate.

Compound 103 is obtained by treating compound 101 and compound 102 with a base (e.g., organic bases such as triethylamine), a condensing agent (e.g., condensing agents such as 1-ethyl-3-(3-dimethylaminopropyl)carbodiimide hydrochloride) and an activator (activators such as N,N-dimethylaminopyridine) in a solvent (e.g., halogen-based solvents such as chloroform).

Compound (IIIb) is obtained by reacting compound 103 with compound 97, 104 or 105 in the presence or absence of a solvent (e.g., halogen-based solvents such as chloroform) at room temperature or a high temperature (e.g., 100° C. or higher). Anion $A^3$ of compound (IIIb) may be converted to another anion, for example, by treating the compound (IIIb) with an appropriate anion-exchange resin.

Compound 98 is obtained by allowing a mesylation reagent (mesyl anhydride or mesyl chloride, etc.), a bromide (magnesium bromide or lithium bromide, etc.), and metal magnesium in order to act on $R^7$—OH (which is a commercially available product or is obtained by a method described in Examples or a method equivalent thereto). Compounds 99 and 100 are obtained in the same way as in compound 98.

Compounds 104 and 105 are obtained in the same way as in compound 23.

Compound 102 is obtained in the same way as in compound 54.

Compounds 108, 109 and 112 can be obtained from ammonia, ethyl formate and compound 99, respectively according to synthesis route 19.

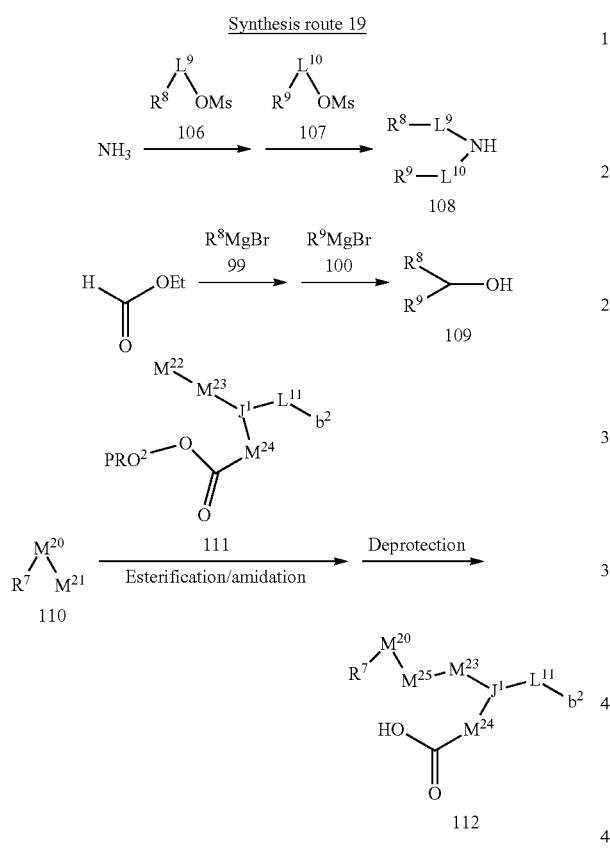

wherein $M^{21}$ is —OH, $M^{22}$ is HO—CO—, and $M^{25}$ is —O—CO—; $M^{21}$ is —$NY^{45C}$—H, $M^{22}$ is HO—CO—, and $M^{25}$ is —$NY^{45C}$—CO—; $M^{21}$ is —CO—OH, $M^{22}$ is HO—, and $M^{25}$ is —CO—O—; or $M^{21}$ is —CO—OH, $M^{22}$ is H—$NY^{14B}$—, and $M^{25}$ is —CO—$NY^{14B}$—; $M^{20}$ is absent, and $M^{23}$ is —$(CY^{39}Y^{40})_{p18}$—; $M^{20}$ is absent, and $M^{23}$ is —$(CY^{41}Y^{42})_{p19}$—$Z^{14}$—$(CY^{43}Y^{44})_{p20}$—; or $M^{20}$ is —$Z^{13}$—$(CY^{41}Y^{42})_{p19}$—, and $M^{23}$ is —$(CY^{43}Y^{44})_{p20}$—; $M^{24}$ is —$(CY^{63}Y^{64})_{p29}$— or —$(CY^{67}Y^{68})_{p31}$—$Z^{20}$—$(CY^{69}Y^{70})_{p32}$—; and the other groups are each as defined above.

Compound 108 is obtained by reacting ammonia with compound 106 and compound 107 by the application of the same reaction conditions as those for the synthesis of compound 4 from ammonia in synthesis route 1.

Compound 109 is obtained by reacting ethyl formate with compound 99 and compound 100 by the application of the same reaction conditions as those for the synthesis of compound 101 from ethyl glyoxylate in synthesis route 18.

Compound 112 can be obtained by condensing compound 110 and compound 111 through esterification or amidation, followed by deprotection.

Compounds 106 and 107 are obtained in the same way as in compound 1.

Compound 110 wherein $M^{21}$ is —OH is obtained in the same way as in $R^1$-$L^1$-OH described in synthesis route 1. Compound 110 wherein $M^{21}$ is —$NY^{45C}$—H is obtained in the same way as in compound 37. Compound 110 wherein $M^{21}$ is —CO—OH is obtained in the same way as in compound 17.

Compound 111 can be obtained as a commercially available product, or by a method described in Examples or a method equivalent thereto, or by a known method described in a literature (e.g., a method described in "The Fourth Series of Experimental Chemistry 20, Synthesis of Organic Compound II", 4th edition, p. 187, Maruzen Co., Ltd. (1992)) or a method equivalent thereto.

Compounds (IIIc) and (IIId) can be obtained from compounds 108 and 112, and compounds 109 and 112, respectively, according to synthesis route 20.

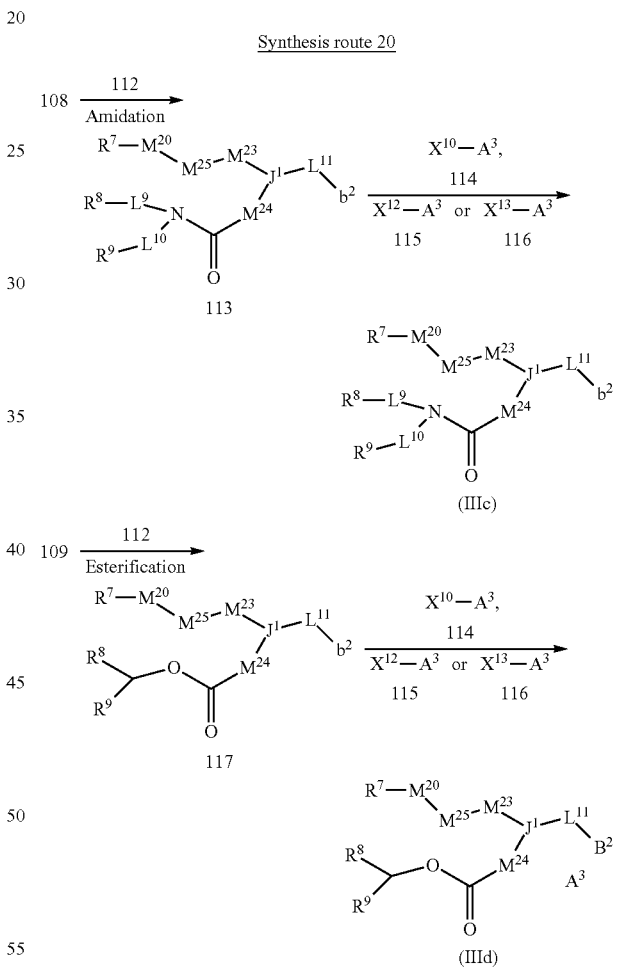

wherein each group is as defined above.

Compound (IIIc) is obtained by condensing compounds 108 and 112 through amidation, and then allowing compound 114, 115, or 116 to act on the condensate.

Compound (IIId) is obtained by condensing compounds 109 and 112 through esterification, and then allowing compound 114, 115, or 116 to act on the condensate.

Anion $A^3$ of compound (IIIc) or (IIId) may be converted to another anion, for example, by treating the compound (IIIc) or (IIId) with an appropriate anion-exchange resin.

Each compound for use in the reactions is as mentioned above.

Compound (IV) can be obtained by any method of synthesis routes 11 and 12 given below, a method equivalent to the method, or the like.

Compound 127 can be obtained according to synthesis route 21.

istry 22, Synthesis of Organic Compound IV", 4th edition, p. 1, Maruzen Co., Ltd. (1992), "The Fourth Series of Experimental Chemistry 20, Synthesis of Organic Compound II", 4th edition, p. 1, Maruzen Co., Ltd. (1992), and "The Fourth Series of Experimental Chemistry 25, Synthesis of Organic Compound VII", 4th edition, p. 59, Maruzen Co., Ltd. (1991)) or a method equivalent thereto.

Synthesis route 21

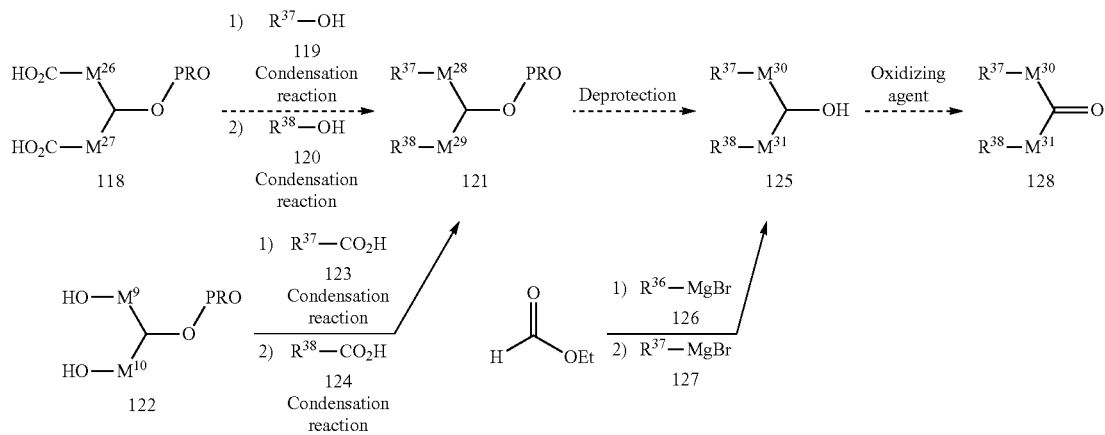

wherein $M^{26}$ and $M^{27}$ are the same or different and are each $-(CY^{91}Y^{92})_{p41}$; $M^{28}$ and $M^{29}$ are the same or different and are each $-O-CO-(CY^{91}Y^{92})_{p41}-$ or $-CO-O-(CY^{91}Y^{92})_{p41}-$; $M^{30}$ and $M^{31}$ are the same or different and are each absent, or $-O-CO-(CY^{91}Y^{92})_{p41}-$ or $-CO-O-(CY^{91}Y^{92})_{p41}-$; and the other groups are each as defined above.

Compound 121 can be obtained by condensing compound 118 with compound 119 and compound 120 in order through esterification reaction, or condensing compound 122 with compound 123 and compound 124 in order through esterification reaction.

Compound 125 can be obtained by allowing a deprotection reagent (e.g., deprotection reagents such as tetra-n-butylammonium fluoride) to act on compound 121 in a solvent (e.g., ether-based solvents such as tetrahydrofuran), or subjecting ethyl formate to addition reaction with compound 126 and compound 127 in order in a solvent (e.g., ether-based solvents such as tetrahydrofuran).

Compound 128 can be obtained by allowing an oxidizing agent (e.g., organic oxidizing agents such as Dess-Martin reagent, and inorganic oxidizing agents such as pyridinium chlorochromate) to act on compound 125 in a solvent (e.g., aprotic solvents such as chloroform).

Each compound such as compound 118, compound 119, compound 120, compound 122, compound 123, compound 124, compound 126 and compound 127, etc. for use in the reaction can be obtained as a commercially available product, or by a method described in Examples or a method equivalent thereto, or by a known method described in a literature (e.g., "The Fourth Series of Experimental Chemistry 22, Synthesis of Organic Compound IV", 4th edition, p. 1, Maruzen Co., Ltd. (1992), "The Fourth Series of Experimental Chemistry 20, Synthesis of Organic Compound II", 4th edition, p. 1, Maruzen Co., Ltd. (1992), and "The Fourth Series of Experimental Chemistry 25, Synthesis of Organic Compound VII", 4th edition, p. 59, Maruzen Co., Ltd. (1991)) or a method equivalent thereto.

Compound (IVa) can be obtained from compound 128 according to synthesis route 22.

Synthesis route 22

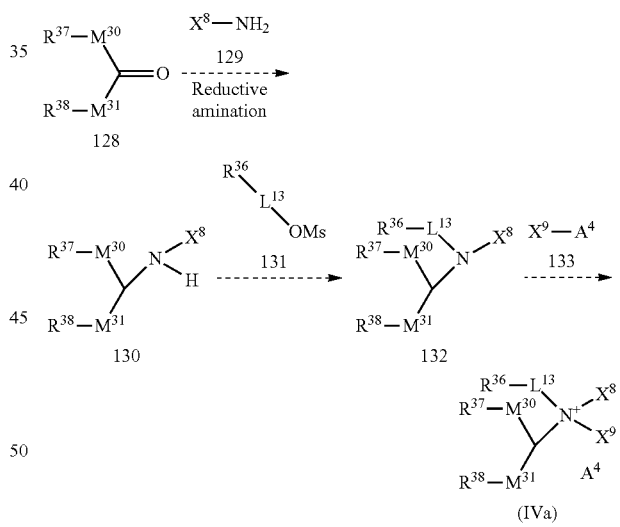

wherein each group is as defined above.

Compound 130 can be obtained by reacting compound 128 with compound 129 in the presence of a reducing agent (e.g., hydride compounds such as sodium borohydride and triacetoxyborohydride) and, in some cases, an additive (e.g., acids such as acetic acid) in a solvent (e.g., halogen-based solvents such as 1,2-dichloroethane).

Compound 132 is obtained by reacting compound 130 with compound 131 in the presence of a base (e.g., inorganic bases such as sodium hydroxide) at a high temperature (e.g., 100° C. or higher). Although no solvent is particularly necessary, a solvent such as ethylene glycol may be used in some cases.

Compound (IVa) is obtained by reacting compound 132 with compound 133 in the presence or absence of a solvent (e.g., halogen-based solvents such as chloroform) at room temperature or a high temperature (e.g., 100° C. or higher). Anion $A^4$ of compound (IVa) may be converted to another anion, for example, by treating the compound (IVa) with an appropriate anion-exchange resin.

Each compound such as compound 129, compound 131 and compound 133, etc. for use in the reaction can be obtained as a commercially available product, or by a method described in Examples or a method equivalent thereto, or by a known method described in a literature (e.g., a method described in WO 2010/042877, WO 2010/054401, or "The Fifth Series of Experimental Chemistry 13, Synthesis of Organic Compound I", 5th edition, p. 374, Maruzen Co., Ltd. (2005)) or a method equivalent thereto.

Compound (IVb) can be obtained according to synthesis route 23.

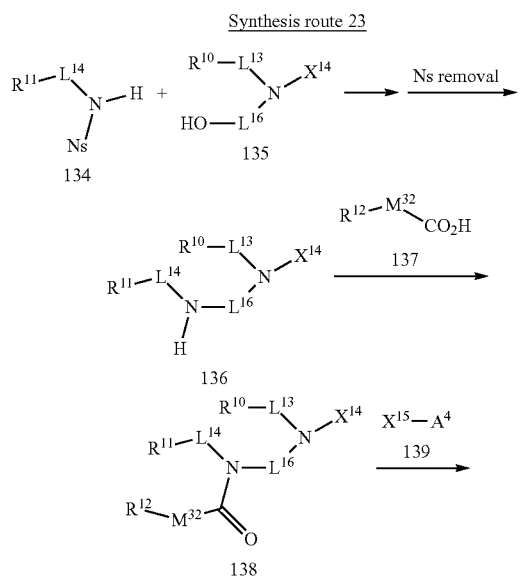

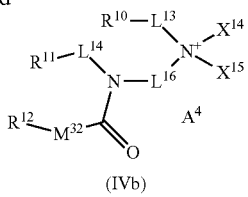

wherein $M^{32}$ is absent, or $-Z^{27}-(CY^{93}Y^{94})_{p42}-$; Ns represents an o-nitrobenzenesulfonyl group; and the other groups are each as defined above.

Compound 136 is obtained by reacting compound 134, compound 135, triphenylphosphine, and diethyl azodicarboxylate, and then removing Ns from the obtained condensate by the action of thiol (e.g., dodecane-1-thiol and thiophenol).

Compound 138 is obtained by amidating compounds 136 and 137.

Compound (IVb) is obtained by allowing compound 139 to act on compound 138. Anion $A^4$ of compound (IVb) may be converted to another anion, for example, by treating the compound (IVb) with an appropriate anion-exchange resin.

Compound 134 is obtained by allowing o-nitrobenzenesulfonyl chloride to act on $R^{11}$-$L^{14}$-$NH_2$. $R^{11}$-$L^{14}$-$NH_2$ can be obtained as a commercially available product, or by a method described in Examples or a method equivalent thereto, or by a known method described in a literature (e.g., a method described in "The Fourth Series of Experimental Chemistry 20, Synthesis of Organic Compound II", 4th edition, p. 279, Maruzen Co., Ltd. (1992)) or a method equivalent thereto.

Each compound such as compounds 135, 137 and 139, etc. for use in the reaction is obtained by any of the methods mentioned above.

Compound (V'a) can be obtained according to synthesis route 24.

Synthesis route 24

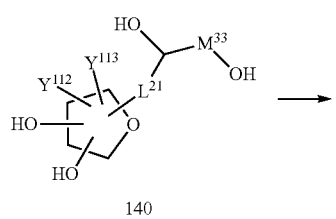

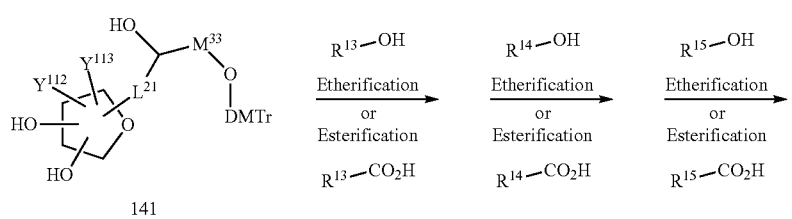

-continued

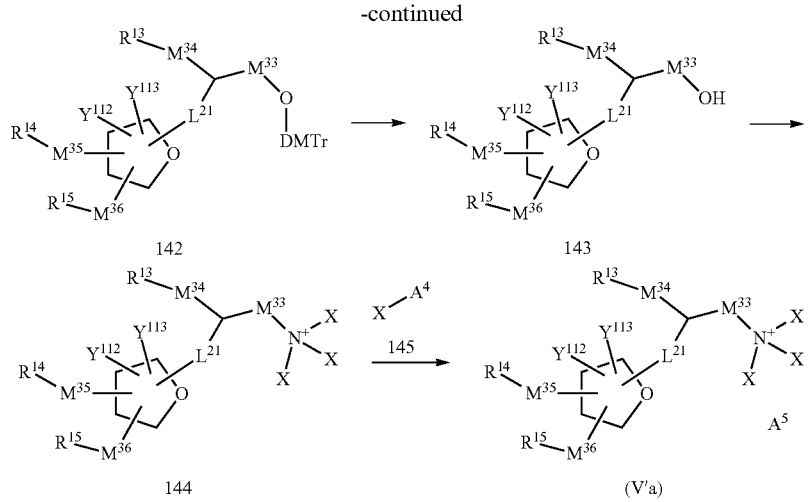

wherein DMTr represents a 2',2''-dimethoxytrityl group; $M^{33}$ represents $-(CY^{123}R^{124})_{p54}-$, $-(CY^{125}Y^{126})_{p55}-Z^{35}-(CY^{127}R^{128})_{p56}-$ or $-(CY^{129}R^{130})_{p57}-Z^{36}-(CY^{131}Y^{132})_{p58}-Z^{37}-(CY^{133}Y^{134})_{p59}-$; $M^{34}$, $M^{35}$ and $M^{36}$ are each independently $-O-$ or $-CO-O-$; and the other groups are each as defined above.

Compound 141 is obtained by allowing 2',2''-dimethoxytrityl chloride to act on compound 140.

Compound 142 is obtained by etherifying or esterifying compound 141 at 3 stages.

Compound 143 is obtained by treating compound 142 with an acid.

Compound 144 is obtained by activating compound 143 with a halogenation reagent, followed by treatment with a corresponding amine compound.

Compound (V'a) is obtained by allowing compound 145 to act on compound 144. Anion $A^5$ of compound (V'a) may be converted to another anion, for example, by treating the compound (V'a) with an appropriate anion-exchange resin.

Compound 140 can be obtained as a commercially available product, as a natural product, or by a method described in Examples or a method equivalent thereto, or by a known method described in a literature (e.g., a method described in "The Organic Chemistry of Sugars", Daniel E. Levy, et al. ed., Taylor & Francis Group, 2005) or a method equivalent thereto.

Compound (V''a) can be obtained in the same way as in synthesis route 25 with compound 146 as a starting material.

Synthesis route 25

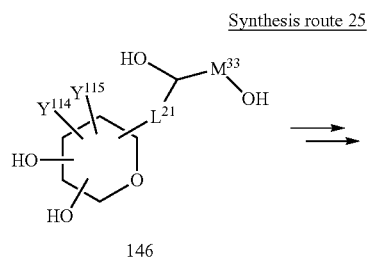

-continued

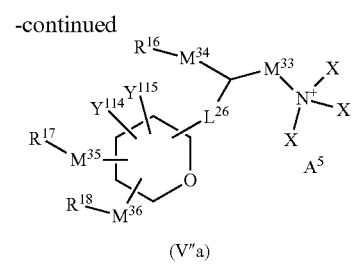

wherein each group is as defined above.

Compound 146 can be obtained as a commercially available product, as a natural product, or by a method described in Examples or a method equivalent thereto, or by a known method described in a literature (e.g., a method described in "The Organic Chemistry of Sugars", Daniel E. Levy, et al. ed., Taylor & Francis Group, 2005) or a method equivalent thereto.

Compounds (I) to (V') can be obtained by any method of synthesis routes 1 to 25 described above, or an appropriate combination of methods equivalent to these methods, or the like.

The lipid represented by compound (CL-I) can be obtained by a method described in WO 2013/089151, or a method equivalent thereto.

The lipid represented by compound (CL-II) can be obtained by a method described in WO 2011/136368, or a method equivalent thereto.

The lipids represented by compound (CL-III), compound (CL-IV) and compound (CL-V) can be obtained by a method described in WO 2014/007398, or a method equivalent thereto.

The lipid represented by compound (CL-VI) can be obtained by a method described in WO 2010/042877, or a method equivalent thereto.

Compound (CL-VII) can be obtained by a method described in WO 2010/054401, a method described in WO 2013/059496, or a method equivalent thereto.

Compound (CL-VIII) can be obtained by a method described in WO 2016/002753, or a method equivalent thereto.

Compound (CL-IX) can be obtained by a method described below, or a method equivalent thereto.

Methods for producing the compound of the present invention will be described. In the production methods shown below, if defined groups react under conditions of the production methods or are unsuitable for carrying out the production methods, the desired compounds can be produced by use of introduction and removal methods of protective groups commonly used in organic synthetic chemistry [e.g., methods described in Protective Groups in Organic Synthesis, third edition, T. W. Greene, John Wiley & Sons Inc. (1999)] or the like. If necessary, the order of reaction steps including substituent introduction or the like may be changed.

Production Method 1

Compounds (CL-IX) wherein both of $X^{115}$ and $X^{116}$ are hydrogen atoms, that is, compound (CL-IXa), and wherein $X^{115}$ and $X^{116}$ are the same, that is, compound (CL-IXb), can be produced by the following method:

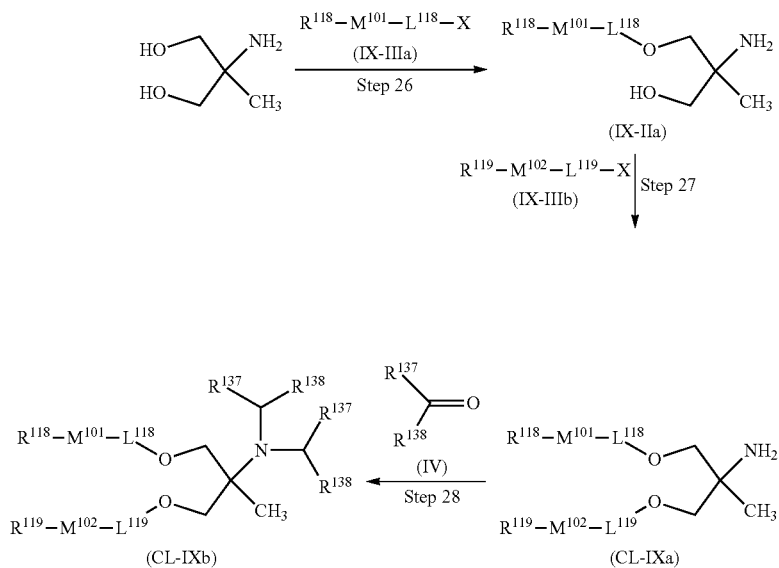

wherein $R^{118}$, $R^{119}$, $M^{101}$, $M^{102}$, $L^{118}$ and $L^{119}$ are each as defined above; X in IX-IIIa and X in IX-IIIb are the same or different and are each a leaving group such as a chlorine atom, a bromine atom, an iodine atom, trifluoromethanesulfonyloxy, methanesulfonyloxy, benzenesulfonyloxy or p-toluenesulfonyloxy; $R^{141}$ is a hydrogen atom, methyl or ethyl; and $R^{142}$ is a hydrogen atom or methyl, or $R^{141}$ and $R^{142}$ form a cyclopropyl ring together with the adjacent carbon (provided that when $R^{141}$ is a hydrogen atom or ethyl, $R^{142}$ is not methyl.

Steps 26 and 27

Compound (IX-IIa) can be produced by reacting compound (IX-IIIa) with 2-amino-2-methyl-1,3-propanediol at a temperature between room temperature and 200° C. for 5 minutes to 100 hours in the presence of 1 to 10 equivalents of a base without a solvent or in a solvent. Compound (CL-IXa) can be produced by reacting compound (IX-IIa) with compound (IX-IIIb) at a temperature between room temperature and 200° C. for 5 minutes to 100 hours in the presence of 1 to 10 equivalents of a base without a solvent or in a solvent.

Examples of the solvent include dichloromethane, 1,2-dichloroethane, toluene, diethyl ether, tetrahydrofuran, 1,2-dimethoxyethane, 1,4-dioxane and pyridine. These solvents can be used alone or as a mixture.

Examples of the base include sodium methoxide, potassium tert-butoxide, sodium hydride, lithium diisopropylamide, lithium hexamethyldisilazane, sodium hexamethyldisilazane and n-butyllithium.

Compound (IX-IIIa) and compound (IX-IIIb) can each be obtained as a commercially available product or by a method known in the art (e.g., "The Fifth Series of Experimental Chemistry 13, Synthesis of Organic Compound I", 5th edition, p. 374, Maruzen Co., Ltd. (2005)) or a method equivalent thereto.

When $R^{118}$-$M^{101}$-$L^{118}$ and $R^{119}$-$M^{102}$-$L^{119}$ are the same, compound (CL-IXa) can be obtained by using 2 equivalents or more of compound (IX-IIIa) in step 26.

2-Amino-2-methyl-1,3-propanediol can be obtained as a commercially available product.

Step 28 Compound (CL-IXb) can be produced by reacting compound (CL-IXa) with 2 to 20 equivalents of compound (IX-IV) at a temperature between −20° C. and 150° C. for 5 minutes to 72 hours in the presence of preferably 1 equivalent to a large excess of a reducing agent and, if necessary, preferably 1 to 10 equivalents of an acid, in a solvent.

Examples of the solvent include methanol, ethanol, tert-butyl alcohol, dichloromethane, chloroform, 1,2-dichloroethane, toluene, ethyl acetate, acetonitrile, diethyl ether, tetrahydrofuran, 1,2-dimethoxyethane, 1,4-dioxane, N,N-dimethylformamide, N,N-dimethylacetamide, ti-methylpyrrolidone and water. These solvents are used alone or as a mixture.

Examples of the reducing agent include sodium triacetoxyborohydride and sodium cyanoborohydride.

Examples of the acid include hydrochloric acid and acetic acid.

Compound (IX-IV) can be obtained as a commercially available product.

Production Method 2

Compounds (CL-IX) wherein $X^{115}$ and $X^{116}$ are different, that is, compounds (CL-IXc) and (CL-IXd), can be produced by the following method:

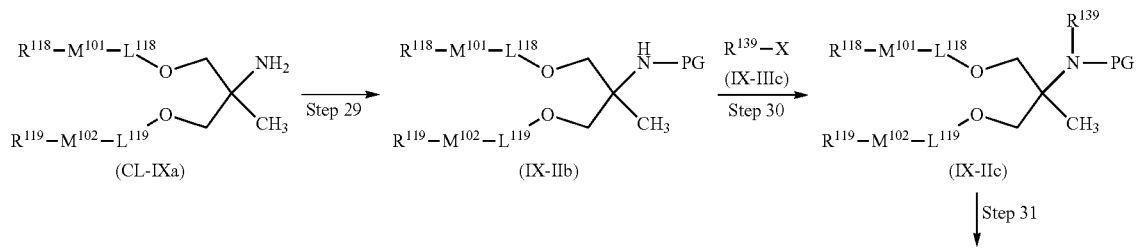

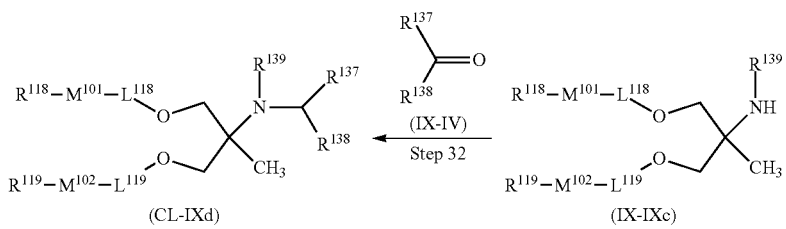

wherein $R^{118}$, $R^{119}$, $M^{101}$, $M^{102}$, $L^{118}$, $L^{119}$, $R^{141}$, $R^{142}$ and X are each as defined above; $R^{143}$ is as defined in $X^{115}$; and PC represents a protective group.

Step 29

Compound (IX-IIb) can be produced by protecting compound (CL-IXa) by a protective group commonly used in organic synthetic chemistry [e.g., protective groups described in Protective Groups in Organic Synthesis, third edition, T. W. Greene, John Wiley & Sons Inc.].

Step 30

Compound (IX-IIc) can be produced by reacting compound (IX-IIb) with compound (IX-IIIc) at a temperature between −20° C. and 150° C. for 5 minutes to 72 hours in the presence of 1 to 10 equivalents of a base without a solvent or in a solvent.

Examples of the solvent include dichloromethane, 1,2-dichloroethane, toluene, diethyl ether, tetrahydrofuran, 1,2-dimethoxyethane, 1,4-dioxane, pyridine, N,N-dimethylformamide and N,N-dimethylacetamide. These solvents can be used alone or as a mixture.

Examples of the base include sodium methoxide, potassium tert-butoxide, sodium hydride, lithium diisopropylamide, lithium hexamethyldisilazane, sodium hexamethyldisilazane, n-butyllithium, potassium carbonate, cesium carbonate and triethylamine.

Compound (IX-IIIc) can be obtained as a commercially available product.

Step 31

Compound (CL-IXc) is obtained by removing the protective group PG on compound (IX-IIc) by an appropriate method. Methods for removing protective groups commonly used in organic synthetic chemistry [e.g., removal methods described in Protective Groups in Organic Synthesis, third edition, T. W. Greene, John Wiley & Sons Inc. (1999)] can be used as the protective group removal method. The compound of interest can thereby be produced.

Step 32

Compound (CL-IXd) can be produced by reacting compound (CL-IXc) with 1 to 10 equivalents of compound (IX-IV) at a temperature between −20° C. and 150° C. for 5 minutes to 72 hours in the presence of preferably 1 equivalent to a large excess of a reducing agent and, if necessary, preferably 1 to 10 equivalents of an acid in a solvent.

Examples of the solvent, the reducing agent and the acid include those listed in step 28.

Production Method 3

Compounds (CL-IX) wherein each of $M^{101}$ and $M^{102}$ is —OC(O)—, that is, compounds (CL-IXc') and (CL-IXd'), can also be produced by the following method:

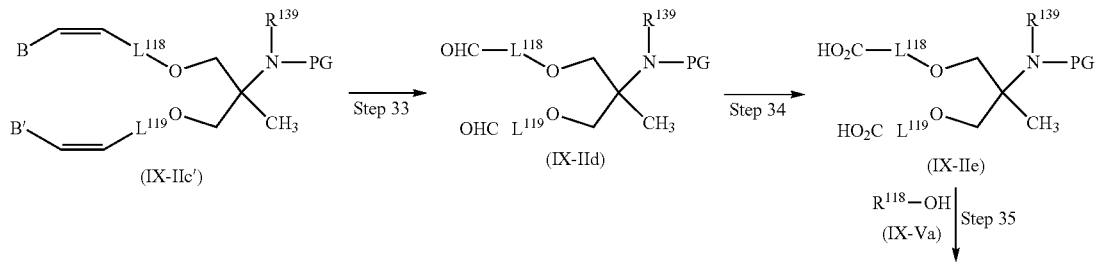

-continued

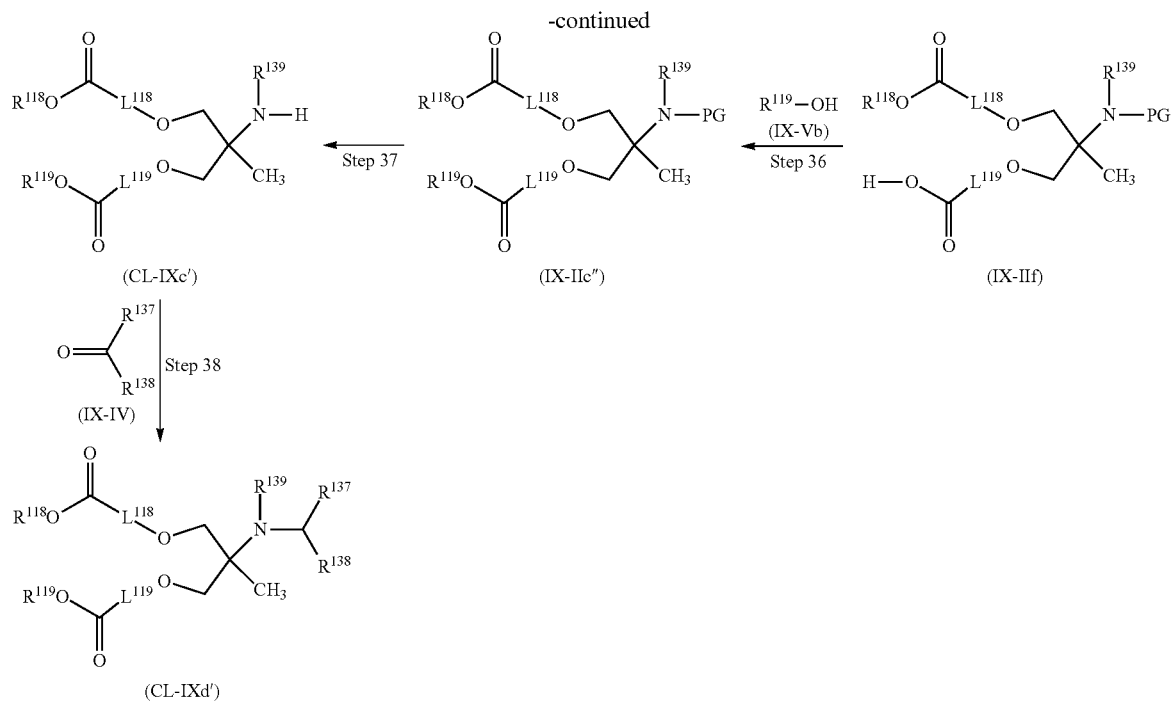

(CL-IXc') (IX-IIc'') (IX-IIf)

(IX-IV)

(CL-IXd')

wherein $R^{118}$, $R^{119}$, $M^{101}$, $M^{102}$, $L^{118}$, $L^{119}$, $R^{141}$, $R^{142}$, $R^{143}$ and PG are each as defined above; and each of B and B' is linear or branched C1-C16 alkyl or C2-C16 alkenyl.

Step 33

Compound (IX-IId) can be produced by reacting compound (IX-IIc') with an oxidizing agent at a temperature between −20° C. and 150° C. for 5 minutes to 72 hours in a solvent.

Examples of the oxidizing agent include ozone, osmium tetroxide/sodium periodate and osmium tetroxide/lead tetraacetate.

Examples of the solvent include those listed in step 28.

Compound (IX-IIc') can be produced by the method described in Production Method 2.

Step 34

Compound (IX-IIe) can be produced by reacting compound (IX-IId) with an oxidizing agent at a temperature between −20° C. and 150° C. for 5 minutes to 72 hours in a solvent.

Examples of the oxidizing agent include Jones reagent, pyridinium dichromate, ruthenium tetroxide and sodium chlorite.

Examples of the solvent include tert-butyl alcohol, dichloromethane, chloroform, 1,2-dichloroethane, toluene, ethyl acetate, acetone, acetonitrile, diethyl ether, tetrahydrofuran, 1,2-dimethoxyethane, 1,4-dioxane, N,N-dimethylformamide, N,N-dimethylacetamide, N-methyl pyrrolidone and water. These solvents can be used alone or as a mixture.

Steps 35 and 36

Compound (IX-IIf) can be produced by reacting compound (IX-IIe) with compound (IX-Va) at a temperature between room temperature and 200° C. for 5 minutes to 100 hours in the presence of 1 to 10 equivalents of a condensing agent and 1 to 10 equivalents of a base without a solvent or in a solvent. Compound (IX-IIc'') can be produced by reacting compound (IX-IIf) with compound (IX-Vb) at a temperature between room temperature and 200° C. for 5 minutes to 100 hours in the presence of 1 to 10 equivalents of a condensing agent and 1 to 10 equivalents of a base without a solvent or in a solvent.

Examples of the solvent include dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methyl pyrrolidone and pyridine. These solvents can be used alone or as a mixture.

Examples of the condensing agent include 1-ethyl-3-(3-dimethylaminopropyl)carbodiimide hydrochloride, N,N'-dicyclohexylcarbodiimide, 4-(4,6-dimethoxy-1,3,5-triazin-2-yl)-4-methylmorpholinium chloride n hydrate, 1H-benzotriazol-1-yloxytris(dimethylamino)phosphonium hexafluorophosphate and O-(7-azabenzotriazol-1-yl)-N,N,N',N'-tetramethyluronium hexafluorophosphate.

Examples of the base include potassium carbonate, cesium carbonate, triethylamine, N,N-diisopropylethylamine, N-methylmorpholine and pyridine.

Each of compound (IX-Va) and compound (IX-Vb) can be obtained as a commercially available product.

Compound (IX-IIc'') wherein $R^{118}$ and $R^{119}$ are the same can be obtained by using 2 or more equivalents of compound (IX-Va) in step 35.

Step 37

Compound (CL-IXc') is obtained by removing the protective group PC on compound (IX-IIc'') by appropriate methods. Methods for removing protective groups commonly used in organic synthetic chemistry [e.g., removal methods described in Protective Groups in Organic Synthesis, third edition, T. W. Greene, John Wiley & Sons Inc. (1999) or the like] can be used as the protective group removal methods, and thus, the compound of interest can be produced.

Step 38

Compound (CL-IXd') can be produced by reacting compound (CL-IXc') with 1 to 10 equivalents of compound (IX-IV) at a temperature between −20° C. and 150° C. for 5 minutes to 72 hours in the presence of preferably 1 equivalent to a large excess of a reducing agent and, if necessary, preferably 1 to 10 equivalents of an acid in a solvent.

Examples of the solvent and the acid include those listed in step 28.

Among compounds (CL-IX), compounds other than compounds (CL-IXa) to (CL-IXd) described above can be produced according to the production methods described above or by the application of general production methods commonly used in organic synthetic chemistry, by adopting starting materials, reagents, or the like suitable for the structures of the compounds of interest.

The intermediates and the desired compounds in the production methods described above can each be isolated and purified by separation and purification methods commonly used in organic synthetic chemistry, for example, filtration, extraction, washing, drying, concentration, recrystallization, various chromatography techniques, or the like. Alternatively, each intermediate may be subjected to the next reaction without being particularly purified.

$R^{115}$ and $R^{116}$ are the same or different and are each a hydrogen atom or C1-C3 alkyl.

$R^{115}$ and $R^{116}$ are the same or different and are each preferably a hydrogen atom, methyl, ethyl or propyl, more preferably a hydrogen atom or methyl.

The combination ($R^{115}, R^{116}$) is preferably (a hydrogen atom, a hydrogen atom), (a hydrogen atom, methyl) or (methyl, methyl), more preferably (a hydrogen atom, methyl) or (methyl, methyl).

$L^{118}$ and $L^{119}$ are the same or different and are each linear or branched C8-C24 alkylene or C8-C24 alkenylene.

When $L^{118}$ and $L^{119}$ are the same or different and are each alkylene, the alkylene is preferably linear C8-C24 alkylene, more preferably linear C8-C20 alkylene, further preferably linear C8-C12 alkylene.

$L^{118}$ and $L^{119}$ are the same or different and are each preferably octylene, nonylene, undecylene, tridecylene or pentadecylene, more preferably octylene, nonylene or undecylene.

When $L^{118}$ and $L^{119}$ are the same or different and are each alkenylene, the alkenylene is preferably linear C8-C24 alkenylene, more preferably linear C10-C20 alkenylene, further preferably linear C10-C12 alkenylene.

$L^{118}$ and $L^{119}$ are the same or different and are each preferably (Z)-undec-9-enylene, (Z)-tridec-11-enylene, (Z)-tetradec-9-enylene, (Z)-hexadec-9-enylene, (Z)-octadec-9-enylene, (Z)-octadec-11-enylene or (9Z,12Z)-octadeca-9,12-dienylene.

$L^{118}$ and $L^{119}$ are preferably the same.

$M^{101}$ and $M^{102}$ are the same or different and are each —C=C—, —OC(O)—C(O)O—, —SC(O)—C(O)S—, —OC(S)—, —C(S)O—, —SS—, —C(R")=N—, —N=C(R")—, —C(R")=N—O—, —O—N=C(R")—, —N(R")C(O)—C(O)N(R")—N(R")C(S)—C(S)N(R")—, —N(R")C(O)N(R'")—, —N(R³)C(O)O—, —OC(O)N(R")— or —OC(O)O—.

$M^{101}$ and $M^{102}$ are the same or different and are each preferably —C=C—, —OC(O)—, —C(O)O—, —C(O)(NR")—, —N(R")C(O)—, —N(R")C(O)—, —N(R")C(O)N(R'")—, —N(R")C(O)O—, —OC(O)N(R")— or —OC(O)O—, more preferably —C=C—, —OC(O)— or —C(O)O—.

Bonds in the structures of $M^{101}$ and $M^{102}$ mean a structure of $R^{118}$—OC(O)-$L^{118}$ when —OC(O)— is taken as an example.

$M^{101}$ and $M^{102}$ are preferably the same.

R" and R'" in $M^{101}$ and $M^{102}$ are the same or different and are each a hydrogen atom or C1-C3 alkyl.

Each of R" and R'" is preferably a hydrogen atom, methyl, ethyl or propyl, more preferably a hydrogen atom or methyl, further preferably a hydrogen atom.

$R^{118}$ and $R^{119}$ are the same or different and are each linear or branched C1-C16 alkyl or C2-C16 alkenyl.

When $R^{118}$ and $R^{119}$ are the same or different and are each alkyl, the alkyl is preferably linear C1-C16 alkyl, more preferably linear C2-C9 alkyl.

$R^{118}$ and $R^{119}$ are the same or different and are each preferably pentyl, octyl, nonyl, decyl or dodecyl.

When $R^{118}$ and $R^{119}$ are the same or different and are each alkenyl, the alkenyl is preferably linear C2-C16 alkenyl, more preferably linear C3-C9 alkenyl.

$R^{118}$ and $R^{119}$ are the same or different and are each preferably (Z)-hept-2-ene, (Z)-oct-2-ene, (Z)-non-2-ene, (Z)-non-3-ene, non-8-ene, (Z)-dodec-2-ene or (Z)-tridec-2-ene.

$R^{118}$ and $R^{119}$ are preferably the same.

$R^{118}$-$M^{101}$-$L^{118}$ and $R^{119}$-$M^{102}$-$L^{119}$ are the same or different, $R^{118}$ and $R^{119}$, $M^{101}$ and $M^{102}$, or $L^{118}$ and $L^{119}$ may be a combination selected from the structures described about each group.

$R^{118}$-$M^{101}$-$L^{118}$ and $R^{119}$-$M^{102}$-$L^{119}$ are preferably the same.

$R^{118}$-$M^{101}$-$L^{118}$ and $R^{119}$-$M^{102}$-$L^{119}$ are the same or different and are each preferably selected from the group consisting of (Z)-tetradec-9-enyl, (Z)-hexadec-9-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl and (Z)-docos-13-enyl, more preferably selected from the group consisting of (Z)-hexadec-9-enyl, (Z)-octadec-9-enyl, (9Z,12Z)-octadeca-9,12-dienyl and (11Z,14Z)-icosa-11,14-dienyl.

$R^{118}$-$M^{101}$-$L^{118}$ and $R^{119}$-$M^{102}$-$L^{119}$ are the same or different and are each preferably any of the following structures (1) to (5), more preferably are the same and any of the following structures (1) to (5):

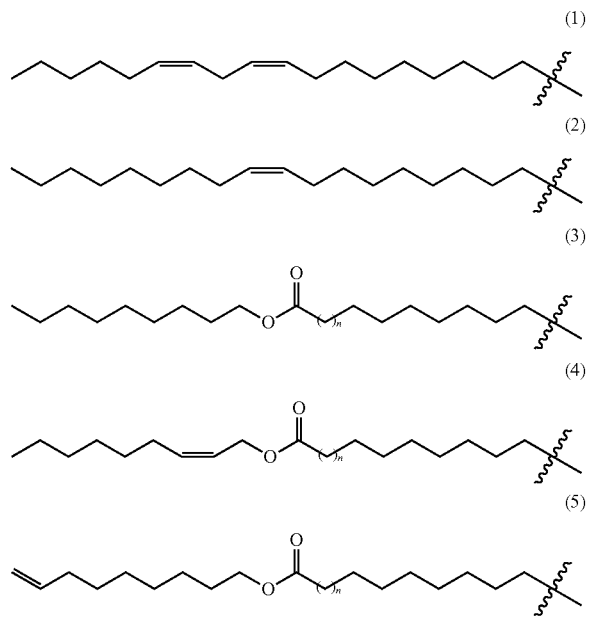

wherein n is an integer from 1 to 4.

The lipid represented by compound (CL-X) can be obtained by a method described in WO 2009/129385, or a method equivalent thereto.

The lipid represented by compound (CL-XI) can be obtained by a method described in WO 2013/1491401, or a method equivalent thereto.

The lipid represented by compound (CL-XII) can be obtained by a method described in WO 2009/129395, or a method equivalent thereto.

The lipid represented by compound (CL-XIII) can be obtained by a method described in WO 2013/059496, or a method equivalent thereto.

The lipid represented by compound (CL-XIV) can be obtained by a method described in WO 2011/149733, or a method equivalent thereto.

The lipid represented by formula (CL-XV) can be obtained by a method described in WO 2011/153493, or a method equivalent thereto.

The lipid represented by formula (CL-XVI) can be obtained by a method described in WO 2015/074085, or a method equivalent thereto.

The lipid represented by formula (CL-XVII) can be obtained by a method described in WO 2012/170952, or a method equivalent thereto.

The lipid represented by formula (CL-XVIII) can be synthesized according to methods given below.

Examples of the method for synthesizing the lipid represented by formula (CL-XVIII) include Synthesis Method I for formula (CL-XVIII) and Synthesis Method II for formula (CL-XVIII) given below.

(Synthesis Method I for Formula (CL-XVIII))

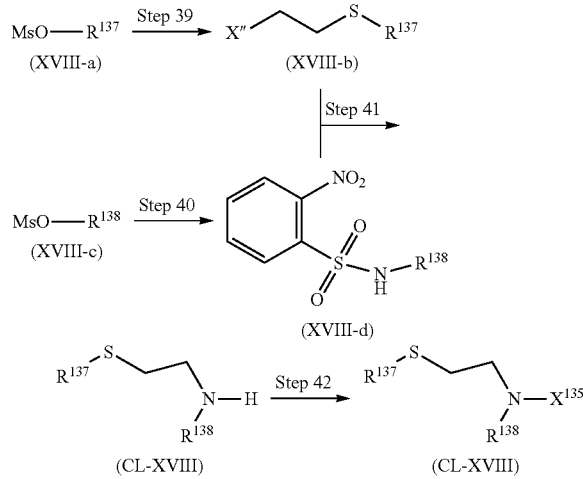

wherein $R^{137}$, $R^{138}$ and $X^{135}$ are each as defined above; Ms in compound (XVIII-a) and compound (XVIII-c) represents a methanesulfonyl group; and X" represents a halogen atom.

Step 39

Compound (XVIII-b) can be obtained by subjecting compound (XVIII-a) and 2-mercaptoethanol to thioetherification reaction for 5 minutes to 100 hours in the presence of 1 to 10 equivalents of a base without a solvent or in a solvent to obtain an alcohol compound, followed by the halogenation reaction of the alcohol. The halogenation reaction is preferably chlorination. Examples thereof can include a method of reaction with methanesulfonyl chloride for 5 minutes to 100 hours in the presence of 1 to 10 equivalents of a base without a solvent or in a solvent.

Examples of the solvent include methanol, ethanol, tert-butyl alcohol, dichloromethane, chloroform, 1,2-dichloroethane, toluene, ethyl acetate, acetonitrile, diethyl ether, tetrahydrofuran, 1,2-dimethoxyethane, 1,4-dioxane, N,N-dimethylformamide, N,N-dimethylacetamide, ti-methylpyrrolidone and water. These solvents are used alone or as a mixture.

Examples of the base include cesium carbonate, triethylamine, sodium methoxide, potassium tert-butoxide, sodium hydride, lithium diisopropylamide, lithium hexamethyldisilazane, sodium hexamethyldisilazane and n-butyllithium.

Compound (XVIII-a) may be obtained as a commercially available product or by a method known in the art (e.g., "The Fifth Series of Experimental Chemistry 13, Synthesis of Organic Compound I", 5th edition, p. 374, Maruzen Co., Ltd. (2005)) or a method equivalent thereto.

Step 40

Compound (XVIII-d) can be produced by reacting compound (XVIII-c) with N-(tert-butoxycarbonyl)-2-nitrobenzenesulfonamide at a temperature between −20° C. and 150° C. for 5 minutes to 72 hours in the presence of a base without a solvent or in a solvent to obtain a carbamate intermediate, and then reacting the intermediate with an acid at a temperature between −20° C. and 150° C. for 5 minutes to 72 hours without a solvent or in a solvent.

A phase transfer catalyst such as tetrabutylammonium iodide may be used at the stage of reacting compound (XVIII-c) with N-(tert-butoxycarbonyl)-2-nitrobenzenesulfonamide.

Examples of the solvent include the same solvents as in step 39.

Examples of the base include the same bases as in step 39.

Examples of the acid include hydrochloric acid, acetic acid and trifluoroacetic acid.

Compound (XVIII-c) may be obtained as a commercially available product or by a method known in the art (e.g., "The Fifth Series of Experimental Chemistry 13, Synthesis of Organic Compound I", 5th edition, p. 374, Maruzen Co., Ltd. (2005)) or a method equivalent thereto.

Step 41

A lipid represented by formula (CL-XVIII) wherein $X^{135}$ is a hydrogen atom can be obtained by reacting compound (XVIII-b) with compound (XVIII-d) at a temperature between −20° C. and 150° C. for 5 minutes to 72 hours in the presence of a base without a solvent or in a solvent.

A phase transfer catalyst such as tetrabutylammonium iodide may be used in the reaction of compound (XVIII-b) with compound (XVIII-d).

Step 42

A lipid represented by formula (CL-XVIII) wherein $X^{135}$ is any of C1-C3 alkyl, hydroxy C2-C4 alkyl, formula (C), formula (D) and formula (E) can be obtained by performing N-alkylation, N-carbonylation, N-acylation or N-sulfonylation reaction by use of a method known in the art (e.g., "The Fifth Series of Experimental Chemistry 13, Synthesis of Organic Compound I", 5th edition, p. 374, Maruzen Co., Ltd. (2005)) or a method equivalent thereto.

(Synthesis Method II for Formula (CL-XVIII))

A lipid represented by formula (CL-XVIII) wherein $R^{138}$ is C8-C24 alkynyl C8-C24 alkylthioethyl, C8-24 alkenylthioethyl or C8-C24 alkynylthioethyl can be suitably produced by Synthesis Method II for formula (CL-XVIII).

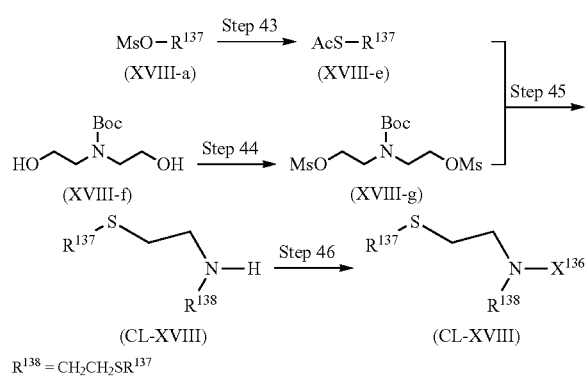

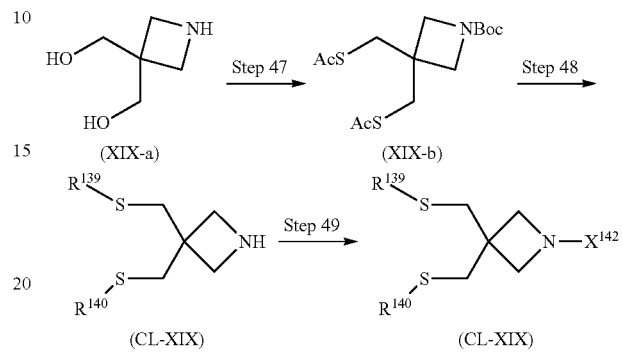

wherein $R^{137}$ and $X^{135}$ are each as defined above; $R^{138}$ is C8-C24 alkynyl C8-C24 alkylthioethyl, C8-24 alkenylthioethyl or C8-C24 alkynylthioethyl; Ms in compound (XVIII-a) and compound (XVIII-g) represents a methanesulfonyl group; and Boc represents a benzyloxycarbonyl group.

Step 43

Compound (XVIII-e) can be obtained by reacting compound (XVIII-a) with S-potassium thioacetate at a temperature between −20° C. and 150° C. for 5 minutes to 72 hours without a solvent or in a solvent.

Examples of the solvent include methanol, ethanol, tert-butyl alcohol, dichloromethane, chloroform, 1,2-dichloroethane, toluene, ethyl acetate, acetonitrile, diethyl ether, tetrahydrofuran, 1,2-dimethoxyethane, 1,4-dioxane, N,N-dimethylformamide, N,N-dimethylacetamide, ti-methylpyrrolidone and water. These solvents are used alone or as a mixture.

Step 44

Compound (XVIII-g) can be obtained by reacting compound (XVIII-f) with methanesulfonyl chloride at a temperature between −20° C. and 150° C. for 5 minutes to 72 hours in the presence of a base without a solvent or in a solvent.

Examples of the solvent include the same solvents as in step 43.

Examples of the base include cesium carbonate, triethylamine, sodium methoxide, potassium tert-butoxide, sodium hydride, lithium diisopropylamide, lithium hexamethyldisilazane, sodium hexamethyldisilazane and n-butyllithium.

Step 45

A lipid represented by formula (CL-XVIII) wherein $X^{135}$ is a hydrogen atom can be obtained by reacting compound (XVIII-e) with compound (XVIII-g) at a temperature between −20° C. and 150° C. for 5 minutes to 72 hours in the presence of a base without a solvent or in a solvent to obtain thioether, and then eliminating the Boc group through reaction at a temperature between −20° C. and 150° C. for 5 minutes to 72 hours in the presence of an acid without a solvent or in a solvent Examples of the solvent include the same solvents as in step 43.

Examples of the base include the same bases as in step 43.

Examples of the acid include hydrochloric acid, acetic acid and trifluoroacetic acid.

Step 46

Step 46 can be performed in the same way as in step 42 described above.

A lipid represented by formula (CL-XIX) can be synthesized according to methods given below.

Examples of the method for synthesizing the lipid represented by formula (CL-XIX) include Synthesis Method I for formula (CL-XIX) and Synthesis Method II for formula (CL-XIX) given below.

(Synthesis Method I for Formula (CL-XIX))

Synthesis Method I for formula (CL-XIX) is suitable for formula (CL-XIX) wherein $L^{133}$ is S.

wherein $R^{139}$, $R^{140}$ and $X^{142}$ are each as defined above; and Boc in compound (XIX-b) represents a benzyloxycarbonyl group.

Step 47

A dimesyl form is obtained by protecting N in azetidine-3,3-diyl dimethanol (XIX-a) with a Boc group according to a routine method, and then allowing methanesulfonyl chloride to act thereon at a temperature between −20° C. and 150° C. for 5 minutes to 72 hours in the presence of a base without a solvent or in a solvent. Compound (XIX-b) can be obtained by reacting the dimesyl form with S-potassium thioacetate for 5 minutes to 72 hours without a solvent or in a solvent.

Examples of the solvent include methanol, ethanol, tert-butyl alcohol, dichloromethane, chloroform, 1,2-dichloroethane, toluene, ethyl acetate, acetonitrile, diethyl ether, tetrahydrofuran, 1,2-dimethoxyethane, 1,4-dioxane, N,N-dimethylformamide, N,N-dimethylacetamide, N-methylpyrrolidone and water. These solvents are used alone or as a mixture.

Examples of the base include cesium carbonate, triethylamine, sodium methoxide, potassium tert-butoxide, sodium hydride, lithium diisopropylamide, lithium hexamethyldisilazane, sodium hexamethyldisilazane and n-butyllithium.

Step 48

A thioether form can be obtained by allowing $R^{139}$—OMs and $R^{140}$—OMs (wherein Ms is a me thane sulfonyl group) to act on compound (XIX-b) at a temperature between −20° C. and 150° C. for 5 minutes to 72 hours in the presence of a base without a solvent or in a solvent.

A lipid represented by formula (CL-XIX) wherein $X^{142}$ is a hydrogen atom can be obtained by eliminating the Boc group from the obtained thioether form through reaction at a temperature between −20° C. and 150° C. for 5 minutes to 72 hours in the presence of an acid without a solvent or in a solvent Examples of the base include the same bases as in step 47.

Examples of the solvent include the same solvents as in step 47.

Examples of the acid include hydrochloric acid, acetic acid and trifluoroacetic acid.

Step 49

A lipid represented by formula (CL-XIX) wherein $X^{142}$ is any of C1-C3 alkyl, hydroxy C2-C4 alkyl, formula (F) and formula (G) can be obtained by performing N-alkylation, N-carbonylation or N-acylation reaction by use of a method known in the art (e.g., "The Fifth Series of Experimental Chemistry 13, Synthesis of Organic Compound I", 5th edition, p. 374, Maruzen Co., Ltd. (2005)) or a method equivalent thereto.

(Synthesis Method II for Formula (CL-XIX))

Synthesis Method II for formula (CL-XIX) is suitable for formula (CL-XIX) wherein $L^{133}$ is 0.

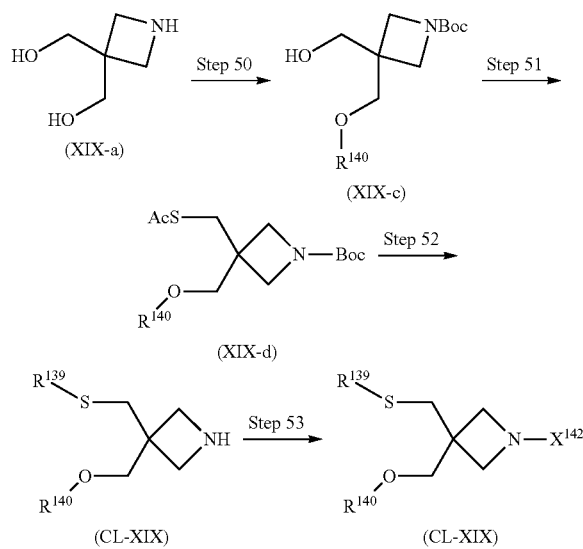

Step 50

Compound (XIX-c) is obtained by protecting N in azetidine-3,3-diyl dimethanol (XIX-a) with a Boc group according to a routine method, and then allowing $R^{140}$—OMs to act thereon at a temperature between −20° C. and 150° C. for 5 minutes to 72 hours in the presence of a base without a solvent or in a solvent.

Examples of the base include cesium carbonate, triethylamine, sodium methoxide, potassium tert-butoxide, sodium hydride, lithium diisopropylamide, lithium hexamethyldisilazane, sodium hexamethyldisilazane and n-butyllithium.

Examples of the solvent include methanol, ethanol, tert-butyl alcohol, dichloromethane, chloroform, 1,2-dichloroethane, toluene, ethyl acetate, acetonitrile, diethyl ether, tetrahydrofuran, 1,2-dimethoxyethane, 1,4-dioxane, N,N-dimethylformamide, N,N-dimethylacetamide, ti-methylpyrrolidone and water. These solvents are used alone or as a mixture.

Step 51

A mesyl form is obtained by allowing methanesulfonyl chloride to act on compound (XIX-c) at a temperature between −20° C. and 150° C. for 5 minutes to 72 hours in the presence of a base without a solvent or in a solvent. Compound (XIX-d) can be obtained by reacting the mesyl form with S-potassium thioacetate for 5 minutes to 72 hours without a solvent or in a solvent.

Examples of the base include the same bases as in step 50.

Examples of the solvent include the same solvents as in step 50.

Step 52

A thioether form can be obtained by allowing $R^{139}$—OMs (wherein Ms is a methanesulfonyl group) to act on compound (XIX-d) at a temperature between −20° C. and 150° C. for 5 minutes to 72 hours in the presence of a base without a solvent or in a solvent.

A lipid represented by formula (CL-XIX) wherein $X^{142}$ is a hydrogen atom can be obtained by eliminating the Boc group from the obtained thioether form through reaction at a temperature between −20° C. and 150° C. for 5 minutes to 72 hours in the presence of an acid without a solvent or in a solvent Examples of the base include the same bases as in step 50.

Examples of the solvent include the same solvents as in step 50.

Examples of the acid include hydrochloric acid, acetic acid and trifluoroacetic acid.

Step 53

Step 53 can be performed in the same way as in step 49 described above.

Specific examples of lipid A according to the present invention will be shown in Tables 16 to 31, though lipid A is not limited thereto.

TABLE 16

| Compound No. | Structural formula |
|---|---|
| I-1 | (structure shown) |
| I-2 | (structure shown) |

TABLE 16-continued
| Compound No. | Structural formula |
|---|---|
| I-3 | 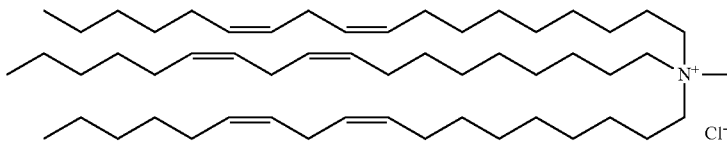 [SMILES: CCCCC/C=C\C/C=C\CCCCCCCC[N+](C)(CCCCCCCC/C=C\C/C=C\CCCCC)CCCCCCCC/C=C\C/C=C\CCCCC ; [Cl-]] |
| I-4 | 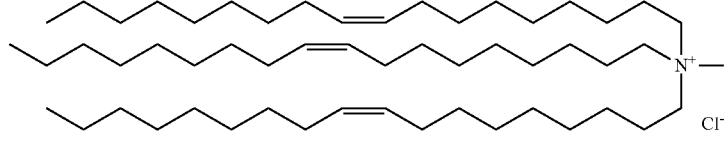 [SMILES: CCCCCCCC/C=C\CCCCCCCC[N+](C)(CCCCCCCC/C=C\CCCCCCCC)CCCCCCCC/C=C\CCCCCCCC ; [Cl-]] |
| I-5 | 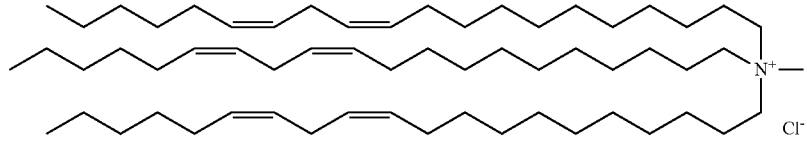 [SMILES: CCCCC/C=C\C/C=C\CCCCCCCCCC[N+](C)(CCCCCCCCCC/C=C\C/C=C\CCCCC)CCCCCCCCCC/C=C\C/C=C\CCCCC ; [Cl-]] |
| I-6 | 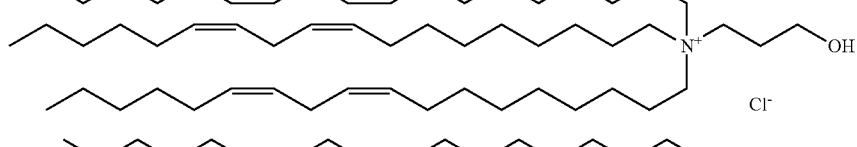 |
| I-7 | 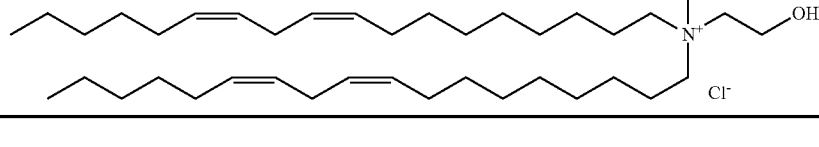 |
TABLE 17
| Compound No. | Structural formula |
|---|---|
| II-1 | 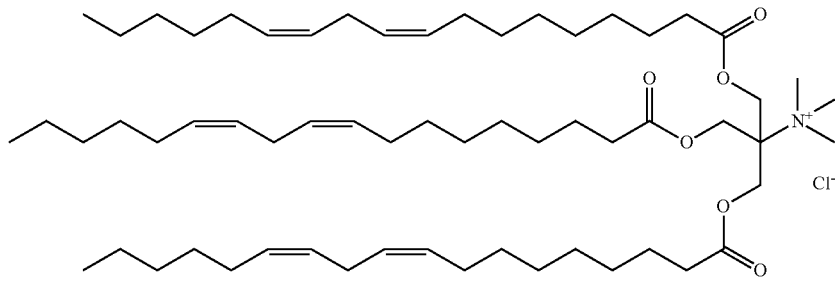 [SMILES: CCCCC/C=C\C/C=C\CCCCCCCC(=O)OCC(COC(=O)CCCCCCC/C=C\C/C=C\CCCCC)(COC(=O)CCCCCCC/C=C\C/C=C\CCCCC)[N+](C)(C)C ; [Cl-]] |
| II-2 | 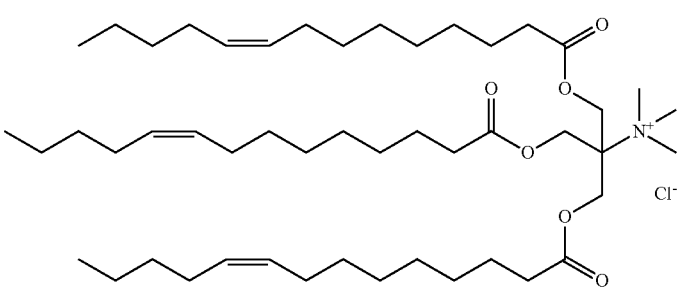 [SMILES: CCCC/C=C\CCCCCCCC(=O)OCC(COC(=O)CCCCCCC/C=C\CCCC)(COC(=O)CCCCCCC/C=C\CCCC)[N+](C)(C)C ; [Cl-]] |

TABLE 17-continued

| Compound No. | Structural formula |
| --- | --- |
| II-3 | |
| II-4 | |
| II-5 | |
| II-6 | |

TABLE 18

| II-7 | |
| --- | --- |
| II-8 | |

TABLE 18-continued
| | |
|---|---|
| II-9 | 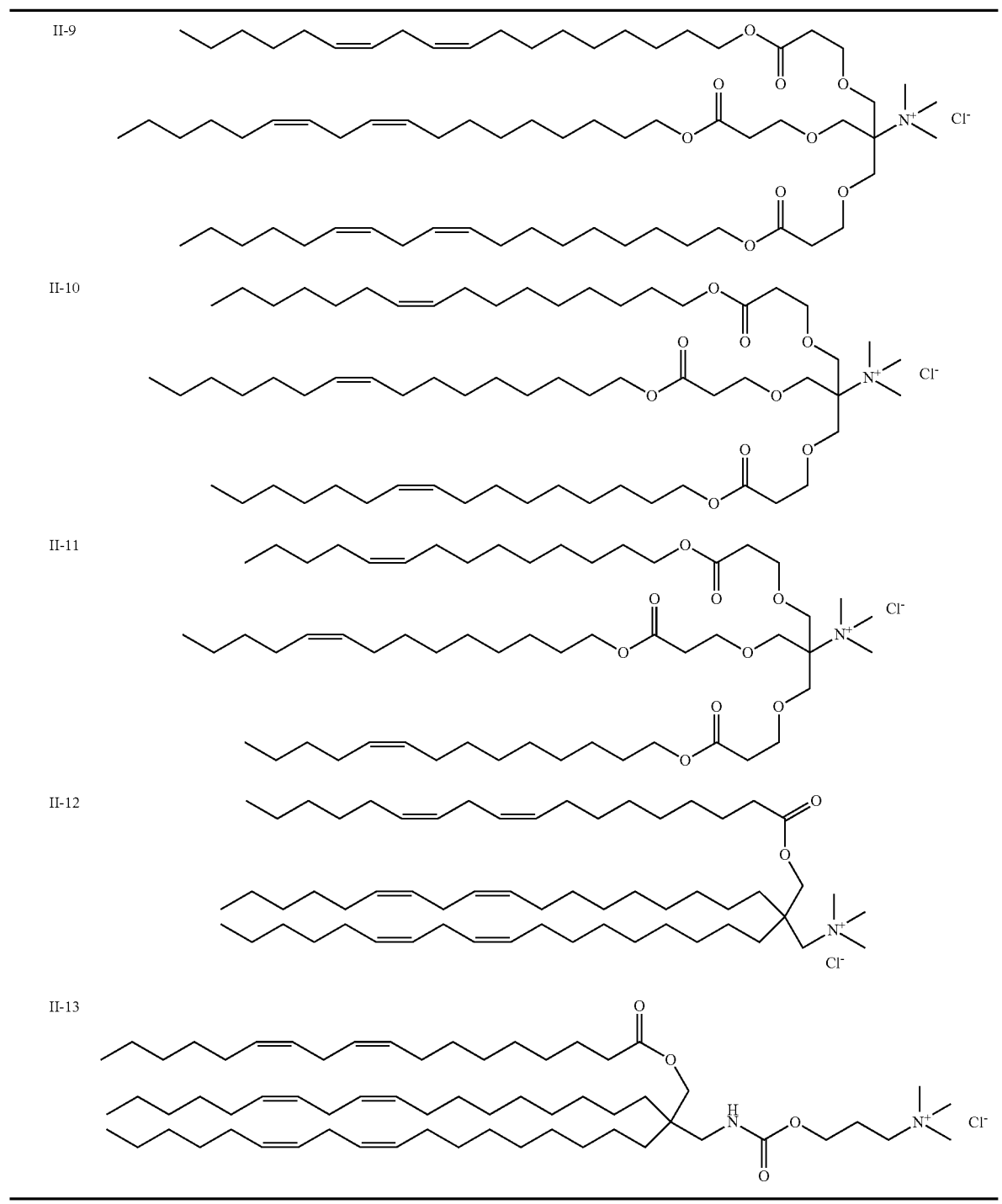 |
| II-10 | |
| II-11 | |
| II-12 | |
| II-13 | |
TABLE 19
| | |
|---|---|
| II-14 | 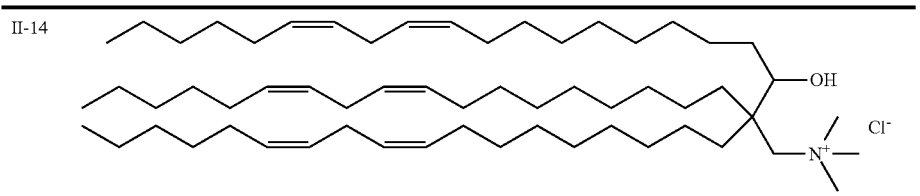 |

TABLE 19-continued
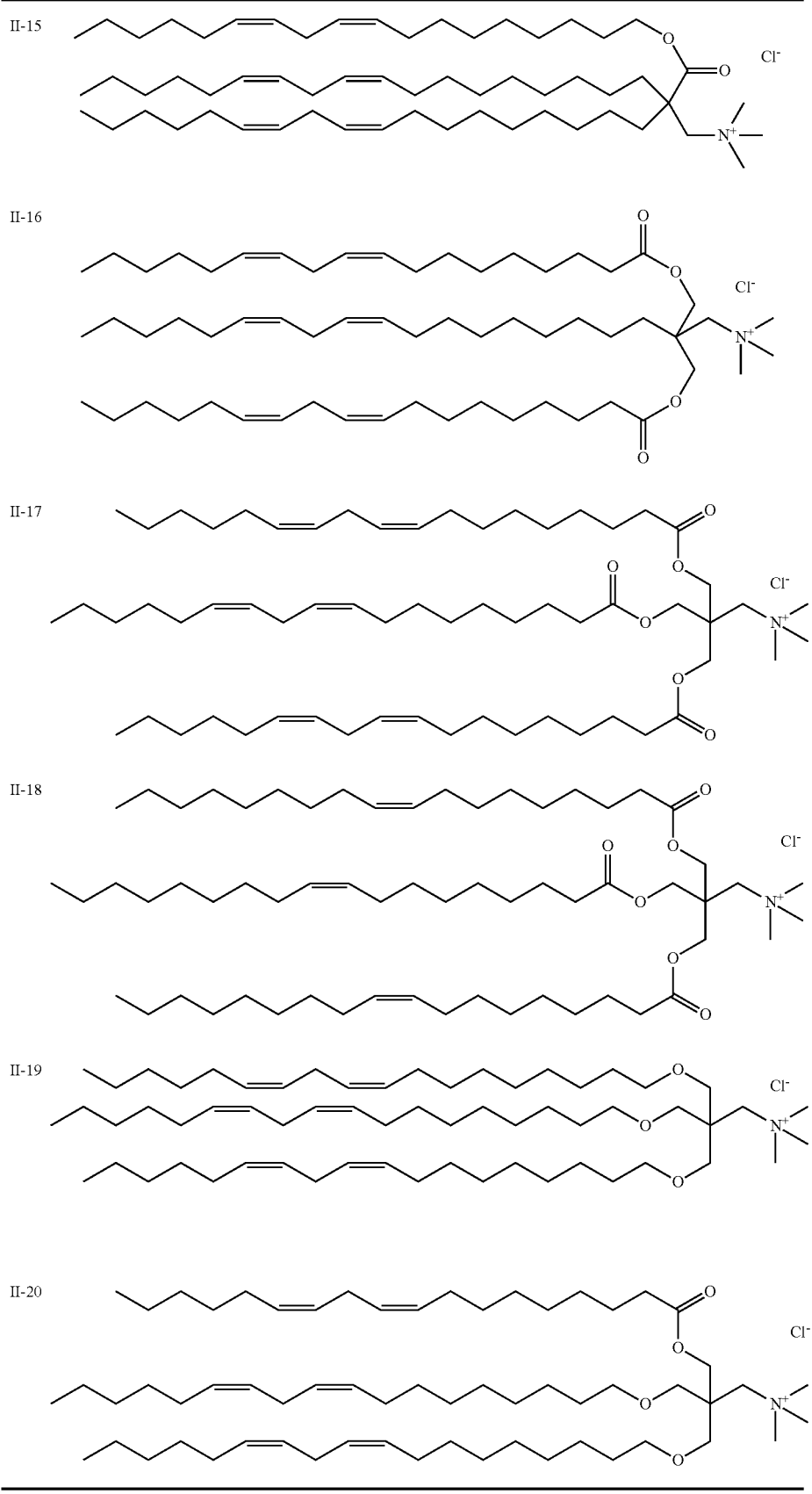

TABLE 20
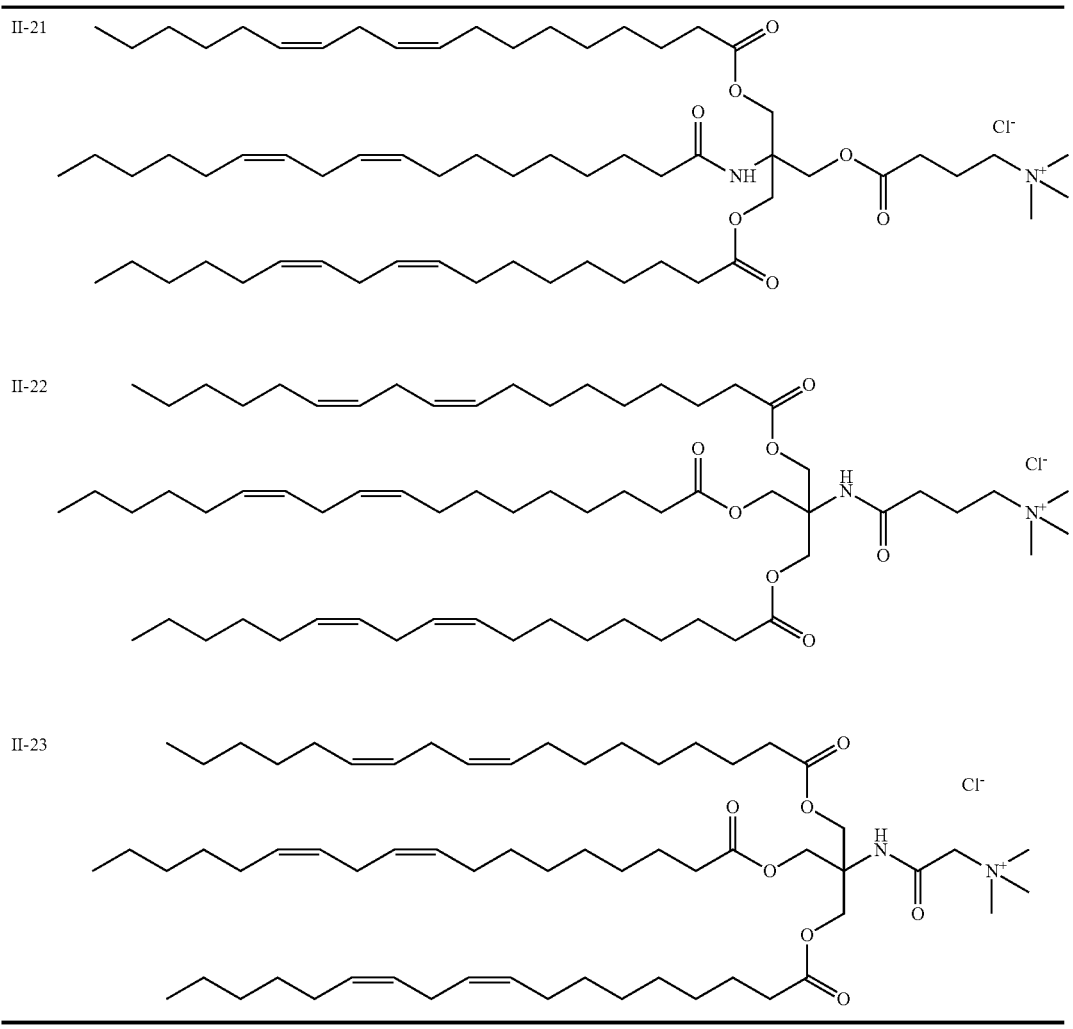
TABLE 21
| Compound No. | Structural formula |
|---|---|
| III-1 | 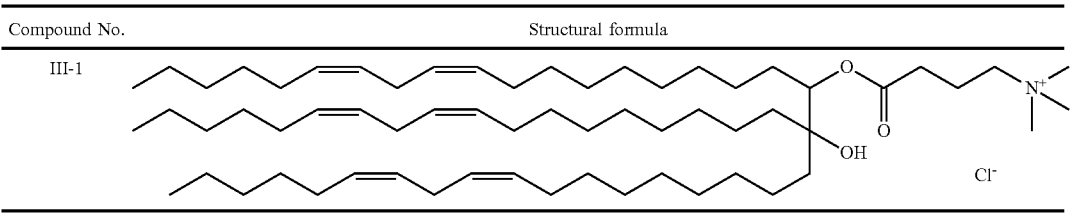 |
TABLE 22
| Compound No. | Structural formula |
|---|---|
| IV-1 | 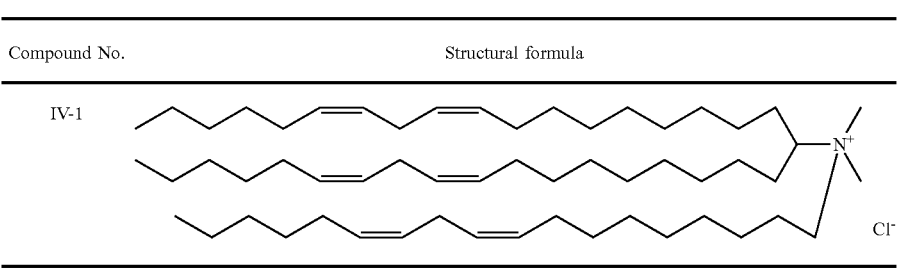 |

TABLE 23

| Compound No. | Structural formula |
|---|---|
| II-24 | |
| II-25 | |
| II-26 | |
| II-27 | |
| II-28 | |

TABLE 23-continued

| Compound No. | Structural formula |
| --- | --- |
| II-29 | |
| II-30 | |

TABLE 24

| II-31 | |
| --- | --- |
| II-32 | |
| II-33 | |

TABLE 24-continued
II-34 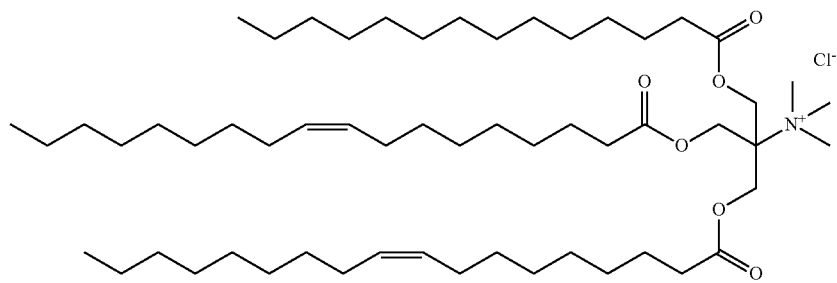 [SMILES: CCCCCCCC/C=C\CCCCCCCC(=O)OCC(COC(=O)CCCCCCC/C=C\CCCCCCCC)(COC(=O)CCCCCCCCCCCCC)[N+](C)(C)C ; [Cl-]]
II-35 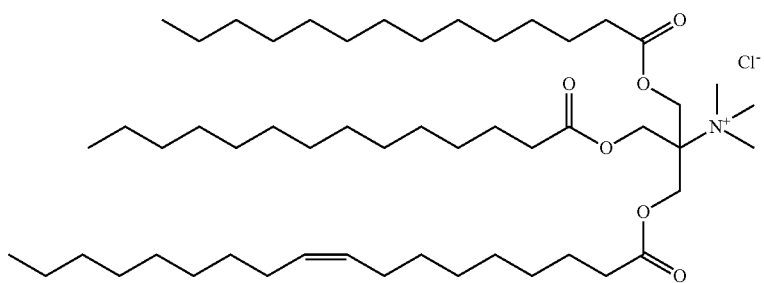 [SMILES: CCCCCCCC/C=C\CCCCCCCC(=O)OCC(COC(=O)CCCCCCCCCCCCC)(COC(=O)CCCCCCCCCCCCC)[N+](C)(C)C ; [Cl-]]
II-36 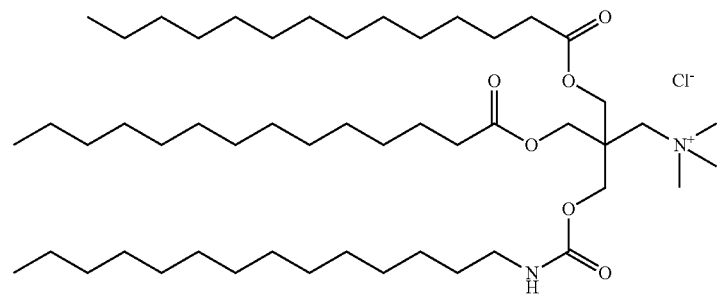 [SMILES: CCCCCCCCCCCCCCNC(=O)OCC(COC(=O)CCCCCCCCCCCCC)(COC(=O)CCCCCCCCCCCCC)C[N+](C)(C)C ; [Cl-]]
II-37 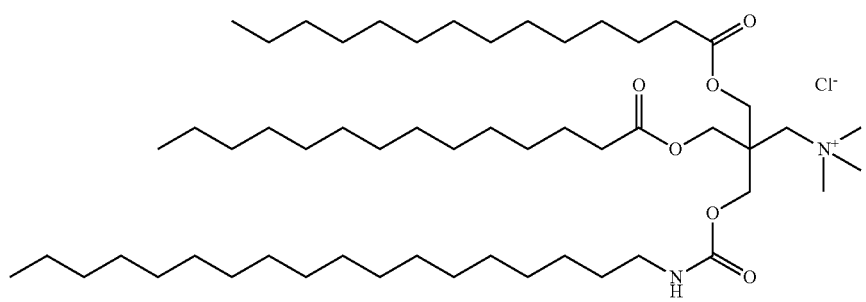 [SMILES: CCCCCCCCCCCCCCCCCCNC(=O)OCC(COC(=O)CCCCCCCCCCCCC)(COC(=O)CCCCCCCCCCCCC)C[N+](C)(C)C ; [Cl-]]
TABLE 25
II-38 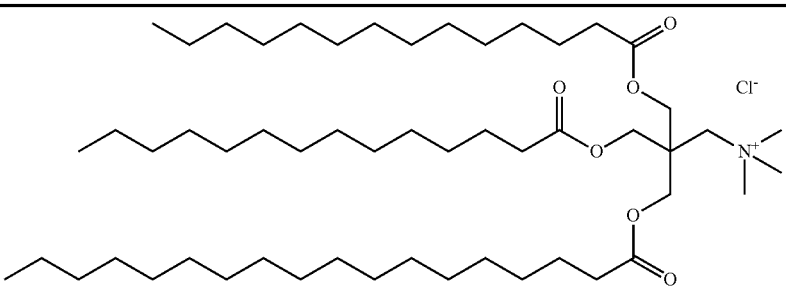

TABLE 25-continued
II-39 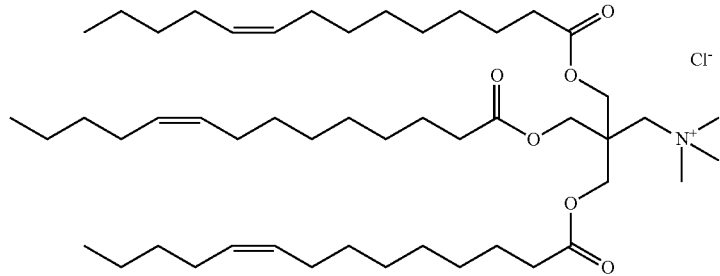 [SMILES: CCCC/C=C\CCCCCCCC(=O)OCC(COC(=O)CCCCCCC/C=C\CCCC)(COC(=O)CCCCCCC/C=C\CCCC)C[N+](C)(C)C ; [Cl-]]
II-40 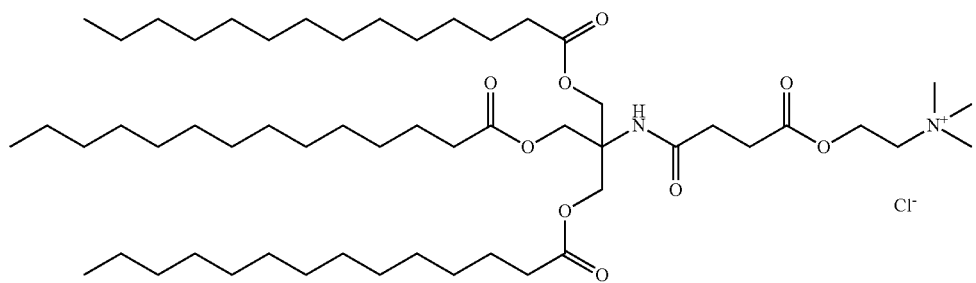 [SMILES: CCCCCCCCCCCCCC(=O)OCC(COC(=O)CCCCCCCCCCCCC)(COC(=O)CCCCCCCCCCCCC)NC(=O)CCC(=O)OCC[N+](C)(C)C ; [Cl-]]
II-41 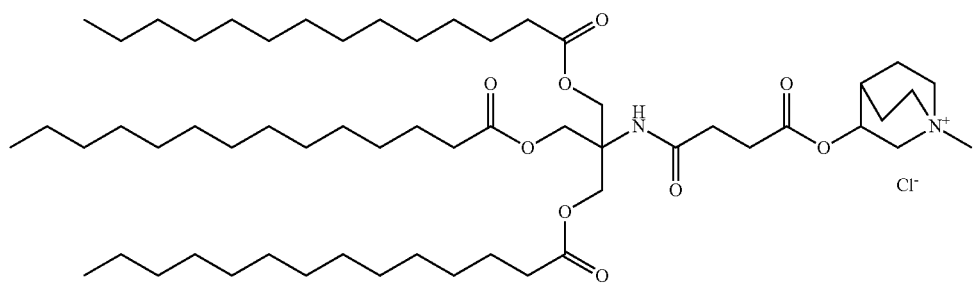 [SMILES: CCCCCCCCCCCCCC(=O)OCC(COC(=O)CCCCCCCCCCCCC)(COC(=O)CCCCCCCCCCCCC)NC(=O)CCC(=O)OC1C[N+]2(C)CCC1CC2 ; [Cl-]]
II-42 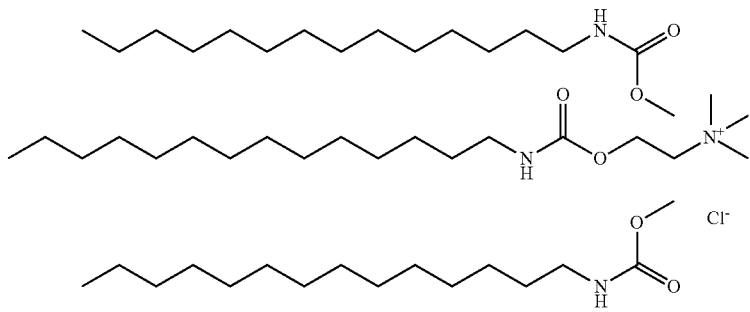
II-43 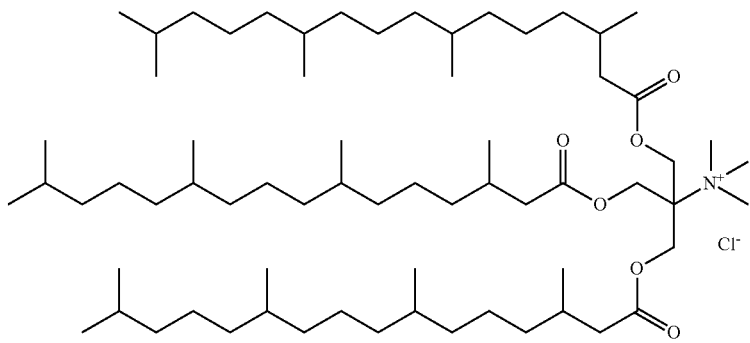 [SMILES: CC(C)CCCC(C)CCCC(C)CCCC(C)CC(=O)OCC(COC(=O)CC(C)CCCC(C)CCCC(C)CCCC(C)C)(COC(=O)CC(C)CCCC(C)CCCC(C)CCCC(C)C)[N+](C)(C)C ; [Cl-]]

TABLE 25-continued
II-44 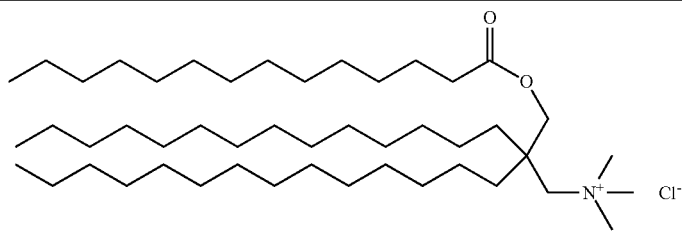
TABLE 26
II-45 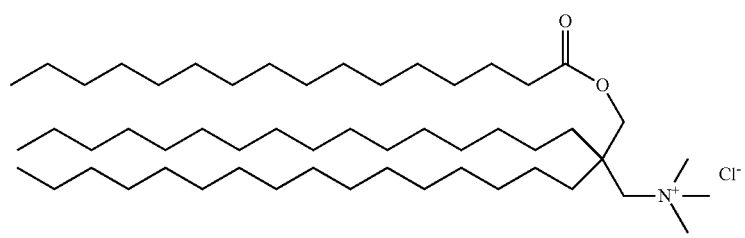 [SMILES: CCCCCCCCCCCCCCCCC(CCCCCCCCCCCCCCCC)(COC(=O)CCCCCCCCCCCCCCC)C[N+](C)(C)C ; [Cl-]]
II-46 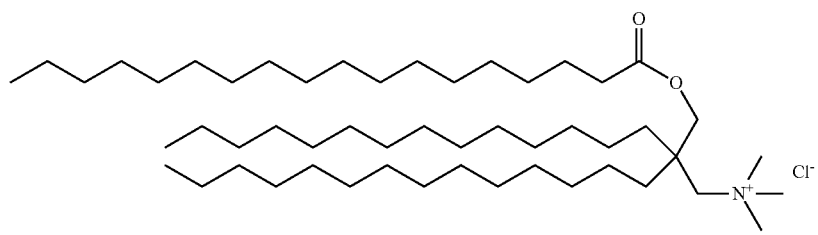 [SMILES: CCCCCCCCCCCCCCCCCC(=O)OCC(CCCCCCCCCCCCCC)(CCCCCCCCCCCCCC)C[N+](C)(C)C ; [Cl-]]
II-47 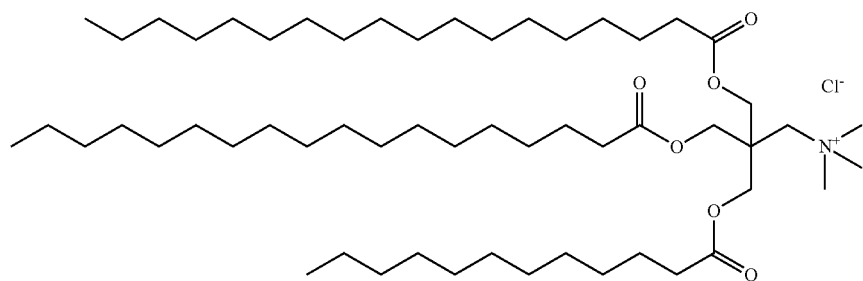 [SMILES: CCCCCCCCCCCCCCCCCC(=O)OCC(COC(=O)CCCCCCCCCCC)(COC(=O)CCCCCCCCCCCCCCCCC)C[N+](C)(C)C ; [Cl-]]
II-48 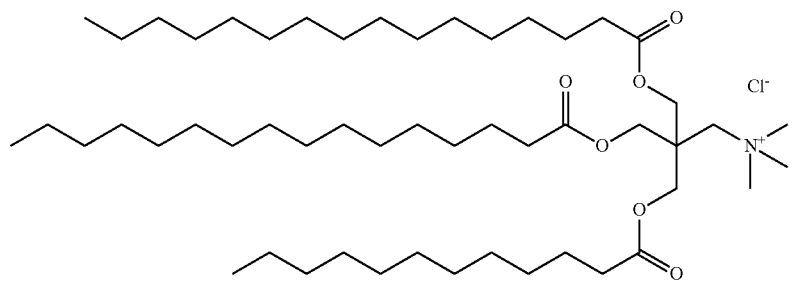 [SMILES: CCCCCCCCCCCCCCCC(=O)OCC(COC(=O)CCCCCCCCCCC)(COC(=O)CCCCCCCCCCCCCCC)C[N+](C)(C)C ; [Cl-]]

TABLE 26-continued
II-49
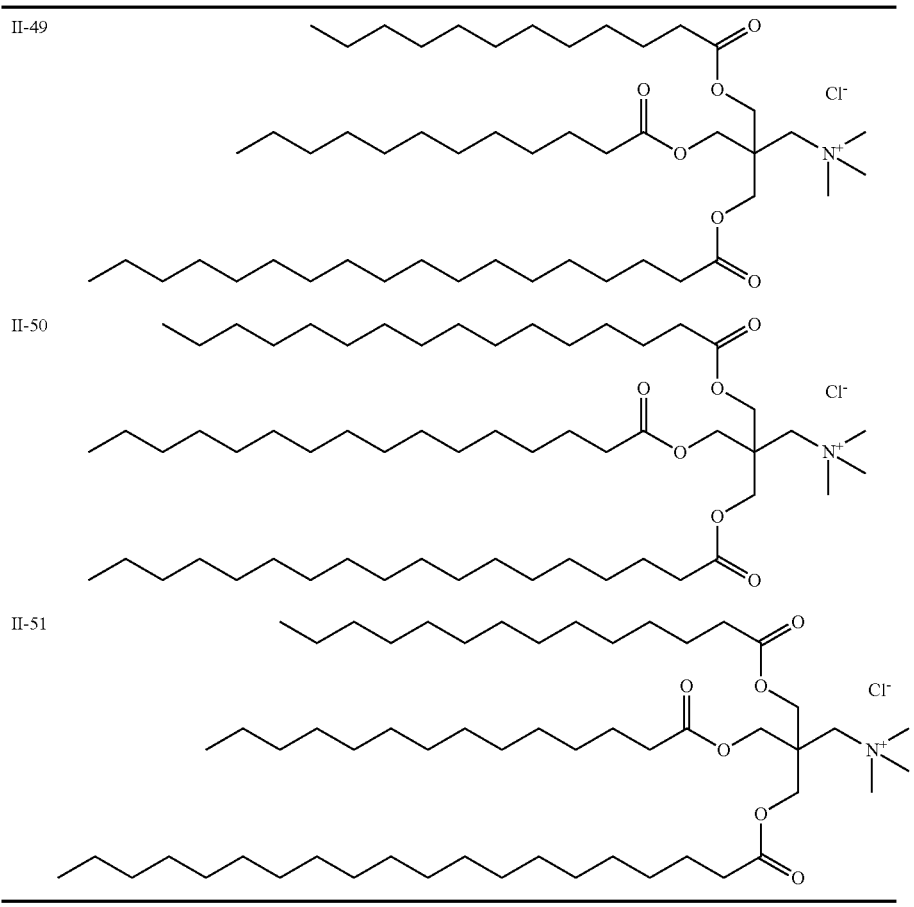
II-50
II-51
TABLE 27
II-52
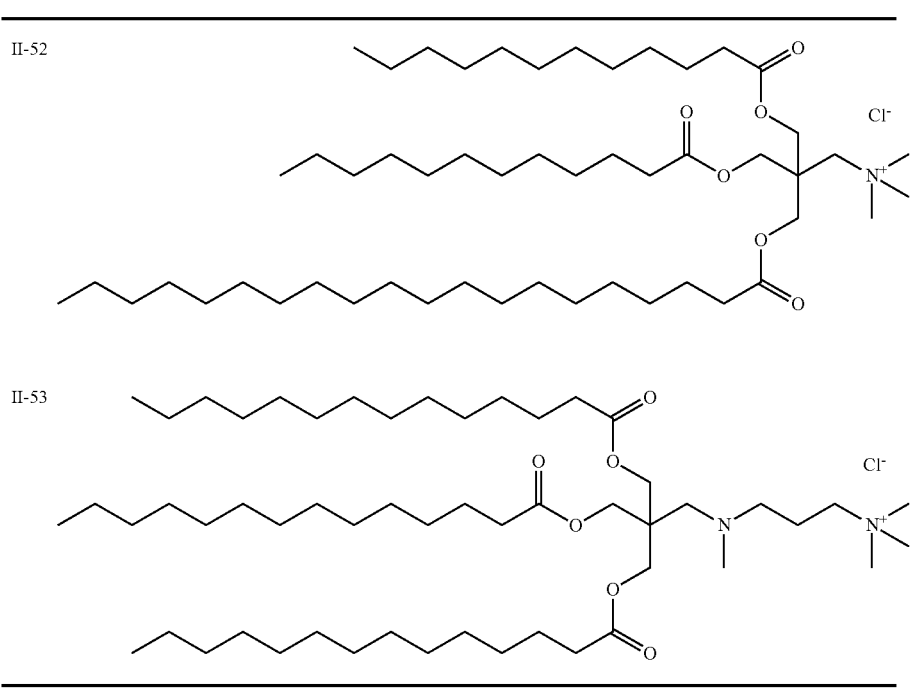
II-53

TABLE 28

| Compound No. | Structural formula |
|---|---|
| III-2 | |
| III-3 | |
| III-4 | |
| III-5 | |
| III-6 | |
| III-7 | |

TABLE 29

| Compound No. | Structural formula |
|---|---|
| IV-2 | |
| IV-3 | |

TABLE 30

| Compound No. | Structural formula |
|---|---|
| V'-1 | |
| V'-2 | |
| V'-3 | |

TABLE 30-continued

| Compound No. | Structural formula |
|---|---|
| V'-4 | (structure) |
| V'-5 | (structure) |

TABLE 31

| Compound No. | Structural formula |
|---|---|
| V'''-1 | (structure) |

Lipid A in the nucleic acid-containing lipid nanoparticle of the present invention is preferably a lipid represented by formula (II), (V') or (V"), more preferably a lipid represented by formula (II) or (V'), among the lipids represented by formulas (I), (II), (III), (IV), (V'), and (V").

The lipid represented by formula (II) is preferably a lipid of formula (II) wherein at least one of $R^4$ to $R^6$ is linear C8-C24 alkyl, more preferably a lipid of formula (II) wherein two of $R^4$ to $R^6$ are each linear C8-C24 alkyl, further preferably a lipid of formula (II) wherein all of $R^4$ to $R^6$ are each linear C8-C24 alkyl.

Lipid B to be combined with a lipid selected from the group consisting of formulas (II), (V') and (V") is preferably a lipid represented by formula (CL-I), (CL-II), (CL-III), (CL-IV), (CL-V), (CL-VI), (CL-VII), (CL-VIII), (CL-IX), (CL-XII), (CL-XIV), (CL-XVIII) or (CL-XIX), more preferably a lipid represented by formula (CL-XVIII) or formula (CL-XIX).

The lipid represented by formula (CL-II) is preferably a lipid of formula (CL-II) wherein $L^{106}$ and $L^{107}$ together form a single bond or C2-C8 alkylene, and each of $p^{101}$ and $p^{102}$ is an integer from 1 to 3, more preferably a lipid of formula (CL-II) wherein $L^{106}$ and $L^{107}$ together form a single bond, and each of $p^{101}$ and $p^{102}$ is 1.

The combination of lipid A and lipid B is more preferably a combination of a lipid represented by formula (II) as the lipid A and a lipid represented by formula (CL-XVIII) and/or formula (CL-XIX) as the lipid B.

The nucleic acid used in the present invention can be any molecule as long as the molecule is obtained by the polymerization of, for example, nucleotides and/or molecules having functions equivalent to nucleotides. Examples thereof include ribonucleic acid (RNA) which is a polymer of ribonucleotides, deoxyribonucleic acid (DNA) which is a polymer of deoxyribonucleotides, chimeric nucleic acids consisting of RNA and DNA, and nucleotide polymers derived from these nucleic acids by the replacement of at least one nucleotide with a molecule having a function equivalent to the nucleotide. A derivative at least partially containing the structure of the molecule obtained by the polymerization of nucleotides and/or molecules having functions equivalent to nucleotides is also included in the nucleic acid of the present invention. In the present invention, uracil U and thymine T can be used interchangeably with each other.

Examples of the molecules having functions equivalent to nucleotides include nucleotide derivatives.

The nucleotide derivative can be any molecule as long as the molecule is, for example, a modified nucleotide. For example, a modified ribonucleotide or deoxyribonucleotide molecule is suitably used for improving nuclease resistance or stabilizing the molecule against the other decomposition factors, for enhancing affinity for a complementary strand nucleic acid, for enhancing cell permeability, or for visualizing the molecule, as compared with RNA or DNA.

Examples of the nucleotide derivative include nucleotides modified at the sugar moiety, nucleotides modified at the phosphodiester bond, and nucleotides modified at the base.

The nucleotide modified at the sugar moiety can be, for example, any nucleotide in which a part or the whole of the chemical structure of its sugar is modified or substituted with an arbitrary substituent or substituted with an arbitrary atom. A 2'-modified nucleotide is preferably used.

Examples of the modifying group in the nucleotide modified at the sugar moiety include 2'-cyano, 2'-alkyl, 2'-substituted alkyl, 2'-alkenyl, 2'-substituted alkenyl, 2'-halogen, 2'-O-cyano, 2'-O-alkyl, 2'-O-substituted alkyl, 2'-O-alkenyl, 2'-O-substituted alkenyl, 2'-S-alkyl, 2'-S-substituted alkyl, 2'-S-alkenyl, 2'-S-substituted alkenyl, 2'-amino, 2'-NH-alkyl, 2'-NH-substituted alkyl, 2'-NH-alkenyl, 2'-NH-substituted alkenyl, 2'-SO-alkyl, 2'-SO-substituted alkyl, 2'-carboxy, 2'-CO-alkyl, 2'-CO-substituted alkyl, 2'-Se-alkyl, 2'-Se-substituted alkyl, 2'-SiH$_2$-alkyl, 2'-SiH$_2$-substituted alkyl, 2'-ONO$_2$, 2'-NO$_2$, 2'-N$_3$, 2'-amino acid residues (which results from the removal of a hydroxy group from the carboxylic acids of amino acids), and 2'-O-amino acid residues (as defined in the amino acid residues).

Examples of the nucleotide modified at the sugar moiety include bridged nucleic acid (BNA) having a structure with the modifying group at position 2' bridged to the carbon atom at position 4', and more specifically include locked nucleic acid (LNA) having the oxygen atom at position 2' and the carbon atom at position 4' bridged via methylene, and ethylene bridged nucleic acid (ENA) [Nucleic Acid Research, 32, e175 (2004)], all of which are included in the 2'-modified nucleotide.

Examples of the nucleotide modified at the sugar moiety also include peptide nucleic acid (PNA) [Acc. Chem. Res., 32, 624 (1999)], oxypeptide nucleic acid (OPNA) [J. Am. Chem. Soc., 123, 4653 (2001)], and peptide ribonucleic acid (PRNA) [J. Am. Chem. Soc., 122, 6900 (2000)].

The modifying group in the nucleotide modified at the sugar moiety is preferably 2'-cyano, 2'-halogen, 2'-O-cyano, 2'-alkyl, 2'-substituted alkyl, 2'-O-alkyl, 2'-O-substituted alkyl, 2'-O-alkenyl, 2'-O-substituted alkenyl, 2'-Se-alkyl, 2'-Se-substituted alkyl or the like, more preferably 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O-[2-(methoxy)ethyl], 2'-O-(3-aminopropyl), 2'-O-[2-(N,N-dimethylaminooxy)ethyl], 2'-O-[3-(N,N-dimethylamino)propyl], 2'-O-{2-[2-(N,N-dimethylamino)ethoxy]ethyl}, 2'-O-[2-(methylamino)-2-oxoethyl], 2'-Se-methyl or the like, further preferably 2'-O-methyl, 2'-O-ethyl, 2'-fluoro or the like, most preferably 2'-O-methyl or 2'-O-ethyl.

The modifying group in the nucleotide modified at the sugar moiety can also be defined from its size, preferably the modifying group corresponds to a size from fluoro to —O-butyl, and more preferably the modifying group corresponds to a size from —O-methyl to —O-ethyl.

Examples of the alkyl in the modifying group in the nucleotide modified at the sugar moiety include C1-C6 alkyl and more specifically include C1-C6 alkyl such as methyl, ethyl, propyl, isopropyl, butyl, isobutyl, sec-butyl, tert-butyl, pentyl, isopentyl, neopentyl and hexyl.

Examples of the alkenyl in the modifying group in the nucleotide modified at the sugar moiety include C3-C6 alkenyl and more specifically include C3-C6 alkenyl such as allyl, 1-propenyl, butenyl, pentenyl and hexenyl.

Examples of the halogen in the modifying group in the nucleotide modified at the sugar moiety include a fluorine atom, a chlorine atom, a bromine atom and an iodine atom.

Examples of the amino acid in the amino acid residue include aliphatic amino acids (specifically, glycine, alanine, valine, leucine, isoleucine, etc.), hydroxyamino acids (specifically, serine, threonine, etc.), acidic amino acids (specifically, aspartic acid, glutamic acid, etc.), acidic amino acid amides (specifically, asparagine, glutamine, etc.), basic amino acids (specifically, lysine, hydroxylysine, arginine, ornithine, etc.), sulfur-containing amino acids (specifically, cysteine, cystine, methionine, etc.), and imino acids (specifically, proline, 4-hydroxyproline etc.).

Examples of the substituent for the substituted alkyl or the substituted alkenyl in the modifying group in the nucleotide modified at the sugar moiety include halogen (as defined above), hydroxy, sulfanyl, amino, oxo, —O-alkyl (the alkyl moiety of the —O-alkyl is as defined in the C1-C6 alkyl in the above-described modifying group), —S-alkyl (the alkyl moiety of the —S-alkyl is as defined in the C1-C6 alkyl in the above-described modifying group), —NH-alkyl (the alkyl moiety of the —NH-alkyl is as defined in the C1-C6 alkyl in the above-described modifying group), dialkylaminooxy (the two alkyl moieties of the dialkylaminooxy are the same or different and are each as defined in the C1-C6 alkyl in the above-described modifying group), dialkylamino (the two alkyl moieties of the dialkylamino are the same or different and are each as defined in the C1-C6 alkyl in the above-described modifying group) and dialkylaminoalkyloxy (the two alkyl moieties of the dialkylaminoalkyloxy are the same or different and are each as defined in the C1-C6 alkyl in the above-described modifying group, and the alkylene moiety means a moiety obtained by removal of one hydrogen atom from the C1-C6 alkyl in the above-described modifying group). The number of substituents is preferably 1 to 3.

The nucleotide modified at the phosphodiester bond can be any nucleotide in which a part or the whole of the chemical structure of its phosphodiester bond is modified or substituted with an arbitrary substituent or substituted with an arbitrary atom. Examples thereof include a nucleotide resulting from the substitution of the phosphodiester bond with a phosphorothioate bond, a nucleotide resulting from the substitution of the phosphodiester bond with a phosphorodithioate bond, a nucleotide resulting from the substitution of the phosphodiester bond with an alkyl phosphonate bond, and a nucleotide resulting from the substitution of the phosphodiester bond with a phosphoramidate bond.

The nucleotide modified at the base can be any nucleotide in which a part or the whole of the chemical structure of its base is modified or substituted with an arbitrary substituent or substituted with an arbitrary atom. Examples thereof include a nucleotide resulting from the substitution of an oxygen atom in the base with a sulfur atom, a nucleotide resulting from the substitution of a hydrogen atom with a C1-C6 alkyl group, a nucleotide resulting from the substitution of a methyl group with a hydrogen atom or a C2-C6 alkyl group, and a nucleotide resulting from the protection of an amino group with a protective group such as a C1-C6 alkyl group or a C1-C6 alkanoyl group.

Further examples of the nucleotide derivative include nucleotide derivatives that are modified nucleotides or each have at least one modified sugar moiety, phosphodiester bond or base, and contain an additional chemical substance, such as lipid, phospholipid, phenazine, folate, phenanthridine, anthraquinone, acridine, fluorescein, rhodamine, coumarin, or dye, added thereto, and specifically include 5'-polyamine-added nucleotide derivatives, cholesterol-added nucleotide derivatives, steroid-added nucleotide derivatives, bile acid-added nucleotide derivatives, vitamin-added nucleotide derivatives, green fluorescent dye (Cy3)-added nucleotide derivatives, red fluorescent dye (Cy5)-added nucleotide derivatives, fluorescein (6-FAM)-added nucleotide derivatives and biotin-added nucleotide derivatives.

In the nucleic acid used in the present invention, the nucleotide or the nucleotide derivative may form a bridged structure, such as an alkylene structure, a peptide structure, a nucleotide structure, an ether structure, an ester structure, and a structure combined with at least one of these structures, with another nucleotide or nucleotide derivative within the nucleic acid.

The molecular weight of the nucleic acid used in the present invention is preferably 1,000 kDa or smaller, more preferably 100 kDa or smaller, further preferably 30 kDa or smaller. Examples of the nucleic acid used in the present invention preferably include nucleic acids silencing a target gene and more preferably include nucleic acids having a silencing effect on a target gene through the use of RNA interference (RNAi).

The target gene in the present invention is not particularly limited as long as the gene is expressed by producing mRNA. For example, a gene related to tumor or inflammation is preferred. Examples thereof include genes encoding proteins such as vascular endothelial growth factor (hereinafter, abbreviated to VEGF), vascular endothelial growth factor receptor (hereinafter, abbreviated to VEGFR), fibroblast growth factor, fibroblast growth factor receptor, platelet-derived growth factor, platelet-derived growth factor receptor, hepatocyte growth factor, hepatocyte growth factor receptor, Kruppel-like factor (hereinafter, abbreviated to KLF), expressed sequence tag (Ets) transcription factor, nuclear factor, hypoxia-inducible factor, cell cycle-related factor, chromosomal replication-related factor, chromosomal repair-related factor, microtubule-related factor, growth signal pathway-related factor, growth-related transcription factor, and apoptosis-related factor, and specifically include VEGF gene, VEGFR gene, fibroblast growth factor gene, fibroblast growth factor receptor gene, platelet-derived growth factor gene, platelet-derived growth factor receptor gene, hepatocyte growth factor gene, hepatocyte growth factor receptor gene, KLF gene, Ets transcription factor gene, nuclear factor gene, hypoxia-inducible factor gene, cell cycle-related factor gene, chromosomal replication-related factor gene, chromosomal repair-related factor gene, microtubule-related factor gene (e.g., CKAP5 gene), growth signal pathway-related factor gene (e.g., KRAS gene), growth-related transcription factor gene and apoptosis-related factor (e.g., BCL-2 gene).

The target gene according to the present invention is preferably, for example, a gene expressed in the liver, the lung, the kidney, or the spleen, more preferably a gene expressed in the liver. Examples thereof include the aforementioned genes related to tumor or inflammation, and genes encoding proteins such as hepatitis B virus genome, hepatitis C virus genome, apolipoprotein (APO), hydroxymethylglutaryl (HMG) CoA reductase, kexin type 9 serine protease (PCSK9), factor 12, glucagon receptor, glucocorticoid receptor, leukotriene receptor, thromboxane A2 receptor, histamine H1 receptor, carbonic anhydrase, angiotensin-converting enzyme, renin, p53, tyrosine phosphatase (PTP), sodium-dependent glucose transport carrier, tumor necrosis factor, interleukin, hepcidin, trans siren, antithrombin, protein C and matriptase enzyme (e.g., TMPRSS6 gene).

Any nucleic acid such as a double-stranded nucleic acid (e.g., siRNA (short interference RNA) and miRNA (micro RNA)) or a single-stranded nucleic acid (e.g., shRNA (short hairpin RNA) antisense nucleic acid and ribozyme) may be used as the nucleic acid silencing a target gene as long as the nucleic acid comprises a nucleotide sequence complementary to, for example, a partial nucleotide sequence of the mRNA of a gene (target gene) encoding a protein or the like and silences the target gene. A double-stranded nucleic acid is preferred.

The nucleic acid comprising a nucleotide sequence complementary to a partial nucleotide sequence of the mRNA of the target gene is referred to as an antisense strand nucleic acid. A nucleic acid comprising a nucleotide sequence complementary to the nucleotide sequence of the antisense strand nucleic acid is also referred to as a sense strand nucleic acid. The sense strand nucleic acid refers to a nucleic acid capable of forming a duplex formation moiety by pairing with the antisense strand nucleic acid, such as a nucleic acid itself consisting of the partial nucleotide sequence of the target gene.

The double-stranded nucleic acid refers to a nucleic acid having a duplex formation moiety composed of paired two strands. The duplex formation moiety refers to a part in which nucleotides constituting the double-stranded nucleic acid, or derivatives thereof have formed a duplex by constituting base pairs. The base pairs constituting the duplex formation moiety are usually 15 to 27 base pairs, preferably 15 to 25 base pairs, more preferably 15 to 23 base pairs, further preferably 15 to 21 base pairs, particularly preferably 15 to 19 base pairs.

For example, a nucleic acid consisting of a partial sequence of the mRNA of the target gene, or a nucleic acid derived from the nucleic acid by the substitution, deletion or addition of 1 to 3 bases, preferably 1 or 2 bases, more preferably 1 base, and having silencing activity against the target protein is suitably used as the antisense strand nucleic acid of the duplex formation moiety. Each single-stranded nucleic acid constituting the double-stranded nucleic acid usually consists of a sequence of 15 to 30 bases (nucleosides), preferably 15 to 29 bases, more preferably 15 to 27 bases, further preferably 15 to 25 bases, particularly preferably 17 to 23 bases, most preferably 19 to 21 bases.

Either of the antisense strand or the sense strand constituting the double-stranded nucleic acid, or both of these nucleic acids may have a non-duplex-forming additional nucleic acid on the 3' or 5' side subsequent to the duplex formation moiety. This non-duplex-forming moiety is also referred to as an overhang.

For example, a double-stranded nucleic acid having an overhang consisting of 1 to 4 bases, usually 1 to 3 bases, at the 3' end or the 5' end of at least one of the strands is used as the double-stranded nucleic acid having the overhang. A double-stranded nucleic acid having an overhang consisting of 2 bases is preferably used, and a double-stranded nucleic acid having an overhang consisting of dTdT or UU is more preferably used. The overhang can be located in only the antisense strand, only the sense strand, and both of the antisense strand and the sense strand. A double-stranded nucleic acid having overhangs in both of the antisense strand and the sense strand is preferably used.

A sequence partially or completely matching the nucleotide sequence of the mRNA of the target gene, or a sequence partially or completely matching the nucleotide sequence of a complementary strand of the mRNA of the target gene may be used subsequently to the duplex formation moiety. Alternatively, for example, a nucleic acid molecule that forms the double-stranded nucleic acid by the action of ribonuclease such as Dicer (WO 2005/089287), or a double-stranded nucleic acid having no 3'-terminal or 5'-terminal overhang can also be used as the nucleic acid silencing the target gene.

When the double-stranded nucleic acid is siRNA, preferably, the antisense strand is an antisense strand in which a sequence of at least the 1st to 17th bases (nucleosides) counted from the 5' end toward the 3' end is a sequence of bases complementary to a sequence of 17 consecutive bases of the mRNA of the target gene. More preferably, the antisense strand is an antisense strand in which a sequence of the 1st to 19th bases counted from the 5' end toward the 3' end is a sequence of bases complementary to a sequence of 19 consecutive bases of the mRNA of the target gene, a sequence of the 1st to 21st bases counted from the 5' end toward the 3' end is a sequence of bases complementary to a sequence of 21 consecutive bases of the mRNA of the target gene, or a sequence of the 1st to 25th bases counted from the 5' end toward the 3' end is a sequence of bases complementary to a sequence of 25 consecutive bases of the mRNA of the target gene.

When the nucleic acid used in the present invention is siRNA, preferably 10 to 70%, more preferably 15 to 60%, further preferably 20 to 50%, of sugars in the nucleic acid is ribose substituted at position 2' with a modifying group. The ribose substituted at position 2' with a modifying group according to the present invention means that the hydroxy group at position 2' of the ribose is substituted with a modifying group. The resulting configuration may be the same as or different from that of the hydroxy group at position 2' of the ribose and is preferably the same as that of the hydroxy group at position 2' of the ribose. Examples of the modifying group in the ribose substituted at position 2' therewith include those listed in the definition of the modifying group in the 2'-modified nucleotide in the nucleotide modified at the sugar moiety, and a hydrogen atom. The modifying group is preferably 2'-cyano, 2'-halogen, 2'-O-cyano, 2'-alkyl, 2'-substituted alkyl, 2'-O-alkyl, 2'-O-substituted alkyl, 2'-O-alkenyl, 2'-O-substituted alkenyl, 2'-Se-alkyl, 2'-Se-substituted alkyl or the like, more preferably 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O-[2-(methoxy)ethyl], 2'-O-(3-aminopropyl), 2'-O-[2-(N,N-dimethyl)aminooxy]ethyl, 2'-O-[3-(N,N-dimethylamino)propyl], 2'-O-{2-[2-(N,N-dimethylamino)ethoxy]ethyl}, 2'-O-[2-(methylamino)-2-oxoethyl], 2'-Se-methyl, a hydrogen atom or the like, further preferably 2'-O-methyl, 2'-O-ethyl, 2'-fluoro, a hydrogen atom or the like, most preferably 2'-O-methyl or 2'-O-fluoro.

The nucleic acid used in the present invention encompasses derivatives in which, for example, an oxygen atom contained in a phosphoric acid moiety, an ester moiety or the like in the structure of the nucleic acid is substituted with a different atom such as a sulfur atom.

The hydroxy group at position 5' of a sugar attached to the 5' terminal base of the antisense strand or the sense strand may be modified with a phosphoric acid group or any of the aforementioned modifying groups, or with a group that is converted to a phosphoric acid group or any of the aforementioned modifying groups by an in vivo nucleolytic enzyme or the like.

The hydroxy group at position 3' of a sugar attached to the 3' terminal base of the antisense strand or the sense strand may be modified with a phosphoric acid group or any of the aforementioned modifying groups, or with a group that is converted to a phosphoric acid group or any of the aforementioned modifying groups by an in vivo nucleolytic enzyme or the like.

The single-stranded nucleic acid can be, for example, any nucleic acid consisting of a sequence complementary to a sequence consisting of 15 to 27 consecutive bases (nucleosides), preferably 15 to 25 consecutive bases, more preferably 15 to 23 consecutive bases, further preferably 15 to 21 consecutive bases, particularly preferably 15 to 19 consecutive bases, of the target gene, or any nucleic acid derived from the nucleic acid by the substitution, deletion or addition of 1 to 3 bases, preferably 1 or 2 bases, more preferably 1 base, and having silencing activity against the target protein. The single-stranded nucleic acid preferably consists of a sequence of 10 to 30 bases (nucleosides). More preferably, a single-stranded nucleic acid of 10 to 27 bases, further preferably 10 to 25 bases, particularly preferably 10 to 23 bases, is suitably used.

A linkage via a spacer sequence (spacer oligonucleotide) of the antisense strand and the sense strand constituting the double-stranded nucleic acid described above may be used as the single-stranded nucleic acid. The spacer oligonucleotide is preferably a single-stranded nucleic acid molecule of 6 to 12 bases. Its 5'-terminal sequence is preferably UU. Examples of the spacer oligonucleotide include a nucleic acid consisting of a sequence UUCAAGAGA. The order in which the antisense strand and the sense strand are linked via the spacer oligonucleotide can be any order in which either of the strands may be positioned on the 5' side. The single-stranded nucleic acid is preferably a single-stranded nucleic acid such as shRNA having a duplex formation moiety by, for example, a stem-loop structure. The single-stranded nucleic acid such as shRNA is usually 50 to 70 bases long.

A nucleic acid of 70 bases or smaller in length, preferably 50 bases or smaller in length, more preferably 30 bases or smaller in length, designed to form the single-stranded nucleic acid or the double-stranded nucleic acid by the action of ribonuclease or the like may be used.

The nucleic acid used in the present invention can be obtained by use of a known RNA or DNA synthesis method and RNA or DNA modification method.

The nucleic acid-containing lipid nanoparticle of the present invention may contain one or two or more lipids A.

The nucleic acid-containing lipid nanoparticle of the present invention may contain one or two or more lipids B.

The nucleic acid-containing lipid nanoparticle of the present invention may also contain a neutral lipid and/or a lipid derivative or a fatty acid derivative of water-soluble polymer.

The nucleic acid-containing lipid nanoparticle of the present invention may contain one or two or more lipids A, and one or two or more lipids B.

The nucleic acid-containing lipid nanoparticle of the present invention may contain not only the nucleic acid but a compound chemically analogous to the nucleic acid (e.g., an anionic polymer such as an anionic peptide).

In the present invention, the nucleic acid is dissolved, with the cationic lipid and other optional lipids (a lipid derivative or a fatty acid derivative of a water-soluble polymer and a neutral lipid), in a water-miscible organic solvent (first lipid solution). In the preparation of the first lipid solution, the nucleic acid is dissolved in water or an aqueous solution of a buffer, and the solution may be added to solutions of lipids in an organic solvent, or solutions of lipids in an organic solvent may be added to water or an aqueous solution of a buffer containing the nucleic acid. Alternatively, solutions of lipids in an organic solvent may be added to the nucleic acid in a freeze-dried state.

An organic solvent solution (first lipid solution) is once prepared using the nucleic acid, the cationic lipid and other optional lipids (a lipid derivative or a fatty acid derivative of a water-soluble polymer and a neutral lipid), and an organic solvent solution supplemented with the analog of the fatty acid ester of glycerol that is not hydrolyzable by a lipase, and optionally the lipid derivative or the fatty acid derivative of the water-soluble polymer (second lipid solution) may then be added to the first lipid solution to prepare a third lipid solution.

In the present invention, the first or third lipid solution is mixed with water or an aqueous solution of a buffer. In this respect, a lipid nanoparticle having a small size is obtained without aggregation by immediately decreasing the organic solvent concentration.

In the mixing of the first or third lipid solution with water or an aqueous solution of a buffer, the former one may be added to the latter one, or the latter one may be added to the former one. The former one and the latter one may be added at the same time to a container with stirring. Alternatively, the former one and the latter one may be mixed in line. In this case, for example, a T-connector can be used as an in-line mixing device.

The average particle size of the nucleic acid-containing lipid nanoparticle of the present invention is freely controllable with various parameters in a production process, though also influenced by the nucleic acid used, and the cationic lipid and other lipids. Those skilled in the art can prepare a particle sample by appropriately changing various parameters in a production process necessary for controlling the average particle size of the nucleic acid-containing lipid nanoparticle of the present invention, and measure and determine the average particle size of the obtained sample. Examples of the parameters necessary for controlling the average particle size include the nucleic acid concentration of an organic solvent solution, the concentration of each lipid, temperature, and the composition of an organic solvent. Examples of the parameters necessary for controlling the average particle size also include temperature, the amount of water or an aqueous solution of a buffer, and the addition rate of each solution at the time of operation of dilution of the organic solvent solution of the nucleic acid and lipids with water or the aqueous solution of a buffer.

The concentration of the cationic lipid in the organic solvent solution before mixing with water or an aqueous solution of a buffer in the case of containing neither phosphatidylcholine (PC) nor cholesterol (Chol) is not particularly limited and is preferably 1 to 2000 µM, more preferably 5 to 400 µM, further preferably 10 to 200 µM, most preferably 20 to 100 µM.

The concentration of the nucleic acid in the organic solvent solution before mixing with water or an aqueous solution of a buffer in the case of containing neither PC nor Choi is not particularly limited and is preferably 0.03 to 15 µM, more preferably 0.15 to 3.0 µM, further preferably 0.3 to 1.5 µM.

The concentration of the lipid derivative or the fatty acid derivative of the water-soluble polymer in the organic solvent solution before mixing with water or an aqueous solution of a buffer in the case of containing neither PC nor Choi is not particularly limited and is preferably 0.5 to 200 µM, more preferably 2.5 to 40 µM, further preferably 5 to 20 µM.

The total concentration of all lipids in the organic solvent solution before mixing with water or an aqueous solution of a buffer in the case of containing neither PC nor Choi is not particularly limited and is preferably 5 to 2000 µM, more preferably 25 to 400 µM, further preferably 50 to 200 µM.

The concentration of the lipid having one quaternary ammonium group as a hydrophilic unit and having optionally substituted three independent hydrocarbon groups (lipid A) in the organic solvent solution before mixing with water or an aqueous solution of a buffer in the case of containing PC and Choi is preferably 0.2 to 1800 µM, more preferably 1 to 360 µM, further preferably 2 to 180 µM, most preferably 5 to 100 µM.

The concentration of the nucleic acid in the organic solvent solution before mixing with water or an aqueous solution of a buffer in the case of containing PC and Choi is preferably 0.02 to 45 µM, more preferably 0.1 to 10 µM, further preferably 0.2 to 5 µM, most preferably 0.3 to 3 µM.

The concentration of the lipid derivative or the fatty acid derivative of the water-soluble polymer in the organic solvent solution before mixing with water or an aqueous solution of a buffer in the case of containing PC and Choi is preferably 0.3 to 1000 µM, more preferably 1.5 to 200 µM, further preferably 3 to 100 µM, most preferably 5 to 50 µM.

The concentration of the cationic lipid in the organic solvent solution before mixing with water or an aqueous solution of a buffer in the case of containing PC and Choi is preferably 2.5 to 4200 µM, more preferably 12.5 to 840 µM, further preferably 25 to 420 µM, most preferably 50 to 210 µM.

The concentration of the neutral lipid in the organic solvent solution before mixing with water or an aqueous solution of a buffer in the case of containing PC and Choi is preferably 2.5 to 5000 µM, more preferably 12.5 to 1000 µM, further preferably 25 to 500 µM, most preferably 50 to 250 µM.

The total concentration of all lipids in the organic solvent solution before mixing with water or an aqueous solution of a buffer in the case of containing PC and Choi is preferably 10 to 8000 µM, more preferably 50 to 1600 µM, further preferably 100 to 800 µM, most preferably 150 to 400 µM.

The temperature for preparing the organic solvent solution containing the nucleic acid and the lipids is not particularly limited as long as the nucleic acid and the lipids are dissolved. The temperature is preferably 10 to 60° C., more preferably 20 to 50° C., further preferably 20 to 30° C. Heating to 30° C. or higher increases the degrees of dissolution of the nucleic acid and the lipids and permits lipid nanoparticle production using a smaller amount of a solvent.

The organic solvent in the organic solvent solution containing the nucleic acid and the lipids is not particularly limited and is preferably a C1-C6 alcohol, such as methanol, ethanol, propanol or butanol, containing 0 to 50% (v/v) of water, or a mixture thereof, more preferably ethanol or propanol containing 0 to 50% (v/v) of water, further preferably ethanol containing 0 to 50% (v/v) of water. In this context, the term "% (v/v)" denotes the volume percentage of a solute occupying the volume of the whole solution. The same holds true for the description below.

The solvent in the organic solvent solution containing the nucleic acid and the lipids may be supplemented with an inorganic acid such as hydrochloric acid, acetic acid or phosphoric acid, or a salt of the acid, etc. In this case, the pH of the solvent is preferably 1 to 7, more preferably 1 to 5, further preferably 2 to 4.

In the operation of adding water or an aqueous solution of a buffer to the organic solvent solution containing the nucleic acid and the lipids, the amount of water or the aqueous solution of a buffer used is not particularly limited and is preferably 0.5 to 100 times, more preferably 1.5 to 20 times, further preferably 2.0 to 10 times, with respect to the amount of the organic solvent solution containing the nucleic acid and the lipids.

In this case, the organic solvent concentration after the addition of water or the aqueous solution of a buffer is not particularly limited and is preferably 50% (v/v) or lower, more preferably 40% (v/v) or lower, further preferably 30% (v/v) or lower, most preferably 20% (v/v) or lower, with respect to the obtained solution. The aqueous solution of a buffer is not particularly limited as long as the aqueous solution of a buffer has a buffering effect. Examples thereof include aqueous phosphate buffer solutions, aqueous citrate buffer solutions and aqueous acetate buffer solutions.

The temperature for performing the addition operation is not particularly limited and is preferably 10 to 60° C., more preferably 20 to 50° C., further preferably 20 to 30° C.

For the addition operation, it is important to immediately decrease the organic solvent solution. Specifically, the organic solvent concentration is preferably changed from 70% (v/v) or higher to 50% (v/v) or lower within 1 minute, more preferably within 0.5 minutes, further preferably within 0.1 minutes, most preferably within 0.05 minutes.

When the nucleic acid-containing lipid nanoparticle of the present invention contains lipid A, the total number of molecules of lipid A is not particularly limited. The molar number of the quaternary ammonium group in lipid A is preferably 0.01-fold molar amount or more, more preferably 0.1- to 10-fold molar amount, further preferably 0.1- to 4-fold molar amount, still further preferably 0.1- to 2-fold molar amount, most preferably 0.1- to 1-fold molar amount, with respect to the molar number of a phosphorus atom in the nucleic acid constituting the nucleic acid-containing lipid nanoparticle of the present invention.

When the nucleic acid-containing lipid nanoparticle of the present invention contains lipid B, the total number of molecules of lipid B is not particularly limited. The molar number of lipid B is preferably 0.1- to 10-fold molar amount, more preferably 0.5- to 9-fold molar amount, further preferably 1- to 8-fold molar amount, most preferably 1.5- to 6-fold molar amount, with respect to the molar number of a phosphorus atom in the nucleic acid constituting the nucleic acid-containing lipid nanoparticle of the present invention.

When the nucleic acid-containing lipid nanoparticle of the present invention contains lipid A and lipid B, the ratio of the molar number of lipid A to the molar number of lipid B (lipid A molar number/lipid B molar number) is preferably 0.001 or more, more preferably 0.003 to 10, further preferably 0.005 to 5, still further preferably 0.01 to 3, most preferably 0.01 to 2.

In the nucleic acid-containing lipid nanoparticle of the present invention, the ratio of the molar number of total lipid to the molar number of the nucleic acid (total lipid molar number/nucleic acid molar number) is preferably 50 or more, more preferably 100 to 1000, further preferably 120 to 800, still further preferably 140 to 600, most preferably 200 to 500.

When the nucleic acid-containing lipid nanoparticle of the present invention contains lipid B, the total number of molecules of lipid B in the nucleic acid-containing lipid nanoparticle is not particularly limited and is preferably 0.1-fold molar amount or more, more preferably 0.15-fold molar amount or more, further preferably 0.2-fold molar amount or more, still further preferably 0.25-fold molar amount or more, with respect to the molar number of total lipid. Also, the total number of molecules of lipid B in the nucleic acid-containing lipid nanoparticle is not particularly limited and is preferably 0.7-fold molar amount or less, more preferably 0.65-fold molar amount or less, further preferably 0.6-fold molar amount or less, with respect to the molar number of total lipid.

The total number of molecules of lipid B in the nucleic acid-containing lipid nanoparticle is preferably 0.10- to 0.70-fold molar amount, more preferably 0.15- to 0.65-fold molar amount, further preferably 0.20- to 0.65-fold molar amount, most preferably 0.25- to 0.60-fold molar amount, among combinations of the preferred ranges of the upper and lower limits described above with respect to the molar number of total lipid.

The nucleic acid-containing lipid nanoparticle of the present invention preferably further comprises a neutral lipid.

The neutral lipid can be any of simple lipids, complex lipids and derived lipids. Examples thereof include, but are not limited to, phospholipid, glyceroglycolipid, sphingoglycolipid, sphingoid and sterol. These neutral lipids may be used alone or in combination of two or more thereof.

In this context, the neutral lipid refers to a neutral lipid other than the analog of the fatty acid ester of glycerol that is not hydrolyzable by a lipase.

When the nucleic acid-containing lipid nanoparticle of the present invention contains a neutral lipid, the total number of molecules of the neutral lipid is not particularly limited and is preferably 0.10- to 0.75-fold molar amount, more preferably 0.20- to 0.70-fold molar amount, further preferably 0.20- to 0.65-fold molar amount, most preferably 0.30- to 0.60-fold molar amount, with respect to the molar number of total lipid (the total lipid includes the analog of the fatty acid ester of glycerol that is not hydrolyzable by a lipase).

In the nucleic acid-containing lipid nanoparticle of the present invention, the analog of the fatty acid ester of glycerol that is not hydrolyzable by a lipase is contained in preferably 0.001-fold molar amount or more, more preferably 0.001- to 0.75-fold molar amount, further preferably 0.05- to 0.70-fold molar amount, still further preferably 0.10- to 0.65-fold molar amount, most preferably 0.12- to 0.60-fold molar amount, with respect to the molar number of total lipid (the total lipid includes the analog of the fatty acid ester of glycerol that is not hydrolyzable by a lipase).

Examples of the phospholipid as the neutral lipid include, but are not limited to, natural or synthetic phospholipids such as phosphatidylcholines (PCs) (specifically, soybean phosphatidylcholine, egg phosphatidylcholine (EPC), distearoyl phosphatidylcholine, 1,2-distearoyl-sn-glycero-3-phosphocholine (DSPC), dipalmitoyl phosphatidylcholine, 1,2-dipalmitoyl-sn-glycero-3-phosphocholine (DPPC), palmitoyl oleoyl phosphatidylcholine (POPC), dimyristoyl phosphatidylcholine (DMPC), dioleoyl phosphatidylcholine (DOPC), etc.), phosphatidylethanolamines (specifically distearoyl phosphatidylethanolamine (DSPE), dipalmitoyl phosphatidylethanolamine (DPPE), dioleoyl phosphatidylethanolamine (DOPE), dimyristoyl phosphatidylethanolamine (DMPE), 16-O-monomethyl PE, 16-0-dimethyl PE, 18-1-trans PE, palmitoyl oleoyl-phosphatidylethanolamine (POPE), 1-stearoyl-2-oleoyl-phosphatidylethanolamine (SOPE), etc.), glycerophospholipids (specifically, phosphatidylserine, phosphatidic acid, phosphatidylglycerol, phosphatidylinositol, palmitoyl oleoyl phosphatidylglycerol (POPG), lysophosphatidylcholine, etc.), sphingophospholipids (specifically, sphingomyelin, ceramide phosphoethanolamine, ceramide phosphoglycerol, ceramide phosphoglycerophosphoric acid, etc.), glycerophosphonolipids, sphingophosphonolipids, natural lecithins (specifically, egg lecithin, soybean lecithin, etc.), and hydrogenated phospholipids (specifically, hydrogenated soybean phosphatidylcholine, etc.).

Examples of the glyceroglycolipid as the neutral lipid include, but are not limited to, sulfoxyribosyl glyceride, diglycosyl diglyceride, digalactosyl diglyceride, galactosyl diglyceride and glycosyl diglyceride.

Examples of the sphingoglycolipid as the neutral lipid include, but are not limited to, galactosyl cerebroside, lactosyl cerebroside and ganglioside.

Examples of the sphingoid as the neutral lipid include, but are not limited to, sphingan, icosasphingan, sphingosine, and derivatives of the foregoing. Examples of the derivatives include, but are not limited to, substances derived from sphingan, icosasphingan, sphingosine, or the like by the conversion of —$NH_2$ to —$NHCO(CH_2)_xCH_3$ wherein x is an integer from 0 to 18 and is particularly preferably 6, 12, or 18.

Examples of the sterol as the neutral lipid include, but are not limited to, cholesterol (Chol), dihydrocholesterol, lanosterol, β-sitosterol, campesterol, stigmasterol, brassicasterol, erugosterol, fucosterol and 3β-[N—(N',N'-dimethylaminoethyl)carbamoyl]cholesterol (DC-Chol).

Examples of the polymer include, but are not limited to, polymers such as proteins, albumin, dextran, polyfect, chitosan, dextran sulfate, poly-L-lysine, polyethylenimine, polyaspartic acid, styrene-maleic acid copolymers, isopropylacrylamide-acrylpyrrolidone copolymers, polyethylene glycol-modified dendrimers, polylactic acid, polylactic acid-polyglycolic acid, and polyethylene glycolated polylactic acid, and micelles consisting of one or more of salts of the foregoing.

In this context, the salt of the polymer encompasses, for example, metal salts, ammonium group salts, acid-addition salts, organic amine-addition salts and amino acid-addition salts. Examples of the metal salts include, but are not limited to: alkali metal salts such as lithium salt, sodium salt, and potassium salt; alkaline earth metal salts such as magnesium salt and calcium salt; aluminum salts; and zinc salts. Examples of the ammonium group salts include, but are not limited to, salts of an ammonium group, a tetramethylammonium group or the like. Examples of the acid-addition salts include, but are not limited to: inorganic acid salts such as hydrochloride, sulfate, nitrate, and phosphate; and organic acid salts such as acetate, maleate, fumarate, and citrate. Examples of the organic amine-addition salts include, but are not limited to, addition salts of morpholine, piperidine or the like. Examples of the amino acid-addition salts include, but are not limited to, addition salts of glycine, phenylalanine, aspartic acid, glutamic acid, lysine or the like.

Any nucleic acid-containing lipid nanoparticle of the present invention may contain, for example, a lipid derivative or a fatty acid derivative of one or more substances selected from a sugar, a peptide, a nucleic acid and a water-soluble polymer, or a surfactant.

Examples of the lipid derivative or the fatty acid derivative of one or more substances selected from a sugar, a peptide, a nucleic acid and a water-soluble polymer, or the surfactant preferably include glycolipids, and lipid derivatives or fatty acid derivatives of water-soluble polymers and more preferably include lipid derivatives or fatty acid derivatives of water-soluble polymers. The lipid derivative or the fatty acid derivative of one or more substances selected from a sugar, a peptide, a nucleic acid and a water-soluble polymer, or the surfactant is preferably a two-faced substance in which a part of the molecule has the properties of binding to other constituents of the composition via, for example, hydrophobic affinity or electrostatic interaction and the other moiety has the properties of binding to a solvent for use in the production of the composition via, for example, hydrophilic affinity or electrostatic interaction.

Examples of the lipid derivatives or the fatty acid derivatives of sugars, peptides or nucleic acids include substances obtained by the binding of sugars such as sucrose, sorbitol, and lactose, peptides such as casein-derived peptides, ovalbumin-derived peptides, soybean-derived peptides, and glutathione, or nucleic acids such as DNA, RNA, plasmids, siRNA, and ODN to the neutral lipids listed in the definition of the composition or to fatty acids such as stearic acid, palmitic acid, myristic acid, and lauric acid.

Examples of the lipid derivatives or the fatty acid derivatives of sugars also include the glyceroglycolipids or the sphingoglycolipids listed in the definition of the composition.

Examples of the lipid derivatives or the fatty acid derivatives of water-soluble polymers include substances obtained by the binding of polyethylene glycol, polyglycerin, polyethylenimine, polyvinyl alcohol, polyacrylic acid, polyacrylamide, oligosaccharide, dextrin, water-soluble cellulose, dextran, chondroitin sulfate, polyglycerin, chitosan, polyvinylpyrrolidone, polyaspartic acid amide, poly-L-lysine, mannan, pullulan, oligoglycerol, or the like or derivatives of the foregoing to the neutral lipids listed in the definition of the composition or to fatty acids such as stearic acid, palmitic acid, myristic acid, and lauric acid, salts of the foregoing. Examples thereof more preferably include lipid derivatives or fatty acid derivatives of polyethylene glycol or polyglycerin, and salts of the foregoing and further preferably include lipid derivatives or fatty acid derivatives of polyethylene glycol and salts of the foregoing.

Examples of the lipid derivatives or the fatty acid derivatives of polyethylene glycol include polyethylene glycolated lipids [specifically, polyethylene glycol-phosphatidylethanolamine (more specifically, 1,2-distearoyl-sn-glycero-3-phosphoethanolamine-N-[methoxy(polyethylene glycol)-2000] (PEG-DSPE), 1,2-dipalmitoyl-sn-glycero-3-phosphoethanolamine-N-[methoxy(polyethylene glycol)-2000] (PEG-DPPE), 1,2-dimyristoyl-sn-glycero-3-phosphoethanolamine-N-[methoxy(polyethylene glycol)-2000] (PEG-DMPE), etc.), polyoxyethylene hydrogenated castor oil 60, CREMOPHOR EL, etc.], and polyethylene glycol sorbitan fatty acid esters (specifically, polyoxyethylene sorbitan monooleate, etc.), and polyethylene glycol fatty acid esters and more preferably include polyethylene glycolated lipids.

Examples of the lipid derivatives or the fatty acid derivatives of polyglycerin include polyglycerinated lipids (specifically, polyglycerin-phosphatidyl ethanol amine, etc.), and polyglycerin fatty acid esters and more preferably include polyglycerinated lipids.

Examples of the surfactant include polyoxyethylene sorbitan monooleate (specifically, polysorbate 80, etc.), polyoxyethylene polyoxypropylene glycol (specifically, Pluronic F68, etc.), sorbitan fatty acid esters (specifically, sorbitan monolaurate, sorbitan monooleate, etc.), polyoxyethylene derivatives (specifically, polyoxyethylene hydrogenated castor oil 60, polyoxyethylene lauryl alcohol, etc.), glycerin fatty acid esters and polyethylene glycol alkyl ethers and preferably include polyoxyethylene polyoxypropylene glycol, glycerin fatty acid esters and polyethylene glycol alkyl ethers.

In the nucleic acid-containing lipid nanoparticle of the present invention, the total number of molecules of the lipid derivatives and the fatty acid derivatives of water-soluble polymers in the nucleic acid-containing lipid nanoparticle is not particularly limited and is preferably 0.005-fold molar amount or more, more preferably 0.01 to 0.30-fold molar amount, further preferably 0.02 to 0.25-fold molar amount, still further preferably 0.03 to 0.20-fold molar amount, even further preferably 0.04 to 0.15-fold molar amount, most preferably 0.04 to 0.12-fold molar amount, with respect to the molar number of total lipid.

In the present invention, the total lipid includes lipid A and lipid derivatives and fatty acid derivatives of water-soluble polymers and optionally includes lipid B and a neutral lipid. Specifically, the molar number of lipid A is fold molar amount obtained by subtracting 1 from the sum of the fold molar amounts of the lipid derivatives and the fatty acid derivatives of water-soluble polymers and, in some cases, the fold molar amount of lipid B and the fold molar amount of the neutral lipid, in terms of fold molar amount with the molar number of the total lipid defined as 1.

The nucleic acid-containing lipid nanoparticle of the present invention may be arbitrarily surface-modified with, for example, a water-soluble polymer [see D. D. Basic and F. Martin ed., "Stealth Liposomes" (USA), CRC Press Inc., 1995, p. 93-102]. Examples of the water-soluble polymer that may be used in the surface modification include, but are not limited to, polyethylene glycol, polyglycerin, polyethylenimine, polyvinyl alcohol, polyacrylic acid, polyacrylamide, oligosaccharides, dextrin, water-soluble cellulose, dextran, chondroitin sulfate, polyglycerin, chitosan, polyvinylpyrrolidone, polyaspartic acid amide, poly-L-lysine, mannan, pullulan and oligoglycerol, preferably polyethylene glycol, polyglycerin, polyethyleneimine, polyvinyl alcohol, polyacrylic acid and polyacrylamide, more preferably polyethylene glycol and polyglycerin. The lipid derivative or the fatty acid derivative of one or more substances selected from a sugar, a peptide, a nucleic acid and a water-soluble polymer (as defined above), or the surfactant, etc. can also be used in the surface modification. The surface modification is a method for allowing the nucleic acid-containing lipid nanoparticle of the present invention to contain the lipid derivative or the fatty acid derivative of one or more substances selected from a sugar, a peptide, a nucleic acid and a water-soluble polymer, or the surfactant.

A targeting ligand can be arbitrarily bonded directly to the surface of the nucleic acid-containing lipid nanoparticle of the present invention through a covalent bond to a polar head residue of a lipid component in the nucleic acid-containing lipid nanoparticle of the present invention (see WO 2006/116107).

The average particle size of the nucleic acid-containing lipid nanoparticle of the present invention may be further adjusted after preparation of the lipid nanoparticle. Examples of a method for adjusting the average particle size include an extrusion method and a method of mechanically pulverizing a large multilamellar vesicle (MLV) or the like (specifically, using Manton Gaulin, Microfluidizer, etc.) [see R. H. Muller, S. Benita and B. Bohm ed., "Emulsion and Nanosuspensions for the Formulation of Poorly Soluble Drugs", Germany, Scientific Publishers Stuttgart, 1998, p. 267-294].

The size of the nucleic acid-containing lipid nanoparticle of the present invention is preferably 1.00 to 2000 nm, more preferably 10.0 to 500 nm, further preferably 20.0 to 300 nm, most preferably 20.0 to 150 nm.

The size of the nucleic acid-containing lipid nanoparticle of the present invention can be measured by, for example, a dynamic light scattering method.

The nucleic acid in the nucleic acid-containing lipid nanoparticle of the present invention can be introduced into a mammalian cell by introducing the nucleic acid-containing lipid nanoparticle of the present invention into the cell.

The in vivo introduction of the nucleic acid-containing lipid nanoparticle of the present invention into a mammalian cell can be performed according to procedures of transfection known in the art that can be performed in vivo. For example, the nucleic acid-containing lipid nanoparticle of the present invention can be intravenously administered to a mammal including a human and thereby delivered to, for example, an organ or a site having tumor or inflammation so that the nucleic acid in the nucleic acid-containing lipid nanoparticle of the present invention is introduced into a cell of the organ or the site that has received the nucleic acid-containing lipid nanoparticle. Examples of the organ or the site having tumor or inflammation include, but are not particularly limited to, the stomach, the large intestine, the liver, the lung, the spleen, the pancreas, the kidney, the bladder, the skin, vascular vessels and eye balls. Also, the nucleic acid-containing lipid nanoparticle of the present invention can be intravenously administered to a mammal including a human and thereby delivered to, for example, the liver, the stomach, the lung, the spleen, the pancreas and/or the kidney so that the nucleic acid in the nucleic acid-containing lipid nanoparticle of the present invention is introduced into a cell of the organ or the site that has received the nucleic acid-containing lipid nanoparticle. The cell of the liver, the lung, the spleen, and/or the kidney can be any of normal cells, cells related to tumor or inflammation, and cells related to the other diseases.

Provided that the nucleic acid in the nucleic acid-containing lipid nanoparticle of the present invention is a nucleic acid having a silencing effect on a target gene through the use of RNA interference (RNAi), for example, the nucleic acid silencing a target gene or the like can be introduced into a mammalian cell in vivo. As a result, the expression of the target gene can be suppressed. The recipient is preferably a human.

Provided that the target gene in the nucleic acid-containing lipid nanoparticle of the present invention is, for example, a gene expressed in the liver, the stomach, the lung, the kidney, the pancreas and/or the spleen, preferably a gene expressed in the liver, the nucleic acid-containing lipid nanoparticle of the present invention can be used as a therapeutic agent or a prophylactic agent for a disease related to the liver, the stomach, the lung, the kidney, the pancreas or the spleen, preferably a therapeutic agent or a prophylactic agent for a disease related to the liver. Specifically, the present invention also provides a method for treating a disease or the like related to the liver, the stomach, the lung, the kidney, the pancreas or the spleen, comprising administering the nucleic acid-containing lipid nanoparticle of the present invention described above to a mammal. The recipient is preferably a human, more preferably a human having the disease or the like related to the liver, the stomach, the lung, the kidney, the pancreas or the spleen.

The nucleic acid-containing lipid nanoparticle of the present invention can also be used as a tool for verifying the effectiveness of suppression of a target gene in an in vivo drug efficacy evaluation model as to a therapeutic agent or a prophylactic agent for a disease or the like related to the liver, the stomach, the lung, the kidney, the pancreas or the spleen.

The nucleic acid-containing lipid nanoparticle of the present invention can also be used as a preparation aimed at, for example, stabilizing the nucleic acid in a biogenic substance such as a blood component (e.g., in blood or the digestive tract), reducing adverse reactions, and enhancing drug accumulation to a tissue or an organ containing an expression site of the target gene.

When the nucleic acid-containing lipid nanoparticle of the present invention is pharmaceutically used as a therapeutic agent or a prophylactic agent for, for example, a disease or the like related to the liver, the lung, the kidney or the spleen, an administration route most effective for treatment is desirably used. Examples of such an administration route can include parenteral or oral administration such as administration into the oral cavity, intratracheal administration, intrarectal administration, subcutaneous administration, intramuscular administration, intravenous administration, or the like. Examples thereof can preferably include intravenous administration, subcutaneous administration, and intramuscular administration and more preferably include intravenous administration.

The dose differs depending on the pathological condition or age of the recipient, the administration route, or the like. For example, the nucleic acid-containing lipid nanoparticle of the present invention can be administered, for example, at a daily dose of approximately 0.1 µg to 1000 mg in terms of the amount of the nucleic acid.

Examples of the preparation suitable for intravenous administration or intramuscular administration include injections. A dispersion of the composition prepared by the aforementioned method may be used directly in the form of, for example, an injection. Alternatively, the dispersion may be used after removal of the solvent by, for example, filtration or centrifugation, or the dispersion may be used after being freeze-dried and/or may be used after being supplemented with, for example, an excipient such as mannitol, lactose, trehalose, maltose or glycine and then freeze-dried.

In the case of an injection, the dispersion of the composition or the solvent-free or freeze-dried composition described above is preferably mixed with, for example, water, an acid, an alkali, various buffer solutions, physiological saline or an amino acid transfusion to prepare the injection. Alternatively, the injection may be prepared by the addition of, for example, an antioxidant such as citric acid, ascorbic acid, cysteine, or EDTA or a tonicity agent such as glycerin, glucose or sodium chloride. Also, the injection can also be cryopreserved by the addition of a cryopreserving agent such as glycerin.

EXAMPLES

Next, the present invention will be specifically described with reference to Examples, Reference Examples, Comparative Examples and Test Examples. However, the present invention is not intended to be limited by these Examples, Reference Examples, Comparative Examples and Test Examples.

Proton nuclear magnetic resonance spectra ($^1$H NMR) shown in Examples and Reference Examples were measured at 270 MHz, 300 MHz or 400 MHz, and no exchangeable proton may be clearly observed depending on compounds and measurement conditions. The multiplicity of signals is indicated as usually used, and br denotes an apparently broad signal.

(Synthesis of Cationic Lipid)

Hereinafter, methods for synthesizing lipid A will be shown in Reference Examples A1 to A71.

Reference Example A1

N-Methyl-2-(oleoyloxy)-N,N-bis(2-(oleoyloxy) ethyl)ethanaminium chloride (Compound I-1)

Step 1

To a solution of triethanolamine (manufactured by Sigma-Aldrich Corp., 0.115 g, 0.771 mmol) in chloroform (5 mL), oleic acid (manufactured by Tokyo Chemical Industry Co., Ltd., 0.784 g, 2.78 mmol), 1-ethyl-3-(3-dimethylaminopropyl)carbodiimide hydrochloride (manufactured by Tokyo Chemical Industry Co., Ltd., 0.591 g, 3.08 mmol), triethylamine (0.430 mL, 3.08 mmol) and N,N-dimethylaminopyridine (manufactured by Nacalai Tesque, Inc., 0.024 g, 0.19 mmol) were added, and the mixture was stirred overnight at room temperature. Water was added to the reaction solution, followed by extraction with chloroform. The organic layer was washed with a saturated aqueous solution of sodium bicarbonate and then saturated saline, dried over anhydrous magnesium sulfate, filtered, and concentrated under reduced pressure. The obtained residue was purified by silica gel column chromatography (chloroform/hexane=50/50 to 100/0) to obtain 2,2',2''-nitrilotris(ethane-2,1-diyl) trioleate (0.439 g, 0.466 mmol, yield: 60%).

ESI-MS m/z: 943 (M+H)$^+$; $^1$H-NMR (CDCl$_3$) δ: 0.88 (t, J=6.9 Hz, 9H), 1.23-1.36 (m, 60H), 1.58-1.63 (m, 6H), 1.98-2.04 (m, 12H), 2.29 (t, J=7.6 Hz, 6H), 2.83 (t, J=6.1 Hz, 6H), 4.11 (t, J=6.1 Hz, 6H), 5.31-5.38 (m, 6H).

Step 2

To 2,2',2''-nitrilotris(ethane-2,1-diyl) trioleate (0.439 g, 0.466 mmol) obtained in step 1, methyl iodide (manufactured by Tokyo Chemical Industry Co., Ltd., 3 mL) was added, and the mixture was stirred overnight at room temperature. The reaction solution was concentrated under reduced pressure. The residue was dissolved in a small amount of methanol-chloroform (1:1), and the solution was loaded to an ion-exchange resin (manufactured by The Dow Chemical Company, Dowex™ 1x-2 100 mesh, Cl type, approximately 20-fold amount, prewashed with water and methanol), followed by elution with methanol-chloroform (1:1). The eluate was concentrated under reduced pressure, and the obtained residue was purified by silica gel column chromatography (chloroform/methanol=100/0 to 88/12) to obtain the title compound (0.342 g, 0.344 mmol, yield: 74%).

ESI-MS m/z: 957 (M)$^+$; $^1$H-NMR (CDCl$_3$) δ: 0.88 (t, J=6.9 Hz, 9H), 1.25-1.35 (m, 60H), 1.59-1.63 (m, 6H), 1.99-2.03 (m, 12H), 2.35 (t, J=7.6 Hz, 6H), 3.56 (s, 3H), 4.21 (t, J=4.9 Hz, 6H), 4.61 (t, J=4.9 Hz, 6H), 5.30-5.38 (m, 6H).

Reference Example A2

N-Methyl-2-((9Z,12Z)-octadeca-9,12-dienoyloxy)-N,N-bis(2-((9Z,12Z)-octadeca-9,12-dienoyloxy) ethyl)ethanaminium chloride (Compound I-2)

The title compound (0.100 g, overall yield: 22%) was obtained in the same way as in Reference Example A1 using (9Z,12Z)-octadeca-9,12-dienoic acid (manufactured by Sigma-Aldrich Corp., 0.704 g, 2.51 mmol) instead of oleic acid.

ESI-MS m/z: 950 (M)$^+$; $^1$H-NMR (CDCl$_3$) 0.89 (t, J=7.0 Hz, 9H), 1.25-1.40 (m, 42H), 1.55-1.66 (m, 6H), 2.05 (q, J=6.9 Hz, 12H), 2.35 (t, J=7.6 Hz, 6H), 2.77 (t, J=6.3 Hz, 6H), 3.54 (s, 3H), 4.21 (t, J=5.1 Hz, 6H), 4.59 (br s, 6H), 5.28-5.43 (m, 12H).

Reference Example A3

(9Z,12Z)—N-Methyl-N,N-di((9Z,12Z)-octadeca-9,12-dienyl)octadeca-9,12-dien-1-aminium chloride (Compound I-3)

Step 1

To ammonia (manufactured by Tokyo Chemical Industry Co., Ltd., approximately 7 mol/L solution in methanol, 8.00 mL, 56.0 mmol), (9Z,12Z)-octadeca-9,12-dienyl methanesulfonate (manufactured by Nu-Chek Prep, Inc., 3.55 g, 10.1 mmol) was added, and the mixture was stirred at 130° C. for 3 hours using a microwave reaction apparatus. A saturated aqueous solution of sodium bicarbonate was added to the reaction solution, followed by extraction with chloroform five times. The organic layers were combined, washed with saturated saline, dried over anhydrous magnesium sulfate, then filtered, and concentrated under reduced pressure to obtain a crude product of (9Z,12Z)-octadeca-9,12-dien-1-amine.

To the obtained crude product, (9Z,12Z)-octadeca-9,12-dienyl methanesulfonate (2.78 g, 8.07 mmol) and a 50% aqueous sodium hydroxide solution (2.00 mL, 50.0 mmol) were added, and the mixture was stirred at 110° C. for 60 minutes in an oil bath. After cooling to room temperature, the reaction solution was diluted with ethyl acetate, washed with water and then saturated saline, dried over anhydrous magnesium sulfate, then filtered, and concentrated under reduced pressure. The obtained residue was purified by silica gel column chromatography (hexane/ethyl acetate=100/0 to 90/10) to obtain (9Z,12Z)-tri(9Z,12Z)-octadeca-9,12-dienylamine (1.09 g, 1.43 mmol, yield: 18%).

ESI-MS m/z: 763 (M+H)$^+$.

Step 2

The title compound (1.06 g, 1.30 mol, yield: 94%) was obtained in the same way as in step 2 of Reference Example A1 using (9Z,12Z)-tri(9Z,12Z)-octadeca-9,12-dienylamine (1.05 g, 1.38 mol) obtained in step 1 instead of 2,2',2"-nitrilotris(ethane-2,1-diyl)trioleate.

ESI-MS m/z: 111 (M)$^+$; $^1$H-NMR (CDCl$_3$) δ: 0.89 (t, J=7.1 Hz, 9H), 1.22-1.45 (m, 48H), 1.61-1.69 (m, 6H), 2.05 (q, J=6.8 Hz, 12H), 2.77 (t, J=6.5 Hz, 6H), 3.35 (s, 3H), 3.44-3.50 (m, 6H), 5.29-5.42 (m, 12H).

Reference Example A4

(Z)—N-Methyl-N,N-di((Z)-octadec-9-enyl)octadec-9-en-1-aminium chloride (Compound I-4)

The title compound (0.410 g, 0.501 mmol, overall yield: 24%) was obtained in the same way as in Reference Example A3 using (Z)-octadec-9-enyl methanesulfonate (manufactured by Nu-Chek Prep, Inc.) instead of (9Z,12Z)-octadeca-9,12-dienyl methanesulfonate.

ESI-MS m/z: 783 (M)$^+$; $^1$H-NMR (CDCl$_3$) δ: 0.88 (t, J=6.9 Hz, 9H), 1.22-1.44 (m, 66H), 1.62-1.69 (m, 6H), 1.98-2.04 (m, 12H), 3.35 (s, 3H), 3.45-3.51 (m, 6H), 5.30-5.39 (m, 6H).

Reference Example A5

(11Z,14Z)—N,N-Di((11Z,14Z)-icosa-11,14-dienyl)-N-methylicosa-11,14-dien-1-aminium chloride (Compound I-5)

The title compound (0.323 g, 0.360 mmol, overall yield: 25%) was obtained in the same way as in Reference Example A3 using (11Z,14Z)-icosa-11,14-dienyl methanesulfonate (manufactured by Nu-Chek Prep, Inc.) instead of (9Z,12Z)-octadeca-9,12-dienyl methanesulfonate.

$^1$H-NMR (CDCl$_3$) δ: 0.89 (t, J=6.9 Hz, 9H), 1.24-1.43 (m, 63H), 1.61-1.69 (m, 6H), 2.05 (q, J=6.8 Hz, 12H), 2.77 (t, J=6.6 Hz, 6H), 3.35 (s, 3H), 3.45-3.50 (m, 6H), 5.30-5.42 (m, 12H).

Reference Example A6

(9Z,12Z)—N-(3-Hydroxypropyl)-N,N-di((9Z,12Z)-octadeca-9,12-dienyl)octadeca-9,12-dien-1-aminium chloride (Compound I-6)

To a solution of tri((9Z,12Z)-octadeca-9,12-dienyl)amine (0.199 g, 0.261 mmol) obtained in step 1 of Reference Example A3 in chloroform (0.3 mL), 3-iodopropan-1-ol (manufactured by Wako Pure Chemical Industries Ltd., 0.194 g, 1.04 mmol) was added, and the mixture was reacted at 130° C. for 40 minutes in a microwave reaction apparatus. The reaction solution was dissolved in a small amount of ethanol, and the solution was loaded to an ion-exchange resin (manufactured by Sigma-Aldrich Corp., Amberlite® IRA-400, Cl type, approximately 20-fold amount, pre-washed with water and ethanol), followed by elution with ethanol. The eluate was concentrated under reduced pressure, and the obtained residue was purified by silica gel column chromatography (chloroform/methanol=100/0 to 88/12) to obtain the title compound (0.146 g, 0.170 mmol, yield: 65%).

ESI-MS m/z: 821 (M)$^+$; $^1$H-NMR (CDCl$_3$) δ: 0.89 (t, J=7.0 Hz, 9H), 1.27-1.39 (m, 49H), 1.67-1.74 (m, 6H), 1.93-1.99 (m, 2H), 2.05 (q, J=6.9 Hz, 12H), 2.77 (t, J=6.2 Hz, 6H), 3.14-3.19 (m, 6H), 3.70-3.74 (m, 2H), 3.79 (t, J=5.1 Hz, 2H), 5.29-5.42 (m, 12H).

Reference Example A7

(9Z,12Z)—N-(2-Hydroxyethyl)-N,N-di((9Z,12Z)-octadeca-9,12-dienyl)octadeca-9,12-dien-1-aminium chloride (Compound I-7)

The title compound (0.211 g, 0.250 mmol, yield: 85%) was obtained in the same way as in Reference Example A6 using 2-iodoethan-1-ol (manufactured by Tokyo Chemical Industry Co., Ltd.) instead of 3-iodopropan-1-ol.

ESI-MS m/z: 807 (M)$^+$; $^1$H-NMR (CDCl$_3$) δ: 0.89 (t, J=7.0 Hz, 9H), 1.27-1.40 (m, 49H), 1.64-1.71 (m, 6H), 2.05 (q, J=6.8 Hz, 12H), 2.77 (t, J=6.3 Hz, 6H), 3.36-3.41 (m, 6H), 3.53-3.56 (m, 2H), 4.08-4.12 (m, 2H), 5.29-5.42 (m, 12H).

Reference Example A8

N,N,N-Trimethyl-1,3-bis((9Z,12Z)-octadeca-9,12-dienoyloxy)-2-(((9Z,12Z)-octadeca-9,12-dienoyloxy)methyl)propan-2-aminium chloride (Compound II-1)

Step 1

To a solution of 2-(dimethylamino)-2-(hydroxymethyl)propane-1,3-diol (manufactured by Zylexa Pharma Ltd., 0.252 g, 1.69 mmol) in chloroform (10 mL), (9Z,12Z)-octadeca-9,12-dienoic acid (2.37 g, 8.45 mmol), 1-ethyl-3-(3-dimethylaminopropyl)carbodiimide hydrochloride (1.62 g, 8.45 mmol) and N,N-dimethylaminopyridine (0.206 g, 1.69 mmol) were added, and the mixture was stirred overnight at 60° C. The reaction mixture was cooled to room temperature and then concentrated under reduced pressure. The obtained residue was purified by silica gel column chromatography (chloroform/methanol=100/0) to obtain (9Z,9'Z,12Z,12'Z)-2-(dimethylamino)-2-(((9Z,12Z)-octadeca-9,12-dienoyloxy)methyl)propane-1,3-diyl dioctadeca-9,12-dienoate (0.334 g, 0.356 mmol, yield: 21%).

ESI-MS m/z: 937 (M+H)$^+$.

Step 2

To a solution of (9Z,9'Z,12Z,12'Z)-2-(dimethylamino)-2-(((9Z,12Z)-octadeca-9,12-dienoyloxy)methyl)propane-1,3-diyl dioctadeca-9,12-dienoate (0.324 g, 0.346 mmol) obtained in step 1 in chloroform (3 mL), methyl iodide (0.216 mL) was added, and the mixture was stirred at room temperature for 5 hours. Methyl iodide (0.216 mL) was added to the reaction solution, and the mixture was stirred overnight at room temperature. The reaction solution was concentrated under reduced pressure. The residue was dissolved in a small amount of methanol-chloroform (1:1), and the solution was loaded to an ion-exchange resin (manufactured by The Dow Chemical Company, Dowex™ 1×-2 100 mesh, Cl type, approximately 20-fold amount, prewashed with water and methanol), followed by elution with methanol-chloroform (1:1). The eluate was concentrated under reduced pressure, and the obtained residue was purified by silica gel column chromatography (chloroform/methanol=100/0 to 90/10) to obtain the title compound (0.161 g, 0.164 mmol, yield: 47%).

ESI-MS m/z: 951 (M)$^+$; $^1$H-NMR (CDCl$_3$) δ: 0.86 (t, J=6.9 Hz, 9H), 1.22-1.36 (m, 42H), 1.54-1.61 (m, 6H), 2.02 (q, J=6.8 Hz, 12H), 2.34 (t, J=7.7 Hz, 6H), 2.74 (t, J=6.8 Hz, 6H), 3.69 (s, 9H), 4.57 (s, 6H), 5.26-5.39 (m, 12H).

Reference Example A9

N,N,N-Trimethyl-1,3-bis((Z)-tetradec-9-enoyloxy)-2-(((Z)-tetradec-9-enoyloxy)methyl)propan-2-aminium chloride (Compound II-2)

The title compound (0.0854 g, 0.104 mmol, overall yield: 16%) was obtained in the same way as in Reference Example A8 using cis-9-tetradecenoic acid (manufactured by Nu-Chek Prep, Inc.) instead of (9Z,12Z)-octadeca-9,12-dienoic acid.

ESI-MS m/z: 789 (M)$^+$; $^1$H-NMR (CDCl$_3$) δ: 0.89 (t, J=7.1 Hz, 9H), 1.27-1.36 (m, 36H), 1.58-1.64 (m, 6H), 2.02 (q, J=6.5 Hz, 12H), 2.37 (t, J=7.6 Hz, 6H), 3.72 (s, 9H), 4.55 (s, 6H), 5.30-5.38 (m, 6H).

Reference Example A10

N,N,N-Trimethyl-1,3-bis(oleoyloxy)-2-(oleoyloxymethyl)propan-2-aminium chloride (Compound II-3)

The title compound (1.14 g, 1.15 mmol, overall yield: 34%) was obtained in the same way as in Reference Example A8 using oleic acid instead of (9Z,12Z)-octadeca-9,12-dienoic acid.

ESI-MS m/z: 957 (M)$^+$; $^1$H-NMR (CDCl$_3$) δ: 0.83 (t, J=6.9 Hz, 9H), 1.17-1.32 (m, 60H), 1.51-1.59 (m, 6H), 1.96 (t, J=5.5 Hz, 12H), 2.32 (t, J=7.6 Hz, 6H), 3.70 (s, 9H), 4.56 (s, 6H), 5.25-5.34 (m, 6H).

Reference Example A11

N,N,N-Trimethyl-1,3-bis(stearoyloxy)-2-(stearoyloxymethyl)propan-2-aminium chloride (Compound II-4)

Step 1

To 2-(dimethylamino)-2-(hydroxymethyl)propane-1,3-diol (0.100 g, 0.670 mmol), toluene (10 mL), stearic acid (manufactured by Tokyo Chemical Industry Co., Ltd., 0.763 g, 2.68 mmol), and p-toluenesulfonic acid monohydrate (0.191 g, 1.01 mmol) were added in order, and the mixture was stirred overnight under conditions of heating to reflux. The reaction solution was concentrated under reduced pressure, and the obtained residue was purified by amino silica gel column chromatography (chloroform) to obtain 2-(dimethylamino)-2-((stearoyloxy)methyl)propane-1,3-diyl distearate (0.120 g, 0.127 mmol, yield: 19%).

ESI-MS m/z: 948 (M+H)$^+$

Step 2

The title compound (0.0260 g, 0.0260 mmol, yield: 21%) was obtained in the same way as in step 2 of Reference Example A1 using 2-(dimethylamino)-2-((stearoyloxy)methyl)propane-1,3-diyl distearate (0.120 g, 0.127 mmol) obtained in step 1.

ESI-MS m/z: 963 (M)$^+$; $^1$H-NMR (CDCl$_3$) δ: 0.88 (t, J=7.0 Hz, 9H), 1.22-1.36 (m, 84H), 1.56-1.65 (m, 6H), 2.37 (t, J=7.6 Hz, 6H), 3.72 (s, 9H), 4.56 (s, 6H).

Reference Example A12

1,3-Bis((Z)-hexadec-9-enoyloxy)-2-(((Z)-hexadec-9-enoyloxy)methyl)-N,N,N-trimethylpropan-2-aminium chloride (Compound II-5)

The title compound (0.680 g, 0.748 mmol, overall yield: 63%) was obtained in the same way as in Reference Example A8 using cis-9-hexadecenoic acid instead of (9Z,12Z)-octadeca-9,12-dienoic acid.

ESI-MS m/z: 873 (M)$^+$; $^1$H-NMR (CDCl$_3$) δ: 0.88 (t, J=7.0 Hz, 9H), 1.24-1.36 (m, 48H), 1.56-1.67 (m, 13H), 1.98-2.05 (m, 12H), 2.37 (t, J=7.6 Hz, 6H), 3.75 (s, 9H), 4.53 (s, 6H), 5.29-5.40 (m, 6H).

Reference Example A13

N,N,N-Trimethyl-1,3-bis((9Z,12Z)-octadeca-9,12-dienyloxy)-2-(((9Z,12Z)-octadeca-9,12-dienyloxy)methyl)propan-2-aminium chloride (Compound II-6)

Step 1

To a solution of 2-dimethylamino-2-hydroxymethylpropane-1,3-diol (manufactured by Zylexa Pharma Ltd., 0.115 g, 0.768 mmol) in toluene (5 mL), sodium hydride (manufactured by Nacalai Tesque, Inc., 60% oil, 0.154 g, 3.84 mmol) and (9Z,12Z)-octadeca-9,12-dienyl methanesulfonate (1.32 g, 3.84 mmol) were added, and the mixture was stirred overnight under heating to reflux. After cooling to room temperature, a saturated aqueous solution of sodium bicarbonate was added to the reaction solution, followed by extraction with hexane. The organic layer was dried over anhydrous magnesium sulfate, filtered, and concentrated under reduced pressure. The obtained residue was purified by amino silica gel column chromatography (hexane/ethyl acetate=100/0 to 95/5) to obtain N,N-dimethyl-1,3-bis((9Z,12Z)-octadeca-9,12-dienyloxy)-2-(((9Z,12Z)-octadeca-9,12-dienyloxy)methyl)propan-2-amine (0.195 g, 0.217 mmol, yield: 28%).

ESI-MS m/z: 895 (M+H)$^+$.

Step 2

To a solution of N,N-dimethyl-1,3-bis((9Z,12Z)-octadeca-9,12-dienyloxy)-2-(((9Z,12Z)-octadeca-9,12-dienyloxy)methyl)propan-2-amine (0.0849 g, 0.0949 mmol) obtained in step 1 in chloroform (1 mL), methyl iodide (0.119 mL) was added, and the mixture was stirred overnight at room temperature. The reaction solution was concentrated under reduced pressure. The residue was dissolved in a small amount of methanol-chloroform (1:1), and the solution was loaded to an ion-exchange resin (manufactured by The Dow Chemical Company, Dowex™ 1x-2 100 mesh, Cl type, approximately 20-fold amount, prewashed with water and methanol), followed by elution with methanol-chloroform (1:1). The eluate was concentrated under reduced pressure, and the obtained residue was purified by silica gel column chromatography (chloroform/methanol=100/0 to 90/10) to obtain the title compound (0.0646 g, 0.0684 mmol, yield: 72%).

ESI-MS m/z: 909 (M)$^+$; $^1$H-NMR (CDCl$_3$) δ: 0.89 (t, J=6.9 Hz, 9H), 1.25-1.40 (m, 48H), 1.55-1.63 (m, 6H), 2.02-2.09 (m, 12H), 2.77 (t, J=6.8 Hz, 6H), 3.44 (t, J=6.6 Hz, 6H), 3.62 (s, 9H), 3.82 (s, 6H), 5.29-5.42 (m, 12H).

Reference Example A14

N,N,N-Trimethyl-1,3-bis((Z)-tetradec-9-enyloxy)-2-(((Z)-tetradec-9-enyloxy)methyl)propan-2-aminium chloride (Compound II-7)

The title compound (0.0729 g, 0.0931 mmol, overall yield: 12%) was obtained in the same way as in Reference Example A13 using myristoleyl methanesulfonate (manufactured by Nu-Chek Prep, Inc.) instead of (9Z,12Z)-octadeca-9,12-dienyl methanesulfonate.

ESI-MS m/z: 747 (M)$^+$; $^1$H-NMR (CDCl$_3$) δ: 0.90 (t, J=7.1 Hz, 9H), 1.27-1.37 (m, 42H), 1.54-1.61 (m, 6H), 2.02 (q, J=6.5 Hz, 12H), 3.43 (t, J=6.6 Hz, 6H), 3.64 (s, 8H), 3.81 (s, 6H), 5.31-5.39 (m, 6H).

Reference Example A15

1,3-Bis((Z)-hexadec-9-enyloxy)-2-(((Z)-hexadec-9-enyloxy)methyl)-N,N,N-trimethylpropan-2-aminium chloride (Compound II-8)

The title compound (0.466 g, 0.538 mmol, overall yield: 71%) was obtained in the same way as in Reference Example A13 using palmitoleyl methanesulfonate (manufactured by Nu-Chek Prep, Inc.) instead of (9Z,12Z)-octadeca-9,12-dienyl methanesulfonate.

ESI-MS m/z: 831 (M)$^+$; $^1$H-NMR (CDCl$_3$) δ: 0.88 (t, J=6.8 Hz, 9H), 1.23-1.37 (m, 54H), 1.53-1.61 (m, 14H), 2.02 (q, J=5.8 Hz, 12H), 3.43 (t, J=6.5 Hz, 6H), 3.65 (s, 9H), 3.81 (s, 6H), 5.30-5.40 (m, 6H).

Reference Example A16

(6Z,9Z,40Z,43Z)—N,N,N-Trimethyl-25-((3-((9Z,12Z)-octadeca-9,12-dienyloxy)-3-oxopropoxy)methyl)-20,30-dioxo-19,23,27,31-tetraoxanonatetraconta-6,9,40,43-tetraen-25-aminium chloride (Compound II-9)

Step 1

Di-tert-butyl 3,3'-((2-amino-2-((3-(tert-butoxy)-3-oxopropoxy)methyl)propane-1,3-diyl)bis(oxy))dipropanoate (0.500 g, 0.989 mmol) synthesized by a method equivalent to the method described in "J. Org. Chem.", 2002, Vol. 67, p. 1411-1413 was dissolved in dichloromethane (5 mL). To the solution, methyl iodide (1.40 g, 9.89 mmol) was added, and the mixture was stirred overnight at room temperature. The reaction solution was concentrated under reduced pressure. The residue was dissolved in a small amount of methanol-chloroform (1:1), and the solution was loaded to an ion-exchange resin (Dowex™ 1x-2 100 mesh, Cl type, approximately 20-fold amount, prewashed with water and methanol), followed by elution with methanol. The eluate was concentrated under reduced pressure, and the obtained residue was purified by silica gel column chromatography (chloroform/methanol=97/3 to 80/20) to obtain 9-((3-(tert-butoxy)-3-oxopropoxy)methyl)-N,N,N,2,2,16,16-heptamethyl-4,14-dioxo-3,7,11,15-tetraoxaheptadecan-9-aminium chloride (0.144 g, 0.246 mmol, yield: 25%).

ESI-MS m/z: 548 (M+H)$^+$.

Step 2

9-((3-(tert-Butoxy)-3-oxopropoxy)methyl)-N,N,N,2,2,16,16-heptamethyl-4,14-dioxo-3,7,11,15-tetraoxaheptadecan-9-aminium chloride (0.350 g, 0.246 mmol) obtained in step 1 was dissolved in dichloromethane (2 mL). To the solution, trifluoroacetic acid (0.380 mL, 4.92 mmol) was added, and the mixture was stirred at room temperature for 3 hours. Toluene was added to the reaction solution, and the mixture was concentrated under reduced pressure to obtain a crude product of 1,3-bis(2-carboxyethoxy)-2-((2-carboxyethoxy)methyl)-N,N,N-trimethylpropan-2-aminium chloride trifluoroacetate (0.102 g, 0.246 mmol, crude yield: 100%).

ESI-MS m/z: 422 (M+H)$^+$

Step 3

The crude product of 1,3-bis(2-carboxyethoxy)-2-((2-carboxyethoxy)methyl)-N,N,N-trimethylpropan-2-aminium chloride trifluoroacetate (0.055 g, 0.13 mmol) obtained in step 2 was dissolved in dichloromethane (2 mL). To the solution, O-(7-aza-1H-benzotriazol-1-yl)-N,N,N',N'-tetramethyluronium hexafluorophosphate (manufactured by Wako Pure Chemical Industries Ltd., 0.20 g, 0.53 mmol), N,N-diisopropylethylamine (0.23 mL, 1.3 mmol), and (9Z,12Z)-octadeca-9,12-dien-1-ol (manufactured by Tokyo Chemical Industry Co., Ltd., 0.141 g, 0.53 mmol) were added, and the mixture was stirred overnight at room temperature. Water was added to the reaction solution, followed by extraction with chloroform. The organic layer was washed with saturated saline, dried over anhydrous magnesium sulfate, filtered, and concentrated under reduced pressure. The obtained residue was purified by silica gel column chromatography (chloroform/methanol=90/10 to 80/20) to obtain the title compound (8.0 mg, 6.9 mmol, yield: 5%).

ESI-MS m/z: 1125 (MH)$^+$; $^1$H-NMR (CDCl$_3$) δ: 0.89 (t, J=7.0 Hz, 9H), 1.25-1.39 (m, 48H), 1.58-1.66 (m, 6H), 2.05 (q, J=6.9 Hz, 12H), 2.59 (t, J=5.7 Hz, 6H), 2.77 (t, J=6.7 Hz, 6H), 3.42 (s, 9H), 3.74 (t, J=5.7 Hz, 6H), 4.00 (s, 6H), 4.07 (t, J=6.8 Hz, 6H), 5.29-5.40 (m, 12H).

Reference Example A17

(7Z,38Z)-23-((3-((Z)-Hexadec-9-enyloxy)-3-oxopropoxy)methyl)-N,N,N-trimethyl-18,28-dioxo-17,21,25,29-tetraoxapentatetraconta-7,38-dien-23-aminium chloride (Compound II-10)

The title compound (0.145 g, 0.134 mmol, overall yield: 17%) was obtained in the same way as in Reference Example A16 using (Z)-hexadec-9-en-1-ol (manufactured by Nu-Chek Prep, Inc.) instead of (9Z,12Z)-octadeca-9,12-dien-1-ol.

ESI-MS m/z: 1047 (M)$^+$; $^1$H-NMR (CDCl$_3$) δ: 0.88 (t, J=7.0 Hz, 9H), 1.24-1.38 (m, 54H), 1.58-1.66 (m, 6H), 1.98-2.05 (m, 12H), 2.58 (t, J=5.7 Hz, 6H), 3.47 (s, 9H), 3.74 (t, J=5.7 Hz, 6H), 4.02 (s, 6H), 4.07 (t, J=6.8 Hz, 6H), 5.30-5.40 (m, 6H).

Reference Example A18

(5Z,36Z)—N,N,N-Trimethyl-16,26-dioxo-21-((3-oxo-3-((Z)-tetradec-9-enyloxy)propoxy)methyl)-15,19,23,27-tetraoxahentetraconta-5,36-dien-21-aminium chloride (Compound II-11)

The title compound (0.189 g, 0.189 mmol, overall yield: 24%) was obtained in the same way as in Reference Example A16 using (Z)-tetradec-9-en-1-ol (manufactured by Nu-Chek Prep, Inc.) instead of (9Z,12Z)-octadeca-9,12-dien-1-ol.

ESI-MS m/z: 963 (M)$^+$; $^1$H-NMR (CDCl$_3$) δ: 0.87-0.92 (m, 9H), 1.25-1.38 (m, 42H), 1.55-1.66 (m, 6H), 1.98-2.05 (m, 12H), 2.58 (t, J=5.7 Hz, 6H), 3.47 (s, 9H), 3.75 (t, J=5.7 Hz, 6H), 4.01 (s, 6H), 4.07 (t, J=6.8 Hz, 6H), 5.30-5.41 (m, 6H).

Reference Example A19

(11Z,14Z)—N,N,N-Trimethyl-2-(((9Z,12Z)-octadeca-9,12-dienoyloxy)methyl)-2-((9Z,12Z)-octadeca-9,12-dienyl)icosa-11,14-dien-1-aminium chloride (Compound II-12)

Step 1
Ethyl cyanoacetate (manufactured by Tokyo Chemical Industry Co., Ltd., 1.00 g, 8.84 mmol) and (9Z,12Z)-octadeca-9,12-dienyl methanesulfonate (7.62 g, 22.1 mmol) were dissolved in tetrahydrofuran (30 mL). To the solution, sodium hydride (60% oil, 1.06 g, 26.5 mmol) and tetra-n-butylammonium iodide (manufactured by Nacalai Tesque, Inc., 3.27 g, 8.84 mmol) were added under ice cooling. After foaming was completed, the mixture was stirred at 60° C. for 3 hours. Water was added to the reaction solution, followed by extraction with hexane. The organic layer was washed with saturated saline, dried over anhydrous magnesium sulfate, and filtered. The filtrate was concentrated under reduced pressure to obtain a crude product of (11Z,14Z)-ethyl 2-cyano-2-((9Z,12Z)-octadeca-9,12-dien-1-yl)icosa-11,14-dienoate (3.50 g, 5.74 mmol, crude yield: 65%).

Step 2
The crude product of (11Z,14Z)-ethyl 2-cyano-2-((9Z,12Z)-octadeca-9,12-dien-1-yl)icosa-11,14-dienoate 1.50 g, 2.46 mmol) obtained in step 1 was dissolved in tetrahydrofuran (10 mL). To the solution, lithium aluminum hydride (manufactured by Junsei Chemical Co., Ltd., 0.467 g, 12.3 mmol) was added under ice cooling, and the mixture was stirred for 30 minutes. Water (0.5 mL), a 15% aqueous sodium hydroxide solution (0.5 mL), water (1.5 mL), and magnesium sulfate were added in order to the reaction solution, and the mixture was stirred for a while and then filtered. The filtrate was concentrated under reduced pressure, and the obtained residue was purified by silica gel column chromatography (chloroform/methanol=99/1 to 85/15) to obtain (11Z,14Z)-2-(aminoethyl)-2-((9Z,12Z)-octadeca-9,12-dien-1-yl)icosa-11,14-dien-1-ol (1.00 g, 2.46 mmol, yield: 71%).

ESI-MS m/z: 573 (M+H)$^+$.

Step 3
(11Z,14Z)-2-(Aminoethyl)-2-((9Z,12Z)-octadeca-9,12-dien-1-yl)icosa-11,14-dien-1-ol (0.350 g, 0.612 mmol) obtained in step 2 was dissolved in acetonitrile (2 mL) and tetrahydrofuran (2 mL). To the solution, a 38% aqueous formaldehyde solution (manufactured by Wako Pure Chemical Industries Ltd., 0.145 mL, 1.84 mmol), acetic acid (0.035 mL, 0.612 mmol), and sodium triacetoxyborohydride (manufactured by Acros Organics B.V.B.A., 0.389 g, 1.84 mmol) were added, and the mixture was stirred overnight at room temperature. Water was added to the reaction solution, followed by extraction with chloroform. The organic layer was washed with saturated saline, dried over anhydrous magnesium sulfate, and filtered. The obtained residue was purified by silica gel column chromatography (chloroform/methanol=99/1 to 85/15) to obtain (11Z,14Z)-2-((dimethylamino)methyl)-2-((9Z,12Z)-octadeca-9,12-dien-1-yl) icosa-11,14-dien-1-ol (0.252 g, 0.420 mmol, yield: 69%).

ESI-MS m/z: 600 (M+H)$^+$

Step 4
To a solution of (11Z,14Z)-2-((dimethylamino)methyl)-2-((9Z,12Z)-octadeca-9,12-dien-1-yl)icosa-11,14-dien-1-ol (0.252 g, 0.420 mmol) obtained in step 3 in dichloromethane (4 mL), (9Z,12Z)-octadeca-9,12-dienoic acid (0.141 g, 0.504 mmol), O-(7-aza-1H-benzotriazol-1-yl)-N,N,N',N'-tetramethyluronium hexafluorophosphate (0.192 mmol, 0.504 mmol), and N,N-diisopropylethylamine (0.147 mL, 0.840 mmol) were added in order, and the mixture was stirred at room temperature for 4 hours. Water was added to the reaction solution, followed by extraction with hexane. The organic layer was washed with water, dried over anhydrous magnesium sulfate, filtered, and concentrated under reduced pressure. The obtained residue was purified by silica gel column chromatography (hexane/ethyl acetate=95/5 to 85/15) to obtain (9Z,12Z)-(11Z,14Z)-2-((dimethylamino) methyl)-2-((9Z,12Z)-octadeca-9,12-dien-1-yl)icosa-11,14-dien-1-yl octadeca-9,12-dienoate (0.307 g, 0.356 mmol, yield: 85%).

ESI-MS m/z: 863 (M+H)$^+$

Step 5
The title compound (0.260 g, 0.285 mmol, yield: 80%) was obtained in the same way as in step 2 of Reference Example A1 using (9Z,12Z)-(11Z,14Z)-2-((dimethylamino) methyl)-2-((9Z,12Z)-octadeca-9,12-dien-1-yl)icosa-11,14-dien-1-yl octadeca-9,12-dienoate (0.307 g, 0.356 mmol) obtained in step 4.

ESI-MS m/z: 877 (M)$^+$; $^1$H-NMR (CDCl$_3$) δ: 0.89 (t, J=7.0 Hz, 9H), 1.22-1.48 (m, 54H), 1.60-1.66 (m, 2H), 2.05 (q, J=6.8 Hz, 12H), 2.38 (t, J=7.6 Hz, 2H), 2.77 (t, J=6.3 Hz, 6H), 3.50 (s, 2H), 3.60 (s, 9H), 4.13 (s, 2H), 5.27-5.44 (m, 12H).

Reference Example A20

N,N,N-Trimethyl-3-((11Z,14Z)-2-(((9Z,12Z)-octadeca-9,12-dienoyloxy)methyl)-2-((9Z,12Z)-octadeca-9,12-dienyl)icosa-11,14-dienylcarbamoyloxy) propan-1-aminium chloride (Compound II-13)

Step 1
(11Z,14Z)-2-(Aminoethyl)-2-((9Z,12Z)-octadeca-9,12-dien-1-yl)icosa-11,14-dien-1-ol (0.918 g, 1.61 mmol) obtained in step 2 of Reference Example A19 was dissolved in tetrahydrofuran (20 mL). To the solution, triethylamine (0.671 mL, 4.81 mmol) and di-tert-butyl dicarbonate (manufactured by Kokusan Chemical Co., Ltd., 0.373 mL, 1.61 mmol) were added, and the mixture was stirred overnight at room temperature. The reaction solution was concentrated under reduced pressure, and the obtained residue was purified by silica gel column chromatography (hexane/ethyl acetate=95/5 to 50/50) to obtain tert-butyl ((11Z,14Z)-2-(hydroxymethyl)-2-((9Z,12Z)-octadeca-9,12-dien-1-yl)icosa-11,14-dien-1-yl)carbamate (0.918 g, 1.37 mmol, yield: 85%).

ESI-MS m/z: 672 (M+H)$^+$.

Step 2 tert-Butyl ((11Z,14Z)-2-(hydroxymethyl)-2-((9Z,12Z)-octadeca-9,12-dien-1-yl)icosa-11,14-dien-1-yl)carbamate (0.357 g, 0.531 mmol) obtained in step 1 was dissolved in dichloromethane (5 mL). To the solution, (9Z,12Z)-octadeca-9,12-dienoic acid (0.223 g, 0.797 mmol), O-(7-aza-1H-benzotriazol-1-yl)-N,N,N',N'-tetramethyluronium hexafluorophosphate (0.303 mmol, 0.797 mmol), N,N-diisopropylethylamine (0.186 mL, 1.06 mmol), and N,N-dimethylaminopyridine (0.0650 g, 0.531 mmol) were added, and the mixture was stirred overnight at room temperature. Water was added to the reaction solution, followed by extraction with chloroform. The organic layer was washed with saturated saline, dried over anhydrous magnesium sulfate, filtered, and concentrated under reduced pressure. The obtained residue was purified by silica gel column chromatography (hexane/ethyl acetate=99/1 to 90/10) to obtain (9Z,12Z)-(11Z,14Z)-2-(((tert-butoxycarbonylamino)methyl)-2-((9Z,12Z)-octadeca-9,12-dien-1-yl)icosa-11,14-dien-1-yl octadeca-9,12-dienoate (0.395 g, 0.423 mmol, yield: 80%).

ESI-MS m/z: 935 (M+H)$^+$.

Step 3

(9Z,12Z)-(11Z,14Z)-2-(((tert-Butoxycarbonylamino)methyl)-2-((9Z,12Z)-octadeca-9,12-dien-1-yl) icosa-11,14-dien-1-yl octadeca-9,12-dienoate (0.395 g, 0.423 mmol) obtained in step 2 was dissolved in dichloromethane (3 mL). To the solution, trifluoroacetic acid (1.00 mL, 4.92 mmol) was added under ice cooling, and the mixture was stirred at 0° C. for 2 hours. 1,2-Dichloroethane was added to the reaction solution, and the mixture was concentrated under reduced pressure to obtain a crude product of (9Z,12Z)-(11Z,14Z)-2-(aminoethyl)-2-((9Z,12Z)-octadeca-9,12-dien-1-yl)icosa-11,14-dien-1-yl octadeca-9,12-dienoate trifluoroacetate (0.394 g, 0.423 mmol, crude yield: 100%).

ESI-MS m/z: 834 (M+H)$^+$.

Step 4

The crude product of (9Z,12Z)-(11Z,14Z)-2-(aminoethyl)-2-((9Z,12Z)-octadeca-9,12-dien-1-yl)icosa-11,14-dien-1-yl octadeca-9,12-dienoate trifluoroacetate (0.200 g, 0.215 mmol) obtained in step 3 was dissolved in acetonitrile (2 mL). To the solution, 3-(dimethylamino)propyl 4-nitrophenyl carbonate hydrochloride (0.279 g, 1.07 mmol) synthesized by a method equivalent to the method described in "J. Am. Chem. Soc.", 1981, Vol. 103, p. 4194-4199, triethylamine (0.299 mL, 2.15 mmol), and N,N-dimethylaminopyridine (0.0520 g, 0.429 mmol) were added, and the mixture was stirred at 60° C. for 2 hours. A saturated aqueous solution of sodium bicarbonate was added to the reaction solution, followed by extraction with chloroform. The organic layer was washed with saturated saline, dried over anhydrous magnesium sulfate, filtered, and concentrated under reduced pressure. The obtained residue was purified by silica gel column chromatography (hexane/ethyl acetate=99/1 to 60/40) to obtain (9Z,12Z)-(11Z,14Z)-2-((((3-(dimethylamino)propoxy)carbonyl)amino)methyl)-2-((9Z,12Z)-octadeca-9,12-dien-1-yl)icosa-11,14-dien-1-yl octadeca-9,12-dienoate (0.0800 g, 0.0830 mmol, yield: 39%).

ESI-MS m/z: 964 (M+H)$^+$.

Step 5

The title compound (0.025 g, 0.025 mmol, yield: 45%) was obtained in the same way as in step 2 of Reference Example A1 using (9Z,12Z)-(11Z,14Z)-2-((((3-(dimethylamino)propoxy)carbonyl)amino)methyl)-2-((9Z,12Z)-octadeca-9,12-dien-1-yl)icosa-11,14-dien-1-yl octadeca-9,12-dienoate (0.053 g, 0.055 mmol) obtained in step 4.

ESI-MS m/z: 978 (M)$^+$; $^1$H-NMR (CDCl$_3$) δ: 0.89 (t, J=7.0 Hz, 9H), 1.17-1.40 (m, 54H), 1.56-1.66 (m, 2H), 2.05 (q, J=6.8 Hz, 12H), 2.09-2.17 (m, 2H), 2.33 (t, J=7.6 Hz, 2H), 2.77 (t, J=6.2 Hz, 6H), 3.05 (d, J=6.6 Hz, 2H), 3.44 (s, 9H), 3.73-3.79 (m, 2H), 3.85 (s, 2H), 4.16 (t, J=5.7 Hz, 2H), 5.27-5.44 (m, 12H), 5.72 (t, J=6.5 Hz, 1H).

Reference Example A21

(12Z,15Z)-3-Hydroxy-N,N,N-trimethyl-2,2-di((9Z,12Z)-octadeca-9,12-dien-1-yl)henicosa-12,15-dien-1-aminium chloride (Compound II-14)

Step 1

(11Z,14Z)-2-(Aminoethyl)-2-((9Z,12Z)-octadeca-9,12-dien-1-yl) icosa-11,14-dien-1-ol (1.35 g, 2.36 mmol) obtained in step 2 of Reference Example A19 was dissolved in tetrahydrofuran (10 mL). To the solution, a 38% aqueous formaldehyde solution (manufactured by Wako Pure Chemical Industries Ltd., 0.559 mL, 7.08 mmol), acetic acid (0.135 mL, 2.36 mmol), and sodium triacetoxyborohydride (1.50 g, 7.08 mmol) were added, and the mixture was stirred at room temperature for 1 hour. Water was added to the reaction solution, followed by extraction with chloroform. The organic layer was washed with saturated saline, dried over anhydrous magnesium sulfate, filtered, and concentrated under reduced pressure. The obtained residue was purified by silica gel column chromatography (chloroform/methanol=99/1 to 85/15) to obtain (11Z,14Z)-2-((dimethylamino)methyl)-2-((9Z,12Z)-octadeca-9,12-dien-1-yl)icosa-11,14-dien-1-ol (0.610 g, 1.02 mmol, yield: 43%).

ESI-MS m/z: 600 (M+H)$^+$.

Step 2

(11Z,14Z)-2-((Dimethylamino)methyl)-2-((9Z,12Z)-octadeca-9,12-dien-1-yl)icosa-11,14-dien-1-ol (0.300 g, 0.500 mmol) obtained in step 1 was dissolved in dichloromethane (3 mL). To the solution, Dess-Martin reagent (manufactured by Tokyo Chemical Industry Co., Ltd., 0.233 g, 0.550 mmol) was added, and the mixture was stirred at room temperature for 1 hour. Water was added to the reaction solution, followed by extraction with chloroform. The organic layer was washed with saturated saline, dried over anhydrous magnesium sulfate, filtered, and concentrated under reduced pressure. The obtained residue was purified by silica gel column chromatography (hexane/ethyl acetate=95/5 to 70/30) to obtain (11Z,14Z)-2-((dimethylamino)methyl)-2-((9Z,12Z)-octadeca-9,12-dien-1-yl)icosa-11,14-dienal (0.160 g, 0.268 mmol, yield: 54%).

ESI-MS m/z: 598 (M+H)$^+$.

Step 3

To magnesium (manufactured by Sigma-Aldrich Corp., 0.0140 g, 0.562 mmol), diethyl ether (1 mL) and iodine (a little piece) were added, and the mixture was stirred at room temperature for 5 minutes. A solution of (6Z,9Z)-18-bromooctadeca-6,9-diene (0.176 g, 0.535 mmol) synthesized by a method equivalent to the method described in WO 2010/

42877 in diethyl ether (1 mL) was added thereto, and the mixture was stirred under heating to reflux. After confirmation that the color of iodine disappeared, a solution of (11Z,14Z)-2-((dimethylamino)methyl)-2-((9Z,12Z)-octadeca-9,12-dien-1-yl)icosa-11,14-dienal (0.160 g, 0.268 mmol) obtained in step 2 in diethyl ether (1 mL) was added thereto, and the mixture was stirred at room temperature for 1 hour. Water was added to the reaction solution, followed by extraction with hexane. The organic layer was washed with saturated saline, dried over anhydrous magnesium sulfate, filtered, and concentrated under reduced pressure. The obtained residue was purified by silica gel column chromatography (hexane/ethyl acetate=99/1 to 85/15) to obtain (6Z,9Z,29Z,32Z)-20-((dimethylamino)methyl)-20-((9Z,12Z)-octadeca-9,12-dien-1-yl)octatriaconta-6,9,29,32-tetraen-19-ol (0.0470 g, 0.0550 mmol, yield: 21%).

ESI-MS m/z: 848 (M+H)$^+$.

Step 4

The title compound (0.0012 g, 0.0013 mmol, yield: 2%) was obtained in the same way as in step 2 of Reference Example A1 using (6Z,9Z,29Z,32Z)-20-((dimethylamino)methyl)-20-((9Z,12Z)-octadeca-9,12-dien-1-yl)octatriaconta-6,9,29,32-tetraen-19-ol (0.047 g, 0.055 mmol) obtained in step 3.

ESI-MS m/z: 863 (M)$^+$; $^1$H-NMR (CDCl$_3$) δ: 0.89 (t, J=7.0 Hz, 9H), 1.17-1.40 (m, 58H), 1.54-1.65 (m, 2H), 2.05 (q, J=6.8 Hz, 12H), 2.77 (t, J=6.5 Hz, 6H), 3.29 (d, J=14.4 Hz, 1H), 3.51 (s, 9H), 3.56 (d, J=14.2 Hz, 1H), 3.62-3.70 (m, 1H), 5.29-5.42 (m, 12H).

Reference Example A22

(11Z,14Z)—N,N,N-Trimethyl-2-((9Z,12Z)-octadeca-9,12-dien-1-yl)-2-(((9Z,12Z)-octadeca-9,12-dienyloxy)carbonyl)icosa-11,14-dien-1-aminium chloride (Compound II-15)

Step 1 tert-Butyl ((11Z,14Z)-2-(hydroxymethyl)-2-((9Z,12Z)-octadeca-9,12-dien-1-yl)icosa-11,14-dien-1-yl)carbamate (0.300 g, 0.448 mmol) obtained in step 1 of Reference Example A20 was dissolved in acetone (2 mL). To the solution, Jones reagent (manufactured by Sigma-Aldrich Corp., 2 mol/L, 0.224 mL, 0.448 mmol) was added under ice cooling, and the mixture was then stirred at room temperature for 1 hour. Water was added to the reaction solution, followed by extraction with ethyl acetate. The organic layer was washed with saturated saline, dried over anhydrous magnesium sulfate, filtered, and concentrated under reduced pressure. The obtained residue was purified by silica gel column chromatography (hexane/ethyl acetate=95/5 to 50/50) to obtain (11Z,14Z)-2-(((tert-butoxycarbonyl)amino)methyl)-2-((9Z,12Z)-octadeca-9,12-dien-1-yl)icosa-11,14-dienoic acid (0.136 g, 0.198 mmol, yield: 44%).

ESI-MS m/z: 684 (M−H)$^−$.

Step 2

(11Z,14Z)-(9Z,12Z)-Octadeca-9,12-dien-1-yl 2-(((tert-butoxycarbonyl)amino)methyl)-2-((9Z,12Z)-octadeca-9,12-dien-1-yl)icosa-11,14-dienoate (0.123 g, 0.132 mmol, yield: 75%) was obtained in the same way as in step 2 of Reference Example A20 using (11Z,14Z)-2-(((tert-butoxycarbonyl)amino)methyl)-2-((9Z,12Z)-octadeca-9,12-dien-1-yl)icosa-11,14-dienoic acid (0.120 g, 0.175 mmol) obtained in step 1 and (9Z,12Z)-octadeca-9,12-dien-1-ol (manufactured by Nu-Chek Prep, Inc., 0.0930 g, 0.350 mmol).

ESI-MS m/z: 935 (M+H)$^+$.

Step 3

(11Z,14Z)-(9Z,12Z)-Octadeca-9,12-dien-1-yl 2-(((tert-butoxycarbonyl)amino)methyl)-2-((9Z,12Z)-octadeca-9,12-dien-1-yl)icosa-11,14-dienoate (0.123 g, 0.132 mmol) obtained in step 2 was dissolved in dichloromethane (1 mL). To the solution, trifluoroacetic acid (0.300 mL, 3.89 mmol) was added under ice cooling, and the mixture was stirred for 1 hour. A saturated aqueous solution of sodium bicarbonate was added to the reaction solution, followed by extraction with hexane. The organic layer was washed with saturated saline, dried over anhydrous magnesium sulfate, filtered, and concentrated under reduced pressure. The obtained residue was purified by silica gel column chromatography (hexane/ethyl acetate=99/1 to 80/20) to obtain (11Z,14Z)-(9Z,12Z)-octadeca-9,12-dien-1-yl 2-(aminomethyl)-2-((9Z,12Z)-octadeca-9,12-dien-1-yl)icosa-11,14-dienoate (0.110 g, 0.132 mmol, yield: 100%).

ESI-MS m/z: 835 (M+H)$^+$.

Step 4

(11Z,14Z)-(9Z,12Z)-Octadeca-9,12-dien-1-yl 2-((dimethylaminomethyl)-2-((9Z,12Z)-octadeca-9,12-dien-1-yl)icosa-11,14-dienoate (0.0720 g, 0.0830 mmol, yield: 63%) was obtained in the same way as in step 1 of Reference Example A21 using (11Z,14Z)-(9Z,12Z)-octadeca-9,12-dien-1-yl 2-(aminomethyl)-2-((9Z,12Z)-octadeca-9,12-dien-1-yl) icosa-11,14-dienoate (0.110 g, 0.132 mmol) obtained in step 3.

ESI-MS m/z: 862 (M+H)$^+$.

Step 5

The title compound (0.052 g, 0.057 mmol, yield: 68%) was obtained in the same way as in step 2 of Reference Example A1 using (11Z,14Z)-(9Z,12Z)-octadeca-9,12-dien-1-yl 2-((dimethylaminomethyl)-2-((9Z,12Z)-octadeca-9,12-dien-1-yl) icosa-11,14-dienoate (0.072 g, 0.083 mmol) obtained in step 4.

ESI-MS m/z: 877 (M)$^+$; $^1$H-NMR (CDCl$_3$) δ: 0.89 (t, J=7.0 Hz, 9H), 1.09-1.42 (m, 52H), 1.52-1.81 (m, 6H), 2.05 (q, J=6.8 Hz, 12H), 2.77 (t, J=6.6 Hz, 6H), 3.46 (s, 9H), 3.79 (s, 2H), 4.14 (t, J=6.8 Hz, 2H), 5.28-5.43 (m, 12H).

Reference Example A23

(11Z,14Z)—N,N,N-Trimethyl-2,2-bis(((9Z,12Z)-octadeca-9,12-dienoyloxy)methyl)icosa-11,14-dien-1-aminium chloride (Compound II-16)

Step 1

Dimethyl malonate (manufactured by Tokyo Chemical Industry Co., Ltd., 1.00 g, 7.57 mmol) was dissolved in acetonitrile (20 mL). To the solution, (9Z,12Z)-octadeca-9,12-dienyl methanesulfonate (2.61 g, 7.57 mmol), cesium carbonate (manufactured by Wako Pure Chemical Industries Ltd., 4.93 g, 15.1 mmol) and tetra-n-butylammonium iodide (2.80 g, 7.57 mmol) were added, and the mixture was stirred overnight at 50° C. Water was added to the reaction solution, followed by extraction with hexane. The organic layer was washed with saturated saline, dried over anhydrous magnesium sulfate, filtered, and concentrated under reduced pressure. The obtained residue was purified by silica gel column chromatography (hexane/ethyl acetate=90/10 to 70/30) to obtain dimethyl 2-((9Z,12Z)-octadeca-9,12-dien-1-yl)malonate (1.22 g, 3.21 mmol, yield: 42%).

ESI-MS m/z: 381 (M+H)$^+$.

Step 2

Dimethyl 2-((9Z,12Z)-octadeca-9,12-dien-1-yl)malonate (0.200 g, 0.526 mmol) obtained in step 1 was dissolved in acetonitrile (3 mL). To the solution, N,N,N',N'-tetramethyldiaminomethane (manufactured by Tokyo Chemical Industry Co., Ltd., 0.0860 mL, 0.631 mmol) and acetic anhydride (0.0600 mL, 0.631 mmol) were added. Then, sodium hydride (60% oil, 0.0320 g, 0.788 mmol) was added thereto under ice cooling, and the mixture was stirred at room temperature for 3 hours. A saturated aqueous solution of ammonium chloride was added to the reaction solution, followed by extraction with ethyl acetate. The organic layer was washed with saturated saline, dried over anhydrous magnesium sulfate, filtered, and concentrated under reduced pressure. The obtained residue was purified by silica gel column chromatography (hexane/ethyl acetate=100/0 to 60/40) to obtain dimethyl 2-((dimethylamino)methyl)-2-((9Z,12Z)-octadeca-9,12-dien-1-yl)malonate (0.0660 g, 0.151 mmol, yield: 29%).

ESI-MS m/z: 438 (M+H)$^+$.

Step 3

2-((Dimethylamino)methyl)-2-((9Z,12Z)-octadeca-9,12-dien-1-yl)propane-1,3-diol (0.013 g, 0.034 mmol, yield: 23%) was obtained in the same way as in step 2 of Reference Example A19 using dimethyl 2-((dimethylamino)methyl)-2-((9Z,12Z)-octadeca-9,12-dien-1-yl)malonate (0.066 g, 0.15 mmol) obtained in step 2.

ESI-MS m/z: 382 (M+H)$^+$.

Step 4

(9Z,9'Z,12Z,12')-2-((Dimethylamino)methyl)-2-((9Z,12Z)-octadeca-9,12-dien-1-yl)propane-1,3-diyl bis(octadeca-9,12-dienoate (0.017 g, 0.019 mmol, yield: 56%) was obtained in the same way as in step 2 of Reference Example A20 using 2-((dimethylamino)methyl)-2-((9Z,12Z)-octadeca-9,12-dien-1-yl)propane-1,3-diol (0.013 g, 0.034 mmol) obtained in step 3.

ESI-MS m/z: 906 (M+H)$^+$.

Step 5

The title compound (5.5 mg, 0.0058 mmol, yield: 31%) was obtained in the same way as in step 2 of Reference Example A1 using (9Z,9'Z,12Z,12'Z)-2-((dimethylamino)methyl)-2-((9Z,12Z)-octadeca-9,12-dien-1-yl) propane-1,3-diyl bis(octadeca-9,12-dienoate (0.017 g, 0.019 mmol) obtained in step 4.

ESI-MS m/z: 921 (M)$^+$. $^1$H-NMR (CDCl$_3$) δ: 0.89 (t, J=7.0 Hz, 9H), 1.23-1.40 (m, 48H), 1.53-1.65 (m, 4H), 2.05 (q, J=6.9 Hz, 12H), 2.38 (t, J=7.6 Hz, 4H), 2.77 (t, J=6.6 Hz, 6H), 3.59 (s, 9H), 3.72 (s, 2H), 4.20 (dd, J=22.1, 12.2 Hz, 4H), 5.28-5.44 (m, 12H).

Reference Example A24

N,N,N-Trimethyl-3-((9Z,12Z)-octadeca-9,12-dienoyloxy)-2,2-bis(((9Z,12Z)-octadeca-9,12-dienoyloxy)methyl)propan-1-aminium chloride (Compound II-17)

Step 1

To 2-(bromomethyl)-2-(hydroxymethyl)propane-1,3-diol (0.200 g, 1.01 mmol), dimethylamine (manufactured by Sigma-Aldrich Corp., 2.0 mol/L solution in tetrahydrofuran, 5.02 mL, 10.1 mmol) was added, and the mixture was stirred at 120° C. for 15 hours under microwave irradiation. Lithium hydroxide monohydrate (0.0290 g, 1.21 mmol) was added to the reaction solution, and the resulting precipitate was filtered off. The filtrate was concentrated under reduced pressure to obtain a crude product of 2-((dimethylamino)methyl)-2-(hydroxymethyl)propane-1,3-diol (0.200 g, 1.23 mmol, quantitative).

ESI-MS m/z: 164 (M+H)$^+$.

Step 2

The title compound (0.0470 g, 0.047 mmol overall yield: 4.4%) was obtained in the same way as in Reference Example A8 using the crude product of 2-((dimethylamino)methyl)-2-(hydroxymethyl)propane-1,3-diol (0.200 g, 1.23 mmol) obtained in step 1.

ESI-MS m/z: 965 (M)$^+$; $^1$H-NMR (CDCl$_3$) δ: 0.85-0.94 (m, 9H), 1.24-1.40 (m, 42H), 1.53-1.63 (m, 6H), 2.00-2.10 (m, 12H), 2.38 (t, J=6.9 Hz, 6H), 2.77 (t, J=6.5 Hz, 6H), 3.64 (s, 9H), 3.95 (s, 2H), 4.30 (s, 6H), 5.27-5.43 (m, 12H).

Reference Example A25

N,N,N-Trimethyl-3-(oleoyloxy)-2,2-bis(oleoyloxymethyl)propan-1-aminium chloride (Compound II-18)

The title compound (0.663 g, 0.658 mmol, overall yield: 28%) was obtained in the same way as in Reference Example A8 using oleic acid instead of (9Z,12Z)-octadeca-9,12-dienoic acid used in step 1 of Reference Example A8.

ESI-MS m/z: 971 (M)$^+$; $^1$H-NMR (CDCl$_3$) δ: 0.88 (t, J=6.8 Hz, 9H), 1.22-1.38 (m, 60H), 1.55-1.65 (m, 6H), 2.01 (q, J=5.9 Hz, 12H), 2.38 (t, J=7.6 Hz, 6H), 3.64 (s, 9H), 3.98 (s, 2H), 4.29 (s, 6H), 5.29-5.39 (m, 6H).

Reference Example A26

N,N,N-Trimethyl-3-((9Z,12Z)-octadeca-9,12-dienyloxy)-2,2-bis(((9Z,12Z)-octadeca-9,12-dienyloxy)methyl)propan-1-aminium chloride (Compound IT-19)

Step 1

To dimethylamine (approximately 2 mol/L solution in tetrahydrofuran, 15.0 mL, 30.0 mmol), 2-(bromomethyl)-2-(hydroxymethyl)propane-1,3-diol (1.52 g, 7.56 mmol) was added, and the mixture was stirred under heating at 120° C. for 15 hours using a microwave reaction apparatus. After cooling to room temperature, lithium hydroxide (0.217 g, 9.07 mmol) was added to the reaction solution, and the mixture was filtered and concentrated under reduced pressure to obtain a crude product of 2-((dimethylamino)methyl)-2-(hydroxymethyl)propane-1,3-diol.

To the obtained crude product, toluene (30 mL), (9Z,12Z)-octadeca-9,12-dienyl methanesulfonate (6.51 g, 18.9 mmol) and sodium hydride (60% oil, 0.756 g, 18.9 mmol) were added, and the mixture was stirred overnight under heating to reflux. After cooling to room temperature, a saturated aqueous solution of sodium bicarbonate was added to the reaction solution, followed by extraction with hexane. The organic layer was dried over anhydrous magnesium sulfate, filtered, and concentrated under reduced pressure. The obtained residue was purified by amino silica gel column chromatography (hexane/ethyl acetate=100/0 to 90/10) to obtain N,N-dimethyl-3-((9Z,12Z)-octadeca-9,12-dienyloxy)-2,2-bis(((9Z,12Z)-octadeca-9,12-dienyloxy)methyl)propan-1-amine (0.196 g, 0.216 mmol, 3%) and 3-(dimethylamino)-2,2-bis(((9Z,12Z)-octadeca-9,12-dienyloxy)methyl)propan-1-ol (1.80 g, 2.73 mmol, yield: 36%). N,N-Dimethyl-3-((9Z,12Z)-octadeca-9,12-dienyloxy)-2,2-bis(((9Z,12Z)-octadeca-9,12-dienyloxy)methyl)propan-1-amine ESI-MS m/z: 909 (M+H)$^+$. 3-(Dimethylamino)-2,2-bis(((9Z,12Z)-octadeca-9,12-dienyloxy)methyl)propan-1-ol ESI-MS m/z: 661 (M+H)$^+$.

Step 2

To a solution of N,N-dimethyl-3-((9Z,12Z)-octadeca-9,12-dienyloxy)-2,2-bis(((9Z,12Z)-octadeca-9,12-dienyloxy)

methyl)propan-1-amine (0.120 g, 0.132 mmol) obtained in step 1 in chloroform (1 mL), methyl iodide (0.500 mL) was added, and the mixture was stirred at room temperature for 3 hours. The reaction solution was concentrated under reduced pressure. The residue was dissolved in a small amount of methanol-chloroform (1:1), and the solution was loaded to an ion-exchange resin (Amberlite® IRA-400, Cl type, approximately 20-fold amount, prewashed with water and ethanol), followed by elution with methanol-chloroform (1:1). The eluate was concentrated under reduced pressure, and the obtained residue was purified by silica gel column chromatography (chloroform/methanol=100/0 to 90/10) to obtain the title compound (0.0654 g, 0.0682 mmol, yield: 57%).

ESI-MS m/z: 923 (M)$^+$; $^1$H-NMR (CDCl$_3$) δ: 0.89 (t, J=6.8 Hz, 9H), 1.22-1.40 (m, 1H), 1.49-1.59 (m, 6H), 2.05 (q, J=6.9 Hz, 12H), 2.77 (t, J=6.7 Hz, 6H), 3.37 (t, J=6.6 Hz, 6H), 3.45 (s, 6H), 3.55 (s, 9H), 3.58 (s, 2H), 5.28-5.42 (m, 12H).

Reference Example A27

N,N,N-Trimethyl-3-((9Z,12Z)-octadeca-9,12-dienoyloxy)-2,2-bis(((9Z,12Z)-octadeca-9,12-dienyloxy)methyl)propan-1-aminium chloride (Compound II-20)

To a solution of 3-(dimethylamino)-2,2-bis(((9Z,12Z)-octadeca-9,12-dienyloxy)methyl)propan-1-ol (0.265 g, 0.401 mmol) obtained in step 1 of Reference Example A26 in 1,2-dichloroethane (4 mL), (9Z,12Z)-octadeca-9,12-dienoic acid (0.169 g, 0.602 mmol), 1-ethyl-3-(3-dimethylaminopropyl)carbodiimide hydrochloride (0.154 g, 0.802 mmol) and N,N-dimethylaminopyridine (0.0250 g, 0.201 mmol) were added, and the mixture was stirred overnight at room temperature. The reaction mixture was concentrated under reduced pressure. The obtained residue was purified by silica gel column chromatography (hexane/ethyl acetate=95/5 to 90/10) to obtain a crude product of (9Z, 12Z)-3-(dimethylamino)-2,2-bis(((9Z,12Z)-octadeca-9,12-dienyloxy)methyl)propyl octadeca-9,12-dienoate.

To the obtained crude product, chloroform (2 mL) and methyl iodide (manufactured by Tokyo Chemical Industry Co., Ltd., 1.00 mL) were added, and the mixture was stirred at room temperature for 5 hours. The reaction solution was concentrated under reduced pressure. The residue was dissolved in a small amount of methanol-chloroform (1:1), and the solution was loaded to an ion-exchange resin (manufactured by Sigma-Aldrich Corp., Amberlite® IRA-400, Cl type, approximately 20-fold amount, prewashed with water and ethanol), followed by elution with methanol-chloroform (1:1). The eluate was concentrated under reduced pressure, and the obtained residue was purified by silica gel column chromatography (chloroform/methanol=100/0 to 90/10) to obtain the title compound (0.220 g, 0.226 mmol, yield: 56%).

ESI-MS m/z: 937 (M)$^+$; $^1$H-NMR (CDCl$_3$) δ: 0.89 (t, J=7.0 Hz, 9H), 1.22-1.41 (m, 51H), 1.50-1.66 (m, 6H), 2.05 (q, J=6.9 Hz, 12H), 2.38 (t, J=7.5 Hz, 2H), 2.77 (t, J=6.1 Hz, 6H), 3.39 (t, J=6.6 Hz, 4H), 3.44-3.48 (m, 2H), 3.54-3.58 (m, 11H), 3.73 (s, 2H), 4.18 (s, 2H), 5.28-5.43 (m, 11H).

Reference Example A28

N,N, N-Trimethyl-4-(2-(9Z,12Z)-octadeca-9,12-dienamido-3-((9Z,12Z)-octadeca-9,12-dienoyloxy)-2-(((9Z,12Z)-octadeca-9,12-dienoyloxy)methyl)propoxy)-4-oxybutan-1-aminium chloride (Compound II-21)

Step 1

To a solution of tert-butyl (1,3-dihydroxy-2-(hydroxymethyl)propan-2-yl)carbamate (manufactured by Key Organics Ltd., 0.505 g, 2.28 mmol) in dichloromethane (15 mL), (9Z,12Z)-octadeca-9,12-dienoic acid (3.23 g, 11.4 mmol), 1-ethyl-3-(3-dimethylaminopropyl)carbodiimide hydrochloride (2.19 g, 11.4 mmol) and N,N-dimethylaminopyridine (0.279 g, 2.28 mmol) were added, and the mixture was stirred at room temperature for 1 hour. A saturated aqueous solution of sodium bicarbonate was added to the reaction solution, followed by extraction with chloroform. The organic layer was dried over anhydrous magnesium sulfate, filtered, and concentrated under reduced pressure. The obtained residue was purified by silica gel column chromatography (hexane/chloroform=100/0 to 95/5) to obtain (9Z, 9'Z,12Z,12'Z)-2-(tert-butoxycarbonylamino-2-(((9Z,12Z)-octadeca-9,12-dienoyloxy)methyl)propane-1,3-diyl dioctadeca-9,12-dienoate (2.08 g, 2.06 mmol, yield: 90%).

$^1$H-NMR (CDCl$_3$) δ: 0.89 (t, J=6.7 Hz, 9H), 1.23-1.40 (m, 9H), 1.43 (s, 9H), 1.57-1.66 (m, 14H), 2.05 (q, J=6.8 Hz, 12H), 2.32 (t, J=7.6 Hz, 6H), 2.77 (t, J=6.5 Hz, 6H), 4.34 (s, 6H), 4.81 (br s, 1H), 5.28-5.43 (m, 12H).

Step 2

To a solution of (9Z,9'Z,12Z,12'Z)-2-(tert-butoxycarbonylamino-2-(((9Z,12Z)-octadeca-9,12-dienoyloxy)methyl) propane-1,3-diyl dioctadeca-9,12-dienoate (2.05 g, 2.03 mmol, 90%) obtained in step 1 in dichloromethane (10 mL), trifluoroacetic acid (2 mL, 26.0 mmol) was added, and the mixture was stirred at room temperature for 1 hour. A saturated aqueous solution of sodium bicarbonate was added to the reaction solution, followed by extraction with chloroform. The organic layer was dried over anhydrous magnesium sulfate, filtered, and concentrated under reduced pressure. The obtained residue was purified by amino silica gel column chromatography (hexane/ethyl acetate=100/0 to 95/5) to obtain (9Z,9'Z,12Z,12'Z)-2-(hydroxymethyl)-2-(9Z,12Z)-octadeca-9,12-dienamidopropane-1,3-diyl dioctadeca-9,12-dienoate (1.70 g, 1.84 mmol, yield: 91%).

ESI-MS m/z: 909 (M+H)$^+$.

Step 3

To a solution of (9Z,9'Z,12Z,12'Z)-2-(hydroxymethyl)-2-(9Z,12Z)-octadeca-9,12-dienamidopropane-1,3-diyl dioctadeca-9,12-dienoate (0.8933 g, 0.983 mmol) obtained in step 2 in dichloromethane (9 mL), (9Z,12Z)-octadeca-9,12-dienoic acid (manufactured by Sigma-Aldrich Corp., 2.37 g, 8.45 mmol), 1-ethyl-3-(3-dimethylaminopropyl)carbodiimide hydrochloride (1.62 g, 8.45 mmol) and N,N-dimethylaminopyridine (0.206 g, 1.69 mmol) were added, and the mixture was stirred at room temperature for 2 hours. The reaction mixture was concentrated under reduced pressure. The obtained residue was purified by amino silica gel column chromatography (hexane/ethyl acetate=90/10 to 75/25) to obtain (9Z,9'Z,12Z,12'Z)-2-((4-(dimethylamino)butanoyloxy)methyl)-2-(9Z,12Z)-octadeca-9,12-dienamidopropane-1,3-diyl dioctadeca-9,12-dienoate (0.900 g, 0.881 mmol, yield: 90%).

ESI-MS m/z: 1022 (M+H)$^+$.

Step 4

To a solution of (9Z,9'Z,12Z,12'Z)-2-((4-(dimethylamino)butanoyloxy)methyl)-2-(9Z,12Z)-octadeca-9,12-dienamidopropane-1,3-diyl dioctadeca-9,12-dienoate (0.805 g, 0.788 mmol) obtained in step 3 in chloroform (4 mL), methyl iodide (0.493 mL) was added, and the mixture was stirred overnight at room temperature. The reaction solution was concentrated under reduced pressure. The residue was dissolved in a small amount of methanol-chloroform (1:1), and the solution was loaded to an ion-exchange resin (Dowex™ 1x-2 100 mesh, Cl type, approximately 20-fold amount, prewashed with water and methanol), followed by elution with methanol-chloroform (1:1). The eluate was concentrated under reduced pressure, and the obtained residue was purified by silica gel column chromatography (chloroform/methanol=90/10 to 80/20) to obtain the title compound (0.740 g, 0.690 mmol, yield: 88%).

ESI-MS m/z: 1036 (M)$^+$; $^1$H-NMR (CDCl$_3$) δ: 0.88 (t, J=6.4 Hz, 9H), 1.21-1.40 (m, 45H), 1.54-1.65 (m, 6H), 2.01-2.08 (m, 12H), 2.09-2.19 (m, 2H), 2.24 (t, J=7.4 Hz, 2H), 2.32 (t, J=7.5 Hz, 4H), 2.57 (t, J=6.2 Hz, 2H), 2.77 (t, J=6.3 Hz, 6H), 3.41 (s, 9H), 3.84 (t, J=8.3 Hz, 2H), 4.37-4.50 (m, 6H), 5.28-5.43 (m, 12H), 6.72 (br s, 1H).

Reference Example A29

4-(1,3-Bis((9Z,12Z)-octadeca-9,12-dienoyloxy)-2-(((9Z,12Z)-octadeca-9,12-dienoyloxy)methyl)propan-2-ylamino)-N,N,N-trimethyl-4-oxobutan-1-aminium chloride (Compound II-22)

Step 1

To a solution of 2-amino-2-(hydroxymethyl)-1,3-propanediol (manufactured by Wako Pure Chemical Industries Ltd., 7.41 g, 61.2 mmol) in dichloromethane (60 mL), tert-butyldimethylsilyl chloride (manufactured by Sigma-Aldrich Corp., 9.43 g, 60.7 mmol) and imidazole (manufactured by Nacalai Tesque, Inc., 5.51 g, 80.9 mmol) were added, and the mixture was stirred overnight at room temperature. Saturated saline was added to the reaction solution, followed by extraction with chloroform. The organic layer was dried over anhydrous magnesium sulfate, filtered, and concentrated under reduced pressure. The obtained residue was purified by amino silica gel column chromatography (hexane/ethyl acetate=100/0 to 95/5) to obtain 6-((tert-butyldimethylsilyloxy)methyl)-2,2,3,3,9,9,10,10-octamethyl-4,8-dioxa-3,9-disilaundecan-6-amine (3.80 g, 8.19 mmol, yield: 40%).

ESI-MS m/z: 464 (M+H)$^+$.

Step 2

To a solution of 6-((tert-butyldimethylsilyloxy)methyl)-2,2,3,3,9,9,10,10-octamethyl-4,8-dioxa-3,9-disilaundecan-6-amine (1.28 g, 2.76 mmol) obtained in step 1 in dichloromethane (10 mL), 4-(dimethylamino)butyric acid hydrochloride (manufactured by Sigma-Aldrich Corp., 0.708 g, 4.14 mmol), 1-ethyl-3-(3-dimethylaminopropyl)carbodiimide hydrochloride (0.810 g, 4.14 mmol), N,N-dimethylaminopyridine (0.0170 g, 0.138 mmol) and N,N-diisopropylethylamine (1.45 mL, 8.31 mmol) were added, and the mixture was stirred overnight at room temperature. The reaction mixture was concentrated under reduced pressure. The obtained residue was purified by amino silica gel column chromatography (hexane/ethyl acetate=95/5 to 90/10) to obtain N-(6-((tert-butyldimethylsilyloxy)methyl)-2,2,3,3,9,9,10,10-octamethyl-4,8-dioxa-3,9-disilaundecan-6-yl)-4-(dimethylamino)butanamide (1.22 g, 2.11 mmol, yield: 76%).

ESI-MS m/z: 578 (M+H)$^+$.

Step 3

To a solution of N-(6-((tert-butyldimethylsilyloxy)methyl)-2,2,3,3,9,9,10,10-octamethyl-4,8-dioxa-3,9-disilaundecan-6-yl)-4-(dimethylamino)butanamide (1.08 g, 1.87 mmol) obtained in step 2 in tetrahydrofuran (10 mL), tetrabutylammonium fluoride (manufactured by Tokyo Chemical Industry Co., Ltd., approximately 1 mol/L solution in tetrahydrofuran, 7.49 mL, 7.49 mmol) was added, and the mixture was stirred at room temperature for 2 hours. (9Z,12Z)—Octadeca-9,12-dienoic acid (2.05 g, 7.31 mmol), 1-ethyl-3-(3-dimethylaminopropyl)carbodiimide hydrochloride (1.44 g, 7.51 mmol) and N,N-dimethylaminopyridine (0.0340 g, 0.278 mmol) were added to the reaction solution, and the mixture was stirred overnight at room temperature. The reaction mixture was concentrated under reduced pressure. The obtained residue was purified by amino silica gel column chromatography (hexane/ethyl acetate=60/40 to 50/50) to obtain (9Z,9'Z,12Z,12'Z)-2-(4-(dimethylamino)butanamido)-2-(((9Z,12Z)-octadeca-9,12-dienoyloxy)methyl)propane-1,3-diyl dioctadeca-9,12-dienoate (0.405 g, 0.396 mmol, yield: 21%).

ESI-MS m/z: 1022 (M+H)$^+$.

Step 4

To a solution of (9Z,9'Z,12Z,12'Z)-2-(4-(dimethylamino)butanamido)-2-(((9Z,12Z)-octadeca-9,12-dienoyloxy)methyl)propane-1,3-diyl dioctadeca-9,12-dienoate (0.335 g, 0.328 mmol) obtained in step 3 in chloroform (3 mL), methyl iodide (manufactured by Tokyo Chemical Industry Co., Ltd., 0.200 mL) was added, and the mixture was stirred at room temperature for 2 hours. The reaction solution was concentrated under reduced pressure. The residue was dissolved in a small amount of methanol-chloroform (1:1), and the solution was loaded to an ion-exchange resin (Dowex™ 1×-2 100 mesh, Cl type, approximately 20-fold amount, prewashed with water and methanol), followed by elution with methanol-chloroform (1:1). The eluate was concentrated under reduced pressure, and the obtained residue was purified by silica gel column chromatography (chloroform/methanol=90/10 to 80/20) to obtain the title compound (0.324 g, 0.302 mmol, yield: 92%).

ESI-MS m/z: 1036 (M)$^+$; $^1$H-NMR (CDCl$_3$) δ: 0.89 (t, J=7.0 Hz, 9H), 1.23-1.40 (m, 45H), 1.55-1.64 (m, 6H), 2.01-2.12 (m, 14H), 2.34 (t, J=7.6 Hz, 6H), 2.43 (t, J=6.3 Hz, 2H), 2.77 (t, J=6.6 Hz, 6H), 3.37 (s, 9H), 3.77-3.83 (m, 2H), 4.43 (s, 6H), 5.28-5.42 (m, 12H), 6.62 (br s, 1H).

Reference Example A30

2-(1,3-Bis((9Z,12Z)-octadeca-9,12-dienoyloxy)-2-(((9Z,12Z)-octadeca-9,12-dienoyloxy)methyl)propan-2-ylamino)-N,N,N-trimethyl-2-oxoethanaminium chloride (Compound II-23)

The title compound (0.356 g, 0.341 mmol, overall yield: 17%) was obtained in the same way as in Reference Example A29 using N,N-dimethylglycine (manufactured by Tokyo Chemical Industry Co., Ltd.) instead of 4-(dimethylamino)butyric acid hydrochloride.

ESI-MS m/z: 1008 (M)$^+$; $^1$H-NMR (CDCl$_3$) δ: 0.89 (t, J=7.0 Hz, 9H), 1.23-1.40 (m, 44H), 1.54-1.64 (m, 26H), 2.01-2.08 (m, 12H), 2.35 (t, J=7.6 Hz, 6H), 2.77 (t, J=6.8 Hz, 6H), 3.40 (s, 9H), 4.46 (s, 6H), 4.70 (s, 2H), 5.28-5.42 (m, 12H), 9.54 (br s, 1H).

Reference Example A31

4-((6Z,9Z,29Z,32Z)-20-Hydroxy-20-((9Z,12Z)-octadeca-9,12-dienyl)octatriaconta-6,9,29,32-tetraen-19-yloxy)-N,N,N-trimethyl-4-oxobutan-1-aminium chloride (Compound III-1)

The title compound (0.146 g, 0.150 mmol, yield: 96%) was obtained in the same way as in step 2 of Reference Example A1 using (6Z,9Z,29Z,32Z)-20-hydroxy-20-((9Z,12Z)-octadeca-9,12-dienyl)octatriaconta-6,9,29,32-tetraen-19-yl 4-(dimethylamino)butanoate (0.144 g, 0.156 mmol)

obtained by a method equivalent to the method described in U.S. Patent Application Publication No. 2012/0172411.

ESI-MS m/z: 935 (M)$^+$; $^1$H-NMR (CDCl$_3$) δ: 0.89 (t, J=6.9 Hz, 9H), 1.16-1.79 (m, 60H), 1.98-2.17 (m, 15H), 2.52-2.59 (m, 2H), 2.77 (t, J=6.6 Hz, 6H), 3.44 (s, 9H), 3.69-3.81 (m, 2H), 4.94-4.98 (m, 1H), 5.29-5.42 (m, 12H).

Reference Example A32

(6Z,9Z,28Z,31Z)—N,N-Dimethyl-N-((9Z,12Z)-octadeca-9,12-dienyl)heptatriaconta-6,9,28,31-tetraen-19-aminium chloride (Compound IV-1)

Step 1

To a solution of (6Z,9Z,28Z,31Z)-heptatriaconta-6,9,28,31-tetraen-19-one (0.194 g, 0.368 mmol) obtained by a method equivalent to the method described in WO 2010/042877 in 1,2-dichloroethane (2 mL), methylamine (manufactured by Tokyo Chemical Industry Co., Ltd., approximately 40% solution in methanol, 0.110 mL, 1.1 mmol) and acetic acid (0.063 mL, 1.1 mmol) were added. Sodium triacetoxyborohydride (0.117 g, 0.552 mmol) was further added thereto, and the mixture was then stirred at room temperature for 2 hours. Methylamine (approximately 40% solution in methanol, 0.110 mL, 1.1 mmol), acetic acid (0.063 mL, 1.1 mmol), and sodium triacetoxyborohydride (0.117 g, 0.552 mmol) were added to the reaction solution, and the mixture was stirred for 2 hours. A saturated aqueous solution of sodium bicarbonate was added to the reaction solution, followed by extraction with hexane twice. The organic layers were combined, dried over anhydrous magnesium sulfate, filtered, and concentrated under reduced pressure. The obtained residue was purified by column chromatography (chloroform/methanol=100/0 to 90/10) to obtain (6Z,9Z,28Z,31Z)—N-methylheptatriaconta-6,9,28,31-tetraen-19-amine (0.121 g, 0.223 mmol, yield: 61%).

ESI-MS m/z: 543 (M+H)$^+$.

Step 2

To (6Z,9Z,28Z,31Z)—N-methylheptatriaconta-6,9,28,31-tetraen-19-amine (0.121 g, 0.223 mmol) obtained in step 1, (9Z,12Z)-octadeca-9,12-dienyl methanesulfonate (0.154 g, 0.446 mmol) and a 50% aqueous sodium hydroxide solution (0.107 g, 1.34 mmol) were added, and the mixture was stirred at 135° C. for 2 hours in an oil bath. The reaction solution was cooled to room temperature. Saturated saline was added thereto, and the mixture was washed with hexane. The organic layer was dried over anhydrous magnesium sulfate, filtered, and concentrated under reduced pressure. The obtained residue was purified by silica gel column chromatography (hexane/ethyl acetate=100/0 to 85/15) to obtain (6Z,9Z,28Z,31Z)—N-methyl-N-((9Z,12Z)-octadeca-9,12-dienyl)heptatriaconta-6,9,28,31-tetraen-19-amine (0.139 g, 0.175 mmol, yield: 79%).

ESI-MS m/z: 792 (M+H)$^+$.

Step 3

The title compound (0.114 g, 0.135 mmol, yield: 77%) was obtained in the same way as in step 2 of Reference Example A1 using (6Z,9Z,28Z,31Z)—N-methyl-N-((9Z,12Z)-octadeca-9,12-dienyl)heptatriaconta-6,9,28,31-tetraen-19-amine (0.139 g, 0.175 mmol) obtained in step 2.

ESI-MS m/z: 806 (M)$^+$; $^1$H-NMR (CDCl$_3$) δ: 0.89 (t, J=7.0 Hz, 9H), 1.26-1.56 (m, 54H), 1.65-1.73 (m, 2H), 1.80-1.88 (m, 2H), 2.05 (q, J=7.0 Hz, 12H), 2.77 (t, J=6.3 Hz, 6H), 3.22-3.27 (m, 1H), 3.31 (s, 6H), 3.58-3.62 (m, 2H), 5.29-5.42 (m, 12H).

Reference Example A33

N,N,N-Trimethyl-3-(palmitoyloxy)-2,2-bis((palmitoyloxy)methyl)propan-1-aminium chloride (Compound II-24)

Step 1

To a solution of 2-((dimethylamino)methyl)-2-(hydroxymethyl)propane-1,3-diol (0.420 g, 2.57 mmol) obtained in step 1 of Reference Example A24 in 1,2-dichloroethane (5 mL), pyridine (3.12 mL, 38.6 mmol) was added, then palmitoyl chloride (manufactured by Tokyo Chemical Industry Co., Ltd., 6.22 mL, 20.6 mmol) was added at room temperature, and the mixture was stirred at 70° C. for 2 hours. The reaction solution was cooled to room temperature, and water was added thereto, followed by extraction with ethyl acetate. The organic layer was washed with saturated saline, dried over anhydrous magnesium sulfate, and filtered. The filtrate was concentrated under reduced pressure, and the obtained residue was purified by silica gel column chromatography (chloroform) to obtain 2-((dimethylamino)methyl)-2-((palmitoyloxy)methyl)propane-1,3-diyl dipalmitate (0.650 g, 0.740 mmol, yield: 29%).

ESI-MS m/z: 879 (M+H)$^+$

Step 2

The title compound (0.056 g, 0.060 mmol, yield: 8%) was obtained in the same way as in step 2 of Reference Example A1 using 2-((dimethylamino)methyl)-2-((palmitoyloxy)methyl)propane-1,3-diyl dipalmitate (0.65 g, 0.74 mmol) obtained in step 1.

ESI-MS m/z: 893 (M)$^+$; $^1$H-NMR (CDCl$_3$) δ: 0.88 (t, J=7.0 Hz, 9H), 1.21-1.34 (m, 72H), 1.54-1.64 (m, 6H), 2.38 (t, J=7.6 Hz, 6H), 3.62 (s, 9H), 3.95 (s, 2H), 4.29 (s, 6H).

Reference Example A34

N,N,N-Trimethyl-3-(tetradecanoyloxy)-2,2-bis((tetradecanoyloxy)methyl)propan-1-aminium chloride (Compound II-25)

The title compound (0.045 g, 0.053 mmol, overall yield: 4%) was obtained in the same way as in Reference Example A33 using myristoyl chloride (Wako Pure Chemical Industries Ltd.) instead of palmitoyl chloride.

ESI-MS m/z: 809 (M)$^+$; $^1$H-NMR (CDCl$_3$) δ: 0.88 (t, J=6.8 Hz, 9H), 1.21-1.34 (m, 60H), 1.54-1.64 (m, 6H), 2.38 (t, J=7.6 Hz, 6H), 3.64 (s, 9H), 3.96 (s, 2H), 4.29 (s, 6H).

Reference Example A35

3-(Dodecanoyloxy)-2,2-bis((dodecanoyloxy)methyl)-N,N,N-trimethylpropan-1-aminium chloride (Compound II-26)

The title compound (0.085 g, 0.112 mmol, overall yield: 9%) was obtained in the same way as in Reference Example A33 using lauroyl chloride (manufactured by Tokyo Chemical Industry Co., Ltd.) instead of palmitoyl chloride.

ESI-MS m/z: 725 (M)$^+$; $^1$H-NMR (CDCl$_3$) δ: 0.88 (t, J=6.8 Hz, 9H), 1.19-1.34 (m, 48H), 1.54-1.64 (m, 6H), 2.38 (t, J=7.6 Hz, 6H), 3.66 (s, 9H), 3.97 (s, 2H), 4.30 (s, 6H).

Reference Example A36

(Z)—N,N,N-Trimethyl-3,3-bis((oleoyloxy)methyl) henicos-12-en-1-aminium chloride (Compound II-27)

Step 1

Dimethyl malonate (1.00 g, 7.57 mmol) was dissolved in acetonitrile (25 mL). To the solution, (Z)-oct-9-en-1-yl methanesulfonate (3.15 g, 9.08 mmol), cesium carbonate (4.93 g, 15.1 mmol) and tetrabutylammonium iodide (3.35 g, 9.08 mmol) were added, and the mixture was stirred at 60° C. for 1 hour. Water was added to the reaction solution, followed by extraction with hexane. The organic layer was washed with saturated saline, dried over anhydrous magnesium sulfate, filtered, and concentrated under reduced pressure. The obtained residue was purified by silica gel column chromatography (hexane/ethyl acetate=90/10 to 70/30) to obtain (Z)-dimethyl 2-(octadec-9-en-1-yl)malonate (2.54 g, 6.64 mmol, yield: 88%).

ESI-MS m/z: 383 (M+H)$^+$

Step 2

(Z)-Dimethyl 2-(octadec-9-en-1-yl)malonate (0.500 g, 1.31 mmol) obtained in step 1 was dissolved in toluene (6 mL). To the solution, sodium hydride (60% oil, 0.209 g, 5.23 mmol) was added under ice cooling, and the mixture was stirred until foaming disappeared. Subsequently, 2-chloro-N,N-dimethylethanamine hydrochloride (manufactured by Tokyo Chemical Industry Co., Ltd., 0.377 g, 2.61 mmol) was added thereto, and the mixture was stirred at 100° C. for 2 hours. Water was added to the reaction solution under ice cooling, followed by extraction with chloroform. The organic layer was washed with saturated saline, dried over anhydrous magnesium sulfate, filtered, and concentrated under reduced pressure. The obtained residue was purified by silica gel column chromatography (chloroform/methanol=99/1 to 90/10) to obtain (Z)-dimethyl 2-(2-(dimethylamino)ethyl)-2-(octadec-9-en-1-yl)malonate (0.258 g, 0.569 mmol, yield: 44%).

ESI-MS m/z: 454 (M+H)$^+$

Step 3

(Z)-2-(2-(Dimethylamino)ethyl)-2-(octadec-9-en-1-yl)propane-1,3-diol (0.220 g, 0.553 mmol, quantitative) was obtained in the same way as in step 2 of Reference Example A19 using (Z)-dimethyl 2-(2-(dimethylamino)ethyl)-2-(octadec-9-en-1-yl)malonate (0.250 g, 0.551 mmol) obtained in step 2.

ESI-MS m/z: 398 (M+H)$^+$

Step 4

(Z)-2-(2-(Dimethylamino)ethyl)-2-(octadec-9-en-1-yl)propane-1,3-diol (0.220 g, 0.553 mmol) obtained in step 3 was dissolved in dichloromethane (2 mL). To the solution, N,N-diisopropylethylamine (0.386 mL, 2.21 mmol) was added, then oleoyl chloride (manufactured by Sigma-Aldrich Corp., 0.457 mL, 1.38 mmol) was added under ice cooling, and the mixture was stirred at room temperature for 10 minutes. Water was added to the reaction solution, followed by extraction with hexane. The organic layer was washed with saturated saline, dried over anhydrous magnesium sulfate, filtered, and concentrated under reduced pressure. The obtained residue was purified by silica gel column chromatography (hexane/ethyl acetate=90/10 to 50/50) to obtain (Z)-2-(2-(dimethylamino)ethyl)-2-((Z)-octadec-9-en-1-yl)propane-1,3-diyl dioleate (0.280 g, 0.302 mmol, yield: 55%).

ESI-MS m/z: 927 (M+H)$^+$

Step 5

The title compound (0.199 g, 0.204 mmol, yield: 67%) was obtained in the same way as in step 2 of Reference Example A1 using (Z)-2-(2-(dimethylamino)ethyl)-2-((Z)-octadec-9-en-1-yl)propane-1,3-diyl dioleate (0.280 g, 0.302 mmol) obtained in step 4.

ESI-MS m/z: 941 (M)$^+$; $^1$H-NMR (CDCl$_3$) δ: 0.88 (t, J=7.0 Hz, 9H), 1.22-1.39 (m, 66H), 1.55-1.65 (m, 4H), 1.70-1.78 (m, 2H), 1.98-2.06 (m, 12H), 2.33 (t, J=7.6 Hz, 4H), 3.46 (s, 9H), 3.58-3.65 (m, 2H), 3.93-4.03 (m, 4H), 5.29-5.39 (m, 6H).

Reference Example A37

(Z)—N,N,N-Trimethyl-4,4-bis((oleoyloxy)methyl)docos-13-en-1-aminium chloride (Compound II-28)

Step 1

(Z)-Dimethyl 2-(3-(dimethylamino)propyl)-2-(octadec-9-en-1-yl)malonate (0.210 g, 0.449 mmol, yield: 34%) was obtained in the same way as in step 2 of Reference Example A36 using 3-chloro-N,N-dimethylpropan-1-amine hydrochloride (manufactured by Tokyo Chemical Industry Co., Ltd.) instead of 2-chloro-N,N-dimethylethanamine hydrochloride.

ESI-MS m/z: 468 (M+H)$^+$

Step 2

The title compound (0.042 g, 0.042 mmol, overall yield: 9%) was obtained in the same way as in steps 3, 4 and 5 of Reference Example A36 using (Z)-dimethyl2-(3-(dimethylamino)propyl)-2-(octadec-9-en-1-yl)malonate (0.210 g, 0.449 mmol) obtained in step 1 instead of (Z)-dimethyl 2-(2-(dimethylamino)ethyl)-2-(octadec-9-en-1-yl)malonate.

ESI-MS m/z: 955 (M)$^+$; $^1$H-NMR (CDCl$_3$) δ: 0.88 (t, J=6.8 Hz, 9H), 1.22-1.36 (m, 68H), 1.56-1.64 (m, 4H), 1.72-1.82 (m, 2H), 1.96-2.07 (m, 12H), 2.32 (t, J=7.5 Hz, 4H), 3.38 (s, 9H), 3.39-3.46 (m, 2H), 3.93 (d, J=11.2 Hz, 2H), 3.99 (d, J=11.2 Hz, 2H), 5.28-5.40 (m, 6H).

Reference Example A38

N,N,N-Trimethyl-3-(stearoyloxy)-2,2-bis((stearoyloxy)methyl)propan-1-aminium chloride (Compound II-29)

The title compound (0.085 g, 0.112 mmol, overall yield: 6%) was obtained in the same way as in Reference Example A33 using stearoyl chloride (manufactured by Tokyo Chemical Industry Co., Ltd.) instead of palmitoyl chloride.

ESI-MS m/z: 977 (M)$^+$; $^1$H-NMR (CDCl$_3$) δ: 0.88 (t, J=6.8 Hz, 9H), 1.21-1.37 (m, 84H), 1.54-1.64 (m, 6H), 2.38 (t, J=7.6 Hz, 6H), 3.65 (s, 9H), 3.96 (s, 2H), 4.30 (s, 6H).

Reference Example A39

N,N,N-Trimethyl-3-oleamido-2,2-bis((oleoyloxy)methyl)propan-1-aminium chloride (Compound II-30)

Step 1

2-((Dimethylamino)methyl)-2-(hydroxymethyl)propane-1,3-diol (0.410 g, 2.51 mmol) obtained in step 1 of Reference Example A24 was dissolved in a mixed solvent of dichloromethane (5 mL) and pyridine (5.08 mL, 62.8 mmol). To the solution, oleoyl chloride (1.25 mL, 3.77 mmol) was added under ice cooling. Water was added to the reaction solution, followed by extraction with chloroform. The organic layer was washed with saturated saline, dried over anhydrous magnesium sulfate, and filtered. The filtrate was concentrated under reduced pressure, and the obtained residue was purified by silica gel column chromatography (chloroform/methanol=99/1 to 90/10) to obtain (Z)-2-((dimethylamino)methyl)-2-(hydroxymethyl)propane-1,3-diyl dioleate (0.190 g, 0.275 mmol, yield: 11%).

ESI-MS m/z: 693 (M+H)$^+$

Step 2

(Z)-2-((Dimethylamino)methyl)-2-(hydroxymethyl)propane-1,3-diyl dioleate (0.190 g, 2.51 mmol) obtained in step 1 was dissolved in toluene (2 mL). To the solution, diphenylphosphoryl azide (manufactured by Tokyo Chemical Industry Co., Ltd., 0.118 mL, 0.549 mmol) and 1,8-diazabicyclo[5.4.0]-7-undecene (0.0830 mL, 0.549 mmol) were added at room temperature, and the mixture was stirred for 1 hour. Since the progression of the reaction was insufficient, diphenylphosphoryl azide (0.118 mL, 0.549 mmol) was further added thereto, and the mixture was stirred under heating at 80° C. for 3 hours. The reaction solution was cooled to room temperature, and water was added thereto, followed by extraction with ethyl acetate. The organic layer was washed with saturated saline, dried over anhydrous magnesium sulfate, and filtered. The filtrate was concentrated under reduced pressure, and the obtained residue was purified by silica gel column chromatography (hexane/ethyl acetate=95/5 to 60/40) to obtain (Z)-2-(azidomethyl)-2-((dimethylamino)methyl)propane-1,3-diyl dioleate (0.135 g, 0.188 mmol, yield: 69%).

ESI-MS m/z: 718 (M+H)$^+$

Step 3

(Z)-2-(Azidomethyl)-2-((dimethylamino)methyl)propane-1,3-diyl dioleate (0.135 g, 2.51 mmol) obtained in step 2 was dissolved in a mixed solution of tetrahydrofuran (1 mL) and water (0.1 mL). To the solution, triphenylphosphine (manufactured by Junsei Chemical Co., Ltd., 0.0740 g, 0.282 mmol) was added, and the mixture was stirred for 3 hours. Water was added to the reaction solution, followed by extraction with ethyl acetate. The organic layer was washed with saturated saline, dried over anhydrous magnesium sulfate, and filtered. The filtrate was concentrated under reduced pressure to obtain a crude product of (Z)-2-(aminoethyl)-2-((dimethylamino)methyl)propane-1,3-diyl dioleate (0.130 g, 0.188 mmol, yield: 100%).

ESI-MS m/z: 691 (M+H)$^+$

Step 4

To a solution of (Z)-2-(aminoethyl)-2-((dimethylamino)methyl)propane-1,3-diyl dioleate (0.130 g, 0.188 mmol) obtained in step 3 in dichloromethane (2 mL), N,N-diisopropylethylamine (0.0990 mL, 0.564 mmol) was added, then oleoyl chloride (0.0850 g, 0.282 mmol) was added under ice cooling, and the mixture was stirred at room temperature for 1 hour. Water was added to the reaction solution, followed by extraction with hexane. The organic layer was washed with saturated saline, dried over anhydrous magnesium sulfate, and filtered. The filtrate was concentrated under reduced pressure, and the obtained residue was purified by silica gel column chromatography (hexane/ethyl acetate=97/3 to 60/40) to obtain (Z)-2-((dimethylamino)methyl)-2-(oleamidomethyl)propane-1,3-diyl dioleate (0.105 g, 0.110 mmol, yield: 58%).

ESI-MS m/z: 956 (M+H)$^+$

Step 5

The title compound (0.0480 g, 0.0480 mmol, yield: 43%) was obtained in the same way as in step 2 of Reference Example A1 using (Z)-2-((dimethylamino)methyl)-2-(oleamidomethyl)propane-1,3-diyl dioleate (0.105 g, 0.110 mmol) obtained in step 4.

ESI-MS m/z: 970 (M)$^+$; $^1$H-NMR (CDCl$_3$) δ: 0.88 (t, J=6.8 Hz, 9H), 1.21-1.37 (m, 60H), 1.56-1.65 (m, 6H), 1.96-2.05 (m, 12H), 2.36 (t, J=7.6 Hz, 6H), 3.51 (s, 9H), 3.51-3.56 (m, 2H), 4.02 (s, 2H), 4.20 (d, J=12.2 Hz, 2H), 4.30 (d, J=12.2 Hz, 2H), 5.27-5.40 (m, 6H), 8.11-8.20 (m, 1H).

Reference Example A40

N,N,N-Trimethyl-4-(oleoyloxy)-3,3-bis(oleoyloxymethyl)butan-1-aminium chloride (Compound II-31)

Step 1

To a solution of 2-(bromomethyl)-2-(hydroxymethyl)propane-1,3-diol (manufactured by Tokyo Chemical Industry Co., Ltd., 1.00 g, 5.02 mmol) in tetrahydrofuran (10 mL), tert-butyldimethylchlorosilane (manufactured by Tokyo Chemical Industry Co., Ltd., 3.79 g, 25.1 mmol), imidazole (manufactured by Nacalai Tesque, Inc., 3.42 g, 50.2 mmol), and N,N-dimethylaminopyridine (0.061 g, 0.502 mmol) were added, and the mixture was stirred overnight at room temperature. A saturated aqueous solution of sodium bicarbonate was added to the reaction solution, followed by extraction with hexane twice. The organic layer was dried over anhydrous magnesium sulfate and then concentrated under reduced pressure. The residue was purified by silica gel column chromatography (hexane) to obtain 6-(bromomethyl)-6-((tert-butyldimethylsilyloxy)methyl)-2,2,3,3,9,9,10,10-octamethyl-4,8-dioxa-3,9-disilaundecane (2.50 g, 4.61 mmol, 92%).

$^1$H-NMR (CDCl$_3$) δ: 0.04 (s, 18H), 0.89 (s, 27H), 3.41 (s, 2H), 3.49 (s, 6H).

Step 2

To a solution of 6-(bromomethyl)-6-((tert-butyldimethylsilyloxy)methyl)-2,2,3,3,9,9,10,10-octamethyl-4,8-dioxa-3,9-disilaundecane (1.849 g, 3.41 mmol) obtained in step 1 in dimethyl sulfoxide (10 mL), sodium cyanide (manufactured by Nacalai Tesque, Inc., 0.529 g, 10.8 mmol) was added, and the mixture was stirred at 85° C. for 3 days. After cooling to room temperature, the reaction solution was diluted with hexane, washed with water and then saturated saline, dried over anhydrous magnesium sulfate, then filtered, and concentrated under reduced pressure. The obtained residue was purified by silica gel column chromatography (hexane/ethyl acetate=90/10) to obtain 4-(tert-butyldimethylsilyloxy)-3,3-bis((tert-butyldimethylsilyloxy)methyl)butanenitrile (1.35 g, 2.77 mmol, yield: 81%).

ESI-MS m/z: 489 (M+H)$^+$; $^1$H-NMR (CDCl$_3$) δ: 0.05 (s, 18H), 0.89 (s, 27H), 2.34 (s, 2H), 3.51 (s, 6H).

Step 3

To a solution of 4-(tert-butyldimethylsilyloxy)-3,3-bis((tert-butyldimethylsilyloxy)methyl)butanenitrile (1.34 g, 2.75 mmol) obtained in step 2 in tetrahydrofuran (10 mL), lithium aluminum hydride (0.104 g, 2.75 mmol) was added under ice cooling, and the mixture was stirred at room temperature for 2 hours. Water (0.495 mL, 27.5 mmol) and sodium fluoride (3.46 g, 82.0 mmol) were added to the reaction solution, and the mixture was stirred overnight at room temperature. Insoluble matter was removed by filtration through celite, and the filtrate was concentrated. The obtained residue was purified by amino silica gel column chromatography (ethyl acetate) to obtain 4-(tert-butyldimethylsilyloxy)-3,3-bis((tert-butyldimethylsilyloxy)methyl)butan-1-amine (0.435 g, 0.884 mmol, yield: 32%).

ESI-MS m/z: 493 (M+H)$^+$; $^1$H-NMR (CDCl$_3$) δ: 0.02 (s, 18H), 0.88 (s, 27H), 1.38-1.43 (m, 2H), 2.71-2.75 (m, 2H), 3.40 (s, 6H).

Step 4

To a solution of 4-(tert-butyldimethylsilyloxy)-3,3-bis((tert-butyldimethylsilyloxy)methyl)butan-1-amine (0.200 g, 0.407 mmol) obtained in step 3 in 1,2-dichloroethane (3 mL), a 38% aqueous formaldehyde solution (0.295 mL) and sodium triacetoxyborohydride (0.431 g, 2.03 mmol) were added, and the mixture was stirred overnight at room temperature. A saturated aqueous solution of sodium bicarbonate was added to the reaction solution, followed by extraction with chloroform twice. The organic layer was dried over anhydrous magnesium sulfate and then concentrated under reduced pressure. The residue was purified by silica gel column chromatography (chloroform/methanol=90/10) to obtain a crude product of 4-(tert-butyldimethylsilyloxy)-3,3-bis((tert-butyldimethylsilyloxy)methyl)-N,N-dimethylbutan-1-amine.

To the obtained crude product, tetrahydrofuran (2 mL) and tetrabutylammonium fluoride (manufactured by Tokyo Chemical Industry Co., Ltd., approximately 1 mol/L solution in tetrahydrofuran, 2.06 mL, 2.06 mmol) were added, and the mixture was stirred at room temperature for 5 hours and then stirred overnight at 60° C. A saturated aqueous solution of sodium bicarbonate was added to the reaction solution, and the mixture was washed twice with chloroform. The aqueous layer was concentrated under reduced pressure. To the obtained residue, acetone (2 mL), sodium hydroxide (manufactured by Wako Pure Chemical Industries Ltd., 2 mol/L aqueous solution, 3 mL, 6 mmol), and oleoyl chloride (0.681 mL, 2.06 mmol) were added, and the mixture was stirred at room temperature for 3 hours. Oleoyl chloride (0.681 mL, 2.06 mmol) was added to the reaction solution, and the mixture was stirred overnight at 60° C. After cooling to room temperature, water was added to the reaction solution, followed by extraction with chloroform twice. The organic layer was dried over anhydrous magnesium sulfate, then filtered, and concentrated under reduced pressure. The obtained residue was purified by silica gel column chromatography (chloroform/methanol=90/10) to obtain a crude product of (Z)-2-(2-(dimethylamino)ethyl)-2-(oleyloxymethyl)propane-1,3-diyl dioleate. The obtained crude product was dissolved in a small amount of methanol-chloroform (9:1), and the solution was loaded to an ion-exchange resin (manufactured by Waters Corp., PoraPack Rxn CX, prewashed with methanol), followed by elution with ammonia (manufactured by Sigma-Aldrich Corp., 2 mol/L solution in methanol). The eluate was concentrated under reduced pressure to obtain (Z)-2-(2-(dimethylamino)ethyl)-2-(oleyloxymethyl)propane-1,3-diyl dioleate (0.387 g, 0.399 mmol, yield: 98%).

ESI-MS m/z: 971 (M+H)$^+$; $^1$H-NMR (CDCl$_3$) δ: 0.88 (t, J=7.0 Hz, 9H), 1.21-1.38 (m, 62H), 1.54-1.65 (m, 6H), 1.97-2.04 (m, 12H), 2.20 (s, 6H), 2.25-2.32 (m, 8H), 4.04 (s, 6H), 5.29-5.39 (m, 6H).

Step 5

The title compound (0.0642 g, 0.0630 mol, yield: 56%) was obtained in the same way as in step 2 of Reference Example A1 using (Z)-2-(2-(dimethylamino)ethyl)-2-(oleyloxymethyl)propane-1,3-diyl dioleate (0.109 g, 0.112 mol) obtained in step 4 instead of 2,2',2''-nitrilotris(ethane-2,1-diyl) trioleate.

ESI-MS m/z: 986 (M)$^+$; $^1$H-NMR (CDCl$_3$) δ: 0.88 (t, J=6.8 Hz, 9H), 1.23-1.37 (m, 74H), 1.55-1.64 (m, 65H), 1.78-1.84 (m, 2H), 1.95-2.06 (m, 13H), 2.35 (t, J=7.6 Hz, 6H), 3.42 (s, 8H), 3.70-3.77 (m, 2H), 4.08 (s, 6H), 5.29-5.39 (m, 6H).

Reference Example A41

N,N,N-Trimethyl-2-(3-(oleoyloxy)-2,2-bis((oleoyloxy)methyl)propoxy)-2-oxyethan-1-aminium chloride (Compound II-32)

Step 1

To a solution of 2,2-(dimethyl-1,3-dioxane-5,5-diyl)dimethanol (0.200 g, 1.14 mmol) synthesized by the method described in U.S. Pat. No. 8,816,099 in tetrahydrofuran (5 mL), triethylamine (0.475 mL, 3.40 mmol) was added, then oleoyl chloride (0.854 g, 2.84 mmol) was added under ice cooling, and the mixture was stirred for 1 hour under this ice cooling. Water was added to the reaction solution, followed by extraction with hexane. The organic layer was washed with saturated saline, dried over anhydrous magnesium sulfate, and filtered. The filtrate was concentrated under reduced pressure, and the obtained residue was purified by silica gel column chromatography (hexane/ethyl acetate=95/5) to obtain (2,2-dimethyl-1,3-dioxane-5,5-diyl)bis(methylene) dioleate (0.500 g, 0.709 mmol, yield: 63%).

ESI-MS m/z: 705 (M+H)$^+$

Step 2

To a solution of (2,2-dimethyl-1,3-dioxane-5,5-diyl)bis(methylene) dioleate (0.500 g, 0.709 mmol) obtained in step 1 in dichloromethane (5 mL), trifluoroacetic acid (2.00 mL, 26.0 mmol) was added in two divided portions under ice cooling, and the mixture was stirred for 1 hour under this ice cooling. A saturated aqueous solution of sodium bicarbonate was added to the reaction solution, followed by extraction with ethyl acetate. The organic layer was washed with saturated saline, dried over anhydrous magnesium sulfate, and filtered. The obtained residue was purified by silica gel column chromatography (hexane/ethyl acetate=90/10 to 50/50) to obtain 2,2-bis(hydroxymethyl)propane-1,3-diyl dioleate (0.207 g, 0.311 mmol, yield: 44%).

ESI-MS m/z: 665 (M+H)$^+$

Step 3

To N,N-dimethylglycine (manufactured by Tokyo Chemical Industry Co., Ltd., 0.049 g, 0.474 mmol), thionyl chloride (1 mL, 13.7 mmol) was added, and the mixture was stirred under heating at 70° C. for 30 minutes. The reaction solution was cooled to room temperature and then concentrated under reduced pressure to obtain a crude product of N,N-dimethylglycinoyl chloride. To a solution of 2,2-bis(hydroxymethyl)propane-1,3-diyl dioleate (0.207 g, 0.311 mmol) obtained in step 2 in dichloromethane (5 mL), N,N-diisopropylethylamine (0.110 mL, 0.632 mmol) and the crude product of N,N-dimethylglycinoyl chloride were added under ice cooling, and the mixture was stirred at room temperature for 1 hour. Water was added to the reaction solution, followed by extraction with ethyl acetate. The organic layer was washed with saturated saline, dried over anhydrous magnesium sulfate, and filtered. The obtained residue was purified by silica gel column chromatography (hexane/ethyl acetate=90/10 to 40/60) to obtain 2-(((dimethylglycyl)oxy)methyl)-2-(hydroxymethyl)propane-1,3-diyl dioleate (0.077 g, 0.103 mmol, yield: 33%).

ESI-MS m/z: 751 (M+H)$^+$

Step 4

To a solution of 2-(((dimethylglycyl)oxy)methyl)-2-(hydroxymethyl)propane-1,3-diyl dioleate (0.0770 g, 0.103 mmol) obtained in step 3 in dichloromethane (3 mL), pyridine (0.0330 mL, 0.411 mmol) was added, then oleoyl chloride (0.0620 g, 0.205 mmol) was added under ice cooling, and the mixture was stirred at room temperature for 30 minutes. Water was added to the reaction solution, followed by extraction with a mixed solvent of hexane/ethyl acetate=1/1. The organic layer was washed with saturated saline, dried over anhydrous magnesium sulfate, and filtered. The obtained residue was purified by silica gel column chromatography (hexane/ethyl acetate=95/5) to obtain 2-(((dimethylglycyl)oxy)methyl)-2-((oleoyl)methyl)propane-1,3-diyl dioleate (0.122 g, 0.0600 mmol, yield: 59%).

ESI-MS m/z: 1015 (M+H)$^+$

Step 5

The title compound (0.017 g, 0.016 mmol, yield: 27%) was obtained in the same way as in step 2 of Reference Example A1 using 2-(((dimethylglycyl)oxy)methyl)-2-((oleoyl)methyl)propane-1,3-diyl dioleate (0.122 g, 0.060 mmol) obtained in step 4.

ESI-MS m/z: 1029 (M)$^+$; $^1$H-NMR (CDCl$_3$) δ: 0.88 (t, J=6.8 Hz, 9H), 1.19-1.38 (m, 58H), 1.54-1.66 (m, 6H), 1.98-2.04 (m, 12H), 2.28-2.35 (m, 6H), 3.60 (s, 9H), 4.11 (d, J=1.8 Hz, 6H), 4.20 (s, 2H), 5.08 (s, 2H), 5.29-5.41 (m, 6H).

Reference Example A42

N,N, N-Trimethyl-1,3-bis(tetradecanoyloxy)-2-((tetradecanoyloxy)methyl)propan-2-aminium chloride (Compound II-33)

Step 1

To 2-(dimethylamino)-2-(hydroxymethyl)propane-1,3-diol (1.50 g, 10.1 mmol) in tetrahydrofuran (10 mL), pyridine (4.07 mL, 50.3 mmol) and then tetradecanoyl chloride (4.09 mL, 15.1 mmol) were added, and the mixture was stirred under heating at 60° C. for 2 hours. Water was added to the reaction solution, followed by extraction with ethyl acetate. The organic layer was washed with saturated saline, dried over anhydrous magnesium sulfate, and filtered. The filtrate was concentrated under reduced pressure, and the obtained residue was purified by silica gel column chromatography (chloroform/methanol=99/1 to 90/10) to obtain 2-(dimethylamino)-2-((tetradecanoyloxy)methyl)propane-1,3-diyl ditetradecanoate (1.50 g, 1.92 mmol, yield: 19%), 2-(dimethylamino)-2-(hydroxymethyl)propane-1,3-diyl ditetradecanoate (0.750 g, 1.32 mmol, yield: 13%), and 2-(dimethylamino)-3-hydroxy-2-(hydroxymethyl)propyl tetradecanoate (0.220 g, 0.612 mmol, yield: 6%).

ESI-MS m/z: 781 (M+H)$^+$
ESI-MS m/z: 570 (M+H)$^+$
ESI-MS m/z: 360 (M+H)$^+$

Step 2

The title compound (0.530 g, 0.638 mmol, yield: 33%) was obtained in the same way as in step 2 of Reference Example A1 using 2-(dimethylamino)-2-((tetradecanoyloxy)methyl)propane-1,3-diyl ditetradecanoate (1.50 g, 1.92 mmol) obtained in step 1.

ESI-MS m/z: 795 (M)$^+$; $^1$H-NMR (CDCl$_3$) δ: 0.88 (t, J=6.8 Hz, 9H), 1.21-1.33 (m, 60H), 1.55-1.65 (m, 6H), 2.37 (t, J=7.6 Hz, 6H), 3.71 (s, 9H), 4.59 (s, 6H).

Reference Example A43

N,N,N-Trimethyl-1,3-bis(oleyloxy)-2-((tetradecanoyloxy)methyl)propan-2-aminium chloride (Compound II-34)

Step 1

To a solution of 2-(dimethylamino)-3-hydroxy-2-(hydroxymethyl)propyl tetradecanoate (0.220 g, 0.612 mmol) obtained in step 1 of Reference Example A42 in 1,2-dichloroethane (3 mL), pyridine (0.297 mL, 3.67 mmol) and then oleoyl chloride (0.552 g, 1.84 mmol) were added, and the mixture was stirred under heating at 60° C. for 1 hour. Water was added to the reaction solution, followed by extraction with ethyl acetate. The organic layer was washed with saturated saline, dried over anhydrous magnesium sulfate, and filtered. The obtained residue was purified by silica gel column chromatography (hexane/ethyl acetate=98/2 to 85/15) to obtain 2-(dimethylamino)-2-((tetradecanoyloxy)methyl)propane-1,3-diyl dioleate (0.250 g, 0.281 mmol, yield: 46%).

ESI-MS m/z: 889 (M+H)$^+$

Step 2

The title compound (0.065 g, 0.069 mmol, yield: 25%) was obtained in the same way as in step 2 of Reference Example A1 using 2-(dimethylamino)-2-((tetradecanoyloxy)methyl)propane-1,3-diyl dioleate (0.250 g, 0.281 mmol) obtained in step 1.

ESI-MS m/z: 903 (M)$^+$; $^1$H-NMR (CDCl$_3$) δ: 0.88 (t, J=7.0 Hz, 9H), 1.22-1.38 (m, 60H), 1.56-1.66 (m, 6H), 1.97-2.05 (m, 8H), 2.39 (t, J=7.6 Hz, 6H), 3.72 (s, 9H), 4.58 (s, 6H), 5.28-5.40 (m, 4H).

Reference Example A44

N,N,N-Trimethyl-1-(oleyloxy)-3-(tetradecanoyloxy)-2-((tetradecanoyloxy)methyl)propan-2-aminium chloride (Compound II-35)

Step 1

To a solution of 2-(dimethylamino)-2-(hydroxymethyl)propane-1,3-diyl ditetradecanoate (0.750 g, 1.32 mmol) obtained in step 1 of Reference Example A42 in 1,2-dichloroethane (3 mL), pyridine (0.532 mL, 6.58 mmol) and then oleoyl chloride (0.792 g, 1.84 mmol) were added, and the mixture was stirred under heating at 60° C. for 1 hour. Water was added to the reaction solution, followed by extraction with ethyl acetate. The organic layer was washed with saturated saline, dried over anhydrous magnesium sulfate, and filtered. The obtained residue was purified by silica gel column chromatography (hexane/ethyl acetate=95/5) to obtain 2-(dimethylamino)-2-((oleyloxy)methyl)propane-1,3-diyl ditetradecanoate (0.750 g, 0.899 mmol, yield: 68%).

ESI-MS m/z: 835 (M+H)$^+$

Step 2

The title compound (0.092 g, 0.104 mmol, yield: 12%) was obtained in the same way as in step 2 of Reference Example A1 using 2-(dimethylamino)-2-((oleyloxy)methyl)propane-1,3-diyl ditetradecanoate (0.750 g, 0.899 mmol) obtained in step 1.

ESI-MS m/z: 849 (M)$^+$; $^1$H-NMR (CDCl$_3$) δ: 0.88 (t, J=6.8 Hz, 9H), 1.19-1.38 (m, 60H), 1.56-1.65 (m, 6H), 1.98-2.06 (m, 4H), 2.39 (t, J=7.6 Hz, 6H), 3.72 (s, 9H), 4.59 (s, 6H), 5.30-5.39 (m, 2H).

Reference Example A45

N,N, N-Trimethyl-3-(tetradecanoyloxy)-2-((tetradecanoyloxy)methyl)-2-(((tetradecylcarbamoyl)oxy)methyl)propan-1-aminium chloride (Compound II-36)

Step 1

To a solution of 2-((dimethylamino)methyl)-2-(hydroxymethyl)propane-1,3-diol (0.820 g, 5.02 mmol) obtained in step 1 of Reference Example A24 in tetrahydrofuran (7 mL), pyridine (2.03 mL, 38.6 mmol) was added, then tetradecanoyl chloride (0.930 mL, 3.77 mmol) was added under ice cooling, and the mixture was stirred at 60° C. for 2 hours. The reaction solution was cooled to room temperature, and water was added thereto, followed by extraction with ethyl acetate. The organic layer was washed with saturated saline, dried over anhydrous magnesium sulfate, and filtered. The filtrate was concentrated under reduced pressure, and the obtained residue was purified by silica gel column chromatography (hexane/ethyl acetate=95/5 to 70/30) to obtain 2-((dimethylamino) methyl)-2-(hydroxymethyl)propane-1,3-diyl ditetradecanoate (0.150 g, 0.257 mmol, yield: 5%).

ESI-MS m/z: 584 (M+H)$^+$

Step 2

To a solution of 2-((dimethylamino)methyl)-2-(hydroxymethyl)propane-1,3-diyl ditetradecanoate (0.060 g, 0.103 mmol) obtained in step 1 in dichloromethane (3 mL), triethylamine (0.017 mL, 0.123 mmol) was added, then 4-nitrophenyl chloroformate (manufactured by Tokyo Chemical Industry Co., Ltd., 0.025 g, 0.123 mmol) and then tetradecylamine (manufactured by Tokyo Chemical Industry Co., Ltd., 0.022 g, 0.103 mmol) were added under ice cooling, and the mixture was stirred overnight at room temperature. Water was added to the reaction solution, followed by extraction with ethyl acetate. The organic layer was washed with saturated saline, dried over anhydrous magnesium sulfate, and filtered. The obtained residue was purified by silica gel column chromatography (hexane/ethyl acetate=95/5 to 70/30) to obtain 2-((dimethylamino) methyl)-2-(((tetradecylcarbamoyl)oxy)methyl)propane-1,3-diyl ditetradecanoate (0.052 g, 0.063 mmol, yield: 62%).

ESI-MS m/z: 824 (M+H)$^+$

Step 3

The title compound (0.012 g, 0.014 mmol, yield: 21%) was obtained in the same way as in step 2 of Reference Example A1 using 2-((dimethylamino)methyl)-2-(((tetradecylcarbamoyl)oxy)methyl)propane-1,3-diyl ditetradecanoate (0.052 g, 0.063 mmol) obtained in step 2.

ESI-MS m/z: 838 (M)$^+$; $^1$H-NMR (CDCl$_3$) δ: 0.88 (t, J=7.0 Hz, 9H), 1.22-1.33 (m, 62H), 1.51-1.61 (m, 6H), 2.38 (t, J=7.6 Hz, 4H), 3.13 (dd, J=14.2, 5.8 Hz, 2H), 3.59 (s, 9H), 4.12 (s, 2H), 4.19 (s, 2H), 4.21 (d, J=12.0 Hz, 2H), 4.25 (d, J=12.0 Hz, 2H), 6.72 (t, J=5.8 Hz, 1H).

Reference Example A46

N,N,N-Trimethyl-3-((octadecylcarbamoyl)oxy)-2,2-bis((tetradecanoyloxy)methyl)propan-1-aminium chloride (Compound II-37)

Step 1

The title compound (0.015 g, 0.016 mmol, overall yield: 0.5%) was obtained in the same way as in Reference Example A45 using stearylamine (manufactured by Tokyo Chemical Industry Co., Ltd.) instead of tetradecylamine.

ESI-MS m/z: 894 (M)$^+$; $^1$H-NMR (CDCl$_3$) δ: 0.88 (t, J=6.8 Hz, 9H), 1.21-1.34 (m, 70H), 1.51-1.62 (m, 6H), 2.38 (t, J=7.6 Hz, 4H), 3.13 (dd, J=14.3, 5.8 Hz, 2H), 3.60 (s, 9H), 4.12 (s, 2H), 4.19 (s, 2H), 4.21 (d, J=12.2 Hz, 2H), 4.25 (d, J=12.2 Hz, 2H), 6.69 (t, J=5.8 Hz, 1H).

Reference Example A47

N,N,N-Trimethyl-3-(stearoyloxy)-2,2-bis((tetradecanoyloxy)methyl)propan-1-aminium chloride (Compound II-37)

Step 1

To a solution of (5-(bromomethyl)-2,2-dimethyl-1,3-dioxan-5-yl)methanol (1.00 g, 4.18 mmol) synthesized by the method described in "Angewandte Chemie International Edition", 2009, Vol. 48, p. 2126-2130 in pyridine (10 mL), stearoyl chloride (2.53 g, 8.36 mmol) was added, and the mixture was stirred at room temperature for 30 minutes. Water was added to the reaction solution, followed by extraction with ethyl acetate. The organic layer was washed with saturated saline, dried over anhydrous magnesium sulfate, and filtered. The obtained residue was purified by silica gel column chromatography (hexane/ethyl acetate=90/10) to obtain (5-(bromomethyl)-2,2-dimethyl-1,3-dioxan-5-yl)methyl stearate (0.95 g, 1.879 mmol, yield: 45%).

$^1$H-NMR (CDCl$_3$) δ: 0.89 (t, J=7.0 Hz, 9H), 1.23-1.40 (m, 44H), 1.54-1.64 (m, 26H), 2.01-2.08 (m, 12H), 2.35 (t, J=7.6 Hz, 6H), 2.77 (t, J=6.8 Hz, 6H), 3.40 (s, 9H), 4.46 (s, 6H), 4.70 (s, 2H), 28-5.42 (m, 12H), 9.54 (br s, 1H).

Step 2

To a solution of (5-(bromomethyl)-2,2-dimethyl-1,3-dioxan-5-yl)methyl stearate (0.95 g, 1.879 mmol) obtained in step 1 in N,N-dimethylformamide (10 mL), dimethylamine (2.0 mol/L solution in tetrahydrofuran, 5.64 mL, 11.3 mmol) was added, and the mixture was stirred at 120° C. for 13 hours under microwave irradiation. Water was added to the reaction solution, followed by extraction with ethyl acetate. The organic layer was washed with saturated saline, dried over anhydrous magnesium sulfate, and filtered. The obtained residue was purified by silica gel column chromatography (chloroform/methanol=99/1 to 90/10) to obtain (5-((dimethylamino)methyl)-2,2-dimethyl-1,3-dioxan-5-yl) methyl stearate (0.14 g, 0.298 mmol, yield: 16%).

ESI-MS m/z: 470 (M+H)$^+$

Step 3

3-(Dimethylamino)-2,2-bis(hydroxymethyl)propyl stearate (0.12 g, 0.279 mmol, yield: 94%) was obtained in the same way as in step 2 of Reference Example A41 using (5-((dimethylamino)methyl)-2,2-dimethyl-1,3-dioxan-5-yl) methyl stearate (0.140 g, 0.298 mmol) obtained in step 1.

ESI-MS m/z: 430 (M+H)$^+$

Step 4

To a solution of 3-(dimethylamino)-2,2-bis(hydroxymethyl)propyl stearate (0.12 g, 0.279 mmol) obtained in step 3 in dichloromethane (2 mL), pyridine (0.122 mL, 1.51 mmol) was added, then tetradecanoyl chloride (0.224 g, 0.98 mmol) was added under ice cooling, and the mixture was stirred at room temperature for 1 hour. Water was added to the reaction solution, followed by extraction with ethyl acetate. The organic layer was washed with saturated saline, dried over anhydrous magnesium sulfate, and filtered. The filtrate was concentrated under reduced pressure, and the obtained residue was purified by silica gel column chromatography (hexane/ethyl acetate=95/5) to obtain 2-((dimethylamino)methyl)-2-((stearoyloxy)methyl)propane-1,3-diyl ditetradecanoate (0.150 g, 0.176 mmol, yield: 63%).

ESI-MS m/z: 851 (M+H)$^+$

Step 5

The title compound (0.032 g, 0.056 mmol, yield: 32%) was obtained in the same way as in step 2 of Reference Example A1 using -((dimethylamino)methyl)-2-((stearoyloxy)methyl)propane-1,3-diyl ditetradecanoate (0.150 g, 0.176 mmol) obtained in step 4.

ESI-MS m/z: 865 (M)$^+$; $^1$H-NMR (CDCl$_3$) δ: 0.88 (t, J=6.8 Hz, 9H), 1.19-1.33 (m, 68H), 1.54-1.65 (m, 6H), 2.38 (t, J=7.6 Hz, 6H), 3.63 (s, 9H), 3.95 (s, 2H), 4.29 (s, 6H).

Reference Example A48

N,N,N-Trimethyl-3-(((Z)-tetradec-9-enoyl)oxy)-2,2-bis((((Z)-tetradec-9-enoyl)oxy)methyl)propan-1-aminium chloride (Compound II-39)

Step 1

To a solution of myristoleic acid (manufactured by Nu-Chek Prep, Inc., 2.50 g, 11.0 mmol) in dichloromethane (20 mL), thionyl chloride (1.61 mL, 22.1 mmol) and N,N-dimethylformamide (8.55 mL, 0.110 mmol) were added, and the mixture was stirred at room temperature for 1 hour. The reaction solution was concentrated under reduced pressure to obtain a crude product of myristoleyl chloride (2.70 g, 11.04 mmol, yield: 100%).

Step 2

The title compound (0.350 g, 0.417 mmol, overall yield: 27%) was obtained in the same way as in Reference Example A33 using myristoleyl chloride (1.88 g, 7.66 mmol) obtained in step 1 instead of palmitoyl chloride.

ESI-MS m/z: 803 (M)$^+$; $^1$H-NMR (CDCl$_3$) δ: 0.86-0.94 (m, 9H), 1.26-1.39 (m, 36H), 1.53-1.64 (m, 6H), 1.97-2.07 (m, 12H), 2.38 (t, J=7.6 Hz, 6H), 3.67 (s, 9H), 3.99 (s, 2H), 4.30 (s, 6H), 5.29-5.39 (m, 6H).

Reference Example A49

2-((4-((1,3-Bis(tetradecanoyloxy)-2-((tetradecanoyloxy)methyl)propan-2-yl)amino)-4-oxobutanoyl)oxy)-N,N,N-trimethylethan-1-aminium chloride (Compound II-40)

Step 1

To a solution of 4-((1,3-bis(tetradecanoyloxy)-2-((tetradecanoyloxy)methyl)propan-2-yl)amino)-4-oxobutanoic acid (0.250 g, 0.293 mmol) synthesized by a method equivalent to the method described in "Australian Journal of Chemistry", 2013, Vol. 66, p. 23-29 in dichloromethane (3 mL), 1-ethyl-3-(3-dimethylaminopropyl)carbodiimide (0.084 g, 0.440 mmol), 2-(dimethylamino)ethan-1-ol (manufactured by Tokyo Chemical Industry Co., Ltd., 0.039 g, 0.440 mmol), and 4-dimethylaminopyridine (0.036 g, 0.293 mmol) were added in order, and the mixture was stirred overnight at room temperature. Water was added to the reaction solution, followed by extraction with ethyl acetate. The organic layer was washed with saturated saline, dried over anhydrous magnesium sulfate, and filtered. The filtrate was concentrated under reduced pressure, and the obtained residue was purified by silica gel column chromatography (chloroform/methanol=99/1 to 90/10) to obtain 2-(4-(2-(dimethylamino)ethoxy)-4-oxobutanamido)-2-((tetradecanoyloxy)methyl)propane-1,3-diyl ditetradecanoate (0.200 g, 0.217 mmol, yield: 74%).

ESI-MS m/z: 924 (M+H)$^+$

Step 2

The title compound (0.150 g, 0.154 mmol, yield: 71%) was obtained in the same way as in step 2 of Reference Example A1 using 2-(4-(2-(dimethylamino)ethoxy)-4-oxobutanamido)-2-((tetradecanoyloxy)methyl)propane-1,3-diyl ditetradecanoate (0.200 g, 0.217 mmol) obtained in step 1.

ESI-MS m/z: 938 (M)$^+$; $^1$H-NMR (CDCl$_3$) δ: 0.88 (t, J=6.8 Hz, 9H), 1.20-1.34 (m, 60H), 1.56-1.65 (m, 6H), 2.34 (t, J=7.6 Hz, 6H), 2.54 (br s, 4H), 3.48 (s, 9H), 4.13-4.21 (m, 2H), 4.40 (s, 6H), 4.57-4.65 (m, 2H), 6.22 (s, 1H).

Reference Example A50

3-((4-((1,3-Bis(tetradecanoyloxy)-2-((tetradecanoyloxy)methyl)propan-2-yl)amino)-4-oxobutanoyl)oxy)-1-methylquinuclidin-1-ium chloride (Compound II-41)

The title compound (0.350 g, 0.417 mmol, overall yield: 46%) was obtained in the same way as in Reference Example A49 using quinuclidin-3-ol (manufactured by Tokyo Chemical Industry Co., Ltd.) instead of 2-(dimethylamino)ethan-1-ol.

ESI-MS m/z: 976 (M)$^+$; $^1$H-NMR (CDCl$_3$) δ: 0.88 (t, J=7.0 Hz, 9H), 1.18-1.35 (m, 66H), 1.55-1.66 (m, 6H), 1.97-2.10 (m, 1H), 2.14-2.26 (m, 2H), 2.45-2.70 (m, 6H), 3.34 (s, 3H), 3.61-4.07 (m, 6H), 4.41 (s, 6H), 5.03-5.10 (m, 1H), 6.50 (s, 1H).

Reference Example A51

N,N,N-Trimethyl-16,22-dioxo-19-(((tetradecylcarbamoyl)oxy)methyl)-17,21-dioxa-15,23-diazaheptatriacontan-19-aminium chloride (Compound II-42)

Step 1

To 2-(dimethylamino)-2-(hydroxymethyl)propane-1,3-diol (0.15 g, 1.01 mmol), toluene (4 mL), triethylamine (0.280 mL, 2.01 mmol), and 1-tetradecane isocyanate (1.66 mL, 6.03 mmol) were added in order, and the mixture was reacted at 100° C. for 4 hours in a microwave reaction apparatus. Water was added to the reaction solution, followed by extraction with chloroform. The organic layer was washed with saturated saline, dried over anhydrous magnesium sulfate, and filtered. The filtrate was concentrated under reduced pressure, and the obtained residue was purified by silica gel column chromatography (chloroform/methanol=99/1 to 90/10) to obtain 2-(dimethylamino)-2-(((tetradecylcarbamoyl)oxy)methyl)propane-1,3-diyl bis(tetradecylcarbamate) (0.872 g, 1.01 mmol, yield: 100%).

ESI-MS m/z: 868 (M+H)$^+$

Step 2

The title compound (0.761 g, 0.829 mmol, yield: 82%) was obtained in the same way as in step 2 of Reference Example A1 using 2-(dimethylamino)-2-(((tetradecylcarbamoyl)oxy)methyl)propane-1,3-diyl bis(tetradecylcarbamate) (0.872 g, 1.01 mmol) obtained in step 1.

ESI-MS m/z: 882 (M)$^+$; $^1$H-NMR (CDCl$_3$) δ: 0.88 (t, J=7.0 Hz, 9H), 1.22-1.32 (m, 66H), 1.47-1.56 (m, 6H), 3.13 (td, J=14.3, 6.0 Hz, 6H), 3.58 (s, 9H), 4.52 (s, 6H), 6.69 (t, J=6.0 Hz, 3H).

Reference Example A52

N,N,N-Trimethyl-1,3-bis(3,7,11,15-tetramethylhexadecanoyloxy)-2-((3,7,11,15-tetramethylhexadecanoyl)methyl)propan-2-aminium chloride (Compound II-43)

To a solution of 2-dimethylamino-2-hydroxymethylpropane-1,3-diol (0.0170 g, 0.112 mmol) in 1,2-dichloroethane (1 mL), 3,7,11,15-tetramethylhexadecanoic acid (0.1826 g, 0.561 mmol), (((((1-cyano-2-ethoxy-2-oxoethylidene)amino)oxy)-4-morpholinomethylene)dimethylammonium hexafluorophosphate (manufactured by Sigma-Aldrich Corp., 0.240 g, 0.561 mmol), and N,N-diisopropylethylamine (0.098 mL, 0.561 mmol) were added, and the mixture was stirred overnight at 60° C. The reaction mixture was cooled to room temperature and then concentrated under reduced pressure. The obtained residue was purified by amino silica gel column chromatography (hexane/ethyl acetate=95/5) to obtain a crude product of 2-(dimethylamino)-2-((3,7,11,15-tetramethylhexadecanoyloxy)methyl)propane-1,3-diyl bis(3,7,11,15-tetramethylhexadecanoate).

To the obtained crude product, methyl iodide (1.00 mL, 16.0 mmol) was added, and the mixture was stirred overnight at room temperature. The reaction solution was concentrated under reduced pressure. The residue was dissolved in a small amount of methanol-chloroform (1:1), and the solution was loaded to an ion-exchange resin (manufactured by The Dow Chemical Company, Dowex™ 1×-2 100 mesh, Cl type, approximately 20-fold amount, prewashed with water and methanol), followed by elution with methanol-chloroform (1:1). The eluate was concentrated under reduced pressure, and the obtained residue was purified by silica gel column chromatography (chloroform/methanol=90/10) to obtain the title compound (0.0766 g, 0.071 mmol, yield: 63%).

ESI-MS m/z: 1043 (M)$^+$; $^1$H-NMR (CDCl$_3$) δ: 0.81-0.87 (m, 36H), 0.92 (d, J=6.7 Hz, 9H), 0.97-1.42 (m, 60H), 1.51 (tt, J=19.8, 6.7 Hz, 3H), 1.84-1.97 (m, 3H), 2.16 (ddd, J=15.5, 8.4, 2.3 Hz, 3H), 2.38 (ddd, J=15.5, 5.6, 1.6 Hz, 3H), 3.72 (s, 9H), 4.55 (s, 6H).

Reference Example A53

N,N,N-Trimethyl-2-((tetradecanoyloxy)methyl)-2-tetradecylhexadecan-1-aminium chloride (Compound II-44)

The title compound (0.292 g, 0.39 mmol, overall yield: 22%) was obtained in the same way as in Reference Example A19 using 1-bromotetradecane (manufactured by Tokyo Chemical Industry Co., Ltd.) and myristic acid (manufactured by Tokyo Chemical Industry Co., Ltd.) instead of (9Z,12Z)-octadeca-9,12-dienyl methanesulfonate used in step 1 of Reference Example A19 and (9Z,12Z)-octadeca-9,12-dienoic acid used in step 4, respectively.

ESI-MS m/z: 721 (M)$^+$; $^1$H-NMR (CD$_3$OD) δ: 0.90 (t, J=6.8 Hz, 9H), 1.28-1.32 (m, 70H), 1.49 (br s, 2H), 1.63-1.66 (m, 2H), 2.42 (t, J=7.2 Hz, 2H), 3.26 (s, 9H), 3.43 (s, 2H), 4.18 (s, 2H).

Reference Example A54

2-Hexadecyl-N,N,N-trimethyl-2-((palmitoyloxy)methyl)octadecan-1-aminium chloride (Compound II-45)

The title compound (0.195 g, 0.23 mmol, overall yield: 5%) was obtained in the same way as in Reference Example A19 using 1-bromohexadecane (manufactured by Tokyo Chemical Industry Co., Ltd.) and palmitic acid (manufactured by Tokyo Chemical Industry Co., Ltd.) instead of (9Z,12Z)-octadeca-9,12-dienyl methanesulfonate used in step 1 of Reference Example A19 and (9Z,12Z)-octadeca-9,12-dienoic acid used in step 4, respectively.

ESI-MS m/z: 805 (M)$^+$; $^1$H-NMR (CD$_3$OD) δ: 0.90 (t, J=6.8 Hz, 9H), 1.28-1.33 (m, 82H), 1.49 (br s, 2H), 1.63-1.67 (m, 2H), 2.43 (t, J=7.2 Hz, 2H), 3.26 (s, 9H), 3.43 (s, 2H), 4.18 (s, 2H).

Reference Example A55

N,N,N-Trimethyl-2-((stearoyloxy)methyl)-2-tetradecylhexadec-1-aminium chloride (Compound II-46)

The title compound (0.421 g, 0.52 mmol, overall yield: 20%) was obtained in the same way as in Reference Example A19 using 1-bromotetradecane (manufactured by Tokyo Chemical Industry Co., Ltd.) and stearic acid (manufactured by Tokyo Chemical Industry Co., Ltd.) instead of (9Z,12Z)-octadeca-9,12-dienyl methanesulfonate used in step 1 of Reference Example A19 and (9Z,12Z)-octadeca-9,12-dienoic acid used in step 4, respectively.

ESI-MS m/z: 111 (M)$^+$; $^1$H-NMR (CD$_3$OD) δ: 0.90 (t, J=6.8 Hz, 9H), 1.29-1.33 (m, 78H), 1.49 (br s, 2H), 1.63-1.67 (m, 2H), 2.43 (t, J=7.2 Hz, 2H), 3.27 (s, 9H), 3.44 (s, 2H), 4.18 (s, 2H).

Reference Example A56

3-(Dodecanoyloxy)-N,N,N-trimethyl-2,2-bis((stearoyloxy)methyl)propan-1-aminium chloride (Compound II-47)

The title compound (0.200 g, 0.417 mmol, overall yield: 0.3%) was obtained in the same way as in Reference Example A46 using lauroyl chloride (manufactured by Tokyo Chemical Industry Co., Ltd.) and stearoyl chloride (manufactured by Tokyo Chemical Industry Co., Ltd.) instead of stearoyl chloride used in step 1 of Reference Example A46 and tetradecanoyl chloride used in step 4, respectively.

ESI-MS m/z: 893 (M)$^+$; $^1$H-NMR (CDCl$_3$) δ: 0.88 (t, J=6.9 Hz, 9H), 1.21-1.32 (m, 72H), 1.57-1.64 (m, 6H), 2.38 (t, J=7.6 Hz, 6H), 3.63 (s, 9H), 3.99 (s, 2H), 4.29 (s, 6H).

Reference Example A57

3-(Dodecanoyloxy)-N,N,N-trimethyl-2,2-bis((palmitoyloxy)methyl)propan-1-aminium chloride (Compound II-48)

The title compound (0.350 g, 0.40 mmol, overall yield: 0.6%) was obtained in the same way as in Reference Example A47 using lauroyl chloride (manufactured by Tokyo Chemical Industry Co., Ltd.) and palmitoyl chloride (manufactured by Wako Pure Chemical Industries Ltd.) instead of stearoyl chloride used in step 1 of Reference Example A47 and tetradecanoyl chloride used in step 4, respectively.

ESI-MS m/z: 837 (M)$^+$; $^1$H-NMR (CDCl$_3$) δ: 0.88 (t, J=6.9 Hz, 9H), 1.21-1.33 (m, 64H), 1.56-1.64 (m, 6H), 2.38 (t, J=7.6 Hz, 6H), 3.66 (s, 9H), 3.98 (s, 2H), 4.29 (s, 6H).

Reference Example A58

3-(Dodecanoyloxy)-2-((dodecanoyloxy)methyl)-N,N,N-trimethyl-2-((stearoyloxy)methyl)propan-1-aminium chloride (Compound II-49)

The title compound (0.210 g, 0.249 mmol, overall yield: 0.3%) was obtained in the same way as in Reference Example A47 using lauroyl chloride (manufactured by Tokyo Chemical Industry Co., Ltd.) instead of tetradecanoyl chloride used in step 4 of Reference Example A47.

ESI-MS m/z: 809 (M)$^+$; $^1$H-NMR (CDCl$_3$) δ: 0.88 (t, J=6.9 Hz, 9H), 1.23-1.34 (m, 60H), 1.53-1.65 (m, 6H), 2.38 (t, J=7.6 Hz, 6H), 3.63 (s, 9H), 3.97 (s, 2H), 4.29 (s, 6H).

Reference Example A59

N,N,N-Trimethyl-3-(palmitoyloxy)-2-((palmitoyloxy)methyl)-2-((stearoyloxy)methyl)propan-1-aminium chloride (Compound II-50)

The title compound (0.420 g, 0.44 mmol, overall yield: 0.5%) was obtained in the same way as in Reference Example A47 using palmitoyl chloride (manufactured by Tokyo Chemical Industry Co., Ltd.) instead of tetradecanoyl chloride used in step 4 of Reference Example A47.

ESI-MS m/z: 921 (M)$^+$; $^1$H-NMR (CDCl$_3$) δ: 0.88 (t, J=6.9 Hz, 9H), 1.21-1.32 (m, 76H), 1.55-1.65 (m, 6H), 2.38 (t, J=7.6 Hz, 6H), 3.67 (s, 9H), 399 (s, 2H), 4.29 (s, 6H).

Reference Example A60

3-(Icosanoyloxy)-N,N,N-trimethyl-2,2-bis((tetradecanoyloxy)methyl)propan-1-aminium chloride (Compound II-51)

The title compound is obtained in the same way as in Reference Example A47 using eicosanoyl chloride (manufactured by Nu-Chek Prep, Inc.) instead of stearoyl chloride used in step 1 of Reference Example A47.

Reference Example A61

3-(Dodecanoyloxy)-2-((dodecanoyloxy)methyl)-2-((icosanoyloxy)methyl)-N,N,N-trimethylpropan-1-aminium chloride (Compound II-52)

The title compound is obtained in the same way as in Reference Example A47 using eicosanoyl chloride (manufactured by Nu-Chek Prep, Inc.) and lauroyl chloride (manufactured by Wako Pure Chemical Industries Ltd.) instead of stearoyl chloride used in step 1 of Reference Example A47 and tetradecanoyl chloride used in step 4, respectively.

Reference Example A62

N,N, N-Trimethyl-3-(methyl(3-(tetradecanoyloxy)-2,2-bis((tetradecanoyloxy)methyl)propyl)amino) propan-1-aminium chloride (Compound II-53)

Step 1

To a solution of 2-(bromomethyl)-2-(hydroxymethyl)propane-1,3-diol (0.15 g, 0.754 mmol) in N,N-dimethylacetamide (1 mL), N,N,N'-trimethylpropane-1,3-diamine (0.263 g, 2.26 mmol) was added, and the mixture was reacted at 100° C. for 2 hours in a microwave reaction apparatus. Then, N,N-diisopropylethylamine (0.395 mL, 2.26 mmol) and then tetradecanoyl chloride (1.12 g, 4.52 mmol) were added thereto under ice cooling, and the mixture was stirred at room temperature for 2 hours. Water was added to the reaction solution, followed by extraction with ethyl acetate. The organic layer was washed with a saturated aqueous solution of sodium bicarbonate and saturated saline, dried over anhydrous magnesium sulfate, and filtered. The filtrate was concentrated under reduced pressure, and the obtained residue was purified by silica gel column chromatography (chloroform/methanol=99/1 to 90/10) to obtain 2-(((3-(dimethylamino)propyl)(methyl)amino)methyl)-2-((tetradecanoyloxy)methyl)propane-1,3-diyl ditetradecanoate (0.040 g, 0.046 mmol, yield: 6%).

ESI-MS m/z: 866 (M+H)$^+$

Step 2

The title compound (0.015 g, 0.016 mmol, yield: 35%) was obtained in the same way as in step 2 of Reference Example A1 using 2-(((3-(dimethylamino)propyl)(methyl)amino)methyl)-2-((tetradecanoyloxy)methyl)propane-1,3-diyl ditetradecanoate (0.040 g, 0.046 mmol) obtained in step 1.

ESI-MS m/z: 880 (M)$^+$; $^1$H-NMR (CDCl$_3$) δ: 0.88 (t, J=6.8 Hz, 9H), 1.20-1.35 (m, 62H), 1.54-1.65 (m, 6H), 1.87-2.03 (m, 2H), 2.21-2.31 (m, 2H), 2.31 (t, J=7.6 Hz, 6H), 2.49 (br s, 3H), 3.40 (s, 9H), 3.52-3.63 (m, 2H), 4.05 (s, 6H).

Reference Example A63

(S)-6-(Di(9Z,12Z)-octadeca-9,12-dienylamino)-N,N, N-trimethyl-5-oleamido-6-oxohexan-1-aminium chloride (Compound III-2)

Step 1

To ammonia (approximately 2 mol/L solution in methanol, 18.0 mL, 36.0 mmol), (9Z,12Z)-octadeca-9,12-dienyl methanesulfonate (1.55 g, 4.50 mmol) was added, and the mixture was stirred at 130° C. for 3 hours using a microwave reaction apparatus. A saturated aqueous solution of sodium bicarbonate was added to the reaction solution, followed by extraction with chloroform five times. The organic layers were combined, washed with saturated saline, dried over anhydrous magnesium sulfate, then filtered, and concentrated under reduced pressure to obtain a crude product of (Z)-octadec-9-enylamine.

To the obtained crude product, (9Z,12Z)-octadeca-9,12-dienyl methanesulfonate (1.24 g, 3.60 mmol) and a 50% aqueous sodium hydroxide solution (1.44 g, 18.0 mmol) were added, and the mixture was stirred at 110° C. for 60 minutes in an oil bath. After cooling to room temperature, the reaction solution was diluted with ethyl acetate, washed with water and then saturated saline, dried over anhydrous magnesium sulfate, then filtered, and concentrated under reduced pressure. The obtained residue was purified by silica gel column chromatography (chloroform/methanol=100/0 to 95/5) to obtain (9Z,12Z)-di(9Z,12Z)-octadeca-9,12-dienylamine (0.838 g, 1.631 mmol, yield: 36%).

ESI-MS m/z: 515 (M+H)$^+$; 1H-NMR (CDCl$_3$) δ: 0.89 (t, J=6.8 Hz, 6H), 1.26-1.38 (m, 32H), 1.45-1.54 (m, 4H), 2.05 (q, J=6.6 Hz, 8H), 2.60 (t, J=7.1 Hz, 4H), 2.77 (t, J=5.9 Hz, 4H), 5.29-5.43 (m, 8H).

Step 2

To a solution of (S)-2-amino-6-(tert-butoxycarbonylamino)hexanoic acid (1.94 g, 7.88 mmol) in acetone (5 mL), sodium hydroxide (2 mol/L aqueous solution, 5 mL) and oleoyl chloride (2.09 g, 6.89 mmol) were added, and the mixture was stirred overnight at room temperature. An aqueous hydrochloric acid solution (6 mol/L) was added to the reaction solution, followed by extraction with chloroform twice. The organic layer was dried over anhydrous magnesium sulfate and then concentrated under reduced pressure. The residue was purified by silica gel column chromatography (chloroform/methanol=90/10 to 80/20) to obtain (S)-6-(tert-butoxycarbonylamino)-2-oleamidohexanoic acid (2.50 g, 4.89 mmol, yield: 71%).

ESI-MS m/z: 510 (M–H)$^-$; $^1$H-NMR (CDCl$_3$) δ: 0.87 (t, J=7.0 Hz, 3H), 1.20-1.54 (m, 33H), 1.57-1.68 (m, 2H), 1.71-1.93 (m, 2H), 1.96-2.05 (m, 4H), 2.18-2.29 (m, 2H), 3.07-3.16 (m, 2H), 4.50-4.60 (m, 1H), 4.63-4.76 (m, 1H), 5.28-5.39 (m, 2H), 6.49-6.57 (m, 1H).

Step 3

To a solution of (S)-6-(tert-butoxycarbonylamino)-2-oleamidohexanoic acid (0.291 g, 0.570 mmol) obtained in step 2 in 1,2-dichloroethane (4 mL), O-(7-aza-1H-benzotriazol-1-yl)-N,N,N',N'-tetramethyluronium hexafluorophosphate (0.433 g, 1.14 mmol), N,N-diisopropylethylamine (0.498 mL, 2.85 mmol), and (9Z,12Z)-di(9Z,12Z)-octadeca-9,12-dienylamine (0.293 g, 0.570 mmol) obtained in step 1 were added, and the mixture was stirred at room temperature for 4 hours. A saturated aqueous solution of sodium bicarbonate was added to the reaction solution, followed by extraction with chloroform twice. The organic layer was dried over anhydrous magnesium sulfate, then filtered, and concentrated under reduced pressure. The residue was purified by silica gel column chromatography (hexane/ethyl acetate=80/20) to obtain tert-butyl (S)-6-(di(9Z,12Z)-octadeca-9,12-dienylamino)-5-oleamido-6-oxohexylcarbamate (0.489 g, 0.486 mmol, yield: 85%).

ESI-MS m/z: 1008 (M+H)$^+$; $^1$H-NMR (CDCl$_3$) δ: 0.85-0.92 (m, 9H), 1.20-1.72 (m, 73H), 1.97-2.08 (m, 12H), 2.18 (t, J=7.6 Hz, 2H), 2.74-2.80 (m, 4H), 3.02-3.34 (m, 5H), 3.44-3.53 (m, 1H), 4.55-4.63 (m, 1H), 4.88 (td, J=8.2, 4.6 Hz, 1H), 5.28-5.43 (m, 10H), 6.30 (d, J=8.4 Hz, 1H).

Step 4

To a solution of tert-butyl (S)-6-(di(9Z,12Z)-octadeca-9,12-dienylamino)-5-oleamido-6-oxohexylcarbamate (0.459 g, 0.456 mmol) obtained in step 3 in 1,2-dichloroethane (2 mL), trifluoroacetic acid (0.500 mL, 6.49 mmol) was added, and the mixture was stirred at room temperature for 1 hour. The reaction solution was concentrated under reduced pressure, and chloroform and a saturated aqueous solution of sodium bicarbonate were then added to the residue, followed by extraction with chloroform twice. The organic layer was dried over anhydrous magnesium sulfate, then filtered, and concentrated under reduced pressure. The residue was purified by silica gel column chromatography (hexane/ethyl acetate=90/10 to 80/20) to obtain N—((S)-6-amino-1-(di((9Z,12Z)-octadeca-9,12-dien-1-yl)amino)-1-oxohexan-2-yl)oleamide (0.259 g, 0.286 mmol, yield: 63%).

ESI-MS m/z: 907 (M+H)$^+$; $^1$H-NMR (CDCl$_3$) δ: 0.86-0.91 (m, 9H), 1.20-1.71 (m, 64H), 1.96-2.09 (m, 12H), 2.21 (t, J=7.5 Hz, 2H), 2.73-2.88 (m, 6H), 3.08-3.47 (m, 4H), 4.81-4.88 (m, 1H), 5.28-5.43 (m, 10H), 6.67 (br s, 1H).

Step 5

To a solution of N—((S)-6-amino-1-(di((9Z,12Z)-octadeca-9,12-dien-1-yl)amino)-1-oxohexan-2-yl)oleamide (0.137 g, 0.151 mmol) obtained in step 4 in 1,2-dichloroethane (1 mL), a 38% aqueous formaldehyde solution (0.300 mL) and sodium triacetoxyborohydride (0.096 g, 0.453 mmol) were added, and the mixture was stirred overnight at room temperature. A saturated aqueous solution of sodium bicarbonate was added to the reaction solution, followed by extraction with chloroform twice. The organic layer was dried over anhydrous magnesium sulfate and then concentrated under reduced pressure. The residue was purified by amino silica gel column chromatography (hexane/ethyl acetate=50/50) to obtain N—((S)-1-(di(9Z,12Z)-octadeca-9,12-dienylamino)-6-(dimethylamino)-1-oxohexan-2-yl)oleamide (0.122 g, 0.130 mmol, yield: 86%).

ESI-MS m/z: 936 (M+H)$^+$; $^1$H-NMR (CDCl$_3$) δ: 0.83-0.93 (m, 9H), 1.12-1.77 (m, 64H), 1.95-2.25 (m, 22H), 2.73-2.80 (m, 4H), 3.04-3.15 (m, 1H), 3.20-3.34 (m, 2H), 3.44-3.54 (m, 1H), 4.85-4.91 (m, 1H), 5.28-5.43 (m, 10H), 6.28 (d, J=8.6 Hz, 1H).

Step 6

The title compound (0.0707 g, 0.0718 mol, 65%) was obtained in the same way as in step 2 of Reference Example A8 using N—((S)-1-(di(9Z,12Z)-octadeca-9,12-dienylamino)-6-(dimethylamino)-1-oxohexan-2-yl)oleamide (0.104 g, 0.111 mol) obtained in step 5 instead of (9Z,9'Z,12Z,12'Z)-2-(dimethylamino)-2-(((9Z,12Z)-octadeca-9,12-dienoyloxy)methyl)propane-1,3-diyl dioctadeca-9,12-dienoate.

ESI-MS m/z: 950 (M)$^+$; $^1$H-NMR (CDCl$_3$) δ: 0.85-0.91 (m, 9H), 1.21-1.83 (m, 64H), 1.97-2.08 (m, 12H), 2.19 (t, J=7.7 Hz, 2H), 2.74-2.80 (m, 4H), 3.05-3.84 (m, 15H), 4.82-4.90 (m, 1H), 5.28-5.43 (m, 10H), 6.41-6.46 (m, 1H).

Reference Example A64

(S)—N,N,N-Trimethyl-5-(nonacosan-15-yloxy)-1,5-dioxo-1-(tetradexyloxy)pentan-2-aminium chloride (Compound III-3)

Step 1

To a solution of ethyl formate (manufactured by Nacalai Tesque, Inc., 2.4 mL, 29.7 mmol) in tetrahydrofuran (9 mL), tetradecyl magnesium chloride (manufactured by Sigma-Aldrich Corp., 1.0 mol/L solution in tetrahydrofuran, 59.4 mL, 59.4 mmol) was added, and the mixture was stirred at 60° C. for 2 hours. The reaction solution was cooled in ice, and water and sulfuric acid (manufactured by Nacalai Tesque, Inc., 2.0 mol/L aqueous solution) were added thereto. The precipitate was collected by filtration to obtain nonacosan-15-ol (6.90 g, 16.2 mmol, yield: 55%).

$^1$H-NMR (CDCl$_3$) δ: 0.88 (t, J=6.8 Hz, 6H), 1.22-1.34 (m, 48H), 1.37-1.49 (m, 2H), 3.54-3.64 (m, 1H).

Step 2

To a solution of 1-tert-butyl 2-aminopentanedioate hydrochloride (manufactured by Watanabe Chemical Industries, Ltd., 10.0 g, 30.3 mmol) in ethanol (150 mL), paraformaldehyde (manufactured by Sigma-Aldrich Corp., 5.50 g, 183 mmol) and sodium cyanoborohydride (5.70 g, 90.7 mmol) were added, and the mixture was stirred overnight at room temperature. A saturated aqueous solution of sodium bicarbonate was added to the reaction solution, followed by extraction with chloroform twice. The organic layer was washed with saturated saline, dried over anhydrous magnesium sulfate, filtered, and concentrated under reduced pressure. The residue was purified by silica gel column chromatography (hexane/ethyl acetate=35/65) to obtain (S)-5-benzyl 1-tert-butyl 2-(dimethylamino)pentanedioate (8.20 g, 25.5 mmol, yield: 84%).

$^1$H-NMR (CDCl$_3$) δ: 1.48 (s, 9H), 1.95-2.00 (m, 2H), 2.32 (s, 6H), 2.43 (t, J=7.8 Hz, 2H), 3.04 (t, J=7.5 Hz, 1H), 5.12 (s, 6H), 7.29-7.40 (m, 5H).

Step 3

To a solution of (S)-5-benzyl 1-tert-butyl 2-(dimethylamino)pentanedioate (8.20 g, 25.5 mmol) in ethanol (200 mL), palladium-carbon (manufactured by Tokyo Chemical Industry Co., Ltd., 10% palladium, product wetted with approximately 55% water, 820 mg) was added, and the mixture was stirred at room temperature for 7 hours in a hydrogen atmosphere. Insoluble matter was removed by filtration through celite, and the filtrate was concentrated. The obtained residue was purified by silica gel column chromatography (dichloromethane/methanol=85/15) to obtain a crude product of (S)-5-tert-butoxy-4-(dimethylamino)-5-oxopentanoic acid (4.83 g, 20.9 mmol, crude yield: 82%).

To the obtained crude product of (S)-5-tert-butoxy-4-(dimethylamino)-5-oxopentanoic acid (4.83 g, 20.9 mmol), 1.2-dichloroethane (200 mL), nonacosan-15-ol (9.75 g, 23.0 mmol) obtained in step 1, 1-ethyl-3-(3-dimethylaminopropyl)carbodiimide hydrochloride (8.01 g, 41.8 mmol), and N,N-dimethylaminopyridine (255 mg, 2.09 mmol) were added, and the mixture was stirred at 50° C. for 3 hours. Water was added to the reaction solution, followed by extraction with dichloromethane twice. The organic layer was washed with saturated saline, dried over anhydrous magnesium sulfate, then filtered, and concentrated under reduced pressure. The obtained residue was purified by silica gel column chromatography (hexane/ethyl acetate=85/15) to obtain (S)-1-tert-butyl 5-nonacosan-15-yl 2-(dimethylamino)pentanedioate (8.13 g, 12.7 mmol, yield: 61%).

¹H-NMR (CDCl₃) δ: 0.88 (t, J=6.8 Hz, 6H), 1.20-1.38 (m, 48H), 1.46-1.57 (m, 4H), 1.91-2.00 (m, 2H), 2.33-2.41 (m, 8H), 3.05 (t, J=7.6 Hz, 1H), 4.82-4.93 (m, 1H).

Step 4

To a solution of (S)-1-tert-butyl 5-nonacosan-15-yl 2-(dimethylamino)pentanedioate (8.13 g, 12.7 mmol) obtained in step 3 in dichloromethane (40 mL), trifluoroacetic acid (20 mL) was added, and the mixture was stirred overnight at 40° C. The reaction solution was concentrated under reduced pressure. The obtained residue was purified by silica gel column chromatography (dichloromethane/methanol=85/15) to obtain (S)-2-(dimethylamino)-5-(nonacosan-15-yloxy)-5-oxopentanoic acid (6.70 g, 11.5 mmol, yield: 90%).

¹H-NMR (CDCl₃) δ: 0.89 (t, J=7.0 Hz, 6H), 1.18-1.37 (m, 48H), 1.44-1.60 (m, 4H), 2.00-2.13 (m, 2H), 2.52-2.74 (m, 2H), 2.87 (s, 6H), 3.62-3.73 (m, 1H), 4.80-4.89 (m, 1H).

Step 5

To a solution of (S)-2-(dimethylamino)-5-(nonacosan-15-yloxy)-5-oxopentanoic acid (100 mg, 0.172 mmol) obtained in step 4 in 1,2-dichloroethane (2.0 mL), (1-cyano-2-ethoxy-2-oxoethylideneaminooxy)dimethylamino-morpholino-carbenium hexafluorophosphate (96.0 mg, 0.224 mmol), N,N-diisopropylethylamine (0.060 mL, 0.344 mmol), and tetradecan-1-ol ( ) were added, and the mixture was stirred overnight at room temperature. Water was added to the reaction solution, followed by extraction with dichloromethane. The organic layer was washed with water, dried over anhydrous magnesium sulfate, filtered, and concentrated under reduced pressure. The obtained residue was purified by silica gel column chromatography (hexane/ethyl acetate=95/5 to 85/15) to obtain (S)-5-nonacosan-15-yl 1-tetradecyl 2-(dimethylamino)pentanedioate (64.0 mg, 0.0822 mmol, yield: 48%).

¹H-NMR (CDCl₃) δ: 0.88 (t, J=6.8 Hz, 9H), 1.12-1.39 (m, 70H), 1.45-1.69 (m, 6H), 1.93-2.03 (m, 2H), 2.29-2.38 (m, 8H), 3.16 (t, J=7.4 Hz, 1H), 4.03-4.17 (m, 2H), 4.80-4.91 (m, 1H).

Step 6

The title compound is obtained in the same way as in step 2 of Reference Example A8 using (S)-5-nonacosan-15-yl 1-tetradecyl 2-(dimethylamino)pentanedioate obtained in step 5 instead of (9Z,9'Z,12Z,12'Z)-2-(dimethylamino)-2-(((9Z,12Z)-octadeca-9,12-dienoyloxy)methyl)propane-1,3-diyl dioctadeca-9,12-dienoate.

Reference Example A65

(S)-1-(Dodecyloxy)-N,N,N-trimethyl-5-(nonacosan-15-yloxy)-1,5-dioxopentan-2-aminium chloride (Compound III-4)

The title compound is obtained in the same way as in Reference Example A64 using dodecan-1-ol instead of tetradecan-1-ol used in step 5 of Reference Example A64.

Reference Example A66

(S)-1-(Hexadecyloxy)-N,N,N-trimethyl-5-(nonacosan-15-yloxy)-1,5-dioxopentan-2-aminium chloride (Compound III-5)

The title compound is obtained in the same way as in Reference Example A64 using hexadecan-1-ol instead of tetradecan-1-ol used in step 5 of Reference Example A64.

Reference Example A67

(S)—N,N,N-Trimethyl-5-(nonacosan-15-yloxy)-1-(octadecyloxy)-1,5-dioxopentan-2-aminium chloride (Compound III-6)

The title compound is obtained in the same way as in Reference Example A64 using octadecan-1-ol instead of tetradecan-1-ol used in step 5 of Reference Example A64.

Reference Example A68

(S,Z)—N,N,N-Triethyl-5-(nonacosan-15-yloxy)-1-(octadec-9-enyloxy)-1,5-dioxopentan-2-aminium chloride (Compound III-7)

The title compound is obtained in the same way as in Reference Example A64 using (Z)-octadec-9-en-1-ol instead of tetradecan-1-ol used in step 5 of Reference Example A64.

Reference Example A69

(6Z,9Z,28Z,31Z)—N,N-Dimethyl-N-(2-(N-methylstearamido)ethyl)heptatriaconta-6,9,28,31-tetraen-19-aminium chloride (Compound IV-2)

Step 1

To a solution of (6Z,9Z,28Z,31Z)-heptatriaconta-6,9,28,31-tetraen-19-one (0.50 g, 0.256 mmol) obtained by a method equivalent to the method described in WO 2010/042877 in 1,2-dichloroethane (2 mL), methanol (2 mL), N1,N2-dimethylethane-1,2-diamine (manufactured by Tokyo Chemical Industry Co., Ltd., 0.085 mL, 0.767 mmol), and sodium triacetoxyborohydride (0.325 g, 1.53 mmol) were added, and the mixture was stirred at 50° C. for 5 hours. A saturated aqueous solution of sodium bicarbonate was added to the reaction solution, followed by extraction with chloroform twice. The organic layer was dried over anhydrous magnesium sulfate, filtered, and concentrated under reduced pressure. The obtained residue was purified by amino silica column chromatography (hexane/ethyl acetate=90/10 to 80/20) to obtain N1-((6Z,9Z,28Z,31Z)-heptatriaconta-6,9,28,31-tetraen-19-yl)-N1,N2-dimethyl-ethane-1,2-diamine (0.0303 g, 0.0506 mmol, yield: 20%).

ESI-MS m/z: 600 (M+H)⁺; ¹H-NMR (CDCl₃) δ: 0.89 (t, J=6.8 Hz, 6H), 1.13-1.45 (m, 40H), 2.01-2.09 (m, 8H), 2.14 (s, 3H), 2.28-2.40 (m, 1H), 2.43 (s, 3H), 2.52-2.60 (m, 4H), 2.75-2.80 (m, 4H), 5.29-5.42 (m, 8H).

Step 2

To a solution of N1-((6Z,9Z,28Z,31Z)-heptatriaconta-6,9,28,31-tetraen-19-yl)-N1,N2-dimethylethane-1,2-diamine (0.0258 g, 0.0431 mmol) obtained in step 1 in 1,2-dichloroethane (1 mL), stearoyl chloride (0.0390 g, 0.129 mmol) and N,N-diisopropylethylamine (0.038 mL, 0.215 mmol) were added, and the mixture was stirred at room temperature for 1 hour. A saturated aqueous solution of sodium bicarbonate was added to the reaction solution, followed by extraction with chloroform twice. The organic layer was dried over anhydrous magnesium sulfate, filtered, and concentrated under reduced pressure. The obtained residue was purified by amino silica column chromatography (hexane/ethyl acetate=90/10) to obtain a crude product of N-(2-((6Z,9Z,28Z,31Z)-heptatriaconta-6,9,28,31-tetraen-19-yl (methyl)amino)ethyl)-N-methylstearamide.

To the obtained crude product, methyl iodide (1.00 mL, 16.0 mmol) was added, and the mixture was stirred at 50° C. for 1 hour. The reaction solution was concentrated under reduced pressure. The residue was dissolved in a small amount of methanol-chloroform (1:1), and the solution was loaded to an ion-exchange resin (manufactured by The Dow Chemical Company, Dowex™ 1×-2 100 mesh, Cl type, approximately 20-fold amount, prewashed with water and methanol), followed by elution with methanol-chloroform (1:1). The eluate was concentrated under reduced pressure, and the obtained residue was purified by silica gel column chromatography (chloroform/methanol=80/20) to obtain the title compound (0.0149 g, 0.0163 mmol, yield: 38%).

ESI-MS m/z: 881 (M)$^+$; $^1$H-NMR (CDCl$_3$) δ: 0.84-0.92 (m, 9H), 1.20-2.09 (m, 78H), 2.27-2.38 (m, 2H), 2.74-2.80 (m, 4H), 3.14-3.45 (m, 9H), 3.77-4.09 (m, 5H), 5.28-5.43 (m, 8H).

Reference Example A70

(9Z,12Z)—N,N-Dimethyl-N-(3-((9Z,12Z)—N-((9Z, 12Z)-octadeca-9,12-dienyl)octadeca-9,12-dienamido)propyl)octadeca-9,12-dien-1-aminium chloride (Compound IV-3)

Step 1

To (9Z,12Z)-octadeca-9,12-dienyl methanesulfonate (0.838 g, 2.43 mmol), 3-aminopropan-1-ol (1.66 g, 21.9 mmol) was added, and the mixture was stirred at 90° C. for 3 hours. The reaction solution was concentrated under reduced pressure, and the obtained residue was purified by amino silica gel chromatography (hexane/ethyl acetate) to obtain 3-((9Z,12Z)-octadeca-9,12-dienylamino)propan-1-ol (0.722 g, 2.23 mmol, yield: 92%).

ESI-MS m/z: 325 (M+H)$^+$; $^1$H-NMR (CDCl$_3$) δ: 0.89 (t, J=6.9 Hz, 3H), 1.26-1.39 (m, 17H), 1.46 (tt, J=7.1, 6.9 Hz, 3H), 1.69 (tt, J=5.7, 5.4 Hz, 2H), 2.02-2.08 (m, 4H), 2.60 (t, J=7.1 Hz, 2H), 2.75-2.80 (m, 2H), 2.88 (t, J=5.7 Hz, 2H), 3.81 (t, J=5.4 Hz, 2H), 5.30-5.42 (m, 4H).

Step 2

3-(Methyl((9Z,12Z)-octadeca-9,12-dienyl)amino)propan-1-ol (0.220 g, 0.652 mol, yield: 90%) was obtained in the same way as in step 5 of Reference Example A63 using 3-((9Z,12Z)-octadeca-9,12-dienylamino) propan-1-ol (0.233 g, 0.722 mol) obtained in step 1 instead of N—((S)-6-amino-1-(di((9Z,12Z)-octadeca-9,12-dien-1-yl)amino)-1-oxohexan-2-yl)oleamide.

ESI-MS m/z: 338 (M+H)$^+$; $^1$H-NMR (CDCl$_3$) δ: $^1$H-NMR (CDCl$_3$) δ: 0.89 (t, J=7.0 Hz, 3H), 1.24-1.40 (m, 16H), 1.47 (tt, J=7.6, 7.0 Hz, 2H), 1.69 (tt, J=5.7, 5.2 Hz, 2H), 2.01-2.08 (m, 4H), 2.23 (s, 3H), 2.34 (t, J=7.6 Hz, 2H), 2.59 (t, J=5.7 Hz, 2H), 2.75-2.80 (m, 2H), 3.80 (t, J=5.2 Hz, 2H), 5.29-5.42 (m, 4H).

Step 3

To a solution of (9Z,12Z)-octadeca-9,12-dienyl methanesulfonate (2.85 g, 8.27 mmol) in acetonitrile (30 mL), cesium carbonate (6.74 g, 20.7 mmol), tetra-n-butylammonium iodide (3.05 g, 8.27 mmol) and N-(tert-butoxycarbonyl)-2-nitrobenzenesulfonamide (2.50 g, 8.27 mmol) were added, and the mixture was stirred for 3 hours under heating to reflux. The reaction solution was cooled to room temperature, and water was added thereto, followed by extraction with ethyl acetate. The organic layer was dried over anhydrous magnesium sulfate, filtered, and concentrated under reduced pressure. The obtained residue was purified by silica gel column chromatography (hexane/ethyl acetate=70/30) to obtain tert-butyl 2-nitrophenylsulfonyl ((9Z,12Z)-octadeca-9,12-dienyl)carbamate (3.21 g, 5.83 mmol).

To a solution of the obtained tert-butyl 2-nitrophenylsulfonyl((9Z,12Z)-octadeca-9,12-dienyl)carbamate (3.21 g, 5.83 mmol) in dichloromethane (23 mL), trifluoroacetic acid (9.63 mL, 126 mmol) was added, and the mixture was stirred at room temperature for 0.5 hours. The reaction solution was diluted with dichloromethane, and an aqueous sodium hydroxide solution (1 mol/L) and a saturated aqueous solution of sodium bicarbonate were added thereto. The organic layer was washed with saturated saline, dried over anhydrous magnesium sulfate, filtered, and concentrated under reduced pressure. The obtained residue was purified by silica gel column chromatography (hexane/ethyl acetate=95/5) to obtain 2-nitro-N-((9Z,12Z)-octadeca-9,12-dienyl)benzenesulfonamide (2.48 g, 5.50 mmol, yield: 67%).

ESI-MS m/z: 338 (M+H)$^+$; $^1$H-NMR (CDCl$_3$) δ: 0.89 (t, J=7.0 Hz, 3H), 1.22-1.39 (m, 16H), 1.52 (m, 2H), 2.01-2.05 (m, 4H), 2.77 (t, J=6.6 Hz, 2H), 3.09 (q, J=6.7 Hz, 2H), 5.23 (m, 1H), 5.31-5.42 (m, 4H), 7.71-7.76 (m, 2H), 7.78-7.87 (1H), 813-8.15 (m, 1H).

Step 4

To a solution of 3-(methyl((9Z,12Z)-octadeca-9,12-dienyl)amino)propan-1-ol (0.220 g, 0.652 mol) obtained in step 2 in tetrahydrofuran (4 mL), 2-nitro-N-((9Z,12Z)-octadeca-9,12-dienyl)benzenesulfonamide (0.441 g, 0.978 mmol) obtained in step 3, triphenylphosphine (0.257 g, 0.978 mmol), and diethyl azodicarboxylate (manufactured by Nacalai Tesque, Inc., 40% solution in toluene, 0.387 mL, 0.851 mmol) were added, and the mixture was stirred at 50° C. for 2 hours. The reaction solution was cooled to room temperature, and saturated saline was added thereto, followed by extraction with hexane twice. The organic layer was dried over anhydrous magnesium sulfate, filtered, and concentrated under reduced pressure. The obtained residue was purified by amino silica gel column chromatography (hexane/ethyl acetate=80/20) to obtain a crude product of N-(3-(methyl((9Z,12Z)-octadeca-9,12-dienyl)amino)propyl)-2-nitro-N-((9Z,12Z)-octadeca-9,12-dienyl)benzenesulfonamide.

To a solution of the obtained crude product of N-(3-(methyl((9Z,12Z)-octadeca-9,12-dienyl)amino)propyl)-2-nitro-N-((9Z,12Z)-octadeca-9,12-dienyl)benzenesulfonamide in acetonitrile (5 mL), dodecane-1-thiol (0.409 mL, 1.63 mmol) and 1,8-diazabicyclo[5.4.0]-7-undecene (0.246 mL, 1.630 mmol) were added, and the mixture was stirred at 60° C. for 2 hours. Water was added to the reaction solution, followed by extraction with hexane twice. The organic layer was washed with saturated saline, dried over anhydrous magnesium sulfate, filtered, and concentrated under reduced pressure. The obtained residue was purified by amino silica gel column chromatography (hexane/ethyl acetate=75/25) to obtain N1-methyl-N1,N3-di ((9Z,12Z)-octadeca-9,12-dienyl)propane-1,3-diamine (0.212 g, 0.363 mmol, yield: 56%).

ESI-MS m/z: 586 (M+H)$^+$; $^1$H-NMR (CDCl$_3$) δ: 0.89 (t, J=7.0 Hz, 6H), 1.22-1.51 (m, 36H), 1.66 (tt, J=7.2, 7.1 Hz, 2H), 2.01-2.08 (m, 8H), 2.20 (s, 3H), 2.29 (t, J=7.6 Hz, 2H), 2.36 (t, J=7.2 Hz, 2H), 2.58 (t, J=7.4 Hz, 2H), 2.62 (t, J=7.1 Hz, 2H), 2.75-2.80 (m, 4H), 5.29-5.43 (m, 8H).

Step 5

To a solution of N1-methyl-N1,N3-di((9Z,12Z)-octadeca-9,12-dienyl)propane-1,3-diamine (0.108 g, 0.185 mmol) obtained in step 4 in 1,2-dichloroethane (1 mL), (9Z,12Z)-octadeca-9,12-dienoic acid (0.104 g, 0.370 mmol), 1-ethyl-3-(3-dimethylaminopropyl)carbodiimide hydrochloride (0.106 g, 0.555 mmol), and N,N-dimethylaminopyridine (0.0023 g, 0.0188 mmol) were added, and the mixture was stirred at room temperature for 1 hour. The reaction solution was concentrated under reduced pressure. The obtained residue was purified by amino silica gel column chromatography (hexane/ethyl acetate=85/15) to obtain (9Z,12Z)—N-(3-(methyl((9Z,12Z)-octadeca-9,12-dienyl)amino)propyl)-N-((9Z,12Z)-octadeca-9,12-dienyl)octadeca-9,12-dienamide (0.146 g, 0.172 mmol, yield: 93%).

ESI-MS m/z: 848 (M+H)$^+$; $^1$H-NMR (CDCl$_3$) δ: 0.89 (t, J=7.0 Hz, 9H), 1.21-1.74 (m, 54H), 2.01-2.08 (m, 12H), 2.18 (s, 3H), 2.24-2.33 (m, 6H), 2.74-2.80 (m, 6H), 3.18-3.35 (m, 4H), 5.29-5.42 (m, 12H).

Step 6

The title compound (0.0804 g, 0.0895 mol, yield: 76%) was obtained in the same way as in step 2 of Reference Example A8 using (9Z,12Z)—N-(3-(methyl((9Z,12Z)-octadeca-9,12-dienyl)amino)propyl)-N-((9Z,12Z)-octadeca-9,12-dienyl)octadeca-9,12-dienamide (0.100 g, 0.118 mmol) obtained in step 5 instead of (9Z,9'Z,12Z,12'Z)-2-(dimethylamino)-2-(((9Z,12Z)-octadeca-9,12-dienoyloxy)methyl)propane-1,3-diyl dioctadeca-9,12-dienoate.

ESI-MS m/z: 862 (M)$^+$; $^1$H-NMR (CDCl$_3$) δ: $^1$H-NMR (CDCl$_3$) δ: 0.88 (t, J=7.0 Hz, 9H), 1.22-1.41 (m, 46H), 1.49-1.78 (m, 6H), 1.93-2.10 (m, 14H), 2.30 (t, J=7.6 Hz, 2H), 2.74-2.79 (m, 6H), 3.24-3.35 (m, 8H), 3.36-3.47 (m, 4H), 3.59-3.67 (m, 2H), 5.28-5.42 (m, 12H).

Reference Example A71

(R)-2-((2R,3R,4S)-3,4-Bis((9Z,12Z)-octadeca-9,12-dienyloxy)tetrahydrofuran-2-yl)-N,N,N-trimethyl-2-((9Z,12Z)-octadeca-9,12-dienyloxy)ethanaminium chloride (Compound V'-1)

Step 1

To a solution of (2R,3R,4S)-2-((R)-1,2-dihydroxyethyl)tetrahydrofuran-3,4-diol (manufactured by Sigma-Aldrich Corp., 0.315 g, 1.92 mmol) in pyridine (manufactured by Wako Pure Chemical Industries Ltd., 10 mL), 4,4'-dimethoxytrityl chloride (0.704 g, 2.02 mmol) and N,N-dimethylaminopyridine (0.047 g, 0.384 mmol) were added, and the mixture was stirred overnight at 50° C. The reaction mixture was cooled to room temperature and then concentrated under reduced pressure. The obtained residue was purified by amino silica gel column chromatography (chloroform/methanol=90/10) to obtain (2R,3R,4S)-2-((R)-2-(bis(4-methoxyphenyl)phenyl)methoxy)-1-hydroxyethyl)tetrahydrofuran-3,4-diol (0.465 g, 0.997 mmol, yield: 52%).

$^1$H-NMR (CDCl$_3$) δ: 1.67-1.74 (m, 1H), 2.73-2.77 (m, 1H), 3.31 (dd, J=9.8, 6.2 Hz, 1H), 3.41-3.50 (m, 2H), 3.70 (dd, J=9.6, 1.3 Hz, 1H), 3.79 (s, 6H), 3.94 (dd, J=6.2, 3.5 Hz, 1H), 4.10-4.24 (m, 3H), 4.26-4.30 (m, 1H), 6.81-6.86 (m, 4H), 7.20-7.36 (m, 7H), 7.41-7.45 (m, 2H).

Step 2

To a solution of (2R,3R,4S)-2-((R)-2-(bis(4-methoxyphenyl)phenyl)methoxy)-1-hydroxyethyl)tetrahydrofuran-3,4-diol (0.0669 g, 0.143 mmol) obtained in step 1 in tetrahydrofuran (1 mL), (9Z,12Z)-octadeca-9,12-dienyl methanesulfonate (0.247 g, 0.717 mmol) and sodium hydride (60% oil, 0.0459 g, 1.15 mmol) were added, and the mixture was stirred overnight under heating to reflux. After cooling to room temperature, saturated saline was added to the reaction solution, followed by extraction with hexane. The organic layer was washed with saturated saline, dried over anhydrous magnesium sulfate, filtered, and concentrated under reduced pressure. The obtained residue was purified by amino silica gel column chromatography (hexane/ethyl acetate=90/10) to obtain a crude product of (2R,3R,4S)-2-((R)-2-(bis(4-methoxyphenyl)(phenyl)methoxy)-1-((9Z,12Z)-octadeca-9,12-dienyloxy)ethyl)-3,4-bis((9Z,12Z)-octadeca-9,12-dienyloxy)tetrahydrofuran.

To the obtained crude product of (2R,3R,4S)-2-((R)-2-(bis(4-methoxyphenyl)(phenyl)methoxy)-1-((9Z,12Z)-octadeca-9,12-dienyloxy)ethyl)-3,4-bis((9Z,12Z)-octadeca-9,12-dienyloxy)tetrahydrofuran, dichloromethane (1 mL) and trifluoroacetic acid (0.0500 mL, 0.649 mmol) were added, and the mixture was stirred at room temperature for 5 minutes. The reaction solution was concentrated under reduced pressure, and the obtained residue was purified by silica gel chromatography (hexane/ethyl acetate=70/30) to obtain (R)-2-((2R,3R,4S)-3,4-bis((9Z,12Z)-octadeca-9,12-dienyloxy)tetrahydrofuran-2-yl)-2-((9Z,12Z)-octadeca-9,12-dienyloxy)ethanol (0.0531 g, 0.0584 mmol, yield: 41%).

$^1$H-NMR (CDCl$_3$) δ: 0.89 (t, J=7.0 Hz, 9H), 1.23-1.43 (m, 48H), 1.50-1.62 (m, 6H), 2.01-2.09 (m, 12H), 2.32 (dd, J=8.2, 4.2 Hz, 1H), 2.74-2.80 (m, 6H), 3.37-3.50 (m, 4H), 3.54-3.69 (m, 3H), 3.69-3.77 (m, 2H), 3.80-3.87 (m, 2H), 3.88-3.95 (m, 2H), 4.06 (dd, J=9.8, 4.7 Hz, 1H), 5.28-5.42 (m, 12H).

Step 3

To a solution of (R)-2-((2R,3R,4S)-3,4-bis((9Z,12Z)-octadeca-9,12-dienyloxy)tetrahydrofuran-2-yl)-2-((9Z,12Z)-octadeca-9,12-dienyloxy)ethanol (0.0491 g, 0.0540 mmol) obtained in step 2 in dichloromethane (1 mL), methanesulfonyl chloride (manufactured by Junsei Chemical Co., Ltd., 0.0500 mL, 0.642 mmol) and triethylamine (0.150 mL, 1.08 mmol) were added, and the mixture was stirred at room temperature for 1 hour. Methanesulfonyl chloride (0.0500 mL, 0.642 mmol) and triethylamine (0.150 mL, 1.08 mmol) were added to the reaction solution, and the mixture was stirred at room temperature for 1 hour. Chloroform (1 mL) was added to the reaction solution, and the mixture was stirred at room temperature for 1 hour. Methanesulfonyl chloride (0.0500 mL, 0.642 mmol) and triethylamine (0.150 mL, 1.08 mmol) were added to the reaction solution, and the mixture was stirred at 40° C. for 2 hours and then stirred for 2 hours under heating to reflux. Saturated saline was added to the reaction solution, followed by extraction with chloroform. The organic layer was dried over anhydrous magnesium sulfate, filtered, and concentrated under reduced pressure. To the obtained residue, tetrahydrofuran (1 mL) and dimethylamine (2.0 mol/L solution in tetrahydrofuran, 2 mL, 2.00 mmol) were added, and the mixture was stirred at 130° C. for 5 hours using a microwave reaction apparatus. The reaction solution was concentrated under reduced pressure. The obtained residue was purified by amino silica gel column chromatography (hexane/ethyl acetate=95/5) to obtain a crude product of (R)-2-((2R,3R,4S)-3,4-bis((9Z,12Z)-octadeca-9,12-dienyloxy)tetrahydrofuran-2-yl)-N,N-dimethyl-2-((9Z,12Z)-octadeca-9,12-dienyloxy) ethanamine. To the obtained crude product of (R)-2-((2R,3R,4S)-3,4-bis((9Z,12Z)-octadeca-9,12-dienyloxy)tetrahydrofuran-2-yl)-N,N-dimethyl-2-((9Z,12Z)-octadeca-9,12-dienyloxy) ethanamine, chloroform (0.5 mL) and methyl iodide (1.00 mL, 16.0 mmol) were added, and the mixture was stirred at room temperature for 2 hours. The reaction solution was concentrated under reduced pressure. The residue was dissolved in a small amount of methanol-chloroform (1:1), and the solution was loaded to an ion-exchange resin (manufactured by The Dow Chemical Company, Dowex™ 1×-2 100 mesh, Cl type, approximately 20-fold amount, prewashed with water and methanol), followed by elution with methanol-chloroform (1:1). The eluate was concentrated under reduced pressure, and the obtained residue was purified by silica gel column chromatography (chloroform/methanol=90/10) to obtain the title compound (0.0130 g, 0.0132 mmol, yield: 24%).

ESI-MS m/z: 951 (M)$^+$; $^1$H-NMR (CDCl$_3$) δ: 0.89 (t, J=7.0 Hz, 9H), 1.23-1.40 (m, 48H), 1.51-1.61 (m, 6H), 2.01-2.09 (m, 12H), 2.74-2.80 (m, 6H), 3.34-3.68 (m, 17H), 3.70-3.74 (m, 1H), 3.81-3.84 (m, 1H), 3.93-4.02 (m, 3H), 4.07-4.12 (m, 1H), 5.28-5.43 (m, 12H).

Hereinafter, methods for producing lipid B will be shown.

Reference Example B1

N,N-Dimethyl-2,3-bis(((9Z,12Z)-octadeca-9,12-dien-1-yl)oxy)propan-1-amine (Compound CL-1)

Compound CL-1 was synthesized by the method described in "J. Control. Release.", 2005, Vol. 107, p. 276-287.

Reference Example B2

N-Methyl-N,N-bis(2-((Z)-hexadec-9-enyloxy)ethyl) amine (Compound CL-2)

To a suspension of sodium hydride (60% oil, 222 mg, 5.55 mmol) in toluene (2 mL), a solution of N-methyldiethanolamine (manufactured by Tokyo Chemical Industry Co., Ltd., 82.6 mg, 0.693 mmol) in toluene (2 mL) was added with stirring, and a solution of (Z)-hexadec-9-enyl methanesulfonate (530 mg, 1.66 mmol) in toluene (2 mL) was then added dropwise. The obtained mixture was stirred for 2 hours under heating to reflux. After cooling to room temperature, the reaction was terminated with water. To the obtained mixture, saturated saline was added, followed by extraction with ethyl acetate. The organic layer was dried over anhydrous magnesium sulfate and then concentrated under reduced pressure. The residue was purified by silica gel column chromatography (chloroform/methanol=100/0 to 98/2) to obtain the title compound (199 mg, 0.353 mmol, yield: 51%).

ESI-MS m/z: 565 (M+H)$^+$;

Reference Example B3 trans-1-Methyl-3,4-bis((((Z)-octadec-9-en-1-yl)oxy) methyl)pyrrolidine (Compound CL-3)

Compound CL-3 was synthesized by the method described in WO 2011/136368.

Reference Example B4 trans-1-Methylpyrrolidine-3,4-diyl)bis(methylene) (9Z,9'Z,12Z,12'Z)-bis(octadeca-9,12-dienoate) (Compound CL-4)

Compound CL-4 was synthesized by the method described in WO 2011/136368.

Reference Example B5

(6Z,9Z,28Z,31Z)-Heptatriaconta-6,9,28,31-tetraen-19-yl 4-(dimethylamino)butanoate (Compound CL-5)

Compound CL-5 was synthesized by a method equivalent to the method described in WO 2010/054401.

ESI-MS m/z: 642

Reference Example B6

3-(Di((9Z,12Z)-octadeca-9,12-dien-1-yl)amino)propan-1-ol (Compound CL-6)

Compound CL-6 was synthesized by the method described in WO 2014/007398.

Reference Example B7

(9Z,12Z)—N-(2-(((Z)-Octadec-9-en-1-yl)oxy)ethyl) octadeca-9,12-dien-1-amine (Compound CL-7)

Compound CL-7 was synthesized by the method described in WO 2014/007398.

Reference Example B8

1-Methyl-3,3-di((9Z,12Z)-octadeca-9,12-dien-1-yl) azetidine (Compound CL-8)

Compound CL-8 was synthesized by the method described in WO 2016/002753.

Reference Example B9

N,2-Dimethyl-1,3-bis(((9Z,12Z)-octadeca-9,12-dien-1-yl)oxy)propan-2-amine (Compound CL-9)

Step 1

2-Amino-2-methylpropane-1,3-diol (manufactured by Tokyo Chemical Industry Co., Ltd., 0.300 g, 4.76 mmol) was dissolved in tetrahydrofuran (3 mL). To the solution, sodium hydride (60% oil, 0.171 g, 7.13 mmol) was added at room temperature. After foaming was completed, (9Z,12Z)-octadeca-9,12-dienyl methanesulfonate (manufactured by Nu-Chek Prep, Inc, 2.458 g, 7.13 mmol) was added thereto, and the mixture was stirred for 2 hours under heating to reflux. A saturated aqueous solution of ammonium chloride was added to the reaction mixture, followed by extraction with ethyl acetate. The organic layer was washed with saturated saline, dried over anhydrous magnesium sulfate, and filtered. The filtrate was concentrated under reduced pressure, and the obtained residue was purified by silica gel column chromatography (chloroform/methanol=100/0 to 90/10) to obtain 2-methyl-1,3-bis((9Z,12Z)-octadeca-9,12-dien-1-yloxy)propan-2-amine (0.280 g, yield: 16%).

ESI-MS m/z: 602 (M+H)$^+$

Step 2

2-Methyl-1,3-bis((9Z,12Z)-octadeca-9,12-dien-1-yloxy) propan-2-amine (0.500 g, 0.831 mmol) obtained in step 1 was dissolved in dichloromethane (3 mL). To the solution, triethylamine (manufactured by Wako Pure Chemical Industries Ltd., 2.55 mL, 18.3 mmol) and 2-nitrobenzene-1-sulfonyl chloride (manufactured by Sigma-Aldrich Corp., 0.368 g, 1.66 mmol) were added under ice cooling, and the mixture was brought back to room temperature and then stirred for 1 hour. Water was added to the reaction mixture, followed by extraction with hexane. The organic layer was washed with saturated saline, dried over anhydrous magnesium sulfate, and filtered. The filtrate was concentrated under reduced pressure, and the obtained residue was purified by silica gel column chromatography (hexane/ethyl acetate=99/1 to 85/15) to obtain N-(2-methyl-1,3-bis((9Z, 12Z)-octadeca-9,12-dien-1-yloxy)propan-2-yl)-2-nitrobenzenesulfonamide (0.400 g, yield: 61%).

ESI-MS m/z: 787 (M+H)+

Step 3

N-(2-Methyl-1,3-bis((9Z,12Z)-octadeca-9,12-dien-1-yloxy) propan-2-yl)-2-nitrobenzenesulfonamide (0.200 g, 0.274 mmol) obtained in step 2 was dissolved in tetrahydrofuran (3 mL). To the solution, cesium carbonate (manufactured by Wako Pure Chemical Industries Ltd., 0.248 g, 0.726 mmol) and methyl iodide (manufactured by Tokyo Chemical Industry Co., Ltd., 0.048 mL, 0.762 mmol) were added, and the mixture was stirred at 70° C. for 1 hour using a microwave reaction apparatus. Water was added to the reaction mixture, followed by extraction with hexane. The organic layer was washed with saturated saline, dried over anhydrous magnesium sulfate, and filtered. The filtrate was concentrated under reduced pressure to obtain N-methyl-N-(2-methyl-1,3-bis(((9Z,12Z)-octadeca-9,12-dien-1-yl)oxy)propan-2-yl)-2-nitrobenzenesulfonamide (0.200 g, yield: 91%) as a crude product.

ESI-MS m/z: 801 (M+H)+

Step 4

N-Methyl-N-(2-methyl-1,3-bis((9Z,12Z)-octadeca-9,12-dien-1-yloxy)propan-2-yl)-2-nitrobenzenesulfonamide (0.200 g, 0.250 mmol) obtained in step 3 was dissolved in acetonitrile (2 mL). To the solution, 1-dodecanethiol (manufactured by Tokyo Chemical Industry Co., Ltd., 0.149 mL, 0.624 mmol) and 1,8-diazabicyclo[5.4.0]-7-undecene (manufactured by Nacalai Tesque, Inc., 0.0940 mL, 0.624 mmol) were added, and the mixture was stirred at 80° C. for 1 hour. Water was added to the reaction mixture, and the aqueous layer was subjected to extraction with ethyl acetate. The organic layer was washed with saturated saline, dried over anhydrous magnesium sulfate, then filtered, and concentrated under reduced pressure. The obtained residue was purified by NH silica gel column chromatography (hexane/ethyl acetate=90/10 to 75/25) to obtain compound CL-9 (0.070 g, yield: 46%).

ESI-MS m/z: 616 (M+H)+; $^1$H-NMR (CDCl$_3$) δ: 0.89 (t, J=6.8 Hz, 6H), 1.02 (s, 3H), 1.25-1.40 (m, 32H), 1.50-1.59 (m, 4H), 2.05 (q, J=6.8 Hz, 8H), 2.32 (s, 3H), 2.77 (t, J=6.3 Hz, 4H), 3.26 (s, 4H), 3.40 (t, J=6.6 Hz, 4H), 5.28-5.43 (m, 8H).

Reference Example B10

Methyl di((9Z,12Z)-octadeca-9,12-dienyl)amine (Compound CL-10)

To methylamine (manufactured by Sigma-Aldrich Corp., approximately 2 mol/L solution in tetrahydrofuran, 10.5 mL, 21.0 mmol), (9Z,12Z)-octadeca-9,12-dienyl methanesulfonate (1.03 g, 3.00 mmol) was added, and the mixture was stirred under heating at 150° C. for 90 minutes using a microwave reaction apparatus. The reaction solution was diluted with ethyl acetate, washed with a 2 mol/L aqueous sodium hydroxide solution and then saturated saline, dried over anhydrous magnesium sulfate, then filtered, and concentrated under reduced pressure to obtain a crude product of methyl((9Z,12Z)-octadeca-9,12-dienyl)amine.

To the obtained crude product, (9Z,12Z)-octadeca-9,12-dienyl methanesulfonate (0.93 g, 2.70 mmol) and a 50% aqueous sodium hydroxide solution (0.960 g, 12.0 mmol) were added, and the mixture was stirred under heating at 135° C. for 60 minutes in an oil bath. After cooling to room temperature, the reaction solution was diluted with ethyl acetate, washed with water and then saturated saline, dried over anhydrous magnesium sulfate, then filtered, and concentrated under reduced pressure. The obtained residue was purified by silica gel column chromatography (chloroform/methanol=100/0 to 97/3) to obtain compound CL-10 (1.07 g, 2.03 mmol, overall yield: 67%).

ESI-MS m/z: 529 (M+H)+; $^1$H-NMR (CDCl$_3$) δ: 0.89 (t, J=6.7 Hz, 6H), 1.29 (br s, 32H), 1.40-1.51 (m, 4H), 1.97-2.06 (m, 8H), 2.20 (s, 3H), 2.30 (t, J=7.6 Hz, 4H), 2.77 (t, J=5.8 Hz, 4H), 5.28-5.43 (m, 8H).

Reference Example B11

N-Methyl-2-(((9Z,12Z)-octadeca-9,12-dien-1-yl)oxy)-N-(2-(((9Z,12Z)-octadeca-9,12-dien-1-yl)oxy)ethyl)ethan-1-amine (Compound CL-11)

Compound CL-11 was synthesized by the method described in WO 2011/136368.

Reference Example B12

(3R,4R)-3,4-Bis(((Z)-hexadec-9-en-1-yl)oxy)-1-methylpyrrolidine (Compound CL-12)

Compound CL-12 was synthesized by the method described in WO 2011/136368.

Reference Example B13

2-(Dimethylamino)-N-((6Z,9Z,28Z,31Z)-heptatriaconta-6,9,28,31-tetraen-19-yl)acetamide (Compound CL-13)

Compound CL-13 was synthesized by the method described in WO 2013/059496.

Reference Example B14

3-(Dimethylamino)propane-1,2-diyl (9Z,9'Z,12Z,12'Z)-bis(octadeca-9,12-dienoate) (Compound CL-14)

Compound CL-14 was synthesized by the method described in "Biochemistry", 1994, Vol. 33, p. 12573-12580.

Reference Example B15

(9Z,12Z)-Di((9Z,12Z)-octadeca-9,12-dien-1-yl)amine (Compound CL-15)

Compound CL-15 was synthesized by the method described in WO 2014/007398.

Reference Example B16

Bis(2-(((9Z,12Z)-octadeca-9,12-dien-1-yl)oxy)ethyl)amine (Compound CL-16)

Compound CL-16 was synthesized by the method described in WO 2011/136368.

Reference Example B17

(9Z,12Z)—N-Methyl-N-(2-(((9Z,12Z)-octadeca-9,12-dien-1-yl)oxy)ethyl)octadeca-9,12-dien-1-amine (Compound CL-17)

2-(Methylamino)ethanol (manufactured by Tokyo Chemical Industry Co., Ltd., 0.125 g, 1.66 mmol) was dissolved in toluene (2.5 mL). To the solution, sodium hydride (60% oil, 0.333 g, 8.32 mmol) and a solution of (9Z,12Z)-octadeca-9,12-dien-1-yl methanesulfonate (manufactured by Nu-Chek Prep, Inc., 1.32 g, 3.83 mmol) in toluene (2.5 mL) were added in order, and the mixture was stirred for 2 hours under heating to reflux. The reaction mixture was cooled to room temperature. Then, ethanol and water were added thereto, and the aqueous layer was subjected to extraction with ethyl acetate. The organic layer was dried over anhydrous magnesium sulfate and then filtered. The filtrate was concentrated under reduced pressure, and the obtained residue was purified by silica gel column chromatography (chloroform/methanol=100/0 to 97/3) to obtain compound CL-17 (0.211 g, yield: 22%).

ESI-MS m/z: 572 (M+H)$^+$; $^1$H-NMR (CDCl$_3$) δ: 0.89 (t, J=6.9 Hz, 6H), 1.24-1.38 (m, 32H), 1.43-1.49 (m, 2H), 1.53-1.59 (m, 2H), 2.05 (q, J=7.2 Hz, 8H), 2.27 (s, 3H), 2.37 (t, J=7.7 Hz, 2H), 2.57 (t, J=6.2 Hz, 2H), 2.78 (t, J=6.8 Hz, 4H), 3.42 (t, J=6.8 Hz, 2H), 3.52 (t, J=6.2 Hz, 2H), 5.30-5.41 (m, 8H).

Reference Example B18

(9Z,12Z)—N-(3-(((9Z,12Z)-Octadeca-9,12-dien-1-yl)oxy)propyl)octadeca-9,12-dien-1-amine (Compound CL-18)

Compound CL-18 was synthesized by a method equivalent to the method described in WO 2014/007398.
ESI-MS m/z: 572

Reference Example B19

(1-Methylpiperidin-3-yl)methyl di((11Z,14Z)-icosa-11,14-dien-1-yl)carbamate (Compound CL-19)

Compound CL-19 was synthesized by the method described in WO 2014/007398.

Reference Example B20

(13Z,16Z)—N,N-Dimethyl-4-((9Z,12Z)-octadeca-9,12-dien-1-yl)docosa-3,13,16-trien-1-amine (Compound CL-20)

Step 1
To a solution of heptatriaconta-6,9,28,31-tetraen-19-one (0.353 g, 0.186 mmol) synthesized by the method described in WO 2009/132131 in tetrahydrofuran (0.882 mL), anhydrous cerium(III) chloride (manufactured by Tokyo Chemical Industry Co., Ltd., 0.174 g, 0.706 mmol) was added in an argon atmosphere. Then, cyclopropyl magnesium bromide (manufactured by Sigma-Aldrich Corp., 0.5 mmol/L. 1.06 mL, 0.529 mmol) was added under ice cooling, and the mixture was stirred for 5 minutes and then stirred at room temperature for 1 hour. A saturated aqueous solution of ammonium chloride was added to the reaction mixture, and the aqueous layer was subjected to extraction with ethyl acetate. The organic layer was dried over anhydrous magnesium sulfate and then filtered. The filtrate was concentrated under reduced pressure, and the obtained residue was purified by silica gel column chromatography (hexane/ethyl acetate=97/3 to 94/6) to obtain (6Z,9Z,28Z,31Z)-19-cyclopropylheptatriaconta-6,9,28,31-tetraen-19-ol (0.141 g, yield: 70%).
ESI-MS m/z: 569

Step 2
To a solution of (6Z,9Z,28Z,31Z)-19-cyclopropylheptatriaconta-6,9,28,31-tetraen-19-ol (0.141 g, 0.248 mmol) obtained in step 1 in dichloromethane (2 mL), lithium bromide (manufactured by Sigma-Aldrich Corp., 0.108 g, 1.24 mmol) and chlorotrimethylsilane (manufactured by Tokyo Chemical Industry Co., Ltd., 0.135 g, 1.24 mmol) were added at room temperature, and the mixture was stirred for 1 hour. Then, lithium bromide (manufactured by Sigma-Aldrich Corp., 0.108 g, 1.24 mmol) and chlorotrimethylsilane (manufactured by Tokyo Chemical Industry Co., Ltd., 0.135 g, 1.24 mmol) were further added thereto, and the mixture was stirred for 1 hour. A saturated aqueous solution of sodium bicarbonate was added to the reaction mixture, and the aqueous layer was subjected to extraction with hexane. The organic layer was dried over anhydrous magnesium sulfate and then filtered. The filtrate was concentrated under reduced pressure, and the obtained residue was purified by silica gel column chromatography (hexane/ethyl acetate=100/0 to 90/10 to obtain (6Z,9Z,28Z,31Z)-19-(3-bromopropylidene)heptatriaconta-6,9,28,31-tetraene (0.074 g, yield: 47%).
ESI-MS m/z: 632

Step 3
To (6Z,9Z,28Z,31Z)-19-(3-bromopropylidene)heptatriaconta-6,9,28,31-tetraene (0.074 g, 0.117 mmol) obtained in step 2, dimethylamine (manufactured by Sigma-Aldrich Corp., 2.0 mmol/L solution in tetrahydrofuran, 1.5 mL, 3.0 mmol) was added, and the mixture was stirred under heating at 130° C. for 90 minutes under microwave irradiation. A saturated aqueous solution of sodium bicarbonate was added to the reaction mixture, and the aqueous layer was subjected to extraction with hexane. The organic layer was washed with saturated saline, dried over anhydrous magnesium sulfate, and then filtered. The filtrate was concentrated under reduced pressure, and the obtained residue was purified by NH silica gel column chromatography (hexane/ethyl acetate=97/3 to 88/12 to obtain CL-20 (0.062 g, yield: 69%).
ESI-MS m/z: 596

Reference Example B21

(S)-2-Amino-3-hydroxy-N,N-bis(2-(((Z)-octadec-9-en-1-yl)oxy)ethyl)propanamide (Compound CL-21)

Compound CL-21 was synthesized by the method described in WO 2011/136368.

Reference Example B22

(3R,4R)-3,4-Bis(((11Z,14Z)-icosa-11,14-dien-1-yl)oxy)pyrrolidine (Compound CL-22)

Compound CL-22 was synthesized by the method described in WO 2011/136368.

Reference Example B23 trans-3,4-Bis((((11Z,14Z)-icosa-11,14-dien-1-yl)oxy)methyl)-1-methylpyrrolidine (Compound CL-23)

Compound CL-23 was synthesized by the method described in WO 2011/136368.

Reference Example B24

1-((S)-2,3-Bis(((9Z,12Z)-octadeca-9,12-dien-1-yl)oxy)propyl)pyrrolidine (Compound CL-24)

Compound CL-24 was synthesized by the method described in WO 2009/129395.

Reference Example B25

2-(2,2-Di((9Z,12Z)-octadeca-9,12-dien-1-yl)-1,3-dioxolan-4-yl)-N,N-dimethylethan-1-amine (Compound CL-25)

Compound CL-25 was synthesized by the method described in WO 2010/042877.

Reference Example B26

3-(Dimethylamino)propyl di((9Z,12Z)-oxadeca-9,12-dien-1-yl)carbamate (Compound CL-26)

Compound CL-26 was synthesized by the method described in WO 2014/007398.

Reference Example B27

4-(Dimethylamino)butyl di((9Z,12Z)-oxadeca-9,12-dien-1-yl)carbamate (Compound CL-27)

Compound CL-27 was synthesized by the method described in WO 2014/007398.

Reference Example B28

2-(Di((9Z,12Z)-octadeca-9,12-dien-1-yl)amino)ethan-1-ol (Compound CL-28)

Compound CL-28 was synthesized by the method described in WO 2014/007398.

Reference Example B29

2-(Dimethylamino)-3-(((9Z,12Z)-octadeca-9,12-dien-1-yl)oxy)-2-((((9Z,12Z)-octadeca-9,12-dien-1-yl)oxy)methyl)propan-1-ol (Compound CL-29)

Compound CL-29 was synthesized by the method described in WO 2011/149733.

Reference Example B30

(6Z,9Z,28Z,31Z)—N,N-Dimethylheptatriaconta-6,9,28,31-tetraen-19-amine (Compound CL-30)

Compound CL-30 was synthesized by the method described in WO 2010/054405.

Reference Example B31

N,N,2-Trimethyl-1,3-bis(((9Z,12Z)-octadeca-9,12-dien-1-yl)oxy)propan-2-amine (Compound CL-31)

2-Methyl-1,3-bis((9Z,12Z)-octadeca-9,12-dien-1-yloxy)propan-2-amine (0.240 g, 0.399 mmol) obtained in step 1 of Reference Example B9 was dissolved in a mixed solvent of 1,2-dichloroethane (1 mL) and methanol (1 mL). To the solution, formaldehyde (manufactured by Wako Pure Chemical Industries Ltd., 37% aqueous solution, 0.144 mL, 1.99 mmol) and sodium triacetoxyborohydride (manufactured by Tokyo Chemical Industry Co., Ltd., 0.211 g, 0.997 mmol) were added, and the mixture was stirred overnight at room temperature. Water was added to the reaction mixture, and the aqueous layer was subjected to extraction with ethyl acetate. The organic layer was washed with saturated sodium bicarbonate, then dried over anhydrous magnesium sulfate, and then filtered. The filtrate was concentrated under reduced pressure, and the obtained residue was purified by NH silica gel column chromatography (hexane/ethyl acetate=99/1 to 80/20) to obtain compound 2 (0.191 g, yield: 76%).

ESI-MS m/z: 630 (M+H)$^+$; $^1$H-NMR (CDCl$_3$) δ: 0.89 (t, J=7.0 Hz, 6H), 0.95 (s, 3H), 1.26-1.39 (m, 32H), 1.53-1.58 (m, 4H), 2.05 (q, J=6.9 Hz, 8H), 2.31 (s, 6H), 2.77 (t, J=6.3 Hz, 4H), 3.33-3.42 (m, 8H), 5.27-5.43 (m, 8H).

Reference Example B32

N-Methyl-2-(((Z)-octadec-6-en-1-yl)oxy)-N-(2-(((Z)-octadec-6-en-1-yl)oxy)ethyl)ethan-1-amine (Compound CL-32)

Compound CL-32 was synthesized by the method described in WO 2011/136368.

Reference Example B33

(3R,4R)-3-(Dimethylamino)propyl 3,4-bis((9Z,12Z)-octadeca-9,12-dienyloxy)pyrrolidine-1-carboxylate (Compound CL-33)

Step 1

To a suspension of sodium hydride (60% oil, 5.80 g, 145 mmol) in toluene (100 mL), a solution of (3R,4R)-1-benzylpyrrolidine-3,4-diol (manufactured by Diverchim S.A., 3.50 g, 18.1 mmol) in toluene (70 mL) was added with stirring, and a solution of (9Z,12Z)-octadeca-9,12-dienyl methanesulfonate (15.6 g, 45.3 mmol) in toluene (30 mL) was then added dropwise. The obtained mixture was stirred overnight under heating to reflux. After cooling to room temperature, the reaction was terminated with a saturated aqueous solution of ammonium chloride. To the obtained mixture, saturated saline was added, followed by extraction with ethyl acetate twice. The organic layers were combined, dried over anhydrous magnesium sulfate, and then concentrated under reduced pressure. The residue was purified by silica gel column chromatography (methanol/chloroform=0/100 to 2/98) to obtain (3R,4R)-1-benzyl-3,4-bis((9Z,12Z)-octadeca-9,12-dienyloxy)pyrrolidine (6.96 g, 10.1 mmol, yield: 56%).

ESI-MS m/z: 691 (M+H)$^+$; $^1$H-NMR (CDCl$_3$) δ: 0.89 (t, J=6.9 Hz, 6H), 1.26-1.38 (m, 30H), 1.52-1.62 (m, 6H), 2.05 (q, J=6.3 Hz, 8H), 2.50 (dd, J=9.9, 4.3 Hz, 2H), 2.77 (t, J=5.8 Hz, 4H), 2.85 (dd, J=9.6, 5.9 Hz, 2H), 3.37-3.45 (m, 4H), 3.52-3.66 (m, 2H), 3.83 (t, J=4.6 Hz, 2H), 5.28-5.43 (m, 8H), 7.23-7.33 (m, 5H).

Step 2

(3R,4R)-1-Benzyl-3,4-bis((9Z,12Z)-octadeca-9,12-dienyloxy)pyrrolidine (6.96 g, 10.1 mmol)) obtained in step 1 was dissolved in 1,2-dichloroethane (100 mL). To the solution, 1-chloroethyl chloroformate (3.30 mL, 30.3 mmol) was added, and the mixture was stirred at 130° C. for 1 hour. Methanol (100 mL) was added to the reaction solution, and the mixture was further stirred at 130° C. for 1 hour. The reaction mixture was cooled to room temperature and then concentrated under reduced pressure, and the obtained residue was purified by silica gel column chromatography (chloroform/methanol=100/0 to 92/8). The obtained organic layer was washed with a saturated aqueous solution of sodium bicarbonate and then a saturated aqueous solution of sodium chloride, dried over anhydrous magnesium sulfate, then filtered, and concentrated under reduced pressure to obtain (3R,4R)-3,4-bis((9Z,12Z)-octadeca-9,12-dienyloxy) pyrrolidine (5.56 g, 9.27 mmol, yield: 92%).

ESI-MS m/z: 601 (M+H)$^+$; $^1$H-NMR (CDCl$_3$) δ: 0.89 (t, J=6.9 Hz, 6H), 1.29-1.41 (m, 30H), 1.49-1.60 (m, 4H), 1.67 (br s, 3H), 2.05 (q, J=6.5 Hz, 8H), 2.75-2.85 (m, 6H), 3.09 (dd, J=12.4, 5.1 Hz, 2H), 3.37-3.49 (m, 4H), 3.76 (dd, J=5.0, 3.3 Hz, 2H), 5.28-5.43 (m, 8H).

Step 3

The title compound (0.101 g, 0.139 mmol, 75%) was obtained in the same way as in step 2 of Reference Example B4 using (3R,4R)-3,4-bis((9Z,12Z)-octadeca-9,12-dienyloxy) pyrrolidine (0.111 g, 0.185 mmol) obtained in step 2 instead of di((Z)-octadec-9-enyl)amine.

ESI-MS m/z: 730 (M+H)$^+$; $^1$H-NMR (CDCl$_3$) δ: 0.89 (t, J=6.9 Hz, 6H), 1.24-1.40 (m, 32H), 1.50-1.57 (m, 4H), 1.77-1.83 (m, 2H), 2.02-2.08 (m, 8H), 2.23 (s, 6H), 2.34 (t, J=7.4 Hz, 2H), 2.77 (t, J=6.8 Hz, 4H), 3.38-3.56 (m, 8H), 3.83-3.86 (m, 2H), 4.11 (t, J=6.5 Hz, 2H), 5.30-5.42 (m, 8H).

Reference Example B34

(9Z,12Z)—N-(2-(((9Z,12Z)-Octadeca-9,12-dien-1-yl)oxy)ethyl)octadeca-9,12-dien-1-amine (Compound CL-34)

Compound CL-34 was synthesized by the method described in WO 2014/007398.

Reference Example B35

(9Z,12Z)—N-(2-(((Z)-Hexadec-9-en-1-yl)oxy)ethyl) octadeca-9,12-dien-1-amine (Compound CL-35)

Compound CL-35 was synthesized by the method described in WO 2014/007398.

Reference Example B36

N,N-Dimethyl-1,3-bis(((9Z,12Z)-octadeca-9,12-dien-1-yl)oxy)propan-2-amine (Compound CL-36)

Compound CL-36 was synthesized by the method described in WO 2009/129385.

Reference Example B37

3-(Dimethylamino)propyl di((Z)-octadec-9-enyl) carbamate (Compound CL-37)

Step 1

To ammonia (manufactured by Tokyo Chemical Industry Co., Ltd., approximately 2 mol/L solution in methanol, 12.0 mL, 24.0 mmol), (Z)-octadec-9-enyl methanesulfonate (1.04 g, 3.00 mmol) was added, and the mixture was stirred at 130° C. for 3 hours using a microwave reaction apparatus. A saturated aqueous solution of sodium bicarbonate was added to the reaction solution, followed by extraction with chloroform five times. The organic layers were combined, washed with saturated saline, dried over anhydrous magnesium sulfate, then filtered, and concentrated under reduced pressure to obtain a crude product of (Z)-octadec-9-enylamine.

To the obtained crude product, (Z)-octadec-9-enyl methanesulfonate (0.832 g, 2.40 mmol) and a 50% aqueous sodium hydroxide solution (0.960 g, 12.0 mmol) were added, and the mixture was stirred at 110° C. for 60 minutes in an oil bath. After cooling to room temperature, the reaction solution was diluted with ethyl acetate, washed with water and then saturated saline, dried over anhydrous magnesium sulfate, then filtered, and concentrated under reduced pressure. The obtained residue was purified by silica gel column chromatography (chloroform/methanol=100/0 to 95/5) to obtain di((Z)-octadec-9-enyl)amine (0.562 g, 1.085 mmol, yield: 36%).

ESI-MS m/z: 519 (M+H)$^+$; $^1$H-NMR (CDCl$_3$) δ: 0.88 (t, J=6.7 Hz, 6H), 1.29 (br s, 45H), 1.41-1.52 (m, 4H), 1.97-2.05 (m, 8H), 2.58 (t, J=7.2 Hz, 4H), 5.28-5.40 (m, 4H).

Step 2

Di((Z)-octadec-9-enyl)amine (0.156 g, 0.301 mmol) obtained in step 1 was dissolved in chloroform (3 mL). To the solution, 3-(dimethylamino)propyl 4-nitrophenyl carbonate hydrochloride (0.138 g, 0.452 mmol) synthesized by a method equivalent to the method described in "J. Am. Chem. Soc.", 1981, Vol. 103, p. 4194-4199 and triethylamine (0.168 mL, 1.21 mmol) were added, and the mixture was stirred at 110° C. for 60 minutes using a microwave reaction apparatus. 3-(Dimethylamino)propyl 4-nitrophenyl carbonate hydrochloride (22.9 mg, 0.0753 mmol) was added to the reaction solution, and the mixture was stirred at 110° C. for 20 minutes using a microwave reaction apparatus. 3-(Dimethylamino)propyl 4-nitrophenyl carbonate hydrochloride (22.9 mg, 0.0753 mmol) was added to the reaction solution, and the mixture was stirred at 110° C. for 20 minutes using a microwave reaction apparatus. 3-(Dimethylamino)propyl 4-nitrophenyl carbonate hydrochloride (22.9 mg, 0.0753 mmol) was added to the reaction solution, and the mixture was stirred at 110° C. for 20 minutes using a microwave reaction apparatus. The reaction solution was diluted with chloroform, washed with a saturated aqueous solution of sodium bicarbonate, then washed with saturated saline, dried over anhydrous magnesium sulfate, then filtered, and concentrated under reduced pressure. The obtained residue was dissolved in a small amount of n-hexane/ethyl acetate (1/4) and adsorbed to a pad of amino-modified silica gel, followed by elution with n-hexane/ethyl acetate (1/4). The eluate was concentrated under reduced pressure. The obtained residue was purified by silica gel column chromatography (chloroform/methanol=100/0 to 95/5) to obtain the title compound (0.173 g, 0.267 mmol, yield: 89%).

ESI-MS m/z: 648 (M+H)$^+$; $^1$H-NMR (CDCl$_3$) δ: 0.88 (t, J=6.6 Hz, 6H), 1.28 (br s, 44H), 1.45-1.55 (m, 4H), 1.75-1.85 (m, 2H), 1.97-2.04 (m, 8H), 2.23 (s, 6H), 2.34 (t, J=7.6 Hz, 2H), 3.13-3.24 (m, 4H), 4.10 (t, J=6.4 Hz, 2H), 5.28-5.40 (m, 4H).

Reference Example B38

(11Z,14Z)—N-(2-(((Z)-Octadec-9-en-1-yl)oxy) ethyl)icosa-11,14-dien-1-amine (Compound CL-38)

Compound CL-38 was synthesized by a method equivalent to the method described in WO 2014/007398.

ESI-MS m/z: 588

Reference Example B39

(9Z,12Z)—N-(2-(((Z)-Icos-11-en-1-yl)oxy)ethyl)
octadeca-9,12-dien-1-amine (Compound CL-39)

Compound CL-39 was synthesized by a method equivalent to the method described in WO 2014/007398.
ESI-MS m/z: 588

Reference Example B40

(11Z,14Z)—N-(2-(((Z)-Icos-11-en-1-yl)oxy)ethyli-
cosa-11,14-dien-1-amine (Compound CL-40)

Compound CL-40 was synthesized by a method equivalent to the method described in WO 2014/007398.
ESI-MS m/z: 616

Reference Example B41

(Z)—N-(2-(((Z)-Octadec-9-en-1-yl)oxy)ethyl)octa-
dec-9-en-1-amine (Compound CL-41)

Compound CL-41 was synthesized by a method equivalent to the method described in WO 2014/007398.
ESI-MS m/z: 562

Reference Example B42

Bis(2-(((11Z,14Z)-icosa-11,14-dien-1-yl)oxy)ethyl)
amine (Compound CL-42)

Compound CL-42 was synthesized by a method equivalent to the method described in WO 2011/136368.
ESI-MS m/z: 658

Reference Example B43

(Z)—N-(2-(((Z)-Octadec-9-en-1-yl)oxy)ethyl)hexa-
dec-9-en-1-amine (Compound CL-43)

Compound CL-43 was synthesized by a method equivalent to the method described in WO 2014/007398.
ESI-MS m/z: 534

Reference Example B44

(Z)—N-(2-(Octadec-9-en-1-yloxy)ethyl)octadecan-
1-amine (Compound CL-44)

Compound CL-44 was synthesized by a method equivalent to the method described in WO 2014/007398.
ESI-MS m/z: 564

Reference Example B45

(Z)—N-(2-(Octadec-9-en-1-yloxy)ethyl)tetradecan-
1-amine (Compound CL-45)

Compound CL-45 was synthesized by a method equivalent to the method described in WO 2014/007398.
ESI-MS m/z: 508

Reference Example B46

3-((3R,4R)-3,4-Bis(((9Z,12Z)-octadeca-9,12-dien-1-
yl)oxy)pyrrolidin-1-yl)propane-1,2-diol (Compound
CL-46)

Compound CL-46 was synthesized by the method described in WO 2011/136368.

Reference Example B47

Bis(2-(((Z)-octadec-9-en-1-yl)oxy)ethyl)amine
(Compound CL-47)

Compound CL-47 was synthesized by the method described in WO 2011/136368.

Reference Example B48

3-(Bis(2-(((Z)-octadec-9-en-1-yl)oxy)ethyl)amino)
propane-1,2-diol (Compound CL-48)

Compound CL-48 was synthesized by the method described in WO 2011/136368.

Reference Example B49

3-(Bis(2-(((Z)-octadec-9-en-1-yl)oxy)ethyl)amino)
propanamide (Compound CL-49)

Compound CL-49 was synthesized by the method described in WO 2011/136368.

Reference Example B50

(9Z,12Z)—N-(2-(2-(((Z)-Octadec-9-en-1-yl)oxy)
ethoxy)ethyl)octadeca-9,12-dien-1-amine (Compound CL-50)

Compound CL-50 was synthesized by a method equivalent to the method described in WO 2014/007398.
ESI-MS m/z: 604

Reference Example B51

Di((Z)-non-2-en-1-yl) 9-((4-(dimethylamino)bu-
tanoyl)oxy)heptadecanedioate (Compound CL-51)

Compound CL-51 was synthesized by the method described in WO 2011/153493.

Reference Example B52

Di((Z)-non-2-en-1-yl) 8,8'-((((2-(dimethylamino)
ethyl)thio)carbonyl)azanediyl)dioctanoate (Compound CL-52)

Compound CL-52 was synthesized by the method described in WO 2017/023817.

Reference Example B53

2-(Dimethylamino)-N-(2-(((Z)-octadec-9-en-1-yl)oxy)ethyl)-N-((9Z,12Z)-octadeca-9,12-dien-1-yl)acetamide (Compound CL-53)

Compound CL-53 was synthesized by a method equivalent to the method described in WO 2014/007398.

Reference Example B54

3-((2-(((Z)-Octadec-9-en-1-yl)oxy)ethyl)((9Z,12Z)-octadeca-9,12-dien-1-yl)amino)propan-1-ol (Compound CL-54)

Compound CL-54 was synthesized by a method equivalent to the method described in WO 2014/007398.

Reference Example B55

1-Methyl-3,3-bis((((9Z,12Z)-octadeca-9,12-dien-1-yl)oxy)methyl)azetidine (Compound CL-55)

Compound CL-55 was synthesized by the method described in WO 2012/108397.

Reference Example B56

1-Methyl-3,3-bis(2-(((9Z,12Z)-octadeca-9,12-dien-1-yl)oxy)ethyl)azetidine (Compound CL-56)

Compound CL-56 was synthesized by the method described in WO 2016/002753.

Reference Example B57

1-Methyl-3,3-bis(2-(((9Z,12Z)-octadeca-9,12-dien-1-yl)oxy)propyl)azetidine (Compound CL-57)

Compound CL-57 was synthesized by the method described in WO 2016/002753.

Reference Example B58

2-(3,3-Di((9Z,12Z)-octadeca-9,12-dien-1-yl)azetidin-1-yl)ethan-1-ol (Compound CL-58)

Compound CL-58 was synthesized by the method described in WO 2016/002753.

Reference Example B59

2-(3,3-Di((9Z,12Z)-octadeca-9,12-dien-1-yl)azetidin-1-yl)propan-1-ol (Compound CL-59)

Compound CL-59 was synthesized by the method described in WO 2016/002753.

Reference Example B60

3-(Dimethylamino)propyl 3,3-di((9Z,12Z)-octadeca-9,12-dien-1-yl)azetidine-1-carboxylate (Compound CL-60)

Compound CL-60 was synthesized by the method described in WO 2016/002753.

Reference Example B61

2-(Di((Z)-octadec-9-en-1-yl)amino)ethan-1-ol (Compound CL-61)

Compound CL-61 was synthesized by the method described in WO 2014/007398.

Reference Example B62

3-(Di((Z)-octadec-9-en-1-yl)amino)propan-1-ol (Compound CL-62)

Compound CL-62 was synthesized by the method described in WO 2014/007398.

Reference Example B63

(11Z,14Z)-2-((Dimethylamino)methyl)-2-((9Z,12Z)-octadeca-9,12-dien-1-yl)icosa-11,14-dien-1-ol (Compound CL-63)

Step 1

To a solution of (9Z,12Z)-octadeca-9,12-dien-1-yl methanesulfonate (7.62 g, 22.1 mmol) in tetrahydrofuran (30.0 mL), ethyl 2-cyanoacetate (0.943 mL, 8.84 mmol), sodium hydride (1.06 g, 26.5 mmol), and tetrabutylammonium iodide (3.27 g, 8.84 mmol) were added, and the mixture was stirred at 60° C. for 2 hours. Water was added to the reaction solution, followed by extraction with heptane. The organic layer was dried over anhydrous magnesium sulfate, filtered, and concentrated under reduced pressure. The obtained residue was purified by silica gel column chromatography (heptane/ethyl acetate=99/1 to 85/15) to obtain ethyl (11Z,14Z)-2-cyano-2-((9Z,12Z)-octadeca-9,12-dien-1-yl)icosa-11,14-dienoate (3.50 g, 5.74 mmol, yield: 64.9%).

To a solution of ethyl (11Z,14Z)-2-cyano-2-((9Z,12Z)-octadeca-9,12-dien-1-yl)icosa-11,14-dienoate (1.50 g, 2.46 mmol) in tetrahydrofuran (10.0 mL), lithium aluminum hydride (0.467 g, 12.3 mmol) was added, and the mixture was stirred for 30 minutes under ice cooling. Water, sodium hydroxide, and water were added at a ratio of 1:1:3 to the reaction solution, and the mixture was dried over anhydrous magnesium sulfate, filtered, and concentrated under reduced pressure. The obtained residue was purified by silica gel column chromatography (chloroform/methanol=90/10) to obtain (11Z,14Z)-2-(aminomethyl)-2-((9Z,12Z)-octadeca-9,12-dien-1-yl)icosa-11,14-dien-1-ol (1.00 g, 1.75 mmol, yield: 71.1%).

ESI-MS m/z: 573 (M+H)$^+$.

Step 2

To a solution of (11Z,14Z)-2-(aminomethyl)-2-((9Z,12Z)-octadeca-9,12-dien-1-yl)icosa-11,14-dien-1-ol (0.200 g, 0.350 mmol) in dichloroethane (2.00 mL), a paraformaldehyde solution (0.276 g, 3.50 mmol, 37% solution in methanol) and sodium triacetoxyborohydride (1.48 g, 6.99 mmol) were added, and the mixture was stirred at room temperature for 3 hours. Water was added to the reaction solution, followed by extraction using chloroform. The organic layer was dried over anhydrous magnesium sulfate, filtered, and concentrated under reduced pressure. The obtained residue was purified by silica gel column chromatography (chloroform/methanol=99/1 to 85/15) to obtain the title compound (0.0280 g, 0.0470 mmol, yield: 13.3%).

ESI-MS m/z: 601 (M)+; 1H-NMR (CDCl3) δ: 0.89 (t, J=6.8 Hz, 6H), 1.23-1.29 (m, 40H), 2.05 (q, J=6.8 Hz, 8H), 2.32 (s, 6H), 2.40 (s, 2H), 2.77 (dd, J=9.8, 3.4 Hz, 4H), 3.53 (s, 2H), 5.29-5.42 (m, 8H).

Reference Example B64

(11Z,14Z)-2-(Dimethylamino)-2-((9Z,12Z)-octadeca-9,12-dien-1-yl)icosa-11,14-dien-1-ol (Compound CL-64)

Step 1

To a solution of sodium hydride (1.21 g, 30.3 mmol) in THF (30.0 mL), tert-butyl ethyl malonate (manufactured by Tokyo Chemical Industry Co., Ltd., 2.00 mL, 10.1 mmol), tetra-n-butylammonium iodide (manufactured by Nacalai Tesque, Inc., 0.746 g, 2.02 mmol), and (9Z,12Z)-octadeca-9,12-dienyl methanesulfonate (manufactured by Nu-Chek Prep, Inc., 8.70 g, 25.2 mmol) were added, and the mixture was stirred for 2 hours under heating to reflux. Saturated saline was added to the reaction solution, followed by extraction with ethyl acetate. The organic layer was dried over anhydrous magnesium sulfate and filtered, and the solvent was distilled off under reduced pressure. The obtained residue was purified by silica gel column chromatography (hexane/ethyl acetate=95/5) to obtain 1-tert-butyl 3-ethyl 2,2-di((9Z,12Z)-octadeca-9,12-dien-1-yl)malonic acid (5.52 g, 80.0%).

Step 2

To a solution of 1-tert-butyl 3-ethyl 2,2-di((9Z,12Z)-octadeca-9,12-dien-1-yl)malonic acid (5.52 g, 8.06 mmol) in dichloromethane (30.0 mL), trifluoroacetic acid (5.00 mL, 64.9 mmol) was added, and the mixture was stirred at room temperature for 30 minutes. The reaction solution was concentrated under reduced pressure. The residue was separated into aqueous and organic layers with chloroform and a saturated aqueous solution of sodium bicarbonate. The organic layer was washed with saturated saline, dried over anhydrous magnesium sulfate, and filtered, and the solvent was distilled off under reduced pressure. The obtained residue was purified by silica gel column chromatography (chloroform/methanol=95/5) to obtain (11Z,14Z)-2-(ethoxycarbonyl)-2-((9Z,12Z)-octadeca-9,12-dien-1-yl)icosa-11,14-dienoic acid (4.04 g, 6.42 mmol, 80.0%).

Step 3

To a solution of (11Z,14Z)-2-(ethoxycarbonyl)-2-((9Z,12Z)-octadeca-9,12-dien-1-yl)icosa-11,14-dienoic acid (0.284 g, 0.452 mmol) in toluene (3.00 mL), triethylamine (0.315 mL, 2.26 mmol) and diphenylphosphoryl azide (manufactured by Tokyo Chemical Industry Co., Ltd., 0.121 mL, 0.542 mmol) were added, and the mixture was stirred at room temperature for 1 hour. Water (0.0200 mL, 1.11 mmol) was added to the reaction solution, and the mixture was stirred for 5 hours under heating to reflux. Water was added to the reaction solution, followed by extraction with ethyl acetate. The organic layer was dried over anhydrous magnesium sulfate and filtered, and the solvent was distilled off under reduced pressure. The obtained residue was purified by silica gel column chromatography (hexane/ethyl acetate=80/20) to obtain ethyl (11Z,14Z)-2-amino-2-((9Z,12Z)-octadeca-9,12-dien-1-yl)icosa-11,14-dienoate (0.0457 g, 0.0762 mmol, 17.0%).

ESI-MS m/z: 601 (M+H)+.

Step 4

To a solution of ethyl (11Z,14Z)-2-amino-2-((9Z,12Z)-octadeca-9,12-dien-1-yl)icosa-11,14-dienoate (0.299 g, 0.498 mmol) in THF (3.00 mL), lithium aluminum hydride (manufactured by Junsei Chemical Co., Ltd., 0.0190 g, 0.498 mmol) was added, and the mixture was stirred at room temperature for 30 minutes. Water and an aqueous sodium hydroxide solution were added to the reaction solution, and insoluble matter was removed by filtration through celite. The filtrate was concentrated under reduced pressure. The obtained residue was purified by amino silica gel column chromatography (hexane/ethyl acetate=50/50) to obtain (11Z,14Z)-2-amino-2-((9Z,12Z)-octadeca-9,12-dien-1-yl) icosa-11,14-dien-1-ol (0.0667 g, 0.120 mmol, 24.0%).

ESI-MS m/z: 559 (M+H)+.

Step 5

To a solution of (11Z,14Z)-2-amino-2-((9Z,12Z)-octadeca-9,12-dien-1-yl)icosa-11,14-dien-1-ol (0.0664 g, 0.119 mmol) in dichloroethane (1.00 mL), formaldehyde (0.500 mL, 6.72 mmol) and sodium triacetoxyborohydride (manufactured by Tokyo Chemical Industry Co., Ltd., 0.101 g, 0.476 mmol) were added, and the mixture was stirred overnight at room temperature. A saturated aqueous solution of sodium bicarbonate was added to the reaction solution, followed by extraction with ethyl acetate. The organic layer was washed with a saturated aqueous solution of sodium chloride, dried over anhydrous magnesium sulfate, then filtered, and concentrated under reduced pressure. The obtained residue was purified by silica gel column chromatography (chloroform/methanol=80/20) to obtain the title compound (0.0474 g, 0.0809 mmol, 68.0%).

ESI-MS m/z: 587 (M+H)+; 1H-NMR (CDCl3) δ: 0.89 (t, J=7.0 Hz, 6H), 1.24-1.39 (m, 40H), 2.05 (q, J=6.8 Hz, 8H), 2.38 (s, 6H), 2.77 (t, J=6.7 Hz, 4H), 5.29-5.42 (m, 8H).

Reference Example B65

3-(Dimethylamino)-2,2-bis((((9Z,12Z)-octadeca-9,12-dien-1-yl)oxy)methyl)propan-1-ol (Compound CL-65)

To 2-(bromomethyl)-2-(hydroxymethyl)propane-1,3-diol (1.52 g, 7.56 mmol), a dimethylamine solution (15.0 mL, 30.0 mmol, 2 M in THF) was added, and the mixture was stirred at 120° C. for 15 hours under microwave irradiation. Lithium hydroxide was added to the reaction solution, and the mixture was filtered. The filtrate was concentrated under reduced pressure to obtain 2-((dimethylamino)methyl)-2-(hydroxymethyl)propane-1,3-diol (1.23 g, quantitative).

To a solution of 2-((dimethylamino)methyl)-2-(hydroxymethyl)propane-1,3-diol (1.23 g, 7.56 mmol) in toluene (30.0 mL), sodium hydride (0.756 g, 18.9 mmol) and (9Z,12Z)-octadeca-9,12-dien-1-yl methanesulfonate (6.51 g, 18.9 mmol) were added, and the mixture was stirred overnight under heating to reflux. Saturated saline was added to the reaction solution, followed by extraction using hexane. The organic layer was dried over anhydrous magnesium sulfate, filtered, and concentrated under reduced pressure. The obtained residue was purified by silica gel column chromatography (chloroform/methanol=90/10) and amino silica gel column chromatography (hexane/ethyl acetate=90/10) to obtain the title compound (1.80 g, 2.73 mmol, yield: 36.1%).

ESI-MS m/z: 661 (M)+; 1H-NMR (CDCl3) δ: 0.89 (t, J=7.0 Hz, 6H), 1.24-1.39 (m, 32H), 1.50-1.56 (m, 4H), 2.05

(q, J=6.8 Hz, 8H), 2.30 (s, 6H), 2.53 (s, 2H), 2.77 (t, J=6.3 Hz, 4H), 3.30-3.41 (m, 8H), 3.71 (s, 2H), 5.29-5.42 (m, 8H).

Reference Example B66

((2-((2-(Dimethylamino)ethyl)thio)acetyl)azanediyl) bis(ethane-2,1-diyl) ditetradecanoate (Compound CL-66)

Compound CL-66 was synthesized by the method described in WO 2012/170952.

Example C1

(9Z,12Z)—N-(2-{[(Z)-Octadec-9-en-1-yl]thio}ethyl) octadeca-9,12-dien-1-amine (Compound CL-67)

Step 1

(Z)-Octadec-9-en-1-yl methanesulfonate (2.00 g, 5.77 mmol) was dissolved in acetonitrile (10.0 mL). To the solution, cesium carbonate (3.76 g, 11.5 mmol) and 2-mercaptoethanol (0.615 mL, 8.66 mmol) were added, and the mixture was stirred overnight at room temperature. Saturated saline was added to the reaction solution, followed by extraction with chloroform. The organic layer was dried over anhydrous magnesium sulfate, then filtered, and concentrated under reduced pressure to obtain (Z)-2-(octadec-9-en-1-ylthio)ethan-1-ol (2.35 g, quantitative).

(Z)-2-(Octadec-9-en-1-ylthio)ethan-1-ol (1.50 g, 4.56 mmol) was dissolved in dichloromethane (10.0 mL). To the solution, triethylamine (1.91 mL, 13.7 mmol) and methanesulfonyl chloride (0.889 mL, 11.4 mmol) were added at 0° C., and the mixture was stirred at room temperature for 2.5 hours. Saturated saline was added to the reaction solution, followed by extraction with chloroform. The organic layer was dried over anhydrous magnesium sulfate, then filtered, and concentrated under reduced pressure. The obtained residue was purified by silica gel column chromatography (heptane/ethyl acetate=100/0 to 90/10) to obtain (Z)-(2-chloroethyl)(octadec-9-en-1-yl)sulfane (0.630 g, yield: 39.8%).

$^1$H-NMR (400 MHz, CDCl$_3$) δ: 5.36-5.33 (m, 2H), 3.64-3.60 (m, 2H), 2.87-2.83 (m, 2H), 2.56 (t, J=7.4 Hz, 2H), 2.03-2.00 (m, 4H), 1.61-1.56 (m, 2H), 1.37-1.29 (m, 22H), 0.88 (t, J=6.8 Hz, 3H).

Step 2

(9Z,12Z)-Octadeca-9,12-dien-1-yl methanesulfonate (6.00 g, 17.4 mmol) was dissolved in acetonitrile (40.0 mL). To the solution, cesium carbonate (14.2 g, 43.5 mmol), tetrabutylammonium iodide (8.36 g, 22.6 mmol), and N-(tert-butoxycarbonyl)-2-nitrobenzenesulfonamide (6.84 g, 22.6 mmol) were added, and the mixture was stirred overnight at 60° C. Saturated saline was added to the reaction solution, followed by extraction with ethyl acetate. The organic layer was dried over anhydrous magnesium sulfate, then filtered, and concentrated under reduced pressure. The obtained residue was purified by silica gel column chromatography (heptane/ethyl acetate=100/0 to 70/30) to obtain tert-butyl [(2-nitrophenyl)sulfonyl][(9Z,12Z)-octadeca-9,12-dien-1-yl]carbamate (7.80 g, yield: 81.0%).

tert-Butyl [(2-nitrophenyl)sulfonyl][(9Z,12Z)-octadeca-9,12-dien-1-yl]carbamate (7.80 g, 14.2 mmol) was dissolved in dichloromethane (25.0 mL). To the solution, trifluoroacetic acid (21.8 mL, 283 mmol) was added, and the mixture was stirred at room temperature for 3 hours. The reaction solution was concentrated under reduced pressure, and the obtained residue was purified by amino silica gel column chromatography (heptane/ethyl acetate=100/0 to 70/30) to obtain 2-nitro-N-[(9Z,12Z)-octadeca-9,12-dien-1-yl]benzenesulfonamide (5.10 g, yield: 80.0%).

$^1$H-NMR (400 MHz, CDCl$_3$) δ: 8.15-8.13 (m, 1H), 7.88-7.85 (m, 1H), 7.77-7.71 (m, 2H), 5.37-5.33 (m, 4H), 5.23 (t, J=5.8 Hz, 1H), 3.09 (td, J=7.1, 5.8 Hz, 2H), 2.77 (t, J=6.2 Hz, 2H), 2.07-2.01 (m, 4H), 1.55-1.50 (m, 2H), 1.39-1.23 (m, 16H), 0.89 (t, J=6.8 Hz, 3H).

Step 3

2-Nitro-N-[(9Z,12Z)-octadeca-9,12-dien-1-yl]benzenesulfonamide (0.200 g, 0.444 mmol) obtained in step 2 was dissolved in acetonitrile (4.00 mL). To the solution, cesium carbonate (0.289 g, 0.888 mmol), tetrabutylammonium iodide (0.164 g, 0.444 mmol), and (Z)-(2-chloroethyl)(octadec-9-en-1-yl)sulfane (0.162 g, 0.466 mmol) obtained in step 1 were added, and the mixture was stirred at 80° C. for 4 hours. Saturated saline was added to the reaction solution, followed by extraction with ethyl acetate. The organic layer was dried over anhydrous magnesium sulfate, then filtered, and concentrated under reduced pressure. The obtained residue was purified by silica gel column chromatography (heptane/ethyl acetate=100/0 to 85/15) to obtain 2-nitro-N-(2-{[(Z)-octadec-9-en-1-yl]thio}ethyl)-N-[(9Z,12Z)-octadeca-9,12-dien-1-yl]benzenesulfonamide (0.277 g, yield: 82.0%).

2-Nitro-N-(2-{[(Z)-octadec-9-en-1-yl]thio}ethyl)-N-[(9Z,12Z)-octadeca-9,12-dien-1-yl]benzenesulfonamide (0.277 g, 0.364 mmol) was dissolved in acetonitrile (4.00 mL). To the solution, diazabicycloundecene (0.137 mL, 0.909 mmol) and 1-dodecanethiol (0.217 mL, 0.909 mmol) were added, and the mixture was stirred at 70° C. for 3 hours. Saturated saline was added to the reaction solution, followed by extraction with ethyl acetate. The organic layer was dried over anhydrous magnesium sulfate, then filtered, and concentrated under reduced pressure. The obtained residue was purified by amino silica gel column chromatography (heptane/ethyl acetate=100/0 to 70/30) and silica gel column chromatography (heptane/ethyl acetate=100/0 to 50/50) to obtain (9Z,12Z)—N-(2-{[(Z)-octadec-9-en-1-yl]thio}ethyl)octadeca-9,12-dien-1-amine (0.0525 g, yield: 25.1%).

ESI-MS m/z: 576 (M+H)$^+$; $^1$H-NMR (400 MHz, CDCl$_3$) δ: 5.42-5.30 (m, 6H), 2.82-2.76 (m, 4H), 2.67 (t, J=6.2 Hz, 2H), 2.60 (t, J=7.4 Hz, 2H), 2.51 (t, J=7.5 Hz, 2H), 2.05-2.01 (m, 8H), 1.59-1.48 (m, 4H), 1.39-1.27 (m, 38H), 0.89-0.88 (m, 6H).

Example C2

(9Z,12Z)—N-Methyl-N-(2-{[(Z)-octadec-9-en-1-yl]thio}ethyl)octadeca-9,12-dien-1-amine (Compound CL-68)

Step 1

(9Z,12Z)—N-Methyl-N-(2-{[(Z)-octadec-9-en-1-yl]thio}ethyl)octadeca-9,12-dien-1-amine (0.0200 g, 37.2%) was obtained by the same approach as in Reference Example B31 using (9Z,12Z)—N-(2-{[(Z)-octadec-9-en-1-yl]thio}ethyl)octadeca-9,12-dien-1-amine instead of 2-methyl-1,3-bis((9Z,12Z)-octadeca-9,12-dien-1-yloxy)propan-2-amine.

ESI-MS m/z: 590 (M+H)$^+$; $^1$H-NMR (400 MHz, CDCl$_3$) δ: 5.42-5.29 (m, 6H), 2.77 (t, J=6.3 Hz, 2H), 2.64-2.55 (m, 4H), 2.52 (t, J=7.5 Hz, 2H), 2.35 (t, J=7.6 Hz, 2H), 2.25 (s,

3H), 2.06-2.00 (m, 8H), 1.62-1.56 (m, 2H), 1.47-1.45 (m, 2H), 1.36-1.30 (m, 38H), 0.91-0.86 (m, 6H).

Example C3

2-(Dimethylamino)-N-(2-{[(Z)-octadec-9-en-1-yl]thio}ethyl)-N-[(9Z,12Z)-octadeca-9,12-dien-1-yl]acetamide (Compound CL-69)

Step 1

(9Z,12Z)—N-(2-{[(Z)-Octadec-9-en-1-yl]thio}ethyl)octadeca-9,12-dien-1-amine (1.54 g, 2.66 mmol) obtained in step 3 of Example C1 was dissolved in dichloromethane (10.0 mL). To the solution, N,N-diisopropylethylamine (1.16 mL, 6.66 mmol), 1-[bis(dimethylamino)methylene]-1H-1,2,3-triazolo[4,5-b]pyridinium 3-oxide hexafluorophosphate (2.53 g, 6.66 mmol), and dimethylglycine (0.550 g, 5.33 mmol) were added, and the mixture was stirred at room temperature for 2 hours. Saturated saline was added to the reaction solution, followed by extraction with ethyl acetate. The organic layer was dried over anhydrous magnesium sulfate, then filtered, and concentrated under reduced pressure. The obtained residue was purified by amino silica gel column chromatography (heptane/ethyl acetate=100/0 to 80/20) and silica gel column chromatography (chloroform/methanol=100/0 to 90/10) to obtain 2-(dimethylamino)-N-(2-{[(Z)-octadec-9-en-1-yl]thio}ethyl)-N-[(9Z,12Z)-octadeca-9,12-dien-1-yl]acetamide (1.41 g, yield: 80.0%).

ESI-MS m/z: 661 (M+H)$^+$; $^1$H-NMR (400 MHz, CDCl$_3$) δ: 5.42-5.29 (m, 6H), 3.57 (dt, J=15.7, 7.9 Hz, 1H), 3.47 (dt, J=15.7, 7.9 Hz, 1H), 3.36 (dt, J=15.7, 7.9 Hz, 1H), 3.29 (dt, J=15.7, 7.9 Hz, 1H), 3.10 (d, J=16.7 Hz, 2H), 2.77 (t, J=6.1 Hz, 2H), 2.69-2.65 (m, 2H), 2.57-2.54 (m, 2H), 2.29 (s, 3H), 2.27 (s, 3H), 2.05-1.99 (m, 8H), 1.60-1.56 (m, 4H), 1.39-1.27 (m, 38H), 0.89-0.88 (m, 6H).

Example C4

Bis(2-{[(Z)-octadec-9-en-1-yl]thio}ethyl)amine (Compound CL-70)

Step 1

(Z)-2-Nitro-N-[2-(octadec-9-en-1-ylthio)ethyl]benzenesulfonamide (0.270 g, quantitative) was obtained by the same approach as in step 2 of Example C1 using (Z)-(2-chloroethyl)(octadec-9-en-1-yl)sulfane obtained in step 1 of Example C1 instead of (9Z,12Z)-octadeca-9,12-dien-1-yl methanesulfonate.

Step 2

Bis(2-{[(Z)-octadec-9-en-1-yl]thio}ethyl)amine (0.0470 g, 57.2%) was obtained by the same approach as in step 3 of Example C1 using (Z)-2-nitro-N-[2-(octadec-9-en-1-ylthio)ethyl]benzenesulfonamide instead of 2-nitro-N-[(9Z,12Z)-octadeca-9,12-dien-1-yl]benzenesulfonamide.

ESI-MS m/z: 638 (M+H)$^+$; $^1$H-NMR (400 MHz, CDCl$_3$) δ: 5.39-5.31 (m, 4H), 2.82 (t, J=6.7 Hz, 4H), 2.68 (t, J=6.5 Hz, 4H), 2.51 (t, J=7.5 Hz, 4H), 2.01 (q, J=6.4 Hz, 8H), 1.59-1.55 (m, 4H), 1.39-1.27 (m, 44H), 0.89 (t, J=7.0 Hz, 6H).

Example C5

2-(Dimethylamino)-N,N-bis(2-{[(9Z,12Z)-octadeca-9,12-dien-1-yl]thio}ethyl)acetamide (Compound CL-71)

Step 1

2-(Dimethylamino)-N,N-bis(2-{[(9Z,12Z)-octadeca-9,12-dien-1-yl]thio}ethyl)acetamide (0.0493 g, yield: 87.0%) was obtained by the same approach as in step 1 of Example C3 using bis(2-{[(9Z,12Z)-octadeca-9,12-dien-1-yl]thio}ethyl)amine obtained by the same approach as in Example C4 instead of (9Z,12Z)—N-(2-{[(Z)-octadec-9-en-1-yl]thio}ethyl)octadeca-9,12-dien-1-amine.

ESI-MS m/z: 719 (M+H)$^+$; $^1$H-NMR (400 MHz, CDCl$_3$) δ: 5.42-5.30 (m, 8H), 3.62 (dt, J=15.0, 7.5 Hz, 2H), 3.48 (dt, J=15.0, 7.5 Hz, 2H), 3.14 (s, 2H), 2.77 (t, J=6.7 Hz, 4H), 2.69 (t, J=7.5 Hz, 4H), 2.55 (dt, J=12.8, 7.6 Hz, 4H), 2.28 (s, 6H), 2.05 (q, J=6.8 Hz, 8H), 1.60-1.58 (m, 4H), 1.39-1.26 (m, 32H), 0.89 (t, J=7.0 Hz, 6H).

Example C6

2-(Dimethylamino)-N-(2-{[(Z)-octadec-9-en-1-yl]thio}ethyl)-N-[(9Z,12Z)-octadeca-9,12-dien-1-yl]ethane-1-sulfonamide (Compound CL-72)

Step 1

(9Z,12Z)—N-(2-{[(Z)-Octadec-9-en-1-yl]thio}ethyl)octadeca-9,12-dien-1-amine (0.183 g, 0.318 mmol) obtained in step 3 of Example C1 was dissolved in dichloromethane (3.00 mL). To the solution, triethylamine (0.260 mL, 1.87 mmol) and 2-chloromethanesulfonyl chloride (0.140 mL, 1.33 mmol) were added at 0° C., and the mixture was stirred overnight at room temperature. 0.01 N hydrochloric acid was added to the reaction solution, and the mixture was diluted with distilled water, followed by extraction with ethyl acetate. The organic layer was dried over anhydrous sodium sulfate, then filtered, and concentrated under reduced pressure. The obtained residue was purified by silica gel column chromatography (heptane/ethyl acetate=100/0 to 86/14) to obtain N-(2-{[(Z)-octadec-9-en-1-yl]thio}ethyl)-N-[(9Z,12Z)-octadeca-9,12-dien-1-yl]ethanesulfonamide (0.160 g, yield: 61.0%).

N-(2-{[(Z)-Octadec-9-en-1-yl]thio}ethyl)-N-[(9Z,12Z)-octadeca-9,12-dien-1-yl]ethanesulfonamide (0.113 g, 0.169 mmol) was dissolved in tetrahydrofuran (0.500 mL). To the solution, a dimethylamine solution (1.08 mL, 2.16 mmol, 2 M in THE) was added, and the mixture was stirred for 3 hours under heating to reflux. The reaction solution was concentrated under reduced pressure, and the obtained residue was purified by amino silica gel column chromatography (chloroform/methanol=100/0 to 96/4) to obtain 2-(dimethylamino)-N-(2-{[(Z)-octadec-9-en-1-yl]thio}ethyl)-N-[(9Z,12Z)-octadeca-9,12-dien-1-yl]ethane-1-sulfonamide (0.113 g, yield: 94.0%).

ESI-MS m/z: 712 (M+H)$^+$; $^1$H-NMR (400 MHz, CDCl$_3$) δ: 5.42-5.30 (m, 6H), 3.36 (t, J=7.8 Hz, 2H), 3.20 (t, J=7.8 Hz, 2H), 3.17-3.11 (m, 2H), 2.80-2.68 (m, 6H), 2.54 (t, J=7.3 Hz, 2H), 2.27 (s, 6H), 2.09-1.93 (m, 8H), 1.63-1.53 (m, 4H), 1.41-1.22 (m, 38H), 0.92-0.85 (m, 6H).

Example C7

2-(Dimethylamino)ethyl(2-{[(Z)-octadec-9-en-1-yl]thio}ethyl)[(9Z,12Z)-octadeca-9,12-dien-1-yl]carbamate (Compound CL-73)

Step 1

(9Z,12Z)—N-(2-{[(Z)-Octadec-9-en-1-yl]thio}ethyl)octadeca-9,12-dien-1-amine (0.127 g, 0.220 mmol) obtained in step 3 of Example C1 was dissolved in dichloromethane (1.10 mL). To the solution, triphosgene (0.0406 g, 0.410 mmol) was added, and the mixture was stirred at room temperature for 30 minutes. Triethylamine (0.150 mL, 1.08 mmol) and 2-dimethylaminoethanol (0.100 mL, 0.998 mmol) were added to the reaction solution, and the mixture was stirred overnight at room temperature. A saturated aqueous solution of sodium bicarbonate was added to the reaction solution, followed by extraction with ethyl acetate. The organic layer was dried over anhydrous magnesium sulfate, then filtered, and concentrated under reduced pressure. The obtained residue was purified by silica gel column chromatography (chloroform/methanol=100/0 to 90/10) to obtain 2-(dimethylamino)ethyl(2-{[(Z)-octadec-9-en-1-yl]thio}ethyl) [(9Z,12Z)-octadeca-9,12-dien-1-yl]carbamate (0.140 g, yield: 92.0%).

ESI-MS m/z: 692 (M+H)$^+$; $^1$H-NMR (400 MHz, CDCl$_3$) δ: 5.42-5.30 (m, 6H), 4.18 (t, J=6.0 Hz, 2H), 3.43-3.32 (m, 2H), 3.28-3.18 (m, 2H), 2.77 (t, J=6.4 Hz, 2H), 2.70-2.60 (m, 2H), 2.60-2.49 (m, 4H), 2.28 (s, 6H), 2.09-1.93 (m, 8H), 1.61-1.47 (m, 4H), 1.42-1.19 (m, 38H), 0.91-0.86 (m, 6H).

Example C8

1-Methyl-3,3-bis({[(Z)-octadec-9-en-1-yl]thio}methyl)azetidine (Compound CL-77)

Step 1
Azetidine-3,3-diyl dimethanol (0.315 g, 2.96 mmol) was dissolved in methanol (5.00 mL). To the solution, di-tert-butyl dicarbonate (0.936 mL, 4.03 mmol) and triethylamine (0.750 mL, 5.38 mmol) were added, and the mixture was stirred overnight at room temperature. The reaction solution was concentrated under reduced pressure to obtain tert-butyl 3,3-bis(hydroxymethyl)azetidine-1-carboxylate (0.584 g, quantitative).

tert-Butyl 3,3-bis(hydroxymethyl)azetidine-1-carboxylate (0.584 g, 2.69 mmol) was dissolved in dichloromethane (10.0 mL). To the solution, methanesulfonyl chloride (0.524 mL, 6.73 mmol) and triethylamine (1.13 mL, 8.07 mmol) were added at 0° C., and the mixture was stirred at room temperature for 2 hours. Saturated saline was added to the reaction solution, followed by extraction with ethyl acetate. The organic layer was dried over anhydrous magnesium sulfate, then filtered, and concentrated under reduced pressure to obtain tert-butyl 3,3-bis{[(methylsulfonyl)oxy]methyl}azetidine-1-carboxylate (1.01 g, quantitative).

tert-Butyl 3,3-bis{[(methylsulfonyl)oxy]methyl}azetidine-1-carboxylate (0.900 g, 2.41 mmol) was dissolved in dimethylformamide (15.0 mL). To the solution, S-potassium thioacetate (0.963 g, 8.44 mmol) was added, and the mixture was stirred overnight at 55° C. Saturated saline was added to the reaction solution, followed by extraction with ethyl acetate. The organic layer was dried over anhydrous magnesium sulfate, then filtered, and concentrated under reduced pressure. The obtained residue was purified by silica gel column chromatography (heptane/ethyl acetate=100/0 to 34/66) to obtain tert-butyl 3,3-bis[(acetylthio)methyl]azetidine-1-carboxylate (0.742 g, yield: 92.0%).

$^1$H-NMR (400 MHz, CDCl$_3$) δ: 3.61 (s, 4H), 3.20 (s, 4H), 2.38 (s, 6H), 1.44 (s, 9H).

Step 2
tert-Butyl 3,3-bis[(acetylthio)methyl]azetidine-1-carboxylate (0.342 g, 1.03 mmol) was dissolved in tetrahydrofuran (6.00 mL). To the solution, (Z)-octadec-9-en-1-yl methanesulfonate (1.07 g, 3.08 mmol) and a solution of 28% sodium methoxide in methanol (0.615 mL, 3.08 mmol) were added, and the mixture was stirred at room temperature for 4 hours. Saturated saline was added to the reaction solution, followed by extraction with ethyl acetate. The organic layer was dried over anhydrous magnesium sulfate, then filtered, and concentrated under reduced pressure. The obtained residue was purified by silica gel column chromatography (heptane/ethyl acetate=100/0 to 90/10) to obtain tert-butyl 3,3-bis({[(Z)-octadec-9-en-1-yl]thio}methyl)azetidine-1-carboxylate (0.487 g, yield: 63.3%).

tert-Butyl 3,3-bis({[(Z)-octadec-9-en-1-yl]thio}methyl)azetidine-1-carboxylate (0.487 g, 0.649 mmol) was dissolved in dichloromethane (3.00 mL). To the solution, trifluoroacetic acid (1.00 mL, 13.0 mmol) was added, and the mixture was stirred at room temperature for 2 hours. A saturated aqueous solution of sodium bicarbonate was added to the reaction solution, followed by extraction with ethyl acetate. The organic layer was dried over anhydrous magnesium sulfate, then filtered, and concentrated under reduced pressure. The obtained residue was purified by silica gel column chromatography (heptane/ethyl acetate=100/0 to 25/75, chloroform/methanol=100/0 to 95/5) to obtain 3,3-bis({[(Z)-octadec-9-en-1-yl]thio}methyl)azetidine (0.310 g, yield: 73.5%).

ESI-MS m/z: 650 (M+H)$^+$; $^1$H-NMR (400 MHz, CDCl$_3$) δ: 5.39-5.31 (m, 4H), 3.47 (s, 4H), 2.95 (s, 4H), 2.56 (t, J=7.5 Hz, 4H), 2.01 (q, J=6.4 Hz, 8H), 1.63-1.56 (m, 4H), 1.37-1.29 (m, 44H), 0.88 (t, J=6.8 Hz, 6H).

Step 3
1-Methyl-3,3-bis({[(Z)-octadec-9-en-1-yl]thio}methyl)azetidine (0.0925 g, yield: 88.0%) was obtained by the same approach as in Reference Example B31 using 3,3-bis({[(Z)-octadec-9-en-1-yl]thio}methyl)azetidine instead of bis(2-{[(Z)-octadec-9-en-1-yl]thio}ethyl)amine.

ESI-MS m/z: 664 (M+H)$^+$; $^1$H-NMR (400 MHz, CDCl$_3$) δ: 5.36-5.33 (m, 4H), 3.07 (s, 4H), 2.92 (s, 4H), 2.54 (t, J=7.5 Hz, 4H), 2.33 (s, 3H), 2.01 (q, J=6.4 Hz, 8H), 1.62-1.55 (m, 4H), 1.36-1.29 (m, 44H), 0.88 (t, J=7.0 Hz, 6H).

Example C9

1-[3,3-Bis({[(Z)-octadec-9-en-1-yl]thio}methyl)azetidin-1-yl]-2-(dimethylamino)ethan-1-one (Compound CL-75)

Step 1
1-[3,3-Bis({[(Z)-octadec-9-en-1-yl]thio}methyl)azetidin-1-yl]-2-(dimethylamino)ethan-1-one (0.0815 g, 72.1%) was obtained by the same approach as in step 1 of Example C3 using 3,3-bis({[(Z)-octadec-9-en-1-yl]thio}methyl)azetidine obtained in step 2 of Example C8 instead of (9Z,12Z)—N-(2-{[(Z)-octadec-9-en-1-yl]thio}ethyl)octadeca-9,12-dien-1-amine.

ESI-MS m/z: 735 (M+H)$^+$; $^1$H-NMR (400 MHz, CDCl$_3$) δ: 5.39-5.31 (m, 4H), 3.97 (s, 2H), 3.80 (s, 2H), 2.96 (s, 2H), 2.89 (s, 4H), 2.56 (t, J=7.5 Hz, 4H), 2.28 (s, 6H), 2.01 (q, J=6.4 Hz, 8H), 1.63-1.55 (m, 4H), 1.36-1.29 (m, 44H), 0.88 (t, J=6.8 Hz, 6H).

Example C10

1-Methyl-3,3-bis({[(9Z,12Z)-octadeca-9,12-dien-1-yl]thio}methyl)azetidine (Compound CL-76)

Step 1
3,3-Bis({[(9Z,12Z)-octadeca-9,12-dien-1-yl]thio}methyl)azetidine (0.338 g, 56.6%) was obtained by the same approach as in step 2 of Example C8 using (9Z,12Z)- octadeca-9,12-dien-1-yl methanesulfonate instead of (Z)-octadec-9-en-1-yl methanesulfonate.

ESI-MS m/z: 646 (M+H)$^+$; $^1$H-NMR (400 MHz, CDCl$_3$) δ: 5.42-5.29 (m, 8H), 3.47 (s, 4H), 2.95 (s, 4H), 2.77 (t, J=6.7 Hz, 4H), 2.56 (t, J=7.4 Hz, 4H), 2.05 (q, J=6.8 Hz, 8H), 1.63-1.56 (m, 4H), 1.39-1.24 (m, 32H), 0.88 (t, J=6.8 Hz, 6H).

Step 2

1-Methyl-3,3-bis({[(9Z,12Z)-octadeca-9,12-dien-1-yl]thio}methyl)azetidine (0.0680 g, yield: 63.4%) was obtained by the same approach as in Reference Example B31 using 3,3-bis({[(9Z,12Z)-octadeca-9,12-dien-1-yl]thio}methyl)azetidine instead of bis(2-{[(Z)-octadec-9-en-1-yl]thio}ethyl)amine.

ESI-MS m/z: 660 (M+H)$^+$; $^1$H-NMR (400 MHz, CDCl$_3$) δ: 5.42-5.29 (m, 8H), 3.07 (s, 4H), 2.92 (s, 4H), 2.77 (t, J=6.6 Hz, 4H), 2.54 (t, J=7.5 Hz, 4H), 2.33 (s, 3H), 2.05 (q, J=6.9 Hz, 8H), 1.62-1.55 (m, 4H), 1.39-1.25 (m, 32H), 0.89 (t, J=6.8 Hz, 6H).

Example C11

1-[3,3-Bis({[(9Z,12Z)-octadeca-9,12-dien-1-yl]thio}methyl)azetidin-1-yl]-2-(dimethylamino)ethan-1-one (Compound CL-74)

Step 1

1-[3,3-Bis({[(9Z,12Z)-octadeca-9,12-dien-1-yl]thio}methyl)azetidin-1-yl]-2-(dimethylamino)ethan-1-one (0.0692 g, 61.1%) was obtained by the same approach as in step 1 of Example C3 using 3,3-bis({[(9Z,12Z)-octadeca-9,12-dien-1-yl]thio}methyl)azetidine obtained in step 1 of Example C10 instead of (9Z,12Z)—N-(2-{[(Z)-octadec-9-en-1-yl]thio}ethyl)octadeca-9,12-dien-1-amine.

ESI-MS m/z: 731 (M+H)$^+$; $^1$H-NMR (400 MHz, CDCl$_3$) δ: 5.42-5.29 (m, 8H), 3.97 (s, 2H), 3.80 (s, 2H), 2.98 (s, 2H), 2.89 (s, 4H), 2.77 (t, J=6.7 Hz, 4H), 2.56 (t, J=7.5 Hz, 4H), 2.29 (s, 6H), 2.05 (q, J=6.8 Hz, 8H), 1.63-1.55 (m, 4H), 1.39-1.24 (m, 32H), 0.89 (t, J=7.0 Hz, 6H).

Example C12

1-Methyl-3-({[(Z)-octadec-9-en-1-yl]oxy}methyl)-3-({[(Z)-octadec-9-en-1-yl]thio}methyl)azetidine (Compound CL-81)

Step 1

Azetidine-3,3-diyl dimethanol (0.315 g, 2.96 mmol) was dissolved in methanol (5.00 mL). To the solution, di-tert-butyl dicarbonate (0.936 mL, 4.03 mmol) and triethylamine (0.750 mL, 5.38 mmol) were added, and the mixture was stirred overnight at room temperature. The reaction solution was concentrated under reduced pressure to obtain tert-butyl 3,3-bis(hydroxymethyl)azetidine-1-carboxylate (0.584 g, quantitative).

tert-Butyl 3,3-bis(hydroxymethyl)azetidine-1-carboxylate (0.292 g, 1.35 mmol) was dissolved in toluene (6.00 mL). To the solution, sodium hydride (0.0810 g, 2.02 mmol) and (Z)-octadec-9-en-1-yl methanesulfonate (0.559 g, 1.61 mmol) were added, and the mixture was stirred at 100° C. for 5 hours. Distilled water and saturated saline were added to the reaction solution, followed by extraction with ethyl acetate. The organic layer was dried over anhydrous magnesium sulfate, then filtered, and concentrated under reduced pressure. The obtained residue was purified by silica gel column chromatography (chloroform/methanol=100/0 to 95/5) to obtain tert-butyl (Z)-3-(hydroxymethyl)-3-[(octadec-9-en-1-yloxy)methyl]azetidine-1-carboxylate (0.296 g, yield: 47.1%).

$^1$H-NMR (400 MHz, CDCl$_3$) δ: 5.35-5.34 (m, 2H), 3.81 (d, J=5.6 Hz, 2H), 3.72 (d, J=8.4 Hz, 2H), 3.66 (s, 2H), 3.63 (d, J=8.4 Hz, 2H), 3.45 (t, J=6.6 Hz, 2H), 2.53 (t, J=5.6 Hz, 1H), 2.01 (q, J=6.4 Hz, 4H), 1.60-1.52 (m, 2H), 1.44 (s, 9H), 1.34-1.28 (m, 22H), 0.88 (t, J=6.8 Hz, 3H).

Step 2 tert-Butyl (Z)-3-(hydroxymethyl)-3-[(octadec-9-en-1-yloxy)methyl]azetidine-1-carboxylate (0.296 g, 0.633 mmol) was dissolved in dichloromethane (5.00 mL). To the solution, methanesulfonyl chloride (0.0640 mL, 0.823 mmol) and triethylamine (0.132 mL, 0.949 mmol) were added, and the mixture was stirred at room temperature for 2.5 hours. Saturated saline was added to the reaction solution, followed by extraction with ethyl acetate. The organic layer was dried over anhydrous magnesium sulfate, then filtered, and concentrated under reduced pressure to obtain tert-butyl (Z)-3-{[(methylsulfonyl)oxy]methyl}-3-[(octadec-9-en-1-yloxy)methyl]azetidine-1-carboxylate (0.345 g, quantitative).

tert-Butyl (Z)-3-{[(methylsulfonyl)oxy]methyl}-3-[(octadec-9-en-1-yloxy)methyl]azetidine-1-carboxylate was dissolved in dimethylformamide (8.00 mL). To the solution, S-potassium thioacetate (0.130 g, 1.14 mmol) was added, and the mixture was stirred overnight at 55° C. Distilled water and saturated saline were added to the reaction solution, followed by extraction with ethyl acetate. The organic layer was dried over anhydrous magnesium sulfate, then filtered, and concentrated under reduced pressure. The obtained residue was purified by silica gel column chromatography (heptane/ethyl acetate=100/0 to 80/20) to obtain tert-butyl (Z)-3-[(acetylthio)methyl]-3-[(octadec-9-en-1-yloxy)methyl]azetidine-1-carboxylate (0.250 g, yield: 75.0%).

$^1$H-NMR (400 MHz, CDCl$_3$) δ: 5.36-5.33 (m, 2H), 3.67 (d, J=8.6 Hz, 2H), 3.60 (d, J=8.6 Hz, 2H), 3.43-3.41 (m, 4H), 3.24 (s, 2H), 2.36 (s, 3H), 2.01 (q, J=6.3 Hz, 4H), 1.58-1.53 (m, 2H), 1.44 (s, 9H), 1.29-1.27 (m, 22H), 0.88 (t, J=7.0 Hz, 3H).

Step 3

3-({[(Z)-Octadec-9-en-1-yl]oxy}methyl)-3-({[(Z)-octadec-9-en-1-yl]thio}methyl)azetidine (0.187 g, yield: 62.6%) was obtained by the same approach as in step 2 of Example C8 using tert-butyl (Z)-3-[(acetylthio)methyl]-3-[(octadec-9-en-1-yloxy)methyl]azetidine-1-carboxylate instead of tert-butyl 3,3-bis[(acetylthio)methyl]azetidine-1-carboxylate.

ESI-MS m/z: 634 (M+H)$^+$; $^1$H-NMR (400 MHz, CDCl$_3$) δ: 5.35-5.34 (m, 4H), 3.57 (s, 2H), 3.46-3.40 (m, 6H), 2.88 (s, 2H), 2.52 (t, J=7.4 Hz, 2H), 2.01 (q, J=6.4 Hz, 8H), 1.59-1.56 (m, 4H), 1.34-1.27 (m, 44H), 0.88 (t, J=6.8 Hz, 6H).

Step 4

1-Methyl-3-({[(Z)-octadec-9-en-1-yl]oxy}methyl)-3-({[(Z)-octadec-9-en-1-yl]thio}methyl)azetidine (0.0760 g, yield: 91.0%) was obtained by the same approach as in Reference Example B31 using 3-({[(Z)-octadec-9-en-1-yl]oxy}methyl)-3-({[(Z)-octadec-9-en-1-yl]thio}methyl)azetidine instead of bis(2-{[(Z)-octadec-9-en-1-yl]thio}ethyl)amine.

ESI-MS m/z: 648 (M+H)$^+$; $^1$H-NMR (400 MHz, CDCl$_3$) δ: 5.39-5.31 (m, 4H), 3.53 (s, 2H), 3.44 (t, J=6.7 Hz, 2H), 3.21-3.14 (m, 4H), 2.88 (s, 2H), 2.52 (t, J=7.5 Hz, 2H), 2.39 (s, 3H), 2.01 (q, J=6.8 Hz, 8H), 1.62-1.53 (m, 4H), 1.34-1.27 (m, 44H), 0.88 (t, J=7.0 Hz, 6H).

Example C13

2-(Dimethylamino)-1-(3-({[(Z)-octadec-9-en-1-yl]oxy}methyl)-3-({[(Z)-octadec-9-en-1-yl]thio}methyl)azetidin-1-yl)ethan-1-one (Compound CL-80)

Step 1

2-(Dimethylamino)-1-(3-({[(Z)-octadec-9-en-1-yl]oxy}methyl)-3-({[(Z)-octadec-9-en-1-yl]thio}methyl)azetidin-1-yl)ethan-1-one (0.0360 g, 34.1%) was obtained by the same approach as in step 1 of Example C3 using 3-({[(Z)-octadec-9-en-1-yl]oxy}methyl)-3-({[(Z)-octadec-9-en-1-yl]thio}methyl)azetidine obtained in step 3 of Example C12 instead of (9Z,12Z)—N-(2-{[(Z)-octadec-9-en-1-yl]thio}ethyl)octadeca-9,12-dien-1-amine.

ESI-MS m/z: 719 (M+H)$^+$; $^1$H-NMR (400 MHz, CDCl$_3$) δ: 5.36-5.33 (m, 4H), 3.98 (d, J=9.1 Hz, 1H), 3.92 (d, J=9.1 Hz, 1H), 3.82 (d, J=9.9 Hz, 1H), 3.74 (d, J=9.9 Hz, 1H), 3.51 (s, 2H), 3.44 (t, J=6.5 Hz, 2H), 2.95 (s, 2H), 2.84 (s, 2H), 2.53 (t, J=7.5 Hz, 2H), 2.28 (s, 6H), 2.01 (q, J=6.3 Hz, 8H), 1.59-1.54 (m, 4H), 1.31-1.28 (m, 44H), 0.88 (t, J=6.8 Hz, 6H).

Example C14

1-Methyl-3-({[(9Z,12Z)-octadeca-9,12-dien-1-yl]oxy}methyl)-3-({[(9Z,12Z)-octadeca-9,12-dien-1-yl]thio}methyl)azetidine (Compound CL-79)

Step 1 tert-Butyl 3-(hydroxymethyl)-3-({[(9Z,12Z)-octadeca-9,12-dien-1-yl]oxy}methyl)azetidine-1-carboxylate (0.166 g, yield: 26.6%) was obtained by the same approach as in step 1 of Example C12 using (9Z,12Z)-octadeca-9,12-dien-1-yl methanesulfonate instead of (Z)-octadec-9-en-1-yl methanesulfonate.

$^1$H-NMR (400 MHz, CDCl$_3$) δ: 5.42-5.29 (m, 4H), 3.81 (d, J=5.3 Hz, 2H), 3.72 (d, J=8.4 Hz, 2H), 3.66 (s, 2H), 3.63 (d, J=8.4 Hz, 2H), 3.45 (t, J=6.6 Hz, 2H), 2.77 (t, J=6.7 Hz, 2H), 2.53 (t, J=5.3 Hz, 1H), 2.05 (q, J=6.8 Hz, 4H), 1.57-1.43 (m, 2H), 1.44 (s, 9H), 1.39-1.25 (m, 16H), 0.89 (t, J=7.0 Hz, 3H).

Step 2 tert-Butyl 3-[(acetylthio)methyl]-3-({[(9Z,12Z)-octadeca-9,12-dien-1-yl]oxy}methyl)azetidine-1-carboxylate (0.0560 g, 29.9%) was obtained by the same approach as in step 2 of Example C12 using tert-butyl 3-(hydroxymethyl)-3-({[(9Z,12Z)-octadeca-9,12-dien-1-yl]oxy}methyl)azetidine-1-carboxylate instead of tert-butyl (Z)-3-(hydroxymethyl)-3-[(octadec-9-en-1-yloxy)methyl]azetidine-1-carboxylate.

$^1$H-NMR (400 MHz, CDCl$_3$) δ: 5.42-5.30 (m, 4H), 3.67 (d, J=8.6 Hz, 2H), 3.60 (d, J=8.6 Hz, 2H), 3.43-3.41 (m, 4H), 3.24 (s, 2H), 2.77 (t, J=6.3 Hz, 2H), 2.36 (s, 3H), 2.05 (q, J=6.8 Hz, 4H), 1.56-1.52 (m, 2H), 1.44 (s, 9H), 1.33-1.29 (m, 16H), 0.89 (t, J=6.8 Hz, 3H).

Step 3

3-({[(9Z,12Z)-Octadeca-9,12-dien-1-yl]oxy}methyl)-3-({[(9Z,12Z)-octadeca-9,12-dien-1-yl]thio}methyl)azetidine (0.0335 g, yield: 68.1%) was obtained by the same approach as in step 2 of Example C8 using tert-butyl 3-[(acetylthio)methyl]-3-({[(9Z,12Z)-octadeca-9,12-dien-1-yl]oxy}methyl)azetidine-1-carboxylate instead of tert-butyl 3,3-bis[(acetylthio)methyl]azetidine-1-carboxylate.

ESI-MS m/z: 630 (M+H)$^+$; $^1$H-NMR (400 MHz, CDCl$_3$) δ: 5.42-5.30 (m, 8H), 3.77 (d, J=9.9 Hz, 2H), 3.72 (d, J=9.9 Hz, 2H), 3.54 (s, 2H), 3.48 (t, J=6.8 Hz, 2H), 2.90 (s, 2H), 2.77 (d, J=6.6 Hz, 4H), 2.54 (t, J=7.5 Hz, 2H), 2.05 (q, J=6.8 Hz, 8H), 1.62-1.54 (m, 4H), 1.39-1.24 (m, 32H), 0.89 (t, J=7.0 Hz, 6H).

Step 4

1-Methyl-3-({[(9Z,12Z)-octadeca-9,12-dien-1-yl]oxy}methyl)-3-({[(9Z,12Z)-octadeca-9,12-dien-1-yl]thio}methyl)azetidine (0.0125 g, yield: 76.0%) was obtained by the same approach as in Reference Example B31 using 3-({[(9Z,12Z)-octadeca-9,12-dien-1-yl]oxy}methyl)-3-({[(9Z,12Z)-octadeca-9,12-dien-1-yl]thio}methyl)azetidine instead of bis(2-{[(Z)-octadec-9-en-1-yl]thio}ethyl)amine.

ESI-MS m/z: 644 (M+H)$^+$; $^1$H-NMR (400 MHz, CDCl$_3$) δ: 5.42-5.30 (m, 8H), 3.52 (s, 2H), 3.44 (t, J=6.7 Hz, 2H), 3.23 (s, 4H), 2.88 (s, 2H), 2.77 (t, J=6.6 Hz, 4H), 2.53 (t, J=7.4 Hz, 2H), 2.40 (s, 3H), 2.05 (q, J=6.8 Hz, 8H), 1.59-1.57 (m, 4H), 1.39-1.25 (m, 32H), 0.89 (t, J=7.0 Hz, 6H).

Example C15

2-(Dimethylamino)-1-[3-({[(9Z,12Z)-octadeca-9,12-dien-1-yl]oxy}methyl)-3-({[(9Z,12Z)-octadeca-9,12-dien-1-yl]thio}methyl)azetidin-1-yl]ethan-1-one (Compound CL-78)

Step 1

2-(Dimethylamino)-1-[3-({[(9Z,12Z)-octadeca-9,12-dien-1-yl]oxy}methyl)-3-({[(9Z,12Z)-octadeca-9,12-dien-1-yl]thio}methyl)azetidin-1-yl]ethan-1-one (0.00830 g, 43.0%) was obtained by the same approach as in step 1 of Example C3 using 3-({[(9Z,12Z)-octadeca-9,12-dien-1-yl]oxy}methyl)-3-({[(9Z,12Z)-octadeca-9,12-dien-1-yl]thio}methyl)azetidine obtained in step 3 of Example C14 instead of (9Z,12Z)—N-(2-{[(Z)-octadec-9-en-1-yl]thio}ethyl)octadeca-9,12-dien-1-amine.

ESI-MS m/z: 715 (M+H)$^+$; $^1$H-NMR (400 MHz, CDCl$_3$) δ: 5.42-5.30 (m, 8H), 3.98 (d, J=9.1 Hz, 1H), 3.92 (d, J=9.1 Hz, 1H), 3.82 (d, J=9.6 Hz, 1H), 3.74 (d, J=9.6 Hz, 1H), 3.51 (s, 2H), 3.44 (t, J=6.6 Hz, 2H), 2.96 (s, 2H), 2.84 (s, 2H), 2.77 (t, J=6.7 Hz, 4H), 2.53 (t, J=7.5 Hz, 2H), 2.28 (s, 6H), 2.05 (q, J=6.8 Hz, 8H), 1.60-1.58 (m, 4H), 1.39-1.26 (m, 32H), 0.89 (t, J=7.0 Hz, 6H).

Example C16

3-[(2-{[(Z)-Octadec-9-en-1-yl]thio}ethyl) [(9Z,12Z)-octadeca-9,12-dien-1-yl]amino]propan-1-ol (Compound CL-82)

Step 1

(9Z,12Z)—N-(2-{[(Z)-Octadec-9-en-1-yl]thio}ethyl)octadeca-9,12-dien-1-amine (0.150 g, 0.260 mmol) was dissolved in dimethylformamide (1.00 mL). To the solution, cesium carbonate (0.255 g, 0.781 mmol) and (3-bromopropoxy)(tert-butyl)dimethylsilane (0.121 mL, 0.521 mmol) were added, and the mixture was stirred at 80° C. for 3 hours under microwave irradiation. Saturated saline was added to the reaction solution, followed by extraction with hexane. The organic layer was dried over anhydrous magnesium sulfate, then filtered, and concentrated under reduced pressure. The obtained residue was purified by silica gel column chromatography (heptane/ethyl acetate=80/20) to obtain (9Z,12Z)—N-{3-[(tert-butyldimethylsilyl)oxy]propyl}-N-(2-{[(Z)-octadec-9-en-1-yl]thio}ethyl)octadeca-9,12-dien-1-amine (0.114 g, yield: 58.5%).

(9Z,12Z)—N-{3-[(tert-Butyldimethylsilyl)oxy]propyl}-N-(2-{[(Z)-octadec-9-en-1-yl]thio}ethyl)octadeca-9,12-dien-1-amine (0.114 g, 0.152 mmol) was dissolved in tetrahydrofuran (1.00 mL). To the solution, tetrabutylammonium fluoride (0.228 mL, 0.228 mmol) was added, and the mixture was stirred at room temperature for 2 hours. Saturated saline was added to the reaction solution, followed by extraction with ethyl acetate. The organic layer was dried over anhydrous magnesium sulfate, then filtered, and concentrated under reduced pressure. The obtained residue was purified by silica gel column chromatography (heptane/ethyl acetate=100/0 to 80/20) and (chloroform/methanol=100/0 to 80/20) to obtain 3-[(2-{[(Z)-octadec-9-en-1-yl]thio}ethyl)[(9Z,12Z)-octadeca-9,12-dien-1-yl]amino]propan-1-ol (0.0640 g, yield: 66.3%).

ESI-MS m/z: 635 (M+H)$^+$; $^1$H-NMR (400 MHz, CDCl$_3$) δ: 5.42-5.30 (m, 6H), 3.79 (t, J=5.2 Hz, 2H), 2.78 (t, J=6.7 Hz, 2H), 2.68-2.60 (m, 6H), 2.52 (t, J=7.4 Hz, 2H), 2.44 (t, J=7.6 Hz, 2H), 2.08-1.96 (m, 8H), 1.71-1.66 (m, 2H), 1.62-1.54 (m, 2H), 1.50-1.46 (m, 2H), 1.39-1.27 (m, 38H), 0.90-0.88 (m, 6H).

Example C17

3-(Dimethylamino)propyl(2-{[(Z)-octadec-9-en-1-yl]thio}ethyl)[(9Z,12Z)-octadeca-9,12-dien-1-yl]carbamate (Compound CL-83)

Step 1

4-Nitrophenyl carbonochloridate (5.16 g, 25.1 mmol) was dissolved in diethyl ether (150 mL). To the solution, 3-(dimethylamino)propan-1-ol (3.00 mL, 25.1 mmol) was added, and the mixture was stirred at room temperature for 2 hours. Ethanol was added to the reaction solution, and the mixture was filtered to obtain 3-(dimethylamino)propyl(4-nitrophenyl)carbonate hydrochloride (5.49 g, 71.8%).

(9Z,12Z)—N-(2-{[(Z)-Octadec-9-en-1-yl]thio}ethyl)octadeca-9,12-dien-1-amine (0.104 g, 0.181 mmol) obtained in step 3 of Example C1 was dissolved in chloroform (2.00 mL). To the solution, triethylamine (0.101 mL, 0.722 mmol) and 3-(dimethylamino)propyl(4-nitrophenyl)carbonate hydrochloride (0.110 g, 0.361 mmol) were added, and the mixture was stirred at 110° C. for 2 hours. Saturated saline was added to the reaction solution, followed by extraction with chloroform. The organic layer was dried over anhydrous magnesium sulfate, then filtered, and concentrated under reduced pressure. The obtained residue was purified by amino silica gel column chromatography (heptane/ethyl acetate=100/0 to 80/20) and silica gel column chromatography (chloroform/methanol=100/0 to 80/20) to obtain 3-(dimethylamino)propyl(2-{[(Z)-octadec-9-en-1-yl]thio}ethyl)[(9Z,12Z)-octadeca-9,12-dien-1-yl]carbamate (0.0510 g, yield: 40.1%).

ESI-MS m/z: 706 (M+H)$^+$; $^1$H-NMR (400 MHz, CDCl$_3$) δ: 5.42-5.29 (m, 6H), 4.12 (t, J=6.5 Hz, 2H), 3.38 (t, J=6.7 Hz, 2H), 3.22 (t, J=6.3 Hz, 2H), 2.77 (t, J=6.7 Hz, 2H), 2.65 (t, J=6.6 Hz, 2H), 2.54 (t, J=6.8 Hz, 2H), 2.35 (t, J=7.5 Hz, 2H), 2.23 (s, 6H), 2.06-2.00 (m, 8H), 1.84-1.77 (m, 2H), 1.60-1.51 (m, 4H), 1.36-1.30 (m, 38H), 0.91-0.86 (m, 6H).

Example C18

2-(Diethylamino)-N-(2-{[(Z)-octadec-9-en-1-yl]thio}ethyl)-N-[(9Z,12Z)-octadeca-9,12-dien-1-yl]acetamide (Compound CL-84)

Step 1

2-(Diethylamino)-N-(2-{[(Z)-octadec-9-en-1-yl]thio}ethyl)-N-[(9Z,12Z)-octadeca-9,12-dien-1-yl]acetamide (0.108 g, yield: 86.0%) was obtained by the same approach as in step 1 of Example C3 using N,N-diethylglycine instead of dimethylglycine.

ESI-MS m/z: 690 (M+H)$^+$; $^1$H-NMR (400 MHz, CDCl$_3$) δ: 5.42-5.30 (m, 6H), 3.60 (t, J=7.8 Hz, 1H), 3.48-3.47 (m, 2H), 3.28 (t, J=7.5 Hz, 1H), 3.25 (d, J=15.5 Hz, 2H), 2.77 (t, J=6.2 Hz, 2H), 2.72-2.64 (m, 2H), 2.61-2.51 (m, 6H), 2.09-1.93 (m, 8H), 1.63-1.48 (m, 4H), 1.42-1.20 (m, 38H), 1.03 (t, J=7.1 Hz, 6H), 0.92-0.84 (m, 6H).

Example C19

3-(Dimethylamino)-N-(2-{[(Z)-octadec-9-en-1-yl]thio}ethyl)-N-[(9Z,12Z)-octadeca-9,12-dien-1-yl]propanamide (Compound CL-85)

Step 1

3-(Dimethylamino)-N-(2-{[(Z)-octadec-9-en-1-yl]thio}ethyl)-N-[(9Z,12Z)-octadeca-9,12-dien-1-yl]propanamide (0.0537 g, yield: 83.0%) was obtained by the same approach as in step 1 of Example C3 using 3-(dimethylamino)propanoic acid instead of dimethylglycine.

ESI-MS m/z: 676 (M+H)$^+$; $^1$H-NMR (400 MHz, CDCl$_3$) δ: 5.42-5.30 (m, 6H), 3.50-3.41 (m, 2H), 3.34-3.23 (m, 2H), 2.77 (t, J=6.2 Hz, 2H), 2.70-2.62 (m, 4H), 2.59-2.46 (m, 4H), 2.27 (s, 6H), 2.11-1.93 (m, 8H), 1.67-1.46 (m, 4H), 1.41-1.22 (m, 38H), 0.91-0.86 (m, 6H).

Example C20

S-[2-(Dimethylamino)ethyl] (2-{[(Z)-octadec-9-en-1-yl]thio}ethyl)[(9Z,12Z)-octadeca-9,12-dien-1-yl]carbamothioate (Compound CL-86)

Step 1

S-[2-(Dimethylamino)ethyl] (2-{[(Z)-octadec-9-en-1-yl]thio}ethyl)[(9Z,12Z)-octadeca-9,12-dien-1-yl]carbamothioate (0.143 g, yield: 94.0%) was obtained by the same approach as in step 1 of Example C7 using 2-(dimethylamino)ethane-1-thiol instead of 2-dimethylaminoethanol.

ESI-MS m/z: 708 (M+H)$^+$; $^1$H-NMR (400 MHz, CDCl$_3$) δ: 5.43-5.29 (m, 6H), 3.54-3.43 (m, 2H), 3.41-3.26 (m, 2H), 3.03 (t, J=7.1 Hz, 2H), 2.77 (t, J=6.4 Hz, 2H), 2.73-2.64 (m, 2H), 2.59-2.50 (m, 4H), 2.28 (s, 6H), 2.09-1.93 (m, 8H), 1.65-1.49 (m, 4H), 1.41-1.21 (m, 38H), 0.92-0.85 (m, 6H).

Example C21

N-Methyl-2-{[(Z)-octadec-9-en-1-yl]thio}-N-(2-{[(Z)-octadec-9-en-1-yl]thio}ethyl)ethan-1-amine (Compound CL-87)

Step 1

Bis(2-{[(Z)-octadec-9-en-1-yl]thio}ethyl)amine (0.0300 g, 0.0470 mmol) was dissolved in a mixed solvent of 1,2-dichloroethane (1.00 mL) and methanol (1.00 mL). To the solution, a 37% formaldehyde solution (0.0170 mL, 0.235 mmol) and sodium triacetoxyborohydride (0.0250 g, 0.118 mmol) were added, and the mixture was stirred at room temperature for 3 hours. Saturated saline was added to the reaction solution, followed by extraction with ethyl acetate. The organic layer was dried over anhydrous magnesium sulfate, then filtered, and concentrated under reduced pressure. The obtained residue was purified by amino silica gel column chromatography (heptane/ethyl acetate=100/0 to 90/10) to obtain N-methyl-2-{[(Z)-octadec-9-en-1-yl]thio}-N-(2-{[(Z)-octadec-9-en-1-yl]thio}ethyl)ethan-1-amine (0.0146 g, yield: 47.6%).

ESI-MS m/z: 652 (M+H)$^+$; $^1$H-NMR (400 MHz, CDCl$_3$) δ: 5.39-5.31 (m, 4H), 2.62 (s, 8H), 2.52 (t, J=7.5 Hz, 4H), 2.29 (s, 3H), 2.01 (q, J=6.4 Hz, 8H), 1.62-1.54 (m, 4H), 1.36-1.29 (m, 44H), 0.89 (t, J=6.8 Hz, 6H).

Example C22

Bis(2-{[(9Z,12Z)-octadeca-9,12-dien-1-yl]thio}ethyl)amine (Compound CL-88)

Step 1
(9Z,12Z)-Octadeca-9,12-dien-1-yl methanesulfonate (1.02 g, 2.96 mmol) was dissolved in dimethylformamide (20.0 mL). To the solution, S-potassium thioacetate (0.440 g, 3.85 mmol) was added, and the mixture was stirred at room temperature for 4 hours. Saturated saline was added to the reaction solution, followed by extraction with ethyl acetate. The organic layer was dried over anhydrous magnesium sulfate, then filtered, and concentrated under reduced pressure to obtain S-[(9Z,12Z)-octadeca-9,12-dien-1-yl] ethanethioate (0.0146 g, yield: 47.6%).

Step 2
tert-Butyl bis(2-hydroxyethyl)carbamate (0.300 g, 1.46 mmol) was dissolved in dichloromethane (5.00 mL). To the solution, methanesulfonyl chloride (0.419 mL, 3.65 mmol) and triethylamine (0.611 mL, 4.38 mmol) were added at 0° C., and the mixture was stirred at room temperature for 1 hour. Saturated saline was added to the reaction solution, followed by extraction with ethyl acetate. The organic layer was dried over anhydrous magnesium sulfate, then filtered, and concentrated under reduced pressure to obtain [(tert-butoxycarbonyl)azanediyl]bis(ethane-2,1-diyl) dimethanesulfonate (0.560 g, quantitative).

Step 3
S-[(9Z,12Z)-Octadeca-9,12-dien-1-yl] ethanethioate (0.269 g, 0.830 mmol) was dissolved in a mixed solvent of methanol (2.00 mL) and tetrahydrofuran (0.500 mL). To the solution, a solution of 28% sodium methoxide in methanol (0.133 mL, 0.664 mmol) and [(tert-butoxycarbonyl)azanediyl]bis(ethane-2,1-diyl) dimethanesulfonate (0.100 g, 0.277 mmol) were added at 0° C., and the mixture was stirred overnight at 50° C. Distilled water and saturated saline were added to the reaction solution, followed by extraction with ethyl acetate. The organic layer was dried over anhydrous magnesium sulfate, then filtered, and concentrated under reduced pressure. The obtained residue was purified by amino silica gel column chromatography (heptane/ethyl acetate=100/0 to 85/15) to obtain tert-butyl bis(2-{[(9Z,12Z)-octadeca-9,12-dien-1-yl]thio}ethyl)carbamate (0.0654 g, yield: 32.2%).

tert-Butyl bis(2-{[(9Z,12Z)-octadeca-9,12-dien-1-yl]thio}ethyl) carbamate (0.0654 g, 0.0890 mmol) was dissolved in dichloromethane (1.00 mL). To the solution, trifluoroacetic acid (0.137 mL, 1.78 mmol) was added, and the mixture was stirred overnight at room temperature. A saturated aqueous solution of sodium bicarbonate was added to the reaction solution, followed by extraction with ethyl acetate. The organic layer was dried over anhydrous magnesium sulfate, then filtered, and concentrated under reduced pressure. The obtained residue was purified by silica gel column chromatography (chloroform/methanol=100/0 to 95/5) to obtain bis(2-{[(9Z,12Z)-octadeca-9,12-dien-1-yl]thio}ethyl)amine (0.0493 g, yield: 87.0%).

ESI-MS m/z: 634 (M+H)$^+$; $^1$H-NMR (400 MHz, CDCl$_3$) δ: 5.42-5.29 (m, 8H), 2.82 (t, J=6.6 Hz, 4H), 2.77 (t, J=6.7 Hz, 4H), 2.68 (t, J=6.5 Hz, 4H), 2.51 (t, J=7.5 Hz, 4H), 2.05 (q, J=6.8 Hz, 8H), 1.61-1.57 (m, 4H), 1.39-1.24 (m, 32H), 0.89 (t, J=7.0 Hz, 6H).

Example C23

3,3-Bis({[(9Z,12Z)-octadeca-9,12-dien-1-yl]thio}methyl)azetidine (Compound CL-89)

Compound CL-89 was obtained by the same approach as in step 1 of Example C10.

Example C24

3,3-Bis({[(Z)-octadec-9-en-1-yl]thio}methyl)azetidine (Compound CL-90)

Compound CL-90 was obtained by the same approach as in step 2 of Example C8.

Example C25

1-Ethyl-3,3-bis({[(Z)-octadec-9-en-1-yl]thio}methyl)azetidine (Compound CL-91)

Step 1
3,3-Bis({[(Z)-octadec-9-en-1-yl]thio}methyl)azetidine (0.0450 g, 0.0690 mmol) obtained in step 2 of Example C8 was dissolved in a mixed solvent of 1,2-dichloroethane (0.500 mL) and methanol (0.500 mL). To the solution, acetaldehyde (0.0200 mL, 0.346 mmol) and sodium triacetoxyborohydride (0.0730 g, 0.346 mmol) were added, and the mixture was stirred overnight at room temperature. Saturated saline was added to the reaction solution, followed by extraction with ethyl acetate. The organic layer was dried over anhydrous magnesium sulfate, then filtered, and concentrated under reduced pressure. The obtained residue was purified by silica gel column chromatography (chloroform/methanol=100/0 to 90/10) to obtain 1-ethyl-3,3-bis({[(Z)-octadec-9-en-1-yl]thio}methyl)azetidine (0.0375 g, yield: 80.0%).

ESI-MS m/z: 678 (M+H)$^+$; $^1$H-NMR (400 MHz, CDCl$_3$) δ: 5.39-5.31 (m, 4H), 3.07 (s, 4H), 2.93 (s, 4H), 2.55 (t, J=7.5 Hz, 4H), 2.50-2.49 (m, 2H), 2.01 (q, J=6.4 Hz, 8H), 1.67-1.55 (m, 4H), 1.37-1.29 (m, 44H), 0.95 (t, J=7.2 Hz, 3H), 0.88 (t, J=7.0 Hz, 6H).

Example C26

3,3-Bis({[(Z)-octadec-9-en-1-yl]thio}methyl)-1-propylazetidine (Compound CL-92)

Step 1
3,3-Bis({[(Z)-octadec-9-en-1-yl]thio}methyl)-1-propylazetidine (0.0374 g, yield: 58.5%) was obtained by the same approach as in step 1 of Reference Example 25 using propionaldehyde instead of acetaldehyde.

ESI-MS m/z: 692 (M+H)$^+$; $^1$H-NMR (400 MHz, CDCl$_3$) δ: 5.39-5.31 (m, 4H), 3.04 (s, 4H), 2.93 (s, 4H), 2.54 (t,

J=7.5 Hz, 4H), 2.39 (t, J=7.6 Hz, 2H), 2.01 (q, J=6.4 Hz, 8H), 1.60-1.57 (m, 4H), 1.39-1.30 (m, 46H), 0.89-0.87 (m, 9H).

Example C27

3,3-Bis(({(Z)-hexadec-9-en-1-yl]thio}methyl)azetidine (Compound CL-93)

Step 1

3,3-Bis(({(Z)-hexadec-9-en-1-yl]thio}methyl)azetidine (0.208 g, yield: 62.3%) was obtained by the same approach as in step 2 of Example C8 using (Z)-hexadec-9-en-1-yl methanesulfonate instead of (Z)-octadec-9-en-1-yl methanesulfonate.

ESI-MS m/z: 595 (M+H)+; $^1$H-NMR (400 MHz, CDCl$_3$) δ: 5.39-5.31 (m, 4H), 3.44 (s, 4H), 2.95 (s, 4H), 2.56 (t, J=7.5 Hz, 4H), 2.01 (q, J=6.4 Hz, 8H), 1.64-1.56 (m, 4H), 1.38-1.32 (m, 36H), 0.88 (t, J=7.0 Hz, 6H).

Example C28

3,3-Bis({[(Z)-hexadec-9-en-1-yl]thio}methyl)-1-methylazetidine (Compound CL-94)

Step 1

3,3-Bis({[(Z)-hexadec-9-en-1-yl]thio}methyl)-1-methylazetidine (0.0910 g, yield: 89.0%) was obtained by the same approach as in Reference Example B31 using 3,3-bis(({(Z)-hexadec-9-en-1-yl]thio}methyl)azetidine instead of bis(2-{[(Z)-octadec-9-en-1-yl]thio}ethyl)amine.

ESI-MS m/z: 609 (M+H)+; $^1$H-NMR (400 MHz, CDCl$_3$) δ: 5.36-5.34 (m, 4H), 3.07 (s, 4H), 2.92 (s, 4H), 2.54 (t, J=7.5 Hz, 4H), 2.33 (s, 3H), 2.01 (q, J=6.8 Hz, 8H), 1.62-1.55 (m, 4H), 1.39-1.32 (m, 36H), 0.88 (t, J=6.8 Hz, 6H).

Example C29

1-[3,3-Bis({[(Z)-hexadec-9-en-1-yl]thio}methyl) azetidin-1-yl]-2-(dimethylamino)ethan-1-one (Compound CL-95)

Step 1

1-[3,3-Bis({[(Z)-hexadec-9-en-1-yl]thio}methyl)azetidin-1-yl]-2-(dimethylamino)ethan-1-one (0.0660 g, yield: 64.1%) was obtained by the same approach as in step 1 of Example C3 using 3,3-bis(({(Z)-hexadec-9-en-1-yl]thio}methyl)azetidine instead of (9Z,12Z)—N-(2-{[(Z)-octadec-9-en-1-yl]thio}ethyl)octadeca-9,12-dien-1-amine.

ESI-MS m/z: 679 (M+H)+; $^1$H-NMR (400 MHz, CDCl$_3$) δ: 5.36-5.34 (m, 4H), 3.97 (s, 2H), 3.80 (s, 2H), 2.98 (s, 2H), 2.89 (s, 4H), 2.56 (t, J=7.5 Hz, 4H), 2.28 (s, 6H), 2.01 (q, J=6.5 Hz, 8H), 1.62-1.55 (m, 4H), 1.42-1.29 (m, 36H), 0.88 (t, J=6.8 Hz, 6H).

Example C30

3,3-Bis({[(Z)-octadec-11-en-1-yl]thio}methyl)azetidine (Compound CL-96)

Step 1

3,3-Bis({[(Z)-octadec-11-en-1-yl]thio}methyl)azetidine (0.365 g, yield: 85.0%) was obtained by the same approach as in step 2 of Example C8 using (Z)-octadec-11-en-1-yl methanesulfonate instead of (Z)-octadec-9-en-1-yl methanesulfonate.

ESI-MS m/z: 651 (M+H)+; $^1$H-NMR (400 MHz, CDCl$_3$) δ: 5.36-5.34 (m, 4H), 3.44 (s, 4H), 2.95 (s, 4H), 2.56 (t, J=7.5 Hz, 4H), 2.01 (q, J=6.4 Hz, 8H), 1.62-1.57 (m, 4H), 1.42-1.27 (m, 44H), 0.88 (t, J=6.8 Hz, 6H).

Example C31

1-Methyl-3,3-bis({[(Z)-octadec-11-en-1-yl]thio}methyl)azetidine (Compound CL-97)

Step 1

1-Methyl-3,3-bis({[(Z)-octadec-11-en-1-yl]thio}methyl)azetidine (0.0780 g, yield: 77.0%) was obtained by the same approach as in Reference Example B31 using 3,3-bis({[(Z)-octadec-11-en-1-yl]thio}methyl)azetidine instead of bis(2-{[(Z)-octadec-9-en-1-yl]thio}ethyl)amine.

ESI-MS m/z: 665 (M+H)+; $^1$H-NMR (400 MHz, CDCl$_3$) δ: 5.39-5.31 (m, 4H), 3.07 (s, 4H), 2.92 (s, 4H), 2.54 (t, J=7.5 Hz, 4H), 2.33 (s, 3H), 2.01 (q, J=6.4 Hz, 8H), 1.62-1.55 (m, 4H), 1.42-1.27 (m, 44H), 0.88 (t, J=7.0 Hz, 6H).

Example C32

1-[3,3-Bis({[(Z)-octadec-11-en-1-yl]thio}methyl) azetidin-1-yl]-2-(dimethylamino)ethan-1-one (Compound CL-98)

Step 1

1-[3,3-Bis({[(Z)-octadec-11-en-1-yl]thio}methyl)azetidin-1-yl]-2-(dimethylamino)ethan-1-one (0.0440 g, yield: 67.1%) was obtained by the same approach as in step 1 of Example C3 using 3,3-bis({[(Z)-octadec-11-en-1-yl]thio}methyl)azetidine instead of (9Z,12Z)—N-(2-{[(Z)-octadec-9-en-1-yl]thio}ethyl)octadeca-9,12-dien-1-amine.

ESI-MS m/z: 735 (M+H)+; $^1$H-NMR (400 MHz, CDCl$_3$) δ: 5.36-5.33 (m, 4H), 3.96 (s, 2H), 3.80 (s, 2H), 2.96 (s, 2H), 2.89 (s, 4H), 2.56 (t, J=7.4 Hz, 4H), 2.27 (s, 6H), 2.01 (q, J=6.8 Hz, 8H), 1.62-1.55 (m, 4H), 1.34-1.28 (m, 44H), 0.88 (t, J=7.0 Hz, 6H).

Example C33

3,3-Bis({[(Z)-tetradec-9-en-1-yl]thio}methyl)azetidine (Compound CL-99)

Step 1

3,3-Bis({[(Z)-tetradec-9-en-1-yl]thio}methyl)azetidine (0.137 g, yield: 73.5%) was obtained by the same approach as in step 2 of Example C8 using (Z)-tetradec-9-en-1-yl methanesulfonate instead of (Z)-octadec-9-en-1-yl methanesulfonate.

ESI-MS m/z: 539 (M+H)+; $^1$H-NMR (400 MHz, CDCl$_3$) δ: 5.39-5.31 (m, 4H), 3.47 (s, 4H), 2.95 (s, 4H), 2.56 (t, J=7.5 Hz, 4H), 2.01-2.00 (m, 8H), 1.63-1.56 (m, 4H), 1.36-1.31 (m, 28H), 0.90 (t, J=7.1 Hz, 6H).

Example C34

1-Methyl-3,3-bis({[(Z)-tetradec-9-en-1-yl] thio}methyl)azetidine (Compound CL-100)

Step 1

1-Methyl-3,3-bis({[(Z)-tetradec-9-en-1-yl]thio}methyl)azetidine (0.0684 g, yield: 71.7%) was obtained by the same approach as in Reference Example B31 using 3,3-bis({[(Z)- tetradec-9-en-1-yl]thio}methyl)azetidine instead of bis(2-{[(Z)-octadec-9-en-1-yl]thio}ethyl)amine.

ESI-MS m/z: 553 (M+H)⁺; ¹H-NMR (400 MHz, CDCl₃) δ: 5.39-5.31 (m, 4H), 3.07 (s, 4H), 2.92 (s, 4H), 2.54 (t, J=7.5 Hz, 4H), 2.33 (s, 3H), 2.03-2.01 (m, 8H), 1.62-1.55 (m, 4H), 1.35-1.32 (m, 28H), 0.90 (t, J=7.1 Hz, 6H).

Example C35

1-[3,3-Bis({[(Z)-tetradec-9-en-1-yl]thio}methyl)azetidin-1-yl]-2-(dimethylamino)ethan-1-one (Compound CL-101)

Step 1

1-[3,3-Bis({[(Z)-tetradec-9-en-1-yl]thio}methyl)azetidin-1-yl]-2-(dimethylamino)ethan-1-one (0.0145 g, yield: 50.1%) was obtained by the same approach as in step 1 of Example C3 using 3,3-bis({[(Z)-tetradec-9-en-1-yl]thio}methyl)azetidine instead of (9Z,12Z)—N-(2-{[(Z)-octadec-9-en-1-yl]thio}ethyl)octadeca-9,12-dien-1-amine.

ESI-MS m/z: 623 (M+H)⁺; ¹H-NMR (400 MHz, CDCl₃) δ: 5.37-5.33 (m, 4H), 3.97 (s, 2H), 3.80 (s, 2H), 2.96 (s, 2H), 2.89 (s, 4H), 2.56 (t, J=7.4 Hz, 4H), 2.28 (s, 6H), 2.02-2.00 (m, 8H), 1.63-1.55 (m, 4H), 1.39-1.29 (m, 28H), 0.90 (t, J=7.1 Hz, 6H).

Example C36

3-({[(Z)-Octadec-9-en-1-yl]oxy}methyl)-3-({[(Z)-octadec-9-en-1-yl]thio}methyl)azetidine (Compound CL-102)

Compound CL-102 was obtained by the same approach as in step 3 of Example C12.

Reference Example C37

2-(Dimethylamino)-N,N-bis(2-(((Z)-octadec-9-en-1-yl)oxy)ethyl)acetamide (Compound CL-103)

Compound CL-103 was synthesized by the method described in WO 2011/136368.
(Synthesis of Analog of Fatty Acid Ester of Glycerol Wherein the Analog is not Hydrolyzable by Lipase)

[Production Example 1] Method for Producing D-α-Phosphatidylcholine, Distearoyl (D-DSPC) ((S)-2,3-bis(stearoyloxy)propyl(2-(trimethylammonio)ethyl)phosphoric acid)

The synthesis scheme of D-DSPC will be shown below. Specific synthesis procedures will be shown in [Step 1] and [Step 2].

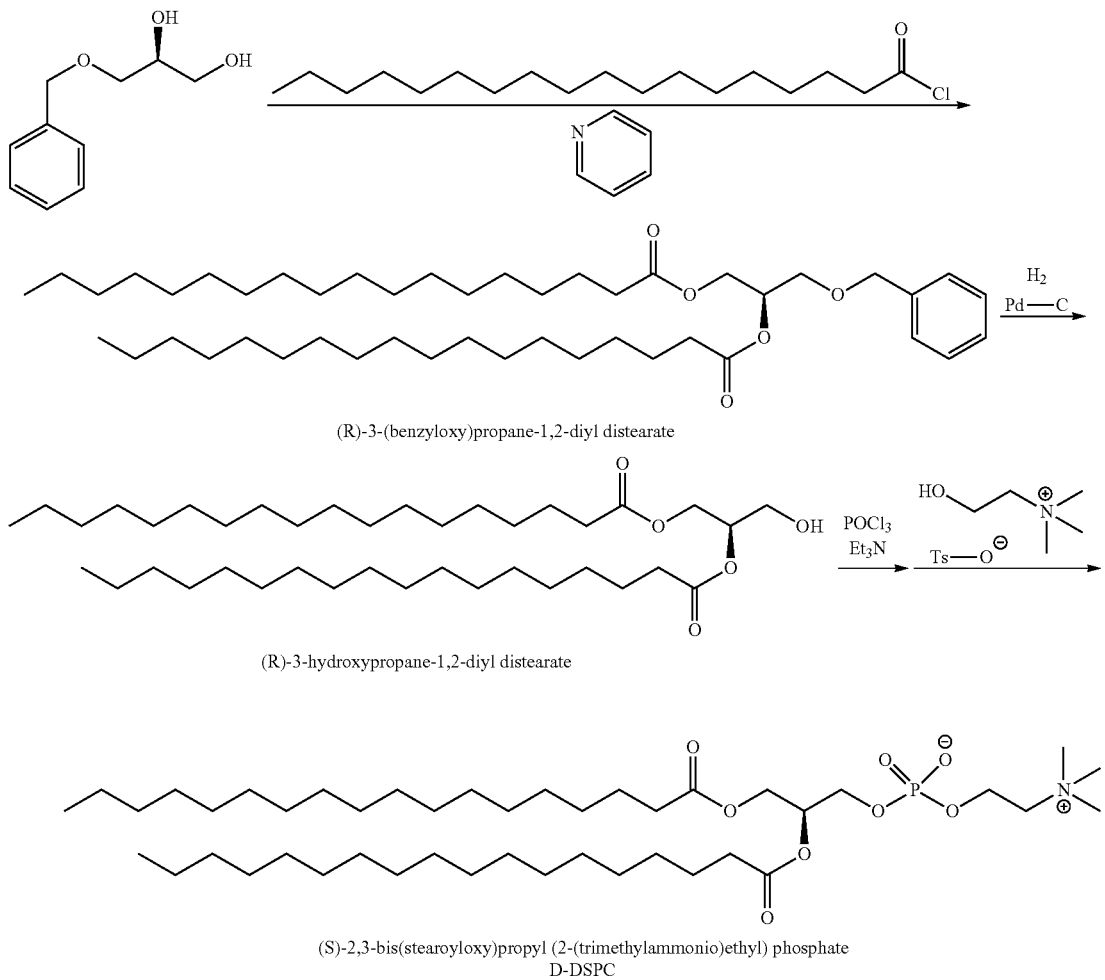

(R)-3-(benzyloxy)propane-1,2-diyl distearate (R)-3-hydroxypropane-1,2-diyl distearate (S)-2,3-bis(stearoyloxy)propyl (2-(trimethylammonio)ethyl) phosphate
D-DSPC

[Step 1]

To a solution of (S)-3-(benzyloxy)propane-1,2-diol (2.36 g, 13.0 mmol) in chloroform (14 mL), a solution of pyridine (2.09 mL, 25.9 mmol) and stearoyl chloride (7.85 g, 25.9 mmol) in chloroform (4 mL) was added, and the mixture was stirred at 55° C. for 7 hours. Hexane was added to the reaction solution, and the organic layer was washed twice with 0.5 mol/L hydrochloric acid, washed with saturated saline, dried over anhydrous magnesium sulfate, and filtered, and the solvent was distilled off under reduced pressure. The obtained residue was crystallized from ethanol, and the crystals were collected by filtration to obtain a crude product of (R)-3-(benzyloxy)propane-1,2-diyl stearate.

To a solution of the obtained crude product in hexane (86 mL), palladium-carbon (10% palladium, product wetted with 50% water, 0.546 g, 0.257 nmol) was added, and the mixture was stirred at 40° C. for 6 hours under hydrogen. The reaction solution was cooled in air to room temperature. Then, insoluble matter was removed by filtration through celite, and the filtrate was concentrated under reduced pressure. The obtained residue was crystallized from hexane, and the crystals were collected by filtration to obtain (R)-3-hydroxypropane-1,2-diyl distearate (5.13 g, 8.21 mmol, 63%).

ESI-MS m/z: 642 (M+NH$_4$)$^+$; $^1$H-NMR (CDCl$_3$) δ: 0.88 (t, J=6.8 Hz, 6H), 1.21-1.36 (m, 56H), 1.57-1.67 (m, 4H), 2.01 (t, J=6.5 Hz, 1H), 2.30-2.37 (m, 4H), 3.71-3.75 (m, 2H), 4.24 (dd, J=11.9, 5.6 Hz, 1H), 4.32 (dd, J=11.9, 4.6 Hz, 1H), 5.05-5.11 (m, 1H).

[Step 2]

To a solution of phosphorus(V) oxychloride (0.767 g, 5.00 mmol) and triethylamine (3.48 mL, 25.0 mmol) in chloroform (15 mL), a solution of (R)-3-hydroxypropane-1,2-diyl distearate (0.313 g, 0.500 mmol) obtained in [Step 1] in chloroform (4 mL) was added under ice cooling, and the mixture was stirred at room temperature for 1 hour. The reaction solution was concentrated under reduced pressure. To the obtained residue, ethyl ether was added, and insoluble matter was removed by filtration. The filtrate was concentrated under reduced pressure. The obtained residue was dissolved in chloroform (5 mL). To the solution, a solution of choline p-toluenesulfonate (0.200 g, 0.725 mmol) in pyridine (7 mL) was added under ice cooling, and the mixture was stirred overnight at room temperature. A 10% aqueous sodium bicarbonate solution was added to the reaction solution, and the mixture was stirred at room temperature for 20 minutes. Ethanol was added to the reaction solution, and the solvent was distilled off under reduced pressure. To the obtained residue, chloroform was added, and insoluble matter was removed by filtration. The filtrate was concentrated under reduced pressure. The obtained residue was purified by silica gel column chromatography (chloroform/methanol/water=60/30/1 to 0/100/0) and crystallized from chloroform/acetone=1/1, and the crystals were collected by filtration to obtain D-DSPC (0.0718 g, 0.0909 mmol, 18%).

ESI-MS m/z: 791 (M+H)$^+$; $^1$H-NMR (CDCl$_3$) δ: 0.88 (t, J=6.8 Hz, 6H), 1.17-1.36 (m, 56H), 1.52-1.63 (m, 4H), 2.24-2.32 (m, 4H), 3.36 (s, 9H), 3.76-3.83 (m, 2H), 3.87-4.00 (m, 2H), 4.12 (dd, J=12.0, 7.5 Hz, 1H), 4.28-4.35 (m, 2H), 4.39 (dd, J=11.9, 2.8 Hz, 1H), 5.16-5.24 (m, 1H).

Example 1

Preparation 1 containing nucleic acid-containing lipid nanoparticles was produced as described below using compound II-3 obtained in Reference Example A10, compound CL-10 obtained in Reference Example B10, 1,2-distearoyl-sn-glycero-3-phosphoethanolamine-N-[methoxy(polyethylene glycol)-2000] (PEG-DSPE), D-α-phosphatidylcholine, dipalmitoyl (D-DPPC) and cholesterol (Chol).

The nucleic acid used was siRNA silencing luciferase (hereinafter, referred to as "Luc") gene and consisting of the nucleotide sequences of a sense strand (5'-CCGU-CGUAUUCGUGAGCAAGA-3') (SEQ ID NO:1) and an antisense strand (5'-UUGCUCACGAAUACGACGGUG-3') (SEQ ID NO:2), and was obtained from Gene Design, Inc. (hereinafter, referred to as "Luc siRNA"). PEG-DSPE and cholesterol were obtained from NOF Corp. D-DPPC was obtained from Sigma-Aldrich Corp.

Compound II-3 was dissolved at 10 mg/mL in 100% ethanol to prepare a lipid stock solution. Compound CL-10, PEG-DSPE, D-DPPC and cholesterol were each dissolved at 20 mg/mL in 100% ethanol to prepare lipid stock solutions. Each lipid stock solution was stored at –20° C. Immediately before formulation, the lipid was dissolved by heating to 60° C., and the resulting solution was brought back to room temperature and then used.

Luc siRNA was dissolved at 1 mg/mL in injectable water to prepare a Luc siRNA solution.

The lipid stock solution of compound II-3 (0.313 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-10, PEG-DSPE, D-DPPC and Chol (1.88 μmol, 0.235 μmol, 0.486 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was concentrated using Amicon Ultra (manufactured by Merck Millipore), further solvent-replaced with physiological saline, and filtered using a 0.2-μm filter (manufactured by Toyo Roshi Kaisha, Ltd.) in a clean bench. The siRNA concentration of the obtained preparation was further measured, and the preparation was diluted with physiological saline such that the siRNA concentration was 0.1 mg/mL to obtain preparation 1.

Example 2

Preparation 2 having a distinct content of D-DPPC was produced as described below.

L-α-Phosphatidylcholine, dipalmitoyl (L-DPPC) was obtained from NOF Corp.

L-DPPC was dissolved at 20 mg/mL in 100% ethanol to prepare a lipid stock solution.

The lipid stock solution of compound II-3 (0.313 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-10, PEG-DSPE, D-DPPC, L-DPPC and Chol (1.88 μmol, 0.235 μmol, 0.364 μmol, 0.121 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 2.

Example 3

Preparation 3 having a distinct content of D-DPPC was produced as described below.

The lipid stock solution of compound II-3 (0.313 μmol) was added to 80% ethanol and a 0.1% aqueous HCl solution.

Subsequently, 200 µL of the Luc siRNA solution was added thereto, and the mixture was stirred for 1 minute. Then, the lipid stock solutions of compound CL-10, PEG-DSPE, D-DPPC, L-DPPC and Choi (1.88 µmol, 0.235 µmol, 0.243 µmol, 0.243 µmol and 1.01 µmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 3.

Example 4

Preparation 4 containing nucleic acid-containing lipid nanoparticles was produced as described below using compound II-12 obtained in Reference Example A19, compound CL-10 obtained in Reference Example B10, 1,2-distearoyl-sn-glycero-3-phosphoethanolamine-N-[methoxy(polyethylene glycol)-2000] (PEG-DSPE), D-α-phosphatidylcholine, dipalmitoyl (D-DPPC) and cholesterol.

Compound II-12 was dissolved at 20 mg/mL in 100% ethanol to prepare a lipid stock solution.

The lipid stock solution of compound II-12 (0.626 µmol) was added to 80% ethanol and a 0.1% aqueous HCl solution. Subsequently, 200 µL of the Luc siRNA solution described above was added thereto, and the mixture was stirred for 1 minute. Then, the lipid stock solutions of compound CL-10, PEG-DSPE, D-DPPC and Choi (1.88 µmol, 0.235 µmol, 0.486 µmol and 1.01 µmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 4.

Example 5

Preparation 5 having a distinct content of D-DPPC was produced as described below.

The lipid stock solution of compound II-12 (0.626 µmol) was added to 80% ethanol and a 0.1% aqueous HCl solution. Subsequently, 200 µL of the Luc siRNA solution was added thereto, and the mixture was stirred for 1 minute. Then, the lipid stock solutions of compound CL-10, PEG-DSPE, D-DPPC, L-DPPC and Choi (1.88 µmol, 0.235 µmol, 0.364 µmol, 0.121 µmol and 1.01 µmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 5.

Example 6

Preparation 6 having a distinct content of D-DPPC was produced as described below.

The lipid stock solution of compound II-12 (0.626 µmol) was added to 80% ethanol and a 0.1% aqueous HCl solution. Subsequently, 200 µL of the Luc siRNA solution was added thereto, and the mixture was stirred for 1 minute. Then, the lipid stock solutions of compound CL-10, PEG-DSPE, D-DPPC, L-DPPC and Choi (1.88 µmol, 0.235 µmol, 0.243 µmol, 0.243 µmol and 1.01 µmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 6.

Example 7

Preparation 7 containing nucleic acid-containing lipid nanoparticles was produced as described below using compound II-4 obtained in Reference Example A11, compound CL-2 obtained in Reference Example B2, 1,2-distearoyl-sn-glycero-3-phosphoethanolamine-N-[methoxy(polyethylene glycol)-2000] (PEG-DSPE), D-α-phosphatidylcholine, dipalmitoyl (D-DPPC) and cholesterol.

Compound II-4 was dissolved at 5 mg/mL in 100% ethanol to prepare a lipid stock solution. Compound CL-2 was dissolved at 20 mg/mL in 100% ethanol to prepare a lipid stock solution.

The lipid stock solution of compound II-4 (0.156 µmol) was added to 80% ethanol and a 0.1% aqueous HCl solution. Subsequently, 200 µL of the Luc siRNA solution was added thereto, and the mixture was stirred for 1 minute. Then, the lipid stock solutions of compound CL-2, PEG-DSPE, D-DPPC and Choi (1.88 µmol, 0.235 µmol, 0.536 µmol and 1.11 µmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 7.

Example 8

Preparation 8 having a distinct content of D-DPPC was produced as described below.

The lipid stock solution of compound II-4 (0.156 µmol) was added to 80% ethanol and a 0.1% aqueous HCl solution. Subsequently, 200 µL of the Luc siRNA solution was added thereto, and the mixture was stirred for 1 minute. Then, the lipid stock solutions of compound CL-2, PEG-DSPE, D-DPPC, L-DPPC and Choi (1.88 µmol, 0.235 µmol, 0.402 µmol, 0.134 µmol and 1.11 µmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 8.

Example 9

Preparation 9 having a distinct content of D-DPPC was produced as described below.

The lipid stock solution of compound II-4 (0.156 µmol) was added to 80% ethanol and a 0.1% aqueous HCl solution. Subsequently, 200 µL of the Luc siRNA solution was added thereto, and the mixture was stirred for 1 minute. Then, the lipid stock solutions of compound CL-2, PEG-DSPE, D-DPPC, L-DPPC and Choi (1.88 µmol, 0.235 µmol, 0.268 µmol, 0.268 µmol and 1.11 µmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 9.

Comparative Example 1

Preparation 10 was obtained in the same way as in Example 1 except that D-DPPC of preparation 1 was changed to L-DPPC.

Comparative Example 2

Preparation 11 was obtained in the same way as in Example 4 except that D-DPPC of preparation 4 was changed to L-DPPC.

Comparative Example 3

Preparation 12 was obtained in the same way as in Example 7 except that D-DPPC of preparation 7 was changed to L-DPPC.

Test Example 1

Average Particle Size Measurement of Nucleic Acid-Containing Lipid Nanoparticle

The average particle size of the nucleic acid-containing lipid nanoparticles in each preparation was measured with a particle size measurement apparatus (Zetasizer Nano ZS, manufactured by Malvern Panalytical Ltd.) (Table 32). PDI in the table represents polydispersity index.

TABLE 32

| Preparation No. | Size (nm) | PDI |
| --- | --- | --- |
| 1 | 39.18 | 0.135 |
| 2 | 39.36 | 0.108 |
| 3 | 38.13 | 0.126 |
| 4 | 46.00 | 0.068 |
| 5 | 44.82 | 0.087 |
| 6 | 45.88 | 0.077 |
| 7 | 44.34 | 0.125 |
| 8 | 53.57 | 0.127 |
| 9 | 51.04 | 0.104 |
| 10 | 39.10 | 0.116 |
| 11 | 43.35 | 0.101 |
| 12 | 49.44 | 0.132 |

As a result, preparations 1 to 12 exhibited an average particle size from 30 to 60 ran and had PDI from 0.06 to 0.14.

Test Example 2

In Vitro Activity Evaluation Test of Nucleic Acid-Containing Lipid Nanoparticle

Preparations 1 to 9 described in Examples 1 to 9 and preparations 10 to 12 described in Comparative Examples 1 to 3 were each introduced to human pancreatic cancer-derived cell line Mia PaCa-2/Luc cells by the following method.

Each preparation was treated with PLA2 and evaluated for its gene suppression ratio according to the method described in [Non Patent Literature 3]. Mia PaCa-2/Luc cells suspended in Dulbecco's modified Eagle's minimal essential medium (DMEM) containing 10% fetal bovine serum (FBS, Gibco/Thermo Fisher Scientific Inc.) were seeded in a 96-well culture plate at 7500 cells/80 µL/well, and cultured at 37° C. for 24 hours under 5% $CO_2$ conditions. Each preparation diluted with Opti-MEM (Gibco/Thermo Fisher Scientific Inc.) so as to have a final nucleic acid concentration from 3 to 100 nM was dispensed to the 96-well culture plate at 20 µL/well, and the cells were cultured at 37° C. under 5% $CO_2$ conditions to introduce each preparation into the Mia PaCa-2/Luc cells. Untreated cells were seeded as a negative control group.

The cells containing each preparation thus introduced were cultured in a 5% $CO_2$ incubator of 37° C. for 24 hours and treated using a luciferase quantification system (Steady-Glo Luciferase Assay System, Promega Corp., E2520) in accordance with the method described in the instructions attached to the product, followed by the measurement of luminescence intensity with a plate reader. The amount of luminescence of the group treated with each preparation was calculated as a relative ratio to the corrected amount of luminescence of the negative control group defined as 1 to obtain an IC50 value.

As is evident from Table 33, the Luc suppression ratios of preparations 1 to 9 containing D-DPPC, introduced in the human pancreatic cancer-derived cell line MIA PaCa-2/Luc cells, were consequently higher than those of preparations 10 to 12 containing L-DPPC instead of D-DPPC. When preparations 1 to 3 were compared, a higher content of D-DPPC resulted in a higher suppression ratio. Similar results were also obtained about preparations 4 to 6 and 7 to 9.

These results demonstrated that the lipid nanoparticle of the present invention containing an analog of a fatty acid ester of glycerol that is not hydrolyzable by a lipase can introduce a nucleic acid into cells, etc. even in the presence of PLA2.

TABLE 33

| Preparation No. | KD % (3 nM) | IC50 (nM) |
| --- | --- | --- |
| 1 | 59.5 | <3.00 |
| 2 | 51.1 | <3.00 |
| 3 | 46.0 | 3.69 |
| 4 | 65.2 | <3.00 |
| 5 | 62.9 | <3.00 |
| 6 | 53.0 | <3.00 |
| 7 | 41.5 | 6.06 |
| 8 | 37.8 | 7.58 |
| 9 | 35.2 | 14.1 |
| 10 | 34.5 | 6.52 |
| 11 | 28.1 | 8.66 |
| 12 | 18.5 | >100 |

Example 10

Preparation 13 containing nucleic acid-containing lipid nanoparticles was produced as described below using compound II-3 obtained in Reference Example A10, compound CL-10 obtained in Reference Example B10, 1,2-distearoyl-sn-glycero-3-phosphoethanolamine-N-[methoxy(polyethylene glycol)-2000] (PEG-DSPE), DL-α-phosphatidylcholine, distearoyl (DL-DSPC) and cholesterol.

DL-DSPC was obtained from Sigma-Aldrich Corp.

DL-DSPC was dissolved at 20 mg/mL in 100% ethanol to prepare a lipid stock solution. Each lipid stock solution was stored at –20° C. Immediately before formulation, the lipid was dissolved by heating to 60° C., and the resulting solution was brought back to room temperature and then used.

The lipid stock solution of compound II-3 (0.313 µmol) was added to 80% ethanol and a 0.1% aqueous HCl solution. Subsequently, 200 µL of the Luc siRNA solution was added thereto, and the mixture was stirred for 1 minute. Then, the lipid stock solutions of compound CL-10, PEG-DSPE, DL-DSPC and Choi (1.88 µmol, 0.235 µmol, 0.486 µmol and 1.01 µmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 13.

Example 11

Preparation 14 having a distinct content of DL-DSPC was produced as described below.

L-α-Phosphatidylcholine, distearoyl (L-DSPC) was obtained from NOF Corp.

L-DSPC was dissolved at 20 mg/mL in 100% ethanol to prepare a lipid stock solution.

The lipid stock solution of compound II-3 (0.313 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-10, PEG-DSPE, DL-DSPC, L-DSPC and Choi (1.88 μmol, 0.235 μmol, 0.243 μmol, 0.243 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 14.

Example 12

Preparation 15 containing nucleic acid-containing lipid nanoparticles was produced as described below using compound II-3 obtained in Reference Example A10, compound CL-8 obtained in Reference Example B8, 1,2-distearoyl-sn-glycero-3-phosphoethanolamine-N-[methoxy(polyethylene glycol)-2000] (PEG-DSPE), DL-α-phosphatidylcholine, distearoyl (DL-DSPC) and cholesterol.

The lipid stock solution of compound II-3 (0.313 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-8, PEG-DSPE, DL-DSPC and Choi (1.88 μmol, 0.235 μmol, 0.486 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 15.

Example 13

Preparation 16 having a distinct content of DL-DSPC was produced as described below.

The lipid stock solution of compound II-3 (0.313 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-8, PEG-DSPE, DL-DSPC, L-DSPC and Choi (1.88 μmol, 0.235 μmol, 0.243 μmol, 0.243 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 16.

Example 14

Preparation 17 containing nucleic acid-containing lipid nanoparticles was produced as described below using compound II-12 obtained in Reference Example A19, compound CL-10 obtained in Reference Example B10, 1,2-distearoyl-sn-glycero-3-phosphoethanolamine-N-[methoxy(polyethylene glycol)-2000] (PEG-DSPE), DL-α-phosphatidylcholine, distearoyl (DL-DSPC) and cholesterol.

The lipid stock solution of compound II-12 (0.626 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-10, PEG-DSPE, DL-DSPC and Choi (1.88 μmol, 0.235 μmol, 0.486 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 17.

Example 15

Preparation 18 having a distinct content of DL-DSPC was produced as described below.

The lipid stock solution of compound II-12 (0.626 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-10, PEG-DSPE, DL-DSPC, L-DSPC and Choi (1.88 μmol, 0.235 μmol, 0.243 μmol, 0.243 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 18.

Example 16

Preparation 19 containing nucleic acid-containing lipid nanoparticles was produced as described below using compound II-4 obtained in Reference Example A11, compound CL-2 obtained in Reference Example B2, 1,2-distearoyl-sn-glycero-3-phosphoethanolamine-N-[methoxy(polyethylene glycol)-2000] (PEG-DSPE), DL-α-phosphatidylcholine, distearoyl (DL-DSPC) and cholesterol.

The lipid stock solution of compound II-4 (0.156 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-2, PEG-DSPE, DL-DSPC and Choi (1.88 μmol, 0.235 μmol, 0.536 μmol and 1.11 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 19.

Example 17

Preparation 20 having a distinct content of DL-DSPC was produced as described below.

The lipid stock solution of compound II-4 (0.156 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-2, PEG-DSPE, DL-DSPC, L-DSPC and Choi (1.88 μmol, 0.235 μmol, 0.268 μmol, 0.268 μmol and 1.11 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 20.

Comparative Example 4

Preparation 21 was obtained in the same way as in Example 10 except that DL-DSPC of preparation 13 was changed to L-DSPC.

Comparative Example 5

Preparation 22 was obtained in the same way as in Example 12 except that DL-DSPC of preparation 15 was changed to L-DSPC.

Comparative Example 6

Preparation 23 was obtained in the same way as in Example 14 except that DL-DSPC of preparation 17 was changed to L-DSPC.

Comparative Example 7

Preparation 24 was obtained in the same way as in Example 16 except that DL-DSPC of preparation 19 was changed to L-DSPC.

Test Example 3

Average Particle Size Measurement of Nucleic Acid-Containing Lipid Nanoparticle

The average particle size of the nucleic acid-containing lipid nanoparticles in each preparation was measured with a particle size measurement apparatus (Zetasizer Nano ZS, manufactured by Malvern Panalytical Ltd.) (Table 34). PDI in the table represents polydispersity index.

TABLE 34

| Preparation No. | Size (nm) | PDI |
|---|---|---|
| 13 | 38.87 | 0.128 |
| 14 | 38.37 | 0.094 |
| 15 | 35.65 | 0.133 |
| 16 | 37.10 | 0.132 |
| 17 | 39.00 | 0.095 |
| 18 | 37.85 | 0.088 |
| 19 | 50.92 | 0.151 |
| 20 | 56.10 | 0.161 |
| 21 | 39.87 | 0.090 |
| 22 | 32.06 | 0.127 |
| 23 | 37.44 | 0.153 |
| 24 | 50.06 | 0.175 |

As a result, preparations 13 to 24 exhibited an average particle size from 30 to 60 nm and had PDI from 0.08 to 0.18.

Test Example 4

In Vitro Activity Evaluation Test of Nucleic Acid-Containing Lipid Nanoparticle

Preparations 13 to 20 described in Examples 10 to 17 and preparations 21 to 24 described in Comparative Examples 4 to 7 were each introduced to human pancreatic cancer-derived cell line Mia PaCa-2/Luc cells by the following method.

Each preparation was treated with PLA2 and evaluated for its gene suppression ratio according to the method described in [Non Patent Literature 3]. Mia PaCa-2/Luc cells suspended in Dulbecco's modified Eagle's minimal essential medium (DMEM) containing 10% fetal bovine serum (FBS, Gibco/Thermo Fisher Scientific Inc.) were seeded in a 96-well culture plate at 7500 cells/80 µL/well, and cultured at 37° C. for 24 hours under 5% $CO_2$ conditions. Each preparation diluted with Opti-MEM (Gibco/Thermo Fisher Scientific Inc.) so as to have a final nucleic acid concentration from 3 to 100 nM was dispensed to the 96-well culture plate at 20 µL/well, and the cells were cultured at 37° C. under 5% $CO_2$ conditions to introduce each preparation into the Mia PaCa-2/Luc cells. Untreated cells were seeded as a negative control group.

The cells containing each preparation thus introduced were cultured in a 5% $CO_2$ incubator of 37° C. for 24 hours and treated using a luciferase quantification system (Steady-Glo Luciferase Assay System, Promega Corp., E2520) in accordance with the method described in the instructions attached to the product, followed by the measurement of luminescence intensity with a plate reader. The amount of luminescence of the group treated with each preparation was calculated as a relative ratio to the corrected amount of luminescence of the negative control group defined as 1 to obtain an IC50 value.

As is evident from Table 35, the Luc suppression ratios of preparations 13 to 20 containing DL-DSPC, introduced in the human pancreatic cancer-derived cell line MIA PaCa-2/Luc cells, were consequently higher than those of preparations 21 to 24 containing L-DSPC instead of DL-DSPC.

These results demonstrated that the lipid nanoparticle of the present invention containing an analog of a fatty acid ester of glycerol that is not hydrolyzable by a lipase can introduce a nucleic acid into cells, etc. even in the presence of PLA2.

TABLE 35

| Preparation No. | KD % (3 nM) | IC50 (nM) |
|---|---|---|
| 13 | 43.0 | 4.26 |
| 14 | 38.7 | 5.22 |
| 15 | 70.0 | <3.00 |
| 16 | 56.3 | <3.00 |
| 17 | 40.5 | 4.91 |
| 18 | 26.3 | 10.1 |
| 19 | 19.3 | 10.3 |
| 20 | 15.3 | 16.6 |
| 21 | 21.6 | 11.4 |
| 22 | 49.3 | 3.15 |
| 23 | 20.0 | 12.0 |
| 24 | 11.1 | 29.2 |

Example 18

A preparation having a distinct content of D-DSPC was produced as described below.

Preparation 25 containing nucleic acid-containing lipid nanoparticles was produced as described below using compound II-3 obtained in Reference Example A10, compound CL-10 obtained in Reference Example B10, 1,2-distearoyl-sn-glycero-3-phosphoethanolamine-N-[methoxy(polyethylene glycol)-2000] (PEG-DSPE), D-α-phosphatidylcholine, distearoyl (D-DSPC) and cholesterol (Chol).

The lipid stock solution of compound II-3 (0.313 µmol) was added to 80% ethanol and a 0.1% aqueous HCl solution. Subsequently, 200 µL of the Luc siRNA solution was added thereto, and the mixture was stirred for 1 minute. Then, the lipid stock solutions of compound CL-10, PEG-DSPE, D-DSPC and Choi (1.88 µmol, 0.235 µmol, 0.486 µmol and 1.01 µmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 25.

Example 19

A preparation having a distinct content of D-DSPC was produced as described below.

Preparation 26 containing nucleic acid-containing lipid nanoparticles was produced as described below using compound II-3 obtained in Reference Example A10, compound CL-10 obtained in Reference Example B10, 1,2-distearoyl-sn-glycero-3-phosphoethanolamine-N-[methoxy(polyethylene glycol)-2000] (PEG-DSPE), D-α-phosphatidylcholine, distearoyl (D-DSPC), L-α-phosphatidylcholine, distearoyl (L-DSPC) and cholesterol.

The lipid stock solution of compound II-3 (0.313 µmol) was added to 80% ethanol and a 0.1% aqueous HCl solution. Subsequently, 200 µL of the Luc siRNA solution was added thereto, and the mixture was stirred for 1 minute. Then, the lipid stock solutions of compound CL-10, PEG-DSPE, D-DSPC, L-DSPC and Choi (1.88 µmol, 0.235 µmol, 0.243 µmol, 0.243 µmol and 1.01 µmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 26.

Example 20

A preparation having a distinct content of D-DSPC was produced as described below.

Preparation 27 containing nucleic acid-containing lipid nanoparticles was produced as described below using compound II-25 obtained in Reference Example A34, compound CL-2 obtained in Reference Example B2, 1,2-distearoyl-sn-glycero-3-phosphoethanolamine-N-[methoxy(polyethylene glycol)-2000] (PEG-DSPE), D-α-phosphatidylcholine, distearoyl (D-DSPC) and cholesterol.

The lipid stock solution of compound II-25 (0.626 µmol) was added to 80% ethanol and a 0.1% aqueous HCl solution. Subsequently, 200 µL of the Luc siRNA solution was added thereto, and the mixture was stirred for 1 minute. Then, the lipid stock solutions of compound CL-2, PEG-DSPE, D-DSPC and Choi (1.88 µmol, 0.235 µmol, 0.384 µmol and 0.797 µmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 27.

Example 21

A preparation having a distinct content of D-DSPC was produced as described below.

Preparation 28 containing nucleic acid-containing lipid nanoparticles was produced as described below using compound II-25 obtained in Reference Example A34, compound CL-2 obtained in Reference Example B2, 1,2-distearoyl-sn-glycero-3-phosphoethanolamine-N-[methoxy(polyethylene glycol)-2000] (PEG-DSPE), D-α-phosphatidylcholine, distearoyl (D-DSPC), L-α-phosphatidylcholine, distearoyl (L-DSPC) and cholesterol.

The lipid stock solution of compound II-25 (0.626 µmol) was added to 80% ethanol and a 0.1% aqueous HCl solution. Subsequently, 200 µL of the Luc siRNA solution was added thereto, and the mixture was stirred for 1 minute. Then, the lipid stock solutions of compound CL-2, PEG-DSPE, D-DSPC, L-DSPC and Choi (1.88 µmol, 0.235 µmol, 0.192 µmol, 0.192 µmol and 0.797 µmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 28.

Example 22

A preparation having a distinct content of D-DSPC was produced as described below.

Preparation 29 containing nucleic acid-containing lipid nanoparticles was produced as described below using compound II-12 obtained in Reference Example A19, compound CL-10 obtained in Reference Example B10, 1,2-distearoyl-sn-glycero-3-phosphoethanolamine-N-[methoxy(polyethylene glycol)-2000] (PEG-DSPE), D-α-phosphatidylcholine, distearoyl (D-DSPC) and cholesterol.

The lipid stock solution of compound II-12 (0.313 µmol) was added to 80% ethanol and a 0.1% aqueous HCl solution. Subsequently, 200 µL of the Luc siRNA solution was added thereto, and the mixture was stirred for 1 minute. Then, the lipid stock solutions of compound CL-10, PEG-DSPE, D-DSPC and Choi (1.88 µmol, 0.235 µmol, 0.486 µmol and 1.01 µmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 29.

Example 23

A preparation having a distinct content of D-DSPC was produced as described below.

Preparation 30 containing nucleic acid-containing lipid nanoparticles was produced as described below using compound II-12 obtained in Reference Example A19, compound CL-10 obtained in Reference Example B10, 1,2-distearoyl-sn-glycero-3-phosphoethanolamine-N-[methoxy(polyethylene glycol)-2000] (PEG-DSPE), D-α-phosphatidylcholine, distearoyl (D-DSPC), L-α-phosphatidylcholine, distearoyl (L-DSPC) and cholesterol.

The lipid stock solution of compound II-12 (0.313 µmol) was added to 80% ethanol and a 0.1% aqueous HCl solution. Subsequently, 200 µL of the Luc siRNA solution was added thereto, and the mixture was stirred for 1 minute. Then, the lipid stock solutions of compound CL-10, PEG-DSPE, D-DSPC, L-DSPC and Choi (1.88 µmol, 0.235 µmol, 0.243 µmol, 0.243 µmol and 1.01 µmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 30.

Example 24

A preparation having a distinct content of D-DSPC was produced as described below.

Preparation 31 containing nucleic acid-containing lipid nanoparticles was produced as described below using compound II-18 obtained in Reference Example A25, compound CL-10 obtained in Reference Example B10, 1,2-distearoyl-sn-glycero-3-phosphoethanolamine-N-[methoxy(polyethylene glycol)-2000] (PEG-DSPE), D-α-phosphatidylcholine, distearoyl (D-DSPC) and cholesterol.

The lipid stock solution of compound II-18 (0.313 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-10, PEG-DSPE, D-DSPC and Chol (1.88 μmol, 0.235 μmol, 0.486 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 31.

Example 25

A preparation having a distinct content of D-DSPC was produced as described below.

Preparation 32 containing nucleic acid-containing lipid nanoparticles was produced as described below using compound II-18 obtained in Reference Example A25, compound CL-10 obtained in Reference Example B10, 1,2-distearoyl-sn-glycero-3-phosphoethanolamine-N-[methoxy(polyethylene glycol)-2000] (PEG-DSPE), D-α-phosphatidylcholine, distearoyl (D-DSPC), L-α-phosphatidylcholine, distearoyl (L-DSPC) and cholesterol.

The lipid stock solution of compound II-18 (0.313 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-10, PEG-DSPE, D-DSPC, L-DSPC and Chol (1.88 μmol, 0.235 μmol, 0.243 μmol, 0.243 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 32.

Comparative Example 8

Preparation 33 was obtained in the same way as in Example 18 except that D-DSPC of preparation 25 was changed to L-DSPC.

Comparative Example 9

Preparation 34 was obtained in the same way as in Example 20 except that D-DSPC of preparation 27 was changed to L-DSPC.

Comparative Example 10

Preparation 35 was obtained in the same way as in Example 22 except that D-DSPC of preparation 29 was changed to L-DSPC.

Comparative Example 11

Preparation 36 was obtained in the same way as in Example 24 except that D-DSPC of preparation 31 was changed to L-DSPC.

Test Example 5

Average Particle Size Measurement of Nucleic Acid-Containing Lipid Nanoparticle

The average particle size of the nucleic acid-containing lipid nanoparticles in each preparation was measured with a particle size measurement apparatus (Zetasizer Nano ZS, manufactured by Malvern Panalytical Ltd.) (Table 36). PDI in the table represents polydispersity index.

TABLE 36

| Preparation No. | Size (nm) | PDI |
|---|---|---|
| 25 | 36.02 | 0.130 |
| 26 | 36.30 | 0.181 |
| 27 | 48.73 | 0.172 |
| 28 | 46.49 | 0.221 |
| 29 | 36.42 | 0.172 |
| 30 | 40.44 | 0.181 |
| 31 | 37.57 | 0.120 |
| 32 | 34.73 | 0.164 |
| 33 | 32.88 | 0.139 |
| 34 | 47.35 | 0.187 |
| 35 | 37.92 | 0.177 |
| 36 | 37.28 | 0.137 |

Test Example 6

In Vitro Activity Evaluation Test of Nucleic Acid-Containing Lipid Nanoparticle

Preparations 25 to 32 described in Examples 18 to 25 and preparations 33 to 36 described in Comparative Examples 8 to 11 were each introduced to human pancreatic cancer-derived cell line Mia PaCa-2/Luc cells by the following method.

Each preparation was treated with PLA2 and evaluated for its gene suppression ratio according to the method described in [Non Patent Literature 3]. Mia PaCa-2/Luc cells suspended in Dulbecco's modified Eagle's minimal essential medium (DMEM) containing 10% fetal bovine serum (FBS, Gibco/Thermo Fisher Scientific Inc.) were seeded in a 96-well culture plate at 7500 cells/80 μL/well, and cultured at 37° C. for 24 hours under 5% $CO_2$ conditions. Each preparation diluted with Opti-MEM (Gibco/Thermo Fisher Scientific Inc.) so as to have a final nucleic acid concentration from 3 to 100 nM was dispensed to the 96-well culture plate at 20 μL/well, and the cells were cultured at 37° C. under 5% $CO_2$ conditions to introduce each preparation into the Mia PaCa-2/Luc cells. Untreated cells were seeded as a negative control group.

The cells containing each preparation thus introduced were cultured in a 5% $CO_2$ incubator of 37° C. for 24 hours and treated using a luciferase quantification system (Steady-Glo Luciferase Assay System, Promega Corp., E2520) in accordance with the method described in the instructions attached to the product, followed by the measurement of luminescence intensity with a plate reader. The amount of luminescence of the group treated with each preparation was calculated as a relative ratio to the corrected amount of luminescence of the negative control group defined as 1 to obtain an IC50 value.

As is evident from Table 37, the Luc suppression ratios of preparations 25 to 32 containing D-DSPC, introduced in the human pancreatic cancer-derived cell line MIA PaCa-2/Luc cells, were consequently higher than those of preparations 33 to 36 containing L-DSPC instead of D-DSPC.

These results demonstrated that the lipid nanoparticle of the present invention containing an analog of a fatty acid ester of glycerol that is not hydrolyzable by a lipase can introduce a nucleic acid into cells, etc. even in the presence of PLA2.

TABLE 37

| Preparation No. | KD % (3 nM) | IC50 (nM) |
|---|---|---|
| 25 | 55.9 | 2.36 |
| 26 | 43.4 | 4.01 |
| 27 | 23.8 | 7.25 |
| 28 | 25.0 | 7.69 |
| 29 | 60.4 | 2.05 |
| 30 | 42.9 | 4.24 |
| 31 | 55.0 | 2.29 |
| 32 | 41.6 | 4.98 |
| 33 | 25.4 | 8.26 |
| 34 | 19.6 | 9.83 |
| 35 | 28.5 | 7.19 |
| 36 | 34.0 | 6.35 |

Example 26

Preparation 37 containing nucleic acid-containing lipid nanoparticles was produced as described below using compound II-3 obtained in Reference Example A10, compound CL-10 obtained in Reference Example B10, 1,2-distearoyl-sn-glycero-3-phosphoethanolamine-N-[methoxy(polyethylene glycol)-2000] (PEG-DSPE), 1,2-dioctadecyl-sn-glycero-3-phosphocholine (Diether-PC) and cholesterol.

Diether-PC was obtained from Avanti Polar Lipids, Inc.

Diether-PC was dissolved at 20 mg/mL in 100% ethanol to prepare a lipid stock solution. Each lipid stock solution was stored at −20° C. Immediately before formulation, the lipid was dissolved by heating to 60° C., and the resulting solution was brought back to room temperature and then used.

The lipid stock solution of compound II-3 (0.313 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-10, PEG-DSPE, Diether-PC and Chol (1.88 μmol, 0.235 μmol, 0.486 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 37.

Example 27

Preparation 38 having a distinct content of Diether-PC was produced as described below.

The lipid stock solution of compound II-3 (0.313 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-10, PEG-DSPE, Diether-PC, L-DSPC and Chol (1.88 μmol, 0.235 μmol, 0.243 μmol, 0.243 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 38.

Example 28

Preparation 39 containing nucleic acid-containing lipid nanoparticles was produced as described below using compound II-3 obtained in Reference Example A10, compound CL-8 obtained in Reference Example B8, 1,2-distearoyl-sn-glycero-3-phosphoethanolamine-N-[methoxy(polyethylene glycol)-2000] (PEG-DSPE), 1,2-dioctadecyl-sn-glycero-3-phosphocholine (Diether-PC) and cholesterol.

The lipid stock solution of compound II-3 (0.313 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-8, PEG-DSPE, Diether-PC and Chol (1.88 μmol, 0.235 μmol, 0.486 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 39.

Example 29

Preparation 40 having a distinct content of Diether-PC was produced as described below.

The lipid stock solution of compound II-3 (0.313 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-8, PEG-DSPE, Diether-PC, L-DSPC and Chol (1.88 μmol, 0.235 μmol, 0.243 μmol, 0.243 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 40.

Example 30

Preparation 41 containing nucleic acid-containing lipid nanoparticles was produced as described below using compound II-12 obtained in Reference Example A19, compound CL-10 obtained in Reference Example B10, 1,2-distearoyl-sn-glycero-3-phosphoethanolamine-N-[methoxy(polyethylene glycol)-2000] (PEG-DSPE), 1,2-dioctadecyl-sn-glycero-3-phosphocholine (Diether-PC) and cholesterol.

The lipid stock solution of compound II-12 (0.626 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-10, PEG-DSPE, Diether-PC and Chol (1.88 μmol, 0.235 μmol, 0.486 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 41.

Example 31

Preparation 42 having a distinct content of Diether-PC was produced as described below.

The lipid stock solution of compound II-12 (0.626 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-10, PEG-DSPE, Diether-PC, L-DSPC and Choi (1.88 μmol, 0.235 μmol, 0.243 μmol, 0.243 μmol and 1.01 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 42.

Example 32

Preparation 43 containing nucleic acid-containing lipid nanoparticles was produced as described below using compound II-4 obtained in Reference Example A11, compound CL-2 obtained in Reference Example B2, 1,2-distearoyl-sn-glycero-3-phosphoethanolamine-N-[methoxy(polyethylene glycol)-2000] (PEG-DSPE), 1,2-dioctadecyl-sn-glycero-3-phosphocholine (Diether-PC) and cholesterol.

The lipid stock solution of compound II-4 (0.156 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-2, PEG-DSPE, Diether-PC and Choi (1.88 μmol, 0.235 μmol, 0.536 μmol and 1.11 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 43.

Example 33

Preparation 44 having a distinct content of Diether-PC was produced as described below.

The lipid stock solution of compound II-4 (0.156 μmol) was added to 80% ethanol and a 0.1% aqueous HCl solution. Subsequently, 200 μL of the Luc siRNA solution was added thereto, and the mixture was stirred for 1 minute. Then, the lipid stock solutions of compound CL-2, PEG-DSPE, Diether-PC, L-DSPC and Choi (1.88 μmol, 0.235 μmol, 0.268 μmol, 0.268 μmol and 1.11 μmol, respectively) were added to the solution. Then, injectable water was added at a flow rate of 62 mL/sec or more such that an aqueous solution of 20% or less ethanol was prepared to form a crude preparation. The obtained crude preparation was treated in the same way as in Example 1 to obtain preparation 44.

Test Example 7

Average Particle Size Measurement of Nucleic Acid-Containing Lipid Nanoparticle

The average particle size of the nucleic acid-containing lipid nanoparticles in each preparation was measured with a particle size measurement apparatus (Zetasizer Nano ZS, manufactured by Malvern Panalytical Ltd.) (Table 38). PDI in the table represents polydispersity index.

TABLE 38

| Preparation No. | Size (nm) | PDI |
| --- | --- | --- |
| 37 | 39.06 | 0.118 |
| 38 | 39.51 | 0.142 |
| 39 | 37.67 | 0.189 |
| 40 | 33.24 | 0.210 |
| 41 | 40.31 | 0.123 |
| 42 | 38.49 | 0.120 |
| 43 | 52.34 | 0.131 |
| 44 | 43.94 | 0.150 |

As a result, preparations 37 to 44 exhibited an average particle size from 30 to 60 nm and had PDI from 0.11 to 0.21.

Test Example 8

In Vitro Activity Evaluation Test of Nucleic Acid-Containing Lipid Nanoparticle

Preparations 37 to 44 described in Examples 26 to 33 and preparations 21 to 24 described in Comparative Examples 4 to 7 were each introduced to human pancreatic cancer-derived cell line Mia PaCa-2/Luc cells by the following method.

Each preparation was treated with PLA2 and evaluated for its gene suppression ratio according to the method described in [Non Patent Literature 3]. Mia PaCa-2/Luc cells suspended in Dulbecco's modified Eagle's minimal essential medium (DMEM) containing 10% fetal bovine serum (FBS, Gibco/Thermo Fisher Scientific Inc.) were seeded in a 96-well culture plate at 7500 cells/80 μL/well, and cultured at 37° C. for 24 hours under 5% $CO_2$ conditions. Each preparation diluted with Opti-MEM (Gibco/Thermo Fisher Scientific Inc.) so as to have a final nucleic acid concentration from 3 to 100 nM was dispensed to the 96-well culture plate at 20 μL/well, and the cells were cultured at 37° C. under 5% $CO_2$ conditions to introduce each preparation into the Mia PaCa-2/Luc cells. Untreated cells were seeded as a negative control group.

The cells containing each preparation thus introduced were cultured in a 5% $CO_2$ incubator of 37° C. for 24 hours and treated using a luciferase quantification system (Steady-Glo Luciferase Assay System, Promega Corp., E2520) in accordance with the method described in the instructions attached to the product, followed by the measurement of luminescence intensity with a plate reader. The amount of luminescence of the group treated with each preparation was calculated as a relative ratio to the corrected amount of luminescence of the negative control group defined as 1 to obtain an IC50 value.

As is evident from Table 39, the Luc suppression ratios of preparations 37 to 44 containing Diether-PC, introduced in the human pancreatic cancer-derived cell line MIA PaCa-2/Luc cells, were consequently higher than those of preparations 21 to 24 containing L-DSPC instead of Diether-PC.

These results demonstrated that the lipid nanoparticle of the present invention containing an analog of a fatty acid ester of glycerol that is not hydrolyzable by a lipase can introduce a nucleic acid into cells, etc. even in the presence of PLA2.

TABLE 39

| Preparation No. | KD % (3 nM) | IC50 (nM) |
| --- | --- | --- |
| 37 | 51.6 | <3.00 |
| 38 | 45.2 | 3.94 |
| 39 | 57.7 | <3.00 |

TABLE 39-continued

| Preparation No. | KD % (3 nM) | IC50 (nM) |
|---|---|---|
| 40 | 60.5 | <3.00 |
| 41 | 63.1 | <3.00 |
| 42 | 54.0 | <3.00 |
| 43 | 32.1 | 9.13 |
| 44 | 34.3 | 6.95 |
| 21 | 21.6 | 11.3 |
| 22 | 49.3 | 3.15 |
| 23 | 20.0 | 12.0 |
| 24 | 11.1 | 29.2 |

Test Example 9

Quantification of Neutral Lipid and Analog of Fatty Acid Ester of Glycerol that is not Hydrolyzable by Lipase in Nucleic Acid-Containing Lipid Nanoparticle Treated with PLA2

The total amount of L-DPPC and D-DPPC in the nucleic acid-containing lipid nanoparticles used in Test Example 2 was quantified with a LC/MS/MS apparatus (ACQUITY UPLC SYSTEM (Waters Corp.) and API4000 Q TRAP (AB Sciex Pte. Ltd.)). The quantification results are shown in FIG. 1. In the LC/MS/MS analysis, 10 mM ammonium acetate/isopropanol/acetonitrile (80:10:10) and isopropanol/acetonitrile (50:50) were used as mobile phases, and ACQUITY UPLC BEH C8 (1.7 µm, 2.1 mm I.D.×50 mm, Waters Corp.) was used as a column.

The amount of the lipids remaining in each preparation was calculated as a relative ratio to the amount of the lipids remaining in a PLA2-untreated group defined as 1.

Test Example 10

Quantification of Neutral Lipid and Analog of Fatty Acid Ester of Glycerol that is not Hydrolyzable by Lipase in Nucleic Acid-Containing Lipid Nanoparticle Treated with PLA2

The total amount of DL-DSPC and L-DSPC in the nucleic acid-containing lipid nanoparticles used in Test Example 4 was quantified with a LC/MS/MS apparatus (ACQUITY UPLC SYSTEM (Waters Corp.) and API4000 (AB Sciex Pte. Ltd.)). The quantification results are shown in FIG. 2. In the LC/MS/MS analysis, 10 mM ammonium acetate/isopropanol/acetonitrile (80:10:10) and isopropanol/acetonitrile (50:50) were used as mobile phases, and ACQUITY UPLC BEH C8 (1.7 µm, 2.1 mm I.D.×50 mm, Waters Corp.) was used as a column.

The amount of the lipids remaining in each preparation was calculated as a relative ratio to the amount of the lipids remaining in a PLA2-untreated group defined as 1.

Test Example 11

Quantification of Neutral Lipid and Analog of Fatty Acid Ester of Glycerol that is not Hydrolyzable by Lipase in Nucleic Acid-Containing Lipid Nanoparticle Treated with PLA2

The total amount of Ether-PC and L-DSPC in the nucleic acid-containing lipid nanoparticles used in Test Example 8 was quantified with a LC/MS/MS apparatus (ACQUITY UPLC SYSTEM (Waters Corp.) and API4000 (AB Sciex Pte. Ltd.)). The quantification results are shown in FIG. 3. In the LC/MS/MS analysis, 10 mM ammonium acetate/isopropanol/acetonitrile (80:10:10) and isopropanol/acetonitrile (50:50) were used as mobile phases, and ACQUITY UPLC BEH C8 (1.7 µm, 2.1 mm I.D.×50 mm, Waters Corp.) was used as a column.

The amount of the lipids remaining in each preparation was calculated as a relative ratio to the amount of the lipids remaining in a PLA2-untreated group defined as 1.

Example 34

Preparation 45 containing nucleic acid-containing lipid nanoparticles was produced as described below using compound II-25 obtained in Reference Example A34, compound CL-67 obtained in Reference Example C1, 1,2-distearoyl-sn-glycero-3-phosphoethanolamine-N-[methoxy(polyethylene glycol)-2000] (PEG-DSPE), DL-α-phosphatidylcholine, distearoyl (DL-DSPC) and cholesterol (Chol).

The nucleic acid used was siRNA silencing luciferase (hereinafter, referred to as "Luc") gene and consisting of the nucleotide sequences of a sense strand (5'-CCGUCGUAUUCGUGAGCAAGA-3') (SEQ ID NO:1) and an antisense strand (5'-UUGCUCACGAAUACGACGGUG-3') (SEQ ID NO:2), and was obtained from Gene Design, Inc. (hereinafter, referred to as "Luc siRNA"). PEG-DSPE and cholesterol were obtained from NOF Corp. DL-DSPC was obtained from Sigma-Aldrich Corp.

Compound II-25 was dissolved at 5 mg/mL in 100% ethanol to prepare a lipid stock solution. Compound CL-67, PEG-DSPE, DL-DSPC and cholesterol were each dissolved at 20 mg/mL in 100% ethanol to prepare lipid stock solutions. Each lipid stock solution was stored at −20° C. Immediately before formulation, the lipid was dissolved by heating to 60° C., and the resulting solution was brought back to room temperature and then used. Luc siRNA was dissolved at 1 mg/mL in injectable water to prepare a Luc siRNA solution.

The lipid stock solution of compound II-25 (0.313 µmol) was added to 80% ethanol and a 0.1% aqueous HCl solution. Subsequently, 200 µL of the Luc siRNA solution was added thereto, and the mixture was stirred for 1 minute. Then, the lipid stock solutions of compound CL-67, PEG-DSPE, DL-DSPC and Choi (1.88 µmol, 0.235 µmol, 0.486 µmol and 1.01 µmol, respectively) were added to the solution. Then, injectable water was added at a flow rate of 62 mL/sec or more such that an aqueous solution of 20% or less ethanol was prepared to form a crude preparation. The obtained crude preparation was concentrated using Amicon Ultra (manufactured by Merck Millipore), further solvent-replaced with physiological saline, and filtered using a 0.2-µm filter (manufactured by Toyo Roshi Kaisha, Ltd.) in a clean bench. The siRNA concentration of the obtained preparation was further measured, and the preparation was diluted with physiological saline such that the siRNA concentration was 0.1 mg/mL to obtain preparation 45.

Example 35

Preparation 46 was obtained in the same way as in Example 34 except that compound CL-67 of preparation 45 was changed to compound CL-69 obtained in Example C3.

Example 36

Preparation 47 was obtained in the same way as in Example 34 except that compound CL-67 of preparation 45 was changed to compound CL-72 obtained in Example C6.

Example 37

Preparation 48 was obtained in the same way as in Example 34 except that compound CL-67 of preparation 45 was changed to compound CL-73 obtained in Example C1.

Example 38

Preparation 49 was obtained in the same way as in Example 34 except that compound CL-67 of preparation 45 was changed to compound CL-86 obtained in Example C20.

Example 39

Preparation 50 was obtained in the same way as in Example 34 except that compound CL-67 of preparation 45 was changed to compound CL-70 obtained in Example C4.

Example 40

Preparation 51 was obtained in the same way as in Example 34 except that compound CL-67 of preparation 45 was changed to compound CL-71 obtained in Example C5.

Example 41

Preparation 52 was obtained in the same way as in Example 34 except that compound CL-67 of preparation 45 was changed to compound CL-74 obtained in Example C11.

Example 42

Preparation 53 was obtained in the same way as in Example 34 except that compound CL-67 of preparation 45 was changed to compound CL-76 obtained in Example C10.

Example 43

Preparation 54 was obtained in the same way as in Example 34 except that compound CL-67 of preparation 45 was changed to compound CL-77 obtained in Example C8.

Example 44

Preparation 55 was obtained in the same way as in Example 34 except that compound CL-67 of preparation 45 was changed to compound CL-80 obtained in Example C13.

Example 45

Preparation 56 was obtained in the same way as in Example 34 except that compound CL-67 of preparation 45 was changed to compound CL-81 obtained in Example C12.

Example 46

Preparation 57 was obtained in the same way as in Example 34 except that compound CL-67 of preparation 45 was changed to compound CL-7 obtained in Reference Example B7.

Example 47

Preparation 58 was obtained in the same way as in Example 34 except that compound CL-67 of preparation 45 was changed to compound CL-47 obtained in Reference Example B47.

Example 48

Preparation 59 was obtained in the same way as in Example 34 except that compound CL-67 of preparation 45 was changed to compound CL-103 obtained in Reference Example C37.

Example 49

Preparation 60 was obtained in the same way as in Example 34 except that compound CL-67 of preparation 45 was changed to compound CL-55 obtained in Reference Example B55.

Test Example 12

Average Particle Size Measurement of Nucleic Acid-Containing Lipid Nanoparticle

The average particle size of the nucleic acid-containing lipid nanoparticles in each preparation was measured with a particle size measurement apparatus (Zetasizer Nano ZS, manufactured by Malvern Panalytical Ltd.) (Table 40). PDI in the table represents polydispersity index.

TABLE 40

| Preparation No. | Size (nm) | PDI |
|---|---|---|
| 45 | 41.98 | 0.106 |
| 46 | 38.83 | 0.170 |
| 47 | 43.41 | 0.136 |
| 48 | 43.62 | 0.164 |
| 49 | 38.97 | 0.173 |
| 50 | 41.79 | 0.095 |
| 51 | 43.89 | 0.112 |
| 52 | 43.84 | 0.121 |
| 53 | 47.83 | 0.130 |
| 54 | 43.98 | 0.131 |
| 55 | 42.78 | 0.208 |
| 56 | 38.77 | 0.214 |
| 57 | 41.41 | 0.172 |
| 58 | 40.92 | 0.201 |
| 59 | 36.30 | 0.246 |
| 60 | 38.12 | 0.196 |

As a result, preparations 45 to 60 exhibited an average particle size from 30 to 50 nm and had PDI from 0.095 to 0.246.

Test Example 13

In Vitro Activity Evaluation Test of Nucleic Acid-Containing Lipid Nanoparticle

Preparations 45 to 49 and 51 to 60 described in Examples 34 to 38 and 40 to 49 were each introduced to human pancreatic cancer-derived cell line Mia PaCa-2/Luc cells forced to express luciferase by the following method.

Each preparation was treated with PLA2 and evaluated for its gene suppression ratio according to the method described in [Non Patent Literature 3]. Mia PaCa-2/Luc cells suspended in Dulbecco's modified Eagle's minimal essential medium (DMEM) containing 10% fetal bovine serum (FBS, Access Biologicals LLC) were seeded in a 96-well culture plate at 7500 cells/80 µL/well, and cultured at 37° C. for 24 hours under 5% $CO_2$ conditions. Each preparation diluted with Opti-MEM (Gibco/Thermo Fisher Scientific Inc.) so as to have a final nucleic acid concentration from 3 to 100 nM was dispensed to the 96-well culture plate at 20 µL/well, and the cells were cultured at 37° C. under 5% $CO_2$ conditions to introduce each preparation into the Mia PaCa-2/Luc cells. Untreated cells were seeded as a negative control group.

The cells containing each preparation thus introduced were cultured in a 5% $CO_2$ incubator of 37° C. for 24 hours and treated using a luciferase quantification system (Steady-Glo Luciferase Assay System, Promega Corp., E2520) in accordance with the method described in the instructions attached to the product, followed by the measurement of luminescence intensity with a plate reader. The amount of luminescence of the group treated with each preparation was calculated as a relative ratio to the corrected amount of luminescence of the negative control group defined as 1 to obtain an IC50 value.

As is evident from Table 41, these results demonstrated that the lipid nanoparticle of the present invention containing an analog of a fatty acid ester of glycerol that is not hydrolyzable by a lipase can introduce a nucleic acid into cells, etc. even in the presence of PLA2.

TABLE 41

| Preparation No. | KD % (3 nM) | IC50 (nM) |
|---|---|---|
| 45 | 51.6 | <3.00 |
| 46 | 68.9 | <3.00 |
| 47 | 9.94 | 11.5 |
| 48 | 58.8 | <3.00 |
| 49 | 19.9 | 12.6 |
| 51 | 53.1 | <3.00 |
| 52 | 10.2 | 13.2 |
| 53 | 38.9 | 5.46 |
| 54 | 42.1 | 4.27 |
| 55 | 1.43 | 22.6 |
| 56 | 67.4 | <3.00 |
| 57 | 24.2 | 8.83 |
| 59 | 2.43 | 27.2 |
| 60 | 26.0 | 7.06 |

Test Example 14

In Vitro Activity Evaluation Test of Nucleic Acid-Containing Lipid Nanoparticle

Preparations 45 to 60 described in Examples 34 to 49 were each introduced to human uterine cervical cancer-derived cell line HeLa cells forced to express luciferase (hereinafter, referred to as Luc2CP-HeLa) by the following method.

Each preparation was treated with PLA2 and evaluated for its gene suppression ratio according to the method described in [Non Patent Literature 3]. Luc2CP-HeLa/Luc cells suspended in Dulbecco's modified Eagle's minimal essential medium (DMEM) containing 10% fetal bovine serum (FBS, Access Biologicals LLC) were seeded in a 96-well culture plate at 7500 cells/80 μL/well, and cultured at 37° C. for 24 hours under 5% $CO_2$ conditions. Each preparation diluted with Opti-MEM (Gibco/Thermo Fisher Scientific Inc.) so as to have a final nucleic acid concentration from 3 to 100 nM was dispensed to the 96-well culture plate at 20 μL/well, and the cells were cultured at 37° C. under 5% $CO_2$ conditions to introduce each preparation into the Luc2CP-HeLa/Luc cells. Untreated cells were seeded as a negative control group.

The cells containing each preparation thus introduced were cultured in a 5% $CO_2$ incubator of 37° C. for 24 hours and treated using a luciferase quantification system (Steady-Glo Luciferase Assay System, Promega Corp., E2520) in accordance with the method described in the instructions attached to the product, followed by the measurement of luminescence intensity with a plate reader. The amount of luminescence of the group treated with each preparation was calculated as a relative ratio to the corrected amount of luminescence of the negative control group defined as 1 to obtain an IC50 value.

As is evident from Table 42, these results demonstrated that the lipid nanoparticle of the present invention containing a fatty acid ester analog of glycerol that is not hydrolyzable by a lipase can introduce a nucleic acid into cells, etc. even in the presence of PLA2.

TABLE 42

| Preparation No. | KD % (3 nM) | IC50 (nM) |
|---|---|---|
| 45 | 57.8 | <3.00 |
| 46 | 86.2 | <3.00 |
| 47 | 4.39 | 22.4 |
| 48 | 63.4 | <3.00 |
| 49 | 9.02 | 16.1 |
| 50 | 55.2 | <3.00 |
| 51 | 67.7 | <3.00 |
| 52 | 3.12 | 14.1 |
| 53 | 32.1 | 4.80 |
| 54 | 39.8 | 3.93 |
| 55 | 7.31 | 14.8 |
| 56 | 81.4 | <3.00 |
| 57 | 10.3 | 18.1 |
| 58 | 47.8 | 3.17 |
| 59 | 1.61 | 17.8 |
| 60 | 14.1 | 7.92 |

Test Example 15

In Vitro Activity Evaluation Test of Nucleic Acid-Containing Lipid Nanoparticle

Preparations 45 to 60 described in Examples 34 to 49 were each introduced to human lung cancer-derived cell line NCI-H358/Luc cells forced to express luciferase by the following method.

Each preparation was treated with PLA2 and evaluated for its gene suppression ratio according to the method described in [Non Patent Literature 3]. NCI-H358/Luc cells suspended in Dulbecco's modified Eagle's minimal essential medium (RPMI1640) containing 10% fetal bovine serum (FBS, Access Biologicals LLC) were seeded in a 96-well culture plate at 7500 cells/80 μL/well, and cultured at 37° C. for 24 hours under 5% $CO_2$ conditions. Each preparation diluted with Opti-MEM (Gibco/Thermo Fisher Scientific Inc.) so as to have a final nucleic acid concentration from 3 to 100 nM was dispensed to the 96-well culture plate at 20 μL/well, and the cells were cultured at 37° C. under 5% $CO_2$ conditions to introduce each preparation into the NCI-H358/Luc cells. Untreated cells were seeded as a negative control group.

The cells containing each preparation thus introduced were cultured in a 5% $CO_2$ incubator of 37° C. for 24 hours and treated using a luciferase quantification system (Steady-Glo Luciferase Assay System, Promega Corp., E2520) in accordance with the method described in the instructions attached to the product, followed by the measurement of luminescence intensity with a plate reader. The amount of luminescence of the group treated with each preparation was calculated as a relative ratio to the corrected amount of luminescence of the negative control group defined as 1 to obtain an IC50 value.

As is evident from Table 43, these results demonstrated that the lipid nanoparticle of the present invention containing a fatty acid ester analog of glycerol that is not hydrolyzable by a lipase can introduce a nucleic acid into cells, etc. even in the presence of PLA2.

TABLE 43

| Preparation No. | KD % (3 nM) | IC50 (nM) |
|---|---|---|
| 45 | 62.3 | 5.81 |
| 46 | 70.4 | 4.11 |
| 47 | 2.36 | 93.1 |
| 48 | 56.9 | 7.58 |
| 49 | 12.4 | 56.1 |
| 51 | 59.8 | 7.09 |
| 52 | 26.1 | 20.8 |
| 53 | 45.7 | 12.7 |
| 54 | 56.6 | 7.95 |
| 55 | 23.0 | 22.8 |
| 56 | 72.7 | 3.22 |
| 57 | 31.8 | 19.5 |
| 59 | 15.3 | 36.4 |
| 60 | 40.5 | 14.6 |

Free Text of Sequence Listing

SEQ ID NO: 1 represents the nucleotide sequence of a Luc siRNA sense strand.

SEQ ID NO: 2 represents the nucleotide sequence of a Luc siRNA antisense strand.

The invention claimed is:

1. A nucleic acid-containing lipid nanoparticle comprising an analog of a fatty acid ester of glycerol wherein the analog is not hydrolyzable by a lipase,
a nucleic acid, and
a cationic lipid,
wherein the cationic lipid is lipid A represented by at least one of the following formulas (I) to (IV), (V') and (V''), and/or lipid B represented by at least one of the following formulas (CL-I) to (CL-XIX):

formula (I)

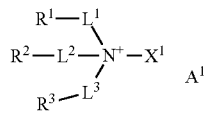

wherein
$R^1$ to $R^3$ are the same or different and are each optionally substituted linear or branched C8-C24 alkyl, C8-C24 alkenyl or C8-C24 alkynyl;
$L^1$ to $L^3$ are the same or different and are each absent, or $-Z^1-(CY^1Y^2)_{p1}-$ or $-Z^2-(CY^3Y^4)_{p2}-Z^3-(CY^5Y^6)_{p3}-$ wherein $Y^1$ to $Y^6$ are the same or different and are each a hydrogen atom or optionally substituted C1-C4 alkyl; $Z^1$ to $Z^3$ are the same or different and are each $-O-$, $-NY^{7A}-$, $-CO-O-$, $-O-CO-$, $-CO-NY^{7B}-$, $-NY^{7C}-CO-$ or $-NY^{7D}-CO-O-$ wherein $Y^{7A}$ to $Y^{7D}$ are the same or different and are each a hydrogen atom or optionally substituted C1-C4 alkyl; and $p^1$ to $p^3$ are the same or different and are each an integer from 1 to 5;
$X^1$ is optionally substituted C1-C4 alkyl; and
$A^1$ is a pharmaceutically acceptable anion, formula (II)

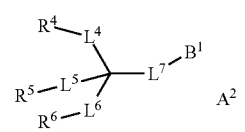

wherein
- $R^4$ to $R^6$ are the same or different and are each optionally substituted linear or branched C8-C24 alkyl, C8-C24 alkenyl or C8-C24 alkynyl;
- $L^4$ to $L^6$ are the same or different and are each absent, or $-Z^4-(CY^8Y^9)_{p4}-$ or $-Z^5-(CY^{10}Y^{11})_{p5}-Z^6-(CY^{12}Y^{13})_{p6}-$ wherein $Y^8$ to $Y^{13}$ are the same or different and are each a hydrogen atom or optionally substituted C1-C4 alkyl; $Z^4$ to $Z^6$ are the same or different and are each $-O-$, $-NY^{14A}-$, $-CO-$, $-O-CO-$, $-CO-NY^{14B}-$, $-NY^{14C}-CO-$ or $-NY^{14D}-CO-O-$ wherein $Y^{14A}$ to $Y^{14D}$ are the same or different and are each a hydrogen atom or optionally substituted C1-C4 alkyl; $p^4$ is an integer from 0 to 5; $p^5$ is an integer from 1 to 5; and $p^6$ is an integer from 0 to 5;
- $L^7$ is absent, or $-(CY^{15}Y^{16})_{p7}-$, $-(CY^{17}Y^{18})_{p8}-Z^7-(CY^{19}Y^{20})_{p9}-$ or $-(CY^{21}Y^{22})_{p10}-Z^8-(CY^{23}Y^{24})_{p11}-Z^9-(CY^{25}Y^{26})_{p12}-$ wherein $Y^{15}$ to $Y^{26}$ are the same or different and are each a hydrogen atom or optionally substituted C1-C4 alkyl; $Z^7$ to $Z^9$ are the same or different and are each $-O-$, $-NY^{27A}-$, $-CO-O-$, $-O-CO-$, $-CO-NY^{27B}-$, $-NY^{27C}-CO-$ or $-NY^{27D}-CO-O-$ wherein $Y^{27A}$ to $Y^{27D}$ are the same or different and are each a hydrogen atom or optionally substituted C1-C4 alkyl; $p^7$ is an integer from 1 to 5; $p^8$ is an integer from 0 to 5; $p^9$ is an integer from 1 to 5; $p^{10}$ is an integer from 0 to 5; $p^{11}$ is an integer from 1 to 5; and $p^{12}$ is an integer from 1 to 5;
- $B^1$ is

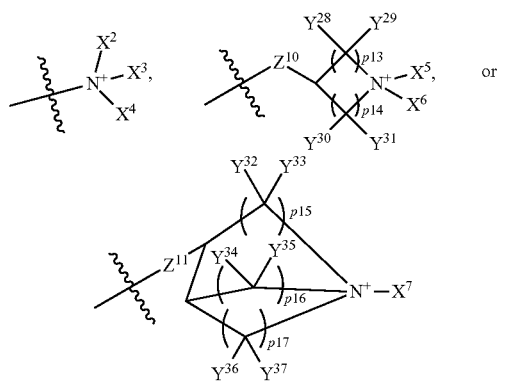

wherein $X^2$ and $X^3$ are the same or different and are each optionally substituted C1-C4 alkyl, or together form an optionally substituted C4-C6 hetero ring with the adjacent nitrogen atom; $X^4$ is optionally substituted C1-C4 alkyl; $X^5$ and $X^6$ are the same or different and are each optionally substituted C1-C4 alkyl, or together form an optionally substituted C4-C6 hetero ring with the adjacent nitrogen atom; $X^7$ is optionally substituted C1-C4 alkyl; $Y^{28}$ to $Y^{37}$ are the same or different and are each a hydrogen atom or optionally substituted C1-C4 alkyl; $Z^{10}$ and $Z^{11}$ are the same or different and are each $-O-$, $-NY^{38A}-$, $-CO-O-$, $-O-CO-$, $-CO-NY^{38B}-$, $-NY^{38C}-CO-$ or $-NY^{38D}-CO-O-$ wherein $Y^{38A}$ to $Y^{38D}$ are the same or different and are each a hydrogen atom or optionally substituted C1-C4 alkyl; $p^{13}$ is an integer from 0 to 5; and $p^{14}$ to $p^{17}$ are the same or different and are each an integer from 1 to 5; and $A^2$ is a pharmaceutically acceptable anion, formula (III)

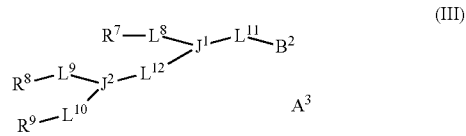

(III)

wherein
- $R^7$ to $R^9$ are the same or different and are each optionally substituted linear or branched C8-C24 alkyl, C8-C24 alkenyl or C8-C24 alkynyl;
- $L^8$ to $L^{10}$ are the same or different and are each absent, or $-Z^{11}-(CY^{39}Y^{40})_{p18}-$ or $-Z^{13}-(CY^{41}Y^{42})_{p19}-Z^{14}-(CY^{43}Y^{44})_{p20}-$ wherein $Y^{39}$ to $Y^{44}$ are the same or different and are each a hydrogen atom or optionally substituted C1-C4 alkyl; $Z^{12}$ to $Z^{14}$ are the same or different and are each $-O-$, $-NY^{45A}-$, $-CO-$, $-O-CO-$, $-CO-NY^{45B}-$, $-NY^{45C}-CO-$, $-NY^{45D}-CO-O-$ or $-CO-$ wherein $Y^{45A}$ to $Y^{45D}$ are the same or different and are each a hydrogen atom or optionally substituted C1-C4 alkyl; $p^{18}$ is an integer from 0 to 5; $p^{19}$ is an integer from 1 to 5; and $p^{20}$ is an integer from 0 to 5;
- $L^{11}$ is absent, or $-(CY^{46}Y^{47})_{p21}-$, $-(CY^{48}Y^{49})_{p22}-Z^{15}-(CY^{50}Y^{51})_{p23}-$ or $-(CY^{52}Y^{53})_{p24}-Z^{16}-(CY^{54}Y^{55})_{p25}-Z^{17}-(CY^{56}Y^{57})_{p26}-$ wherein $Y^{46}$ to $Y^{57}$ are the same or different and are each a hydrogen atom or optionally substituted C1-C4 alkyl; $Z^{15}$ to $Z^{17}$ are the same or different and are each $-O-$, $-NY^{58A}-$, $-CO-O-$, $-O-CO-$, $-CO-NY^{58B}-$, $-NY^{58C}-CO-$, $-NY^{58D}-CO-O-$ or $-CO-$ wherein $Y^{58A}$ to $Y^{58D}$ are the same or different and are each a hydrogen atom or optionally substituted C1-C4 alkyl; $p^{21}$ is an integer from 1 to 5; $p^{22}$ is an integer from 0 to 5; $p^{23}$ is an integer from 1 to 5; $p^{24}$ is an integer from 0 to 5; $p^{25}$ is an integer from 1 to 5; and $p^{26}$ is an integer from 1 to 5;
- $L^{12}$ is absent, or $-(CY^{59}Y^{60})_{p27}-$, $-(CY^{61}Y^{62})_{p28}-Z^{18}-(CY^{63}Y^{64})_{p29}-$ or $-(CY^{65}Y^{66})_{p30}-Z^{19}-(CY^{67}Y^{68})_{p31}-Z^{20}-(CY^{69}Y^{70})_{p32}-$ wherein $Y^{59}$ to $Y^{70}$ are the same or different and are each a hydrogen atom or optionally substituted C1-C4 alkyl; $Z^{18}$ to $Z^{20}$ are the same or different and are each $-O-$, $-NY^{71A}-$, $-CO-O-$, $-O-CO-$, $-CO-NY^{71B}-$, $-NY^{71C}-CO-$, $-NY^{71D}-CO-O-$ or $-CO-$ wherein $Y^{71A}$ to $Y^{71D}$ are the same or different and are each a hydrogen atom or optionally substituted C1-C4 alkyl; $p^{27}$ is an integer from 1 to 5; $p^{28}$ is an integer from 0 to 5; $p^{29}$ is an integer from 0 to 5; $p^{30}$ is an integer from 0 to 5; $p^{31}$ is an integer from 1 to 5; and $p^{32}$ is an integer from 0 to 5;
- $J^1$ and $J^2$ are the same or different and are each $CY^{72}$ or N wherein $Y^{72}$ is a hydrogen atom, hydroxy, optionally substituted C1-C4 alkyl, optionally substituted C1-C4 alkoxy, or optionally substituted C1-C4 acyloxy;
- $B^2$ is

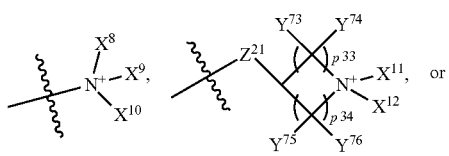

-continued

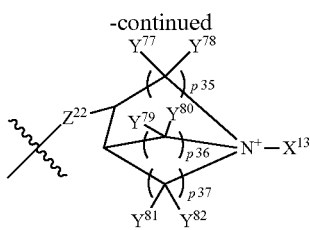

wherein $X^8$ and $X^9$ are the same or different and are each optionally substituted C1-C4 alkyl, or together form an optionally substituted C4-C6 hetero ring with the adjacent nitrogen atom; $X^{10}$ is optionally substituted C1-C4 alkyl; $X^{11}$ and $X^{12}$ are the same or different and are each optionally substituted C1-C4 alkyl, or together form an optionally substituted C4-C6 hetero ring with the adjacent nitrogen atom; $X^{13}$ is optionally substituted C1-C4 alkyl; $Y^{73}$ to $Y^{82}$ are the same or different and are each a hydrogen atom or optionally substituted C1-C4 alkyl; $Z^{21}$ and $Z^{22}$ are the same or different and are each —O—, —NY$^{83A}$—, —CO—O—, —O—CO—, —CO—NY$^{83B}$—, —NY$^{83C}$—CO— or —NY$^{83D}$—CO—O— wherein $Y^{83A}$ to $Y^{83D}$ are the same or different and are each a hydrogen atom or optionally substituted C1-C4 alkyl; $p^{33}$ is an integer from 0 to 5; and $p^{34}$ to $p^{37}$ are the same or different and are each an integer from 1 to 5; and $A^3$ is a pharmaceutically acceptable anion, formula (IV)

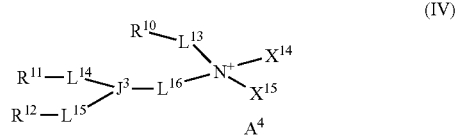

wherein
R$^{10}$ to R$^{12}$ are the same or different and are each optionally substituted linear or branched C8-C24 alkyl, C8-C24 alkenyl or C8-C24 alkynyl;
L$^{13}$ is absent, or —Z$^{23}$—(CY$^{83}$Y$^{84}$)$_{p38}$— or —Z$^{24}$—(CY$^{85}$Y$^{86}$)$_{p39}$—Z$^{25}$—(CY$^{87}$Y$^{88}$)$_{p40}$— wherein Y$^{83}$ to Y$^{88}$ are the same or different and are each a hydrogen atom or optionally substituted C1-C4 alkyl; Z$^{23}$ to Z$^{25}$ are the same or different and are each —O—, —NY$^{89A}$—, —CO—O—, —O—CO—, —CO—NY$^{89B}$—, —NY$^{89C}$—CO— or —NY$^{89D}$—CO—O— wherein Y$^{89A}$ to Y$^{89D}$ are the same or different and are each a hydrogen atom or optionally substituted C1-C4 alkyl; and $p^{38}$ to $p^{40}$ are the same or different and are each an integer from 1 to 5;
L$^{14}$ and L$^{15}$ are the same or different and are each absent, or —Z$^{26}$—(CY$^{90}$Y$^{91}$)$_{p41}$— or —Z$^{27}$—(CY$^{92}$Y$^{93}$)$_{p42}$—Z$^{28}$—(CY$^{94}$Y$^{95}$)$_{p43}$— wherein Y$^{90}$ to Y$^{95}$ are the same or different and are each a hydrogen atom or optionally substituted C1-C4 alkyl; Z$^{26}$ to Z$^{28}$ are the same or different and are each —O—, —NY$^{96A}$—, —CO—O—, —O—CO—, —CO—NY$^{96B}$—, —NY$^{96C}$—CO—, —NY$^{96D}$—CO—O— or —CO— wherein Y$^{96A}$ to Y$^{96D}$ are the same or different and are each a hydrogen atom or optionally substituted C1-C4 alkyl; $p^{41}$ is an integer from 0 to 5; $p^{42}$ is an integer from 1 to 5; and $p^{43}$ is an integer from 0 to 5;
L$^{16}$ is absent, or —(CY$^{97}$Y$^{98}$)$_{p44}$—, —(CY$^{99}$Y$^{100}$)$_{p45}$—Z$^{29}$—(CY$^{101}$Y$^{102}$)$_{p46}$— or —(CY$^{103}$Y$^{104}$)$_{p47}$—Z$^{30}$—(CY$^{105}$Y$^{106}$)$_{p48}$—Z$^{31}$—(CY$^{107}$Y$^{108}$)$_{p49}$— wherein Y$^{97}$ to Y$^{108}$ are the same or different and are each a hydrogen atom or optionally substituted C1-C4 alkyl; Z$^{29}$ to Z$^{31}$ are the same or different and are each —O—, —NY$^{109A}$—, —CO—O—, —O-CO—, —CO—NY$^{109B}$—, —NY$^{109C}$—CO—, —NY$^{109D}$—CO—O— or —CO— wherein Y$^{109A}$ to Y$^{109D}$ are the same or different and are each a hydrogen atom or optionally substituted C1-C4 alkyl; $p^{44}$ is an integer from 1 to 5; $p^{45}$ is an integer from 0 to 5; $p^{46}$ is an integer from 1 to 5; $p^{47}$ is an integer from 0 to 5; $p^{48}$ is an integer from 1 to 5; and $p^{49}$ is an integer from 1 to 5;
J$^3$ is CY$^{110}$ or N wherein Y$^{110}$ is a hydrogen atom, hydroxy, optionally substituted C1-C4 alkyl, optionally substituted C1-C4 alkoxy, or optionally substituted C1-C4 acyloxy;
X$^{14}$ and X$^{15}$ are the same or different and are each optionally substituted C1-C4 alkyl, or together form an optionally substituted C4-C6 hetero ring with the adjacent nitrogen atom; and
$A^4$ is a pharmaceutically acceptable anion, formula (V') or formula (V'')

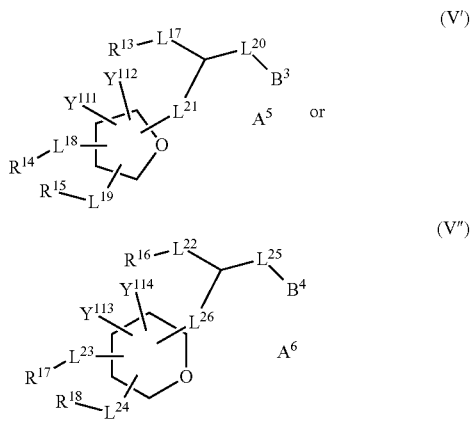

wherein
R$^{13}$ to R$^{18}$ are the same or different and are each optionally substituted linear or branched C8-C24 alkyl, C8-C24 alkenyl or C8-C24 alkynyl;
Y$^{111}$ to Y$^{114}$ are the same or different and are each a hydrogen atom, hydroxy or optionally substituted C1-C4 alkyl;
L$^{17}$ to L$^{19}$ and L$^{22}$ to L$^{24}$ are the same or different and are each absent, or —Z$^{32}$—(CY$^{115}$Y$^{116}$)$_{p51}$— or —Z$^{33}$—(CY$^{117}$Y$^{118}$)$_{p52}$—Z$^{34}$—(CY$^{119}$Y$^{120}$)$_{p53}$— wherein Y$^{115}$ to Y$^{120}$ are the same or different and are each a hydrogen atom or optionally substituted C1-C4 alkyl; Z$^{32}$ to Z$^{34}$ are the same or different and are each —O—, —NY$^{121A}$—, —CO—O—, —O—CO—, —CO—NY$^{121B}$—, —NY$^{121C}$—CO—, —NY$^{121D}$—CO—O— or —CO— wherein Y$^{121A}$ to Y$^{121D}$ are the same or different and are each a hydrogen atom or optionally substituted C1-C4 alkyl; $p^{51}$ is an integer from 0 to 5; $p^{52}$ is an integer from 1 to 5; and $p^{53}$ is an integer from 0 to 5;
L$^{20}$ and L$^{25}$ are the same or different and are each absent, or —(CY$^{122}$Y$^{123}$)$_{p54}$—, —(CY$^{124}$Y$^{125}$)$_{p55}$—Z$^{35}$—(CY$^{126}$Y$^{127}$)$_{p56}$— or —(CY$^{128}$Y$^{129}$)$_{p57}$—Z$^{36}$—(CY$^{130}$Y$^{131}$)$_{p58}$—Z$^{37}$—(CY$^{132}$Y$^{133}$)$_{p59}$— wherein Y$^{122}$ to Y$^{133}$ are the same or different and are each a hydrogen atom or optionally substituted C1-C4 alkyl; $Z^{35}$ to $Z^{37}$ are the same or different and are each —O—, —$NY^{134A}$—, —CO—O—, —O—CO—, —CO—$NY^{134B}$—, —$NY^{134C}$—CO—, —$NY^{134D}$—CO—O— or —CO— wherein $Y^{134A}$ to $Y^{134D}$ are the same or different and are each a hydrogen atom or optionally substituted C1-C4 alkyl; $p^{54}$ is an integer from 1 to 5; $p^{55}$ is an integer from 0 to 5; $p^{56}$ is an integer from 1 to 5; $p^{57}$ is an integer from 0 to 5; $p^{58}$ is an integer from 1 to 5; and $p^{59}$ is an integer from 1 to 5;

$L^{21}$ and $L^{26}$ are the same or different and are each absent, or —$(CY^{135}Y^{136})_{p60}$—, —$(CY^{137}Y^{138})_{p61}$—$Z^{38}$—$(CY^{139}Y^{140})_{p62}$— or —$(CY^{141}Y^{142})_{p63}$—$Z^{39}$—$(CY^{143}Y^{144})_{p64}$—$Z^{40}$—$(CY^{145}Y^{146})_{p65}$— wherein $Y^{135}$ to $Y^{146}$ are the same or different and are each a hydrogen atom or optionally substituted C1-C4 alkyl; $Z^{38}$ to $Z^{40}$ are the same or different and are each —O—, —$NY^{147A}$—CO—O—, —O—CO—, —CO—$NY^{147B}$—, —$NR^{147C}$—CO—, —$NY^{147D}$—CO—O— or —CO— wherein $Y^{147A}$ to $Y^{147D}$ are the same or different and are each a hydrogen atom or optionally substituted C1-C4 alkyl; $p^{60}$ is an integer from 1 to 5; $p^{61}$ is an integer from 0 to 5; $p^{62}$ is an integer from 0 to 5; $p^{63}$ is an integer from 0 to 5; $p^{64}$ is an integer from 1 to 5; and $p^{65}$ is an integer from 0 to 5;

$B^3$ and $B^4$ are the same or different and are each

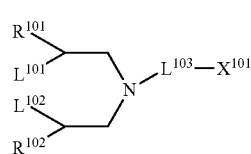
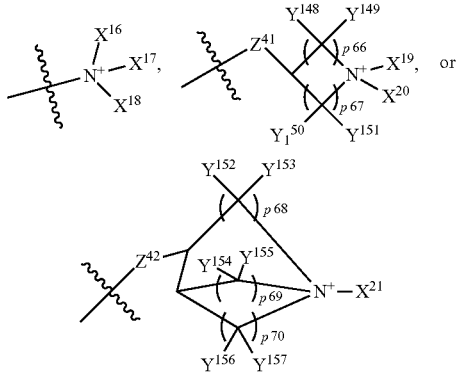

wherein $X^{16}$ and $X^{17}$ are the same or different and are each optionally substituted C1-C4 alkyl, or together form an optionally substituted C4-C6 hetero ring with the adjacent nitrogen atom; $X^{18}$ is optionally substituted C1-C4 alkyl; $X^{19}$ and $X^{20}$ are the same or different and are each optionally substituted C1-C4 alkyl, or together form an optionally substituted C4-C6 hetero ring with the adjacent nitrogen atom; $X^{21}$ is optionally substituted C1-C4 alkyl; $Y^{148}$ to $Y^{157}$ are the same or different and are each a hydrogen atom or optionally substituted C1-C4 alkyl; $Z^{41}$ and $Z^{42}$ are the same or different and are each —O—, —$NY^{158A}$—, —CO—, —O—CO—, —CO—$NY^{158B}$—, —$NY^{158C}$—CO— or —$NY^{158D}$—CO—O— wherein $Y^{158A}$ to $Y^{158D}$ are the same or different and are each a hydrogen atom or optionally substituted C1-C4 alkyl; $p^{66}$ is an integer from 0 to 5; and $p^{67}$ to $p^{70}$ are the same or different and are each an integer from 1 to 5; and $A^5$ and $A^6$ are the same or different and are each a pharmaceutically acceptable anion, formula (CL-I)

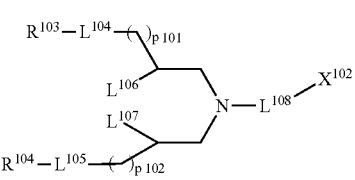

(CL-I)

wherein
$R^{101}$ and $R^{102}$ are the same or different and are each linear or branched C10-C24 alkyl, C10-C24 alkenyl or C10-C24 alkynyl;
$L^{101}$ and $L^{102}$ are each a hydrogen atom, or together form a single bond or C2-C8 alkylene;
$L^{103}$ is a single bond, —CO— or —CO—O—;
when $L^{103}$ is a single bond,
$X^{101}$ is a hydrogen atom, C1-C6 alkyl, C3-C6 alkenyl, pyrrolidin-3-yl, piperidin-3-yl, piperidin-4-yl, or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl; and
when $L^{103}$ is —CO— or —CO—O—,
$X^{101}$ is pyrrolidin-2-yl, pyrrolidin-3-yl, piperidin-2-yl, piperidin-3-yl, piperidin-4-yl, morpholin-2-yl, morpholin-3-yl, or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl, and at least one of the substituents is amino, monoalkylamino, dialkylamino, trialkylammonio, pyrrolidinyl, piperidyl or morpholinyl, formula (CL-II)

(CL-II)

wherein
$R^{103}$ and $R^{104}$ are the same or different and are each linear or branched C12-C24 alkyl, C12-C24 alkenyl or C12-C24 alkynyl;
$p^{101}$ and $p^{102}$ are the same or different and are each an integer from 0 to 3;
$L^{106}$ and $L^{107}$ are each a hydrogen atom, or together form a single bond or C2-C8 alkylene;
$L^{104}$ and $L^{105}$ are the same or different and are each —O—, —CO—O— or —O—CO—;
$L^{108}$ is a single bond, —CO— or —CO—O—;
when $L^{108}$ is a single bond,
$X^{102}$ is a hydrogen atom, C1-C6 alkyl, C3-C6 alkenyl, pyrrolidin-2-yl, pyrrolidin-3-yl, piperidin-3-yl, piperidin-4-yl, or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl; and when $L^{108}$ is —CO— or —CO—O—, $X^{102}$ is pyrrolidin-2-yl, pyrrolidin-3-yl, piperidin-2-yl, piperidin-3-yl, piperidin-4-yl, morpholin-2-yl, morpholin-3-yl, or C1-C6 alkyl or C3-C6 alkenyl substituted with one to three same or different substituents selected from amino, monoalkylamino, dialkylamino, trialkylammonio, hydroxy, alkoxy, carbamoyl, monoalkylcarbamoyl, dialkylcarbamoyl, pyrrolidinyl, piperidyl and morpholinyl, and at least one of the substituents is amino, monoalkylamino, dialkylamino, trialkylammonio, pyrrolidinyl, piperidyl or morpholinyl, formula (CL-III)

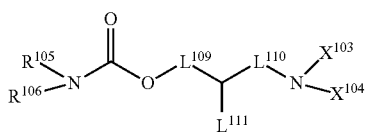

(CL-III)

wherein $R^{105}$ is linear or branched C8-C24 alkyl, C8-C24 alkenyl or C8-C24 alkynyl;

$R^{106}$ is linear or branched C8-C24 alkyl, C8-C24 alkenyl, C8-C24 alkynyl, C8-C24 alkyloxyethyl, C8-C24 alkyloxypropyl, C8-C24 alkenyloxyethyl, C8-C24 alkenyloxypropyl, C8-C24 alkynyloxyethyl or C8-C24 alkynyloxypropyl;

$X^{103}$ and $X^{104}$ are the same or different and are each C1-C3 alkyl, or together form C2-C8 alkylene, or $X^{103}$ forms C2-C8 alkylene together with $L^{111}$;

$L^{111}$ is a hydrogen atom, C1-C6 alkyl, C3-C6 alkenyl, amino, monoalkylamino, hydroxy, alkoxy, carbamoyl, monoalkylcarbamoyl, dialkylcarbamoyl, or C1-C6 alkyl or C3-C6 alkenyl substituted with one to three same or different substituents selected from amino, monoalkylamino, hydroxy, alkoxy, carbamoyl, monoalkylcarbamoyl and dialkylcarbamoyl, or forms C2-C8 alkylene together with $X^{103}$;

$L^{109}$ is C1-C6 alkylene;

$L^{110}$ is a single bond, or C1-C6 alkylene, provided that the sum of the numbers of carbon atoms of $L^{109}$ and $L^{110}$ is 7 or less; when $L^{111}$ is a hydrogen atom, $L^{110}$ is a single bond; and when $L^{111}$ forms C2-C6 alkylene together with $X^{103}$, $L^{110}$ is a single bond, or methylene or ethylene, formula (CL-IV)

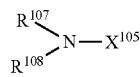

(CL-IV)

wherein $R^{107}$ is linear or branched C8-C24 alkyl, C8-C24 alkenyl or C8-C24 alkynyl;

$R^{108}$ is linear or branched C8-C24 alkyl, C8-C24 alkenyl, C8-C24 alkynyl, C8-C24 alkyloxyethyl, C8-C24 alkyloxypropyl, C8-C24 alkenyloxyethyl, C8-C24 alkenyloxypropyl, C8-C24 alkynyloxyethyl, C8-C24 alkynyloxypropyl, C8-C24 alkyloxyethoxyethyl, C8-C24 alkenyloxyethoxyethyl or C8-C24 alkynyloxyethoxyethyl; and $X^{105}$ is a hydrogen atom or optionally substituted C1-C4 alkyl, formula (CL-V)

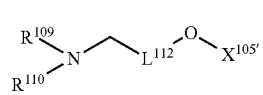

(CL-V)

wherein $R^{109}$ is linear or branched C8-C24 alkyl, C8-C24 alkenyl or C8-C24 alkynyl;

$R^{110}$ is linear or branched C8-C24 alkyl, C8-C24 alkenyl, C8-C24 alkynyl, C8-C24 alkyloxyethyl, C8-C24 alkyloxypropyl, C8-C24 alkenyloxyethyl, C8-C24 alkenyloxypropyl, C8-C24 alkynyloxyethyl or C8-C24 alkynyloxypropyl;

$L^{112}$ is C1-C3 alkylene; and $X^{105'}$ is a hydrogen atom or C1-C3 alkyl, formula (CL-VI)

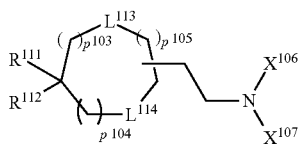

(CL-VI)

wherein $R^{111}$ and $R^{112}$ are the same or different and are each optionally substituted linear or branched C8-C24 alkyl, C8-C24 alkenyl or C8-C24 alkynyl;

$X^{106}$ and $X^{107}$ are the same or different and are each C1-C3 alkyl, or together form C2-C8 alkylene;

$p^{103}$, $p^{104}$ and $p^{105}$ are the same or different and are each 0 or 1, provided that $p^{103}$, $p^{104}$ and $p^{105}$ are not 0 at the same time; and $L^{113}$ and $L^{114}$ are the same or different and are each O, S or NH, formula (CL-VII)

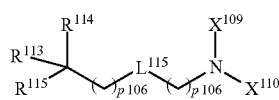

(CL-VII)

wherein $R^{113}$ and $R^{114}$ are the same or different and are each optionally substituted linear or branched C8-C24 alkyl, C8-C24 alkenyl or C8-C24 alkynyl;

$R^{105}$ is a hydrogen atom, hydroxy, optionally substituted C1-C4 alkyl, C1-C4 alkoxy or C1-C4 acyloxy;

$X^{109}$ and $X^{10}$ are the same or different and are each C1-C3 alkyl, or together form C2-C8 alkylene;

$L^{105}$ is —CO—O—, —O—CO—, —NHCO— or —CONH—;

$p^{106}$ is an integer from 0 to 3; and $p^{107}$ is an integer from 1 to 4,
formula (CL-VIII)

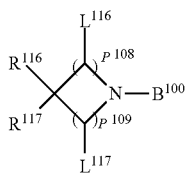
(CL-VIII)

wherein
$R^{116}$ and $R^{17}$ are the same or different and are each optionally substituted linear or branched C8-C24 alkyl, C8-C24 alkenyl, C8-C24 alkynyl, C7-C20 alkyloxy C1-C3 alkyl, C7-C20 alkenyloxy C1-C3 alkyl or C7-C20 alkynyloxy C1-C3 alkyl;
$B^{100}$ is a hydrogen atom, C1-C3 alkyl, hydroxy C2-C4 alkyl, C1-C3 dialkylamino C2-C4 alkyl, formula (A):

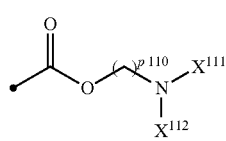
(A)

wherein $X^{111}$ and $X^{112}$ are the same or different and are each a hydrogen atom or C1-C3 alkyl, or $X^{111}$ and $X^{112}$ optionally form a C2-C6 nitrogen-containing hetero ring together with the nitrogen atom to which they are bonded; and $p^{110}$ is an integer from 2 to 6,
or formula (B):

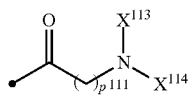
(B)

wherein $X^{113}$ and $X^{114}$ are the same or different and are each a hydrogen atom or C1 to C3 alkyl, or $X^{113}$ and $X^{114}$ optionally form a C2-C6 nitrogen-containing hetero ring together with the nitrogen atom to which they are bonded; and $p^{111}$ is an integer from 1 to 6;
$P^{108}$ is an integer from 0 to 4; $P^{109}$ is an integer from 1 to 4, provided that when $P^{108}$ is 0, $P^{109}$ is not 1;
$L^{116}$ is the same or different on each carbon to which it is bonded and is a hydrogen atom or C1-C3 alkyl; and
$L^{17}$ is the same or different on each carbon to which it is bonded and is a hydrogen atom or C1-C3 alkyl,
formula (CL-IX)

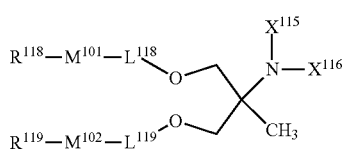
(CL-IX)

wherein
$X^{115}$ and $X^{116}$ are the same or different and are each a hydrogen atom or C1-C3 alkyl;
$L^{118}$ and $L^{119}$ are the same or different and are each optionally substituted linear or branched C8-C24 alkylene or C8-C24 alkenylene;
$M^{101}$ and $M^{102}$ are the same or different and are each selected from the group consisting of —C=C—, —OC(O)—, —C(O)O—, —SC(O)—, —C(O)S—, —OC(S)—, —C(S)O—, —SS—, —C(R")=N—, —N=C(R")—, —C(R")=N—O—, —O—N=C(R")—, —N(R")C(O)—, —C(O)N(R")—, —N(R")C(S)—, —C(S)N(R")—, —N(R")C(O)N(R''')—, —N(R")C(O)O—, —OC(O)N(R")— and —OC(O)O—;
R" and R''' are the same or different and are each a hydrogen atom or C1-C3 alkyl; and
$R^{118}$ and $R^{119}$ are the same or different and are each optionally substituted linear or branched C1-C16 alkyl or C2-C16 alkenyl,
formula (CL-X)

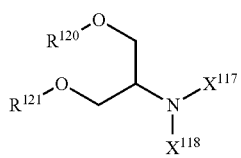
(CL-X)

wherein
$X^{117}$ and $X^{118}$ are the same or different and are each a hydrogen atom, optionally substituted C1-C6 alkyl, heterocyclyl or polyamine, or $X^{117}$ and $X^{118}$ optionally form, together with the nitrogen to which they are bonded, a 4- to 7-membered monocyclic hetero ring optionally containing one or two additional heteroatoms selected from N, O and S in addition to the nitrogen; and
$R^{120}$ and $R^{121}$ are the same or different and are each optionally substituted linear or branched C4-C24 alkyl or C4-C24 alkenyl,
formula (CL-XI)

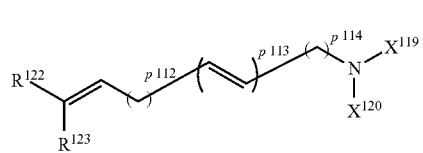
(CL-XI)

wherein
$X^{119}$ and $X^{120}$ are the same or different and are each a hydrogen atom, optionally substituted linear or branched C1-C20 alkyl, C1-C20 alkenyl, C1-C20 alkynyl or C6-C20 acyl;
$R^{122}$ and $R^{123}$ are the same or different and are each optionally substituted linear or branched C1-C30 alkyl, C2-C30 alkenyl or C2-C30 alkynyl; and
$p^{112}$, $p^{113}$ and $p^{114}$ are the same or different and are each 0, or an arbitrary positive integer, formula (CL-XII)

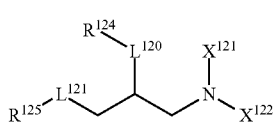

(CL-XII)

wherein $X^{121}$ and $X^{122}$ are the same or different and are each a hydrogen atom, C1-C6 alkyl, cycloalkyl or cycloalkenyl, or $X^{121}$ and $X^{122}$ optionally form a C2-C6 nitrogen-containing hetero ring together with the nitrogen atom to which they are bonded;

$L^{120}$ and $L^{121}$ are the same or different and are each —O—, —OC(O)— or —(O)CO—; and $R^{124}$ and $R^{125}$ are the same or different and are each optionally substituted linear or branched C8-C24 alkyl or C8-C24 alkenyl, formula (CL-XIII)

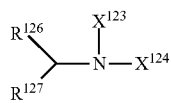

(CL-XIII)

wherein $R^{126}$ and $R^{127}$ are the same or different and are each optionally substituted linear or branched C8-C24 alkyl, C8-C24 alkenyl, C8-C24 alkynyl, C8-C24 heteroalkyl, C8-C24 heteroalkenyl or C8-C24 heteroalkynyl;

$X^{123}$ is a hydrogen atom or optionally substituted C1-C6 alkyl;

$X^{124}$ is C1-C6 alkyl, substituted C1-C6 alkyl which is substituted with —$NR^{4a}R^{4b}$, or optionally substituted C3-C7 heterocyclyl;

$R^{4a}$ and $R^{4b}$ are the same or different and are each a hydrogen atom, C(=NH)NH$_2$ or optionally substituted C1-C6 alkyl, or $R^{4a}$ and $R^{4b}$ optionally form optionally substituted C3-C7 heterocyclyl;

$X^{123}$ and $X^{124}$ optionally form optionally substituted C3-C7 heterocyclyl together with the nitrogen atom to which they are bonded, provided that $X^{123}$ and $X^{124}$ do not form imidazolyl, benzimidazolyl, or succinimidyl, and only one primary amine is allowed to be present on any one of $X^{123}$ and $X^{124}$, or any primary amine is not present on any one of $X^{123}$ and $X^{124}$, and neither $X^{123}$ nor $X^{124}$ is substituted amide;

when each of $R^{126}$ and $R^{127}$ is C11 alkyl or C15 alkyl, $X^{123}$ is not a hydrogen atom;

when each of $R^{126}$ and $R^{127}$ is C16 alkyl or C17 alkyl, $R^{126}$ and $R^{127}$ are not substituted with OH;

when each of $R^{126}$ and $R^{127}$ is C17 alkyl, $X^{123}$ and $X^{124}$ are not substituted with OH; and when each of $R^{126}$ and $R^{127}$ is C18 alkyl, $X^{124}$ is not substituted with optionally substituted imidazolyl, formula (CL-XIV)

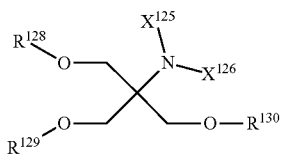

(CL-XIV)

wherein $X^{125}$ and $X^{126}$ are the same or different and are each a hydrogen atom, optionally substituted C1-C6 alkyl, heterocyclyl or polyamine, or $X^{125}$ and $X^{126}$ optionally form, together with the nitrogen to which they are bonded, a 4- to 7-membered monocyclic hetero ring optionally containing one or two additional heteroatoms selected from N, O and S in addition to the nitrogen;

$R^{130}$ is a hydrogen atom or C1-C6 alkyl; and $R^{128}$ and $R^{129}$ are the same or different and are each optionally substituted linear or branched C4-C24 alkyl or C4-C24 alkenyl, formula (CL-XV)

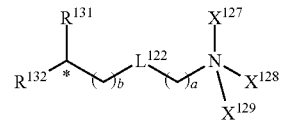

(CL-XV)

wherein $X^{127}$ and $X^{128}$ are each independently C1-C6 alkyl, C2-C6 alkenyl or C2-C6 alkynyl, or $X^{127}$ and $X^{128}$ form, together with the nitrogen atom to which they are bonded, a hetero ring having one or two nitrogen atoms;

$L^{122}$ is —C(O)O—, —OC(O)—, —C(O)N($X^{130}$)—, —N($X^{130}$)C(O)—, —OC(O)O—, —OC(O)N($X^{130}$)—, —N($X^{130}$)C(O)N($X^{130}$)—, or —N($X^{130}$)C(O)O—;

each $X^{130}$ present is independently a hydrogen atom or C1-C3 alkyl;

a is 1, 2, 3, 4, 5, or 6;

b is 0, 1, 2, or 3;

$X^{129}$ is absent, or hydrogen or C1-C3 alkyl;

$R^{131}$ and $R^{132}$ are each independently alkyl having 12 to 24 carbon atoms, alkenyl having 12 to 24 carbon atoms, or alkoxy having 12 to 24 carbon atoms, which has one or more biodegradable groups; each biodegradable group independently interrupts the alkyl group, the alkenyl group, or the alkoxy group having 12 to 24 carbon atoms, or substitutes a terminal of the alkyl group, the alkenyl group, or the alkoxy group having 12 to 24 carbon atoms (wherein the interrupting biodegradable group is —C(O)O—, —OC(O)—, —C(O)N($X^{130}$)—, or —N($X^{130}$)C(O)—, and the group having the terminal biodegradable group is —C(O)O-C1-C4 alkyl, —OC(O)—C1-C4 alkyl, —C(O)N($X^{130}$)—C1-C4 alkyl, or —N($X^{130}$)C(O)—C1-C4 alkyl); and $R^{131}$ and $R^{132}$ each have at least four carbon atoms between the biodegradable group and the asterisked (*) tertiary carbon atom, formula (CL-XVI)

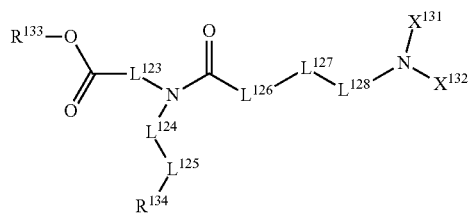
(CL-XVI)

wherein
- $R^{133}$ and $R^{134}$ are the same or different and are each linear or branched C1-C9 alkyl, C2—C11 alkenyl or C2-C11 alkynyl;
- $L^{123}$ and $L^{124}$ are the same or different and are each linear C5-C18 alkylene or linear C5—C18 alkenylene, or forms a hetero ring with N;
- $L^{125}$ is a single bond, or —CO—O—, thereby forming -$L^{124}$-CO—O$R^{134}$;
- $L^{127}$ is S or O;
- $L^{126}$ is a single bond or linear or branched C1-C6 alkylene, or forms a hetero ring with N;
- $L^{128}$ is linear or branched C1-C6 alkylene; and
- $X^{131}$ and $X^{132}$ are the same or different and are each hydrogen or linear or branched C1—C6 alkyl, formula (CL-XVII)

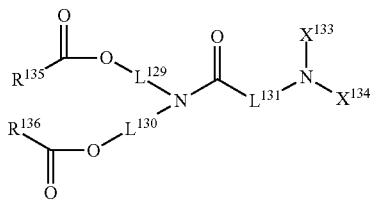
(CL-XVII)

wherein
- $L^{131}$ is C2-C4 alkylene or —CH$_2$—S—CH$_2$CH$_2$—;
- $L^{129}$ and $L^{130}$ are the same or different and are each C1-C6 alkyl;
- $R^{135}$ and $R^{136}$ are the same or different and are each C10-C30 alkyl or C10-C30 alkenyl; and
- $X^{133}$ and $X^{134}$ are the same or different and are each hydrogen, C1-C6 alkyl or —CH$_2$CH$_2$OH, formula (CL-XVIII)

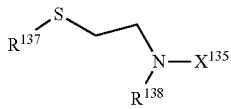
(CL-XVIII)

wherein
- $R^{137}$ and $R^{38}$ are the same or different and are each linear or branched C8-C24 alkyl, C8—C24 alkenyl, C8-C24 alkynyl, C8-C24 alkylthioethyl, C8-24 alkenylthioethyl, or C8-C24 alkynylthioethyl;
- $X^{135}$ is a hydrogen atom, C1-C3 alkyl, hydroxy C2-C4 alkyl, formula (C):

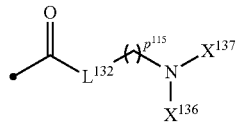
(C)

wherein $X^{136}$ and $X^{137}$ are the same or different and are each a hydrogen atom or C1-C3 alkyl, or $X^{136}$ and $X^{137}$ optionally form a C2-C6 nitrogen-containing hetero ring together with the nitrogen atom to which they are bonded; $L^{132}$ is S or O; and $p^{115}$ is an integer from 2 to 4, formula (D):

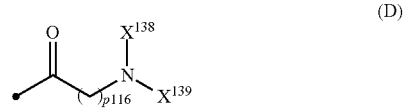
(D)

wherein $X^{138}$ and $X^{139}$ are the same or different and are each a hydrogen atom or C1 to C3 alkyl, or $X^{138}$ and $X^{139}$ optionally form a C3-C6 nitrogen-containing hetero ring together with the nitrogen atom to which they are bonded; and $p^{116}$ is an integer from 1 to 4, or formula (E):

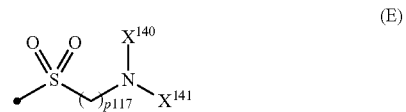
(E)

wherein $X^{140}$ and $X^{141}$ are the same or different and are each a hydrogen atom or C1 to C3 alkyl, or $X^{140}$ and $X^{141}$ optionally form a C3-C6 nitrogen-containing hetero ring together with the nitrogen atom to which they are bonded; and $p^{117}$ is an integer from 1 to 4, and formula (CL-XIX)

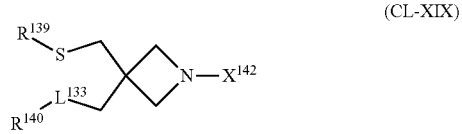
(CL-XIX)

wherein
- $R^{139}$ and $R^{140}$ are the same or different and are each linear or branched C8-C24 alkyl, C8—C24 alkenyl or C8-C24 alkynyl;
- $L^{133}$ is S or O; and
- $X^{142}$ is a hydrogen atom, C1-C3 alkyl, hydroxy C2-C4 alkyl, formula (F):

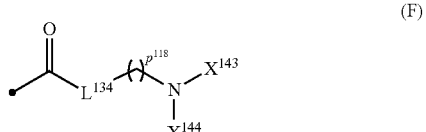
(F)

wherein $X^{143}$ and $X^{144}$ are the same or different and are each a hydrogen atom or C1-C3 alkyl, or $X^{143}$ and $X^{144}$ optionally form a C2-C6 nitrogen-containing hetero ring together with the nitrogen atom to which they are bonded; $L^{134}$ is S or O; and $p^{118}$ is an integer from 2 to 4, or formula (G):

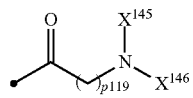
(G)

wherein $X^{145}$ and $X^{146}$ are the same or different and are each a hydrogen atom or C1 to C3 alkyl, or $X^{145}$ and $X^{146}$ optionally form a C3-C6 nitrogen-containing hetero ring together with the nitrogen atom to which they are bonded; and $p^{119}$ is an integer from 1 to 4.

2. The nucleic acid-containing lipid nanoparticle according to claim 1, wherein the analog of the fatty acid ester of glycerol is an analog of a glycerophospholipid.

3. The nucleic acid-containing lipid nanoparticle according to claim 1, wherein the lipase is phospholipase A2.

4. The nucleic acid-containing lipid nanoparticle according to claim 1, wherein the analog of the fatty acid ester of glycerol is a lipid represented by the following formula (1) or (2):

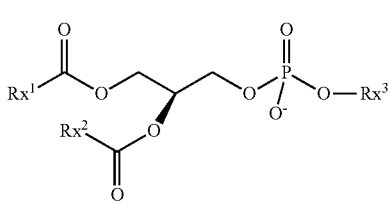
(1)

wherein
$Rx^1$ and $Rx^2$ are the same or different and are each optionally substituted linear or branched C7-C23 alkyl, C7-C23 alkenyl or C7-C23 alkynyl; and
$Rx^3$ is a negative charge, a hydrogen atom, or any of the following groups:

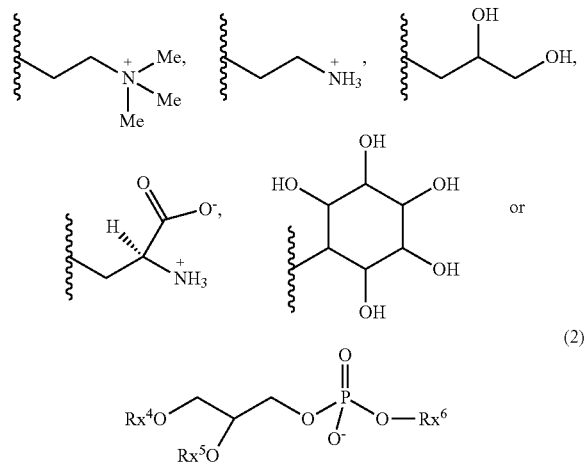
(2)

wherein
$Rx^4$ is optionally substituted linear or branched C8-C24 alkyl, C8-C24 alkenyl or C8-C24 alkynyl or $Rx^{41}$-CO—;

$Rx^{41}$ is optionally substituted linear or branched C7-C23 alkyl, C7-C23 alkenyl or C7—C23 alkynyl;
$Rx^5$ is optionally substituted linear or branched C8-C24 alkyl, C8-C24 alkenyl or C8-C24 alkynyl; and
$Rx^6$ is a negative charge, a hydrogen atom, or any of the following groups:

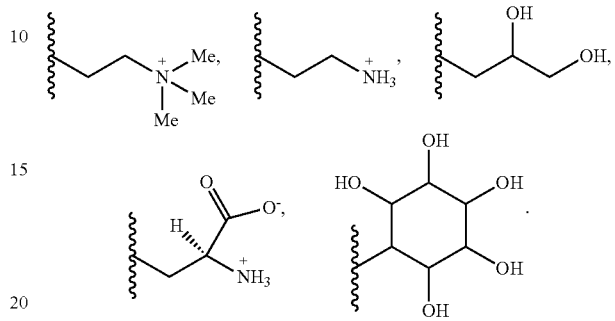

5. The nucleic acid-containing lipid nanoparticle according to claim 1, wherein the cationic lipid is the lipid B.

6. The nucleic acid-containing lipid nanoparticle according to claim 1, further comprising a lipid derivative or a fatty acid derivative of a water-soluble polymer.

7. The nucleic acid-containing lipid nanoparticle according to claim 1, further comprising a neutral lipid.

8. The nucleic acid-containing lipid nanoparticle according to claim 1, wherein the nucleic acid is a nucleic acid having a silencing effect on a target gene through the use of RNA interference (RNAi).

9. A method for introducing a nucleic acid into a cell comprising administering intravenously or subcutaneously the nucleic acid-containing lipid nanoparticle according to claim 1 to a human in need thereof,
wherein the cell is a human cell from a liver, stomach, lung, kidney, pancreas or spleen.

10. The method according to claim 9, wherein the cell is a cell residing at a tumor or inflammation site.

11. A method for treating a cancer of the liver, stomach, lungs, kidneys, pancreas or spleen or an inflammatory disease of the liver, stomach, lungs, kidneys, pancreas or spleen, comprising administering the nucleic acid-containing lipid nanoparticle according to claim 1 to a human in need thereof.

12. The method for treating according to claim 11, wherein the administration is intravenous administration or subcutaneous administration.

13. A medicament comprising the nucleic acid-containing lipid nanoparticle according to claim 1.

14. The medicament according to claim 13, wherein the medicament is intended for intravenous administration or subcutaneous administration.

15. A therapeutic agent for a cancer of the liver, stomach, lungs, kidneys, pancreas or spleen or an inflammatory disease of the liver, stomach, lungs, kidneys, pancreas or spleen, comprising the nucleic acid-containing lipid nanoparticle according to claim 1.

16. The therapeutic agent according to claim 15, wherein the therapeutic agent is intended for intravenous administration or subcutaneous administration.

17. A compound represented by formula (CL-XVIII), or a pharmaceutically acceptable salt thereof:

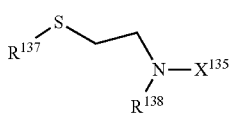

(CL-XVIII)

wherein
R$^{137}$ and R$^{38}$ are the same or different and are each linear or branched C8-C24 alkyl, C8—C24 alkenyl, C8-C24 alkynyl, C8-C24 alkylthioethyl, C8-24 alkenylthioethyl, or C8-C24 alkynylthioethyl; and
X$^{135}$ is a hydrogen atom, C1-C3 alkyl, hydroxy C2-C4 alkyl, formula (C):

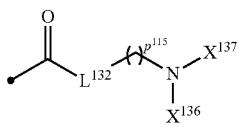

(C)

wherein X$^{136}$ and X$^{137}$ are the same or different and are each a hydrogen atom or C1-C3 alkyl, or X$^{136}$ and X$^{137}$ optionally form a C2-C6 nitrogen-containing hetero ring together with the nitrogen atom to which they are bonded; L$^{132}$ is S or O; and p$^{115}$ is an integer from 2 to 4,
formula (D):

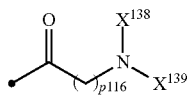

(D)

wherein X$^{138}$ and X$^{139}$ are the same or different and are each a hydrogen atom or C1 to C3 alkyl, or X$^{138}$ and X$^{139}$ optionally form a C3-C6 nitrogen-containing hetero ring together with the nitrogen atom to which they are bonded; and p$^{116}$ is an integer from 1 to 4, or formula (E):

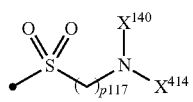

(E)

wherein X$^{140}$ and X$^{141}$ are the same or different and are each a hydrogen atom or C1 to C3 alkyl, or X$^{140}$ and X$^{141}$ optionally form a C3-C6 nitrogen-containing hetero ring together with the nitrogen atom to which they are bonded; and p$^{117}$ is an integer from 1 to 4.

18. A compound represented by formula (CL-XIX), or a pharmaceutically acceptable salt thereof:

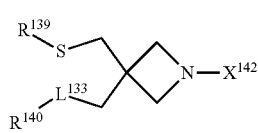

(CL-XIX)

wherein
R$^{139}$ and R$^{140}$ are the same or different and are each linear or branched C8-C24 alkyl, C8—C24 alkenyl or C8-C24 alkynyl;
L$^{133}$ is S or O; and
X$^{142}$ is a hydrogen atom, C1-C3 alkyl, hydroxy C2-C4 alkyl, formula (F):

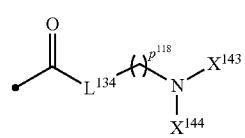

(F)

wherein X$^{143}$ and X$^{144}$ are the same or different and are each a hydrogen atom or C1-C3 alkyl, or X$^{143}$ and X$^{144}$ optionally form a C2-C6 nitrogen-containing hetero ring together with the nitrogen atom to which they are bonded; L$^{134}$ is S or O; and p$^{118}$ is an integer from 2 to 4,
or formula (G):

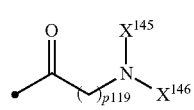

(G)

wherein X$^{145}$ and X$^{146}$ are the same or different and are each a hydrogen atom or C1 to C3 alkyl, or X$^{145}$ and X$^{146}$ optionally form a C3-C6 nitrogen-containing hetero ring together with the nitrogen atom to which they are bonded; and p$^{119}$ is an integer from 1 to 4.

* * * * *

SEQUENCE LISTING

```
<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: Luc siRNA sense

<400> SEQUENCE: 1
ccgucguauu cgugagcaag a                                              21

<210> SEQ ID NO 2
<211> LENGTH: 21
<212> TYPE: RNA
<213> ORGANISM: Artificial Sequence
<220> FEATURE:
<223> OTHER INFORMATION: Luc siRNA antisense

<400> SEQUENCE: 2
uugcucacga auacgacggu g                                              21
```